US010137190B2

(12) United States Patent
Nabel et al.

(10) Patent No.: US 10,137,190 B2
(45) Date of Patent: Nov. 27, 2018

(54) NUCLEIC ACID MOLECULES ENCODING FERRITIN-HEMAGGLUTININ FUSION PROTEINS

(71) Applicant: The United States of America, as represented by the Secretary, Department of Health and Human Services, Washington, DC (US)

(72) Inventors: Gary J. Nabel, Chestnut Hill, MA (US); Masaru Kanekiyo, Chevy Chase, MD (US); Chih-Jen Wei, Potomac, MD (US); Patrick M. McTamney, Bethesda, MD (US); Hadi M. Yassine, Rockville, MD (US); Jeffrey C. Boyington, Clarksburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/244,321

(22) Filed: Aug. 23, 2016

(65) Prior Publication Data
US 2017/0189518 A1    Jul. 6, 2017

Related U.S. Application Data

(62) Division of application No. 14/346,849, filed as application No. PCT/US2012/056822 on Sep. 24, 2012, now Pat. No. 9,441,019.

(60) Provisional application No. 61/538,663, filed on Sep. 23, 2011, provisional application No. 61/661,209, filed on Jun. 18, 2012.

(51) Int. Cl.
| A61K 39/145 | (2006.01) |
| A61K 39/12 | (2006.01) |
| A61K 39/02 | (2006.01) |
| C07K 14/11 | (2006.01) |
| C07K 14/205 | (2006.01) |
| C12N 7/00 | (2006.01) |
| G01N 33/569 | (2006.01) |
| C07K 14/005 | (2006.01) |
| A61K 39/00 | (2006.01) |

(52) U.S. Cl.
CPC ............ *A61K 39/145* (2013.01); *A61K 39/12* (2013.01); *C07K 14/005* (2013.01); *C07K 14/205* (2013.01); *C12N 7/00* (2013.01); *G01N 33/56983* (2013.01); *A61K 39/105* (2013.01); *A61K 2039/55555* (2013.01); *A61K 2039/55566* (2013.01); *A61K 2039/575* (2013.01); *A61K 2039/6031* (2013.01); *A61K 2039/70* (2013.01); *C07K 2319/00* (2013.01); *C07K 2319/21* (2013.01); *C07K 2319/35* (2013.01); *C07K 2319/40* (2013.01); *C07K 2319/735* (2013.01); *C12N 2760/16022* (2013.01); *C12N 2760/16034* (2013.01); *C12N 2760/16071* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 7,094,598 | B2 | 8/2006 | Nabel et al. |
| 7,097,841 | B2 | 8/2006 | Carter et al. |
| 7,608,268 | B2 | 10/2009 | Carter et al. |
| 2002/0054882 | A1 | 5/2002 | Okuno et al. |
| 2005/0042229 | A1 | 2/2005 | Yang et al. |
| 2005/0108791 | A1 | 5/2005 | Edgerton |
| 2006/0251679 | A1 | 11/2006 | Carter et al. |
| 2007/0082054 | A1 | 4/2007 | Mooter et al. |
| 2007/0224205 | A1 | 9/2007 | Powell et al. |
| 2008/0299151 | A1 | 12/2008 | Fomsgaard |

(Continued)

FOREIGN PATENT DOCUMENTS

| EP | 1504037 | 12/2009 |
| WO | WO 2003/094849 | 11/2003 |

(Continued)

OTHER PUBLICATIONS

GenBank Accession No. 3EGM_A (submitted Sep. 11, 2008).*
GenBank Accession No. AAP34324 (submitted May 1, 2003).*
Kossovsky et al. "Nanocrystalline Epstein-Barr virus decoys," Journal of Applied Biomaterials: An Official Journal of the Society for Biomaterials, Jan. 1991, vol. 2, No. 4, pp. 251-259.
Pulford et al. "Expression of the Epstein-Barr Virus Envelope Fusion Glycoportien GB85 Gene by a Recombinant Baculovirus," Journal of General Virology, Nov. 1994, vol. 75, No. 11, pp. 3241-3248.

(Continued)

*Primary Examiner* — Nicole Kinsey White
(74) *Attorney, Agent, or Firm* — Sheridan Ross PC

(57) ABSTRACT

Novel vaccines are provided that elicit broadly neutralizing anti-influenza antibodies. Some vaccines comprise nanoparticles that display hemagglutinin trimers from influenza virus on their surface. The nanoparticles comprise fusion proteins comprising a monomeric subunit of ferritin joined to at least a portion of an influenza hemagglutinin protein. Some portions comprise the ectodomain while some portions are limited to the stem region. The fusion proteins self-assemble to form the hemagglutinin-displaying nanoparticles. Some vaccines comprise only the stem region of an influenza hemagglutinin protein joined to a trimerization domain. Such vaccines can be used to vaccinate an individual against infection by heterologous influenza viruses and influenza virus that are antigenically divergent from the virus from which the nanoparticle hemagglutinin protein was obtained. Also provided are fusion proteins and nucleic acid molecules encoding such proteins.

17 Claims, 91 Drawing Sheets
Specification includes a Sequence Listing.

(56) References Cited

U.S. PATENT DOCUMENTS

| | | |
|---|---|---|
| 2009/0233377 A1 | 9/2009 | Iwahori et al. |
| 2010/0137412 A1 | 6/2010 | Zhou et al. |
| 2010/0285982 A1 | 11/2010 | Golding et al. |
| 2010/0297174 A1 | 11/2010 | Garcia-Sastre et al. |
| 2011/0038025 A1 | 2/2011 | Naitou et al. |
| 2011/0059130 A1 | 3/2011 | Yusibov |
| 2011/0177122 A1 | 7/2011 | Nabel et al. |
| 2011/0212128 A1 | 9/2011 | Galarza et al. |
| 2014/0302079 A1 | 10/2014 | Nabel et al. |
| 2016/0303224 A1 | 10/2016 | Kanekiyo et al. |

FOREIGN PATENT DOCUMENTS

| | | |
|---|---|---|
| WO | WO 2010/036948 | 4/2010 |
| WO | WO 2010/117786 | 10/2010 |
| WO | WO 2011/035422 | 3/2011 |
| WO | WO 2011/044152 | 4/2011 |
| WO | WO 2013/044203 | 3/2013 |

OTHER PUBLICATIONS

Vallhov et al. "Exosomes Containing Glycoprotein 350 Released by EBV-Transformed B Cells Selectively Target B Cells thorugh CD21 and Block EBV Infection in Vitro," The Journal of Immunology, Jan. 2011, vol. 186, No. 1, pp. 73-82.

Yassine et al. "Hemagglutinin-stem nanoparticles generate heterosubypic influenza protection." Nature Medicine, Sep. 2015, vol. 21, No. 9, pp. 1065-1070.

Official Action for Canada Patent Application No. 2,849,822, dated Sep. 1, 2016 4 pages.

Notice of Allowance with English Translation for China Patent Application No. 201280057703.7, dated Sep. 27, 2016 5 pages.

A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

Bachmann, M.F., et al., "Neutralizing antiviral B cell responses," Annu Rev Immunol, 1997, 15:235-270.

Caton, A.J., et al., "The antigenic structure of the influenza virus A/PR/8/34 hemagglutinin (H1 subtype)," Cell, 1982, 31:417-427.

Cohen et al., "Ferritin as an Endogenous MRI Reporter for Noninvasive Imaging Neoplasia of Gene Expression in C6 Glioma Tumors," Neoplasia, Feb. 2005, 7(2):109-117.

COLT38, UniProtKB COLT38_91NFB, Sep. 21, 2011 [online]. [Retrieved on Feb. 26, 2013]. Retrieved from the internet <URL: http://www.uniprotorg/uniprot/C0LT38.txt?version=18>.

Corti, D., et al., "Heterosubtypic neutralizing antibodies are produced by individuals immunized with a seasonal influenza vaccine," J Clin Invest, 2010, 120:1663-1673.

Corti, D., et al., "A neutralizing antibody selected from plasma cells that binds to group 1 and group 2 influenza A hemagglutinins," Science, 2011, 333:850-856.

Dintzis, H.M. et al., "Molecular determinants of immunogenicity: the immunon model of immune response," Proc Natl Acad Sci USA, 1976, 73:3671-3675.

Ekiert, D.C., et al., "A highly conserved neutralizing epitope on group 2 influenza A viruses," Science, 2011, 333:843-850.

Ekiert, D.C., et al., "Antibody recognition of a highly conserved influenza virus epitope," Science, 2009, 324:246-251.

Haynes, J.R., "Influenza virus-like particle vaccines," Expert Rev Vaccines, 2009, 8:435-445.

Kashyap, A.K., et al., "Combinatorial antibody libraries from survivors of the Turkish H5N1 avian influenza outbreak reveal virus neutralization strategies," Proc Natl Acad Sci USA, 2008, 105:5986-5991.

Kong, W.P., et al., "Protective immunity to lethal challenge of the 1918 pandemic influenza virus by vaccination," Proc Natl Acad Sci USA, 2006, 103:15987-15991.

Krause, J.C., et al., "A broadly neutralizing human monoclonal antibody that recognizes a conserved, novel epitope on the globular head of the influenza H1N1 virus hemagglutinin," J Virol, 2011, 85:10905-10908.

Lambert, L.C., et al., "Influenza vaccines for the future," N Engl J Med, 2010, 363, 2036-2044.

Li, C.Q. et al., "Ferritin nanoparticle technology: A new platform for antigen presentation and vaccine development," Industrial Biotechnol 2, 143-147 (2006).

Meldrum, F.C., et al., "Magnetoferritin: in vitro synthesis of a novel magnetic protein," Science, 1992, 257:522-523.

Nabel, G.J., et al., "Induction of unnatural immunity: prospects for a broadly protective universal influenza vaccine," Nat Med, 2010, 16:1389-1391.

Okuno, Y., et al., "A common neutralizing epitope conserved between the hemagglutinins of influenza A virus H1 and H2 strains," J Virol, 1993, 67:2552-2558.

Roldao, A., et al., "Virus-like particles in vaccine development," Expert Rev Vaccines, 2010, 9:1149-1176.

Sheridan, C., "Flu vaccine makers upgrade technology—and pray for time," Nat Biotechnol, 2009, 27:489-491.

Steel, J. et al., "Influenza Virus Vaccine Based on the Conserved Hemagglutinin Stalk Domain," MBio 1, e0018 (2010).

Sui, J., et al., "Structural and functional bases for broad-spectrum neutralization of avian and human influenza A viruses," Nat Struct Mol Biol, 2009, 16:265-273.

Treanor, J.J., et al., "Safety and immunogenicity of a recombinant hemagglutinin vaccine for H5 influenza in humans," Vaccine, 2001, 19:1732-1737.

Treanor, J.J., "Safety and immunogenicity of a baculovirus-expressed hemagglutinin influenza vaccine: a randomized controlled trial," JAMA,2007, 297:1577-1582.

Wang, T.T., et al., "Broadly protective monoclonal antibodies against H3 influenza viruses following sequential immunization with different hemagglutinins," PLoS Pathog, 2010, vol. 6, Issue 2, e1000796.

Wei, C.J., et al., Cross-neutralization of 1918 and 2009 influenza viruses: role of glycans in viral evolution and vaccine design. Sci Transl Med, 2010, 2, 24ra21.

Wei, C.J., et al., "Induction of broadly neutralizing H1N1 influenza antibodies by vaccination," Science, 2010, 329:1060-1064.

Wei, C.J., et al., "Comparative efficacy of neutralizing antibodies elicited by recombinant hemagglutinin proteins from avian H5N1 influenza virus," J Virol, 2008, 82:6200-6208.

Whittle, J.R., et al., "Broadly neutralizing human antibody that recognizes the receptor-binding pocket of influenza virus hemagglutinin," Proc Natl Aced Sci USA, 2011, 108:14216-14221.

WHO Reference on Animal Influenza Diagnosis and Surveillance, 2002, Department of Communicable Disease Surveillance and Response, World Health Organization).

Wu, C.Y., et al., "Mammalian expression of virus-like particles for advanced mimicry of authentic influenza virus," PLoS One 5, 2010, e9784.

Xiong, A.S., et al., "PCR-based accurate synthesis of long DNA sequences," Nat Protoc, 2006, 1(2):791-797.

Yamashita, I., et al., "Ferritin in the field of nanodevices," Biochim Biophys Acta, 2010, 1800:846-857.

Yang, Z.Y., et al., "Immunization by avian H5 influenza hemagglutinin mutants with altered receptor binding specificity," Science, 2007, 317:825-828).

Zhang, Y., et al., "Self-Assembly in the Ferritin Nano-Cage Protein Super Family," Int. J. Mol. Sci., 2011, 12:5406-5421.

PCT Publication No. WO 2013 044203 A3, with International Search Report, dated Mar. 11, 2013, for PCT Application No. PCT/US12/56822.

Invitation to remedy deficiencies pursuant to Rule 30(3) EPC / Rules 163(3) EPC, dated May 23, 2014, in European Patent Application No. 12834398.5.

Official Action for U.S. Appl. No. 14/346,849, dated May 22, 2015 13 pages Restriction Requirement.

Official Action for U.S. Appl. No. 14/346,849, dated Sep. 28, 2015 9 pages.

Notice of Allowance for U.S. Appl. No. 14/346,849, dated May 4, 2016 8 pages.

Kang, S.M., et al., "Influenza vaccines based on virus-like particles", Virus Research, Amsterdam, NL, vol. 143, No. 2, Aug. 1, 2009 (Aug. 1, 2009), pp. 140-146.

(56) References Cited

OTHER PUBLICATIONS

Lee, L.A., et al., "Adaptations of nanoscale viruses and other protein cages for medical applications", Nanomedicine: Nanotechnology, Biology and Medicine, Elsevier, NL, vol. 2, No. 3, Sep. 1, 2006 (Sep. 1, 2006), pp. 137-149.
Kanekiyo, Masaru, et al., "Self-assembling influenza nanoparticle vaccines elicit broadly neutralizing H1N1 antibodies", Nature, Nature Publishing Group, United Kingdom, vol. 499, No. 7456, Jul. 4, 2013 (Jul. 4, 2013), pp. 102-106.
Official Action for Canada Patent Application No. 2,849,822, dated Nov. 10, 2015 6 pages.
English Translation of China Patent Application No. 201280057703.7, dated Jun. 26, 2015 8 pages.
English Translation of China Patent Application No. 201280057703.7, dated Mar. 15, 2016 7 pages.
Partial Supplementary Search Report for European Patent Application No. 12834398.5, dated Jun. 8, 2015 7 pages.
Extended Search Report for European Patent Application No. 12834398.5, dated Oct. 2, 2015 10 pages.
Official Action for European Patent Application No. 12834398.5, dated Jul. 5, 2016 4 pages.
Greenstone et al. "Chimeric papillomavirus virus-like particles elecit antitumor immunity against the E7 oncoprotein in an HPV16 tumor model," Proc. Natl. Acad. Sci. USA, Feb. 1998, vol. 95, pp. 1800-1805.
Harrison "The Structure and Function of Ferritin," Biochemical Education, 1986, vol. 14, No. 4, pp. 154-162.
He et al. "Presenting native-like trimeric HIV-1 antigens with self-assembling nanoparticles," Nature Communications, Jun. 2016, vol. 7, 12041, 15 pages.
Kanekiyo et al. "Rational Design of an Epstein-Barr Virus Vaccine Targeting the Receptor-Binding Site," Cell, Aug. 2015, vol. 162, No. 5, pp. 1090-1100.
Lee et al. "Viruses and Virus-Like Protein Assemblies—Chemically Programmable Nanoscale Building Blocks," Nano Res, 2009, vol. 2, pp. 349-364.
Lopez-Sagaseta et al. "Self-assembling protein nanoparticles in the design of vaccines," Computational and Structural Biotechnology Journal, 2016, vol. 14, pp. 58-68.
Ruiss et al. "A Virus-Like Particle-Based Epstein-Barr Virus Vaccine," Journal of Virology, Dec. 2011, vol. 85, No. 24, pp. 13105-13113.
Zhang et al. "Universal Influenza Vaccines, a Dream to Be Realized Soon," Viruses, 2014, vol. 6, pp. 1974-1991.
Result of Consultation for European Patent Application No. 12834398.5, dated Sep. 15, 2017 3 pages.

* cited by examiner

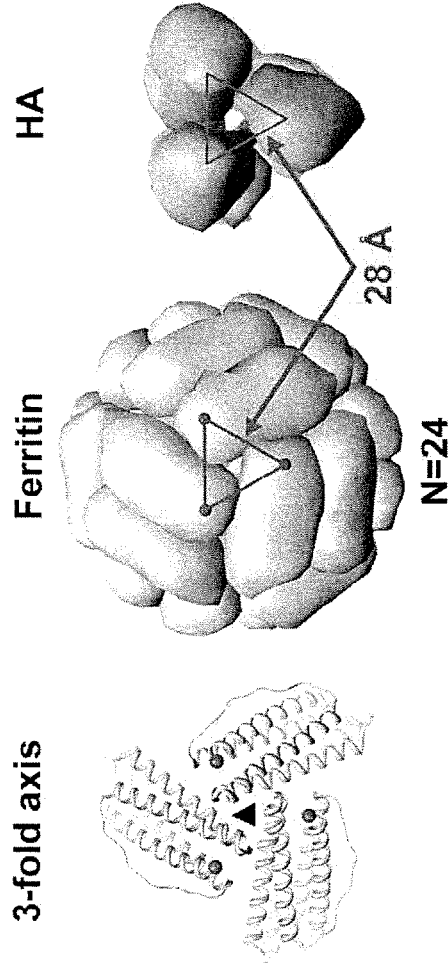
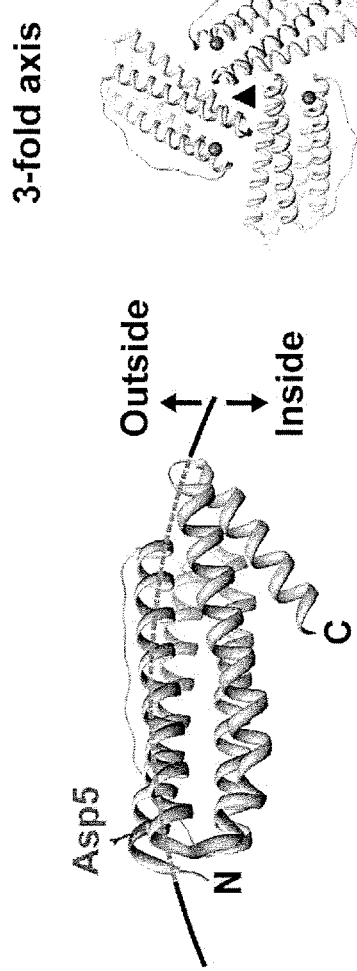
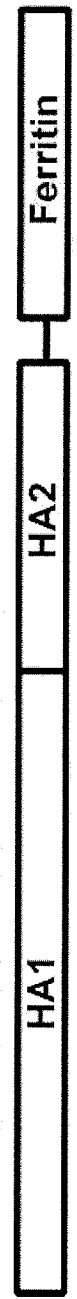
FIG. 1A
FIG. 1B
FIG. 1C
FIG. 1D

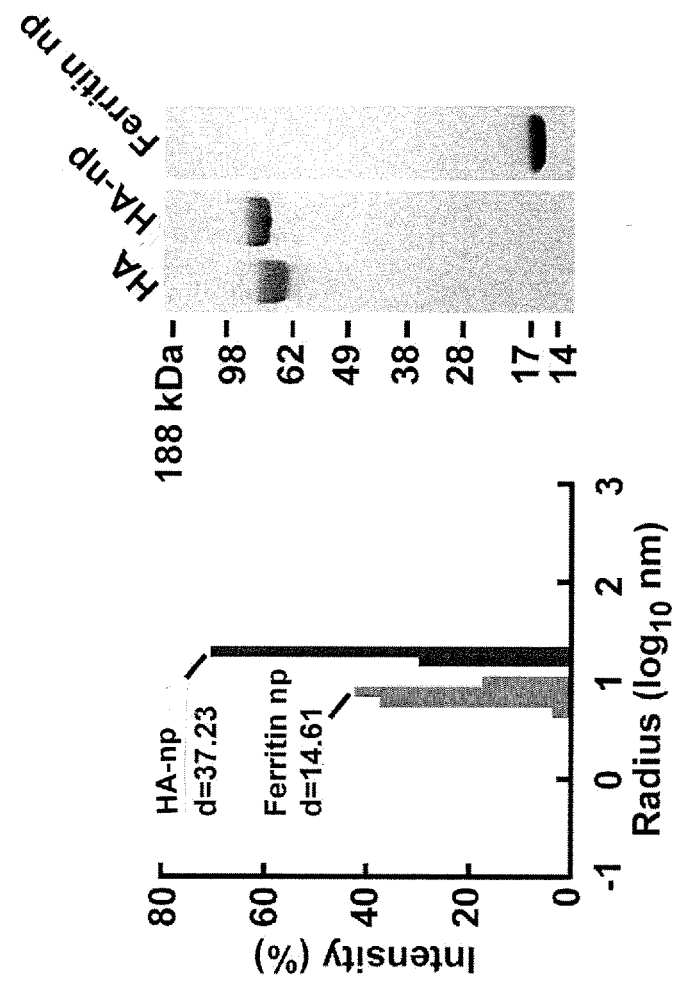
FIG. 1G
FIG. 1F
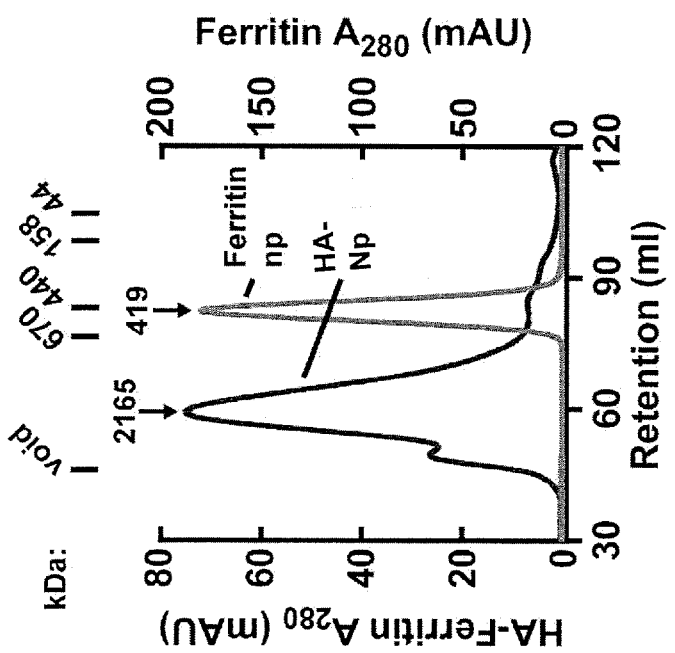
FIG. 1E

H. pylori vs Mouse (L)    H. pylori vs Human (L)    Mouse (L) vs Human (L)

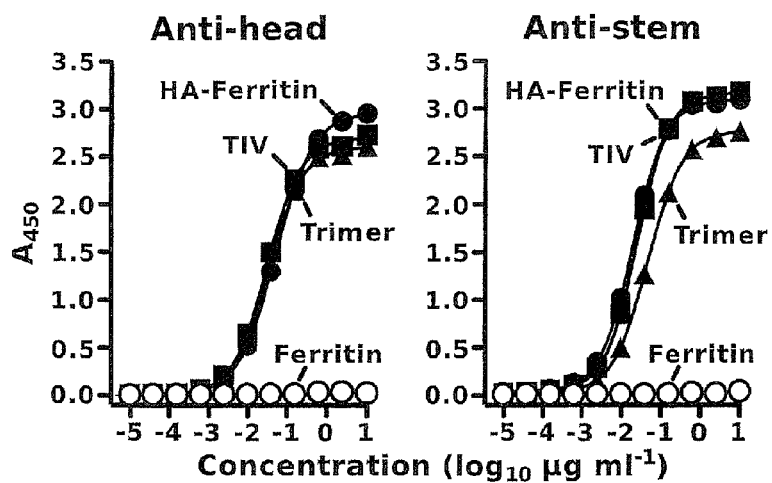
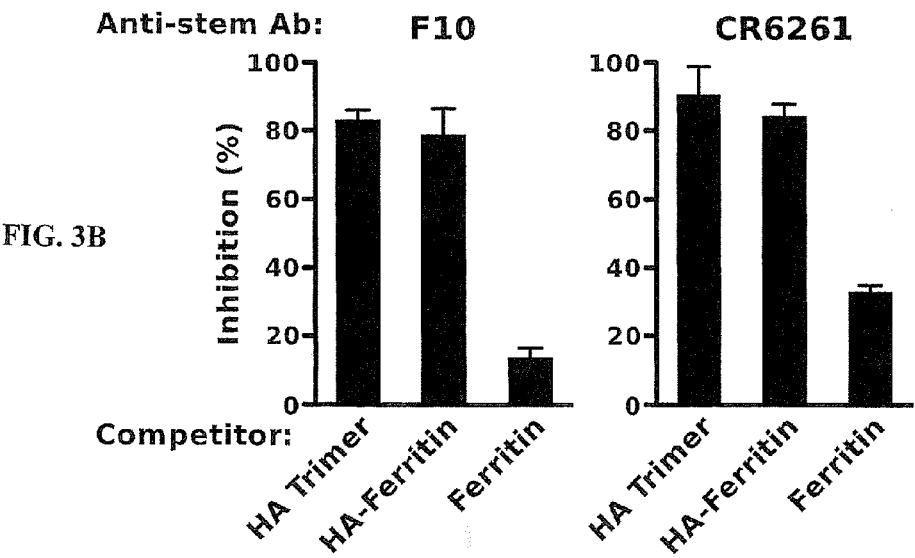
FIG. 3A
FIG. 3B

|  | 1918 SC | 1934 PR8 | 1986 Sing | 1995 Beijing | 1999 NC | 2006 SI | 2007 Bris |
|---|---|---|---|---|---|---|---|
| HA-Trimer | n.d. | <50 | n.d. | n.d. | 956 | n.d. | n.d. |
| TIV | <50 | <100 | <100 | 1654 | 4215 | 677 | 311 |
| HA-np | <50 | 210 | 114 | >6400 | >12800 | >3200 | 4286 |

FIG. 4D

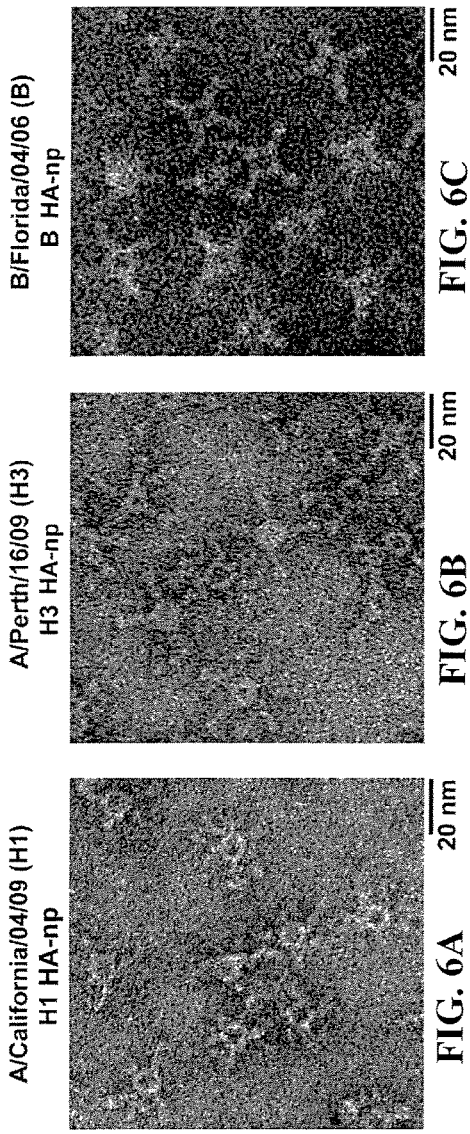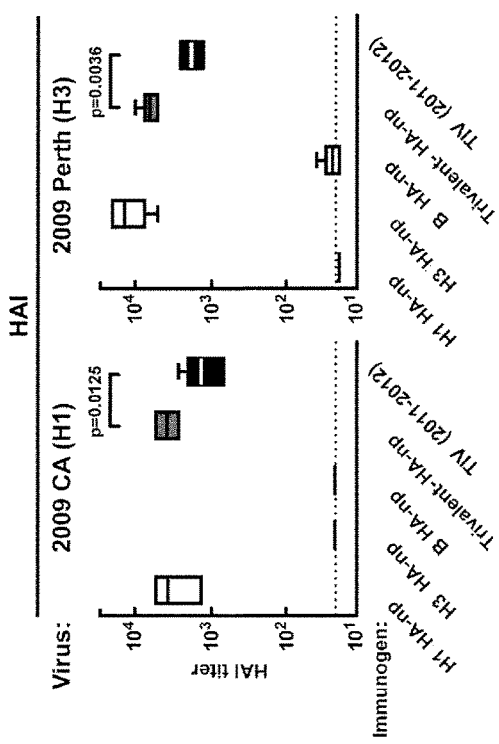

IP: — CH65 CR6261 VRC01
HA: WT ΔRBS WT ΔRBS WT ΔRBS WT ΔRBS
220 kDa
160
100
80 ← HA
60
50 ← HC
30 ← LC
20

2007 Bris

IP: — CH65 CR6261 VRC01
HA: WT ΔRBS WT ΔRBS WT ΔRBS WT ΔRBS
← HA
← HC
← LC

Immunization of Pan-Group1 HA-Ferritin nanoparticles in Mice and Ferrets

Pan-group1 HA-np vaccine:

H1 A/NC/20/1999
H1 A/CA/04/2009
H2 A/Singapore/1/1957
H5 A/Indonesia/05/2005

Dose:
Mice: 6.8 μg (1.67 μg of each HA-np) + Ribi adjuvant
Ferrets: 10 μg (2.5 μg of each HA-np) + Ribi adjuvant
Injection: Intramuscular, weeks 0 and 3 (mice) or 4 (ferrets)

Fig. 11

Immunogenicity of Pan-Group1 HA-np In Mice

| | H1 | | | | | | | | | |
|---|---|---|---|---|---|---|---|---|---|---|
| Virus | 1918 SC | 1934 PR8 | 1947 FM | 1954 MAL | 1986 SG | 1995 BJ | 1999 NC | 2006 SI | 2007 Bris | 2009 CA |
| Animal ID | | | | | | | | | | |
| 5726 | 2978 | <50 | <50 | <50 | <50 | <50 | 8306 | 690 | 423 | 9040 |
| 5727 | >3200 | <50 | <50 | <50 | <50 | 261 | 6208 | <50 | <50 | >12800 |
| 5728 | >3200 | <50 | 76 | <50 | <50 | 221 | >12800 | 1360 | 825 | >12800 |
| 5729 | >3200 | <50 | <50 | <50 | <50 | 989 | >12800 | <50 | 121 | >12800 |
| 5730 | 2521 | <50 | <50 | <50 | <50 | 4390 | 10906 | <50 | <50 | 11137 |

| | H2 | | |
|---|---|---|---|
| Virus | 1957 SG | 2006 MO (Swine) | 2007 NED (Avian) |
| Animal ID | | | |
| 5726 | >12800 | >12800 | >12800 |
| 5727 | >12800 | >12800 | >12800 |
| 5728 | >12800 | >12800 | >12800 |
| 5729 | >12800 | >12800 | >12800 |
| 5730 | >12800 | >12800 | >12800 |

| | H9 |
|---|---|
| | 1999 HK |
| Animal ID | |
| 5726 | <50 |
| 5727 | <50 |
| 5728 | <50 |
| 5729 | <50 |
| 5730 | <50 |

| | H5 | | | |
|---|---|---|---|---|
| Virus | 2004 VN1203 | 2005 Indo | 2006 Nigeria (Avian) | 2007 Anhui |
| | Clade 1 | Clade 2.1.3 | Clade 2.2 | Clade 2.3.4 |
| Animal ID | | | | |
| 5726 | 488 | 1128 | 1438 | <50 |
| 5727 | 100 | 537 | 1192 | <50 |
| 5728 | 112 | 461 | 1002 | <50 |
| 5729 | 112 | 335 | 2539 | <50 |
| 5730 | 105 | 424 | 1105 | <50 |

IC50 titers are shown

Fig. 12

Immunogenicity of Pan-Group1 HA-np In Ferrets

| | H1 | | | | | | | |
|---|---|---|---|---|---|---|---|---|
| Virus | 1918 SC | 1934 PR8 | 1947 FM | 1954 Mal | 1986 SG | 1999 NC | 2007 Bris | 2009 CA |
| Animal ID | | | | | | | | |
| 456 | <50 | <50 | <50 | <50 | 751 | 5726 | 888 | >6400 |
| 457 | 215 | <50 | 474 | 982 | 1438 | >6400 | >6400 | >6400 |
| 487 | <50 | <50 | <50 | <50 | 393 | 3568 | 402 | 2417 |
| 488 | <50 | <50 | <50 | <50 | 646 | >6400 | 851 | >6400 |
| 492 | 138 | <50 | 401 | <50 | 1342 | >6400 | 1755 | >6400 |
| 493 | <50 | <50 | 331 | 437 | 815 | >6400 | 3193 | >6400 |
| 444 | 140 | <50 | <50 | <50 | 421 | 6400 | 1223 | 5547 |
| 445 | <50 | <50 | <50 | <50 | 596 | 2978 | 741 | 3825 |
| 485 | <50 | <50 | <50 | <50 | 501 | 1962 | 762 | 794 |
| 486 | <50 | <50 | 50 | <50 | 441 | 6400 | 1079 | 1707 |
| 489 | <50 | <50 | <50 | <50 | 501 | 4712 | 455 | 1172 |
| 490 | 258 | <50 | 709 | 885 | >6400 | >6400 | 5569 | >6400 |

| | H2 | | |
|---|---|---|---|
| Virus | 1957 SG | 2006 MO (Swine) | 2007 NED (Avian) |
| Animal ID | | | |
| 456 | 2193 | 247 | 2351 |
| 457 | >6400 | 1035 | >6400 |
| 487 | 2740 | 284 | 1637 |
| 488 | >6400 | 663 | >6400 |
| 492 | >6400 | 682 | >6400 |
| 493 | 3423 | 365 | 3720 |
| 444 | 6400 | 482 | 2628 |
| 445 | 762 | <50 | 751 |
| 485 | 1425 | 127 | 762 |
| 486 | 3329 | 331 | 1638 |
| 489 | 4276 | 365 | 2133 |
| 490 | 4276 | 577 | 1856 |

| | H5 | | | |
|---|---|---|---|---|
| Virus | 2004 VN1203 Clade 1 | 2005 Indo Clade 2.1.3 | 2006 Nigeria (Avian) Clade 2.2 | 2007 Anhui Clade 2.3.4 |
| Animal ID | | | | |
| 456 | TBD | 546 | 1571 | 806 |
| 457 | TBD | 1189 | 4276 | 2384 |
| 487 | TBD | <50 | 365 | <50 |
| 488 | TBD | 258 | 900 | 482 |
| 492 | TBD | 380 | 1780 | 731 |
| 493 | TBD | 335 | 992 | 523 |
| 444 | TBD | 296 | 817 | 585 |
| 445 | TBD | <50 | 272 | <50 |
| 485 | TBD | <50 | <50 | <50 |
| 486 | TBD | <50 | 577 | 112 |
| 489 | TBD | 50 | 828 | 292 |
| 490 | TBD | 370 | 1348 | 449 |

IC50 titers are shown

Fig. 13

HAI Titers from Pan-Group1 HA-np Immunized Ferrets

| Virus | H1 1986 S

Fig. 17

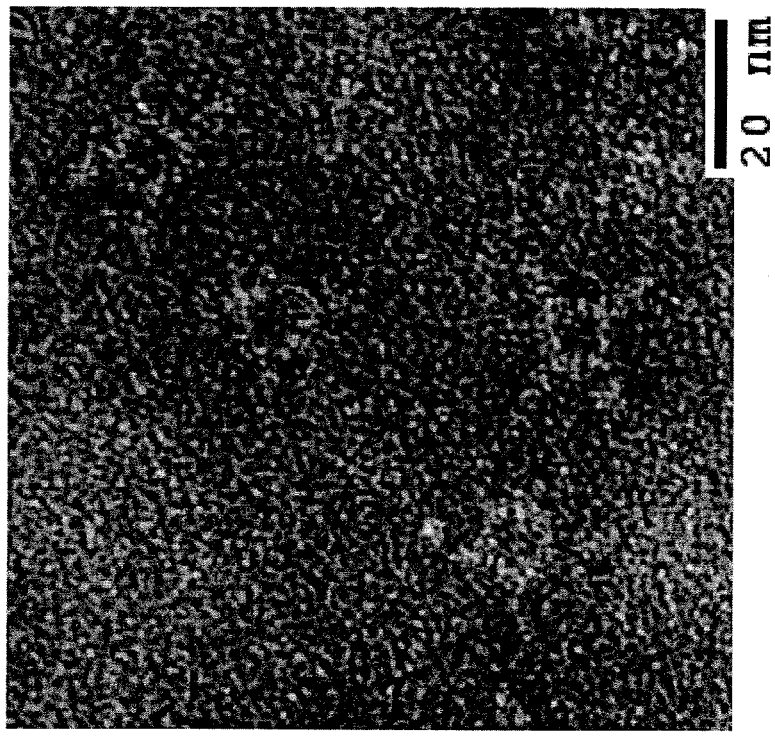
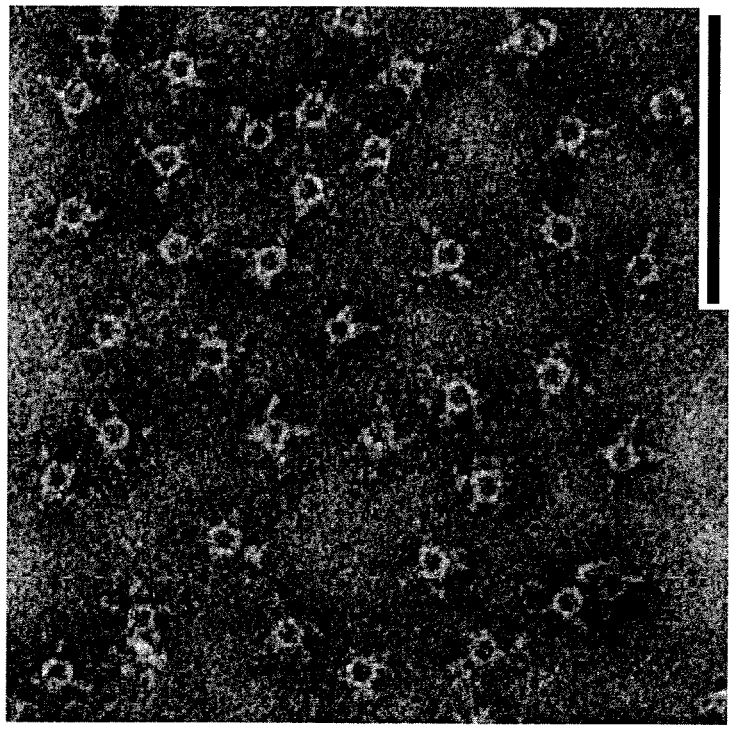
FIG. 20B
FIG. 20A

H1NC HA(517)_SGG_egm (H1 1999NC HA-ferritin)

Plasmid DNA sequence
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 25-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCAAACTGCTGGTGCTGCTGTGTA
CCTTTACCGCCACCTACGCCGACACAATCTGTATCGGCTACCACGCCAACAATAGCACCGACACCGTGGAT
ACAGTGCTGGAGAAGAACGTGACCGTGACCCACTCTGTGAACCTGCTGGAGGACAGCCACAATGGCAAGCT
GTGTCTGCTGAAAGGCATTGCCCCTCTGCAGCTGGGCAATTGTTCTGTGGCCGGATGGATTCTGGGCAACC
CCGAGTGTGAGCTGCTGATTTCTAAGGAGAGCTGGAGCTACATCGTGGAGACCCCCAATCCTGAGAATGGC
ACCTGCTACCCTGGCTACTTCGCCGATTACGAGGAGCTGCGCGAGCAGCTGTCTAGCGTGTCCAGCTTCGA
GAGATTCGAGATCTTCCCCAAGGAGTCCAGCTGGCCTAATCACACAGTGACAGGCGTGTCTGCCAGCTGTA
GCCACAACGGCAAAAGCAGCTTCTACCGGAACCTGCTGTGGCTGACAGGCAAGAATGGCCTGTACCCCAAC
CTGAGCAAGAGCTACGTGAACAACAAGGAAAAGGAAGTGCTGGTGCTGTGGGGAGTGCACCACCCTCCCAA
CATCGGAAATCAGCGGGCCCTGTACCACACAGAGAACGCCTATGTGAGCGTGGTGTCCAGCCACTACAGCA
GAAGATTCACCCCCGAGATCGCCAAGAGACCCAAAGTGAGAGACCAGGAGGGCCGGATCAATTACTACTGG
ACCCTGCTGGAGCCTGGCGATACCATCATCTTCGAGGCCAACGGCAATCTGATCGCCCCTTGGTATGCCTT
TGCCCTGAGCAGAGGCTTTGGCAGCGGCATCATCACAAGCAACGCCCCCATGGATGAGTGTGATGCCAAGT
GCCAGACACCTCAGGGCGCCATCAATAGCAGCCTGCCCTTCCAGAATGTGCACCCTGTGACCATCGGCGAG
TGCCCCAAGTATGTGAGAAGCGCCAAGCTGAGAATGGTGACCGGCCTGAGAAACATCCCTCAGAGGGAGAC
CAGAGGACTGTTTGGAGCCATCGCCGGATTCATCGAGGGAGGATGGACAGGCATGGTGGATGGCTGGTACG
GCTACCACCACCAGAATGAGCAGGGCTCTGGATATGCCGCCGATCAGAAGTCTACCCAGAACGCCATCAAC
GGCATCACCAACAAGGTGAACAGCGTGATCGAGAAGATGAACACCCAGTTTACCGCTGTGGGCAAGGAGTT
CAACAAGCTGGAGCGGAGGATGGAGAACCTGAACAAGAAGGTGGACGACGGCTTTCTGGACATCTGGACCT
ACAATGCCGAACTCCTGGTCCTCCTCGAGAATGAGAGGACCCTGGACTTCCACGACAGCAACGTGAAGAAC
CTGTATGAGAAGGTGAAGAGCCAGCTGAAGAACAACGCCAAGGAGATCGGCAACGGCTGCTTCGAGTTCTA
CCACAAGTGTAACAACGAGTGTATGGAGAGCGTGAAGAACGGCACCTACGACTACCCTAAGTACAGCGAGG
AGAGCAAGCTGAACCGGGAGAAGATCGATTCCGGAGGCGACATCATCAAGCTGCTGAACGAGCAGGTGAAC
AAGGAGATGCAGAGCAGCAACCTGTACATGAGCATGAGCAGCTGGTGCTACACCCACAGCCTGGACGGCGC
CGGCCTGTTCCTGTTCGACCACGCCGCCGAGGAGTACGAGCACGCCAAGAAGCTGATCATCTTCCTGAACG
AGAACAACGTGCCCGTGCAGCTGACCAGCATCAGCGCCCCGAGCACAAGTTCGAGGGCCTGACCCAGATC
TTCCAGAAGGCCTACGAGCACGAGCAGCACATCAGCGAGAGCATCAACAACATCGTGGACCACGCCATCAA
GAGCAAGGACCACGCCACCTTCAACTTCCTGCAGTGGTACGTGGCCGAGCAGCACGAGGAGGAGGTGCTGT
TCAAGGACATCCTGGACAAGATCGAGCTGATCGGCAACGAGAACCACGGCCTGTACCTGGCCGACCAGTAC
GTGAAGGGCATCGCCAAGAGCAGGAAGAGCGGATCCTAGCATCATCATCATCATTAGTCTGGAAGGGCGAA
TTGATCCAGATCTGCTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCTGGGCAGAA
AGAAGCAGGCACATCCCCTTCTCTGTGACACACCCTGTCCACGCCCCTGGTTCTTAGTTCCAGCCCCACTC
ATAGGACACTCATAGCTCAGGAGGGCTCCGCCTTCAATCCCACCCGCTAAAGTACTTGGAGCGGTCTCTCC
CTCCCTCATCAGCCCACCAAACCAAACCTAGCCTCCAAGAGTGGGAAGAAATTAAAGCAAGATAGGCTATT
AAGTGCAGAGGGAGAGAAAATGCCTCCAACATGTGAGGAAGTAATGAGAGAAATCATAGAATTTTAAGGCC
ATGATTTAAGGCCATCATGGCCTTAATCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCC
ATAGGCTCCGCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCC
```

Fig. 25-2

```
TTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCGGGGGGGGGGGCGCTGAGGTCTGC
CTCGTGAAGAAGGTGTTGCTGACTCATACCAGGCGTGAATCGCCCCATCATCCAGCCAGAAAGTGAGGGAG
CCACGGTTGATGAGAGCTTTGTTGTAGGTGGACCAGTTGGTGATTTTGAACTTTTGCTTTGCCACGGAACG
GTCTGCGTTGTCGGGAAGATGCGTGATCTGATCCTTCAACTCAGCAAAAGTTCGATTTATTCAACAAAGCC
GCCGTCCCGTCAAGTCAGCGTAATGCTCTGCCAGTGTTACAACCAATTAACCAATTCTGATTAGAAAAACT
CATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGAT
TCCGACTCGTCCAACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCAGACTTGTTCAACA
GGCCAGCCATTACGCTCGTCATCAAAATCACTCGCATCAACCAAACCGTTATTCATTCGTGATTGCGCCTG
AGCGAGACGAAATACGCGATCGCTGTTAAAAGGACAATTACAAACAGGAATCGAATGCAACCGGCGCAGGA
ACACTGCCAGCGCATCAACAATATTTTCACCTGAATCAGGATATTCTTCTAATACCTGGAATGCTGTTTTC
CCGGGGATCGCAGTGGTGAGTAACCATGCATCATCAGGAGTACGGATAAAATGCTTGATGGTCGGAAGAGG
CATAAATTCCGTCAGCCAGTTTAGTCTGACCATCTCATCTGTAACATCATTGGCAACGCTACCTTTGCCAT
GTTTCAGAAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCGAGCAAGA
CGTTTCCCGTTGAATATGGCTCATAACACCCCTTGTATTACTGTTTATGTAAGCAGACAGTTTTATTGTTC
ATGATGATATATTTTTATCTTGTGCAATGTAACATCAGAGATTTTGAGACACAACGTGGCTTTCCCCCCCC
CCCCATTATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAACCATTATTATCA
TGACATTAACCTATAAAAATAGGCGTATCACGAGGCCCTTTCGTC
```

<u>Coding sequence</u>
```
ATGAAGGCCAAACTGCTGGTGCTGCTGTGTACCTTTACCGCCACCTACGCCGACACAATCTGTATCGGCTA
CCACGCCAACAATAGCACCGACACCGTGGATACAGTGCTGGAGAAGAACGTGACCGTGACCCACTCTGTGA
ACCTGCTGGAGGACAGCCACAATGGCAAGCTGTGTCTGCTGAAAGGCATTGCCCCTCTGCAGCTGGGCAAT
TGTTCTGTGGCCGGATGGATTCTGGGCAACCCCGAGTGTGAGCTGCTGATTTCTAAGGAGAGCTGGAGCTA
CATCGTGGAGACCCCCAATCCTGAGAATGGCACCTGCTACCCTGGCTACTTCGCCGATTACGAGGAGCTGC
GCGAGCAGCTGTCTAGCGTGTCCAGCTTCGAGAGATTCGAGATCTTCCCCAAGGAGTCCAGCTGGCCTAAT
CACACAGTGACAGGCGTGTCTGCCAGCTGTAGCCACAACGGCAAAAGCAGCTTCTACCGGAACCTGCTGTG
GCTGACAGGCAAGAATGGCCTGTACCCCAACCTGAGCAAGAGCTACGTGAACAACAAGGAAAAGGAAGTGC
TGGTGCTGTGGGGAGTGCACCACCCTCCCAACATCGGAAATCAGCGGGCCCTGTACCACACAGAGAACGCC
TATGTGAGCGTGGTGTCCAGCCACTACAGCAGAAGATTCACCCCCGAGATCGCCAAGAGACCCAAAGTGAG
AGACCAGGAGGGCCGGATCAATTACTACTGGACCCTGCTGGAGCCTGGCGATACCATCATCTTCGAGGCCA
ACGGCAATCTGATCGCCCCTTGGTATGCCTTTGCCCTGAGCAGAGGCTTTGGCAGCGGCATCATCACAAGC
AACGCCCCCATGGATGAGTGTGATGCCAAGTGCCAGACACCTCAGGGCGCCATCAATAGCAGCCTGCCCTT
CCAGAATGTGCACCCTGTGACCATCGGCGAGTGCCCCAAGTATGTGAGAAGCGCCAAGCTGAGAATGGTGA
CCGGCCTGAGAAACATCCCTCAGAGGGAGACCAGAGGACTGTTTGGAGCCATCGCCGGATTCATCGAGGGA
GGATGGACAGGCATGGTGGATGGCTGGTACGGCTACCACCACCAGAATGAGCAGGGCTCTGGATATGCCGC
CGATCAGAAGTCTACCCAGAACGCCATCAACGGCATCACCAACAAGGTGAACAGCGTGATCGAGAAGATGA
ACACCCAGTTTACCGCTGTGGGCAAGGAGTTCAACAAGCTGGAGCGGAGGATGGAGAACCTGAACAAGAAG
GTGGACGACGGCTTTCTGGACATCTGGACCTACAATGCCGAACTCCTGGTCCTCCTGAGAATGAGAGGAC
CCTGGACTTCCACGACAGCAACGTGAAGAACCTGTATGAGAAGGTGAAGAGCCAGCTGAAGAACAACGCCA
AGGAGATCGGCAACGGCTGCTTCGAGTTCTACCACAAGTGTAACAACGAGTGTATGGAGAGCGTGAAGAAC
GGCACCTACGACTACCCTAAGTACAGCGAGGAGAGCAAGCTGAACCGGGAGAAGATCGATTCCGGAGGCGA
CATCATCAAGCTGCTGAACGAGCAGGTGAACAAGGAGATGCAGAGCAGCAACCTGTACATGAGCATGAGCA
GCTGGTGCTACACCCACAGCCTGGACGGCGCCGGCCTGTTCCTGTTCGACCACGCCGCCGAGGAGTACGAG
```

Fig. 25-3

```
CACGCCAAGAAGCTGATCATCTTCCTGAACGAGAACAACGTGCCCGTGCAGCTGACCAGCATCAGCGCCCC
CGAGCACAAGTTCGAGGGCCTGACCCAGATCTTCCAGAAGGCCTACGAGCACGAGCAGCACATCAGCGAGA
GCATCAACAACATCGTGGACCACGCCATCAAGAGCAAGGACCACGCCACCTTCAACTTCCTGCAGTGGTAC
GTGGCCGAGCAGCACGAGGAGGAGGTGCTGTTCAAGGACATCCTGGACAAGATCGAGCTGATCGGCAACGA
GAACCACGGCCTGTACCTGGCCGACCAGTACGTGAAGGGCATCGCCAAGAGCAGGAAGAGCGGATCCTAG
```

Translation
```
MKAKLLVLLCTFTATYADTICIGYHANNSTDTVDTVLEKNVTVTHSVNLLEDSHNGKLCLLKGIAPLQLGN
CSVAGWILGNPECELLISKESWSYIVETPNPENGTCYPGYFADYEELREQLSSVSSFERFEIFPKESSWPN
HTVTGVSASCSHNGKSSFYRNLLWLTGKNGLYPNLSKSYVNNKEKEVLVLWGVHHPPNIGNQRALYHTENA
YVSVVSSHYSRRFTPEIAKRPKVRDQEGRINYYWTLLEPGDTIIFEANGNLIAPWYAFALSRGFGSGIITS
NAPMDECDAKCQTPQGAINSSLPFQNVHPVTIGECPKYVRSAKLRMVTGLRNIPQRETRGLFGAIAGFIEG
GWTGMVDGWYGYHHQNEQGSGYAADQKSTQNAINGITNKVNSVIEKMNTQFTAVGKEFNKLERRMENLNKK
VDDGFLDIWTYNAELLVLLENERTLDFHDSNVKNLYEKVKSQLKNNAKEIGNGCFEFYHKCNNECMESVKN
GTYDYPKYSEESKLNREKIDSGGDIIKLLNEQVNKEMQSSNLYMSMSSWCYTHSLDGAGLFLFDHAAEEYE
HAKKLIIFLNENNVPVQLTSISAPEHKFEGLTQIFQKAYEHEQHISESINNIVDHAIKSKDHATFNFLQWY
VAEQHEEEVLFKDILDKIELIGNENHGLYLADQYVKGIAKSRKSGS
```

Fig. 25-4

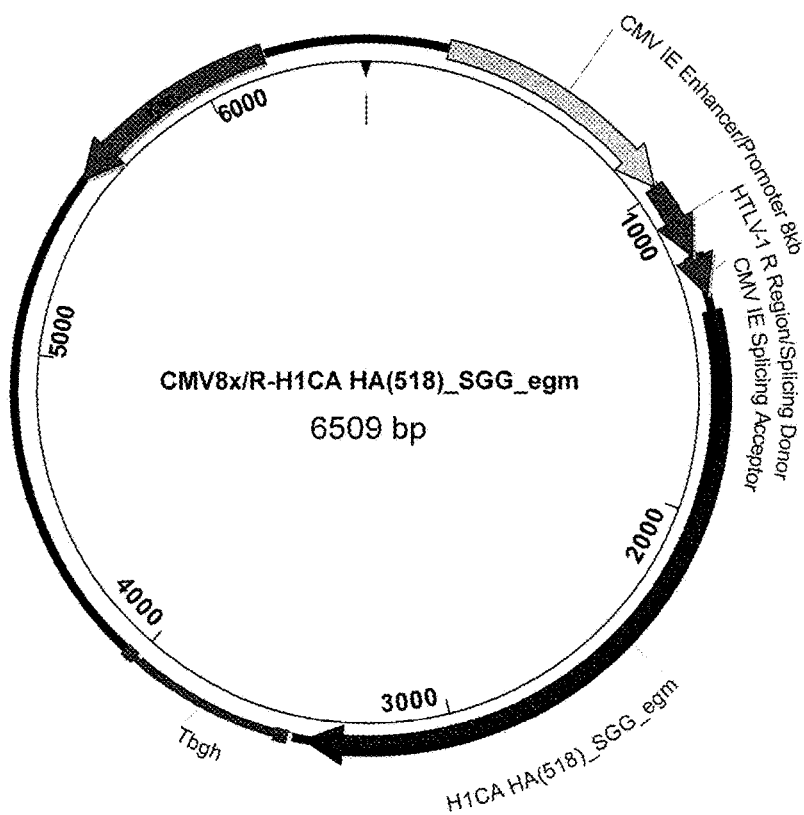
H1CA HA(518)_SGG_egm (H1 2009CA HA-ferritin)

<u>Plasmid DNA sequence</u>
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 26-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCCTGGTGGTGCTGCTGTACA
CCTTCGCCACCGCCAACGCCGACACCCTGTGCATCGGCTACCACGCCAACAACAGCACCGACACCGTGGAC
ACCGTGCTGGAGAAGAACGTGACCGTGACCCACAGCGTGAACCTGCTGGAGGACAAGCACAACGGCAAGCT
GTGCAAGCTGCGGGCGTGGCCCCCCTGCACCTGGGCAAGTGCAACATCGCCGGCTGGATTCTGGGCAACC
CCGAGTGCGAGAGCCTGAGCACCGCCAGCAGCTGGAGCTACATCGTGGAGACCCCCAGCAGCGACAACGGC
ACCTGCTACCCCGGCGACTTCATCGACTACGAGGAGCTGCGGGAGCAGCTGAGCAGCGTGAGCAGCTTCGA
GCGGTTCGAGATCTTCCCCAAGACCAGCAGCTGGCCCAACCACGACAGCAACAAGGGCGTGACCGCCGCCT
GCCCCCACGCCGGCGCCAAGAGCTTCTACAAGAACCTGATCTGGCTGGTGAAGAAGGGCAACAGCTACCCC
AAGCTGAGCAAGAGCTACATCAACGACAAGGGCAAGGAGGTGCTGGTGCTGTGGGGCATCCACCACCCCAG
CACCAGCGCCGACCAGCAGAGCCTGTACCAGAACGCCGACACCTACGTGTTCGTGGGCAGCAGCCGGTACA
GCAAGAAGTTCAAGCCCGAGATCGCCATCCGGCCCAAGGTGCGGGACCAGGAGGGCCGGATGAACTACTAC
TGGACCCTGGTGGAGCCCGGCGACAAGATCACCTTCGAGGCCACCGGCAACCTGGTGGTGCCCCGGTACGC
CTTCGCCATGGAGCGGAACGCCGGCAGCGGCATCATCATCAGCGACACCCCCGTGCACGACTGCAACACA
CCTGCCAGACCCCCAAGGGCGCCATCAACACCAGCCTGCCCTTCCAGAACATCCACCCCATCACCATCGGC
AAGTGCCCCAAGTACGTGAAGAGCACCAAGCTGCGGCTGGCCACCGGCCTGCGGAACATCCCCAGCATCCA
GAGCCGGGGCCTGTTCGGCGCCATCGCCGGCTTCATCGAGGGCGGCTGGACCGGCATGGTGGACGGCTGGT
ACGGCTACCACCACCAGAACGAGCAGGGCAGCGGCTACGCCGCCGACCTGAAGAGCACCCAGAACGCCATC
GACGAGATCACCAACAAGGTGAACAGCGTGATCGAGAAGATGAACACCCAGTTCACCGCCGTGGGCAAGGA
GTTCAACCACCTGGAGAAGCGGATCGAGAACCTGAACAAGAAGGTGGACGACGGCTTCCTGGACATCTGGA
CCTACAACGCCGAGCTGCTGGTGCTGCTGGAGAACGAGCGGACCCTGGACTACCACGACAGCAACGTGAAG
AACCTGTACGAGAAGGTGCGGAGCCAGCTGAAGAACAACGCCAAGGAGATCGGCAACGGCTGCTTCGAGTT
CTACCACAAGTGCGACAACACCTGCATGGAGAGCGTGAAGAACGGCACCTACGACTACCCCAAGTACAGCG
AGGAGGCCAAGCTGAACCGGGAGGAGATCGACTCCGGAGGCGACATCATCAAGCTGCTGAACGAGCAGGTG
AACAAGGAGATGCAGAGCAGCAACCTGTACATGAGCATGAGCAGCTGGTGCTACACCCACAGCCTGGACGG
CGCCGGCCTGTTCCTGTTCGACCACGCCGCCGAGGAGTACGAGCACGCCAAGAAGCTGATCATCTTCCTGA
ACGAGAACAACGTGCCCGTGCAGCTGACCAGCATCAGCGCCCCCGAGCACAAGTTCGAGGGCCTGACCCAG
ATCTTCCAGAAGGCCTACGAGCACGAGCAGCACATCAGCGAGAGCATCAACAACATCGTGGACCACGCCAT
CAAGAGCAAGGACCACGCCACCTTCAACTTCCTGCAGTGGTACGTGGCCGAGCAGCACGAGGAGGAGGTGC
TGTTCAAGGACATCCTGGACAAGATCGAGCTGATCGGCAACGAGAACCACGGCCTGTACCTGGCCGACCAG
TACGTGAAGGGCATCGCCAAGAGCAGGAAGAGCGGATCCTAGCATCATCATCATCATTAGTCTGGAAGGGC
GAATTGATCCAGATCTGCTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTGTCTGAGT
AGGTGTCATTCTATTCTGGGGGGTGGGGTGGGGCAGGACAGCAAGGGGGAGGATTGGGAAGACAATAGCAG
GCATGCTGGGGATGCGGTGGGCTCTATGGGTACCCAGGTGCTGAAGAATTGACCCGGTTCCTCCTGGGCCA
GAAAGAAGCAGGCACATCCCCTTCTCTGTGACACACCCTGTCCACGCCCCTGGTTCTTAGTTCCAGCCCCA
CTCATAGGACACTCATAGCTCAGGAGGGCTCCGCCTTCAATCCCACCCGCTAAAGTACTTGGAGCGGTCTC
TCCCTCCCTCATCAGCCCACCAAACCAAACCTAGCCTCCAAGAGTGGGAAGAAATTAAAGCAAGATAGGCT
ATTAAGTGCAGAGGGAGAGAAAATGCCTCCAACATGTGAGGAAGTAATGAGAGAAATCATAGAATTTTAAG
GCCATGATTTAAGGCCATCATGGCCTTAATCTTCCGCTTCCTCGCTCACTGACTCGCTGCGCTCGGTCGTT
CGGCTGCGGCGAGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCCGTTCAGCCCGACCGCTGC
```

Fig. 26-2

GCCTTATCCGGTAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGTGGCCTAACTACG
GCTACACTAGAAGAACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCTTTTAAATTAAAAATGA
AGTTTTAAATCAATCTAAAGTATATATGAGTAAACTTGGTCTGACAGTTACCAATGCTTAATCAGTGAGGC
ACCTATCTCAGCGATCTGTCTATTTCGTTCATCCATAGTTGCCTGACTCGGGGGGGGGGGCGCTGAGGTC
TGCCTCGTGAAGAAGGTGTTGCTGACTCATACCAGGCCTGAATCGCCCCATCATCCAGCCAGAAAGTGAGG
GAGCCACGGTTGATGAGAGCTTTGTTGTAGGTGGACCAGTTGGTGATTTTGAACTTTTGCTTTGCCACGGA
ACGGTCTGCGTTGTCGGGAAGATGCGTGATCTGATCCTTCAACTCAGCAAAAGTTCGATTTATTCAACAAA
GCCGCCGTCCCGTCAAGTCAGCGTAATGCTCTGCCAGTGTTACAACCAATTAACCAATTCTGATTAGAAAA
ACTCATCGAGCATCAAATGAAACTGCAATTTATTCATATCAGGATTATCAATACCATATTTTTGAAAAAGC
CGTTTCTGTAATGAAGGAGAAAACTCACCGAGGCAGTTCCATAGGATGGCAAGATCCTGGTATCGGTCTGC
GATTCCGACTCGTCCAACATCAATACAACCTATTAATTTCCCCTCGTCAAAAATAAGGTTATCAAGTGAGA
AATCACCATGAGTGACGACTGAATCCGGTGAGAATGGCAAAAGCTTATGCATTTCTTTCCAGACTTGTTCA
ACAGGCCAGCCATTACGCTCGTCATCAAAATCACTCGCATCAACCAAACCGTTATTCATTCGTGATTGCGC
CTGAGCGAGACGAAATACGCGATCGCTGTTAAAAGGACAATTACAAACAGGAATCGAATGCAACCGGCGCA
GGAACACTGCCAGCGCATCAACAATATTTTCACCTGAATCAGGATATTCTTCTAATACCTGGAATGCTGTT
TTCCCGGGGATCGCAGTGGTGAGTAACCATGCATCATCAGGAGTACGGATAAAATGCTTGATGGTCGGAAG
AGGCATAAATTCCGTCAGCCAGTTTAGTCTGACCATCTCATCTGTAACATCATTGGCAACGCTACCTTTGC
CATGTTTCAGAAACAACTCTGGCGCATCGGGCTTCCCATACAATCGATAGATTGTCGCACCTGATTGCCCG
ACATTATCGCGAGCCCATTTATACCCATATAAATCAGCATCCATGTTGGAATTTAATCGCGGCCTCGAGCA
AGACGTTTCCCGTTGAATATGGCTCATAACACCCCTTGTATTACTGTTTATGTAAGCAGACAGTTTTATTG
TTCATGATGATATATTTTTATCTTGTGCAATGTAACATCAGAGATTTTGAGACACAACGTGGCTTTCCCCC
CCCCCCCATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTC

Coding sequence
ATGAAGGCCATCCTGGTGGTGCTGCTGTACACCTTCGCCACCGCCAACGCCGACACCCTGTGCATCGGCTA
CCACGCCAACAACAGCACCGACACCGTGGACACCGTCTGGAAGCTGCCCGCCGTGACCGTGACCCACAGCGTGA
ACCTGCTGGAGGACAAGCACAACGGCAAGCTGTGCAAGCTGCGGGGCGTGGCCCCCCTGCACCTGGGCAAG
TGCAACATCGCCGGCTGGATTCTGGGCAACCCCGAGTGCGAGAGCCTGAGCACCGCCAGCAGCTGGAGCTA
CATCGTGGAGACCCCCAGCAGCGACAACGGCACCTGCTACCCCGGCGACTTCATCGACTACGAGGAGCTGC
GGGAGCAGCTGAGCAGCGTGAGCAGCTTCGAGCGGTTCGAGATCTTCCCCAAGACCAGCAGCTGGCCCAAC
CACGACAGCAACAAGGGCGTGACCGCCGCCTGCCCCCACGCCGGCGCCAAGAGCTTCTACAAGAACCTGAT
CTGGCTGGTGAAGAAGGGCAACAGCTACCCCAAGCTGAGCAAGAGCTACATCAACGACAAGGGCAAGGAGG
TGCTGGTGCTGTGGGGCATCCACCACCCCAGCACCAGCGCCGACCAGCAGAGCCTGTACCAGAACGCCGAC
ACCTACGTGTTCGTGGGCAGCAGCCGGTACAGCAAGAAGTTCAAGCCCGAGATCGCCATCCGGCCCAAGGT
GCGGGACCAGGAGGGCCGGATGAACTACTACTGGACCCTGGTGGAGCCCGGCGACAAGATCACCTTCGAGG
CCACCGGCAACCTGGTGGTGCCCCGGTACGCCTTCGCCATGGAGCGGAACGCCGGCAGCGGCATCATCATC
AGCGACACCCCCGTGCACGACTGCAACACCACCTGCCAGACCCCCAAGGGCGCCATCAACACCAGCCTGCC
CTTCCAGAACATCCACCCCATCACCATCGGCAAGTGCCCCAAGTACGTGAAGAGCACCAAGCTGCGGCTGG
CCACCGGCCTGCGCAACATCCCCAGCATCCAGAGCCGGGGCCTGTTCGGCGCCATCGCCGGCTTCATCGAG
GGCGGCTGGACCGGCATGGTGGACGGCTGGTACGGCTACCACCACCAGAACGAGCAGGGCAGCGGCTACGC
CGCCGACCTGAAGAGCACCCAGAACGCCATCGACGAGATCACCAACAAGGTGAACAGCGTGATCGAGAAGA
TGAACACCCAGTTCACCGCCGTGGGCAAGGAGTTCAACCACCTGGAGAAGCGGATCGAGAACCTGAACAAG
AAGGTGGACGACGGCTTCCTGGACATCTGGACCTACAACGCCGAGCTGCTGGTGCTGCTGGAGAACGAGCG
GACCCTGGACTACCACGACAGCAACGTGAAGAACCTGTACGAGAAGGTGCGGAGCCAGCTGAAGAACAACG
CCAAGGAGATCGGCAACGGCTGCTTCGAGTTCTACCACAAGTGCGACAACACCTGCATGGAGAGCGTGAAG
AACGGCACCTACGACTACCCCAAGTACAGCGAGGAGGCCAAGCTGAACCGGGAGGAGATCGACTCCGGAGG
CGACATCATCAAGCTGCTGAACGAGCAGGTGAACAAGGAGATGCAGAGCAGCAACCTGTACATGAGCATGA
GCAGCTGGTGCTACACCCACAGCCTGGACGGCGCCGGCCTGTTCCTGTTCGACCACGCCGCCGAGGAGTAC

Fig. 26-3

```
GAGCACGCCAAGAAGCTGATCATCTTCCTGAACGAGAACAACGTGCCCGTGCAGCTGACCAGCATCAGCGC
CCCCGAGCACAAGTTCGAGGGCCTGACCCAGATCTTCCAGAAGGCCTACGAGCACGAGCAGCACATCAGCG
AGAGCATCAACAACATCGTGGACCACGCCATCAAGAGCAAGGACCACGCCACCTTCAACTTCCTGCAGTGG
TACGTGGCCGAGCAGCACGAGGAGGAGGTGCTGTTCAAGGACATCCTGGACAAGATCGAGCTGATCGGCAA
CGAGAACCACGGCCTGTACCTGGCCGACCAGTACGTGAAGGGCATCGCCAAGAGCAGGAAGAGCGGATCC
```

Translation
```
MKAILVVLLYTFATANADTLCIGYHANNSTDTVDTVLEKNVTVTHSVNLLEDKHNGKLCKLRGVAPLHLGK
CNIAGWILGNPECESLSTASSWSYIVETPSSDNGTCYPGDFIDYEELREQLSSVSSFERFEIFPKTSSWPN
HDSNKGVTAACPHAGAKSPYKNLIWLVKKGNSYPKLSKSYINDKGKEVLVLWGIHHPSTSADQQSLYQNAD
TYVFVGSSRYSKKFKPEIAIRPKVRDQEGRMNYYWTLVEPGDKITFEATGNLVVPRYAFAMERNAGSGIII
SDTPVHDCNTTCQTPKGAINTSLPFQNIHPITIGKCPKYVKSTKLRLATGLRNIPSIQSRGLFGAIAGFIE
GGWTGMVDGWYGYHHQNEQGSGYAADLKSTQNAIDEITNKVNSVIEKMNTQFTAVGKEFNHLEKRIENLNK
KVDDGFLDIWTYNAELLVLLENERTLDYHDSNVKNLYEKVRSQLKNNAKEIGNGCFEFYHKCDNTCMESVK
NGTYDYPKYSEEAKLNREEIDSGGDIIKLLNEQVNKEMQSSNLYMSMSSWCYTHSLDGAGLFLFDHAAEEY
EHAKKLIIFLNENNVPVQLTSISAPEHKFEGLTQIFQKAYEHEQHISESINNIVDHAIKSKDHATFNFLQW
YVAEQHEEEVLFKDILDKIELIGNENHGLYLADQYVKGIAKSRKSGS
```

Fig. 26-4

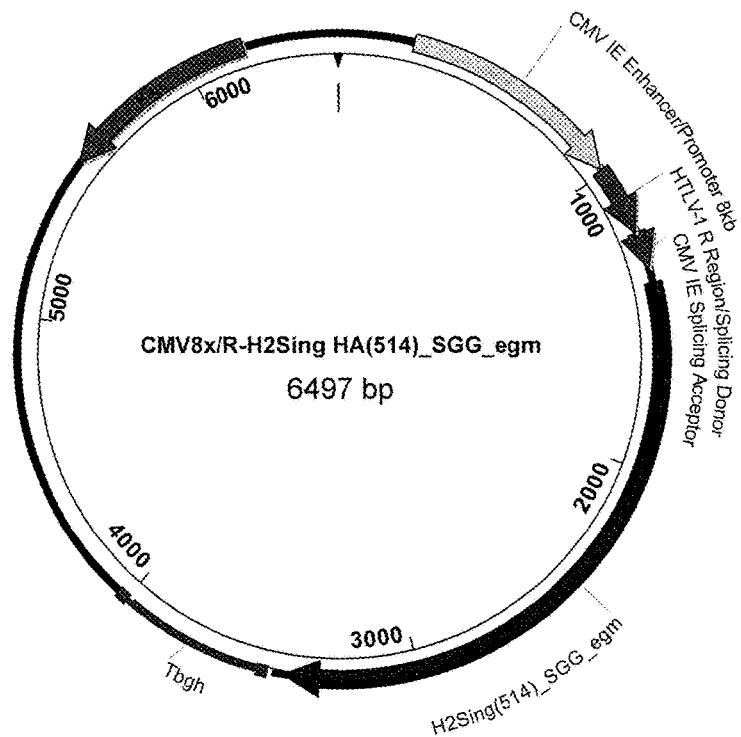
H2 Sing HA(514)_SGG_egm (H2 1957Sing HA-ferritin)
Plasmid DNA sequence

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 27-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCATGGGTCTTTTCTGCAGTCACCGTCGTCGACACG
TGTGATCAGATATCGCGGCCGCTCTAGAGATATCGCCACCATGGCCATCATCTACCTGATCCTGCTGTTTA
CAGCTGTGCGGGGCGATCAGATCTGTATCGGCTACCACGCCAACAATAGCACCGAGAAGGTGGACACCATC
CTGGAAAGAAATGTGACCGTGACCGTGACCCACGCCAAGGATATTCTGGAAAAGACCCACAACGGCAAGCTGTGCAA
GCTGAATGGCATTCCTCCTCTGGAACTGGGCGATTGTTCTATTGCTGGCTGGCTGCTGGGAAATCCTGAGT
GCGATAGACTGCTGTCTGTGCCTGAGTGGAGCTACATCATGGAAAAAGAGAACCCTAGGGACGGACTGTGT
TACCCCGGCAGCTTCAACGATTACGAGGAACTGAAGCACCTGCTGTCCAGCGTGAAGCACTTCGAGAAAGT
GAAGATCCTGCCCAAGGATAGATGGACCCAGCATACAACAACAGGCGGAAGCAGAGCTTGTGCTGTGTCCG
GCAACCCCAGCTTCTTCAGAAATATGGTCTGGCTGACCAAGAAGGGCTCTAATTATCCTGTGGCCAAGGGC
AGCTACAATAATACAAGCGGCGAGCAGATGCTGATTATTTGGGGCGTGCACCACCCTAATGATGAGACAGA
GCAGAGAACCCTGTACCAGAATGTGGGCACATACGTGTCTGTGGGCACCAGCACACTGAATAAGAGAAGCA
CCCCCGATATTGCCACCAGACCCAAAGTGAATGGACAGGGCGGCAGAATGGAATTTTCCTGGACCCTGCTG
GATATGTGGGACACCATCAACTTTGAGAGCACCGGGAATCTGATTGCCCCTGAGTACGGCTTCAAGATCAG
CAAGAGAGGCAGCAGCGGCATCATGAAAACAGAGGGCACCCTGGAAAACTGTGAAACCAAGTGTCAGACAC
CTCTGGGCGCCATTAATACCACCCTGCCCTTCCATAATGTGCACCCTCTGACAATCGGCGAGTGCCCTAAG
TACGTGAAGTCTGAGAAACTGGTGCTGGCCACAGGACTGAGAAATGTGCCCCAGATCGAGTCAAGAGGCCT
GTTTGGAGCCATTGCCGGCTTTATTGAAGGCGGATGGCAGGGAATGGTGGATGGGTGGTACGGCTATCACC
ACAGCAATGATCAGGGATCTGGCTATGCCGCCGATAAAGAGAGCACCCAGAAGGCCTTTGACGGCATCACC
AACAAAGTGAACAGCGTGATCGAGAAGATGAACACCCAGTTTGAGGCCGTGGGCAAAGAGTTCAGCAATCT
GGAAAGACGGCTGGAAAACCTGAACAAGAAAATGGAAGATGGCTTCCTGGACGTGTGGACATATAATGCCG
AGCTGCTGGTGCTGATGGAAAACGAGAGGACCCTGGACTTTCACGACAGCAACGTGAAGAACCTGTACGAC
AAAGTGCGGATGCAGCTGAGAGACAATGTGAAAGAGCTGGGCAACGGCTGCTTTGAGTTCTACCACAAGTG
CGACGACGAGTGCATGAATAGCGTGAAGAACGGCACCTACGACTACCCTAAGTATGAGGAAGAGAGCAAGC
TGAACAGAAACGAGATCAAGTCCGGAGGCGACATCATCAAGCTGCTGAACGAGCAGGTGAACAAGGAGATG
CAGAGCAGCAACCTGTACATGAGCATGAGCAGCTGGTGCTACACCCACAGCCTGGACGGCGCCGGCCTGTT
CCTGTTCGACCACGCCGCCGAGGAGTACGAGCACGCCAAGAAGCTGATCATCTTCCTGAACGAGAACAACG
TGCCCGTGCAGCTGACCAGCATCAGCGCCCCCGAGCACAAGTTCGAGGGCCTGACCCAGATCTTCCAGAAG
GCCTACGAGCACGAGCAGCACATCAGCGAGAGCATCAACAACATCGTGGACCACGCCATCAAGAGCAAGGA
CCACGCCACCTTCAACTTCCTGCAGTGGTACGTGGCCGAGCAGCACGAGGAGGAGGTGCTGTTCAAGGACA
TCCTGGACAAGATCGAGCTGATCGGCAACGAGAACCACGGCCTGTACCTGGCCGACCAGTACGTGAAGGGC
ATCGCCAAGAGCAGGAAGAGCGGATCCTAGCATCATCATCATCATTAGTCTGGAAGGGCGAATTGATCCAG
ATCTGCTGTGCCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAGGTGTCATTCT
ATTCTGGGGGGTGGGGTGGGCAGGACAGCAAGGGGGAGGATTGGGAAGACAATAGCAGGCATGCTGGGA
TGCGGTGGGCTCTATGGGTACCCAGGTGCTGAAGAATTGACCCGGTTCCTCCTGGGCCAGAAAGAAGCAGG
CACATCCCCTTCTCTGTGACACACCCTGTCCACGCCCTGGTTCTTAGTTCCAGCCCCACTCATAGGACAC
TCATAGCTCAGGAGGGCTCCGCCTTCAATCCCACCCGCTAAAGTACTTGGAGCGGTCTCTCCCTCCCTCAT
CAGCCCACCAAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATAGAATTTTAAGGCCATGATTTAA
GGCCATCATGGCCTTAATCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAACGCAGGAAAGAACAT
GTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGT
```

Fig. 27-2

```
AACTATCGTCTTGAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAAAGG
ATCTCAAGAAGATCCTTTGATCTTTTCTACGGGTCTGACGCTCAGTGGAACGAAAACTCACGTTAAGGGA
TTTTGGTCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGC
GATCTGTCTATTTCGTTCATCCATAGTTGCCTGACTCGGGGGGGGGGGGCGCTGAGGTCTGCCTCGTGAAG
AAGGTGTTGCTGACTCATACCAGGCCTGAATCGCCCCATCATCCAGCCAGAAAGTGAGGGAGCCACGGTTG
ATGAGAGCTTTGTTGTAGGTGGACCAGTTGGTGATTTTGAACTTTTGCTTTGCCACGGAACGGTCTGCGTT
GTCGGGAAGATGCGTGATCTGATCCTTCAACTCAGCAAAAGTTCGATTTATTCAACAAAGCCGCCGTCCCG
TCAAGTCAGCGTAATGCTCTGCCAGTGTTACAACCAATTAACCAATTCTGATTAGAAAAACTCATCGAGCA
TCAAATGAAACTGCAATTTATTCATATCAGGATTATCAATACCATATTTTTGAAAAAGCCGTTTCTGTAAT
GAAGGAGAAAACTCACCGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGTGAGAAATCACCATGAG
TGACGACTGAATCCGGTGAGAATGGCAAAAGCTTATGCATTTCTTTCCAGACTTGTTCAACAGGCCAGCCA
TTACGCTCGTCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATC
GCAGTGGTGAGTAACCATGCATCATCAGGAGTACGGATAAAATGCTTGATGGTCGGAAGAGGCATAAATTC
CGTCAGCCAGTTTAGTCTGACCATCTCATCTGTAACATCATTGGCAACGCTACCTTTGCCATGTTTCAGAA
ACAACTCTGGCGCATCGGGCTTCCCATACAATCGATAGATTGTCGCACCTGATTGCCCGACATTATCGCGA
GCCCATTTATACCCATATAAATCAGCATCCATGTTGGAATTTAATCGCGGCCTCGAGCAAGACGTTTCCCG
TTGAATATGGCTCATAACACCCCTTGTATTACTGTTTATGTAAGCAGACAGTTTTATTGTTCATGATGATA
TATTTTTATCTTGTGCAATGTAACATCAGAGATTTTGAGACACAACGTGGCTTTCCCCCCCCCCCATTAT
TGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTATTATCATGACATTAA
CCTATAAAAATAGGCGTATCACGAGGCCCTTTCGTC

Coding sequence
ATGGCCATCATCTACCTGATCCTGCTGTTTACAGCTGTGCGGGGCGATCAGATCTGTATCGGCTACCACGC
CAACAATAGCACCGAGAAGGTGGACACCATCCTGGAAAGAAATGTGACCGTGACCCACGCCAAGGATATTC
TGGAAAAGACCCACAACGGCAAGCTGTGCAAGCTGAATGGCATTCCTCCTCTGGAACTGGGCGATTGTTCT
ATTGCTGGCTGGCTGCTGGGAAATCCTGAGTGCGATAGACTGGCTGTCTGTGCCTGAGTGGAGCTACATCAT
GGAAAAAGAGAACCCTAGGGACGGACTGTGTTACCCCGGCGACTTCAACGATTACGAGGAACTGAAGCACC
TGCTGTCCAGCGTGAAGCACTTCGAGAAAGTGAAGATCCTGCCCAAGGATAGATGGACCCAGCATACAACA
ACAGGCGGAAGCAGAGCTTGTGCTGTGTCCGGCAACCCCAGCTTCTTCAGAAATATGGTCTGGCTGACCAA
GAAGGGCTCTAATTATCCTGTGGCCAAGGGCAGCTACAATAATACAAGCGGCGAGCAGATGCTGATTATTT
GGGGCGTGCACCACCCTAATGATGAGACAGAGCAGAGAACCCTGTACCAGAATGTGGGCACATACGTGTCT
GTGGGCACCAGCACACTGAATAAGAGAAGCACCCCCGATATTGCCACCAGACCCAAAGTGAATGGACAGGG
CGGCAGAATGGAATTTTCCTGGACCCTGCTGGATATGTGGGACACCATCAACTTTGAGAGCACCGGGAATC
TGATTGCCCCTGAGTACGGCTTCAAGATCAGCAAGAGAGGCAGCAGCGGCATCATGAAAACAGAGGGCACC
CTGGAAAACTGTGAAACCAAGTGTCAGACACCTCTGGGCGCCATTAATACCACCCTGCCCTTCCATAATGT
GCACCCTCTGACAATCGGCGAGTGCCCTAAGTACGTGAAGTCTGAGAAACTGGTGCTGGCCACAGGACTGA
GAAATGTGCCCCAGATCGAGTCAAGAGGCCTGTTTGGAGCCATTGCCGGCTTTATTGAAGGCGGATGGCAG
GGAATGGTGGATGGGTGGTACGGCTATCACCACAGCAATGATCAGGGATCTGGCTATGCCGCCGATAAAGA
GAGCACCCAGAAGGCCTTTGACGGCATCACCAACAAAGTGAACAGCGTGATCGAGAAGATGAACACCCAGT
TTGAGGCCGTGGGCAAAGAGTTCAGCAATCTGGAAAGACGGCTGGAAAACCTGAACAAGAAAATGGAAGAT
GGCTTCCTGGACGTGTGGACATATAATGCCGAGCTGCTGGTGCTGATGGAAAACGAGAGGACCCTGGACTT
TCACGACAGCAACGTGAAGAACCTGTACGACAAAGTGCGGATGCAGCTGAGAGACAATGTGAAAGAGCTGG
GCAACGGCTGCTTTGAGTTCTACCACAAGTGCGACGACGAGTGCATGAATAGCGTGAAGAACGGCACCTAC
GACTACCCTAAGTATGAGGAAGAGAGCAAGCTGAACAGAAACGAGATCAAGTCCGGAGGCGACATCATCAA
GCTGCTGAACGAGCAGGTGAACAAGGAGATGCAGAGCAGCAACCTGTACATGAGCATGAGCAGCTGGTGCT
ACACCCACAGCCTGGACGGCGCCGGCCTGTTCCTGTTCGACCACGCCGCCGAGGAGTACGAGCACGCCAAG
```

Fig. 27-3

```
AAGCTGATCATCTTCCTGAACGAGAACAACGTGCCCGTGCAGCTGACCAGCATCAGCGCCCCCGAGCACAA
GTTCGAGGGCCTGACCCAGATCTTCCAGAAGGCCTACGAGCACGAGCAGCACATCAGCGAGAGCATCAACA
ACATCGTGGACCACGCCATCAAGAGCAAGGACCACGCCACCTTCAACTTCCTGCAGTGGTACGTGGCCGAG
CAGCACGAGGAGGAGGTGCTGTTCAAGGACATCCTGGACAAGATCGAGCTGATCGGCAACGAGAACCACGG
CCTGTACCTGGCCGACCAGTACGTGAAGGGCATCGCCAAGAGCAGGAAGAGCGGATCC
```

Translation
```
MAIIYLILLFTAVRGDQICIGYHANNSTEKVDTILERNVTVTHAKDILEKTHNGKLCKLNGIPPLELGDCS
IAGWLLGNPECDRLLSVPEWSYIMEKENPRDGLCYPGSFNDYEELKHLLSSVKHFEKVKILPKDRWTQHTT
TGGSRACAVSGNPSFFRNMVWLTKKGSNYPVAKGSYNNTSGEQMLIIWGVHHPNDETEQRTLYQNVGTYVS
VGTSTLNKRSTPDIATRPKVNGQGGRMEFSWTLLDMWDTINFESTGNLIAPEYGFKISKRGSSGIMKTEGT
LENCETKCQTPLGAINTTLPFHNVHPLTIGECPKYVKSEKLVLATGLRNVPQIESRGLFGAIAGFIEGGWQ
GMVDGWYGYHHSNDQGSGYAADKESTQKAFDGITNKVNSVIEKMNTQFEAVGKEFSNLERRLENLNKKMED
GFLDVWTYNAELLVLMENERTLDFHDSNVKNLYDKVRMQLRDNVKELGNGCFEFYHKCDDECMNSVKNGTY
DYPKYEEESKLNRNEIKSGGDIIKLLNEQVNKEMQSSNLYMSMSSWCYTHSLDGAGLFLFDHAAEEYEHAK
KLIIFLNENNVPVQLTSISAPEHKFEGLTQIFQKAYEHEQHISESINNIVDHAIKSKDHATFNFLQWYVAE
QHEEEVLFKDILDKIELIGNENHGLYLADQYVKGIAKSRKSGS
```

Fig. 27-4

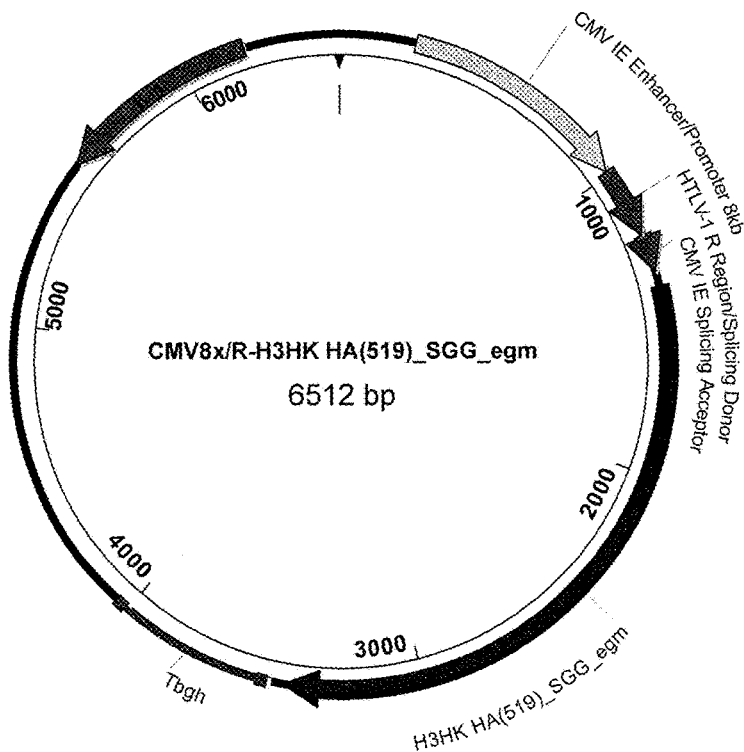
H3 HK HA(519)_SGG_egm (H3 1968HK HA-ferritin)
Plasmid DNA sequence
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 28-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAACCATCATTGCCCTGAGCTACATCT
TTTGTCTGGCTCTGGGCCAGGATCTGCCCGGCAATGATAATAGCACCGCCACCCTGTGTCTGGGACACCAC
GCCGTGCCTAATGGCACCCTGGTGAAAACCATTACCGACGACCAGATCGAAGTGACCAATGCCACCGAGCT
GGTGCAGAGCAGCAGCACCGGCAAGATCTGCAACAACCCCACAGAATCCTGGATGGCATCGACTGTACCC
TGATCGATGCCCTGCTGGGCGATCCTCACTGCGACGTGTTCCAGAACGAGACATGGGACCTGTTCGTGGAG
AGAAGCAAGGCCTTCAGCAACTGCTACCCCTACGATGTGCCCGATTACGCCTCTCTGAGAAGCCTGGTGGC
CAGCAGCGGCACACTGGAATTCATCACCGAGGGCTTTACCTGGACAGGCGTGACCCAGAATGGCGGCAGCA
ATGCCTGTAAAAGAGGCCCTGGCAGCGGCTTCTTCAGCAGACTGAACTGGCTGACCAAGTCCGGCAGCACC
TACCCTGTGCTGAACGTGACCATGCCCAACAACGACAACTTCGACAAGCTGTACATCTGGGGCGTGCACCA
CCCTAGCACCAATCAGGAACAGACCAGCCTGTACGTGCAGGCCAGCGGCAGAGTGACCGTGTCTACCAGAC
GGTCCCAGCAGACCATCATCCCCAACATCGAGTCAAGACCTTGGGTGCGCGGCCTGAGCAGCAGAATCAGC
ATCTACTGGACCATCGTGAAACCTGGCGACGTGCTGGTGATCAACAGCAATGGCAACCTGATCGCCCCCAG
AGGCTACTTCAAGATGCGGACCGGCAAGAGCAGCATCATGAGAAGCGACGCCCCCATCGATACCTGTATCA
GCGAGTGCATCACCCCCAACGGCAGCATCCCCAACGACAAGCCCTTCCAGAACGTGAACAAGATCACCTAC
GGCGCTGCCCTAAGTACGTGAAGCAGAACACCCTGAAGCTGGCCACCGGCATGAGAAATGTGCCCGAGAA
GCAGACAAGAGGCCTGTTTGGCGCCATTGCCGGCTTTATCGAGAACGGCTGGGAGGGCATGATCGATGGGT
GGTACGGCTTCAGACACCAGAATTCTGAGGGCACAGGACAGGCCGCCGATCTGAAGTCTACACAGGCCGCC
ATCGACCAGATCAACGGCAAGCTGAACAGAGTGATCGAGAAAACCAACGAGAAGTTCCACCAGATCGAGAA
AGAATTCAGCGAGGTGGAGGGCAGAATCCAGGACCTGGAAAAATACGTGGAGGACACCAAGATCGACCTGT
GGAGCTACAATGCCGAACTGCTGGTCGCCCTGGAAAACCAGCACACCATCGACCTGACCGACAGCGAGATG
AATAAGCTGTTCGAAAAGACCAGACGGCAGCTGAGAGAAAACGCCGAGGACATGGGCAACGGCTGCTTCAA
GATCTACCACAAGTGCGACAACGCCTGCATCGAGAGCATCAGAAACGGCACCTACGACCACGATGTGTACA
GGGACGAGGCCCTGAACAACAGATTCCAGATCAAGTCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACGTGCCCGTGCAGCTGACCGAGCATCAGCGCCCCGAGCACAAGTTCGAGGGCCTGACC
CAGATCTTCCAGAAGGCCTACGAGCAGCAGCACATCAGCAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGGCCTGTACCTGGCCGAC
CAGTACGTGAAGGGCATCGCCAAGAGCAGGAAGAGCGGATCCTAGCATCATCATCATCATTAGTCTGGAAG
GGCGAATTGATCCAGATCTGCTGTGCCTTCTAGTTGCCAGCCATCTGTTGTTTGCCCCTCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 28-2

TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTC

Coding sequence
ATGAAAACCATCATTGCCCTGAGCTACATCTTTTGTCTGGCTCTGGGCCAGGATCTGCCCGGCAATGATAA
TAGCACCGCCACCCTGTGTCTGGACACCACGCCGTGCCTAATGGCACCCTGGTGAAAACCATTACCGACG
ACCAGATCGAAGTGACCAATGCCACCGAGCTGGTGCAGAGCAGCAGCACCGGCAAGATCTGCAACAACCCC
CACAGAATCCTGGATGGCATCGACTGTACCCTGATCGATGCCCTGCTGGGCGATCCTCACTGCGACGTGTT
CCAGAACGAGACATGGGACCTGTTCGTGGAGAGAAGCAAGGCCTTCAGCAACTGCTACCCCTACGATGTGC
CCGATTACGCCTCTCTGAGAAGCCTGGTGGCCAGCAGCGGCACACTGGAATTCATCACCGAGGGCTTTACC
TGGACAGGCGTGACCCAGAATGGCGGCAGCAATGCCTGTAAAAGAGGCCCTGGCAGCGGCTTCTTCAGCAG
ACTGAACTGGCTGACCAAGTCCGGCAGCACCTACCCTGTGCTGAACGTGACCATGCCCAACAACGACAACT
TCGACAAGCTGTACATCTGGGGCGTGCACCACCCTAGCACCAATCAGGAACAGACCAGCCTGTACGTGCAG
GCCAGCGGCAGAGTGACCGTGTCTACCAGACGGTCCCAGCAGACCATCATCCCCAACATCGAGTCAAGACC
TTGGGTGCGCGGCCTGAGCAGCAGAATCAGCATCTACTGGACCATCGTGAAACCTGGCGACGTGCTGGTGA
TCAACAGCAATGGCAACCTGATCGCCCCCAGAGGCTACTTCAAGATGCGGACCGGCAAGAGCAGCATCATG
AGAAGCGACGCCCCCATCGATACCTGTATCAGCGAGTGCATCACCCCCAACGGCAGCATCCCCAACGACAA
GCCCTTCCAGAACGTGAACAAGATCACCTACGGCGCCTGCCCTAAGTACGTGAAGCAGAACACCCTGAAGC
TGGCCACCGGCATGAGAAATGTGCCCGAGAAGCAGACAAGAGGCCTGTTTGGCGCCATTGCCGGCTTTATC
GAGAACGGCTGGGAGGGCATGATCGATGGGTGGTACGGCTTCAGACACCAGAATTCTGAGGGCACAGGACA
GGCCGCCGATCTGAAGTCTACACAGGCGGCCATCGACCAGATCAACGGCAAGCTGAACAGAGTGATCGAGA
AAACCAACGAGAAGTTCCACCAGATCGAGAAGAATTCAGCGAGGTGGAGGGCAGAATCCAGGACCTGGAA
AAATACGTGGAGGACACCAAGATCGACCTGTGGAGCTACAATGCCGAACTGCTGGTCGCCCTGGAAAACCA
GCACACCATCGACCTGACCGACAGCGAGATGAATAAGCTGTTCGAAAAGACCAGACGGCAGCTGAGAGAAA
ACGCCGAGGACATGGGCAACGGCTGCTTCAAGATCTACCACAAGTGCGACAACGCCTGCATCGAGAGCATC
AGAAACGGCACCTACGACCACGATGTGTACAGGGACGAGGCCCTGAACAACAGATTCCAGATCAAGTCCGG
AGGCGACATCATCAAGCTGCTGAACGAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG

Fig. 28-3

```
TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC
```

Translation
```
MKTIIALSYIFCLALGQDLPGNDNSTATLCLGHHAVPNGTLVKTITDDQIEVTNATELVQSSSTGKICNNP
HRILDGIDCTLIDALLGDPHCDVFQNETWDLFVERSKAFSNCYPYDVPDYASLRSLVASSGTLEFITEGFT
WTGVTQNGGSNACKRGPGSGFFSRLNWLTKSGSTYPVLNVTMPNNDNFDKLYIWGVHHPSTNQEQTSLYVQ
ASGRVTVSTRRSQQTIIPNIESRPWVRGLSSRISIYWTIVKPGDVLVINSNGNLIAPRGYFKMRTGKSSIM
RSDAPIDTCISECITPNGSIPNDKPFQNVNKITYGACPKYVKQNTLKLATGMRNVPEKQTRGLFGAIAGFI
ENGWEGMIDGWYGFRHQNSEGTGQAADLKSTQAAIDQINGKLNRVIEKTNEKFHQIEKEFSEVEGRIQDLE
KYVEDTKIDLWSYNAELLVALENQHTIDLTDSEMNKLFEKTRRQLRENAEDMGNGCFKIYHKCDNACIESI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNFLQ
WYVAEQHEEEVLFKDILDKIELIGNENHGLYLADQYVKGIAKSRKSGS
```

Fig. 28-4

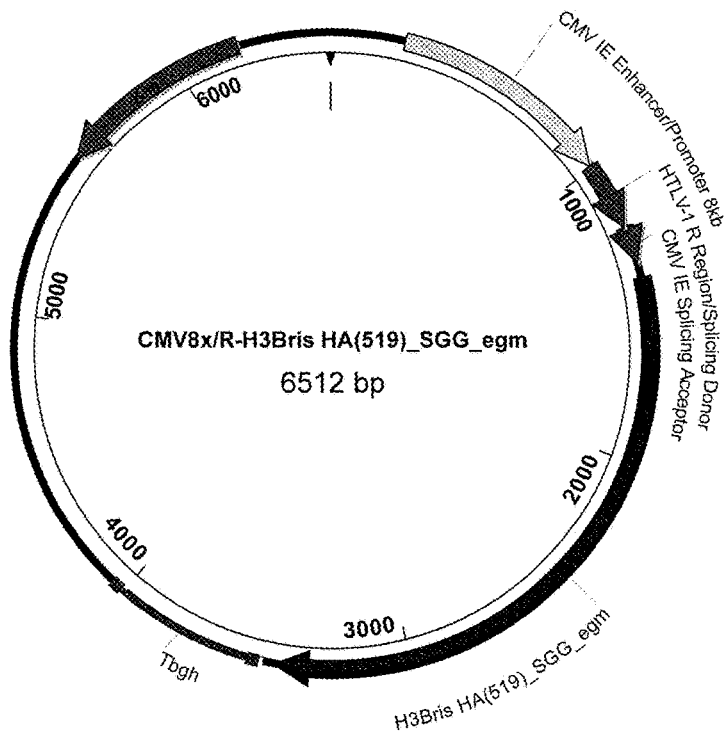
H3 Bris HA(519)_SGG_egm (H3 2007Bris HA-ferritin)
Plasmid DNA sequence

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 29-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAACCATCATTGCCCTGAGCTACATCC
TGTGCCTGGTGTTCACACAGAAGCTGCCCGGCAACGATAATAGCACCGCCACACTGTGTCTGGGACACCAC
GCCGTGCCTAATGGCACCATCGTGAAAACAATCACCAACGACCAGATCGAAGTGACCAATGCCACAGAGCT
GGTGCAGAGCAGCAGCACAGGCGAGATCTGTGACAGCCCCCACCAGATCCTGGATGGCGAGAACTGTACCC
TGATCGATGCCCTGCTGGGCGATCCTCAGTGCGACGGCTTCCAGAACAAGAAATGGGACCTGTTCGTGGAG
AGAAGCAAGGCCTACAGCAACTGCTACCCCTACGACGTGCCTGATTACGCCAGCCTGAGAAGCCTGGTGGC
CTCTAGCGGCACCCTGGAATTCAACAACGAGAGCTTCAACTGGACCGGCGTGACACAGAATGGCACCAGCA
GCGCCTGCATCAGACGGTCCAACAACAGCTTCTTCAGTAGACTGAATTGGCTGACCCACCTGAAGTTCAAG
TACCCCGCCCTGAACGTGACCATGCCCAACAATGAGAAGTTCGACAAGCTGTACATCTGGGGAGTGCACCA
CCCTGGCACCGACAACGATCAGATCTTCCCTTACGCCCAGGCCAGCGGCAGAATCACCGTGTCCACCAAGA
GAAGCCAGCAGACCGTGATCCCCAATATCGGCAGCAGACCCAGAGTGCGGAACATCCCCAGCAGGATCAGC
ATCTACTGGACAATCGTGAAGCCTGGCGACATCCTGCTGATCAACAGCACCGGCAACCTGATCGCCCCTCG
GGGCTACTTTAAGATCAGAAGCGGCAAGAGCAGCATCATGAGATCCGACGCCCCCATCGGCAAGTGCAACA
GCGAGTGCATCACCCCAAACGGCAGCATCCCCAACGACAAGCCCTTCCAGAACGTGAACAGGATCACCTAC
GGCGCCTGCCCTAGATACGTGAAGCAGAACACCCTGAAGCTGGCCACCGGCATGAGAAATGTGCCCGAGAA
GCAGACCAGAGGCATCTTTGGCGCCATTGCCGGCTTTATCGAGAATGGCTGGGAGGGAATGGTGGATGGGT
GGTACGGCTTCAGACACCAGAATAGCGAGGGAATTGGACAGGCCGCCGATCTGAAATCTACCCAGGCCGCC
ATCGACCAGATCAACGGCAAGCTGAACAGGCTGATCGGCAAGACCAACGAGAAGTTCCACCAGATCGAGAA
AGAATTCAGCGAGGTGGAGGGCAGAATCCAGGACCTGGAAAAATACGTGGAGGACACCAAGATCGACCTGT
GGAGCTACAATGCCGAACTGCTGGTCGCCCTGGAAAACCAGCACACAATTGATCTGACAGACAGTGAGATG
AATAAGCTGTTCGAGAAAACCAAGAAGCAGCTGAGAGAAAACGCCGAGGACATGGGCAACGGCTGCTTCAA
GATCTACCACAAGTGCGACAACGCCTGCATCGGCAGCATCAGAAACGGCACCTACGACCACGACGTGTACA
GAGATGAGGCCCTGAACAACCGGTTTCAGATCAAGTCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACAACGTGCCCGTGCAGCTGACCAGCATCAGCGCCCCCGAGCACAAGTTCGAGGGCCTGACC
CAGATCTTCCAGAAGGCCTACGAGCACGAGCAGCACATCAGCGAGAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGGCCTGTACCTGGCCGAC
CAGTACGTGAAGGGCATCGCCAAGAGCAGGAAGAGCGGATCCTAGCATCATCATCATCATTAGTCTGGAAG
GGCGAATTGATCCAGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 29-2

```
TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTC
```

Coding sequence
```
ATGAAAACCATCATTGCCCTGAGCTACATCCTGTGCCTGGTGTTCACACAGAAGCTGCCCGGCAACGATAA
TAGCACCGCCACACTGTGTCTGGGACACCACGCCGTGCCTAATGGCACCATCGTGAAAACAATCACCAACG
ACCAGATCGAAGTGACCAATGCCACAGAGCTGGTGCAGAGCAGCAGCACAGGCGAGATCTGTGACAGCCCC
CACCAGATCCTGGATGGCGAGAACTGTACCCTGATCGATGCCCTGCTGGGCGATCCTCAGTGCGACGGCTT
CCAGAACAAGAAATGGGACCTGTTCGTGGAGAGAAGCAAGGCCTACAGCAACTGCTACCCCTACGACGTGC
CTGATTACGCCAGCCTGAGAAGCCTGGTGGCCTCTAGCGGCACCCTGGAATTCAACAACGAGAGCTTCAAC
TGGACCGGCGTGACACAGAATGGCACCAGCAGCGCCTGCATCAGACGGTCCAACAACAGCTTCTTCAGTAG
ACTGAATTGGCTGACCCACCTGAAGTTCAAGTACCCCGCCCTGAACGTGACCATGCCCAACAATGAGAAGT
TCGACAAGCTGTACATCTGGGGAGTGCACCACCCTGGCACCGACAACGATCAGATCTTCCCTTACGCCCAG
GCCAGCGGCAGAATCACCGTGTCCACCAAGAGAAGCCAGCAGACCGTGATCCCCAATATCGGCAGCAGACC
CAGAGTGCGGAACATCCCCAGCAGGATCAGCATCTACTGGACAATCGTGAAGCCTGGCGACATCCTGCTGA
TCAACAGCACCGGCAACCTGATCGCCCCTCGGGGCTACTTTAAGATCAGAAGCGGCAAGAGCAGCATCATG
AGATCCGACGCCCCATCGGCAAGTGCAACAGCGAGTGCATCACCCCAAACGGCAGCATCCCCAACGACAA
GCCCTTCCAGAACGTGAACAGGATCACCTACGGCGCCTGCCCTAGATACGTGAAGCAGAACACCCTGAAGC
TGGCCACCGGCATGAGAAATGTGCCCGAGAAGCAGACCAGAGGCATCTTTGGCGCCATTGCCGGCTTTATC
GAGAATGGCTGGGAGGGAATGGTGGATGGGTGGTACGGCTTCAGACACCAGAATAGCGAGGGAATTGGACA
GGCCGCCGATCTGAAATCTACCCAGGCCGCCATCGACCAGATCAACGGCAAGCTGAACAGGCTGATCGGCA
AGACCAACGAGAAGTTCCACCAGATCGAGAAAGAATTCAGCGAGGTGGAGGGCAGAATCCAGGACCTGGAA
AAATACGTGGAGGACACCAAGATCGACCTGTGGAGCTACAATGCCGAACTGCTGGTCGCCCTGGAAAACCA
GCACACAATTGATCTGACAGACAGTGAGATGAATAAGCTGTTCGAGAAAACCAAGAAGCAGCTGAGAGAAA
ACGCCGAGGACATGGGCAACGGCTGCTTCAAGATCTACCACAAGTGCGACAACGCCTGCATCGGCAGCATC
AGAAACGGCACCTACGACCACGACGTGTACAGAGATGAGGCCCTGAACAACCGGTTCCAGATCAAGTCCGG
AGGCGACATCATCAAGCTGCTGAACGAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG
```

Fig. 29-3

```
TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC
```

Translation
```
MKTIIALSYILCLVFTQKLPGNDNSTATLCLGHHAVPNGTIVKTITNDQIEVTNATELVQSSSTGEICDSP
HQILDGENCTLIDALLGDPQCDGFQNKKWDLFVERSKAYSNCYPYDVPDYASLRSLVASSGTLEFNNESFN
WTGVTQNGTSSACIRRSNNSFFSRLNWLTHLKFKYPALNVTMPNNEKFDKLYIWGVHHPGTDNDQIFPYAQ
ASGRITVSTKRSQQTVIPNIGSRPVRNIPSRISIYWTIVKPGDILLINSTGNLIAPRGYFKIRSGKSSIM
RSDAPIGKCNSECITPNGSIPNDKPFQNVNRITYGACPRYVKQNTLKLATGMRNVPEKQTRGIFGAIAGFI
ENGWEGMVDGWYGFRHQNSEGIGQAADLKSTQAAIDQINGKLNRLIGKTNEKFHQIEKEFSEVEGRIQDLE
KYVEDTKIDLWSYNAELLVALENQHTIDLTDSEMNKLFEKTKKQLRENAEDMGNGCFKIYHKCDNACIGSI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNFLQ
WYVAEQHEEEVLFKDILDKIELIGNENHGLYLADQYVKGIAKSRKSGS
```

Fig. 29-4

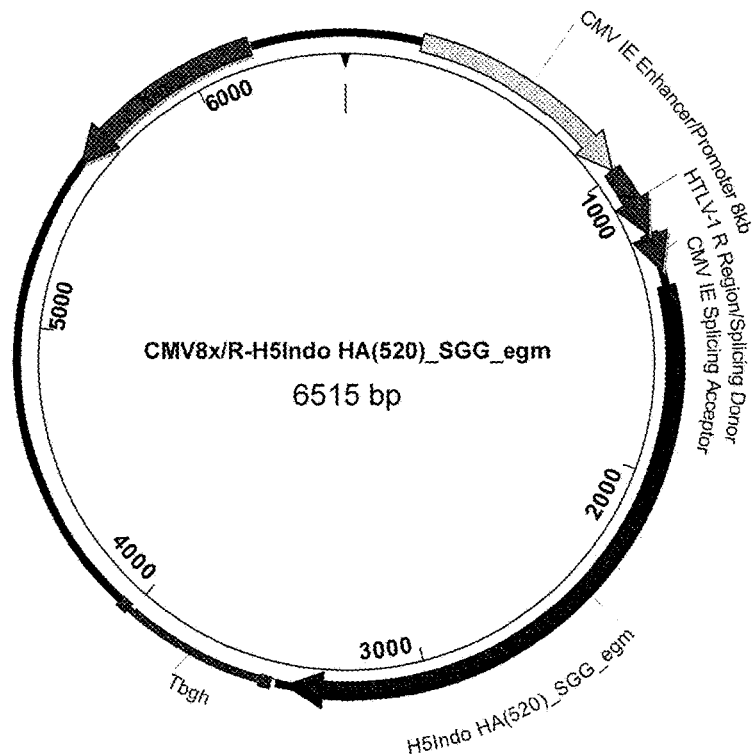
H5 Indo HA(520)_SGG_egm (H5 2005Indo HA-ferritin)
Plasmid DNA sequence

```
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG
```

Fig. 30-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGCCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGGAAAAGATCGTGCTGCTGCTGGCCATTG
TGAGCCTGGTGAAGAGCGACCAGATCTGCATTGGCTACCACGCCAACAATAGCACAGAGCAGGTGGACACC
ATCATGGAAAAAACGTGACCGTGACCCACGCTCAGGACATCCTGGAAAAGACCCACAACGGCAAGCTGTG
TGATCTGGACGGCGTGAAGCCTCTGATCCTGAGAGATTGTAGCGTGGCTGGATGGCTGCTGGGCAACCCTA
TGTGCGACGAGTTCATCAACGTGCCCGAGTGGAGCTATATCGTGGAGAAGGCCAACCCCACCAACGATCTG
TGTTACCCCGGCAGCTTCAACGATTACGAGGAACTGAAGCACCTGCTGTCCCGGATCAACCACTTCGAGAA
GATCCAGATCATCCCCAAGTCCTCTTGGAGCGATCACGAAGCCTCTAGCGGAGTGTCTAGCGCCTGTCCTT
ACCTGGGCAGCCCCAGCTTCTTCAGAAACGTGGTGTGGCTGATCAAGAAGAACAGCACCTACCCCACCATC
AAGAAGAGCTACAACAACACCAACCAGGAAGATCTGCTGGTCCTGTGGGGAATCCACCACCCTAATGATGC
CGCCGAGCAGACCAGACTGTACCAGAACCCCACCACCTATATCAGCATCGGCACCAGCACCCTGAATCAGA
GACTGGTGCCCAAGATCGCCACCAGATCCAAGGTGAACGGCCAGAGCGGCAGGATGGAATTCTTCTGGACC
ATCCTGAAGCCCAACGACGCCATCAACTTCGAGAGCAACGGCAACTTTATCGCCCCTGAGTACGCCTACAA
GATCGTGAAGAAGGGCGACAGCGCCATCATGAAGAGCGAGCTGGAATACGGCAACTGCAACACCAAGTGCC
AGACACCTATGGGCGCCATCAACAGCAGCATGCCCTTCCACAACATCCACCCTCTGACCATCGGCGAGTGC
CCTAAGTACGTGAAGAGCAACAGACTGGTGCTGGCCACAGGCCTGAGAAATAGCCCCCAGCGGGAGAGCAG
AAGAAAGAAGAGGGGCCTGTTTGGAGCCATCGCCGGCTTTATTGAAGGCGGCTGGCAGGGAATGGTGGATG
GCTGGTACGGCTACCACCACAGCAATGAGCAGGGCTCTGGATATGCCGCCGACAAAGAGTCTACCCAGAAG
GCCATCGACGGCGTCACCAACAAGGTGAACAGCATCATCGACAAGATGAACACCCAGTTCGAGGCTGTGGG
CAGAGAGTTCAACAACCTGGAACGGCGGATCGAGAACCTGAACAAGAAAATGGAAGATGGCTTCCTGGATG
TGTGGACCTACAATGCCGAACTGCTGGTGCTGATGGAAAACGAGCGGACCCTGGACTTCCACGACAGCAAC
GTGAAGAACCTGTACGACAAAGTGCGGCTGCAGCTGAGAGACAACGCCAAAGAGCTGGGCAACGGCTGCTT
CGAGTTCTACCACAAGTGCGACAACGAGTGCATGGAAAGCATCAGGAACGGCACCTACAACTACCCTCAGT
ACAGCGAGGAAGCCAGGCTGAAGAGGGAAGAGATCAGCTCCGGAGGCGACATCATCAAGCTGCTGAACGAG
CAGGTGAACAAGGAGATGCAGAGCAGCAACCTGTACATGAGCATGAGCAGCTGGTGCTACACCCACAGCCT
GGACGGCGCCGGCCTGTTCCTGTTCGACCACGCCGCCGAGGAGTACGAGCACGCCAAGAAGCTGATCATCT
TCCTGAACGAGAACAACGTGCCCGTGCAGCTGACCAGCATCAGCGCCCCCGAGCACAAGTTCGAGGGCCTG
ACCCAGATCTTCCAGAAGGCCTACGAGCACGAGCAGCACATCAGCGAGAGCATCAACAACATCGTGGACCA
CGCCATCAAGAGCAAGGACCACGCCACCTTCAACTTCCTGCAGTGGTACGTGGCCGAGCAGCACGAGGAGG
AGGTGCTGTTCAAGGACATCCTGGACAAGATCGAGCTGATCGGCAACGAGAACCACGGCCTGTACCTGGCC
GACCAGTACGTGAAGGGCATCGCCAAGAGCAGGAAGAGCGGATCCTAGCATCATCATCATCATTAGTCTGG
AAGGGCGAATTGATCCAGATCTGCTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGCAGGACAGCAAGGGGGAGGATTGGGAAGACAA
TAGCAGGCATGCTGGGGATGCGGTGGGCTCTATGGGTACCCAGGTGCTGAAGAATTGACCCGGTTCCTCCT
GGGCCAGAAAGAAGCAGGCACATCCCCTTCTCTGTGACACACCCTGTCCACGCCCCTGGTTCTTAGTTCCA
GCCCCACTCATAGGACACTCATAGCTCAGGAGGGCTCCGCCTTCAATCCCACCCGCTAAAGTACTTGGAGC
GGTCTCTCCCTCCCTCATCAGCCCACCAAACCAAACCTAGCCTCCAAGAGTGGGAAGAAATTAAAGCAAGA
TAGGCTATTAAGTGCAGAGGGAGAGAAAATGCCTCCAACATGTGAGGAAGTAATGAGAGAAATCATAGAAT
TTTAAGGCCATGATTTAAGGCCATCATGGCCTTAATCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCCCCGTTCAGCCCGAC
```

Fig. 30-2

```
CGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGTTACCTTCGGAAAAGA
GTTGGTAGCTCTTGATCCGGCAAACAAACCACCGCTGGTAGCGGTGGTTTTTTTGTTTGCAAGCAGCAGAT
TACGCGCAGAAAAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCGGGGGGGGGGGCGCT
GAGGTCTGCCTCGTGAAGAAGGTGTTGCTGACTCATACCAGGCCTGAATCGCCCCATCATCCAGCCAGAAA
GTGAGGGAGCCACGGTTGATGAGAGCTTTGTTGTAGGTGGACCAGTTGGTGATTTTGAACTTTTGCTTTGC
CACGGAACGGTCTGCGTTGTCGGGAAGATGCGTGATCTGATCCTTCAACTCAGCAAAAGTTCGATTTATTC
AACAAAGCCGCCGTCCCGTCAAGTCAGCGTAATGCTCTGCCAGTGTTACAACCAATTAACCAATTCTGATT
AGAAAAACTCATCGAGCATCAAATGAAACTGCAATTTATTCATATCAGGATTATCAATACCATATTTTGA
AAAAGCCGTTTCTGTAATGAAGGAGAAAACTCACCGAGGCAGTTCCATAGGATGGCAAGATCCTGGTATCG
GTCTGCGATTCCGACTCGTCCAACATCAATACAACCTATTAATTTCCCCTCGTCAAAATAAGGTTATCAA
GTGAGAAATCACCATGAGTGACGACTGAATCCGGTGAGAATGGCAAAAGCTTATGCATTTCTTTCCAGACT
TGTTCAACAGGCCAGCCATTACGCTCGTCATCAAAATCACTCGCATCAACCAAACCGTTATTCATTCGTGA
TTGCGCCTGAGCGAGACGAAATACGCGATCGCTGTTAAAGGACAATTACAAACAGGAATCGAATGCAACC
GGCGCAGGAACACTGCCAGCGCATCAACAATATTTTCACCTGAATCAGGATATTCTTCTAATACCTGGAAT
GCTGTTTTCCCGGGGATCGCAGTGGTGAGTAACCATGCATCATCAGGAGTACGGATAAAATGCTTGATGGT
CGGAAGAGGCATAAATTCCGTCAGCCAGTTTAGTCTGACCATCTCATCTGTAACATCATTGGCAACGCTAC
CTTTGCCATGTTTCAGAAACAACTCTGGCGCATCGGGCTTCCCATACAATCGATAGATTGTCGCACCTGAT
TGCCCGACATTATCGCGAGCCCATTTATACCCATATAAATCAGCATCCATGTTGGAATTTAATCGCGGCCT
CGAGCAAGACGTTTCCCGTTGAATATGGCTCATAACACCCCTTGTATTACTGTTTATGTAAGCAGACAGTT
TTATTGTTCATGATGATATATTTTTATCTTGTGCAATGTAACATCAGAGATTTTGAGACACAACGTGGCTT
TCCCCCCCCCCCCATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTC
```

Coding sequence
```
ATGGAAAAGATCGTGCTGCTGCTGGCCATTGTGAGCCTGGTGAAGAGCGACCAGATCTGCATTGGCTACCA
CGCCAACAATAGCACAGAGCAGGTGGACACCATCATGGAAAAAAACGTGACCGTGACCCACGCTCAGGACA
TCCTGGAAAAGACCCACAACGGCAAGCTGTGTGATCTGGACGGCGTGAAGCCTCTGATCCTGAGAGATTGT
AGCGTGGCTGGATGGCTGCTGGGCAACCCTATGTGCGACGAGTTCATCAACGTGCCCGAGTGGAGCTATAT
CGTGGAGAAGGCCAACCCCACCAACGATCTGTGTTACCCCGGCAGCTTCAACGATTACGAGGAACTGAAGC
ACCTGCTGTCCCGGATCAACCACTTCGAGAAGATCCAGATCATCCCCAAGTCCTCTTGGAGCGATCACGAA
GCCTCTAGCGGAGTGTCTAGCGCCTGTCCTTACCTGGGCAGCCCCAGCTTCTTCAGAAACGTGGTGTGGCT
GATCAAGAAGAACAGCACCTACCCCACCATCAAGAAGAGCTACAACAACACCAACCAGGAAGATCTGCTGG
TCCTGTGGGGAATCCACCACCCTAATGATGCCGCCGAGCAGACCAGACTGTACCAGAACCCCACCACCTAT
ATCAGCATCGGCACCAGCACCCTGAATCAGAGACTGGTGCCAAGATCGCCACCAGATCCAAGGTGAACGG
CCAGAGCGGCAGGATGGAATTCTTCTGGACCATCCTGAAGCCCAACGACGCCATCAACTTCGAGAGCAACG
GCAACTTTATCGCCCCTGAGTACGCCTACAAGATCGTGAAGAAGGGCGACAGCGCCATCATGAAGAGCGAG
CTGGAATACGGCAACTGCAACACCAAGTGCCAGACACCTATGGGCGCCATCAACAGCAGCATGCCCTTCCA
CAACATCCACCCTCTGACCATCGGCGAGTGCCCTAAGTACGTGAAGAGCAACAGACTGGTGCTGGCCACAG
GCCTGAGAAATAGCCCCCAGCGGGAGAGCAGAAGAAAGAAGAGGGGCCTGTTTGGAGCCATCGCCGGCTTT
ATTGAAGGCGGCTGGCAGGGAATGGTGGATGGCTGGTACGGCTACCACCACAGCAATGAGCAGGGCTCTGG
ATATGCCGCCGACAAAGAGTCTACCCAGAAGGCCATCGACGGCGTCACCAACAAGGTGAACAGCATCATCG
ACAAGATGAACACCCAGTTCGAGGCTGTGGGCAGAGAGTTCAACAACCTGGAACGGCGGATCGAGAACCTG
AACAAGAAAATGGAAGATGGCTTCCTGGATGTGTGGACCTACAATGCCGAACTGCTGGTGCTGATGGAAAA
CGAGCGGACCCTGGACTTCCACGACAGCAACGTGAAGAACCTGTACGACAAAGTGCGGCTGCAGCTGAGAG
ACAACGCCAAAGAGCTGGGCAACGGCTGCTTCGAGTTCTACCACAAGTGCGACAACGAGTGCATGGAAAGC
ATCAGGAACGGCACCTACAACTACCCTCAGTACAGCGAGGAAGCCAGGCTGAAGAGGGAAGAGATCAGCTC
CGGAGGCGACATCATCAAGCTGCTGAACGAGCAGGTGAACAAGGAGATGCAGAGCAGCAACCTGTACATGA
GCATGAGCAGCTGGTGCTACACCCACAGCCTGGACGGCGCCGGCCTGTTCCTGTTCGACCACGCCGCCGAG
```

Fig. 30-3

```
GAGTACGAGCACGCCAAGAAGCTGATCATCTTCCTGAACGAGAACAACGTGCCCGTGCAGCTGACCAGCAT
CAGCGCCCCCGAGCACAAGTTCGAGGGCCTGACCCAGATCTTCCAGAAGGCCTACGAGCACGAGCAGCACA
TCAGCGAGAGCATCAACAACATCGTGGACCACGCCATCAAGAGCAAGGACCACGCCACCTTCAACTTCCTG
CAGTGGTACGTGGCCGAGCAGCACGAGGAGGAGGTGCTGTTCAAGGACATCCTGGACAAGATCGAGCTGAT
CGGCAACGAGAACCACGGCCTGTACCTGGCCGACCAGTACGTGAAGGGCATCGCCAAGAGCAGGAAGAGCG
GATCC
```

Translation
```
MEKIVLLLAIVSLVKSDQICIGYHANNSTEQVDTIMEKNVTVTHAQDILEKTHNGKLCDLDGVKPLILRDC
SVAGWLLGNPMCDEFINVPEWSYIVEKANPTNDLCYPGSFNDYEELKHLLSRINHFEKIQIIPKSSWSDHE
ASSGVSSACPYLGSPSFFRNVVWLIKKNSTYPTIKKSYNNTNQEDLLVLWGIHHPNDAAEQTRLYQNPTTY
ISIGTSTLNQRLVPKIATRSKVNGQSGRMEFFWTILKPNDAINFESNGNFIAPEYAYKIVKKGDSAIMKSE
LEYGNCNTKCQTPMGAINSSMPFHNIHPLTIGECPKYVKSNRLVLATGLRNSPQRESRRKKRGLFGAIAGF
IEGGWQGMVDGWYGYHHSNEQGSGYAADKESTQKAIDGVTNKVNSIIDKMNTQFEAVGREFNNLERRIENL
NKKMEDGFLDVWTYNAELLVLMENERTLDFHDSNVKNLYDKVRLQLRDNAKELGNGCFEFYHKCDNECMES
IRNGTYNYPQYSEEARLKREEISSGGDIIKLLNEQVNKEMQSSNLYMSMSSWCYTHSLDGAGLFLFDHAAE
EYEHAKKLIIFLNENNVPVQLTSISAPEHKFEGLTQIFQKAYEHEQHISESINNIVDHAIKSKDHATFNFL
QWYVAEQHEEEVLFKDILDKIELIGNENHGLYLADQYVKGIAKSRKSGS
```

Fig. 30-4

B Florida HA(534)_SGG_egm (B 2006FL HA-ferritin)

Plasmid DNA sequence
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 31-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCATCGTGCTGCTGATGGTGG
TGACCAGCAACGCCGATAGAATCTGCACCGGCATCACCAGCAGCAATAGCCCCCATGTGGTGAAAACAGCC
ACCCAGGGCGAAGTGAATGTGACAGGCGTGATCCCTCTGACCACCACCCCCACCAAGAGCTACTTCGCCAA
CCTGAAGGGCACCAGAACCAGAGGCAAGCTGTGCCCCGATTGCCTGAACTGCACCGATCTGGATGTGGCTC
TGGGCAGACCTATGTGTGTGGGCACCACACCATCTGCCAAGGCCAGCATCCTGCACGAAGTGAAGCCTGTG
ACCAGCGGCTGCTTCCCCATCATGCACGACCGGACCAAGATCAGACAGCTGCCCAACCTGCTGAGAGGCTA
CGAGAACATCCGGCTGTCCACCCAGAATGTGATCGATGCCGAGAAGCCCCTGGCGGACCTTATAGACTGG
GCACCAGCGGCTCTTGTCCCAATGCCACCTCCAAGAGCGGCTTTTTTGCCACAATGGCCTGGGCCGTGCCT
AAGGACAACAACAAGAACGCCACCAACCCTCTGACCGTGGAGGTGCCCTACATCTGTACAGAGGGCGAGGA
TCAGATCACAGTGTGGGGCTTCCACAGCGACGACAAGACCCAGATGAAGAACCTGTACGGCGACAGCAACC
CCCAGAAGTTTACCAGCAGCGCCAATGGCGTGACCACCCACTACGTGTCCCAGATCGGCAGCTTTCCCGAT
CAGACAGAGGATGGCGGACTGCCTCAGTCTGGCAGGATCGTGGTGGACTACATGATGCAGAAGCCTGGCAA
GACCGGCACCATCGTGTATCAGAGAGGCGTGCTGCTGCCTCAGAAAGTGTGGTGTGCCAGCGGCAGGTCTA
AAGTGATCAAGGGCAGCCTGCCTCTGATTGGCGAGGCCGACTGTCTGCACGAAAAGTACGGCGGCCTGAAC
AAGAGCAAGCCCTACTACACAGGCGAGCACGCCAAGGCCATCGGCAATTGCCCCATCTGGGTGAAAACCCC
CCTGAAGCTGGCCAATGGCACCAAGTACAGACCTCCCGCCAAGCTGCTGAAAGAGAGAGGCTTCTTTGGCG
CCATTGCCGGATTTCTGGAAGGCGGCTGGGAGGGAATGATTGCCGGCTGGCACGGCTATACATCTCATGGG
GCCCATGGCGTGGCTGTGGCCGCCGATCTGAAGTCTACCCAGGAAGCCATCAACAAGATCACCAAGAACCT
GAACAGCCTGAGCGAGCTGGAAGTGAAGAATCTGCAGAGACTGAGCGGCGCCATGGATGAGCTGCACAACG
AGATCCTGGAACTGGACGAGAAAGTGGATGATCTCCGCGCCGATACAATTTCCTCCCAGATTGAACTGGCC
GTGCTGCTGTCCAACGAGGGCATCATCAACAGCGAGGATGAACACCTGCTGGCCCTGGAACGGAAGCTGAA
GAAGATGCTGGGCCCTTCTGCCGTGGAGATCGGCAACGGCTGCTTCGAGACAAAGCACAAGTGCAACCAGA
CCTGCCTGGATAGAATCGCCGCTGGCACCTTCAATGCCGGCGAGTTCAGCCTGCCTACCTTCGACAGCCTG
AATATCACCTCCGGAGGCGACATCATCAAGCTGCTGAACGAGCAGGTGAACAAGGAGATGCAGAGCAGCAA
CCTGTACATGAGCATGAGCAGCTGGTGCTACACCCACAGCCTGGACGGCGCCGGCCTGTTCCTGTTCGACC
ACGCCGCCGAGGAGTACGAGCACGCCAAGAAGCTGATCATCTTCCTGAACGAGAACAACGTGCCCGTGCAG
CTGACCAGCATCAGCGCCCCCGAGCACAAGTTCGAGGGCCTGACCCAGATCTTCCAGAAGGCCTACGAGCA
CGAGCAGCACATCAGCGAGAGCATCAACAACATCGTGGACCACGCCATCAAGAGCAAGGACCACGCCACCT
TCAACTTCCTGCAGTGGTACGTGGCCGAGCAGCACGAGGAGGAGGTGCTGTTCAAGGACATCCTGGACAAG
ATCGAGCTGATCGGCAACGAGAACCACGGCCTGTACCTGGCCGACCAGTACGTGAAGGGCATCGCCAAGAG
CAGGAAGAGCGGATCCTAGCATCATCATCATCATTAGTCTGGAAGGGCGAATTGATCCAGATCTGCTGTGC
CTTCTAGTTGCCAGCCATCTGTTGTTTGCCCCTCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTATTCTGGGGGG
TGGGGTGGGGCAGGACAGCAAGGGGGAGGATTGGGAAGACAATAGCAGGCATGCTGGGGATGCGGTGGGCT
CTATGGGTACCCAGGTGCTGAAGAATTGACCCGGTTCCTCCTGGGCCAGAAAGAAGCAGGCACATCCCCTT
CTCTGTGACACACCCTGTCCACGCCCTGGTTCTTAGTTCCAGCCCCACTCATAGGACACTCATAGCTCAG
GAGGGCTCCGCCTTCAATCCACCACCGCTAAAGTACTTGGAGCGGTCTCTCCCTCCCTCATCAGCCCACCAA
ACCAAACCTAGCCTCCAAGAGTGGGAAGAAATTAAAGCAAGATAGGCTATTAAGTGCAGAGGGAGAGAAAA
TGCCTCCAACATGTGAGGAAGTAATGAGAGAAATCATAGAATTTTAAGGCCATGATTTAAGGCCATCATGG
CCTTAATCTTCCGCTTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGTGTAGGTCGTTCGC
```

Fig. 31-2

```
TCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATG
AGATTATCAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTAT
TTCGTTCATCCATAGTTGCCTGACTCGGGGGGGGGGGCGCTGAGGTCTGCCTCGTGAAGAAGGTGTTGCT
GACTCATACCAGGCCTGAATCGCCCCATCATCCAGCCAGAAAGTGAGGGAGCCACGGTTGATGAGAGCTTT
GTTGTAGGTGGACCAGTTGGTGATTTTGAACTTTTGCTTTGCCACGGAACGGTCTGCGTTGTCGGGAAGAT
GCGTGATCTGATCCTTCAACTCAGCAAAAGTTCGATTTATTCAACAAAGCCGCCGTCCCGTCAAGTCAGCG
TAATGCTCTGCCAGTGTTACAACCAATTAACCAATTCTGATTAGAAAAACTCATCGAGCATCAAATGAAAC
TGCAATTTATTCATATCAGGATTATCAATACCATATTTTGAAAAAGCCGTTTCTGTAATGAAGGAGAAAA
CTCACCGAGGCAGTTCCATAGGATGGCAAGATCCTGGTATCGGTCTGCGATTCCGACTCGTCCAACATCAA
TACAACCTATTAATTTCCCCTCGTCAAAAATAAGGTTATCAAGTGAGAAATCACCATGAGTGACGACTGAA
TCCGGTGAGAATGGCAAAAGCTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCGAGACGAAATACGCGAT
CGCTGTTAAAAGGACAATTACAAACAGGAATCGAATGCAACCGGCGCAGGAACACTGCCAGCGCATCAACA
ATATTTTCACCTGAATCAGGATATTCTTCTAATACCTGGAATGCTGTTTCCCGGGGATCGCAGTGGTGAG
TAACCATGCATCATCAGGAGTACGGATAAAATGCTTGATGGTCGGAAGAGGCATAAATTCCGTCAGCCAGT
TTAGTCTGACCATCTCATCTGTAACATCATTGGCAACGCTACCTTTGCCATGTTTCAGAAACAACTCTGGC
GCATCGGGCTTCCCATACAATCGATAGATTGTCGCACCTGATTGCCCGACATTATCGCGAGCCCATTTATA
CCCATATAAATCAGCATCCATGTTGGAATTTAATCGCGGCCTCGAGCAAGACGTTTCCCGTTGAATATGGC
TCATAACACCCCTTGTATTACTGTTTATGTAAGCAGACAGTTTTATTGTTCATGATGATATATTTTTATCT
TGTGCAATGTAACATCAGAGATTTTGAGACACAACGTGGCTTTCCCCCCCCCCCATTATTGAAGCATTTA
TCAGGGTTATTGTCTCATGAGCGGATACATATTTGAATGTATTTAGAAAAATAAACAAATAGGGGTTCCGC
GCACATTTCCCCGAAAAGTGCCACCTGACGTCTAAGAAACCATTATTATCATGACATTAACCTATAAAAAT
AGGCGTATCACGAGGCCCTTTCGTC
```

Coding sequence
```
ATGAAGGCCATCATCGTGCTGCTGATGGTGGTGACCAGCAACGCCGATAGAATCTGCACCGGCATCACCAG
CAGCAATAGCCCCCATGTGGTGAAAACAGCCACCCAGGGCGAAGTGAATGTGACAGGCGTGATCCCTCTGA
CCACCACCCCCACCAAGAGCTACTTCGCCAACCTGAAGGGCACCAGAACCAGAGGCAAGCTGTGCCCCGAT
TGCCTGAACTGCACCGATCTGGATGTGGCTCTGGGCAGACCTATGTGTGTGGGCACCACACCATCTGCCAA
GGCCAGCATCCTGCACGAAGTGAAGCCTGTGACCAGCGGCTGCTTCCCCATCATGCACGACCGGACCAAGA
TCAGACAGCTGCCCAACCTGCTGAGAGGCTACGAGAACATCCGGCTGTCCACCCAGAATGTGATCGATGCC
GAGAAAGCCCCTGGCGGACCTTATAGACTGGGCACCAGCGGCTCTTGTCCCAATGCCACCTCCAAGAGCGG
CTTTTTTGCCACAATGGCCTGGGCCGTGCCTAAGGACAACAACAAGAACGCCACCAACCCTCTGACCGTGG
AGGTGCCCTACATCTGTACAGAGGGCGAGGATCAGATCACAGTGTGGGGCTTCCACAGCGACGACAAGACC
CAGATGAAGAACCTGTACGGCGACAGCAACCCCCAGAAGTTTACCAGCAGCGCCAATGGCGTGACCACCCA
CTACGTGTCCCAGATCGGCAGCTTTCCCGATCAGACAGAGGATGGCGGACTGCCTCAGTCTGGCAGGATCG
TGGTGGACTACATGATGCAGAAGCCTGGCAAGACCGGCACCATCGTGTATCAGAGAGGCGTGCTGCTGCCT
CAGAAAGTGTGGTGTGCCAGCGGCAGGTCTAAAGTGATCAAGGGCAGCCTGCCTCTGATTGGCGAGGCCGA
CTGTCTGCACGAAAAGTACGGCGGCCTGAACAAGAGCAAGCCCTACTACACAGGCGAGCACGCCAAGGCCA
TCGGCAATTGCCCCATCTGGGTGAAAACCCCCTGAAGCTGGCCAATGGCACCAAGTACAGACCTCCCGCC
AAGCTGCTGAAAGAGAGAGGCTTCTTTGGCGCCATTGCCGGATTTCTGGAAGGCGGCTGGGAGGGAATGAT
TGCCGGCTGGCACGGCTATACATCTCATGGGGCCCATGGCGTGGCTGTGGCCGCCGATCTGAAGTCTACCC
AGGAAGCCATCAACAAGATCACCAAGAACCTGAACAGCCTGAGCGAGCTGGAAGTGAAGAATCTGCAGAGA
CTGAGCGGCGCCATGGATGAGCTGCACAACGAGATCCTGGAACTGGACGAGAAGTGGATGATCTCCGCGC
CGATACAATTTCCTCCCAGATTGAACTGGCCGTGCTGCTGTCCAACGAGGGCATCATCAACAGCGAGGATG
AACACCTGCTGGCCCTGGAACGGAAGCTGAAGAAGATGCTGGGCCCTTCTGCCGTGGAGATCGGCAACGGC
TGCTTCGAGACAAAGCACAAGTGCAACCAGACCTGCCTGGATAGAATCGCCGCTGGCACCTTCAATGCCGG
CGAGTTCAGCCTGCCTACCTTCGACAGCCTGAATATCACCTCCGGAGGCGACATCATCAAGCTGCTGAACG
```

Fig. 31-3

```
AGCAGGTGAACAAGGAGATGCAGAGCAGCAACCTGTACATGAGCATGAGCAGCTGGTGCTACACCCACAGC
CTGGACGGCGCCGGCCTGTTCCTGTTCGACCACGCCGCCGAGGAGTACGAGCACGCCAAGAAGCTGATCAT
CTTCCTGAACGAGAACAACGTGCCCGTGCAGCTGACCAGCATCAGCGCCCCCGAGCACAAGTTCGAGGGCC
TGACCCAGATCTTCCAGAAGGCCTACGAGCACGAGCAGCACATCAGCGAGAGCATCAACAACATCGTGGAC
CACGCCATCAAGAGCAAGGACCACGCCACCTTCAACTTCCTGCAGTGGTACGTGGCCGAGCAGCACGAGGA
GGAGGTGCTGTTCAAGGACATCCTGGACAAGATCGAGCTGATCGGCAACGAGAACCACGGCCTGTACCTGG
CCGACCAGTACGTGAAGGGCATCGCCAAGAGCAGGAAGAGCGGATCC
```

Translation
```
MKAIIVLLMVVTSNADRICTGITSSNSPHVVKTATQGEVNVTGVIPLTTTPTKSYFANLKGTRTRGKLCPD
CLNCTDLDVALGRPMCVGTTPSAKASILHEVKPVTSGCFPIMHDRTKIRQLPNLLRGYENIRLSTQNVIDA
EKAPGGPYRLGTSGSCPNATSKSGFFATMAWAVPKDNNKNATNPLTVEVPYICTEGEDQITVWGFHSDDKT
QMKNLYGDSNPQKFTSSANGVTTHYVSQIGSFPDQTEDGGLPQSGRIVVDYMMQKPGKTGTIVYQRGVLLP
QKVWCASGRSKVIKGSLPLIGEADCLHEKYGGLNKSKPYYTGEHAKAIGNCPIWVKTPLKLANGTKYRPPA
KLLKERGFFGAIAGFLEGGWEGMIAGWHGYTSHGAHGVAVAADLKSTQEAINKITKNLNSLSELEVKNLQR
LSGAMDELHNEILELDEKVDDLRADTISSQIELAVLLSNEGIINSEDEHLLALERKLKKMLGPSAVEIGNG
CFETKHKCNQTCLDRIAAGTFNAGEFSLPTFDSLNITSGGDIIKLLNEQVNKEMQSSNLYMSMSSWCYTHS
LDGAGLFLFDHAAEEYEHAKKLIIFLNENNVPVQLTSISAPEHKFEGLTQIFQKAYEHEQHISESINNIVD
HAIKSKDHATFNFLQWYVAEQHEEEVLFKDILDKIELIGNENHGLYLADQYVKGIAKSRKSGS
```

Fig. 31-4

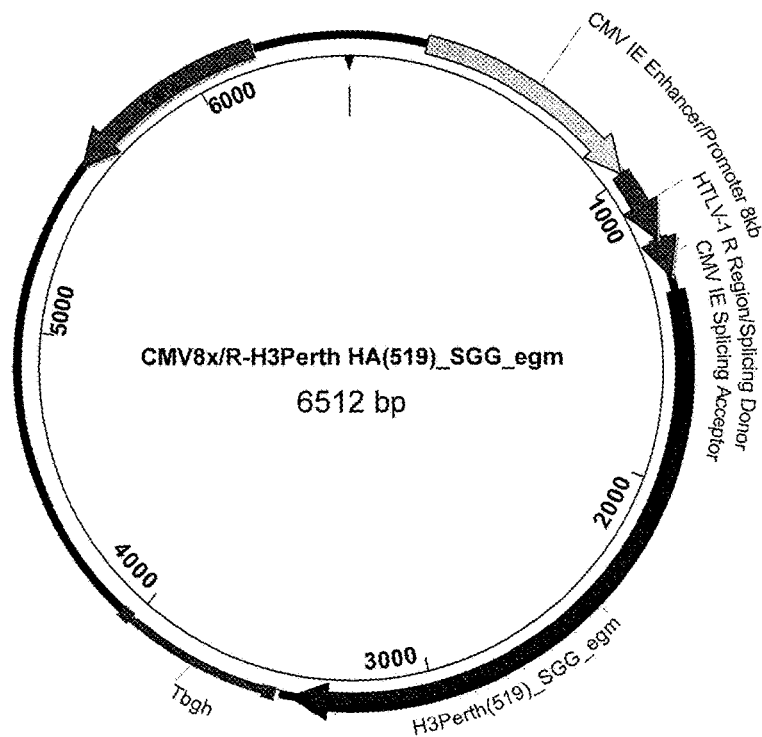
H3 Perth HA(519)_SGG_egm (H3 2009Perth HA-ferritin)

Plasmid DNA sequence

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 32-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTCTGCAGTCACCGTCGTCGACACG
TGTGATCAGATATCGCGGCCGCTCTAGAGATATCGCCACCATGAAAACCATAATTGCGCTGTCCTACATAC
TGTGTCTGGTGTTTGCCCAGAAACTGCCGGGCAATGACAACTCAACAGCCACGCTCTGCTTGGGGCACCAT
GCCGTCCCTAACGGGACCATTGTGAAAACCATTACTAACGATCAGATAGAGGTGACTAATGCCACCGAGCT
GGTGCAAAGTAGCTCCACAGGAGAGATCTGCGATAGTCCCCACCAGATTCTGGACGGAAAGAATTGTACGC
TGATCGACGCGCTGTTGGGCGACCCTCAGTGTGACGGATTTCAGAATAAGAAGTGGGATCTGTTTGTGGAA
AGGTCAAAGGCTTATTCAAATTGCTACCCTTACGATGTGCCTGATTATGCCAGCCTGCGGTCCCTCGTCGC
GTCTAGTGGGACTCTGGAGTTCAACAACGAGTCATTTAACTGGCTGGCGTTACACAGAACGGGACTAGTT
CCGCTTGCATAAGGAGAAGCAAAAATAGTTTCTTCAGCAGACTGAATTGGCTGACACATCTGAACTTCAAG
TACCCTGCACTGAATGTAACCATGCCCAACAACGAGCAGTTCGATAAGCTTTACATTTGGGGAGTTCATCA
TCCTGGCACTGACAAGGATCAGATCTTTCTGTATGCCCAGGCTTCCGGCAGGATTACCGTGTCTACAAAGA
GAAGCCAGCAAACTGTGTCTCCCAATATCGGCAGTAGACCCAGAGTACGGAACATCCCTAGTCGCATCAGT
ATTTACTGGACCATCGTGAAACCAGGCGATATTCTCCTGATTAACAGTACTGGCAACCTGATCGCCCCCG
GGGATACTTTAAAATCCGCTCTGGAAAGTCCTCCATTATGAGATCAGATGCACCGATCGGAAAATGCAACT
CTGAGTGTATCACACCCAATGGGAGCATTCCCAATGACAAACCTTTCCAGAACGTTAATCGAATAACTTAT
GGGGCCTGTCCACGGTACGTGAAGCAAAATACCTTGAAACTGGCGACCGGTATGCGCAATGTCCCCGAAAA
ACAGACCCGCGGGATATTTGGGGCTATCGCAGGCTTATCGAGAATGGCTGGGAAGGGATGGTGGATGGTT
GGTATGGTTTTAGACATCAAAACTCCGAAGGCAGAGGCCAGGCTGCCGATCTCAAGAGCACGCAGGCCGCT
ATAGATCAGATCAATGGAAAGCTCAACAGACTGATCGGGAAAACCAACGAAAAATTCCATCAGATCGAGAA
AGAGTTCTCCGAAGTCGAGGGGCGCATACAGGACCTGGAGAAGTATGTTGAGGATACAAAGATTGATCTGT
GGTCCTACAATGCCGAGCTGCTGGTGGCTCTGGAGAATCAGCACACTATTGACCTGACCGATTCAGAGATG
AACAAACTTTTTGAGAAGACGAAGAAGCAGCTTAGAGAAAATGCAGAGGACATGGGGAACGGATGCTTTAA
AATATATCATAAGTGTGATAATGCCTGCATCGGATCAATTAGAAATGGTACCTATGATCACGATGTTTACA
GGGACGAAGCGCTGAATAACAGGTTCCAGATAAAATCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACAACGTGCCCGTGCAGCTGACCAGCATCAGCGCCCCCGAGCACAAGTTCGAGGGCCTGACC
CAGATCTTCCAGAAGGCCTACGAGCACGAGCAGCACATCAGCGAGAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGGCCTGTACCTGGCCGAC
CAGTACGTGAAGGGCATCGCCAAGAGCAGGAAGAGCGGATCCTAGCATCATCATCATTAGTCTGGAAG
GGCGAATTGATCCAGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 32-2

```
TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTC
```

Coding sequence

```
ATGAAAACCATAATTGCGCTGTCCTACATACTGTGTCTGGTGTTTGCCCAGAAACTGCCGGGCAATGACAA
CTCAACAGCCACGCTCTGCTTGGGGCACCATGCCGTCCCTAACGGGACCATTGTGAAAACCATTACTAACG
ATCAGATAGAGGTGACTAATGCCACCGAGCTGGTGCAAAGTAGCTCCACAGGAGAGATCTGCGATAGTCCC
CACCAGATTCTGGACGGAAAGAATTGTACGCTGATCGACGCGCTGTTGGGCGACCCTCAGTGTGACGGATT
TCAGAATAAGAAGTGGGATCTGTTTGTGGAAAGGTCAAAGGCTTATTCAAATTGCTACCCTTACGATGTGC
CTGATTATGCCAGCCTGCGGTCCCTCGTCGCGTCTAGTGGGACTCTGGAGTTCAACAACGAGTCATTTAAC
TGGACTGGCGTTACACAGAACGGGACTAGTTCCGCTTGCATAAGGAGAAGCAAAAATAGTTTCTTCAGCAG
ACTGAATTGGCTGACACATCTGAACTTCAAGTACCCTGCACTGAATGTAACCATGCCCAACAACGAGCAGT
TCGATAAGCTTTACATTTGGGGAGTTCATCATCCTGGCACTGACAAGGATCAGATCTTTCTGTATGCCCAG
GCTTCCGGCAGGATTACCGTGTCTACAAAGAGAAGCCAGCAAACTGTGTCTCCCAATATCGGCAGTAGACC
CAGAGTACGAACATCCCTAGTCGCATCAGTATTTACTGGACCATCGTGAAACCAGGCGATATTCTCCTGA
TTAACAGTACTGGCAACCTGATCGCCCCCGGGGATACTTTAAAATCCGCTCTGGAAAGTCCTCCATTATG
AGATCAGATGCACCGATCGGAAAATGCAACTCTGAGTGTATCACACCCAATGGGAGCATTCCCAATGACAA
ACCTTTCCAGAACGTTAATCGAATAACTTATGGGGCCTGTCCACGGTACGTGAAGCAAATACCTTGAAAC
TGGCGACCGGTATGCGCAATGTCCCCGAAAAACAGACCCGCGGGATATTTGGGCTATCGCAGGCTTTATC
GAGAATGGCTGGGAAGGGATGGTGGATGGTTGGTATGGTTTTAGACATCAAAACTCCGAAGGCAGAGGCCA
GGCTGCCGATCTCAAGAGCACGCAGGCCGCTATAGATCAGATCAATGGAAAGCTCAACAGACTGATCGGA
AAACCAACGAAAAATTCCATCAGATCGAGAAAGAGTTCTCCGAAGTCGAGGGGCGCATACAGGACCTGGAG
AAGTATGTTGAGGATACAAAGATTGATCTGTGGTCCTACAATGCCGAGCTGCTGGTGGCTCTGGAGAATCA
GCACACTATTGACCTGACCGATTCAGAGATGAACAAACTTTTTGAGAAGACGAAGAAGCAGCTTAGAGAAA
ATGCAGAGGACATGGGGAACGGATGCTTTAAAATATATCATAAGTGTGATAATGCCTGCATCGGATCAATT
AGAAATGGTACCTATGATCACGATGTTTACAGGGACGAAGCGCTGAATAACAGGTTCCAGATAAAATCCGG
AGGCGACATCATCAAGCTGCTGAACAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG
```

Fig. 32-3

```
TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC
```

Translation
```
MKTIIALSYILCLVFAQKLPGNDNSTATLCLGHHAVPNGTIVKTITNDQIEVTNATELVQSSSTGEICDSP
HQILDGKNCTLIDALLGDPQCDGFQNKKWDLFVERSKAYSNCYPYDVPDYASLRSLVASSGTLEFNNESFN
WTGVTQNGTSSACIRRSKNSFFSRLNWLTHLNFKYPALNVTMPNNEQFDKLYIWGVHHPGTDKDQIFLYAQ
ASGRITVSTKRSQQTVSPNIGSRPRVRNIPSRISIYWTIVKPGDILLINSTGNLIAPRGYFKIRSGKSSIM
RSDAPIGKCNSECITPNGSIPNDKPFQNVNRITYGACPRYVKQNTLKLATGMRNVPEKQTRGIFGAIAGFI
ENGWEGMVDGWYGFRHQNSEGRGQAADLKSTQAAIDQINGKLNRLIGKTNEKFHQIEKEFSEVEGRIQDLE
KYVEDTKIDLWSYNAELLVALENQHTIDLTDSEMNKLFEKTKKQLRENAEDMGNGCFKIYHKCDNACIGSI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNPLQ
WYVAEQHEEEVLFKDILDKIELIGNENHGLYLADQYVKGIAKSRKSGS
```

Fig. 32-4

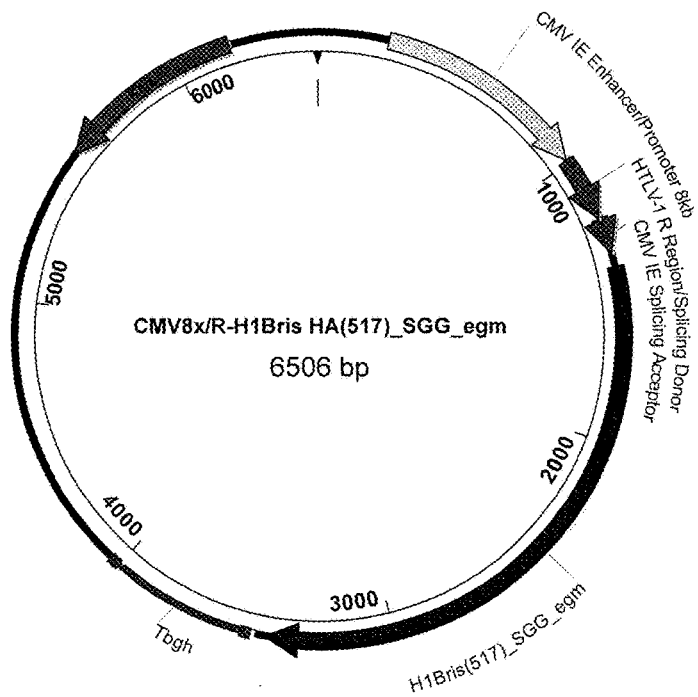
H1 Bris HA(517)_SGG_egm (H1 2007Bris HA-ferritin)

Plasmid DNA sequence

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 33-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAGTGAAGCTGCTGGTGCTGCTGTGTA
CCTTTACCGCCACCTACGCCGATACCATCTGTATCGGCTACCACGCCAACAATAGCACCGACACCGTGGAT
ACCGTGCTGGAAAAGAACGTGACCGTGACCCACAGCGTGAACCTGCTGGAAAACAGCCACAACGGCAAGCT
GTGTCTGCTGAAAGGCATTGCCCCTCTGCAGCTGGGAAATTGTAGCGTGGCCGGCTGGATTCTGGGCAATC
CTGAGTGCGAGCTGCTGATTTCCAAAGAGTCCTGGTCCTACATCGTGGAGAAGCCCAACCCTGAGAATGGC
ACCTGCTACCCTGGCCACTTCGCCGATTACGAGGAACTGAGAGAACAGCTGTCCAGCGTGTCCAGCTTCGA
GAGATTCGAGATCTTCCCCAAAGAGAGCAGCTGGCCCAATCATACAGTGACCGGCGTGAGCGCCTCTTGTA
GCCACAATGGCGAGAGCAGCTTCTACAGAAACCTGCTGTGGCTGACCGGCAAGAACGGCCTGTACCCCAAC
CTGAGCAAGAGCTACGCCAACAACAAAGAAAAAGAAGTGCTGGTCCTCTGGGGAGTGCACCACCCTCCTAA
CATCGGCATCCAGAAGGCCCTGTACCACACCGAGAATGCCTACGTGTCCGTGGTGTCCAGCCACTACAGCA
GAAAGTTCACCCCCGAGATCGCCAAAAGACCCAAAGTGCGGGACCAGGAAGGCAGGATCAACTACTACTGG
ACCCTGCTGGAACCTGGCGACACCATCATCTTCGAGGCCAACGGCAATCTGATCGCCCCTAGATACGCCTT
TGCCCTGAGCAGAGGCTTTGGCAGCGGCATCATCAACAGCAACGCCCCCATGGACAAGTGTGACGCCAAGT
GTCAGACACCACAGGGAGCTATCAATAGCAGCCTGCCCTTCCAGAATGTGCACCCTGTGACCATCGGCGAG
TGTCCTAAATACGTGCGGAGCGCCAAGCTGAGAATGGTGACCGGCCTGAGGAATATCCCCAGCATCCAGAG
CAGAGGCCTGTTTGGCGCCATTGCCGGCTTTATCGAGGGCGGATGGACAGGCATGGTGGATGGGTGGTACG
GCTACCACCACCAGAATGAGCAGGGATCTGGCTATGCCGCCGATCAGAAGAGCACCCAGAACGCCATCAAC
GGCATCACCAACAAAGTGAACAGCGTGATCGAGAAGATGAACACCCAGTTCACCGCCGTGGGCAAAGAGTT
CAACAAGCTGGAACGGCGGATGGAAAACCTGAACAAGAAGGTGGACGACGGCTTCATCGACATCTGGACCT
ACAACGCCGAACTCCTGGTCCTCCTGGAAAATGAGAGGACCCTGGACTTCCACGACAGCAACGTGAAGAAC
CTGTACGAGAAAGTGAAGAGCCAGCTGAAGAACAACGCCAAAGAGATCGGCAACGGCTGCTTCGAGTTCTA
CCACAAGTGCAACGACGAGTGCATGGAAAGCGTGAAGAACGGCACCTACGACTACCCCAAGTACAGCGAGG
AAAGCAAGCTGAACCGGGAGAAGATCGATTCCGGAGGCGACATCATCAAGCTGCTGAACGAGCAGGTGAAC
AAGGAGATGCAGAGCAGCAACCTGTACATGAGCATGAGCAGCTGGTGCTACACCCACAGCCTGGACGGCGC
CGGCCTGTTCCTGTTCGACCACGCCGCCGAGGAGTACGAGCACGCCAAGAAGCTGATCATCTTCCTGAACG
AGAACAACGTGCCCGTGCAGCTGACCAGCATCAGCGCCCCCGAGCACAAGTTCGAGGGCCTGACCCAGATC
TTCCAGAAGGCCTACGAGCACGAGCAGCACATCAGCGAAGGCATCAACAATCGTGAACCACGCCATCAA
GAGCAAGGACCACGCCACCTTCAACTTCCTGCAGTGGTACGTGGCCGAGCAGCACGAGGAGGAGGTGCTGT
TCAAGGACATCCTGGACAAGATCGAGCTGATCGGCAACGAGAACCACGGCCTGTACCTGGCCGACCAGTAC
GTGAAGGGCATCGCCAAGAGCAGGAAGAGCGGATCCTAGCATCATCATCATCATTAGTCTGGAAGGGCGAA
TTGATCCAGATCTGCTGTGCCTTCTAGTTGCCAGCCATCTGTTGTTTGCCCCTCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCTGGGCCAGAA
AGAAGCAGGCACATCCCCTTCTCTGTGACACACCCTGTCCACGCCCCTGGTTCTTAGTTCCAGCCCCACTC
ATAGGACACTCATAGCTCAGGAGGGCTCCGCCTTCAATCCCACCCGCTAAAGTACTTGGAGCGGTCTCTCC
CTCCCTCATCAGCCCACCAAACCAAACCTAGCCTCCAAGAGTGGGAAGAAATTAAAGCAAGATAGGCTATT
AAGTGCAGAGGGAGAGAAAATGCCTCCAACATGTGAGGAAGTAATGAGAGAAATCATAGAATTTTAAGGCC
ATGATTTAAGGCCATCATGGCCTTAATCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCC
```

Fig. 33-2

```
TTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCGGGGGGGGGGCGCTGAGGTCTGC
CTCGTGAAGAAGGTGTTGCTGACTCATACCAGGCCTGAATCGCCCCATCATCCAGCCAGAAAGTGAGGGAG
CCACGGTTGATGAGAGCTTTGTTGTAGGTGGACCAGTTGGTGATTTTGAACTTTTGCTTTGCCACGGAACG
GTCTGCGTTGTCGGGAAGATGCGTGATCTGATCCTTCAACTCAGCAAAAGTTCGATTTATTCAACAAAGCC
GCCGTCCCGTCAAGTCAGCGTAATGCTCTGCCAGTGTTACAACCAATTAACCAATTCTGATTAGAAAAACT
CATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGAT
TCCGACTCGTCCAACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCAGACTTGTTCAACA
GGCCAGCCATTACGCTCGTCATCAAAATCACTCGCATCAACCAAACCGTTATTCATTCGTGATTGCCCTG
AGCGAGACGAAATACGCGATCGCTGTTAAAAGGACAATTACAAACAGGAATCGAATGCAACCGGCGCAGGA
ACACTGCCAGCGCATCAACAATATTTTCACCTGAATCAGGATATTCTTCTAATACCTGGAATGCTGTTTTC
CCGGGGATCGCAGTGGTGAGTAACCATGCATCATCAGGAGTACGGATAAAATGCTTGATGGTCGGAAGAGG
CATAAATTCCGTCAGCCAGTTTAGTCTGACCATCTCATCTGTAACATCATTGGCAACGCTACCTTTGCCAT
GTTTCAGAAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCGAGCAAGA
CGTTTCCCGTTGAATATGGCTCATAACACCCCTTGTATTACTGTTTATGTAAGCAGACAGTTTTATTGTTC
ATGATGATATATTTTTATCTTGTGCAATGTAACATCAGAGATTTTGAGACACAACGTGGCTTTCCCCCCCC
CCCCATTATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAACCATTATTATCA
TGACATTAACCTATAAAAATAGGCGTATCACGAGGCCCTTTCGTC

Coding sequence
ATGAAAGTGAAGCTGCTGGTGCTGCTGTGTACCTTTACCGCCACCTACGCCGATACCATCTGTATCGGCTA
CCACGCCAACAATAGCACCGACACCGTGGATACCGTGCTGGAAAAGAACGTGACCGTGACCCACAGCGTGA
ACCTGCTGGAAAACAGCCACAACGGCAAGCTGTGTCTGCTGAAAGGCATTGCCCCTCTGCAGCTGGGAAAT
TGTAGCGTGGCCGGCTGGATTCTGGGCAATCCTGAGTGCGAGCTGCTGATTTCCAAAGAGTCCTGGTCCTA
CATCGTGGAGAAGCCCAACCCTGAGAATGGCACCTGCTACCCTGGCCACTTCGCCGATTACGAGGAACTGA
GAGAACAGCTGTCCAGCGTGTCCAGCTTCGAGAGATTCCCCAAAGAGAGCAGCTGGCCCAAT
CATACAGTGACCGGCGTGAGCGCCTCTTGTAGCCACAATGGCGAGAGCAGCTTCTACAGAAACCTGCTGTG
GCTGACCGGCAAGAACGGCCTGTACCCCAACCTGAGCAAGAGCTACGCCAACAACAAAGAAAAAGAAGTGC
TGGTCCTCTGGGAGTGCACCACCCTCCTAACATCGGCATCCAGAAGGCCCTGTACCACACCGAGAATGCC
TACGTGTCCGTGGTGTCCAGCCACTACAGCAGAAAGTTCACCCCCGAGATCGCCAAAAGACCCAAAGTGCG
GGACCAGGAAGGCAGGATCAACTACTACTGGACCCTGCTGGAACCTGGCGACACCATCATCTTCGAGGCCA
ACGGCAATCTGATCGCCCCTAGATACGCCTTTGCCCTGAGCAGAGGCTTTGGCAGCGGCATCATCAACAGC
AACGCCCCCATGGACAAGTGTGACGCCAAGTGTCAGACACCACAGGGAGCTATCAATAGCAGCCTGCCCTT
CCAGAATGTGCACCCTGTGACCATCGGCGAGTGTCCTAAATACGTGCGGAGCGCCAAGCTGAGAATGGTGA
CCGGCCTGAGGAATATCCCCAGCATCCAGAGCAGAGGCCTGTTTGGCGCCATTGCCGGCTTTATCGAGGGC
GGATGGACAGGCATGGTGGATGGGTGGTACGGCTACCACCACCAGAATGAGCAGGGATCTGGCTATGCCGC
CGATCAGAAGAGCACCCAGAACGCCATCAACGGCATCACCAACAAAGTGAACAGCGTGATCGAGAAGATGA
ACACCCAGTTCACCGCCGTGGGCAAAGAGTTCAACAAGCTGGAACGGCGGATGGAAAACCTGAACAAGAAG
GTGGACGACGGCTTCATCGACATCTGGACCTACAACGCCGAACTCCTGGTCCTCCTGGAAAATGAGAGGAC
CCTGGACTTCCACGACAGCAACGTGAAGAACCTGTACGAGAAAGTGAAGAGCCAGCTGAAGAACAACGCCA
AAGAGATCGGCAACGGCTGCTTCGAGTTCTACCACAAGTGCAACGACGAGTGCATGGAAAGCGTGAAGAAC
GGCACCTACGACTACCCCAAGTACAGCGAGGAAAGCAAGCTGAACCGGGAGAAGATCGATTCCGGAGGCGA
CATCATCAAGCTGCTGAACGAGCAGGTAACAAGGAGATGCAGAGCAGCAACCTGTACATGAGCATGAGCA
GCTGGTGCTACACCCACAGCCTGGACGGCGCCGGCCTGTTCCTGTTCGACCACGCCGCCGAGGAGTACGAG
```

Fig. 33-3

```
CACGCCAAGAAGCTGATCATCTTCCTGAACGAGAACAACGTGCCCGTGCAGCTGACCAGCATCAGCGCCCC
CGAGCACAAGTTCGAGGGCCTGACCCAGATCTTCCAGAAGGCCTACGAGCACGAGCAGCACATCAGCGAGA
GCATCAACAACATCGTGGACCACGCCATCAAGAGCAAGGACCACGCCACCTTCAACTTCCTGCAGTGGTAC
GTGGCCGAGCAGCACGAGGAGGAGGTGCTGTTCAAGGACATCCTGGACAAGATCGAGCTGATCGGCAACGA
GAACCACGGCCTGTACCTGGCCGACCAGTACGTGAAGGGCATCGCCAAGAGCAGGAAGAGCGGATCC
```

Translation
```
MKVKLLVLLCTFTATYADTICIGYHANNSTDTVDTVLEKNVTVTHSVNLLENSHNGKLCLLKGIAPLQLGN
CSVAGWILGNPECELLISKESWSYIVEKPNPENGTCYPGHFADYEELREQLSSVSSFERFEIFPKESSWPN
HTVTGVSASCSHNGESSFYRNLLWLTGKNGLYPNLSKSYANNKEKEVLVLWGVHHPPNIGIQKALYHTENA
YVSVVSSHYSRKFTPEIAKRPKVRDQEGRINYYWTLLEPGDTIIFEANGNLIAPRYAFALSRGFGSGIINS
NAPMDKCDAKCQTPQGAINSSLPFQNVHPVTIGECPKYVRSAKLRMVTGLRNIPSIQSRGLFGAIAGFIEG
GWTGMVDGWYGYHHQNEQGSGYAADQKSTQNAINGITNKVNSVIEKMNTQFTAVGKEFNKLERRMENLNKK
VDDGFIDIWTYNAELLVLLENERTLDFHDSNVKNLYEKVKSQLKNNAKEIGNGCFEFYHKCNDECMESVKN
GTYDYPKYSEESKLNREKIDSGGDIIKLLNEQVNKEMQSSNLYMSMSSWCYTHSLDGAGLFLFDHAAEEYE
HAKKLIIFLNENNVPVQLTSISAPEHKFEGLTQIFQKAYEHEQHISESINNIVDHAIKSKDHATFNFLQWY
VAEQHEEEVLFKDILDKIELIGNENHGLYLADQYVKGIAKSRKSGS
```

Fig. 33-4

B Bris HA(535)_SGG_egm (B 2008Bris HA-ferritin)

Plasmid DNA sequence
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 34-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTCGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCATCGTGCTGCTGATGGTGG
TCACAAGCAACGCCGATAGAATCTGTACCGGCATCACCAGCAGCAATAGCCCTCACGTCGTGAAAACAGCT
ACACAGGGCGAAGTGAATGTGACCGGCGTGATCCCTCTGACCACAACACCTACAAAGAGCCACTTCGCCAA
TCTGAAGGGCACAGAGACAAGAGGCAAGCTGTGTCCCAAGTGCCTGAATTGCACAGATCTGGATGTGGCTC
TGGGCAGACCTAAGTGTACAGGCAAAATCCCTAGCGCCAGAGTGTCCATTCTGCATGAAGTGCGACCTGTG
ACCAGCGGCTGTTTTCCTATTATGCACGACCGGACCAAGATCAGACAGCTGCCTAATCTGCTGAGAGGCTA
CGAGCACATCAGACTGAGCACCCACAATGTGATCAACGCCGAAAATGCTCCTGGCGGCCCTTATAAGATCG
GCACATCTGGCAGCTGCCCCAACATTACAAATGGCAATGGCTTCTTTGCCACCATGGCTTGGGCCGTGCCT
AAGAACGATAAGAACAAGACCGCCACCAACCCCCTGACAATCGAGGTGCCATATATCTGTACAGAGGGCGA
GGATCAGATCACCGTGTGGGGATTTCACAGCGACAACGAAACACAGATGGCCAAGCTGTACGGCGATAGCA
AGCCTCAGAAGTTTACCAGCTCTGCCAATGGCGTGACCACACACTATGTGTCTCAGATCGGCGGCTTCCCT
AATCAGACAGAAGATGGCGGACTGCCTCAGTCTGGAAGAATCGTGGTGGATTACATGGTGCAGAAGTCTGG
CAAGACCGGCACCATCACATATCAGAGAGGAATCCTGCTGCCCCAGAAAGTGTGGTGCGCTTCTGGAAGAT
CCAAAGTGATCAAGGGCAGCCTGCCTCTGATTGGAGAAGCCGATTGTCTGCACGAGAAATACGGCGGCCTG
AACAAGAGCAAGCCTTACTATACAGGCGAGCACGCCAAGGCCATCGGCAATTGTCCTATTTGGGTCAAGAC
CCCTCTGAAGCTGGCCAATGGCACAAAGTATAGACCTCCAGCCAAGCTGCTGAAAGAGAGAGGCTTTTTTG
GAGCTATCGCCGGCTTTCTGGAAGGCGGATGGGAGGGAATGATTGCTGGATGGCATGGCTACACATCTCAT
GGCGCACATGGCGTGGCAGTGGCTGCTGATCTGAAATCTACACAGGAAGCCATCAACAAGATCACCAAGAA
CCTGAACAGCCTGAGCGAGCTGGAAGTGAAGAATCTGCAGAGACTGTCTGGCGCCATGGACGAACTGCACA
ATGAGATCCTGGAACTGGACGAGAAGGTGGACGATCTGAGAGCCGATACAATCAGCAGCCAGATTGAACTG
GCTGTGCTGCTGTCTAACGAGGGCATCATCAATAGCGAAGACGAACATCTGCTGGCCCTGGAAAGAAAGCT
GAAGAAGATGCTGGGACCTAGCGCCGTGGAAATCGGCAATGATGCTTTGAGACAAAGCACAAGTGCAACC
AGACCTGCCTGGATAGAATTGCCGCCGGAACATTTGATGCCGGCGAGTTTTCTCTGCCCACCTTCGATAGC
CTGAATATCACATCCGGAGGCGACATCATCAAGCTGCTGAACGAGCAGGTGAACAAGGAGATGCAGAGCAG
CAACCTGTACATGAGCATGAGCAGCTGGTGCTACACCCACAGCCTGGACGGCGCCGGCCTGTTCCTGTTCG
ACCACGCCGCCGAGGAGTACGAGCACGCCAAGAAGCTGATCATCTTCCTGAACGAGAACAACGTGCCCGTG
CAGCTGACCAGCATCAGCGCCCCCGAGCACAAGTTCGAGGGCCTGACCCAGATCTTCCAGAAGGCCTACGA
GCACGAGCAGCACATCAGCGAGAGCATCAACAACATCGTGGACCACGCCATCAAGAGCAAGGACCACGCCA
CCTTCAACTTCCTGCAGTGGTACGTGGCCGAGCAGCACGAGGAGGAGGTGCTGTTCAAGGACATCCTGGAC
AAGATCGAGCTGATCGGCAACGAGAACCACGGCCTGTACCTGGCCGACCAGTACGTGAAGGGCATCGCCAA
GAGCAGGAAGAGCGGATCCTAGCATCATCATCATCATTAGTCTGGAAGGGCAATTGATCCAGATCTGCTG
TGCCTTCTAGTTGCCAGCCATCTGTTGTTTGCCCCTCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGGG
GGGTGGGGTGGGGCAGGACAGCAAGGGGGAGGATTGGGAAGACAATAGCAGGCATGCTGGGGATGCGGTGG
GCTCTATGGGTACCCAGGTGCTGAAGAATTGACCCGGTTCCTCCTGGGCCAGAAAGAAGCAGGCACATCCC
CTTCTCTGTGACACACCCTGTCCACGCCCCTGGTTCTTAGTTCCAGCCCCACTCATAGGACACTCATAGCT
CAGGAGGGCTCCGCCTTCAATCCCACCCGCTAAAGTACTTGGAGCGGTCTCTCCCTCCCTCATCAGCCCAC
CAAACCAAACCTAGCCTCCAAGAGTGGGAAGAAATTAAAGCAAGATAGGCTATTAAGTGCAGAGGGAGAGA
AAATGCCTCCAACATGTGAGGAAGTAATGAGAGAAATCATAGAATTTTAAGGCCATGATTTAAGGCCATCA
TGGCCTTAATCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTCCGCCCCCCT
GACGAGCATCACAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGGTCGTT
```

Fig. 34-2

CGCTCCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTAGAAGAACAGTA
TTTGGTATCTGCGCTCTGCTGAAGCCAGTTACCTTCGGAAAAGAGTTGGTAGCTCTTGATCCGGCAAACA
AACCACCGCTGGTAGCGGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGCGATCTGTC
TATTTCGTTCATCCATAGTTGCCTGACTCGGGGGGGGGGGCGCTGAGGTCTGCCTCGTGAAGAAGGTGTT
GCTGACTCATACCAGGCCTGAATCGCCCCATCATCCAGCCAGAAAGTGAGGGAGCCACGGTTGATGAGAGC
TTTGTTGTAGGTGGACCAGTTGGTGATTTTGAACTTTTGCTTTGCCACGGAACGGTCTGCGTTGTCGGGAA
GATGCGTGATCTGATCCTTCAACTCAGCAAAAGTTCGATTTATTCAACAAAGCCGCCGTCCCGTCAAGTCA
GCGTAATGCTCTGCCAGTGTTACAACCAATTAACCAATTCTGATTAGAAAAACTCATCGAGCATCAAATGA
AACTGCAATTTATTCATATCAGGATTATCAATACCATATTTTTGAAAAAGCCGTTTCTGTAATGAAGGAGA
AAACTCACCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGTGACGACT
GAATCCGGTGAGAATGGCAAAAGCTTATGCATTTCTTTCCAGACTTGTTCAACAGGCCAGCCATTACGCTC
GTCATCAAAATCACTCGCATCAACCAAACCGTTATTCATTCGTGATTGCGCCTGAGCGAGACGAAATACGC
GATCGCTGTTAAAGGACAATTACAAACAGGAATCGAATGCAACCGGCGCAGGAACACTGCCAGCGCATCA
ACAATATTTTCACCTGAATCAGGATATTCTTCTAATACCTGGAATGCTGTTTTCCCGGGGATCGCAGTGGT
GAGTAACCATGCATCATCAGGAGTACGGATAAAATGCTTGATGGTCGGAAGAGGCATAAATTCCGTCAGCC
AGTTTAGTCTGACCATCTCATCTGTAACATCATTGGCAACGCTACCTTTGCCATGTTTCAGAAACAACTCT
GGCGCATCGGGCTTCCCATACAATCGATAGATTGTCGCACCTGATTGCCCGACATTATCGCGAGCCCATTT
ATACCCATATAAATCAGCATCCATGTTGGAATTTAATCGCGGCCTCGAGCAAGACGTTTCCCGTTGAATAT
GGCTCATAACACCCCTTGTATTACTGTTTATGTAAGCAGACAGTTTTATTGTTCATGATGATATATTTTTA
TCTTGTGCAATGTAACATCAGAGATTTTGAGACACAACGTGGCTTTCCCCCCCCCCCCATTATTGAAGCAT
TTATCAGGGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACCATTATTATCATGACATTAACCTATAAA
AATAGGCGTATCACGAGGCCCTTTCGTC

<u>Coding sequence</u>
ATGAAGGCCATCATCGTGCTGCTGATGGTGGTCACAAGCAACGCCGATAGAATCTGTACCGGCATCACCAG
CAGCAATAGCCCTCACGTCGTGAAAACAGCTACACAGGGCGAAGTGAATGTGACCGGCGTGATCCCTCTGA
CCACAACACCTACAAAGAGCCACTTCGCCAATCTGAAGGGCACAGAGACAAGAGGCAAGCTGTGTCCCAAG
TGCCTGAATTGCACAGATCTGGATGTGGCTCTGGGCAGACCTAAGTGTACAGGCAAAATCCCTAGCGCCAG
AGTGTCCATTCTGCATGAAGTGCGACCTGTGACCAGCGGCTGTTTTCCTATTATGCACGACCGGACCAAGA
TCAGACAGCTGCCTAATCTGCTGAGAGGCTACGAGCACATCAGACTGAGCACCCACAATGTGATCAACGCC
GAAAATGCTCCTGGCGGCCCTTATAAGATCGGCACATCTGGCAGCTGCCCCAACATTACAAATGGCAATGG
CTTCTTTGCCACCATGGCTTGGGCCGTGCCTAAGAACGATAAGAACAAGACCGCCACCAACCCCCTGACAA
TCGAGGTGCCATATATCTGTACAGAGGGCGAGGATCAGATCACCGTGTGGGATTTCACAGCGACAACGAA
ACACAGATGGCCAAGCTGTACGGCGATAGCAAGCCTCAGAAGTTTACCAGCTCTGCCAATGGCGTGACCAC
ACACTATGTGTCTCAGATCGGCGGCTTCCCTAATCAGACAGAAGATGGCGGACTGCCTCAGTCTGGAAGAA
TCGTGGTGGATTACATGGTGCAGAAGTCTGGCAAGACCGGCACCATCACATATCAGAGAGGAATCCTGCTG
CCCCAGAAAGTGGTGCGCTTCTGGAAGATCCAAAGTGATCAAGGGCAGCAGCCTGCCTCTGATTGGAGAGC
CGATTGTCTGCACGAGAAATACGCGGCCTGAACAAGAGCAAGCCTTACTATACAGGCGAGCACGCCAAGG
CCATCGGCAATTGTCCTATTTGGGTCAAGACCCCTCTGAAGCTGGCCAATGGCACAAAGTATAGACCTCCA
GCCAAGCTGCTGAAAGAGAGGCTTTTTTGGAGCTATCGCCGGCTTTCTGGAAGGCGGATGGGAGGGAAT
GATTGCTGGATGGCATGGCTACACATCTCATGGCGCACATGGCGTGGCAGTGGCTGCTGATCTGAAATCTA
CACAGGAAGCCATCAACAAGATCACCAAGAACCTGAACAGCCTGAGCGAGCTGGAAGTGAAGAATCTGCAG
AGACTGTCTGGCGCCATGGACGAACTGCACAATGAGATCCTGGAACTGGACGAGAAGGTGGACGATCTGAG
AGCCGATACAATCAGCAGCCAGATTGAACTGGCTGTGCTGCTGTCTAACGAGGGCATCATCAATAGCGAGG
ACGAACATCTGCTGGCCCTGGAAAGAAAGCTGAAGAAGATGCTGGGACCTAGCGCCGTGGAAATCGGCAAT
GGATGCTTTGAGACAAAGCACAAGTGCAACCAGACCTGCCTGGATAGAATTGCCGCCGGAACATTTGATGC
CGGCGAGTTTTCTCTGCCCACCTTCGATAGCCTGAATATCACATCCGGAGGCGACATCATCAAGCTGCTGA

Fig. 34-3

```
ACGAGCAGGTGAACAAGGAGATGCAGAGCAGCAACCTGTACATGAGCATGAGCAGCTGGTGCTACACCCAC
AGCCTGGACGGCGCCGGCCTGTTCCTGTTCGACCACGCCGCCGAGGAGTACGAGCACGCCAAGAAGCTGAT
CATCTTCCTGAACGAGAACAACGTGCCCGTGCAGCTGACCAGCATCAGCGCCCCCGAGCACAAGTTCGAGG
GCCTGACCCAGATCTTCCAGAAGGCCTACGAGCACGAGCAGCACATCAGCGAGAGCATCAACAACATCGTG
GACCACGCCATCAAGAGCAAGGACCACGCCACCTTCAACTTCCTGCAGTGGTACGTGGCCGAGCAGCACGA
GGAGGAGGTGCTGTTCAAGGACATCCTGGACAAGATCGAGCTGATCGGCAACGAGAACCACGGCCTGTACC
TGGCCGACCAGTACGTGAAGGGCATCGCCAAGAGCAGGAAGAGCGGATCC
```

Translation
```
MKAIIVLLMVVTSNADRICTGITSSNSPHVVKTATQGEVNVTGVIPLTTTPTKSHFANLKGTETRGKLCPK
CLNCTDLDVALGRPKCTGKIPSARVSILHEVRPVTSGCFPIMHDRTKIRQLPNLLRGYEHIRLSTHNVINA
ENAPGGPYKIGTSGSCPNITNGNGFFATMAWAVPKNDKNKTATNPLTIEVPYICTEGEDQITVWGFHSDNE
TQMAKLYGDSKPQKFTSSANGVTTHYVSQIGGFPNQTEDGGLPQSGRIVVDYMVQKSGKTGTITYQRGILL
PQKVWCASGRSKVIKGSLPLIGEADCLHEKYGGLNKSKPYYTGEHAKAIGNCPIWVKTPLKLANGTKYRPP
AKLLKERGFFGAIAGFLEGGWEGMIAGWHGYTSHGAHGVAVAADLKSTQEAINKITKNLNSLSELEVKNLQ
RLSGAMDELHNEILELDEKVDDLRADTISSQIELAVLLSNEGIINSEDEHLLALERKLKKMLGPSAVEIGN
GCFETKHKCNQTCLDRIAAGTFDAGEFSLPTFDSLNITSGGDIIKLLNEQVNKEMQSSNLYMSMSSWCYTH
SLDGAGLFLFDHAAEEYEHAKKLIIFLNENNVPVQLTSISAPEHKFEGLTQIFQKAYEHEQHISESINNIV
DHAIKSKDHATFNFLQWYVAEQHEEEVLFKDILDKIELIGNENHGLYADQYVKGIAKSRKSGS
```

Fig. 34-4

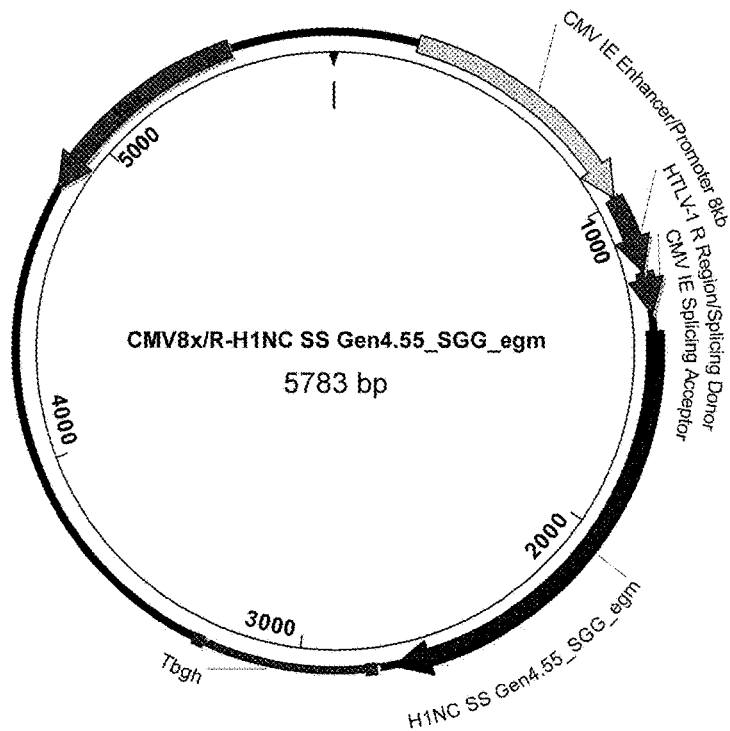

H1 NC Stabilized Stem Gen4.55_SGG_egm (H1 1999NC SS Gen4.55-ferritin)

Plasmid DNA sequence
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 35-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCAAGCTGCTGGTGCTGCTGTGCA
CCTTTACCGCCACCTACGCCGACACCATCTGCATTGGCTACCACGCCAACAACAGCACCGACACCGTGGAT
ACCGTGCTGGAAAAGAACGTGACCGTGACCCACAGCGTGAACCTGGGATCCGGACTGAGAATGGTCACCGG
CCTGAGAAACATCCCCAGCATCCAGAGCAGAGGCCTGTTTGGAGCCATTGCCGGCTTTATTGAGGGCGGAT
GGACCGGAATGGTGGATGGGTGGTACGGCTACCACCACCAGAATGAGCAGGGCTCTGGCTATGCCGCCGAT
CAGAAGTCTACCCAGAACGCCATCAACGGCATCACCAACAAAGTGAACAGCGTGATCGAGAAGATGGGCGG
CGATCCTGAATGGGACAGAGAGATCAACAACTACACCAGCATCATCTACAGCCTGATCGAGGAAAGCCAGA
ACCAGCAGGAAAACGGCACAGGCGGCGGATCTGGAATTGTGCAGCAGCAGAACAACCTGCTGAGAGCCATT
GAGGCCCAGCAGCATCTGCTGCAGCTGACAGTGTGGGGCATCAAGCAGCTGCAGACCTACAATGCCGAGCT
GCTGGTCCTCCTGGAAAACGAGAGAACCCTGGACTTCCACGACAGCAACGTGAAGAACCTGTACGAGAAAG
TGAAGTCCCAGCTGAAGAACAACGCCAAAGAGATCGGCAACGGCTGCTTCGAGTTCTACCACAAGTGCAAC
AACGAGTGCATGGAAAGCGTGAAGAACGGCACCTACGACTACCCCAAGTACAGCGAGGAAAGCAAGCTGAA
CAGAGAGAAGATCGACTCCGGAGGCGACATCATCAAGCTGCTGAACGAGCAGGTGAACAAGGAGATGCAGA
GCAGCAACCTGTACATGAGCATGAGCAGCTGGTGCTACACCCACAGCCTGGACGGCGCCGGCCTGTTCCTG
TTCGACCACGCCGCCGAGGAGTACGAGCACGCCAAGAAGCTGATCATCTTCCTGAACGAGAACAACGTGCC
CGTGCAGCTGACCAGCATCAGCGCCCCCGAGCACAAGTTCGAGGGCCTGACCCAGATCTTCCAGAAGGCCT
ACGAGCACGAGCAGCACATCAGCGAGAGCATCAACAACATCGTGGACCACGCCATCAAGAGCAAGGACCAC
GCCACCTTCAACTTCCTGCAGTGGTACGTGGCCGAGCAGCACGAGGAGGAGGTGCTGTTCAAGGACATCCT
GGACAAGATCGAGCTGATCGGCAACGAGAACCACGGCCTGTACCTGGCCGACCAGTACGTGAAGGGCATCG
CCAAGAGCAGGAAGAGCGGATCCTAGCATCATCATCATCATTAGTCTGGAAGGGCGAATTGATCCAGATCT
GCTGTGCCTTCTAGTTGCCAGCCATCTGTTGTTTGCCCCTCCCCGTGCCTTCCTTGACCCTGGAAGGTGC
CACTCCCACTGTCCTTTCCTAATAAAATGAGGAAATTGCATCGCATTGTCTGAGTAGGTGTCATTCTATTC
TGGGGGGTGGGGTGGGCAGGACAGCAAGGGGGAGGATTGGGAAGACAATAGCAGGCATGCTGGGGATGCG
GTGGGCTCTATGGGTACCCAGGTGCTGAAGAATTGACCCGGTTCCTCCTGGGCCAGAAAGAAGCAGGCACA
TCCCCTTCTCTGTGACACACCCTGTCCACGCCCCTGGTTCTTAGTTCCAGCCCCACTCATAGGACACTCAT
AGCTCAGGAGGGCTCCGCCTTCAATCCCACCCGCTAAAGTACTTGGAGCGGTCTCTCCCTCCCTCATCAGC
CCACCAAACCAAACCTAGCCTCCAAGAGTGGGAAGAAATTAAAGCAAGATAGGCTATTAAGTGCAGAGGGA
GAGAAAATGCCTCCAACATGTGAGGAAGTAATGAGAGAAATCATAGAATTTTAAGGCCATGATTTAAGGCC
ATCATGGCCTTAATCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATC
TGTCTATTTCGTTCATCCATAGTTGCCTGACTCGGGGGGGGGGGCGCTGAGGTCTGCCTCGTGAAGAAGG
TGTTGCTGACTCATACCAGGCCTGAATCGCCCCATCATCCAGCCAGAAAGTGAGGGAGCCACGGTTGATGA
GAGCTTTGTTGTAGGTGGACCAGTTGGTGATTTTGAACTTTTGCTTTGCCACGGAACGGTCTGCGTTGTCG
```

Fig. 35-2

```
GGAAGATGCGTGATCTGATCCTTCAACTCAGCAAAAGTTCGATTTATTCAACAAAGCCGCCGTCCCGTCAA
GTCAGCGTAATGCTCTGCCAGTGTTACAACCAATTAACCAATTCTGATTAGAAAAACTCATCGAGCATCAA
ATGAAACTGCAATTTATTCATATCAGGATTATCAATACCATATTTTTGAAAAAGCCGTTTCTGTAATGAAG
GAGAAAACTCACCGAGGCAGTTCCATAGGATGGCAAGATCCTGGTATCGGTCTGCGATTCCGACTCGTCCA
ACATCAATACAACCTATTAATTTCCCCTCGTCAAAAATAAGGTTATCAAGTGAGAAATCACCATGAGTGAC
GACTGAATCCGGTGAGAATGGCAAAAGCTTATGCATTTCTTTCCAGACTTGTTCAACAGGCCAGCCATTAC
GCTCGTCATCAAAATCACTCGCATCAACCAAACCGTTATTCATTCGTGATTGCGCCTGAGCGAGACGAAAT
ACGCGATCGCTGTTAAAAGGACAATTACAAACAGGAATCGAATGCAACCGGCGCAGGAACACTGCCAGCGC
ATCAACAATATTTTCACCTGAATCAGGATATTCTTCTAATACCTGGAATGCTGTTTTCCCGGGGATCGCAG
TGGTGAGTAACCATGCATCATCAGGAGTACGGATAAAATGCTTGATGGTCGGAAGAGGCATAAATTCCGTC
AGCCAGTTTAGTCTGACCATCTCATCTGTAACATCATTGGCAACGCTACCTTTGCCATGTTTCAGAAACAA
CTCTGGCGCATCGGGCTTCCCATACAATCGATAGATTGTCGCACCTGATTGCCCGACATTATCGCGAGCCC
ATTTATACCCATATAAATCAGCATCCATGTTGGAATTTAATCGCGGCCTCGAGCAAGACGTTTCCCGTTGA
ATATGGCTCATAACACCCCTTGTATTACTGTTTATGTAAGCAGACAGTTTTATTGTTCATGATGATATATT
TTTATCTTGTGCAATGTAACATCAGAGATTTTGAGACACAACGTGGCTTTCCCCCCCCCCCCATTATTGAA
GCATTTATCAGGGTTATTGTCTCATGAGCGGATACATATTTGAATGTATTTAGAAAAATAAACAAATAGGG
GTTCCGCGCACATTTCCCCGAAAAGTGCCACCTGACGTCTAAGAAACCATTATTATCATGACATTAACCTA
TAAAAATAGGCGTATCACGAGGCCCTTTCGTC
```

Coding sequence
```
ATGAAGGCCAAGCTGCTGGTGCTGCTGTGCACCTTTACCGCCACCTACGCCGACACCATCTGCATTGGCTA
CCACGCCAACAACAGCACCGACACCGTGGATACCGTGCTGGAAAAGAACGTGACCGTGACCCACAGCGTGA
ACCTGGGATCCGGACTGAGAATGGTCACCGGCCTGAGAAACATCCCCAGCATCCAGAGCAGAGGCCTGTTT
GGAGCCATTGCCGGCTTTATTGAGGGCGGATGGACCGGAATGGTGGATGGGTGGTACGGCTACCACCACCA
GAATGAGCAGGGCTCTGGCTATGCCGCCGATCAGAAGTCTACCCAGAACGCCATCAACGGCATCACCAACA
AAGTGAACAGCGTGATCGAGAAGATGGGCGGCGATCCTGAATGGGACAGAGAGATCAACAACTACACCAGC
ATCATCTACAGCCTGATCGAGGAAAGCCAGAACCAGCAGGAAAACGGCACAGGCGGCGGATCTGGAATTGT
GCAGCAGCAGAACAACCTGCTGAGAGCCATTGAGGCCCAGCAGCATCTGCTGCAGCTGACAGTGTGGGGCA
TCAAGCAGCTGCAGACCTACAATGCCGAGCTGCTGGTCCTCCTGGAAAACGAGAGAACCCTGGACTTCCAC
GACAGCAACGTGAAGAACCTGTACGAGAAAGTGAAGTCCCAGCTGAAGAACAACGCCAAAGAGATCGGCAA
CGGCTGCTTCGAGTTCTACCACAAGTGCAACAACGAGTGCATGGAAAGCGTGAAGAACGGCACCTACGACT
ACCCCAAGTACAGCGAGGAAAGCAAGCTGAACAGAGAGAAGATCGACTCCGGAGGCGACATCATCAAGCTG
CTGAACGAGCAGGTGAACAAGGAGATGCAGAGCAGCAACCTGTACATGAGCATGAGCAGCTGGTGCTACAC
CCACAGCCTGGACGGCGCCGGCCTGTTCCTGTTCGACCACGCCGCCGAGGAGTACGAGCACGCCAAGAAGC
TGATCATCTTCCTGAACGAGAACAACGTGCCCGTGCAGCTGACCAGCATCAGCGCCCCCGAGCACAAGTTC
GAGGGCCTGACCCAGATCTTCCAGAAGGCCTACGAGCACGAGCAGCACATCAGCGAGAGCATCAACAACAT
CGTGGACCACGCCATCAAGAGCAAGGACCACGCCACCTTCAACTTCCTGCAGTGGTACGTGGCCGAGCAGC
ACGAGGAGGAGGTGCTGTTCAAGGACATCCTGGACAAGATCGAGCTGATCGGCAACGAGAACCACGGCCTG
TACCTGGCCGACCAGTACGTGAAGGGCATCGCCAAGAGCAGGAAGAGCGGATCC
```

Translation
MKAKLLVLLCTFTATYADTICIGYHANNSTDTVDTVLEKNVTVTHSVNLGSGLRMVTGLRNIPSIQSRGLF
GAIAGFIEGGWTGMVDGWYGYHHQNEQGSGYAADQKSTQNAINGITNKVNSVIEKMGGDPEWDREINNYTS
IIYSLIEESQNQQENGTGGGSGIVQQQNNLLRAIEAQQHLLQLTVWGIKQLQTYNAELLVLLENERTLDFH
DSNVKNLYEKVKSQLKNNAKEIGNGCFEFYHKCNNECMESVKNGTYDYPKYSEESKLNREKIDSGGDIIKL
LNEQVNKEMQSSNLYMSMSSWCYTHSLDGAGLFLFDHAAEEYEHAKKLIIFLNENNVPVQLTSISAPEHKF
EGLTQIFQKAYEHEQHISESINNIVDHAIKSKDHATFNFLQWYVAEQHEEEVLFKDILDKIELIGNENHGL
YLADQYVKGIAKSRKSGS

Fig. 35-3

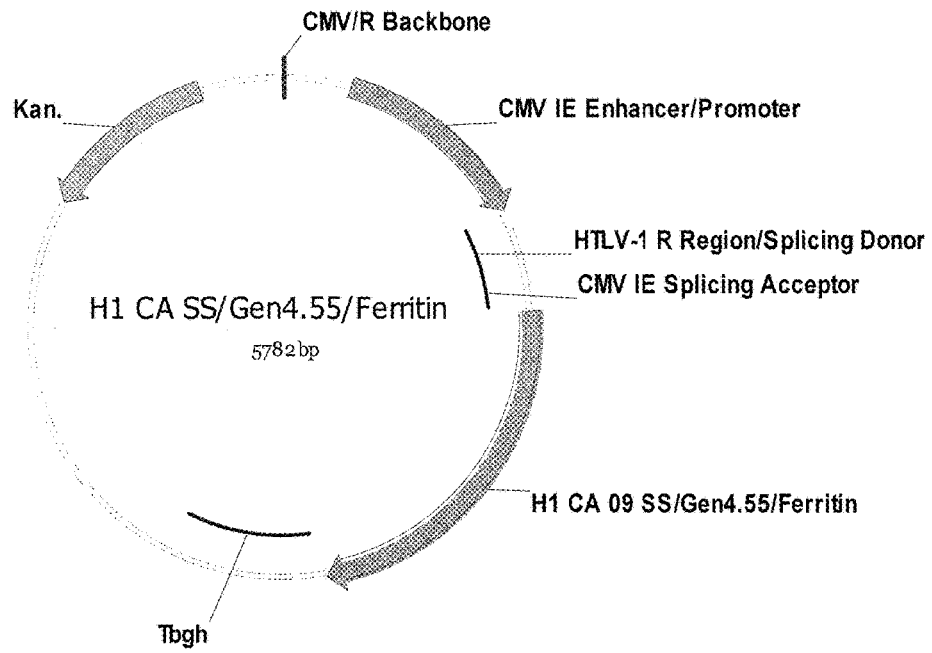

H1 CA SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgaccccgcccattgacgtcaataatgacgtatgt
tcccatagtaacgccaatagggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccaccccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactctagttaacggtggagggcagtgtagtct
gagcagtactcgttgctgccgcgcgcgccaccagacataatagctgacagactaacagactgttcctttccatgggtcttttctgcagtcaccgtc
gtcgacacgtgtgatcagatatcgcggccgctctagagatatcgccaccatgaaggctatcctggtggtgctgctgtacacctttgccaccgccaa
tgccgacaccctgtgtattggctaccacgccaacaacagcaccgacaccgtggataccgtgctggaaaagaacgtgaccgtgacccacagcgt
gaacctgggctccggcctgagactggccaccggcctgagaaacatcccagcattcagagcagaggcctgtttggagccattgccggctttattg
agggcggatggaccggaatggtggatgggtggtacggctaccaccaccagaatgagcagggctctggctatgccgccgacctgaagtctaccc
agaacgccatcgacgagatcaccaacaaagtgaacagcgtgatcgagaagatgggcggctgggacccatgggacagagagatcaacaacta
caccagcatcatctacagcctgatcgaggaaagccagaaccagcaggaaaacggcacaggcggcggatctggaattgtgcagcagcagaaca
acctgctgagagccattgaggcccagcagcatctgctgcagctgacagtgtggggcatcaagcagctgcagacctacaacgccgagctgctggt
gctgctcgagaatgagagaacctggactaccacgacagcaacgtgaagaacctgtacgagaaagtgcggagccagctgaagaacaacgcc
aaagagatcggcaacggctgcttcgagttctaccacaagtgcgacaatacctgcatggaaagcgtgaagaacggcacctacgactaccccaag
tacagcgaggaagccaagctgaaccgggaagagatcgattccggaggcgacatcatcaagctgctgaacgagcaggtgaacaaggagatgc
agagcagcaacctgtacatgagcatgagcagctggtgctacacccacagcctggacggcgccggcctgttcctgttcgaccacgccgccgagga

Fig. 36-1

```
gtacgagcacgccaagaagctgatcatcttcctgaacgagaacaacgtgcccgtgcagctgaccagcatcagcgcccccgagcacaagttcga
gggcctgacccagatcttccagaaggcctacgagcacgagcagcacatcagcgagagcatcaacaacatcgtggaccacgccatcaagagca
aggaccacgccaccttcaacttcctgcagtggtacgtggccgagcagcacgaggaggaggtgctgttcaaggacatcctggacaagatcgagct
gatcggcaacgagaaccacgcctgtacctggccgaccagtacgtgaagggcatcgccaagagcaggaagagcggatcctagcatcatcatc
atcatcattagtctgaagggcgaattgatccagctgtgccttctagttgccagccatctgttgtttgcccctccccgtgccttccttgaccctggaa
ggtgccactcccactgtcctttcctaataaaatgaggaaattgcatcgcattgtctgagtaggtgtcattctattctggggggtggggtggggcag
gacagcaaggggggaggattgggaagacaatagcaggcatgctggggatgcggtgggctctatgggtacccaggtgctgaagaattgacccggt
tcctcctgggccagaaagaagcaggcacatcccctctctgtgacacaccctgtccacgcccctggttcttagttccagccccactcataggacac
tcatagctcaggagggctccgccttcaatcccaccgctaaagtacttggagcggtctctcctccctcatcagcccaccaaaccaaacctagcct
ccaagagtgggaagaaattaaagcaagataggctattaagtgcagagggagagaaaatgcctccaacatgtgaggaagtaatgagagaaat
catagaattttaaggccatgatttaaggccatcatggccttaatcttccgcttcctcgctcactgactcgctgcgctcggtcgttcggctgcggcga
gcggtatcagctcactcaaaggcggtaatacggttatccacagaatcaggggataacgcaggaaagaacatgtgagcaaaaggccagcaaaa
ggccaggaaccgtaaaaaggccgcgttgctggcgtttttccataggctccgcccccctgacgagcatcacaaaaatcgacgctcaagtcagagg
tggcgaaacccgacaggactataaagataccaggcgtttccccctggaagctccctcgtgcgctctcctgttccgaccctgccgcttaccggatac
ctgtccgcctttctcccttcgggaagcgtggcgctttctcatagctcacgctgtaggtatctcagttcggtgtaggtcgttcgctccaagctgggctg
tgtgcacgaaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacactagaaga
acagtatttggtatctgcgctctgctgaagccagttaccttcggaaaaagagttggtagctcttgatccggcaaacaaaccaccgctggtagcggt
ggtttttttgtttgcaagcagcagattacgcgcagaaaaaaaggatctcaagaagatcctttgatcttttctacggggtctgacgctcagtggaac
gaaaactcacgttaagggattttggtcatgagattatcaaaaaggatcttcacctagatcctttaaattaaaaatgaagtttaaatcaatctaa
agtatatatgagtaaacttggtctgacagttaccaatgcttaatcagtgaggcacctatctcagcgatctgtctatttcgttcatccatagttgcctg
actcgggggggggggggcgctgaggtctgcctcgtgaagaaggtgttgctgactcataccaggcctgaatcgccccatcatccagccagaaagtg
agggagccacggttgatgagagctttgttgtaggtggaccagttggtgattttgaacttttgctttgccacggaacggtctgcgttgtcgggaagat
gcgtgatctgatccttcaactcagcaaaagttcgatttattcaacaaagccgccgtcccgtcaagtcagcgtaatgctctgccagtgttacaacca
attaaccaattctgattagaaaaactcatcgagcatcaaatgaaactgcaatttattcatatcaggattatcaataccatatttttgaaaaagccg
tttctgtaatgaaggagaaaactcaccgaggcagttccataggatggcaagatcctggtatcggtctgcgattccgactcgtccaacatcaatac
aacctattaatttcccctcgtcaaaaataaggttatcaagtgagaaatcaccatgagtgacgactgaatccggtgagaatggcaaaagcttatgc
atttctttccagacttgttcaacaggccagccattacgctcgtcatcaaaatcactcgcatcaaccaaaccgttattcattcgtgattgcgcctgag
cgagacgaaatacgcgatcgctgttaaaaggacaattacaaacaggaatcgaatgcaaccggcgcaggaacactgccagcgcatcaacaata
ttttcacctgaatcaggatattcttctaatacctggaatgctgttttcccggggatcgcagtggtgagtaaccatgcatcatcaggagtacggataa
aatgcttgatggtcggaagaggcataaaattccgtcagccagtttagtctgaccatctcatctgtaacatcattggcaacgctacctttgccatgttt
cagaaacaactctggcgcatcgggcttcccatacaatcgatagattgtcgcacctgattgcccgacattatcgcgagcccatttatacccatataa
atcagcatccatgttgaatttaatcgcggcctcgagcaagacgtttcccgttgaatatggctcataacacccccttgtattactgtttatgtaagca
gacagttttattgttcatgatgatatattttttatcttgtgcaatgtaacatcagagattttgagacacaacgtggctttccccccccccccattattga
agcatttatcaggggttattgtctcatgagcggatacatatttgaatgtatttagaaaaataaacaaatagggggttccgcgcacatttccccgaaaa
gtgccacctgacgtctaagaaaccattattatcatgacattaacctataaaaataggcgtatcacgaggccctttcgtc
```

Fig. 36-2

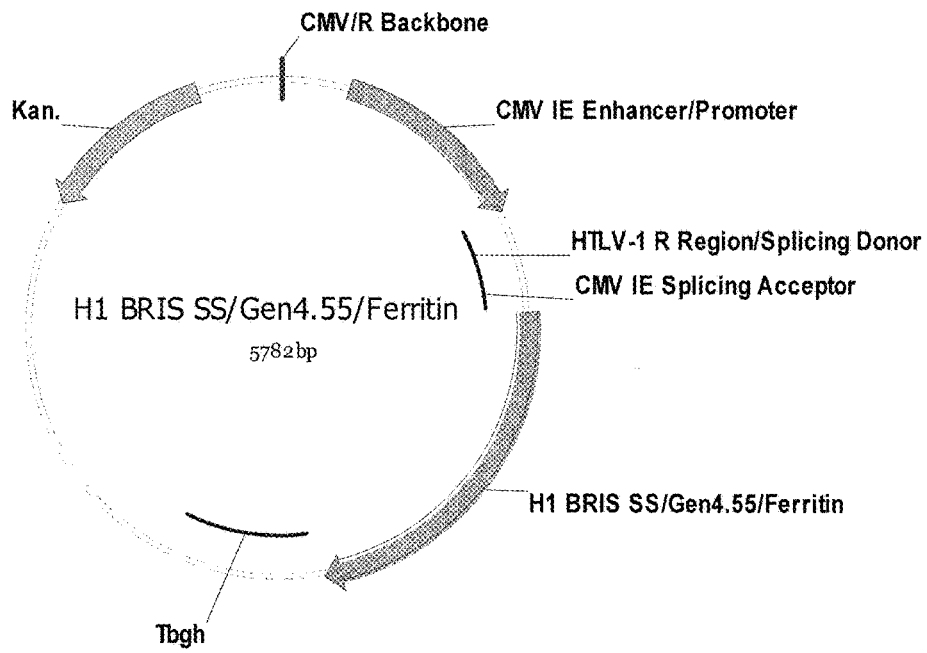

H1 Bris SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgaccccgcccattgacgtcaataatgacgtatgt
tcccatagtaacgccaataggggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccacccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctccc

```
cagagcagcaacctgtacatgagcatgagcagctggtgctacacccacagcctggacggcgccggcctgttcctgttcgaccacgccgccgagg
agtacgagcacgccaagaagctgatcatcttcctgaacgagaacaacgtgcccgtgcagctgaccagcatcagcgcccccgagcacaagttcg
agggcctgacccagatcttccagaaggcctacgagcacgagcagcacatcagcgagagcatcaacaacatcgtggaccacgccatcaagagc
aaggaccacgccaccttcaacttcctgcagtggtacgtggccgagcagcacgaggaggaggtgctgttcaaggacatcctggacaagatcgag
ctgatcggcaacgagaaccacggcctgtacctggccgaccagtacgtgaagggcatcgccaagagcaggaagagcggatcctagcatcatcat
catcatcattagtctgaagggcgaattgatccagctgtgcctctagttgccagccatctgttgtttgcccctcccccgtgccttccttgaccctgga
aggtgccactcccactgtccttcctaataaaatgaggaaattgcatcgcattgtctgagtaggtgtcattctattctgggggggtggggtggggca
ggacagcaaggggaggattgggaagacaatagcaggcatgctggggatgcggtgggctctatgggtacccaggtgctgaagaattgacccg
gttcctcctgggccagaaagaagcaggcacatccccttctctgtgacacaccctgtccacgccctggttcttagttccagcccactcataggac
actcatagctcaggagggctccgccttcaatcccaccgctaaagtacttggagcggtctctccctccctcatcagcccaccaaaccaaacctag
cctccaagagtgggaagaaattaaagcaagataggctattaagtgcagagggagagaaaatgcctccaacatgtgaggaagtaatgagagaa
atcatagaattttaaggccatgatttaaggccatcatggccttaatcttccgcttcctcgctcactgactcgctgcgctcggtcgttcggctgcggcg
agcggtatcagctcactcaaaggcggtaatacggttatccacagaatcaggggataacgcaggaaagaacatgtgagcaaaaggccagcaaa
aggccaggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccggata
cctgtccgcctttctcccttcgggaagcgtggcgctttctcatagctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtggcctaactacggctacactagaag
aacagtatttggtatctgcgctctgctgaagccagttaccttcggaaaaagagttggtagctcttgatccggcaaacaaaccaccgctggtagcg
gtggtttttttgtttgcaagcagcagattacgcgcagaaaaaaaggatctcaagaagatcctttgatcttttctacggggtctgacgctcagtgga
acgaaaactcacgttaagggattttggtcatgagattatcaaaaaggatcttcacctagatcctttta aattaaaaatgaagttttaaatcaatct
aaagtatatatgagtaaacttggtctgacagttaccaatgcttaatcagtgaggcacctatctcagcgatctgtctatttcgttcatccatagttgcc
tgactcggggggggggggcgctgaggtctgcctcgtgaagaaggtgttgctgactcataccaggcctgaatcgccccatcatccagccagaaag
tgagggagccacggttgatgagagctttgttgtaggtggaccagttggtgattttgaacttttgctttgccacggaacggtctgcgttgtcgggaag
atgcgtgatctgatccttcaactcagcaaaagttcgatttattcaacaaagccgccgtcccgtcaagtcagcgtaatgctctgccagtgttacaac
caattaaccaattctgattagaaaaactcatcgagcatcaaatgaaactgcaatttattcatatcaggattatcaataccatatttttgaaaaagc
cgtttctgtaatgaaggagaaaactcaccgaggcagttccataggatggcaagatcctggtatcggtctgcgattccgactcgtccaacatcaat
acaacctattaatttcccctcgtcaaaaataaggttatcaagtgagaaatcaccatgagtgacgactgaatccggtgagaatggcaaaagcttat
gcatttctttccagacttgttcaacaggccagccattacgctcgtcatcaaaatcactcgcatcaaccaaaccgttattcattcgtgattgcgcctg
agcgagacgaaatacgcgatcgctgttaaaaggacaattacaaacaggaatcgaatgcaaccggcgcaggaacactgccagcgcatcaacaa
tattttcacctgaatcaggatattcttctaatacctggaatgctgttttcccggggatcgcagtggtgagtaaccatgcatcatcaggagtacggat
aaaatgcttgatggtcggaagaggcataaattccgtcagccagtttagtctgaccatctcatctgtaacatcattggcaacgctacctttgccatgt
ttcagaaacaactctggcgcatcgggcttcccatacaatcgatagattgtcgcacctgattgcccgacattatcgcgagcccatttatacccatat
aaatcagcatccatgttggaatttaatcgcggcctcgagcaagacgtttcccgttgaatatggctcataacacccccttgtattactgtttatgtaag
cagacagttttattgttcatgatgatatattttatcttgtgcaatgtaacatcagagattttgagacacaacgtggctttccccccccccccattatt
gaagcatttatcagggttattgtctcatgagcggatacatatttgaatgtatttagaaaaataaacaaatagggggttccgcgcacatttccccgaa
aagtgccacctgacgtcaagaaaccattattatcatgacattaacctataaaaataggcgtatcacgaggccctttcgtc
```

Fig. 37-2

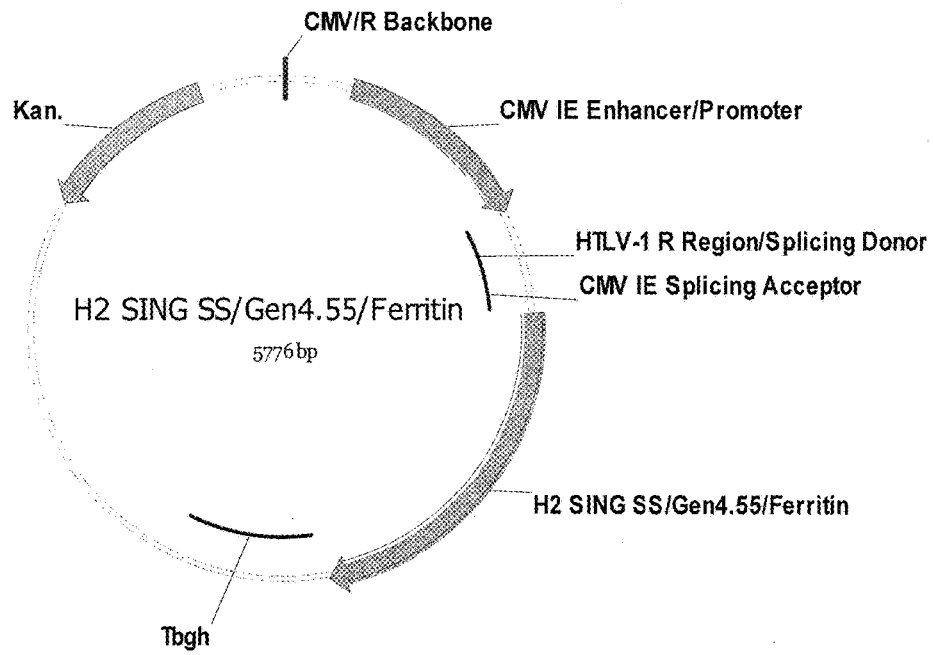

H2 Sing SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgacccccgcccattgacgtcaataatgacgtatgt
tcccatagtaacgccaataggggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccaccccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactctagttaacggtggagggcagtgtagtct
gagcagtactcgttgctgccgcgcgccaccagacataatagctgacagactaacagactgttccttttccatgggtctttctgcagtcaccgtc
gtcgacacgtgtgatcagatatcgcggccgctctagagatatcgccaccatggccatcatctacctgattctgctgtttacagccgtcagaggcga
tcagatctgtattggctaccacgccaacaatagcaccgagaaagtggataccatcctggaaagaaatgtgacagtgacacacgccaaggatatt
ggatcaggactggtgctggctacaggactgagaaatgtgcctcagattgagagcagaggcctgtttggagccattgctggctttattgaaggcgg
atggcagggaatgattgatgggtggtacggctaccaccactctaatgatcagggatctggatatgccgccgacaaagaatctacacagaaagc
cttcgacggcatcaccaacaaagtgaatagcgtgatcgagaagatgggcggagatcccgaatgggacagagagatcaacaactacaccagca
tcatctcacagcctgatcgaggaaagccagaatcagcaggaaaatggaacaggcggaggatctggaattgtgcagcagcagaacaatctgctg
agagctattgaagctcagcagcatctgctgaatctgacagtgtggggaatcaaacagctgcagacatacaatgctgagctgctggtgctgatgg
aaaatgagagaaccctggacttccacgacagcaatgtgaagaacctgtacgacaaagtgcggatgcagctgagagacaatgtgaaagaactg
ggcaatggctgcttcgagttctaccacaagtgcgacgatgagtgtatgaacagcgtgaagaacggcacctacgactaccctaagtacgaggaa
gagagcaagctgaacagaaatgagatcaagtccggaggcgacatcatcaagctgctgaacgagcaggtgaacaaggagatgcagagcagca

Fig. 38-1 acctgtacatgagcatgagcagctggtgctacacccacagcctggacggcgccggcctgttcctgttcgaccacgccgccgaggagtacgagca
cgccaagaagctgatcatcttcctgaacgagaacaacgtgcccgtgcagctgaccagcatcagcgcccccgagcacaagttcgagggcctgac
ccagatcttccagaaggcctacgagcacgagcagcacatcagcgagagcatcaacaacatcgtggaccacgccatcaagagcaaggaccacg
ccaccttcaacttcctgcagtggtacgtggccgagcagcacgaggaggaggtgctgttcaaggacatcctggacaagatcgagctgatcggcaa
cgagaaccacggcctgtacctggccgaccagtacgtgaagggcatcgccaagagcaggaagagcggatcctagcatcatcatcatcatcatta
gtctgaagggcgaattgatccagctgtgccttctagttgccagccatctgttgtttgccctccccgtgccttccttgaccctggaaggtgccactc
ccactgtcctttcctaataaaatgaggaaattgcatcgcattgtctgagtaggtgtcattctattctgggggtggggtggggcaggacagcaagg
gggaggattgggaagacaatagcaggcatgctggggatgcggtgggctctatgggtacccaggtgctgaagaattgacccggttcctcctgggc
cagaaagaagcaggcacatcccccttctctgtgacacaccctgtccacgcccctggttcttagttccagccccactcataggacactcatagctcag
gagggctccgccttcaatcccacccgctaaagtacttggagcggtctctcctccctcatcagcccaccaaaccaaacctagcctccaagagtgg
gaagaaattaaagcaagataggctattaagtgcagagggagagaaaatgcctccaacatgtgaggaagtaatgagagaaatcatagaatttt
aaggccatgatttaaggccatcatggccttaatcttccgcttcctcgctcactgactcgctcgcgtcggtcgttcggctgcggcgagcggtatcagc
tcactcaaaggcggtaatacggttatccacagaatcaggggataacgcaggaaagaacatgtgagcaaaaggccagcaaaaggccaggaac
cgtaaaaaggccgcgttgctggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgcttaccggatacctgtccgcctt
tctcccttcgggaagcgtggcgctttctcatagctcacgctgtaggtatctcagttcggtgtaggtcgttcgctccaagctgggctgtgtgcacgaa
ccccccgttcagcccgaccgctgcgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaagaacagtatttg
gtatctgcgctctgctgaagccagttaccttcggaaaaagagttggtagctcttgatccggcaaacaaaccaccgctggtagcggtggtttttttgt
ttgcaagcagcagattacgcgcagaaaaaaaggatctcaagaagatcctttgatcttttctacggggtctgacgctcagtggaacgaaaactca
cgttaagggattttggtcatgagattatcaaaaaggatcttcacctagatccttttaaattaaaaatgaagttttaaatcaatctaaagtatatatg
agtaaacttggtctgacagttaccaatgcttaatcagtgaggcacctatctcagcgatctgtctatttcgttcatccatagttgcctgactcggggg
ggggggggcgctgaggtctgcctcgtgaagaaggtgttgctgactcataccaggcctgaatcgccccatcatccagccagaaagtgagggagcc
acggttgatgagagctttgttgtaggtggaccagttggtgattttgaacttttgctttgccacggaacggtctgcgttgtcgggaagatgcgtgatc
tgatccttcaactcagcaaaagttcgatttattcaacaaagccgccgtcccgtcaagtcagcgtaatgctctgccagtgttacaaccaattaacca
attctgattagaaaaactcatcgagcatcaaatgaaactgcaatttattcatatcaggattatcaataccatatttttgaaaaagccgtttctgtaa
tgaaggagaaaactcaccgaggcagttccataggatggcaagatcctggtatcggtctgcgattccgactcgtccaacatcaatacaacctatta
atttcccctcgtcaaaaataaggttatcaagtgagaaatcaccatgagtgacgactgaatccggtgagaatggcaaaagctttatgcatttcttcc
agacttgttcaacaggccagccattacgctcgtcatcaaaatcactcgcatcaaccaaaccgttattcattcgtgattgcgcctgagcgagacga
aatacgcgatcgctgttaaaaggacaattacaaacaggaatcgaatgcaaccggcgcaggaacactgccagcgcatcaacaatatttcacct
gaatcaggatattcttctaatacctggaatgctgttttcccggggatcgcagtggtgagtaaccatgcatcatcaggagtacggataaaatgcttg
atggtcggaagaggcataaattccgtcagccagtttagtctgaccatctcatctgtaacatcattggcaacgctacctttgccatgtttcagaaac
aactctggcgcatcgggcttcccatacaatcgatagattgtcgcacctgattgcccgacattatcgcgagcccatttatacccatataaatcagca
tccatgttggaatttaatcgcggcctcgagcaagacgtttcccgttgaatatggctcataacaccccttgtattactgtttatgtaagcagacagttt
tattgttcatgatgatatattttttatcttgtgcaatgtaacatcagagattttgagacacaacgtggctttccccccccccccattattgaagcatta
tcagggttattgtctcatgagcggatacatatttgaatgtatttagaaaaataaacaaatagggggttccgcgcacatttccccgaaaagtgccacc
tgacgtctaagaaaccattattcatgacattaacctataaaaataggcgtatcacgaggccctttcgtc

Fig. 38-2

Plasmid map: H3 Bris SS/Gen4.55/Ferritin, 5810 bp

Labels: CMV8x/R-H1NC SS4.55(517) SGG egm; CMV IE Enhancer/Promoter 8kb; HTLV-1 R Region/Splicing Donor; CMV IE Splicing Acceptor; H3 Bris SS/Gen4.55/ferritin; Tbgh; Kan.

H3 Bris SS/Gen4.55/ferritin tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgcccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
acccattgacgtcaatgggagtttgttttggactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgcgccaccagacataatagctgacagactaacagactgttcctttccatgggtcttttctgcagtcaccgtcgt
cgacacgtgtgatcagatatcgcggccgctctagagatatcgccaccatgaaaaccatcattgccctgagctacatcctgtgcctggtgttcacac
agaagctgcccggcaacgataatagcaccgccacactgtgtctgggacaccacgccgtgcctaatggcaccatcgtgaaaacaatcaccaacg
accagatcgaagtgaccaatgccacagagctgggctccggcctgaagctggccaccggcatgagaaatgtgcccgagaagcagaccagaggc
atctttggcgccattgccggctttatcgagaatggctgggagggaatggtggatggtggtacggcttcagacaccagaatagcgagggaattg
gacaggccgccgatctgaaatctacccaggccgccatcgaccagatcaacggcaagctgaacaggctgatcggcaagaccggcggcgatccc
gagtgggaccgggagatcaacaactacaccagcatcatctacagcctgatcgaggagagccagaaccagcaggagaacggcaccggcggcg
gcagcggcatcgtgcagcagcagaacaacctgctgcgggccatcgaggcccagcagcacctgctgcagctgaccgtgtggggcatcaagcagc
tgcagagctacaatgccgaactgctggtcgccctggaaaaccagcacacaattgatctgacagacagtgagatgaataagctgttcgagaaaa
ccaagaagcagctgagagaaaacgccgaggacatgggcaacggctgcttcaagatctaccacaagtgcgacaacgcctgcatcggcagcatc
agaaacgcacctacgaccacgacgtgtacagagatgaggccctgaacaaccggtttcagatcaagggctccggaggcgacatcatcaagctg
ctgaacgagcaggtgaacaaggagatgcagagcagcaacctgtacatgagcatgagcagctggtgctacacccacagcctggacggcgccgg
cctgttcctgttcgaccacgccgccgaggagtacgagcacgccaagaagctgatcatcttcctgaacgagaacaacgtgcccgtgcagctgacc

Fig. 39-1

```
agcatcagcgcccccgagcacaagttcgagggcctgacccagatcttccagaaggcctacgagcacgagcagcacatcagcgagagcatcaa
caacatcgtggaccacgccatcaagagcaaggaccacgccaccttcaacttcctgcagtggtacgtggccgagcagcacgaggaggaggtgct
gttcaaggacatcctggacaagatcgagctgatcggcaacgagaaccacgccctgtacctggccgaccagtacgtgaagggcatcgccaagag
caggaagagcggatcctagcatcatcatcatcatcattagtctgaagggcgaattgatccagctgtgccttctagttgccagccatctgttgtttgc
ccctcccccgtgccttccttgaccctggaaggtgccactcccactgtcctttcctaataaaatgaggaaattgcatcgcattgtctgagtaggtgtc
attctattctgggggtggggtggggcaggacagcaaggggggaggattgggaagacaatagcaggcatgctggggatgcggtgggctctatgg
gtacccaggtgctgaagaattgacccggttcctcctgggccagaaagaagcaggcacatccccttctctgtgacacaccctgtccacgccctgg
ttcttagttccagccccactcataggacactcatagctcaggagggctccgccttcaatcccacccgctaaagtacttggagcggtctctccctccc
tcatcagcccaccaaaccaaacctagcctccaagagtgggaagaaattaaagcaagataggctattaagtgcagagggagagaaaatgcctc
caacatgtgaggaagtaatgagagaaatcatagaattttaaggccatgatttaaggccatcatggccttaatcttccgcttcctcgctcactgact
cgctgcgctcggtcgttcggctgcggcgagcggtatcagctcactcaaaggcggtaatacggttatccacagaatcaggggataacgcaggaaa
gaacatgtgagcaaaaggccagcaaaaggccaggaaccgtaaaaaggccgcgttgctggcgtttttccataggctccgcccccctgacgagca
tcacaaaaatcgacgctcaagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccggtaactatcgtcttgagtccaa
cccggtaagacacgacttatcgccactggcagcagccactggtaacaggattagcagagcgaggtatgtaggcggtgctacagagttcttgaag
tggtggcctaactacggctacactagaagaacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaaaaaggatcttcacctagatccttta
aattaaaaatgaagttttaaatcaatctaaagtatatatgagtaaacttggtctgacagttaccaatgcttaatcagtgaggcacctatctcagcg
atctgtctatttcgttcatccatagttgcctgactcgggggggggggggcgctgaggtctgcctcgtgaagaaggtgttgctgactcataccaggcct
gaatcgccccatcatccagccagaaagtgagggagccacggttgatgagagctttgttgtaggtggaccagttggtgattttgaacttttgctttg
ccacggaacgtctgcgttgtcgggaagatgcgtgatctgatccttcaactcagcaaaagttcgatttattcaacaaagccgccgtcccgtcaagt
cagcgtaatgctctgccagtgttacaaccaattaaccaattctgattagaaaaactcatcgagcatcaaatgaaactgcaatttattcatatcagg
attatcaataccatatttttgaaaaagccgtttctgtaatgaaggagaaaactcaccgaggcagttccataggatggcaagatcctggtatcggt
ctgcgattccgactcgtccaacatcaatacaacctattaatttcccctcgtcaaaaataaggttatcaagtgagaaatcaccatgagtgacgactg
aatccggtgagaatggcaaaagcttatgcatttctttccagacttgttcaacaggccagccattacgctcgtcatcaaaatcactcgcatcaacca
aaccgttattcattcgtgattgcgcctgagcgagacgaaatacgcgatcgctgttaaaaggacaattacaaacaggaatcgaatgcaaccggcg
caggaacactgccagcgcatcaacaatatttttcacctgaatcaggatattcttctaatacctggaatgctgttttcccggggatcgcagtggtgag
taaccatgcatcatcaggagtacggataaaatgcttgatggtcggaagaggcataaattccgtcagccagtttagtctgaccatctcatctgtaac
atcattggcaacgctacctttgccatgtttcagaaacaactctggcgcatcgggcttcccatacaatcgatagattgtcgcacctgattgcccgac
attatcgcgagcccatttatacccatataaatcagcatccatgttggaatttaatcgcggcctcgagcaagacgtttcccgttgaatatggctcata
acacccccttgtattactgtttatgtaagcagacagttttattgttcatgatgatatatttttatcttgtgcaatgtaacatcagagattttgagacaca
acgtggctttccccccccccccattattgaagcatttatcagggttattgtctcatgagcggatacatatttgaatgtatttagaaaaataaacaaa
taggggttccgcgcacatttccccgaaaagtgccacctgacgtctaagaaaccattattatcatgacattaacctataaaaataggcgtatcacg
aggccctttcgtc
```

Fig. 39-2

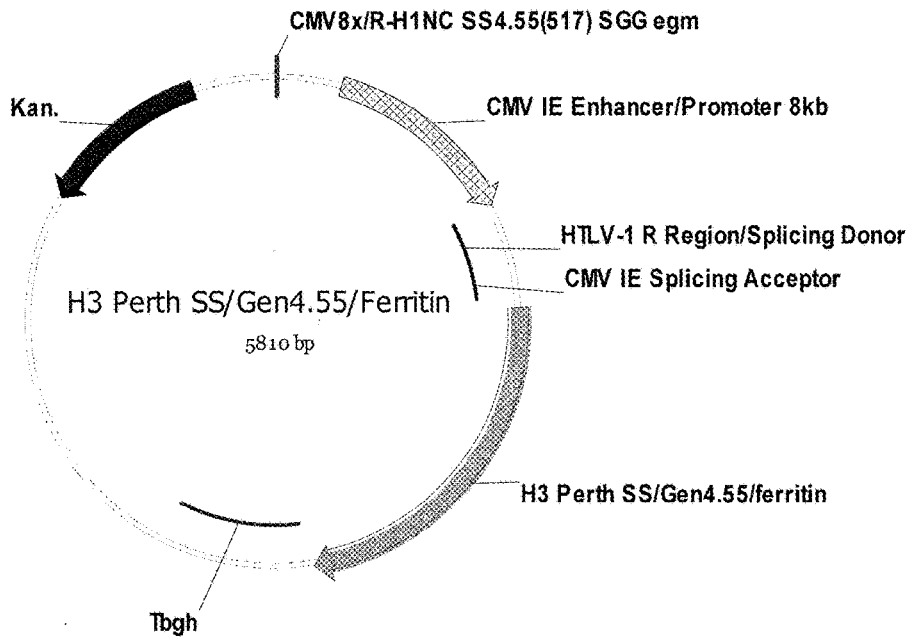

H3 Perth SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacggggaacttccaagtctcc
acccccattgacgtcaatgggagtttgttttgactcaccaaaatcaacgggaatttccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgccaccagacataatagctgacagactaacagactgttcctttccatgggtcttttctgcagtcaccgtcgt
cgacacgtgtgatcagatatcgcggccgctctagagatatcgccaccatgaaaaccataattgcgctgtcctacatactgtgtctggtgtttgccc
agaaaactgccgggcaatgacaactcaacagccacgctctgcttggggcaccatgccgtccctaacgggaccattgtgaaaaccattactaacga
tcagatagaggtgactaatgccaccgagctgggctccggcttgaaactggcgaccggtatgcgcaatgtccccgaaaaacagacccgcgggat
atttgggctatcgcaggctttatcgagaatggctgggaagggatggtggatggttggtatggttttagacatcaaaactccgaaggcagaggcc
aggctgccgatctcaagagcacgcaggccgctatagatcagatcaatggaaagctcaacagactgatcgggaaaaccggcggcgatcccgag
tgggaccgggagatcaacaactacaccagcatcatctacagcctgatcgaggagagccagaaccagcaggagaacggcaccggcggcggca
gcggcatcgtgcagcagcagaacaacctgctgcgggccatcgaggcccagcagcacctgctgcagctgaccgtgtggggcatcaagcagctgc
agtcctacaatgccgagctgctggtggctctggagaatcagcacactattgacctgaccgattcagagatgaacaaactttttgagaagacgaa
gaagcagcttagagaaaat

```
ctgttcgaccacgccgccgaggagtacgagcacgccaagaagctgatcatcttcctgaacgagaacaacgtgcccgtgcagctgaccagcatc
agcgcccccgagcacaagttcgagggcctgacccagatcttccagaaggcctacgagcacgagcagcacatcagcgagagcatcaacaacat
cgtggaccacgccatcaagagcaaggaccacgccaccttcaacttcctgcagtggtacgtggccgagcagcacgaggaggaggtgctgttcaa
ggacatcctggacaagatcgagctgatcggcaacgagaaccacggcctgtacctggccgaccagtacgtgaagggcatcgccaagagcagga
agagcggatcctagcatcatcatcatcatcattagtctgaagggcgaattgatccagctgtgccttctagttgccagccatctgttgtttgcccctcc
cccgtgccttccttgaccctggaaggtgccactcccactgtcctttcctaataaaatgaggaaattgcatcgcattgtctgagtaggtgtcattctat
tctgggggtggggtggggcaggacagcaaggggggaggattgggaagacaatagcaggcatgctggggatgcggtgggctctatgggtaccc
aggtgctgaagaattgacccggttcctcctgggccagaaagaagcaggcacatcccctctctgtgacacaccctgtccacgccctggttcttag
ttccagccccactcataggacactcatagctcaggagggctccgccttcaatcccaccccgctaaagtacttggagcggtctctccctccctcatca
gcccaccaaaccaaacctagcctccaagagtgggaagaaattaaagcaagataggctattaagtgcagagggagagaaaatgcctccaacat
gtgaggaagtaatgagagaaatcatagaattttaaggccatgatttaaggccatcatggccttaatcttccgcttcctcgctcactgactcgctgc
gctcggtcgttcggctgcggcgagcggtatcagctcactcaaaggcggtaatacggttatccacagaatcaggggataacgcaggaaagaaca
tgtgagcaaaaggccagcaaaaggccaggaaccgtaaaaaggccgcgttgctggcgtttttccataggctccgcccccctgacgagcatcaca
aaaatcgacgctcaagtcagaggtggcgaaacccgacaggactataaagataccaggcgtttccccctggaagctccctcgtgcgctctcctgtt
ccgaccctgccgcttaccggatacctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaactatcgtcttgagtccaacccggt
aagacacgacttatcgccactggcagcagccactggtaacaggattagcagagcgaggtatgtaggcggtgctacagagttcttgaagtggtgg
cctaactacggctacactagaagaacagtatttggtatctgcgctctgctgaagccagttaccttcggaaaaagagttggtagctcttgatccggc
aaacaaaccaccgctggtagcggtggtttttttgtttgcaagcagcagattacgcgcagaaaaaaaggatctcaagaagatcctttgatctttct
acggggtctgacgctcagtggaacgaaaactcacgttaagggattttggtcatgagattatcaaaaaggatcttcacctagatcctttaaattaa
aaatgaagttttaaatcaatctaaagtatatatgagtaaacttggtctgacagttaccaatgcttaatcagtgaggcacctatctcagcgatctgt
ctatttcgttcatccatagttgcctgactcgggggggggggggcgctgaggtctgcctcgtgaagaaggtgttgctgactcataccaggcctgaatc
gccccatcatccagccagaaagtgagggagccacggttgatgagagctttgttgtaggtggaccagttggtgattttgaacttttgctttgccacg
gaacggtctgcgttgtcgggaagatgcgtgatctgatccttcaactcagcaaaagttcgatttattcaacaaagccgccgtcccgtcaagtcagc
gtaatgctctgccagtgttacaaccaattaaccaattctgattagaaaactcatcgagcatcaaatgaaactgcaatttattcatatcaggatta
tcaataccatattttgaaaaagccgtttctgtaatgaaggagaaaactcaccgaggcagttccataggatggcaagatcctggtatcggtctgc
gattccgactcgtccaacatcaatacaacctattaatttccctcgtcaaaaataaggttatcaagtgagaaatcaccatgagtgacgactgaat
ccggtgagaatggcaaaagcttatgcatttctttccagacttgttcaacaggccagccattacgctcgtcatcaaaatcactcgcatcaaccaaac
cgttattcattcgtgattgcgcctgagcgagacgaaatacgcgatcgctgttaaaaggacaattacaaacaggaatcgaatgcaaccggcgcag
gaacactgccagcgcatcaacaatattttcacctgaatcaggatattcttctaatacctggaatgctgttttcccggggatcgcagtggtgagtaa
ccatgcatcatcaggagtacggataaaatgcttgatggtcggaagaggcataaattccgtcagccagtttagtctgaccatctcatctgtaacatc
attggcaacgctacctttgccatgtttcagaaacaactctggcgcatcgggcttcccatacaatcgatagattgtcgcacctgattgcccgacatta
tcgcgagcccatttatacccatataaatcagcatccatgttggaatttaatcgcggcctcgagcaagacgtttcccgttgaatatggctcataaca
ccccttgtattactgtttatgtaagcagacagttttattgttcatgatgatatattttatcttgtgcaatgtaacatcagagattttgagacacaacg
tggctttccccccccccccattattgaagcatttatcagggttattgtctcatgagcggatacatatttgaatgtatttagaaaaataaacaaatag
gggttccgcgcacatttccccgaaaagtgccacctgacgtctaagaaaccattattatcatgacattaacctataaaaataggcgtatcacgagg
ccctttcgtc
```

Fig. 40-2

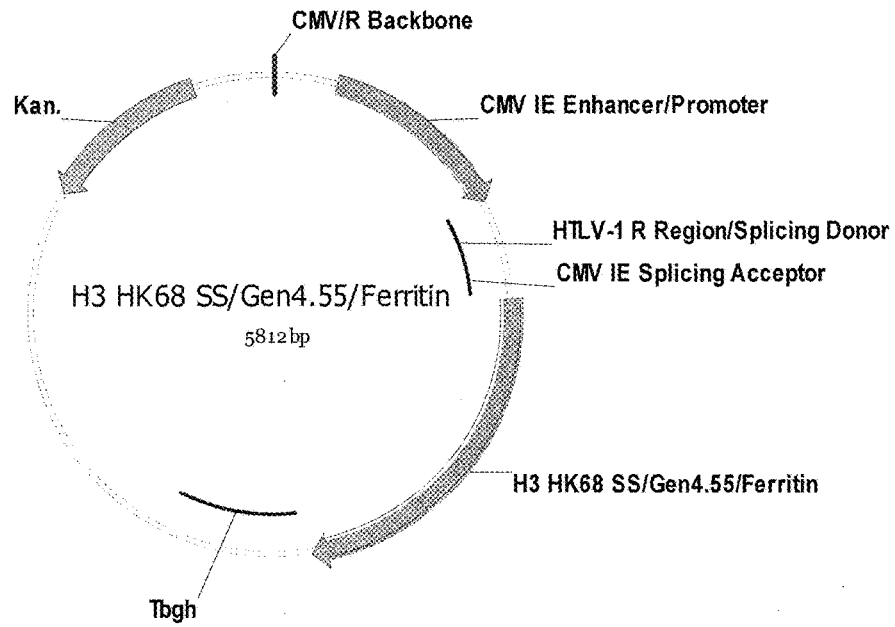

H3 HK SS/Gen4.55/ferritin
tcgcgcgtttcggtgatgacggtgaaaacctctgacacatgcagctcccggagacggtcacagcttgtctgtaagcggatgccggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgacccccgcccattgacgtcaataatgacgtatgt
tcccatagtaacgccaataggggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccacccattgacgtcaatggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccggggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactctagttaacggtggagggcagtgtagtct
gagcagtactcgttgctgccgcgcgcgccaccagacataatagctgacagactaacagactgttcctttccatgggtcttttctgcagtcaccgtc
gtcgacacgtgtgatcagatatcgcggccgctctagagatatcgccaccatgaagaccatcatcgccctgagctacatcttctgcctggccctggg
ccaggacctgcccggcaacgacaacagcaccgccacccctgtgcctgggccaccacgccgtgcccaacggcaccctggtgaagaccatcaccga
cgaccagatcgaggtgaccaacgccaccgagctgggctccggcctgaagctggccaccggcatgcggaacgtgcccgagaagcagacccggg
gcctgttcggcgccatcgccggcttcatcgagaacggctggggagggcatgatcgacggctggtacggcttccggcaccagaacagcgagggca
ccggccaggccgccgacctgaagagcacccaggccgccatcgaccagatcaacggcaagctgaaccggggtgatcgagaagaccggcggcgat
cccgagtgggaccgggagatcaacaactacaccagcatcatctacagcctgatcgaggagagccagaaccagcaggagaacggcaccggcg
gcggcagcggcatcgtgcagcagcagaacaacctgctgcgggccatcgaggcccagcagcacctgctgcagctgaccgtgtggggcatcaagc
agctgcagagctacaacgccgagctgctggtggccctggagaaccagcacaccatcgacctgaccgacagcgagatgaacaagctgttcgaga
gacccggcggcagctgcgggagaacgccgaggacatgggcaacggctgcttcaag

```
gaccagcatcagcgcccccgagcacaagttcgagggcctgacccagatcttccagaaggcctacgagcacgagcagcacatcagcgagagca
tcaacaacatcgtggaccacgccatcaagagcaaggaccacgccaccttcaacttcctgcagtggtacgtggccgagcagcacgaggaggagg
tgctgttcaaggacatcctggacaagatcgagctgatcggcaacgagaaccacggcctgtacctggccgaccagtacgtgaagggcatcgcca
agagcaggaagagcggatcctagcatcatcatcatcatcattagtctgaagggcgaattgatccagctgtgccttctagttgccagccatctgttg
tttgccccteccccgtgccttccttgaccctggaaggtgccactcccactgtccttcctaataaaatgaggaaattgcatcgcattgtctgagtagg
tgtcattctattctgggggtgggtgtgggcaggacagcaaggggggaggattgggaagacaatagcaggcatgctggggatgcggtgggctct
atgggtacccaggtgctgaagaattgaccggttcctcctgggccagaaagaagcaggcacatcccettctctgtgacacaccctgtccacgccc
ctggttcttagttccagccccactcataggacactcatagctcaggagggctccgccttcaatcccacccgctaaagtacttggagcggtctctccc
tccctcatcagcccaccaaaccaaacctagcctccaagagtgggaagaaattaaagcaagataggctattaagtgcagagggagagaaaatg
cctccaacatgtgaggaagtaatgagagaaatcatagaattttaaggccatgatttaaggccatcatggccttaatcttccgcttcctcgctcact
gactcgctgcgctcggtcgttcggctgcggcgagcggtatcagctcactcaaaggcggtaatacggttatccacagaatcaggggataacgcag
gaaagaacatgtgagcaaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgctgtaggtatctc
agttcggtgtaggtcgttcgctccaagctgggctgtgtgcacgaaccccccgttcagcccgaccgctgcgccttatccggtaactatcgtcttgagt
ccaacccggtaagacacgacttatcgccactggcagcagccactggtaacaggattagcagagcgaggtatgtaggcggtgctacagagttctt
gaagtggtggcctaactacggctacactagaagaacagtatttggtatctgcgctctgctgaagccagttaccttcggaaaaagagttggtagct
cttgatccggcaaacaaaccaccgctggtagcggtggtttttttgtttgcaagcagcagattacgcgcagaaaaaaaggatctcaagaagatcct
ttgatcttttctacggggtctgacgctcagtggaacgaaaactcacgttaagggattttggtcatgagattatcaaaaaggatcttcacctagatc
cttttaaattaaaaatgaagttttaaatcaatctaaagtatatatgagtaaacttggtctgacagttaccaatgcttaatcagtgaggcacctatct
cagcgatctgtctatttcgttcatccatagttgcctgactccccccccccccccccccctgaggtctgcctcgtgaagaaggtgttgctgactcatacc
aggcctgaatcgccccatcatccagccagaaagtgagggagccacggttgatgagagctttgttgtaggtggaccagttggtgattttgaactttt
gctttgccacggaacggtctgcgttgtcgggaagatgcgtgatctgatccttcaactcagcaaaagttcgatttattcaacaaagccgccgtcccg
tcaagtcagcgtaatgctctgccagtgttacaaccaattaaccaattctgattagaaaaactcatcgagcatcaaatgaaactgcaatttattcat
atcaggattatcaataccatattttgaaaaagccgtttctgtaatgaaggagaaaactcaccgaggcagttccataggatggcaagatcctggt
atcggtctgcgattccgactcgtccaacatcaatacaacctattaatttcccctcgtcaaaaataaggttatcaagtgagaaatcaccatgagtga
cgactgaatccggtgagaatggcaaaagcttatgcatttctttccagacttgttcaacaggccagccattacgctcgtcatcaaaatcactcgcat
caaccaaaccgttattcattcgtgattgcgcctgagcgagacgaaatacgcgatcgctgttaaaaggacaattacaaacaggaatcgaatgcaa
ccggcgcaggaacactgccagcgcatcaacaatattttcacctgaatcaggatattcttctaatacctggaatgctgtttteccggggatcgcagt
ggtgagtaaccatgcatcatcaggagtacggataaaatgcttgatggtcggaagaggcataaattccgtcagccagtttagtcgaccatctcat
ctgtaacatcattggcaacgctacctttgccatgtttcagaaacaactctggcgcatcgggcttcccatacaatcgatagattgtcgcacctgattg
cccgacattatcgcgagccatttataccatataaatcagcatccatgttggaatttaatcgcggcctcgagcaagacgtttcccgttgaatatg
gctcataacaccccttgtattactgtttatgtaagcagacagttttattgttcatgatgatatatttttatcttgtgcaatgtaacatcagagatttga
gacacaacgtggctttccccccccccccattattgaagcatttatcaggttattgtctcatgagcggatacatatttgaatgtatttagaaaaata
aacaaatagggttccgcgcacatttccccgaaaagtgccacctgacgtctaagaaaccattattatcatgacattaacctataaaaataggcgt
atcacgaggccctttcgtc
```

Fig. 41-2

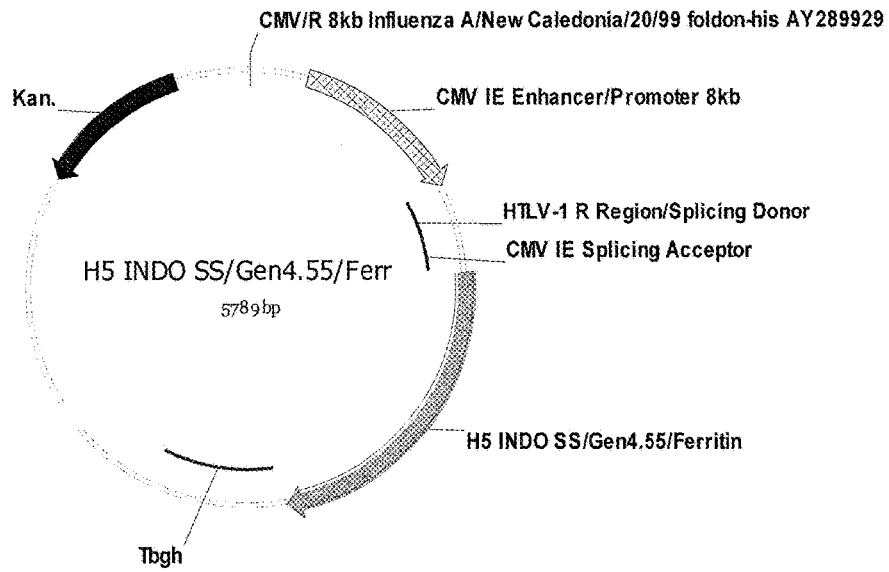
H5 Indo SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgacccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgcgccaccagacataatagctgacagactaacagactgttcctttccatgggtcttttctgcagtcaccgtcgt
cgacacgtgtgatcagatatcgcggccgctctagagatatcgccaccatggagaagatcgtgctgctgctggccatcgtgagcctggtgaagag
cgaccagatctgcatcggctaccacgccaacaacagcaccgagcaggtggacaccatcatggagaagaacgtgaccgtgacccacgcccagg
acatcggctccggcctggtgctggccaccggcctgcggaacagcccccagcgggagagccggcggaagaagcggggcctgttcggcgccatcg
ccggcttcatcgagggcggctggcagggcatggtggacggctggtacggctaccaccacagcaacgagcagggcagcggctacgccgccgac
aaggagagcacccagaaggccatcgacggcgtgaccaacaaggtgaacagcatcatcgacaagatgggcggcgatcccgagtgggaccggg
agatcaacaactacaccagcatcatctacagcctgatcgaggagagccagaaccagcaggagaacggcaccggcggcggcagcggcatcgtg
cagcagcagaacaacctgctgcgggccatcgaggcccagcagcacctgctgcagctgaccgtgtggggcatcaagcagctgcagacctacaac
gccgagctgctggtgctgatggagaacgagcggaccctggacttccacgacagcaacgtgaagaacctgtacgacaaggtgcggctgcagctg
cgggacaacgccaaggagctgggcaacggctgcttcgagttctaccacaagtgcgacaacgagtgcatggagagcatccggaacggcaccta
caactacccccagtacagcgaggaggcccggctgaagcgggaggagatcagctccggaggcgacatcatcaagctgctgaacgagcaggtga
acaaggagatgcagagcagcaacctgtacatgagcatgagcagctggtgctacacccacagcctggacggcgccggcctgttcctgttcgacca
cgccgccgaggagtacgagcacgccaagaagctgatcatcttcctgaacgagaacaacgtgcccgtgcagctgaccagcatcagcgcccccga
gcacaagttcgagggcctgacccagatcttccagaaggcctacgagcacgagcagcacatcagcgagagcatcaacaacatcgtggaccacg
ccatcaagagcaaggaccacgccaccttcaacttcctgcagtggtacgtggccgagcagcacgaggaggaggtgctgttcaaggacatcctgg

Fig. 42-1 acaagatcgagctgatcggcaacgagaaccacggcctgtacctggccgaccagtacgtgaagggcatcgccaagagcaggaagagcggatcc
tagcatcatcatcatcatcattagtctgaagggcgaattgatccagctgtgccttctagttgccagccatctgttgtttgcccctccccgtgccttcc
ttgaccctggaaggtgccactcccactgtcctttcctaataaaatgaggaaattgcatcgcattgtctgagtaggtgtcattctattctgggggtg
gggtggggcaggacagcaaggggggaggattgggaagacaatagcaggcatgctggggatgcggtgggctctatgggtacccaggtgctgaag
aattgacccggttcctcctgggccagaaagaagcaggcacatccccttctctgtgacacaccctgtccacgccccctggttcttagttccagcccca
ctcataggacactcatagctcaggagggctccgccttcaatcccacccgctaaagtacttggagcggtctctccctccctcatcagcccaccaaac
caaacctagcctccaagagtgggaagaaattaaagcaagataggctattaagtgcagaggagagagaaaatgcctccaacatgtgaggaagta
atgagagaaatcatagaattttaaggccatgatttaaggccatcatggccttaatcttccgcttcctcgctcactgactcgctgcgctcggtcgttc
ggctgcggcgagcggtatcagctcactcaaaggcggtaatacggttatccacagaatcaggggataacgcaggaaagaacatgtgagcaaaa
ggccagcaaaaggccaggaaccgtaaaaaggccgcgttgctggcgttttccataggctccgcccccctgacgagcatcacaaaaatcgacgct
caagtcagaggtggcgaaacccgacaggactataaagataccaggcgtttccccctggaagctccctcgtgcgctctcctgttccgaccctgccg
cttaccggatacctgtccgcctttctcccttcgggaagcgtggcgctttctcatagctcacgctgtaggtatctcagttcggtgtaggtcgttcgctcc
aagctgggctgtgtgcacgaacccccccgttcagcccgaccgctgcgccttatccggtaactatcgtcttgagtccaacccggtaagacacgactt
atcgccactggcagcagccactggtaacaggattagcagagcgaggtatgtaggcggtgctacagagttcttgaagtggtggcctaactacggc
tacactagaagaacagtatttggtatctgcgctctgctgaagccagttaccttcggaaaaagagttggtagctcttgatccggcaaacaaaccac
cgctggtagcggtggtttttttgtttgcaagcagcagattacgcgcagaaaaaaaggatctcaagaagatcctttgatctttttctacggggtctga
cgctcagtggaacgaaaactcacgttaagggattttggtcatgagattatcaaaaaggatcttcacctagatccttttaaattaaaaatgaagttt
taaatcaatctaaagtatatatgagtaaacttggtctgacagttaccaatgcttaatcagtgaggcacctatctcagcgatctgtctatttcgttcat
ccatagttgcctgactcgggggggggggggcgctgaggtctgcctcgtgaagaaggtgttgctgactcataccaggcctgaatcgccccatcatcc
agccagaaagtgagggagccacggttgatgagagctttgttgtaggtggaccagttggtgattttgaacttttgctttgccacggaacggtctgcg
ttgtcgggaagatgcgtgatctgatccttcaactcagcaaaagttcgatttattcaacaaagccgccgtcccgtcaagtcagcgtaatgctctgcc
agtgttacaaccaattaaccaattctgattagaaaaactcatcgagcatcaaatgaaactgcaatttattcatatcaggattatcaataccatatt
tttgaaaagccgtttctgtaatgaaggagaaaactcaccgaggcagttccataggatggcaagatcctggtatcggtctgcgattccgactcgt
ccaacatcaatacaacctattaatttcccctcgtcaaaaataaggttatcaagtgagaaatcaccatgagtgacgactgaatccggtgagaatgg
caaaagcttatgcatttcttttccagacttgttcaacaggccagccattacgctcgtcatcaaaatcactcgcatcaaccaaaccgttattcattcgt
gattgcgcctgagcgagacgaaatacgcgatcgctgttaaaaggacaattacaaacaggaatcgaatgcaaccggcgcaggaacactgccag
cgcatcaacaatattttcacctgaatcaggatattcttctaatacctggaatgctgttttcccggggatcgcagtggtgagtaaccatgcatcatca
ggagtacggataaaatgcttgatggtcggaagaggcataaattccgtcagccagtttagtctgaccatctcatctgtaacatcattggcaacgct
acctttgccatgtttcagaaacaactctggcgcatcgggcttcccatacaatcgatagattgtcgcacctgattgcccgacattatcgcgagcccat
ttatacccatataaatcagcatccatgttgaatttaatcgcggcctcgagcaagacgtttcccgttgaatatggctcataacaccccttgtattac
tgtttatgtaagcagacagttttattgttcatgatgatatattttatcttgtgcaatgtaacatcagagattttgagacacaacgtggctttcccccc
cccccattattgaagcatttatcagggttattgtctcatgagcggatacatatttgaatgtatttagaaaaataaacaatagggggttccgcgca
catttccccgaaaagtgccacctgacgtctaagaaaccattattatcatgacattaacctataaaaataggcgtatcacgaggccctttcgtc

Fig. 42-2

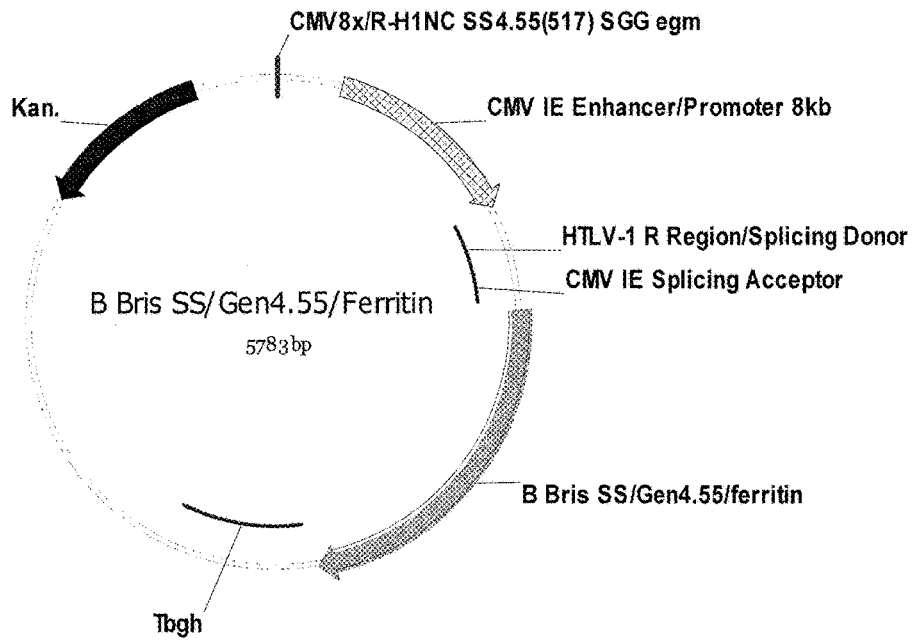

B Bris SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgcccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctccccttggagcctacctagactcagccggctctccacgctttgcctgaccctgcttgctcaactctagttaacggtggagggcagtgtagtctg
agcagtactcgttgctgccgcgcgccaccagacataatagctgacagactaacagactgttcctttccatgggtcttttctgcagtcaccgtcgt
cgacacgtgtgatcagatatcgcggccgctctagagatatcgccaccatgaaggccatcatcgtgctgctgatggtggtcacaagcaacgccga
tagaatctgtaccggcatcaccagcagcaatagccctcacgtcgtgaaaacagctacacagggcgaagtgaatgtgaccggcgtgatccctctg
ggatcaggactgaagctggccaatggcacaaagtatagacctccagccaagctgctgaaagagagaggcttttttggagctatcgccggctttct
ggaaggcggatgggagggaatgattgctggatggcatggctacacatctcatggcgcacatggcgtggcagtggctgctgatctgaaatctaca
caggaagccatcaacaagatcaccaagaacctgaacagcctgagcgagctggaaggaggcgaccccgagtgggatcgcgaaatcaacaact
acacatctatcatctacagtctgattgaggaaagccagaaccagcaggagaatgggactggggaggctccggaatcgtgcagcagcagaac
aatctgctgcgagccattgaagctcagcagcacctgctgcagctgacagtgtggggcatcaagcagctgcaggggagccagattgaactggctg
tgctgctgtctaacgagggcatcatcaatagcgaggacgaacatctgctggccctggaaagaaagctgaagaagatgctgggacctagcgccg
tggaaatcggcaatggatgctttgagacaaagcacaagtgcaaccagacctgcctggatagaattgccgccggaacatttgatgccggcgagtt
ttctctgcccaccttcgatagcctgaatatcacatccggaggcgacatcatcaagctgctgaacgagcaggtgaacaaggagatgcagagcagc
aacctgtacatgagcatgagcagctggtgctacacccacagcctggacggcgccggcctgttcctgttcgaccacgccgccgaggagtacgagc

Fig. 43-1

```
acgccaagaagctgatcatcttcctgaacgagaacaacgtgcccgtgcagctgaccagcatcagcgcccccgagcacaagttcgagggcctga
cccagatcttccagaaggcctacgagcacgagcagcacatcagcgagagcatcaacaacatcgtggaccacgccatcaagagcaaggaccac
gccaccttcaacttcctgcagtggtacgtggccgagcagcacgaggaggaggtgctgttcaaggacatcctggacaagatcgagctgatcggca
acgagaaccacggcctgtacctggccgaccagtacgtgaagggcatcgccaagagcaggaagagcggatcctagtagcatcatcatcatcatc
attagtctgaagggcgaattgatccagctgtgtgccttctagttgccagccatctgttgtttgccccctccccgtgccttccttgaccctggaaggtgcc
actcccactgtcctttcctaataaaatgaggaaattgcatcgcattgtctgagtaggtgtcattctattctgggggtggggtggggcaggacagc
aaggggggaggattgggaagacaatagcaggcatgctggggatgcggtgggctctatgggtacccaggtgctgaagaattgacccggttcctcct
gggccagaaagaagcaggcacatccccttctctgtgacacaccctgtccacgcccctggttcttagttccagcccactcataggacactcatag
ctcaggagggctccgccttcaatcccacccgctaaagtacttggagcggtctctccctccctcatcagcccaccaaaccaaacctagcctccaag
agtgggaagaaattaaagcaagataggctattaagtgcagagggagagaaaatgcctccaacatgtgaggaagtaatgagagaaatcatag
aattttaaggccatgatttaaggccatcatggccttaatcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagcaaaaggcca
ggaaccgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacctgtc
cgcctttctcccttcgggaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaagaacag
tatttggtatctgcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagtggaacgaa
aactcacgttaagggattttggtcatgagattatcaaaaaggatcttcacctagatccttttaaattaaaaatgaagtttaaatcaatctaaagta
tatatgagtaaacttggtctgacagttaccaatgcttaatcagtgaggcacctatctcagcgatctgtctatttcgttcatccatagttgcctgactc
ggggggggggggcgctgaggtctgcctcgtgaagaaggtgttgctgactcataccaggcctgaatcgccccatcatccagccagaaagtgagg
gagccacggttgatgagagctttgttgtaggtggaccagttggtgattttgaacttttgctttgccacggaacggtctgcgttgtcgggaagatgcg
tgatctgatccttcaactcagcaaaagttcgatttattcaacaaagccgccgtcccgtcaagtcagcgtaatgctctgccagtgttacaaccaatt
aaccaattctgattagaaaaactcatcgagcatcaaatgaaactgcaatttattcatatcaggattatcaataccatatttttgaaaaagccgttt
ctgtaatgaaggagaaaactcaccgaggcagttccataggatggcaagatcctggtatcggtctgcgattccgactcgtccaacatcaatacaa
cctattaatttcccctcgtcaaaaataaggttatcaagtgagaaatcaccatgagtgacgactgaatccggtgagaatggcaaaagcttatgcat
ttctttccagacttgttcaacaggccagccattacgctcgtcatcaaaatcactcgcatcaaccaaaccgttattcattcgtgattgcgcctgagcg
agacgaaatacgcgatcgctgttaaaaggacaattacaaacaggaatcgaatgcaaccggcgcaggaacactgccagcgcatcaacaatattt
tcacctgaatcaggatattcttctaatacctggaatgctgttttcccggggatcgcagtggtgagtaaccatgcatcatcaggagtacggataaaa
tgcttgatggtcggaagaggcataaattccgtcagccagtttagtctgaccatctcatctgtaacatcattggcaacgctaccttgccatgtttca
gaaacaactctggcgcatcgggcttcccataccaatcgatagattgtcgcacctgattgcccgacattatcgcgagcccatttatacccatataaat
cagcatccatgttggaatttaatcgcggcctcgagcaagacgtttcccgttgaatatggctcataacaccccttgtattactgtttatgtaagcaga
cagtttattgttcatgatgatatattttatcttgtgcaatgtaacatcagagattttgagacacaacgtggctttccccccccccccccattattgaag
catttatcagggttattgtctcatgagcggatacatatttgaatgtatttagaaaaataaacaaatagggggttccgcgcacatttccccgaaaagt
gccacctgacgtctaagaaaccattattatcatgacattaacctataaaaataggcgtatcacgaggccctttcgtc
```

Fig. 43-2

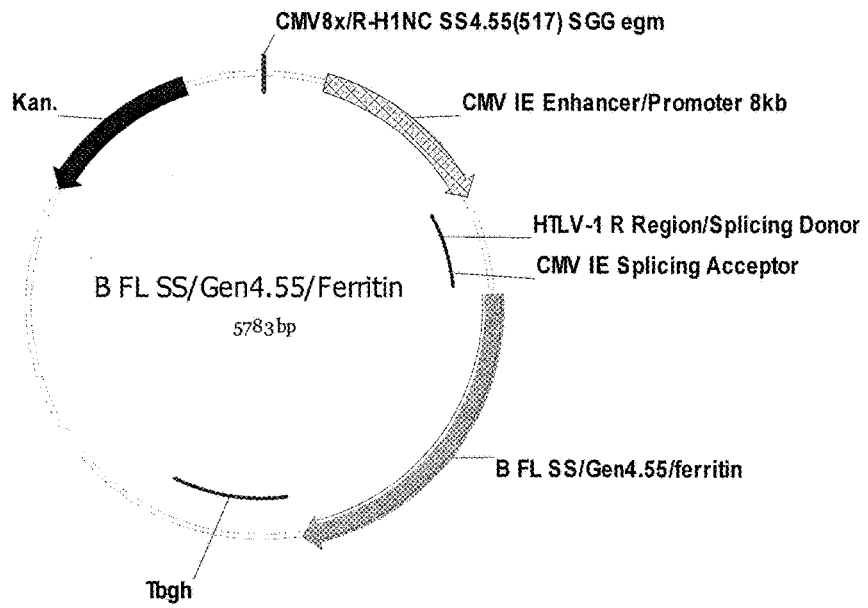

B FL SS/Gen4.55/ferritin
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgccggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaataggggaacttccattgacgtcaatgggtggagtatttacggtaaactgcccacttgggaatttccaagtgtatcatatgccaa
gtacgccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaatttcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgccaccagacataatagctgacagactaacagactgttccttttccatgggtcttttctgcagtcaccgtcgt
cgacacgtgtgatcagatatcgcggccgctctagagatatcgccaccatgaaggccatcatcgtgctgctgatggtggtgaccagcaacgccgat
agaatctgcaccggcatcaccagcagcaatagccccatgtggtgaaaacagccacccagggcgaagtgaatgtgacaggcgtgatccctctg
ggatcaggactgaagctggccaatggcaccaagtacagaacctcccgccaagctgctgaaagagagaggcttctttggcgccattgccggatttc
tggaaggcggctgggagggaatgattgccggctggcacggctatacatctcatgggcccatggcgtggctgtggccgccgatctgaagtctac
ccaggaagccatcaacaagatcaccaagaacctgaacagcctgagcgagctggaaggaggcgaccccgagtgggatcgcgaaatcaacaac
tacacatctatcatctacagtctgattgaggaaagccagaaccagcaggagaatggaactggggggaggctccggaatcgtgcagcagcagaac
aatctgctgcgagccattgaagctcagcagcacctgctgcagctgacagtgtggggcatcaagcagctgcaggggtcccagattgaactggccg
tgctgctgtccaacgagggcatcatcaacagcgaggatgaacacctgctggccctgggaacggaagctgaagaagatgctgggcccttctgccgt
gggagatcggcaacggctgcttcgagacaaagcacaagtgcaaccagacctgcctggatagaatcgccgctggcaccttcaatgccggcgagtt
cagcctgcctaccttcgacagcctgaatatcacctccggaggcgacatcatcaagctgctgaacgagcaggtgaacaaggagatgcagagcag
caacctgtacatgagcatgagcagctggtgctacacccacagcctggacggcgccggcctgttcctgttcgaccacgccgccgaggagtacgag
cacgccaagaagctgatcatcttcctgaacgagaacaacgtgcccgtgcagctgaccagcatcagcgccccgagcacaagttcgagggcctg

Fig. 44-1

```
acccagatcttccagaaggcctacgagcacgagcagcacatcagcgagagcatcaacaacatcgtggaccacgccatcaagagcaaggacca
cgccaccttcaacttcctgcagtggtacgtggccgagcagcacgaggaggaggtgctgttcaaggacatcctggacaagatcgagctgatcggc
aacgagaaccacggcctgtacctggccgaccagtacgtgaagggcatcgccaagagcaggaagagcggatcctagtagcatcatcatcatcat
cattagtctgaagggcgaattgatccagctgtgccttctagttgccagccatctgttgtttgccctccccgtgccttccttgaccctggaaggtgc
cactcccactgtcctttcctaataaaatgaggaaattgcatcgcattgtctgagtaggtgtcattctattctgggggtggggtggggcaggacag
caaggggggaggattgggaagacaatagcaggcatgctggggatgcggtgggctctatgggtacccaggtgctgaagaattgacccggttcctc
ctgggccagaaagaagcaggcacatccccttctctgtgacacaccctgtccacgcccctggttcttagttccagccccactcataggacactcata
gctcaggagggctccgccttcaatcccaccgctaaagtacttggagcggtctctccctccctcatcagcccaccaaaccaaacctagcctccaa
gagtgggaagaaattaaagcaagataggctattaagtgcagagggagagaaaatgcctccaacatgtgaggaagtaatgagagaaatcatag
aattttaaggccatgatttaaggccatcatggccttaatcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagcaaaaggcca
ggaaccgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacctgtc
cgcctttctcccttcgggaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaagaacag
tatttggtatctgcgctctgctgaagccagttaccttcggaaaaagagttggtagctcttgatccggcaaacaaaccaccgctggtagcggtggtt
ttttgtttgcaagcagcagattacgcgcagaaaaaaaggatctcaagaagatcctttgatcttttctacggggtctgacgctcagtggaacgaa
aactcacgttaagggattttggtcatgagattatcaaaaaggatcttcacctagatccttttaaattaaaaatgaagttttaaatcaatctaaagta
tatatgagtaaacttggtctgacagttaccaatgcttaatcagtgaggcacctatctcagcgatctgtctatttcgttcatccatagttgcctgactc
ggggggggggggcgctgaggtctgcctcgtgaagaaggtgttgctgactcataccaggcctgaatcgccccatcatccagccagaaagtgagg
gagccacggttgatgagagctttgttgtaggtggaccagttggtgattttgaacttttgctttgccacggaacggtctgcgttgtcgggaagatgcg
tgatctgatccttcaactcagcaaagttcgatttattcaacaaagccgccgtcccgtcaagtcagcgtaatgctctgccagtgttacaaccaatt
aaccaattctgattagaaaaactcatcgagcatcaaatgaaactgcaatttattcatatcaggattatcaataccatatttttgaaaaagccgttt
ctgtaatgaaggagaaaactcaccgaggcagttccataggatggcaagatcctggtatcggtctgcgattccgactcgtccaacatcaatacaa
cctattaatttcccctcgtcaaaaataaggttatcaagtgagaaatcaccatgagtgacgactgaatccggtgagaatggcaaaagcttatgcat
ttctttccagacttgttcaacaggccagccattacgctcgtcatcaaaatcactcgcatcaaccaaaccgttattcattcgtgattgcgcctgagcg
agacgaaatacgcgatcgctgttaaaaggacaattacaaacaggaatcgaatgcaaccggcgcaggaacactgccagcgcatcaacaatattt
tcacctgaatcaggatattcttctaatacctggaatgctgttttcccggggatcgcagtggtgagtaaccatgcatcatcaggagtacggataaaa
tgcttgatggtcggaagaggcataaattccgtcagccagtttagtctgaccatctcatctgtaacatcattggcaacgctacctttgccatgtttca
gaaacaactctggcgcatcgggcttcccatacaatcgatagattgtcgcacctgattgcccgacattatcgcgagcccatttatacccatataat
cagcatccatgttgaatttaatcgcggcctcgagcaagacgtttcccgttgaatatggctcataacaccccttgtattactgtttatgtaagcaga
cagtttattgttcatgatgatatattttatcttgtgcaatgtaacatcagagattttgagacacaacgtggctttccccccccccccattattgaag
catttatcagggttattgtctcatgagcggatacatatttgaatgtatttagaaaaataaacaatagggggttccgcgcacatttccccgaaaagt
gccacctgacgtctaagaaaccattattatcatgacattaacctataaaaataggcgtatcacgaggccctttcgtc
```

Fig. 44-2

NUCLEIC ACID MOLECULES ENCODING FERRITIN-HEMAGGLUTININ FUSION PROTEINS

CROSS REFERENCE TO RELATED APPLICATIONS

This application is a divisional of U.S. patent application Ser. No. 14/346,849, filed Mar. 24, 2014; which is a national stage application under 35 U.S.C. 371 and claims the benefit of PCT Application No. PCT/US2012/056822 having an international filing date of Sep. 24, 2012, which designated the United States; which PCT application claimed the benefit of U.S. Provisional Application No. 61/538,663, filed Sep. 23, 2011, and U.S. Provisional Application No. 61/661,209, filed Jun. 18, 2012; the disclosure of each of which are incorporated herein by reference.

REFERENCE TO SEQUENCE LISTING

This application contains a Sequence Listing submitted as an electronic text file named "6137NIAID-26-C1-PCT_sequence_listing_ST25.txt", having a size in bytes of 529 KB, and created on Aug. 20, 2014. The information contained in this electronic file is hereby incorporated by reference in its entirety pursuant to 37 CFR § 1.52(e)(5).

SUMMARY OF THE INVENTION

The present invention provides novel hemagglutinin protein-based influenza vaccines that are easily manufactured, potent, and which elicit broadly neutralizing influenza antibodies. In particular, the present invention provides influenza hemagglutinin proteins, and portions thereof, that are useful in inducing the production of neutralizing antibodies. It also provides novel HA-ferritin nanoparticle (np) vaccines. Such nanoparticles comprise fusion proteins, each of which comprises a monomeric subunit of ferritin joined to an immunogenic portion of an influenza hemagglutinin protein. Because such nanoparticles display influenza hemagglutinin protein on their surface, they can be used to vaccinate an individual against influenza virus.

In one embodiment, the invention is a nanoparticle that comprises a fusion protein, and in this embodiment the fusion protein comprises at least 25 contiguous amino acids from a monomeric ferritin subunit protein joined to a first influenza hemagglutinin (HA) protein, such that the nanoparticle comprises influenza virus HA protein trimers on its surface. The nanoparticle can form an octahedron, which can consist of 24 subunits having 432 symmetry. Further, the monomeric ferritin subunit protein can be selected from a bacterial ferritin, a plant ferritin, an algal ferritin, an insect ferritin, a fungal ferritin and a mammalian ferritin, and in a preferred embodiment, is a *Helicobacter pylori* ferritin protein.

In this embodiment, the monomeric ferritin subunit protein can comprise at least 25 contiguous amino acids of an amino acid sequence selected from SEQ ID NO:2 and SEQ ID NO:5 or can comprise an amino acid at least about 80% identical, at least about 85% identical, at least about 90% identical, at least about 95% identical, at least about 97% identical, at least about 99% identical to those sequences or can comprise those sequences. In another embodiment, the monomeric subunit comprises a region corresponding to amino acids 5-167 of SEQ ID NO:2.

In this embodiment, the hemagglutinin protein can comprise at least 25 contiguous amino acids from the hemagglutinin protein of an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). Also, the hemagglutinin protein can comprise an amino acid sequence that is selected from the amino acid sequences of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least 80% identical, at least about 85% identical, at least about 90% identical, at least about 95% identical, at least about 97% identical, at least about 99% identical thereto. Alternatively, the hemagglutinin protein can comprise an amino acid sequence that is selected from the amino acid sequences of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98 or one that is at least 80% identical, at least about 85% identical, at least about 90% identical, at least about 95% identical, at least about 97% identical, at least about 99% identical thereto.

In this embodiment, the hemagglutinin protein can be capable of eliciting an immune response to a protein comprising an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or it can comprise a region selected from a region capable of allowing formation of a hemagglutinin trimer, a stem region, an ectodomain, and a region comprising the amino acid sequence from the amino acid residue immediately distal to the last amino acid of the second helical coiled coil to the amino acid residue proximal to the first amino acid of the transmembrane domain.

The hemagglutinin protein can also comprise a hemagglutinin spike domain, a region corresponding to amino acids 1-519 of SEQ ID NO:8 or an amino acid sequence selected from the group consisting of amino acids 1-519 of SEQ ID NO:8 and SEQ ID NO:11.

In this embodiment, the fusion protein can comprise a linker sequence.

In this embodiment, the nanoparticle can elicit an immune response against a stem region of influenza hemagglutinin, a spike of influenza hemagglutinin, an influenza virus strain that is heterologous to the strain influenza virus from which the hemagglutinin protein was obtained or an influenza virus that is antigenically divergent from the influenza virus from which the hemagglutinin protein was obtained.

In this embodiment, the fusion protein can comprise an amino acid sequence at least about 80% identical, at least about 85% identical, at least about 90% identical, at least about 95% identical, at least about 97% identical, at least about 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68, wherein the nanoparticle elicits an immune response against an influenza virus or can comprise an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. The fusion protein can also comprise an amino acid sequence at least 80% identical, at least about 85% identical, at least about 90% identical, at least about 95% identical, at least about 97% identical, at least about 99% identical to a sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the nanoparticle elicits an immune response against an influenza virus.

In this embodiment, the nanoparticle can comprise a second fusion protein comprising a second influenza hemagglutinin protein, wherein the first and second influenza hemagglutinin proteins are from different Types, from different sub-types or different strains of influenza viruses.

Another embodiment of the present invention is a vaccine composition comprising any of the foregoing nanoparticle. The vaccine composition can further comprise at least one additional nanoparticle that comprises at least one hemagglutinin protein from a different strain of influenza than the first hemagglutinin protein and the second hemagglutinin protein.

A further embodiment of the invention is a method to produce a vaccine against influenza virus. The method includes expressing a fusion protein comprising a monomeric ferritin protein joined to an influenza hemagglutinin protein under conditions such that the fusion proteins form a nanoparticle displaying hemagglutinin trimers on its surface and recovering the nanoparticle.

The invention also includes a method to vaccinate an individual against influenza that includes administering a nanoparticle to an individual such that the nanoparticle elicits an immune response against influenza virus. In this embodiment, the nanoparticle comprises a monomeric subunit of ferritin joined to an influenza hemagglutinin protein and the nanoparticle displays influenza hemagglutinin trimers on its surface. In this embodiment, the nanoparticle can elicit an immune response to an influenza virus strain that is heterologous to the sub-type or strain of or that is antigenically divergent from the influenza virus from which the hemagglutinin protein was obtained.

This method can further include administering to the individual a first vaccine composition and then at a later time, administering a second vaccine composition comprising a nanoparticle that comprises an HA-SS-ferritin fusion protein. The HA SS-ferritin fusion protein can comprise an amino acid sequence selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98 or one that is at least 80% identical, at least 85% identical, at least 90% identical, at least 95% identical, at least 97% identical or at least 99% identical thereto, wherein the HA SS-ferritin fusion protein elicits an immune response to an influenza virus. The HA SS-ferritin fusion protein can comprise an amino acid sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, or one at least 80% identical, at least 85% identical, at least 90% identical, at least 95% identical, at least 97% identical or at least 99% identical thereto, wherein the HA SS-ferritin fusion protein elicits an immune response to an influenza virus.

In this method, the first vaccine composition can comprise a nanoparticle comprising an ectodomain from the hemagglutinin protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). Alternatively, the hemagglutinin of the first vaccine composition protein can comprise an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least about 80% identical, at least about 85% identical, at least about 90% identical, at least about 95% identical, at least about 97% identical, at least about 99% identical thereto. Further, the first vaccine composition can comprise an HA-ferritin fusion protein comprising an amino acid sequence selected from SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68 or an amino acid sequence that is at least 80% identical, at least about 85% identical, at least about 90% identical, at least about 95% identical, at least about 97% identical, at least about 99% identical thereto, wherein the nanoparticle elicits an immune response against an influenza virus.

Administration of the boosting composition is generally weeks or months after administration of the priming composition.

A further embodiment of the present invention is a fusion protein comprising a monomeric ferritin subunit protein joined to an influenza hemagglutinin protein. The monomeric ferritin subunit protein can be selected from a bacterial ferritin, a plant ferritin, an algal ferritin, an insect ferritin, a fungal ferritin and a mammalian ferritin or can be a monomeric subunit of a *Helicobacter pylori* ferritin protein. The monomeric ferritin subunit protein can comprise a domain that allows the fusion protein to self-assemble into nanoparticles. In this embodiment, the monomeric ferritin subunit protein can comprise SEQ ID NO:2 or SEQ ID NO:5 or comprise at least 25 contiguous amino acids from or be at least about 80% identical, at least about 85% identical, at least about 90% identical, at least about 95% identical, at least about 97% identical, at least about 99% identical to a sequence selected from SEQ ID NO:2 and SEQ ID NO:5 and the fusion protein can be capable of self-assembling into nanoparticles. Additionally, the monomeric subunit can comprise a region corresponding to amino acids 5-167 of SEQ ID NO:2.

In this embodiment, the hemagglutinin protein can comprise at least 25 amino acids from an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B). Alternatively, the hemagglutinin protein can be capable of eliciting an immune response to a protein comprising an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least about 80% identical, at least about 85% identical, at least about 90% identical, at least about 95% identical, at least about 97% identical, at least about 99% thereto.

In this embodiment, the fusion protein can comprise an amino acid sequence selected from SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68 or one that is at least about 80% identical, at least about 85% identical, at least about 90% identical, at least about 95% identical, at least about 97% identical, at least about 99% thereto.

Further in this embodiment, the hemagglutinin protein can comprise a region selected from a region capable of allowing trimerization of the hemagglutinin protein, a stem region, an ectodomain, and a region comprising the amino acid sequence from the amino acid residue immediately distal to the last amino acid of the second helical coiled coil to the amino acid residue proximal to the first amino acid of the transmembrane domain. The hemagglutinin protein alternatively can comprise a region corresponding to amino acids 1-519 of SEQ ID NO:8, an amino acid sequence selected from the group consisting of amino acids 1-519 of SEQ ID NO:8 and SEQ ID NO:11, or a hemagglutinin spike domain. Further, the hemagglutinin protein can comprise the stem region from an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), or B/Brisbane/60/2008 (2008 Bris, B). The hemagglutinin protein can also comprise an amino acid sequence at least about 80% identical, at least about 85% identical, at least about 90% identical, at least about 95% identical, at least about 97% identical, at least about 99% to SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In this embodiment, the fusion protein can comprise one or more linker sequences or an amino acid sequence of selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128 or a sequence that is at least about 80% identical, at least about 85% identical, at least about 90% identical, at least about 95% identical, at least about 97% identical, at least about 99% thereto.

A further embodiment of the present invention is a nucleic acid molecule encoding any of the fusion proteins described above. In this embodiment, the nucleic acid molecule can be functionally linked to a promoter. Other embodiments of the invention include recombinant cells and viruses that comprise such nucleic acid molecules.

Another embodiment of the invention is a protein comprising an amino acid sequence at least 80% identical, at least about 85% identical, at least about 90% identical, at least about 95% identical, at least about 97% identical, at least about 99% to an amino acid selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98, wherein the protein is joined to one or more trimerization domains. In this embodiment, the protein can be joined to at least a portion of the head region of an influenza hemagglutinin protein, comprise one or more linker regions or elicit an immune response against an influenza virus. A further embodiment is a nucleic acid molecule encoding such a protein.

BACKGROUND

Protective immune responses induced by vaccination against influenza virus are primarily directed to the viral hemagglutinin (HA) protein, which is a glycoprotein on the surface of the virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HAL The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 Å$^2$ per trimer that is 95% conserved between A/South Carolina/1/1918 (1918 SC) and A/California/04/2009 (2009 CA) pandemic strains. The globular head includes several antigenic sites that include immunodominant epitopes. Examples include the Sa, Sb, Ca$_1$, Ca$_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, gene segments of the viral genome can undergo reassortment (antigenic shift) in host species, creating new viruses with altered antigenicity that are capable of becoming pandemics [Salomon, R. et al. *Cell* 136, 402-410 (2009)]. Until now, each year, influenza vaccine is updated to reflect the predicted HA and neuraminidase (NA) for upcoming circulating viruses.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs that often comprise HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as current vaccines do, and thus, does not likely improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Recently, entirely new classes of broadly neutralizing antibodies against influenza viruses were isolated. One class of antibodies recognizes the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)], and another class of antibodies precisely recognizes the sialic acid binding site of the RBD on the variable HA head [Whittle, J. R. et al. *Proc Natl Acad Sci USA* 108, 14216-14221 (2011); Krause, J. C. et al. *J Virol* 85, 10905-10908 (2011)]. Unlike strain-specific antibodies, those antibodies are capable of neutralizing multiple antigenically distinct viruses, and hence inducing such antibodies has been a focus of next generation universal vaccine [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLoS Pathog* 6, e1000796 (2010); Wei, C. J. et al. *Science* 329, 1060-1064 (2010)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. *Science* 257, 522-523 (1992); Naitou, M. et al. U.S. Patent 2011/0038025 (2011); Yamashita, I. *Biochim Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that protects individuals from heterologous strains of influenza virus, including evolving seasonal and pandemic influenza virus strains of the future. The present invention meets this need by providing a novel HA-ferritin nanoparticle (HA-ferritin np) influenza vaccine that is easily manufactured, potent, and elicits broadly neutralizing influenza antibodies

BRIEF DESCRIPTION OF THE FIGURES

FIG. 1A-1J. Molecular design and construction of ferritin particles displaying influenza virus hemagglutinin. (A) Ribbon diagram of a subunit of *H. pylori* nonheme ferritin (PDB: 3bve). Amino- and carboxyl-termini are labeled as N and C, respectively. (B) Three ferritin subunits surrounding an octahedral three-fold axis are shown as a ribbon diagram. Residue Asp5 is indicated. (C) The octahedral assembly of the ferritin particle (viewed at 8 Å resolution along an octahedral three-fold axis) and A/Solomon Islands/3/2006 (H1N1) HA trimer (PDB: 3sm5) (viewed down from membrane proximal side). The measured average distance between the Asp5 residues in each ferritin subunit surrounding an octahedral three-fold axis is shown as a triangle. The same equilateral triangle (a=b=c=28 Å) is also drawn on the HA trimer (right). (D) Schematic representation of the HA-ferritin expression vector used for protein production. (E) Chromatogram of the size exclusion chromatography of ferritin nanoparticles (np) and HA-np. Molecular weights (kDa) of calibration standards are indicated above the curves with vertical lines. Calculated molecular weights for ferritin nanoparticles and HA-np were 419 and 2,165 kDa, respectively, and were within 10% of the predicted molecular weights (408 and 2,040 kDa, respectively). (F) Particle size distribution (radius) of purified ferritin nanoparticles and HA-np was determined by dynamic light scattering. Measured mean diameters (d) are indicated. The polydispersity indices of purified ferritin np and HA-np were 0.035 and 0.011, respectively. (G) Purified HA trimer (thrombin uncleaved), HA-np and ferritin nanoparticles were analyzed by SDS-PAGE. (H and I) Negatively stained transmission electron microscopy images of ferritin nanoparticles (left) and HA-np. Images were originally recorded at 67,000× magnification. (J) Models representing octahedral four-, three- and two-fold symmetries of HA-ferritin np (top panels) and actual TEM image (bottom panels) are shown. Visible HA spikes are numbered in the images.

FIG. 3A-3B. Antigenic characterization of HA-ferritin np. (A) Binding of mAbs directed to globular head and stem of HA was measured by ELISA. Equal amount (200 ng of HA per well) of HA trimer (▲), TIV (■), HA-ferritin (●) or Ferr (equimolar amount as HA-Ferr) (○) were coated on the plates and wells were probed with anti-head mAb (3u-u) and anti-stem mAb CR6261. The half maximal effective concentrations ($EC_{50}$) of binding were calculated for each antibody and showed as ng $ml^{-1}$ (B) Inhibition of antibody-mediated neutralization of 1999 NC pseudotyped virus by using HA trimer, HA-Ferr or Ferr as a competitor. Inhibition of neutralization was plotted as percent inhibition respect to no competitor control. The anti-stem neutralizing mAbs, F10 (left) and CR6261 (right) were used at 3.125 and 25 μg $ml^{-1}$, respectively. Competitor proteins were added to the reactions at a final concentration of 20 μg $ml^{-1}$.

FIG. 4A-4F. Immune responses in HA-np-immunized mice. (A) HAI, (B) $IC_{90}$ neutralization, and (C) anti-HA ab endpoint titers against 1999 NC HA after two immunizations with 0.17 μg (amount of H1 HA) of TIV or HA-np with or without Ribi adjuvant and a 3-week interval. The immune sera were collected 2 weeks after the second immunization. The data are presented as box-and-whiskers plots (boxed from lower to upper quartile with whiskers from minimum to maximum) with lines at the mean (n=5). (D) Neutralization breadth of the immune sera elicited by HA-trimer, TIV, or HA-np. An additional group of mice (n=4) was immunized twice with 20 μg of trimeric HA protein using Ribi adjuvant and a 4-week interval. The immune sera were collected 2 weeks after the second immunization. $IC_{50}$ neutralization titers against a panel of H1N1 pseudotyped viruses were determined. (E) Cellular and humoral immune responses against *H. pylori* (top) and mouse (bottom) ferritins. Mice were immunized twice with 1.67 μg (amount of H1 HA) of TIV or HA-np, or 0.57 μg of ferritin nanoparticles (equimolar to HA-np) using Ribi adjuvant and a 3-week interval. The splenocytes and immune sera were harvested 11 days after the second immunization. Cytokine-producing $CD4^+$ (left) and $CD8^+$ (right)_T cells were measured by ICS, (F) ab response was detected by ELISA. All cells expressing IFN-γ, TNFα, or IL-2 were identified as $cytokine^+$ cells. The percentage of $cytokine^+$ cells in $CD4^+$ and $CD8^+$ T cells that were activated in response to stimulation with specific peptides covering the entire *H. pylori* or mouse ferritins (heavy and light chains combined) were plotted. Recombinant *H. pylori* and purified mouse (liver) ferritins were used for detecting anti-ferritin ab responses. The data are presented as box-and-whiskers plots with lines at the mean (n=5).

FIG. 6A-6D. Development of trivalent HA-np. (A-C) HA-np consisting of HAs from (A) 2009 CA (H1), (B) 2009 Perth (H3) or (C) 2006 FL (type B) were purified and visualized by TEM. (D) HAI titers against 2009 CA (H1N1) and 2009 Perth (H3N2) viruses in immunized mice. Mice were immunized twice with 1.67 μg (amount of HA) of monovalent H1, monovalent H3, monovalent type B, or 5.0 μg (total amount of HA) of trivalent HA-np or TIV (2011-2012 season) using Ribi adjuvant with a 3-week interval. Immune sera were collected 2 weeks after the second immunization. The data are presented as box-and-whiskers plots with lines at the mean (n=5).

FIG. 8A-8D. Improved neutralization breadth and detection of stem- and RBS-directed abs. Neutralization breadth of immune sera in ferrets. (A) $IC_{50}$ neutralization titers against a panel of H1N1 pseudotyped viruses and (B) HAI titers against 1934 PR8 and 2007 Bris H1N1 viruses were determined. The HAI titers are presented as box-and-whiskers plots with lines at the mean (n=6). (C) Stem- (left) and RBS-directed (middle) abs elicited by HA-np immunization. Ferret immune sera (diluted 1:100) were pre-absorbed with ΔStem HA-expressing cells and their binding to WT or ΔStem HA were analyzed by ELISA (left). The immune sera (diluted 1:1,000) were pre-absorbed with ΔRBS HA-expressing cells and their binding to WT or ΔRBS HA were analyzed by ELISA (middle). The mean endpoint dilution titers were plotted with s.d. (n=6). Competition ELISA with stem-directed mAb CR6261 (right). The immune sera pre-absorbed with ΔStem were tested for binding to HA in the presence of an isotype control IgG or CR6261. Each symbol represents the titer of an individual ferret (n=6). (D) Neutralization competition with WT, ΔStem or ΔRBS HA protein. The neutralization of HA-np immune sera against 1986 Sing, 1995 Beijing, 1999 NC and 2007 Bris was measured in the presence of irrelevant protein (control), WT, ΔStem or ΔRBS HA as a competitor. Percent neutralizations at serum dilution 1:200 (1986 Sing, 2007 Bris), 1:800 (1995 Beijing) or 1:3,200 (1999 NC) were plotted. Each symbol represents the individual ferret serum and mean is indicated as a red line with s.d. (n=6 for 1986 Sing, 1995 Beijing and 1999 NC; n=3 for 2007 Bris). The relative contribution of the stem- and RBS-directed neutralization was determined by the inhibition of neutralization for each competitor protein (right most panel). Mean percent contributions in neutralizing each virus were plotted as pile-up bars (n=6).

FIG. 9A-9B. Characterization of ΔRBS HA probe. (A) Crystal structure of HA (A/Solomon Islands/3/2006) complex with an anti-RBS mAb CH65 Fab (PDB: 3sm5) (J. R. Whittle et al., Broadly neutralizing human antibody that recognizes the receptor-binding pocket of influenza virus hemagglutinin. *Proc Natl Acad Sci USA* 108, 14216-14221 (2011)) (left). Close up view of CH65 contact area (right). The residue HA1 190 which has been mutated to be glycosylated in ΔRBS mutant is highlighted. The CH65 Fab-bound HA1 protomer is darkened. (B) Characterization of the soluble trimer of WT and ΔRBS HAs from 1999 NC (left) and 2007 Bris (right). The WT and ΔRBS HA proteins were immunoprecipitated with anti-RBS (CH65), stem (CR6261) and control (anti-HIV, VRC01) mAbs. Immune complexes were then dissolved in Lamini buffer and analyzed by SDS-PAGE. Antibody heavy and light chains are labeled as HC and LC, respectively.

FIG. 11. Protocol for immunization of mice and ferrets using pan-group 1 HA-ferritin np. Mice were injected intramuscularly twice (Week 0 and week 4) with PBS (control) or 6.8 ug (1.7 ug of each HA-ferritin np) pan-group 1 vaccine in Ribi. Ferrets were injected intramuscularly twice (Week 0 and week 4) with PBS (control) or 10 ug (2.5 ug of each HA-ferritin np) pan-group 1 vaccine in Ribi.

FIG. 12. Neutralization activity of mouse antisera against Group1 HA pseudotyped viruses. Neutralization activity of murine antisera from control or pan Group1 HA-np immunized mice against the indicated HA pseudotyped viruses. IC50 titers are shown for all panels.

FIG. 13. Neutralization activity of ferret antisera against Group1 HA pseudotyped viruses. Neutralization activity of ferret antisera from control or pan Group1 HA np immunized ferrets against the indicated HA pseudotyped viruses. IC50 titers are shown for all panels.

FIG. 14. H1 HAI assays were performed using the sera obtained from the ferritin immunization studies. These studies were performed using actual H1 virus, and H2 and H5 HAI were performed using HA-ferritin np FIG. 15. Protection of ferrets from viral challenge with Influenza A/Brisbane/59/2007 Brisbane (H1N1) (2007 Bris). Two groups of ferrets (n=6 for control and n=5 for pan-group 1 immune) were immunized with pan Group1 HA np vaccine or PBS (control) and challenged with heterologous 2007 Bris virus ($10^{6.5}$ $EID_{50}$). Virus titers were measured in nasal swabs collected on day 3 and day 5 post challenge. Titers were determined using end-point titration in MDCK cells.

FIG. 17. Conservation of the influenza HA stem region. (left, right) Neutralizing antibodies that react with both Group 1 and Group 2 viruses act at the sites of vulnerability shown in the Figure. (Right) Space filling model of influenza HA protein illustrating amino acid sequence conservation in over 800 human H1N1 strains. Light residues indicate residues that are 100% conserved. Dark residues as indicate sites of variation.

FIG. 20A-20B. Electron microscopic analysis of nanoparticles. Purified SS-np were subjected to transmission electron microscopic analysis. The samples were negatively stained with ammonium molybdate and images were recorded on a Tecnai T12 microscope (FEI) at 80 kV with a CCD camera (AMT Corp.). Images of lower (A) and higher (B) magnifications are shown. The SS spikes were protruding perpendicularly from the particle core and clearly visible.

FIGS. 25-1 through 25-4. Map and sequence of CMV8x/R-H1NC HA(517)_SGG-egm (SEQ ID NO:130), the nucleic acid sequence encoding the related HA-ferritin fusion protein (SEQ ID NO:131) and the amino acid sequence of the encoded HA-ferritin fusion protein.

FIGS. 26-1 through 26-4. Map and sequence of CMV8x/R-H1CA HA(518)_SGG-egm (SEQ ID NO:132), the nucleic acid sequence encoding the related HA-ferritin fusion protein (SEQ ID NO:133) and the amino acid sequence of the encoded HA-ferritin fusion protein.

FIGS. 27-1 through 27-4. Map and sequence of CMV8x/R-H2Sing HA(514)_SGG-egm (SEQ ID NO:134), the nucleic acid sequence encoding the related HA-ferritin fusion protein (SEQ ID NO:135) and the amino acid sequence of the encoded HA-ferritin fusion protein.

FIGS. 28-1 through 28-4. Map and sequence of CMV8x/R-H3HK HA(519)_SGG-egm (SEQ ID NO:136), the nucleic acid sequence encoding the related HA-ferritin fusion protein (SEQ ID NO:137) and the amino acid sequence of the encoded HA-ferritin fusion protein.

FIGS. 29-1 through 29-4. Map and sequence of CMV8x/R-H3Bris HA(519)_SGG-egm (SEQ ID NO:138), the nucleic acid sequence encoding the related HA-ferritin fusion protein (SEQ ID NO:139) and the amino acid sequence of the encoded HA-ferritin fusion protein.

FIGS. 30-1 through 30-4. Map and sequence of CMV8x/R-H5Indo HA(520)_SGG-egm (SEQ ID NO:140), the nucleic acid sequence encoding the related HA-ferritin fusion protein (SEQ ID NO:141) and the amino acid sequence of the encoded HA-ferritin fusion protein.

FIGS. 31-1 through 31-4. Map and sequence of CMV8x/R-B.Florida HA(534)_SGG-egm (SEQ ID NO:142), the nucleic acid sequence encoding the related HA-ferritin fusion protein (SEQ ID NO:143) and the amino acid sequence of the encoded HA-ferritin fusion protein.

FIGS. 32-1 through 32-4. Map and sequence of CMV8x/R-H3Perth HA(519)_SGG-egm (SEQ ID NO:144), the nucleic acid sequence encoding the related HA-ferritin fusion protein (SEQ ID NO:145) and the amino acid sequence of the encoded HA-ferritin fusion protein.

FIGS. 33-1 through 33-4. Map and sequence of CMV8x/R-H1Bris HA(517)_SGG-egm (SEQ ID NO:146), the nucleic acid sequence encoding the related HA-ferritin fusion protein (SEQ ID NO:147) and the amino acid sequence of the encoded HA-ferritin fusion protein.

FIGS. 34-1 through 34-4. Map and sequence of CMV8x/R-B.Bris HA(535)_SGG-egm (SEQ ID NO:148), the nucleic acid sequence encoding the related HA-ferritin fusion protein (SEQ ID NO:149) and the amino acid sequence of the encoded HA-ferritin fusion protein.

FIGS. 35-1 through 35-3. Map and sequence of CMV8x/R-H1NC SS Gen4.55_SGG-egm (SEQ ID NO:150), the nucleic acid sequence encoding the related HA-ferritin fusion protein (SEQ ID NO:151) and the amino acid sequence of the encoded HA-ferritin fusion protein.

FIGS. 36-1 through 36-2. Map and sequence of CMV/R H1 CA SS/Gen4.55/ferritin (SEQ ID NO:152).

FIGS. 37-1 through 37-2. Map and sequence of CMV/R H1 Bris SS/Gen4.55/ferritin (SEQ ID NO:153).

FIGS. 38-1 through 38-2. Map and sequence of CMV/R H2 Sing SS/Gen4.55/ferritin (SEQ ID NO:154).

FIGS. 39-1 through 39-2. Map and sequence of CMV/R H3 Bris SS/Gen4.55/ferritin (SEQ ID NO:155).

FIGS. 40-1 through 40-2. Map and sequence of CMV/R H3 Perth SS/Gen4.55/ferritin (SEQ ID NO:156).

FIGS. 41-1 through 41-2. Map and sequence of CMV/R H3 HK68 SS/Gen4.55/ferritin (SEQ ID NO:157).

FIGS. 42-1 through 42-2. Map and sequence of CMV/R H5 Indo SS/Gen4.55/ferritin (SEQ ID NO:158).

FIGS. 43-1 through 43-2. Map and sequence of CMV/R B Bris SS/Gen4.55/ferritin (SEQ ID NO:159).

FIGS. 44-1 through 44-2. Map and sequence of CMV/R B FL SS/Gen4.55/ferritin (SEQ ID NO:160).

DETAILED DESCRIPTION OF THE INVENTION

Figures 1H, 1I, 1J:
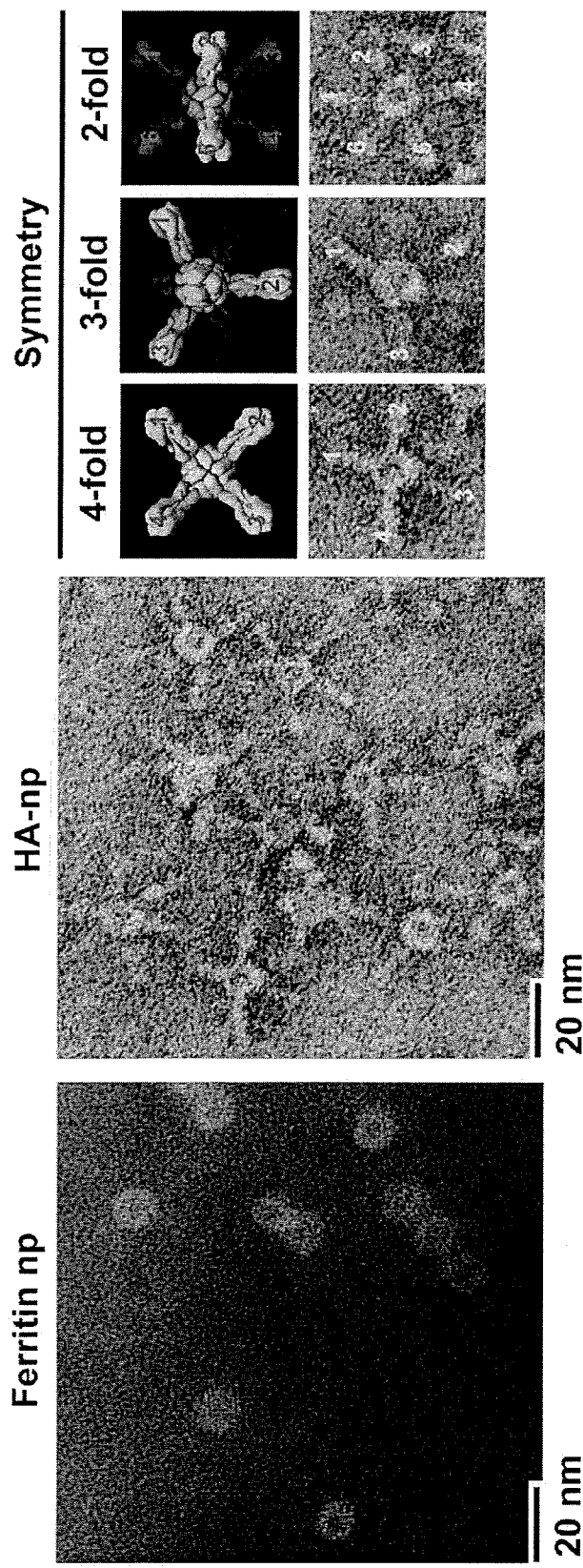

The present invention relates to a novel vaccine for influenza virus. More specifically, the present invention relates to novel, influenza hemagglutinin protein-based vaccines that elicit an immune response against a broad range of influenza viruses. It also relates to self-assembling ferritin-based, nanoparticles that display immunogenic portions of influenza hemagglutinin protein on their surface. Such nanoparticles are useful for vaccinating individuals against influenza virus. Accordingly, the present invention also relates to fusion proteins for producing such nanoparticles and nucleic acid molecules encoding such proteins. Additionally, the present invention relates to, methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical.

As used herein, an immune response to a vaccine, or nanoparticle, of the present invention is the development in a subject of a humoral and/or a cellular immune response to a hemagglutinin protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a hemagglutinin protein present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as s specific Type relates to sequence difference in the respective M1 (matrix) protein or NP (nucleoprotein). Type A influenza viruses are further divided into Group1 and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15 or H16. Group 1 influenza subtypes are H1, H2, H5, H7 and H9. Group 2 influenza subtypes are H4, H4, H6, H8, H10, H11, H12, H13, H14, H15 and H16. Finally, the term strain refers to viruses within a subtype that differ from one another in that they have small, genetic variations in their genome.

As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group I influenza virus may neutralize a Group 2 vim. AS an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15 or H16.

As used herein, an influenza hemagglutinin protein, or HA protein, refers to a full-length influenza hemagglutinin protein or any portion thereof, that is capable of eliciting an immune response. Preferred HA proteins are those that are capable of forming a trimer. An epitope of a full-length influenza hemagglutinin protein refers to a portion of such protein that can elicit a neutralizing antibody response against the homologous influenza strain, i.e., a strain from which the HA is derived. In some embodiments, such an epitope can also elicit a neutralizing antibody response against a heterologous influenza strain, i.e., a strain having an HA that is not identical to that of the HA of the immunogen.

With regard to hemagglutinin proteins, it is understood by those skilled in the art that hemagglutinin proteins from different influenza viruses may have different lengths due to mutations (insertions, deletions) in the protein. Thus, reference to a corresponding region refers to a region of another proteins that is identical, or nearly so (e.g., at least 95%, identical, at least 98% identical or at least 99% identical), in sequence, structure and/or function to the region being compared. For example, with regard to the stem region of a hemagglutinin protein, the corresponding region in another hemagglutinin protein may not have the same residue numbers, but will have a nearly identical sequence and will perform the same function. To better clarify sequences comparisons between viruses, numbering systems are used by those in the field, which relate amino acid positions to a reference sequence. Thus, corresponding amino acid residues in hemagglutinin proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the $100^{th}$ residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. Unless otherwise noted, reference to amino acids in hemagglutinin proteins herein is made using the H3 numbering system.

According to the present invention, a trimerization domain is a series of amino acids that when joined (also referred to as fused) to a protein or peptide, allow the fusion protein to interact with other fusion proteins containing the trimerization domain, such that a trimeric structure is formed. Any known trimerization domain can be used in the present invention. Examples of trimerization domains include, but are not limited to, the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit neutralizing antibodies against an influenza virus. Such activity may be measured by measuring the titer of such antibodies against influenza virus, or by measuring the number of types, subtypes or strains neutralized by the elicited antibodies. Methods of determining antibody titers and methods of performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of influenza hemagglutinin proteins are not normally found joined together via a peptide bond.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

According to the present invention, vaccines are provided that elicit a broad immune response against influenza viruses. Some vaccines disclosed herein may elicit an immune response against the entire HA protein, while others may elicit an immune response against a specific region or portion of an influenza HA protein. Moreover, the inventors have discovered that specific fusion proteins comprising portions of hemagglutinin protein are useful for eliciting a broad immune response against influenza viruses. Each of these embodiments will now be disclosed in detail below.

Vaccines Against the Stem Region of Influenza HA Protein

As stated previously, the amino acid sequence of the stem region of the hemagglutinin protein is highly conserved across types, sub-types and strains of influenza viruses and contains a site of vulnerability for group 1 viruses. Thus, an immune response directed this region of the HA protein may protect individuals against influenza viruses from several types, sub-types and/or strains.

Consequently, one embodiment of the present invention is a protein that elicits an immune response against the stem region of an influenza HA protein. In one embodiment, the immune response can be directed against the stem region of an HA protein from a virus selected from the group consisting of influenza A viruses, influenza B viruses and influenza C viruses. In one embodiment, the immune response can be directed against the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. In one embodiment, the immune response can be directed against the stem region of an HA protein from a strain of virus selected from the group of viruses listed in Table 2.

TABLE 2

| SEQ ID NO | Comments |
|---|---|
| | FERRITIN |
| 1 | Coding sequence for ferritin monomeric subunit protein from *H. pylori* |
| 2 | Amino acid sequence encoded by SEQ ID NO: 1 |
| 3 | Complement of SEQ ID NO1 |

TABLE 2-continued

| SEQ ID NO | Comments |
|---|---|
| 4 | Nucleic acid sequence encoding amino acids 5-167 from SEQ ID NO: 2; Asn19 has been replaced with Gln |
| 5 | Amino acid sequence encoded by SEQ ID NO: 3 |
| 6 | Complement of SEQ ID NO3 |
| | FULL LENGTH HA |
| 7 | Nucleic acid sequence encoding full length hemagglutinin protein from A/New Caledonia/20/1999 (1999 NC, H1)(GenBank: AY289929) |
| 8 | Amino acid sequence encoded by SEQ ID NO: 7 (full length hemagglutinin protein from A/New Caledonia/20/1999 (1999 NC, H1)(GenBank: AY289929)) |
| 9 | Complement of SEQ ID NO: 7 |
| | ECTODOMAINS |
| 10 | Nucleic acid sequence encoding ectodomain from hemagglutinin protein from A/New Caledonia/20/1999 (1999 NC, H1). |
| 11 | Amino acid sequence encoded by SEQ ID NO: 10 (ectodomain from hemagglutinin protein from A/New Caledonia/20/1999 (1999 NC, H1). Amino acids 1-517 from SEQ ID NO: 8. |
| 12 | Complement of SEQ ID NO: 10 |
| 13 | Nucleic acid sequence encoding ectodomain from hemagglutinin protein from A/California/04/2009 (2009 CA, H1). |
| 14 | Amino acid sequence encoded by SEQ ID NO: 13 (ectodomain from hemagglutinin protein from A/California/04/2009 (2009 CA, H1)) |
| 15 | Complement of SEQ ID NO: 13 |
| 16 | Nucleic acid sequence encoding ectodomain from hemagglutinin protein from A/Singapore/1/1957 (1957 Sing, H2). |
| 17 | Amino acid sequence encoded by SEQ ID NO: 16 (ectodomain from hemagglutinin protein from A/Singapore/1/1957 (1957 Sing, H2)) |
| 18 | Complement of SEQ ID NO: 16 |
| 19 | Nucleic acid sequence encoding ectodomain from hemagglutinin protein from A/Hong Kong/1/1968 (1968 HK, H3) |
| 20 | Amino acid sequence encoded by SEQ ID NO: 19) ectodomain from hemagglutinin protein from A/Hong Kong/1/1968 (1968 HK, H3)) |
| 21 | Complement of SEQ ID NO: 19 |
| 22 | Nucleic acid sequence encoding ectodomain from hemagglutinin protein from A/Brisbane/10/2007 (2007 Bris, H3). |
| 23 | Amino acid sequence encoded by SEQ ID NO: 22 (ectodomain from hemagglutinin protein from A/Brisbane/10/2007 (2007 Bris, H3)) |
| 24 | Complement of SEQ ID NO: 22 |
| 25 | Nucleic acid sequence encoding ectodomain from hemagglutinin protein from A/Indonesia/05/2005 (2005 Indo, H5) |
| 26 | Amino acid sequence encoded by SEQ ID NO: 25 (ectodomain from hemagglutinin protein from A/Indonesia/05/2005 (2005 Indo, H5)) |
| 27 | Complement of SEQ ID NO: 25 |
| 28 | Nucleic acid sequence encoding ectodomain from hemagglutinin protein from B/Florida/4/2006 (2006 Flo, B) |
| 29 | Amino acid sequence encoded by SEQ ID NO: 28 (ectodomain from hemagglutinin protein from B/Florida/4/2006 (2006 Flo, B)) |
| 30 | Complement of SEQ ID NO: 28 |
| 31 | Nucleic acid sequence encoding ectodomain from hemagglutinin protein from A/Perth/16/2009 (2009 Per, H3) |
| 32 | Amino acid sequence encoded by SEQ ID NO: 31 (ectodomain from hemagglutinin protein from A/Perth/16/2009 (2009 Per, H3)) |
| 33 | Complement of SEQ ID NO: 31 |
| 34 | Nucleic acid sequence encoding ectodomain from hemagglutinin protein from A/Brisbane/59/2007 (2007 Bris, H1) |
| 35 | Amino acid sequence encoded by SEQ ID NO: 34 (ectodomain from hemagglutinin protein from A/Brisbane/59/2007 (2007 Bris, H1)) |
| 36 | Complement of SEQ ID NO: 34 |
| 37 | Nucleic acid sequence encoding ectodomain from hemagglutinin protein from B/Brisbane/60/2008 (2008 Bris, B) |
| 38 | Amino acid sequence encoded by SEQ ID NO: 37 (ectodomain from hemagglutinin protein from B/Brisbane/60/2008 (2008 Bris, B)) |
| 39 | Complement of SEQ ID NO: 37 |
| | FERRITIN-HA ECTODOMAIN FUSION |
| 40 | Nucleic acid sequence encoding SEQ ID NO: 41 |
| 41 | Amino acid sequence of ferritin-HA fusion (ectodomain from hemagglutinin protein from A/New Caledonia/20/1999 (1999 NC, H1)) |
| 42 | Complement of SEQ ID NO: 40 |
| 43 | Nucleic acid sequence encoding SEQ ID NO: 44 |
| 44 | Amino acid sequence of ferritin-HA fusion (ectodomain from hemagglutinin protein from A/California/04/2009 (2009 CA, H1)) |
| 45 | Complement of SEQ ID NO: 43 |
| 46 | Nucleic acid sequence encoding SEQ ID NO: 47 |

TABLE 2-continued

| SEQ ID NO | Comments |
|---|---|
| 47 | Amino acid sequence of ferritin-HA fusion (ectodomain from hemagglutinin protein from A/Singapore/1/1957 (1957 Sing, H2)) |
| 48 | Complement of SEQ ID NO: 46 |
| 49 | Nucleic acid sequence encoding SEQ ID NO: 50 |
| 50 | Amino acid sequence of ferritin-HA fusion (ectodomain from hemagglutinin protein from A/Hong Kong/1/1968 (1968 HK, H3)) |
| 51 | Complement of SEQ ID NO: 49 |
| 52 | Nucleic acid sequence encoding SEQ ID NO: 53 |
| 53 | Amino acid sequence of ferritin-HA fusion (ectodomain from hemagglutinin protein from A/Brisbane/10/2007 (2007 Bris, H3)) |
| 54 | Complement of SEQ ID NO: 52 |
| 55 | Nucleic acid sequence encoding SEQ ID NO: 56 |
| 56 | Amino acid sequence of ferritin-HA fusion (ectodomain from hemagglutinin protein from A/Indonesia/05/2005 (2005 Indo, H5)) |
| 57 | Compliment of SEQ ID NO: 55 |
| 58 | Nucleic acid sequence encoding SEQ ID NO: 59 |
| 59 | Amino acid sequence of ferritin-HA fusion protein (ectodomain from hemagglutinin protein from B/Florida/4/2006 (2006 Flo, B)) |
| 60 | Complement of SEQ ID NO: 58 |
| 61 | Nucleic acid sequence encoding SEQ ID NO: 62 |
| 62 | Amino acid sequence of ferritin-HA fusion protein (ectodomain from hemagglutinin protein from A/Perth/16/2009 (2009 Per, H3)) |
| 63 | Complement of SEQ ID NO: 61 |
| 64 | Nucleic acid sequence encoding SEQ ID NO: 65 |
| 65 | Amino acid sequence of ferritin-HA fusion protein (ectodomain from hemagglutinin protein from A/Brisbane/59/2007 (2007 Bris, H1)) |
| 66 | Complement of SEQ ID NO: 64 |
| 67 | Nucleic acid sequence encoding SEQ ID NO: 68 |
| 68 | Amino acid sequence of ferritin-HA fusion protein (ectodomain from hemagglutinin protein from B/Brisbane/60/2008 (2008 Bris, B)) |
| 69 | Complement of SEQ ID NO: 67 |
| | STEM REGION |
| 70 | Nucleic acid molecule encoding SEQ ID NO: 71 |
| 71 | Amino acid sequence of stem region from A/New Caledonia/20/1999 (1999 NC, H1)(GenBank: AY289929) |
| 72 | Complement of SEQ ID NO: 70 |
| 73 | Nucleic acid sequence encoding SEQ ID NO: 74 |
| 74 | Amino acid sequence of stem region from A/California/04/2009 (2009 CA, H1) |
| 75 | Complement of SEQ ID NO: 73 |
| 76 | Nucleic acid sequence encoding SEQ ID NO: 77 |
| 77 | Amino acid sequence of stem region fro A/Singapore/1/1957 (1957 Sing, H2) |
| 78 | Complement of SEQ ID NO: 76 |
| 79 | Nucleic acid sequence encoding SEQ ID NO: 80 |
| 80 | Amino acid sequence of stem region from A/Hong Kong/1/1968 (1968 HK, H3) |
| 81 | Complement of SEQ ID NO: 79 |
| 82 | Nucleic acid sequence encoding SEQ ID NO: 83 |
| 83 | Amino acid sequence of stem region from A/Brisbane/10/2007 (2007 Bris, H3) |
| 84 | Complement of SEQ ID NO: 82 |
| 85 | Nucleic acid sequence encoding SEQ ID NO: 86 |
| 86 | Amino acid sequence of stem region from A/Indonesia/05/2005 (2005 Indo, H5) |
| 87 | Complement of SEQ ID NO: 85 |
| 88 | Nucleic acid sequence encoding SEQ ID NO: 89 |
| 89 | Amino acid sequence of stem region from B/Florida/4/2006 (2006 Flo, B) |
| 90 | Complement of SEQ ID NO: 88 |
| 91 | Nucleic acid sequence encoding SEQ ID NO: 92 |
| 92 | Amino acid sequence of stem region from A/Perth/16/2009 (2009 Per, H3) |
| 93 | Complement of SEQ ID NO: 91 |
| 94 | Nucleic acid sequence encoding SEQ ID NO: 95 |
| 95 | Amino acid sequence of stem region from A/Brisbane/59/2007 (2007 Bris, H1) |
| 96 | Complement of SEQ ID NO: 94 |
| 97 | Nucleic acid sequence encoding SEQ ID NO: 98 |
| 98 | Amino acid sequence of stem region from B/Brisbane/60/2008 (2008 Bris, B) |
| 99 | Complement of SEQ ID NO: 97 |
| | FERRITIN- HA STEM REGION FUSION |
| 100 | Nucleic acid sequence encoding SEQ ID NO: 101 |
| 101 | Amino acid sequence of ferritin-HA stem region fusion protein A/New Caledonia/20/1999 (1999 NC, H1) |

TABLE 2-continued

| SEQ ID NO | Comments |
|---|---|
| 102 | Complement of SEQ ID NO: 100 |
| 103 | Nucleic acid sequence encoding SEQ ID NO: 104 |
| 104 | Amino acid sequence of ferritin-HA stem region fusion protein (H1 CA) |
| 105 | Complement of SEQ ID NO: 103 |
| 106 | Nucleic acid sequence encoding SEQ ID NO: 107 |
| 107 | Amino acid sequence of ferritin-HA stem region fusion protein (H2 Sing ) |
| 108 | Complement of SEQ ID NO: 106 |
| 109 | Nucleic acid sequence encoding SEQ ID NO: 110 |
| 110 | Amino acid sequence of ferritin-HA stem region fusion protein (H3 Hong Kong) |
| 111 | Complement of SEQ ID NO: 109 |
| 112 | Nucleic acid sequence encoding SEQ ID NO: 113 |
| 113 | Amino acid sequence of ferritin-HA stem region fusion protein (H5 Indonesia) |
| 114 | Complement of SEQ ID NO: 112 |
| 115 | Nucleic acid sequence encoding SEQ ID NO: 116 |
| 116 | Amino acid sequence of ferritin-HA stem region fusion protein (A/Brisbane/59/2007 (2007 Bris, H1)) |
| 117 | Complement of SEQ ID NO: 115 |
| 118 | Nucleic acid sequence encoding SEQ ID NO: 119 |
| 119 | Amino acid sequence of ferritin-HA stem region fusion protein (A/Brisbane/10/2007 (2007 Bris, H3)) |
| 120 | Complement of SEQ ID NO: 118 |
| 121 | Nucleic acid sequence encoding SEQ ID NO: 122 |
| 122 | Amino acid sequence of ferritin-HA stem region fusion protein (A/Perth/16/2009 (2009 Per, H3)) |
| 123 | Complement of SEQ ID NO: 121 |
| 124 | Nucleic acid sequence encoding SEQ ID NO: 125 |
| 125 | Amino acid sequence of ferritin-HA stem region fusion protein (B/Brisbane/60/2008 (2008 Bris, B)) |
| 126 | Complement of SEQ ID NO: 124 |
| 127 | Nucleic acid sequence encoding SEQ ID NO: 128 |
| 128 | Amino acid sequence of ferritin-HA stem region fusion protein (B/Florida/4/2006 (2006 Flo, B)) |
| 129 | Complement of SEQ ID NO: 127 |
| 130 | Sequence of plasmid CMV8x/R-H1NC HA(517)_SGG_egm Synthetic sequence (FIG. 25) |
| 131 | Nucleic acid sequence encoding SEQ ID NO: 41. Contains stop codon. Identical to SEQ ID NO: 40, Synthetic (FIG. 25) |
| 132 | Sequence of plasmid CMV8x/R-H1CA HA(518)_SGG_egm Synthetic sequence (FIG. 26) |
| 133 | Nucleic acid sequence encoding SEQ ID NO: 44. Nearly identical to SEQ ID NO: 43 but lacks stop codon. (FIG. 26) |
| 134 | Sequence of plasmid CMV8x/R-H2S1NG HA(514)_SGG_egm, Synthetic sequence (FIG. 27) |
| 135 | Nucleic acid sequence encoding SEQ ID NO: 47. Nearly identical to SEQ ID NO: 46 but lacks stop codon, Synthetic (FIG. 27) |
| 136 | Sequence of plasmid CMV8x/R-H3HK HA(519)_SGG_egm Synthetic sequence (FIG. 28) |
| 137 | Nucleic acid sequence encoding SEQ ID NO: 50. Nearly identical to SEQ ID NO: 49 but lacks stop codon. Synthetic (FIG. 28) |
| 138 | Sequence of plasmid CMV8x/R-H3Bris HA(519)_SGG_egm Synthetic sequence (FIG. 29) |
| 139 | Nucleic acid sequence encoding SEQ ID NO: 53. Nearly identical to SEQ ID NO: 52 but lacks stop codon. Synthetic (FIG. 29) |
| 140 | Sequence of plasmid CMV8x/R-H5Indo HA(520)_SGG_egm, Synthetic sequence (FIG. 30) |
| 141 | Nucleic acid sequence encoding SEQ ID NO: 56. Nearly identical to SEQ ID NO: 55 but lacks stop codon. Synthetic (FIG. 30) |
| 142 | Sequence of plasmid CMV8x/R-B. Florida HA(534)_SGG_egm, Synthetic sequence (FIG. 31) |
| 143 | Nucleic acid sequence encoding SEQ ID NO: 59. Nearly identical to SEQ ID NO: 58 but lacks stop codon. Synthetic (FIG. 31) |
| 144 | Sequence of plasmid CMV8x/R-H3-Perth HA(519)_SGG_egm, Synthetic sequence (FIG. 32) |
| 145 | Nucleic acid sequence encoding SEQ ID NO: 62. Nearly identical to SEQ ID NO: 61 but lacks stop codon. Synthetic (FIG. 32) |
| 146 | Sequence of plasmid CMV8x/R-H1Bris HA(517)_SGG_egm Synthetic sequence (FIG. 33) |
| 147 | Nucleic acid sequence encoding SEQ ID NO: 65. Nearly identical to SEQ ID NO: 64 but lacks stop codon. Synthetic (FIG. 33) |
| 148 | Sequence of plasmid CMV8x/R-B. Bris HA(535)_SGG_egm Synthetic sequence (FIG. 34) |
| 149 | Nucleic acid sequence encoding SEQ ID NO: 68. Nearly identical to SEQ ID NO: 67 but lacks stop codon. Synthetic (FIG. 34) |

TABLE 2-continued

| SEQ ID NO | Comments |
|---|---|
| 150 | Sequence of plasmid CMV8x/R-H1NC SS Gen4.55__SGG__egm, Synthetic sequence (FIG. 35) |
| 151 | Nucleic acid sequence encoding SEQ ID NO: 101. Identical to SEQ ID NO: 100. Both lack stop codon. (FIG. 35) |
| 152 | Sequence of plasmid H1CA SS/Gen4.55/Ferritin Synthetic sequence (FIG. 36) |
| 153 | Sequence of plasmid H1Bris SS/Gen4.55/Ferritin Synthetic sequence (FIG. 37) |
| 154 | Sequence of plasmid H1Sing SS/Gen4.55/Ferritin Synthetic sequence (FIG. 38) |
| 155 | Sequence of plasmid H3Bris SS/Gen4.55/Ferritin Synthetic sequence (FIG. 39) |
| 156 | Sequence of plasmid H1Perth SS/Gen4.55/Ferritin Synthetic sequence (FIG. 40) |
| 157 | Sequence of plasmid H3 HK68 SS/Gen4.55/Ferritin Synthetic sequence (FIG. 41) |
| 158 | Sequence of plasmid H5Indo SS/Gen4.55/Ferritin Synthetic sequence FIG. (42) |
| 159 | Sequence of plasmid B Bris SS/Gen4.55/Ferritin Synthetic sequence (FIG. 43) |
| 160 | Sequence of plasmid B FL SS/Gen4.55/Ferritin Synthetic sequence Synthetic sequence (FIG. 44) |

One type of immune response is a B-cell response, which results in the production of antibodies against the antigen that elicited the immune response. Thus, one embodiment of the present invention is a protein that elicits antibodies that bind to the stem region of influenza HA protein from a virus selected from the group consisting of influenza A viruses, influenza B viruses and influenza C viruses. One embodiment of the present invention is a protein that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein that elicits antibodies that bind to the stem region of influenza HA protein from a strain of virus selected from the viruses listed in Table 2.

While all antibodies are capable of binding to the antigen which elicited the immune response that resulted in antibody production, preferred antibodies are those that neutralize an influenza virus. Thus, one embodiment of the present invention is a protein that elicits neutralizing antibodies that bind to the stem region of influenza HA protein from a virus selected from the group consisting of influenza A viruses, influenza B viruses and influenza C viruses. One embodiment of the present invention is a protein that elicits neutralizing antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein that elicits neutralizing antibodies that bind to the stem region of influenza HA protein from a strain of virus selected from the viruses listed in Table 2. One embodiment of the present invention is a protein that elicits neutralizing antibodies that bind to a protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein that elicits neutralizing antibodies that bind to a protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

Neutralizing antibodies elicited by proteins of the present invention can neutralize viral infections by affecting any step in the life cycle of the virus. For example, neutralizing antibodies may prevent an influenza virus from attaching to a cell, entering a cell, releasing viral ribonucleoproteins into the cytoplasm, forming new viral particles in the infected cell and budding new viral particles from the infected host cell membrane. In one embodiment, neutralizing antibodies elicited by proteins of the present invention prevent influenza virus from attaching to the host cell. In one embodiment, neutralizing antibodies elicited by proteins of the present invention prevent influenza virus from entering the host cell. In one embodiment, neutralizing antibodies elicited by proteins of the present invention prevent fusion of viral membranes with endosomal membranes. In one embodiment, neutralizing antibodies elicited by proteins of the present invention prevent release of ribonucleoproteins into the cytoplasm of the host cell. In one embodiment, neutralizing antibodies elicited by proteins of the present invention prevent assembly of new virus in the infected host cell. In one embodiment, neutralizing antibodies elicited by proteins of the present invention prevent release of newly formed virus from the infected host cell.

Because the amino acid sequence of the stem region of influenza virus is highly conserved, neutralizing antibodies elicited by proteins of the present invention may be broadly neutralizing. That is, neutralizing antibodies elicited by proteins of the present invention may neutralize influenza viruses of more than one type, subtype and/or strain, Thus, one embodiment of the present invention is a protein that elicits broadly neutralizing antibodies that bind the stem region of influenza HA protein. One embodiment is a protein that elicits antibodies that bind the stem region of an HA protein from more than one type of influenza virus selected from the group consisting of influenza type A viruses, influenza type B viruses and influenza type C viruses. One embodiment is a protein that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment is a protein that elicits antibodies that bind the stem region of an HA protein from more than strain of influenza virus. One embodiment is a protein that elicits antibodies that bind the stem region of an HA protein from more than one strain of influenza virus selected from the viruses listed in Table 2. One embodiment of the present invention is a protein that elicits antibodies that bind more than one protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein that elicits neutralizing antibodies that bind to more than one protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

Particularly useful proteins of the present invention are those comprising an immunogenic portion of an influenza HA protein. Thus, one embodiment of the present invention is a protein comprising at least one immunogenic portion from the stem region of influenza HA protein, wherein the protein elicits neutralizing antibodies against an influenza virus. Such a protein is referred to as a stem-region protein (or a stem-region immunogen). One embodiment of the present invention is a protein comprising at least one immunogenic portion from the stem region of an HA protein from a virus selected from the group consisting of influenza type A viruses, influenza type B viruses and influenza type C viruses, wherein the protein elicits neutralizing antibodies against an influenza virus. One embodiment of the present invention is a protein comprising at least one immunogenic portion from the stem region of an HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein comprising at least one immunogenic portion from the stem region of an HA protein from the viruses listed in Table 2. One embodiment of the present invention is a protein comprising at least one immunogenic portion from a protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein comprising at least one immunogenic portion from a protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, such proteins comprising immunogenic portions of the HA protein elicit the production of broadly neutralizing antibodies against influenza virus.

Immunogenic portions of proteins comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in one embodiment the immunogenic portion from the influenza HA protein comprises at least one epitope. One embodiment of the present invention is a protein comprising at least 6 amino acids, at least 10 amino acids, at least 25 amino acids, at least 50 amino acids, at least 75 amino acids or at least 100 amino acids from the stem region of influenza HA protein. One embodiment of the present invention is a protein comprising at least 6 amino acids, at least 10 amino acids, at least 25 amino acids, at least 50 amino acids, at least 75 amino acids or at least 100 amino acids from the stem region of an HA protein from a virus selected from the group consisting of influenza type A viruses, influenza type B viruses and influenza type C viruses. One embodiment of the present invention is a protein comprising at least 6 amino acids, at least 10 amino acids, at least 25 amino acids, at least 50 amino acids, at least 75 amino acids or at least 100 amino acids from the stem region of an HA protein selected from the group consisting an H1 influenza virus HA protein, an H2 influenza virus HA protein, an influenza H3 virus HA protein, an influenza H4 virus HA protein, an influenza H5 virus HA protein, an H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein comprising at least 6 amino acids, at least 10 amino acids, at least 25 amino acids, at least 50 amino acids, at least 75 amino acids or at least 100 amino acids from the stem region of an HA protein from a strain of virus selected from the viruses listed in Table 2. In one embodiment, the amino acids are contiguous amino acids from the stem region of the HA protein. In one embodiment, such proteins comprising at least 6 amino acids, at least 10 amino acids, at least 25 amino acids, at least 50 amino acids, at least 75 amino acids or at least 100 amino acids from the stem region of an HA protein elicit the production of broadly neutralizing antibodies against influenza virus. One embodiment of the present invention is a protein comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the amino acids are contiguous amino acids from the stem region of the HA protein. In one embodiment, the amino acids are non-contiguous, but are in close spatial proximity in the final protein.

While the present application discloses the use of stem regions from several exemplary HA proteins having specific sequences, the invention may also be practiced using stem regions from proteins comprising variations of the disclosed HA sequences. Thus, one embodiment of the present invention is a stem-region protein comprising an amino acid sequence at least 80%, at least 85%, at least 90%, at least 92%, at least 94%, at least 96%, at least 98% or at least 99% identical the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a stem-region protein comprising an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. One embodiment of the present invention is a stem-region protein comprising the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a stem-region protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

While the proteins disclosed thus far may elicit broadly neutralizing antibodies against an influenza virus, the inventors have discovered that such proteins are more stable and easier to purify when they exist in a trimeric form. Thus, one embodiment is a protein comprising the stem-region protein of the present invention joined to a trimerization domain. In one embodiment, the stem region is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the trimerization domain is selected from the group consisting of the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain. In one embodiment, the trimerization domain is an HIV gp41 trimerization domain.

The inventors have also found that, in some instances, stem region proteins of the present invention may be more stable when joined to at least part of the head region of the HA protein. Thus, one embodiment of the present invention is a protein comprising a stem region protein joined to the head region of an HA protein and a trimerization domain. In one embodiment, the stem region protein is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In some embodiments of the present invention, the various protein domains (e.g., stem region protein, trimerization domain, head region, etc.) may be joined directly to one another. In other embodiments, it may be necessary to employ linkers (also referred to as a spacer sequences) so that the various domains are in the proper special orientation. The linker sequence is designed to position the hemagglutinin protein in such a way to that it maintains the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SGG, GSG, GG and NGTGGSG (SEQ ID NO:162). Amino acids can be added or subtracted as needed. Those skilled in the art are capable of determining appropriate linker sequences for proteins of the present invention.

One embodiment of the present invention is a fusion protein comprising a stem region protein joined to at least a portion of the head region of an HA protein and a trimerization domain, wherein the fusion protein comprises one or more linker sequences. In one embodiment, the stem region protein is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the linker is selected from the group consisting of GG, GSG and NGTGGSG (SEQ ID NO:162). In one embodiment, the protein elicits antibodies that neutralize at least one virus that is a different Type, sub-type or strain than the Type, sub-type or strain of the virus from which the HA protein was obtained.

Vaccines Comprising HA-Ferritin Fusion Proteins

The inventors have also discovered that fusion of influenza HA protein with ferritin protein (HA-ferritin fusion protein) results in a vaccine that elicits a robust immune response to influenza virus. Such HA-ferritin fusion proteins self-assemble into nanoparticles that display immunogenic portions of influenza hemagglutinin protein on their surface. These nanoparticles are useful for vaccinating individuals against a broad range of influenza viruses. Thus, one embodiment of the present invention is an HA-ferritin fusion protein comprising a monomeric ferritin subunit disclosed herein joined to an influenza hemagglutinin protein disclosed herein, wherein the HA-ferritin fusion protein is capable of self-assembling into nanoparticles.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. It is expected that one or both of these pores represent the point by which the hydrated iron diffuses into and out of the capsid. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Amino acid sequences from monomeric ferritin subunits of any known ferritin protein can be used to produce fusion proteins of the present invention, so long as the monomeric ferritin subunit is capable of self-assembling into a nanoparticle displaying hemagglutinin on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori*.

HA-ferritin fusion proteins of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from a monomeric ferritin subunit, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from the region of a ferritin protein corresponding to the amino acid sequences of the *Helicobacter pylori* ferritin monomeric subunit that direct self-assembly of the monomeric subunits into the globular form of the ferritin protein, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from SEQ ID NO:2 that are capable of directing self-assembly of the monomeric subunits into the globular ferritin protein, wherein the HA-ferritin fusion protein is capable of self-assembling into nanoparticles. One embodiment of the present invention is an HA-ferritin fusion protein comprising an HA-protein of the present invention joined to at least 25 contiguous amino acids, at least 50 contiguous amino acids, at least 75 contiguous amino acids, at least 100 contiguous amino acids, or at least 150 contiguous amino acids from amino acid residues 5-167 of SEQ ID NO:2, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from SEQ ID NO:5, wherein the HA-ferritin fusion protein is capable of self-assembling into nanoparticles. One embodiment of the present invention is an HA-ferritin fusion protein comprising an HA protein of the present invention joined to amino acid residues 5-167 from SEQ ID NO:2, or SEQ ID NO:5, wherein the HA-ferritin fusion protein is capable of self-assembling into nanoparticles. As has been previously discussed, it is well-known in the art that some variations can be made in the amino acid sequence of a protein without affecting the activity of the protein. Such variations include insertion of amino acid residues, deletions of amino acid residues, and substitutions of amino acid residues. Thus, in one embodiment, the sequence of the monomeric ferritin subunit is divergent enough from the sequence of a ferritin subunit naturally found in a mammal, such that when the variant monomeric ferritin subunit is introduced into the mammal, it does not result in the production of antibodies that react with the mammal's natural ferritin protein. According to the present invention, such a monomeric subunit is referred to as immunogenically neutral. One embodiment of the present invention is an HA-ferritin fusion protein comprising an HA protein of the present invention joined to an amino acid sequence at least 80%, at least 85%, at least 90%, at least 95%, and at least 97% identical to the amino acid sequence of a monomeric ferritin subunit that is responsible for directing self-assembly of the monomeric ferritin subunits into the globular form of the protein, wherein the HA-ferritin fusion protein is capable of self-assembling into nanoparticles. In one embodiment, the HA-ferritin fusion protein comprises a polypeptide sequence identical in sequence to a monomeric ferritin subunit. One embodiment of the present invention is an HA-ferritin fusion protein comprising an HA protein of the present invention joined to an amino acid sequence at least 80%, at least 85%, at least 90%, at least 95%, and at least 97% identical to the amino acid sequence of a monomeric ferritin subunit from *Helicobacter pylori*, wherein the HA-ferritin fusion protein is capable of self-assembling into nanoparticles. One embodiment of the present invention is an HA-ferritin fusion protein comprising an HA protein of the present invention joined to an amino acid sequence at least 80%, at least 85%, at least 90%, at least 95%, and at least 97% identical to a sequence selected from amino acid residues 5-167 from SEQ ID NO:2 and SEQ ID NO:5, wherein the HA-ferritin fusion protein is capable of self-assembling into nanoparticles. One embodiment of the present invention is an HA-ferritin fusion protein comprising an HA protein of the present invention joined to a sequence selected from amino acid residues 5-167 from SEQ ID NO:2 and SEQ ID NO:5.

In some embodiments, it may be useful to engineer mutations into the amino acid sequences of proteins of the present invention. For example, it may be useful to alter sites such as enzyme recognition sites or glycosylation sites in the monomeric ferritin subunit, the trimerization domain, or linker sequences, in order to give the fusion protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:5.

According to the present invention, the hemagglutinin protein portion of HA-ferritin fusion proteins of the present invention can be from any influenza virus, so long as the HA-ferritin fusion protein elicits an immune response against an influenza virus. Thus, one embodiment of the preset invention is an HA-ferritin fusion protein comprising a ferritin protein of the present invention joined to an amino acid sequence from an HA protein from an influenza A virus, an influenza B virus or an influenza C virus. One embodiment of the preset invention is an HA-ferritin fusion protein comprising a ferritin protein of the present invention joined to an amino acid sequence from an influenza A Group 1 virus HA protein. One embodiment of the preset invention is an HA-ferritin fusion protein comprising a ferritin protein of the present invention joined to an amino acid sequence from an influenza A Group 2 virus HA protein. One embodiment of the preset invention is an HA-ferritin fusion protein comprising a ferritin protein of the present invention joined to an amino acid sequence from an HA protein selected from the group consisting of an H1 influenza virus HA protein, an H2 influenza virus HA protein, an H5 influenza virus HA protein, an H7 virus influenza HA protein and an H9 influenza virus HA protein. One embodiment of the preset invention is an HA-ferritin fusion protein comprising a ferritin protein of the present invention joined to an amino acid sequence from an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H15 influenza virus HA protein. One embodiment of the preset invention is an HA-ferritin fusion protein comprising a ferritin protein of the present invention joined to an amino acid sequence of an HA protein from a virus listed in Table 2.

Preferred hemagglutinin proteins to use in constructing HA-ferritin fusion proteins of the present invention are those that elicit an immune response against an influenza virus. Even more preferred hemagglutinin proteins are those that are capable of eliciting antibodies to an influenza virus. One embodiment of the present invention is an HA-ferritin fusion protein that elicits antibodies to a virus selected from the group consisting of influenza A viruses, influenza B viruses and influenza C viruses. One embodiment of the present invention is a HA-ferritin fusion protein that elicits antibodies to a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment of the present invention is an HA-ferritin fusion protein that elicits antibodies to a virus listed in Table 2. Preferred antibodies elicited by HA-ferritin fusion proteins of the present invention are those that neutralize an influenza virus. Thus, one embodiment of the present invention is an HA-ferritin fusion protein that elicits neutralizing antibodies to a virus selected from the group consisting of influenza A viruses, influenza B viruses and influenza C viruses. One embodiment of the present invention is an HA-ferritin fusion protein that elicits neutralizing antibodies to a virus having a subtype selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment of the present invention is an HA-ferritin fusion protein that elicits neutralizing antibodies to a virus listed in Table 2.

As has been discussed, neutralizing antibodies elicited by a HA-ferritin fusion protein of the present invention can neutralize viral infections by affecting any step in the life cycle of the virus. Thus, in one embodiment of the present invention, an HA-ferritin fusion protein elicits neutralizing antibodies that prevent influenza virus from attaching to the host cell. In one embodiment of the present invention, an HA-ferritin fusion protein may elicit neutralizing antibodies that prevent influenza virus from entering the host cell. In one embodiment of the present invention, an HA-ferritin fusion protein may elicit neutralizing antibodies that prevent fusion of viral membranes with endosomal membranes. In one embodiment of the present invention, an HA-ferritin fusion protein may elicit neutralizing antibodies that prevent influenza virus from releasing ribonucleoproteins into the cytoplasm of the host cell. In one embodiment of the present invention, an HA-ferritin fusion protein may elicit neutralizing antibodies that prevent assembly of new virus in the infected host cell. In one embodiment of the present invention, an HA-ferritin fusion protein may elicit neutralizing antibodies that prevent release of newly formed virus from the infected host cell.

Preferred HA-ferritin fusion proteins of the present invention are those that elicit broadly neutralizing antibodies. Thus, one embodiment is an HA-ferritin fusion protein that elicits antibodies that neutralizes more than one type of influenza virus selected from the group consisting of influenza type A viruses, influenza type B viruses and influenza type C viruses. One embodiment is an HA-ferritin fusion protein that elicits antibodies that neutralize more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment is an HA-ferritin protein that elicits antibodies that neutralize from more than one strain of influenza virus selected from the viruses listed in Table 2.

It will be understood by those skilled in the art that particularly useful HA-ferritin useful proteins of the present invention are those comprising an immunogenic portion of influenza HA protein. Thus, one embodiment of the present invention is an HA-ferritin fusion protein comprising a ferritin protein of the present invention joined to at least one immunogenic portion of an influenza HA protein. One embodiment of the present invention is an HA-ferritin protein comprising a ferritin protein of the present invention joined to at least one immunogenic portion of an HA protein from a virus selected from the group consisting of influenza type A viruses, influenza type B viruses and influenza type C viruses. One embodiment of the present invention is an HA-ferritin protein comprising a ferritin protein of the present invention joined to at least one immunogenic portion of an HA protein selected from the group consisting of an H1 influenza virus HA protein, an H2 influenza virus HA protein, an H5 influenza virus HA protein, an H7 virus influenza HA protein and an H9 influenza virus HA protein. One embodiment of the preset invention is an HA-ferritin fusion protein comprising a ferritin protein of the present invention joined to at least one immunogenic portion of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention. One embodiment of the present invention is an HA-ferritin protein comprising a ferritin protein of the present invention joined to at least one immunogenic portion of an HA protein from virus listed in Table 2. In one embodiment, an HA-ferritin fusion protein comprising an immunogenic portion of an HA protein elicits the production of broadly neutralizing antibodies against influenza virus.

Immunogenic portions of proteins comprise epitopes, which are clusters of amino acid residues that are recognized by the immune system, thus eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that such epitopes require a minimum of six amino acid residues in order to be recognized by the immune system. Thus, one embodiment of the present invention is an HA-ferritin fusion comprising an immunogenic portion from the influenza HA protein, wherein the immunogenic portion comprises at least one epitope.

It is known in the art that some variation in a protein sequence can be tolerated without significantly affecting the activity of the protein. Thus, one embodiment of the present invention is an HA-ferritin fusion protein comprising a ferritin protein of the present invention joined to an amino acid sequence that is a variant of an HA protein from a virus selected from the group consisting of influenza Type A viruses influenza Type B viruses and influenza type C viruses. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein selected from the group consisting of an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein from a virus listed in Table 2, wherein the HA-ferritin fusion protein elicits the production of neutralizing antibodies against an influenza protein. One embodiment of the present invention is an HA-ferritin fusion protein comprising a ferritin protein of the present invention joined to amino acid sequence at least about 80%, at least about 85%, at least about 90%, at least about 95%, at least about 97% or at least about 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, wherein the HA-ferritin fusion protein elicits the production of neutralizing antibodies against an influenza protein. One embodiment of the present invention is an HA-ferritin fusion protein comprising a ferritin protein of the present invention joined to amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

One embodiment of the present invention is an HA-ferritin fusion protein comprising an amino acid sequence at least 80%, at least about 85%, at least about 90%, at least about 95%, at least about 97% or at least about 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. One embodiment of the present invention is an HA-ferritin fusion protein comprising an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68.

It is known in the art that influenza hemagglutinin proteins have various regions, or domains, each possessing specific activities. For example, the globular head extends out from the lipid membrane and comprises two domains: the receptor binding domain (RBD) and the vestigial esterase domain. The RB domain is involved in binding of the HA protein to receptors. The globular head also includes several antigenic sites that include immunodominant epitopes. The stem region is responsible for anchoring the HA protein into the viral lipid envelope. Thus, it will be understood by those skilled in the art that HA-ferritin fusion proteins of the present invention need not comprise the entire sequence of the HA protein. Instead, an HA-ferritin fusion protein can comprise only those portions, regions, domains, and the like, that contain the necessary activities for practicing the present invention. For example, an HA-ferritin fusion protein may contain only those amino acid sequences from the HA protein that contain antigenic sites, epitopes, immunodominant epitopes, and the like.

One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein selected from the group consisting an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from and HA protein from a virus listed in Table 2, wherein the HA-ferritin fusion protein elicits the production of neutralizing antibodies against in influenza virus. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

One embodiment of the present invention is an HA-ferritin fusion protein comprising a ferritin protein of the present invention joined to at least one domain from a HA protein from a virus listed in Table 2, wherein the domain is selected from the group consisting of an ectodomain, an RDB domain, a stem domain, and a domain comprising the region stretching from the amino acid residue immediately distal to the last amino acid of second helical coil to the amino acid residue proximal to the first amino acid of the transmembrane domain. According to the present invention, an ectodomain of an influenza hemagglutinin protein refers to the portion of the hemagglutinin protein that lies outside its transmembrane domain. In one embodiment, the HA-ferritin fusion protein comprises a ferritin protein of the present invention joined to a region of a HA protein from a virus listed in Table 2, wherein the region consists of the amino acid immediately distal to the last amino acid of the second helical coiled coil and proximal to the first amino acid of the transmembrane domain. In one embodiment, the HA-ferritin fusion protein comprises a ferritin protein of the present invention joined to a region of a HA protein from a virus listed in Table 2, wherein the region comprises an amino acid sequence distal to the second helical coiled coil and proximal to the transmembrane domain. In one embodiment, the HA-ferritin fusion protein comprises a ferritin protein of the present invention joined to the ectodomain of a HA protein from a virus listed in Table 2. One embodiment of the present invention is an HA-ferritin fusion protein comprising a ferritin protein of the present invention joined a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

The stem region of an influenza HA protein is a particularly useful domain for constructing fusion proteins of the present invention. Thus, one embodiment of the present invention is a ferritin protein of the present invention joined to at least one immunogenic portion from the stem region of influenza HA protein. According to the preset invention, such a protein is referred to an HA SS-ferritin fusion protein. As used herein, the HA stem region of the hemagglutinin protein consists of the amino acids from the membrane up to the head region of the protein. More specifically, the stem region consists of the amino terminal amino acid up to the cysteine at position 52, and all residues after the cysteine residue at position 277 (using standard H3 numbering). Sequences of exemplary stem regions are represented by SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein selected from the group consisting an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein from a virus listed in Table 2, wherein the HA-ferritin fusion protein elicits the production of neutralizing antibodies against in influenza virus. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein comprising a sequence selected from the group consisting of SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region comprising a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein from a virus selected from the group consisting of influenza Type A viruses influenza Type B viruses and influenza type C viruses, wherein the Ha-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein selected from the group consisting an H1 influenza virus HA protein, an H2 influenza virus HA protein, an H5 influenza virus HA protein, an H7 virus influenza HA protein and an H9 influenza virus HA protein, wherein the Ha-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein from a virus listed in Table 2, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the stem region of an HA protein comprising an amino acid sequence selected from the group consisting of SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

As has been described for stem region proteins of the present invention, the inventors have found that HA-ferritin fusion proteins are more stable and easier to purify when they exist in a trimeric form. Thus, in one embodiment of the present invention the HA portion of the HA-ferritin fusion protein is joined to one or more trimerization domains. In one embodiment, the HA protein comprises an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, joined to one or more trimerization domains. In one embodiment, the HA protein comprises an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 joined to one or more trimerization domains. In one embodiment, the HA protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98 joined to one or more trimerization domains. In one embodiment, the HA protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98 joined to one or more trimerization domains. In one embodiment, the trimerization domain is selected from the group consisting of the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain. In one embodiment, the trimerization domain is an HIV gp41 trimerization domain.

Additionally, the inventors have found that, in some instances, HA-ferritin fusion proteins in which the HA portion is limited to HA stem region sequences may be more stable when joined to at least part of the head region of the HA protein. Thus, one embodiment of the present invention is an HA SS-ferritin fusion protein, wherein, the HA portion of the fusion protein is joined to an amino acid sequence from at least a portion of an HA protein head region.

HA-ferritin proteins of the present invention are constructed by joining ferritin proteins of the present invention with HA proteins of the present invention. In addition, HA-ferritin fusion proteins may contain other domains (e.g., stem region protein, trimerization domain, head region, etc.) that improve the functionality of the final HA-ferritin fusion protein. In some embodiments, joining of the various proteins and/or domains can be done such that the sequences are directly linked. In other embodiments, it may be necessary to employ linkers (also referred to as a spacer sequences) between the various proteins and/or domains so that the so that they are in the proper special orientation. More specifically, linker sequence can be inserted so that the hemagglutinin protein is positioned in such a way to maintain the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SGG, GSG, GG and NGTGGSG (SEQ ID NO:162). Amino acids can be added or subtracted as needed. Those skilled in the art are capable of determining appropriate linker sequences for proteins of the present invention.

In accordance with the invention, suitable portions of the hemagglutinin protein can be joined to the ferritin protein either as an exocapsid product by fusion with the N-terminal sequence lying adjacent to the capsid three-fold axis, as an endocapsid product by fusion with the C-terminus extending inside the capsid core, or a combination thereof. In one embodiment, the hemagglutinin portion of the fusion protein is joined to the N-terminal sequence of the ferritin portion of the fusion protein.

One embodiment of the present invention is an HA-ferritin fusion protein comprising an amino acid sequence at least about 80%, at least about 85%, at least about 90%, at least about 95%, at least about 97% or at least about 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the HA-ferritin fusion protein elicits the production of neutralizing antibodies against an influenza protein. One embodiment of the present invention is an HA-ferritin fusion protein comprising SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual,* 3$^{rd}$ edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a stem region immunogen, a ferritin monomeric subunit, a hemagglutinin protein, and/or an HA-ferritin fusion protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

Preferred nucleic acid molecules are those that encode a stem-region protein, a ferritin monomeric subunit, a hemagglutinin protein, and/or an HA-ferritin fusion protein comprising a monomeric subunit of a ferritin protein joined to an influenza hemagglutinin protein. Thus, one embodiment of the present invention is a nucleic acid molecule comprising a nucleic acid sequence encoding a protein that comprises a monomeric subunit of a ferritin protein joined to an influenza hemagglutinin protein. In one embodiment, the monomeric subunit of ferritin is from the ferritin protein of *Helicobacter pylori*. In one embodiment, the monomeric subunit comprises an amino acid sequence at least 80%, at least 85%, at least 90%, at least 92%, at least 94%, at least 96%, at least 98% or at least 99% identical to a sequence selected from the group consisting of SEQ ID NO:2 and SEQ ID NO:5. In one embodiment, the monomeric subunit comprises an amino acid sequence selected from the group consisting of SEQ ID NO:2 and SEQ ID NO:5. In one embodiment the influenza hemagglutinin protein comprises an amino acid sequence at least 80%, at least 85%, at least 90%, at least 92%, at least 94%, at least 96%, at least 98% or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment the influenza hemagglutinin protein comprises a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment the influenza hemagglutinin protein comprises at least 25 amino acids, at least 50 amino acids, at least 75 amino acids, at least 100 amino acids, at least 150 amino acids, or at least 200 amino acids from a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises at least 25 amino acids, at least 50 amino acids, at least 75 amino acids, at least 100 amino acids, at least 150 amino acids, or at least 200 amino acids from a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. One embodiment of the present invention is a nucleic acid molecule comprising a nucleic sequence encoding an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. One embodiment of the present invention is a nucleic acid molecule comprising a nucleic sequence encoding an amino acid sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Also embodied in the present invention are nucleic acid sequences that are variants of nucleic acid sequence encoding protein of the present invention. Such variants include nucleotide insertions, deletions, and substitutions, so long as they do not affect the ability of fusion proteins of the present invention to self-assemble into nanoparticles, or significantly affect the ability of the hemagglutinin portion of fusion proteins to elicit an immune response to an influenza virus. Thus, one embodiment of the present invention is a nucleic acid molecule encoding a fusion protein of the present invention, wherein the monomeric subunit is encoded by a nucleotide sequence at least 85%, at least 90%, at least 95%, or at least 97% identical to a nucleotide sequence selected from the group consisting of SEQ ID NO:1 and SEQ ID NO:4. One embodiment of the present invention is a nucleic acid molecule encoding an HA-ferritin fusion protein of the present invention, wherein the HA protein is encoded by a nucleotide sequence at least 85%, at least 90%, at least 95%, at least 97% identical or at least 99% identical to a nucleic acid sequence encoding an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a nucleic acid molecule encoding an HA-ferritin fusion protein of the present invention, wherein the HA protein is encoded by a nucleotide sequence at least 85%, at least 90%, at least 95%, at least 97% identical or at least 99% identical to a nucleic acid sequence encoding an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, and SEQ ID NO:37. One embodiment of the present invention is a nucleic acid molecule comprising a nucleic acid sequence selected from the group consisting of SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, and SEQ ID NO:37.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:40, SEQ ID NO:43, SEQ ID NO:46, SEQ ID NO:49, SEQ ID NO:52, SEQ ID NO:55, SEQ ID NO:58, SEQ ID NO:61, SEQ ID NO:64, and SEQ ID NO:67. One embodiment of the present invention is a nucleic acid molecule comprising a nucleic acid sequence selected from the group consisting of SEQ ID NO:40, SEQ ID NO:43, SEQ ID NO:46, SEQ ID NO:49, SEQ ID NO:52, SEQ ID NO:55, SEQ ID NO:58, SEQ ID NO:61, SEQ ID NO:64, and SEQ ID NO:67.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, and SEQ ID NO:97. One embodiment of the present invention is a nucleic acid molecule comprising a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, and SEQ ID NO:97.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:100, SEQ ID NO:103, SEQ ID NO:106, SEQ ID NO:109, SEQ ID NO:112, SEQ ID NO:115, SEQ ID NO:121, SEQ ID NO:124, and SEQ ID NO:127. One embodiment of the present invention is a nucleic acid molecule comprising a nucleic acid sequence selected from the group consisting of SEQ ID NO:100, SEQ ID NO:103, SEQ ID NO:106, SEQ ID NO:109, SEQ ID NO:112, SEQ ID NO:115, SEQ ID NO:121, SEQ ID NO:124, and SEQ ID NO:127.

Also encompassed by the present invention are expression systems for producing fusion proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the ferritin fusion proteins of the present invention can take place using any suitable conventional recombinant technology currently known in the field. For example, molecular cloning a fusion protein, such as ferritin with a suitable protein such as the recombinant influenza hemagglutinin protein, can be carried out via expression in *E. coli* with the suitable monomeric subunit protein, such as the *helicobacter pylori* ferritin monomeric subunit. The construct may then be transformed into protein expression cells, grown to suitable size, and induced to produce the fusion protein.

As has been described, because HA-ferritin fusion proteins of the present invention comprise a monomeric subunit of ferritin, they can self-assemble. According to the present invention, the supramolecule resulting from such self-assembly is referred to as a hemagglutinin expressing ferritin based nanoparticle. For ease of discussion, the hemagglutinin expressing ferritin based nanoparticle will simply be referred to as a, or the, nanoparticle (np). Nanoparticles of the present invention have the same structural characteristics as the ferritin proteins described earlier. That is, they contain 24 subunits and have 432 symmetry. In the case of nanoparticles of the present invention, the subunits are the fusion proteins comprising a ferritin monomeric subunit joined to an influenza hemagglutinin protein. Such nanoparticles display at least a portion of the hemagglutinin protein on their surface as hemagglutinin trimers. In such a construction, the hemagglutinin trimer is accessible to the immune system and thus can elicit an immune response. Thus, one embodiment of the present invention is a nanoparticle comprising an HA-ferritin fusion protein, wherein the fusion protein comprises a monomeric ferritin subunit joined to an influenza hemagglutinin protein. In one embodiment, the nanoparticle is an octahedron. In one embodiment, the nanoparticle displays the hemagglutinin protein on its surface as a hemagglutinin trimer. In one embodiment, the influenza hemagglutinin protein is capable of eliciting neutralizing antibodies to an influenza virus. In one embodiment, the monomeric ferritin subunit comprises at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the monomeric ferritin subunit comprises SEQ ID NO:2 or SEQ ID NO:5.

In one embodiment, the influenza hemagglutinin protein comprises at least one epitope from an influenza hemagglutinin protein listed in Table 2. In one embodiment, the influenza hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a hemagglutinin protein of a virus listed in Table 2. In one embodiment, the hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the hemagglutinin protein comprises a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

In one embodiment, the influenza hemagglutinin protein comprises an amino acid sequence at least 80%, at least 85%, at least 90%, at least 95%, at least 97%, at least 99% identical to the sequence of an hemagglutinin protein from a virus listed in Table 2. In one embodiment, the influenza hemagglutinin protein comprises an amino acid sequence at least 80%, at least 85%, at least 90%, at least 95%, at least 97%, at least 99% identical to a protein sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

In one embodiment, the hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the influenza hemagglutinin protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the hemagglutinin protein comprises a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In one embodiment, the HA-ferritin fusion protein comprises an amino acid sequence at least 80%, at least 85%, at least 90%, at least 95%, at least 97%, at least 99% identical to a protein sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence at least 80%, at least 85%, at least 90%, at least 95%, at least 97%, at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the HA-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Because stem region immunogens, HA-ferritin fusion proteins and nanoparticles of the present invention can elicit an immune response to an influenza virus, they can be used as vaccines to protect individuals against infection by influenza virus. According to the present invention a vaccine can be a stem region immunogen, an HA-ferritin fusion protein, or a nanoparticle of the present invention. Thus, one embodiment of the present invention is a vaccine comprising a stem region immunogen, an HA-ferritin fusion protein, or a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the disclosure is a ferritin-based nanoparticle vaccine that includes more than one influenza hemagglutinin protein. Such a vaccine can include a combination of different influenza hemagglutinin proteins, either on a single nanoparticle or as a mixture of nanoparticles, at least two of which have a unique influenza hemagglutinin proteins. A multivalent vaccine can comprise as many influenza hemagglutinin proteins as necessary in order to result in production of the immune response necessary to protect against a desired breadth of virus strains. In one embodiment, the vaccine comprises a hemagglutinin protein from at least two different influenza strains (bi-valent). In one embodiment, the vaccine comprises a hemagglutinin protein from at least three different influenza strains (tri-valent). In one embodiment, the vaccine comprises a hemagglutinin protein from at least four different influenza strains (tetra-valent). In one embodiment, the vaccine comprises a hemagglutinin protein from at least five different influenza strains (penta-valent). In one embodiment, the vaccine comprises a hemagglutinin protein from at least six different influenza strains (hexa-valent). In various embodiments, a vaccine comprises a hemagglutinin protein from each of 7, 8, 9, or 10 different strains of influenza virus. An example of such a combination is a ferritin-based nanoparticle vaccine that comprises influenza A group 1 hemagglutinin protein, an influenza A group 2 hemagglutinin protein, and an influenza B hemagglutinin protein. In one embodiment, the influenza hemagglutinin proteins are H1 HA, H3 HA, and B HA. In one embodiment, the influenza hemagglutinin proteins are those included in the 2011-2012 influenza vaccine. Another example of a multivalent vaccine is a ferritin based nanoparticle vaccine that comprises hemagglutinin proteins from four different influenza viruses. In one embodiment, the multivalent vaccine comprises hemagglutinin proteins from H1 A/NC/20/1999, H1 A/CA/04/2009, H2 A/Singapore/1/1957 and H5 A/Indonesia/05/2005. Such a vaccine is described in Example 2.

One embodiment of the present invention is a method to vaccinate an individual against influenza virus, the method comprising administering a nanoparticle to an individual such that an immune response against influenza virus is produced in the individual, wherein the nanoparticle comprises a monomeric subunit from ferritin joined to an influenza hemagglutinin protein, and wherein the nanoparticle displays the influenza hemagglutinin on its surface. In one embodiment, the nanoparticle is a monovalent nanoparticle. In one embodiment, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits comprise a ferritin protein joined to an influenza hemagglutinin protein, and wherein the nanoparticle displays the influenza hemagglutinin on its surface; and, b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit from ferritin joined to an influenza hemagglutinin protein, and wherein the nanoparticle displays the influenza hemagglutinin on its surface. In one embodiment, the vaccine is a stem region immunogen. In one embodiment, the vaccine is a nanoparticle. In one embodiment, the vaccine is a monovalent vaccine. In one embodiment, the vaccine is multivalent vaccine. Another embodiment of the present invention is a method to vaccinate an individual against infection with influenza virus, the method comprising:

a) obtaining a vaccine comprising at least one nanoparticle comprising an HA-ferritin fusion protein, wherein the fusion protein comprises a ferritin protein joined to an influenza HA protein, and wherein the nanoparticle displays the influenza HA on its surface; and, b) administering the vaccine to an individual such that an immune response against an influenza virus is produced.

In one embodiment, the nanoparticle is a monovalent nanoparticle. In one embodiment, the nanoparticle is multivalent nanoparticle.

In one embodiment, the nanoparticle is an octahedron. In one embodiment, the influenza hemagglutinin protein is capable of eliciting neutralizing antibodies to an influenza virus. In one embodiment, the influenza HA protein is capable of eliciting broadly neutralizing antibodies to an influenza virus. In one embodiment, the ferritin portion of the fusion protein comprise at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the HA portion of the fusion protein comprises at least one epitope from an influenza hemagglutinin protein listed in Table 2. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a hemagglutinin protein of a virus listed in Table 2. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the HA portion of the fusion protein comprises an amino acid sequence at least 80%, at least 85%, at least 90%, at least 95%, at least 97%, at least 99% identical to the sequence of an HA protein from a virus listed in Table 2. In one embodiment, the HA portion of the fusion protein comprises an amino acid sequence at least 80%, at least 85%, at least 90%, at least 95%, at least 97%, at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the HA portion of the fusion protein comprises an amino acid sequence at least 80%, at least 85%, at least 90%, at least 95%, at least 97%, at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the HA-ferritin fusion protein comprises an amino acid sequence at least 80%, at least 85%, at least 90%, at least 95%, at least 97%, at least 99% identical to a protein sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence at least 80%, at least 85%, at least 90%, at least 95%, at least 97%, at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the HA-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle comprising an HA-ferritin fusion protein of the present invention. In one embodiment, the first vaccine composition comprises a nanoparticle comprising an ectodomain from the hemagglutinin protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the hemagglutinin of the first vaccine composition comprises an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the first vaccine composition comprises an HA-ferritin fusion protein comprising an amino acid sequence at least 80% identical, at least 85% identical, at least 90% identical, at least 95% identical, at least 97% identical or at least 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68, wherein the nanoparticle elicits an immune response against an influenza virus. In one embodiment, the first vaccine composition comprises an HA-ferritin fusion protein comprising an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, second vaccine composition comprises a nanoparticle comprising an HA SS-ferritin fusion protein of the present invention. In one embodiment, the HA SS-ferritin fusion protein comprises an amino acid sequence at least 80% identical, at least 85% identical, at least 90% identical, at least 95% identical, at least 97% identical or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, the HA SS-ferritin fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, the HA SS-ferritin fusion protein comprises an amino acid sequence at least 80% identical, at least 85% identical, at least 90% identical, at least 95% identical, at least 97% identical or at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the HA SS-ferritin fusion protein elicits an immune response to an influenza virus. In one embodiment, the HA SS-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the individual is at risk for infection with influenza virus. In one embodiment, the individual has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18$^{th}$ ed., 1990, Mack Publishing Co., Easton, Pa. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using hemagglutinin protein from one strain of influenza virus is capable of protecting an individual against infection by different strains of influenza. For example, a vaccine made using hemagglutinin protein from influenza A/New Caledonia/20/1999 (1999 NC, H1), can be used to protect an individual against infection by an influenza virus including, but not limited to A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 indo, H5), A/Perth/16/2009 (2009 Per, H3), and/or A/Brisbane/59/2007 (2007 Bris, H1).

In one embodiment, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using hemagglutinin protein from a A/New Caledonia/20/1999 (1999 NC, H1) strain of influenza virus is capable of protecting an individual against infection by earlier, antigenically divergent New Caledonia strains of influenza, and by evolving (or diverging) influenza strains of the future.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1. Design and Production of Ferritin-Based Nanoparticles Expressing Influenza Virus HA This Example demonstrates the ability of HA-ferritin fusion proteins to form nanoparticles. Analysis of ferritin structure suggested that it was possible to insert a heterologous protein, specifically influenza virus HA, so that it mimics a physiologically relevant trimeric viral spike (FIG. 1A). Ferritin forms a nearly spherical particle consisting of 24 subunits arranged with octahedral symmetry around a hollow interior. The symmetry of the ferritin nanoparticles includes eight three-fold axes on the surface. The aspartic acid (Asp) at residue 5 near the $NH_2$ terminus is readily accessible, and the distance (28 Å) between each Asp5 on the three-fold axis is almost identical to the distance between the central axes of each HA2 subunit of trimeric HA (FIG. 1A, right).

Vector Construction.

The HA-ferritin fusion proteins were constructed by joining the ectodomain of A/New Caledonia/20/1999 (1999 NC) HA to ferritin (FIG. 1B). Specifically, the gene encoding *H. pylori* nonheme iron-containing ferritin (GenBank NP_223316) with a point mutation (N19Q) to abolish a potential N-linked glycosylation site was synthesized by PCR-based accurate synthesis (M. F. Bachmann, R. M. Zinkernagel, Neutralizing antiviral B cell responses. *Annu Rev Immunol* 15, 235-270 (1997)) using human-preferred codons. The human CD5 leader sequence and a serine-glycine-glycine (SGG) spacer were joined to the gene fragment encoding ferritin (residues 5-167) to generate a secreted protein. The plasmids encoding various influenza virus HAs, including A/South Carolina/1/1918 (1918 SC), GenBank AF117241; A/Puerto Rico/8/1934 (1934 PR8), UniProt P03452; A/Singapore/6/1986 (1986 Sing), GenBank AB038395; A/Beijing/262/1995 (1995 Beijing), GenBank AAP34323; A/New Caledonia/20/1999 (1999 NC), GenBank AY289929; A/Solomon Islands/3/2006 (2006 SI), GenBank ABU99109; A/Brisbane/59/2007 (2007 Bris), GenBank ACA28844; A/California/04/2009 (2009 CA), GenBank ACP41105; A/Perth/16/2009 (H3 2009 Perth), GenBank ACS71642; B/Florida/04/2006 (B 2006 Florida), GenBank ACA33493 and their corresponding NAs with human preferred codons were synthesized as previously reported (C. J. Wei et al., Induction of broadly neutralizing H1N1 influenza antibodies by vaccination. *Science* 329, 1060-1064 (2010)). The gene fragments encoding HAs (residues HA1 1-HA2 174, H3 numbering) from 1999 NC HA, 2009 CA HA, 2009 Perth H3 and 2006 Florida B were amplified and joined to the ferritin gene fragment (residues 5-167) with an SGG linker to give rise to the HA-ferritin fusion gene. To produce soluble trimeric HA, the 1999 NC HA gene fragment (residues HA1 1-HA2 174, H3 numbering) was joined to a thrombin cleavage site followed by a foldon trimerization motif and a poly-histidine tag as described previously (A. S. Xiong et al., PCR-based accurate synthesis of long DNA sequences. *Nat Protoc* 1, 791-797 (2006)). Both full length and soluble forms of 1999 NC ΔStem (C. J. Wei et al., Induction of broadly neutralizing H1N1 influenza antibodies by vaccination. *Science* 329, 1060-1064 (2010)) and ΔRBS HA mutants were generated by introducing an N-linked glycosylation site at residues HA2 45 (I45N/G47T) and HA1 190 (Q192T), respectively. The soluble form of 2007 Bris ΔRBS HA mutant was generated by introducing an N-linked glycosylation site at the same site. All genes were then cloned into mammalian expression vectors for efficient expression (C. J. Wei et al., Comparative efficacy of neutralizing antibodies elicited by recombinant hemagglutinin proteins from avian H5N1 influenza virus. *J Virol* 82, 6200-6208 (2008)). Plasmids encoding the mAbs, CR6261 (D. C. Ekiert et al., Antibody recognition of a highly conserved influenza virus epitope. *Science* 324, 246-251 (2009)), CH65 (J. R. Whittle et al., Broadly neutralizing human antibody that recognizes the receptor-binding pocket of influenza virus hemagglutinin. *Proc Natl Acad Sci USA* 108, 14216-14221 (2011)) and a single-chain variable fragment F10 (J. Sui et al., Structural and functional bases for broad-spectrum neutralization of avian and human influenza A viruses. *Nat Struct Mol Biol* 16, 265-273 (2009)) were also synthesized as described by C. J. Wei et al., (*Science* 329, 1060-1064 (2010).

Protein Biosyntheses and Purifications.

To produce ferritin nanoparticles, HA-np and trimeric HA, the expression vectors were transfected into 293F cells (Invitrogen), a human embryonic kidney cell line using 293fectin (Invitrogen) according to the manufacturer's instructions. Matched NAs were co-transfected at 20:1 HA:NA (wt:wt). The cells were grown in Freestyle 293 expression medium (Invitrogen) and the culture supernatants were collected 4 days post-transfection by centrifugation and filtered through a 0.22 μm pore filter unit (Nalgene) to remove cell debris. The supernatants were concentrated with a 30 kDa molecular weight cut-off filter unit (Pall Corp.) and then buffer exchanged to a Tris buffer (20 mM Tris, 50 mM NaCl, pH 7.5 for ferritin nanoparticles; 20 mM Tris, 500 mM NaCl, pH 7.5 for HA-np). The ferritin nanoparticles were purified by ion-exchange chromatography using a HiLoad 16/10 Q Sepharose HP column (GE Healthcare). The HA-np were purified by affinity column chromatography using *Erythrina cristagalli* agglutinin (ECA, coral tree lectin; EY Laboratories, Inc.) specific for galactose β(1,4) N-acetylglucosamine. The ferritin nanoparticles and HA-np were further purified by size exclusion chromatography with a Superose 6 PG XK 16/70 column (GE Healthcare) in PBS. The peak fraction was collected and used for further studies. The molecular weights of the ferritin nanoparticle and HA-np were calculated based on two equations generated by least squares linear regression on a semi-log plot using gel filtration low and high molecular weight standards (Bio-Rad), respectively. The yield of 1999 NC HA-np is ~4 mg liter$^{-1}$ and appears stable at 4° C. or frozen at −80° C. The trimeric HA proteins were purified as described by A. S. Xiong et al (*Nat Protoc* 1, 791-797 (2006)) with slight modifications. Briefly, HA proteins were first purified by affinity chromatography using Ni Sepharose HP resin (GE Healthcare), and then were separated by size exclusion chromatography with a HiLoad 16/60 Superdex 200 PG column (GE Healthcare). To remove the foldon trimerization motif and poly-histidine tag, HA proteins were digested with thrombin (EMD Chemicals, Inc.) (3 U mg ml$^{-1}$) overnight at 4° C. Undigested proteins were removed by passing over Ni Sepharose HP resin and the digested HAs were purified on a HiLoad 16/60 Superdex 200 PG column. All purified proteins were verified by SD S-PAGE. Protein purity and size distribution were examined by dynamic light scattering using a DynaPro system (Wyatt Technology). All human mAbs and a single-chain variable fragment were also produced in 293F cells and purified as described previously (C. J. Wei et al., Induction of broadly neutralizing H1N1 influenza antibodies by vaccination. *Science* 329, 1060-1064 (2010); W. P. Kong et al., Protective immunity to lethal challenge of the 1918 pandemic influenza virus by vaccination. *Proc Natl Acad Sci USA* 103, 15987-15991 (2006)). MAbs against 1999 NC HA were purified from hybridoma supernatants as previously described (C. J. Wei et al., Induction of broadly neutralizing H1N1 influenza antibodies by vaccination. *Science* 329, 1060-1064 (2010)).

Iodixanol-Based Gradient Centrifugation.

Figure 10:
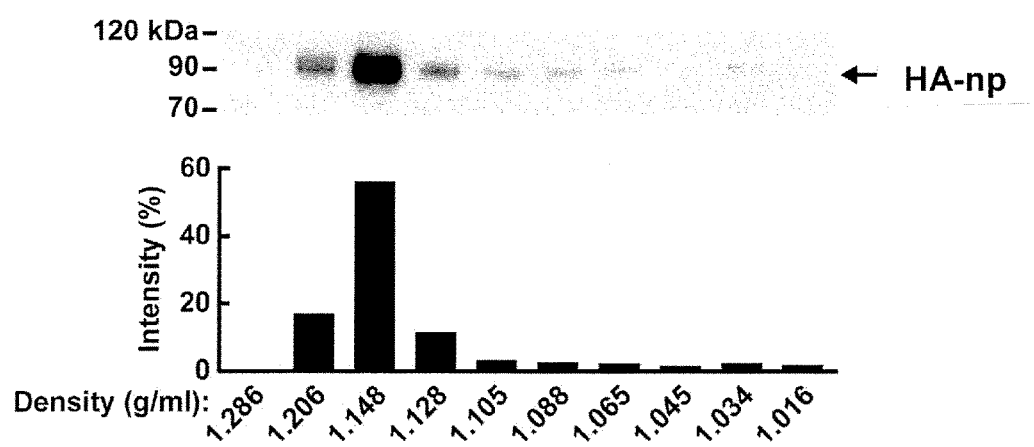
FIG. 10. Purification of HA-np. HA-np were purified by routine iodixanol gradient ultracentrifugation routinely. Fractions containing HA-np were confirmed by SDS-PAGE and Western blotting using a mAb against 1999 NC HA. The HA-np were enriched in the fraction with density of ~1.15 g/ml.

Alternatively, HA-np were purified by iodixanol gradient ultracentrifugation (FIG. 10) routinely used for virus and VLP purifications (C. J. Wei et al., Cross-neutralization of 1918 and 2009 influenza viruses: role of glycans in viral evolution and vaccine design. *Sci Transl Med* 2, 24ra21 (2010)). Fractions containing HA np were confirmed by SDS-PAGE and Western blotting using a mAb against 1999 NC HA.

Electron Microscopic Analysis.

Purified ferritin nanoparticles and HA-np were subjected to transmission electron microscopic analysis. The samples were negatively stained with phosphotungstic acid (ferritin nanoparticles) or ammonium molybdate (HA-np) and images were recorded on a Tecnai T12 microscope (FEI) at 80 kV with a CCD camera (AMT Corp.).

Analysis of HA-Ferritin np.

Figure 2A:
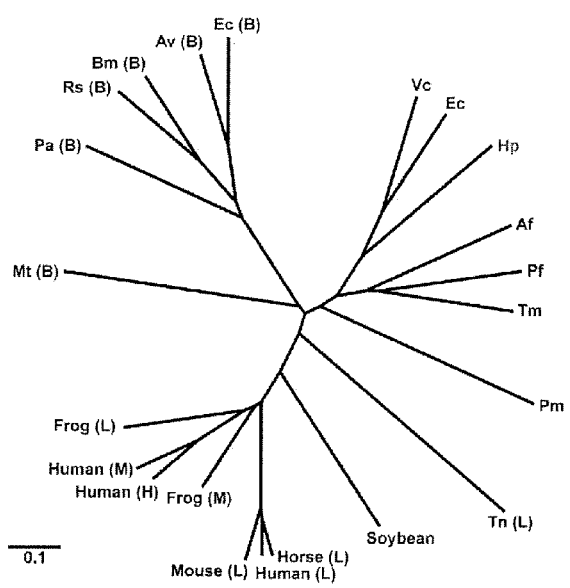
FIG. 2A-2B. Genetic and structural comparison of ferritins. (A) Phylogenetic tree analysis of ferritins found in RSCB PDB. Twenty-two sequences contain 16 ferritins including Vc (*Vibrio cholerae*), Ec (*E. coli*), Hp (*H. pylori*), Af (*Archaeoglobus fulgidus*), Pf (*Pyrococcus furiosus*), Tm (*Thermatoga maritime*), Pm (*Pseudo-nitzschia multiseries*), Tn (L) (*Trichoplusia ni* light chain), Soybean (chloroplastic), Horse (L) (light chain), Human (L), (H) and (M) (light, heavy chains and mitochondrial, respectively), Mouse (L) (light chain), and Frog (M) and (L) (middle and lower subunits, respectively), and 6 bacterioferritins (B) including Mt (B) (*Mycobacterium tuberculosis*), Pa (B) (*Pseudomonas aeruginosa*), Rs (B) (*Rhodabacter sphaeroides*), Bm (B) (*Brucella melitensis*), Av (B) (*Azobacter vinelandii*), and Ec (B). Protein sequences were aligned using Clustal W2 (www.ebi.ac.uk/Tools/msa/clustalw2) with Gonnet matrix and a phylogenetic tree was generated with the Phylodendron program (http://iubio.bio.indiana.edu/treeapp/treeprint-form.html) using the neighbor-joining method. (B) Comparison of surface exposed residues between *H. pylori* and mouse (light chain) (left) or human (light chain) (middle), and mouse and human (light chains) (right). Conservation of surface exposed residues was rendered by UCSF Chimera using a protein sequence alignment generated by Clustal W2. Conserved and varied residues between the two ferritins are shown as light and dark residues, respectively. PDB files 3bve (*H. pylori*) (left and middle) and 1 h96 (mouse light chain) (right) were used for surface rendering.
Figure 2B:
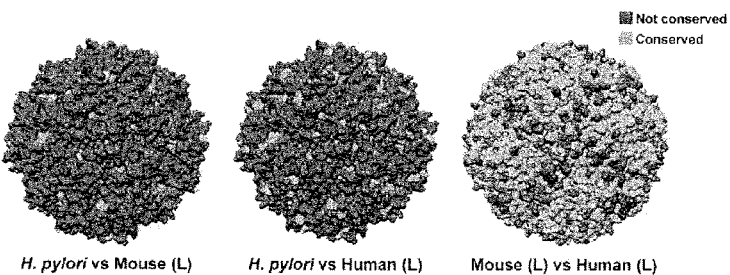

Among the various ferritins, *Helicobacter* (H.) *pylori* nonheme ferritin (K. J. Cho et al., The crystal structure of ferritin from *Helicobacter pylori* reveals unusual conformational changes for iron uptake. *J Mol Biol* 390, 83-98 (2009)) was selected as a prototype because of its highly divergent sequence compared to mammalian ferritins (FIG. 2), thus minimizing the likelihood of inducing autoimmunity after vaccination. The final purification step for recombinant HA-ferritin was size exclusion chromatography (FIG. 1C, left) and dynamic light scattering was used to confirm that both ferritin and HA-ferritin self-assembled into supramolecules with diameters of 14.61 and 37.23 nm, respectively (FIG. 1C, middle). HA-ferritin and ferritin subunits from these nanoparticles migrated at the expected respective molecular weights of 85 and 17 kDa by SDS-PAGE compared to 68 kDa for purified HA (FIG. 1C, right). While the morphology of the ferritin nanoparticles was smooth, as visualized by transmission electron microscopy (TEM), HA-ferritin formed np that exhibited clearly visible spikes around the spherical core (FIG. 1D, Ferritin np vs. HA-np). Remarkably, the placement of these spikes clearly illustrated the octahedral symmetry of the HA-np design. Octahedral two-, three- and four-fold axes were distinctly observed in the TEM image (FIG. 1E, right). These data demonstrated the formation of HA spikes on self-assembling HA-ferritin nanoparticles. More importantly, this design enabled HAs from different subtypes or influenza B viruses to be readily joined to a ferritin core without substantial modification.

Example 2. Antigenicity and Immunogenicity of HA-np in Mice

To verify the antigenicity of the HA spikes on the np, HA-ferritin np were analyzed for their ability to react with anti-HA head ab and a conformation-dependent monoclonal ab (mAb), CR6261, that recognizes a highly conserved structure in the trimeric HA stem and neutralizes diverse influenza A group 1 viruses D. C. Ekiert et al., Antibody recognition of a highly conserved influenza virus epitope. Science 324, 246-251 (2009)), using ELISA and a virus neutralization assay.
Analysis by ELISA.
Purified trimeric HA, HA-np, and TIV (2 µg of H1 HA ml$^{-1}$), ferritin nanoparticles (0.68 µg ml$^{-1}$ for FIG. 3 or 2 µg ml$^{-1}$ for the rest), mouse liver ferritin (2 µg ml$^{-1}$, Alpha Diagnostic International, Inc.), ΔStem and ΔRB S HA trimer (2 µg ml$^{-1}$) were coated (100 µl/well) onto MaxiSorp™ plates (Nunc) and the wells were probed with the anti-HA mAbs, anti-mouse liver ferritin IgG (Alpha Diagnostic International, Inc.) or immune sera followed by peroxidase-conjugated secondary antibodies (anti-mouse IgG and anti-human IgG, SouthernBiotech; anti-ferret IgG, Rockland Immunochemicals, Inc.). The wells were developed using a SureBlue chromogen (KPL) and the reaction was stopped by adding 0.5 M sulfuric acid. For the ELISA-based competition assay, HA trimer (2 µg ml$^{-1}$) was coated onto the plates. Plates were incubated with an anti-stem mAb, CR6261 (8 µg ml$^{-1}$) or an isotype control Ab, VRC01 (8 µg ml$^{-1}$) (Z. Y. Yang et al., Immunization by avian H5 influenza hemagglutinin mutants with altered receptor binding specificity. Science 317, 825-828 (2007); X. Wu et al., Rational design of envelope identifies broadly neutralizing human monoclonal antibodies to HIV-1. Science 329, 856-861 (2010)) before adding serially diluted pre-absorbed ferret immune sera. The wells were probed with anti-ferret IgG and developed as described above. Absorbance at 450 nm was measured by SpectraMax M2e (Molecular Devices). The endpoint titers were determined by calculating the intersection of the observed binding curve and the absorbance threshold (four times background).
Neutralization Assays.
HA/NA-pseudotyped lentiviral vectors encoding luciferase were used. Immune sera used for the assay were pretreated with RDE as described above. Pre-titrated pseudotyped viruses (Gag p24≈6.25 ng ml$^{-1}$) were incubated with serially diluted sera for 20 minutes at room temperature and added to 293A cells (10,000 cells/well in a 96-well plate; 50 µl/well; in triplicate). Plates were then washed and replaced with fresh media 2 hours later, and luciferase activity was measured after 24 hours. For the protein competition assay, neutralizing activity of the mAbs F10, CR6261 or immune sera was measured in the presence of competitor proteins, trimeric HA (WT, 4Stem or ΔRBS), HA-np, ferritin nanoparticles or irrelevant protein (HIV-1 gp120) at final concentration of 20 and 25 µg ml$^{-1}$ for mAbs and immune sera, respectively. The HA-np was able to bind to anti-head or anti-stem mAbs with affinities similar to trimeric HA or trivalent inactivated vaccine (TIV) containing the same 1999 NC HA at equimolar concentrations of HA, in contrast to a ferritin nanoparticle control (FIG. 3A). Analogous to trimeric HA, the HA-np also blocked neutralization by CR6261 and another stem-directed mAb, F10 (4 J. Sui et al., Structural and functional bases for broad-spectrum neutralization of avian and human influenza A viruses. Nat Struct Mol Biol 16, 265-273 (2009)) (FIG. 3B). These results indicated that HA molecules on the HA-np antigenically resembled the physiological trimeric viral spike.

Example 3. Immunogenicity of HA-Ferritin np In Vivo

Figures 4A, 4B, 4C:
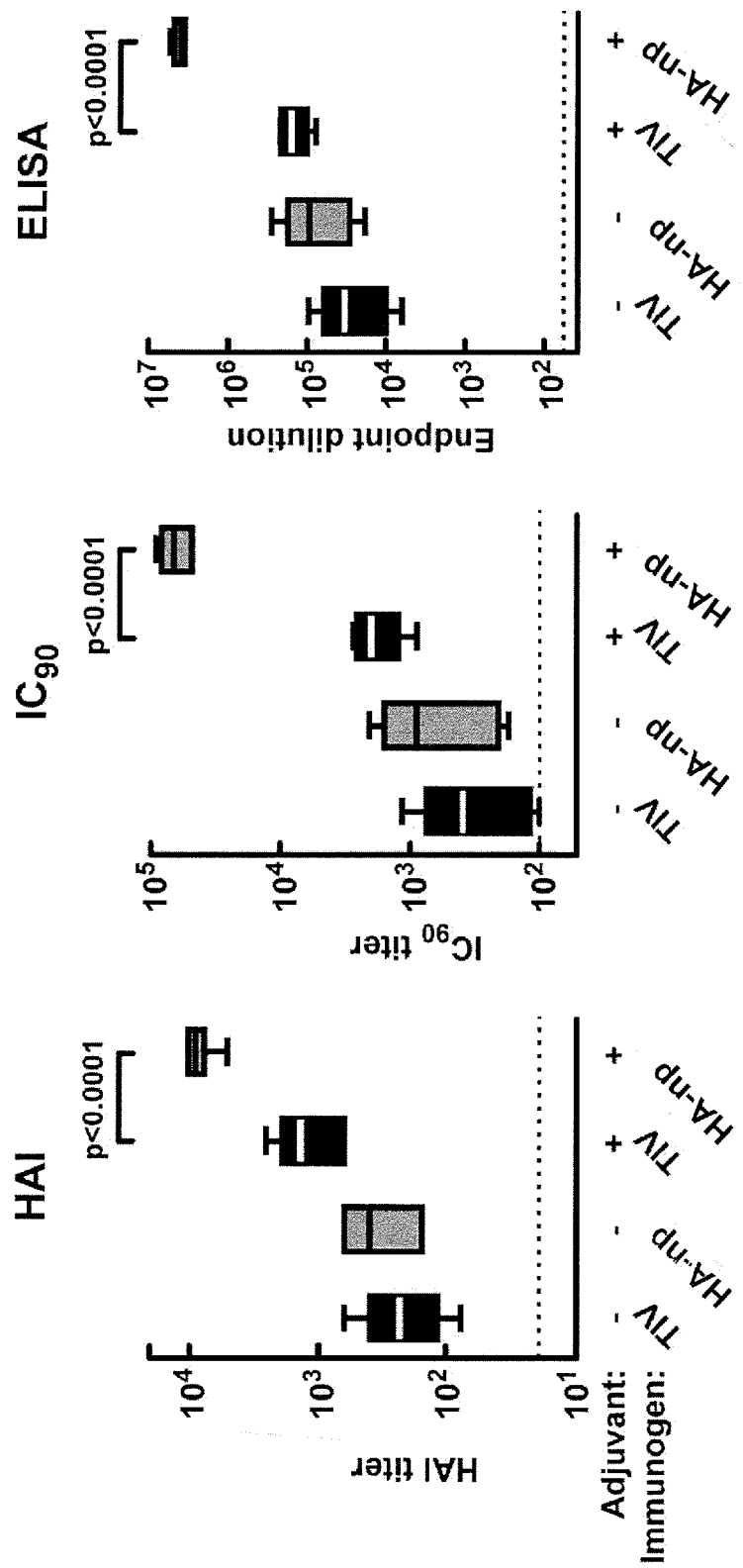
Figures 4E, 4F:
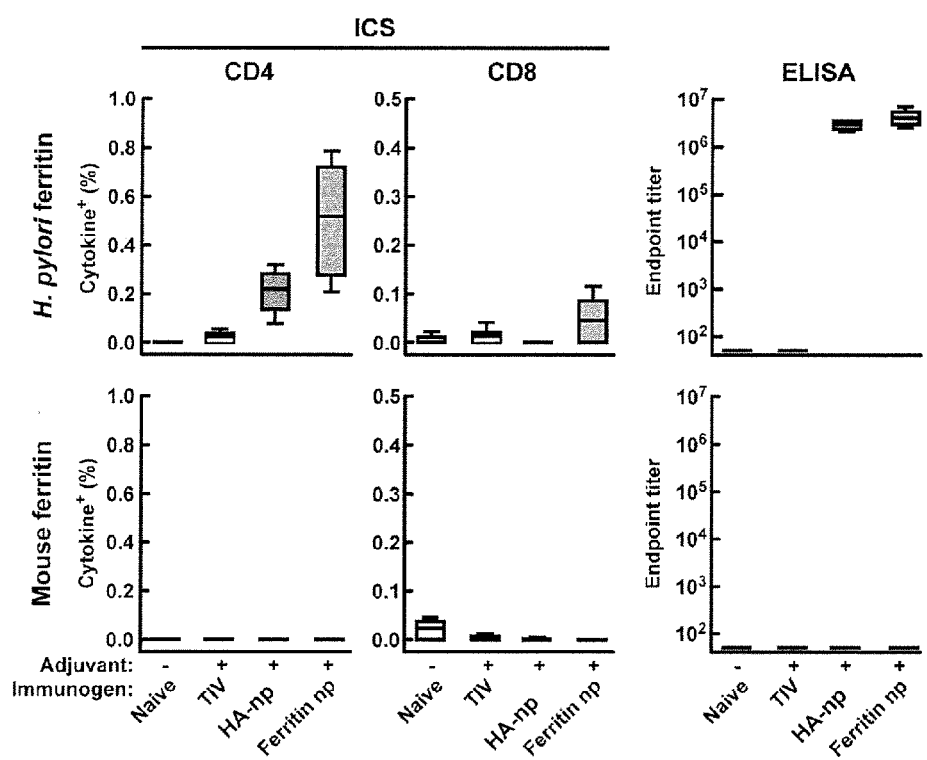

This Example demonstrates the ability of HA-ferritin np of the present invention to elicit neutralizing antibodies.
To assess the immunogenicity of the HA-ferritin np in vivo, mice were immunized twice with HA-np or TIV's from the 2006-2007 season, with HAs from A/New Caledonia/20/1999 (H1N1), A/Wisconsin/67/2005 (H3N2) and B/Malaysia/2504/04 (type B), or from the 2011-2012 season, with HAs from A/California/07/09-like (H1N1), A/Perth/16/09 (H3N2) and B/Brisbane/60/08 (type B). Briefly, female BALB/c mice (6-8 weeks old; Charles River Laboratories) were immunized (5 mice/group) intramuscularly with 5 or 0.5 µg (1.67 or 0.17 µg of H1 HA) of TIV, 2.24 or 0.22 µg (1.67 or 0.17 µg of HA) of HA-np or 0.57 µg of ferritin nanoparticles (equimolar to 2.24 µg of HA-np) in 100 µl of PBS or in 100 µl of 50% (v/v) mixture of Ribi adjuvant (Sigma) in PBS at weeks 0 and 3. A group of BALB/c mice (n=4) was immunized with 20 µg of trimeric HA (thrombin cleaved) in 100 µl of 50% (v/v) mixture of Ribi adjuvant in PBS at weeks 0 and 4. For the experiment using trivalent HA-np, mice were immunized (n=5) with 6.72 µg (1.67 µg of each HA component) of trivalent HA-np in 100 µl of 50% (v/v) mixture of Ribi adjuvant in PBS at weeks 0 and 3. Blood samples were collected prior to the first dose, and at 2 weeks after each immunization.
The resulting antibody titers were determined as described in Example 2. The HA-np induced significantly higher HAI titers than TIV (FIG. 4A, left; p<0.0001), and a similar effect was observed in the neutralization assay and ELISA (FIG. 4A, middle and right; p<0.0001). For example, neutralization titers elicited by HA-np as assessed by the concentration of ab needed to inhibit viral entry by 90% (IC$_{90}$) were ~34 times higher than TIV (FIG. 4A, middle). Because higher titers were observed in groups with the adjuvant Ribi, further comparisons were performed with this adjuvant. Neutralization against a panel of H1N1 strains revealed not only increased potency but also enhanced breadth stimulated by HA-np compared with TIV or trimeric HA (FIG. 4B). Neutralization against two highly divergent H1N1 viruses, A/Puerto Rico/8/1934 (1934 PR8) and A/Singapore/6/1986 (1986 Sing) were only observed in mice immunized with the HA-np, and the titer against the contemporary virus A/Brisbane/59/2007 (2007 Bris) was more than one log higher in mice immunized with HA-np than with TIV (FIG. 4B).

Figure 5A:
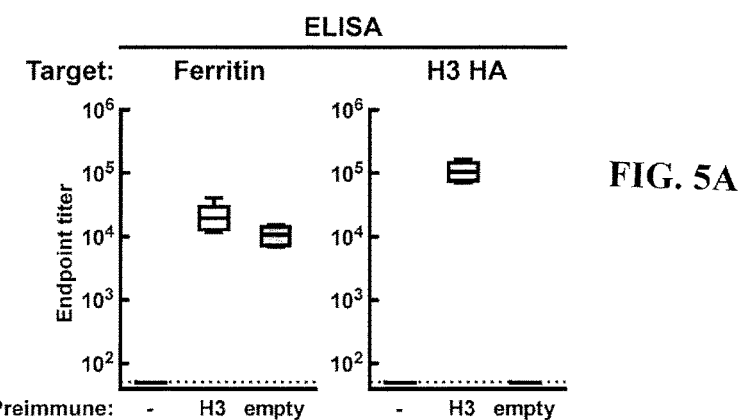
FIG. 5A-5B. Successive immunization of HA-nanoparticles in mice. Mice were pre-immunized with 1.67 μg (amount of HA) of 2009 Perth (H3) HA-nanoparticles or 0.57 μg (equimolar to HA-nanoparticle) of empty ferritin nanoparticles at week 0 and then immunized with 1.67 μg (amount of HA) of 1999 NC (H1) HA-nanoparticles at week 3. Ribi was used as an adjuvant. Another group of mice was immunized with 1999 NC (H1) HA-nanoparticles without pre-immunization of empty ferritin nanoparticles or H3 HA-nanoparticles. (A) Ab responses to *H. pylori* ferritin (left) and 2009 Perth H3 HA (right). Immune sera collected 2 weeks after the immunization with H3 HA-nanoparticles or empty ferritin nanoparticles were analyzed by ELISA. (B) Immune responses to 1999 NC (H1) after 1999 NC (H1) HA-nanoparticle immunization. Naïve mice or mice with pre-immunity to ferritin or H3 HA were immunized with H1 HA-nanoparticles at week 3 and HAI (left), $IC_{90}$ neutralization (middle) and ELISA (right) Ab titers were measured 2 weeks after the immunization. The data are presented as box-and-whiskers plots with lines at the mean (n=5).
Figure 5B:
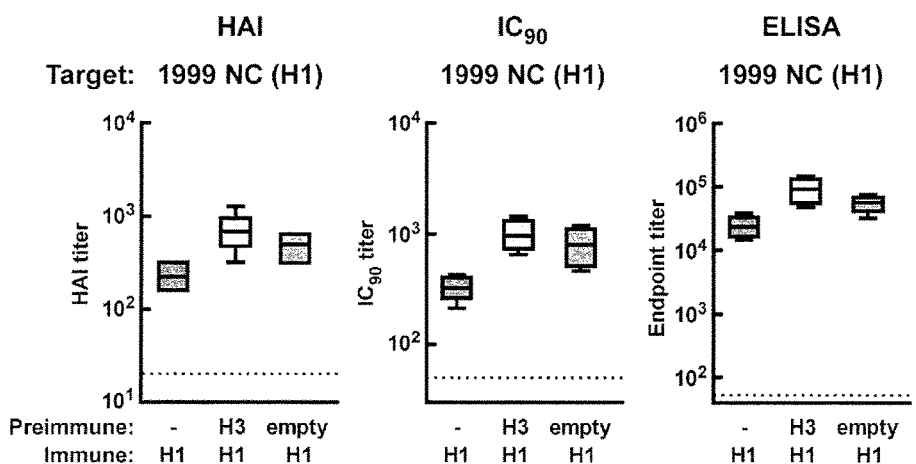

To assess whether the preexisting immune responses to ferritin nanoparticles or to other HA subtypes would attenuate the immunogenicity of the subsequent immunization of HA-np, mice were pre-immunized with either H3 (A/Perth/16/09, 2009 Perth) HA-np or empty ferritin nanoparticles to elicit anti-H3 HA and/or anti-*H. pylori* ferritin immune responses (FIG. 5A). These animals were then immunized with H1 (1999 NC) HA-np. Comparable HAI, $IC_{90}$ neutralization and ELISA titers against 1999 NC HA were observed in naïve animals as well as in groups pre-immunized with H3 HA-np or empty ferritin nanoparticles (FIG. 5B). These results indicated that preexisting anti-*H. pylori* ferritin immunity did not diminish the HA-specific ab response.

Example 4. Lack of Autoreactivity of *H. pylori* Ferritin Nanoparticles

This Example demonstrates analyzes the ability of HA-ferritin np of the present invention to elicit an auto-immune response against autologous ferritin in mice.

Although the overall structural architecture and physiological functions of ferritin are conserved across organisms, murine ferritin has only 27% amino acid sequence identity to *H. pylori* ferritin. This homology nonetheless raised the possibility that immunization with *H. pylori* ferritin in mice might abrogate immune tolerance and induce autoimmunity. To address this concern, CD4, CD8 T-cell and ab responses against both murine and *H. pylori* ferritins were analyzed by intracellular cytokine staining (ICS) and ELISA in mice immunized with HA-np. ELISAs were performed according to the procedure in Example 2. For intracellular cytokine analysis, $CD4^+$ and $CD8^+$ T-cell responses were evaluated for interferon-γ (IFN-γ), tumor necrosis factor α (TNFα), and interleukin-2 (IL-2) as described by T. Zhou et al. (*Science* 329, 811-817 (2010)). Individual peptide pools (15-mer overlapping by 11 residues, 2.5 µg ml$^{-1}$ for each peptide) covering *H. pylori* ferritin or mouse ferritin light and heavy chains were used to stimulate cells. After stimulation, cells were fixed, permeabilized and stained using anti-mouse CD3, CD4, CD8, IFN-γ, TNFα and IL-2 mAbs (BD Pharmingen) together with aqua blue dye for live/dead stain (Invitrogen). The data were collected by LSR II Flow Cytometer (BD Biosciences) and IFN-γ-, TNFα- and IL-2-positive cells in the $CD4^+$ and $CD8^+$ cell populations were analyzed with FlowJo software (Tree Star).

Although an increase in the ICS staining of $CD4^+$ T cells stimulated with *H. pylori* ferritin peptides (FIG. 4C, top left) was observed, no increases in the $CD4^+$ and $CD8^+$ ICS responses were seen with murine ferritin peptide stimulation (FIG. 4C, bottom left and middle). In addition, while high titers (>$10^6$) of anti-*H. pylori* ferritin abs were detected in ferritin nanoparticle- and HA-np-immune sera, abs to mouse ferritin were undetectable (FIG. 4C, right). These results demonstrate that HA-ferritin np of the present invention do not elicit autoreactivity to autologous ferritin in mice.

Example 5. Generation of Trivalent HA-np and Immunogenicity in Mice

The Example analyzes whether multivalent HA-np were similar in immunogenicity to monovalent np.

HA-np expressing HAs from H1 (A/California/04/09, 2009 CA), H3 (2009 Perth) or influenza B (B/Florida/04/06, 2006 FL) were generated. The 2009 CA (H1)-, 2009 Perth (H3)- and 2006 FL (type B)-HA-np self-assembled and displayed the same morphology observed for 1999 NC HA-np (FIG. 6A). Trivalent HA-np were generated by combining three monovalent HA-np, and their immunogenicity was compared to a seasonal TIV containing the same H1 and H3 strains and a mismatched type B (B/Brisbane/60/08). HAI titers against homologous H1N1 and H3N2 viruses were significantly increased in animals immunized with trivalent HA-np relative to TIV-immunized animals (FIG. 6B; p=0.0125 and 0.0036, respectively). When compared to animals immunized with the corresponding monovalent HA-np, HAI titers against 2009 CA (H1) and 2009 Perth (H3) induced by trivalent HA-np were comparable (FIG. 6B). These results demonstrate that no substantial antigenic competition between H1 and H3 HA-np was observed with a trivalent HA-np vaccine.

Example 6. Cross-Protective Immunity Elicited by HA-np in Ferrets

This Example demonstrates that vaccination of ferrets with 1999 NC HA-np elicits a protective immunity similar to that observed in human disease.

Male Fitch ferrets (6 months old; Triple F Farms), seronegative for exposure to H1N1, H3N2 and type B influenza viruses, were housed and cared for at BIOQUAL, Inc. (Rockville, Md.). Prior to study start, a temperature transponder (Biomedic Data Systems, Inc.) was implanted into the neck of each ferret. Ferrets were immunized (6 ferrets/group) intramuscularly with 500 µl of PBS, 7.5 µg (2.5 µg of H1 HA) of TIV or 3.35 µg (2.5 µg of HA) of HA-np in 500 µl of 50% (v/v) mixture of Ribi adjuvant in PBS at weeks 0 and 4. Blood was collected 3 and 2 weeks after the first and the second immunization, respectively.

Figure 7A:
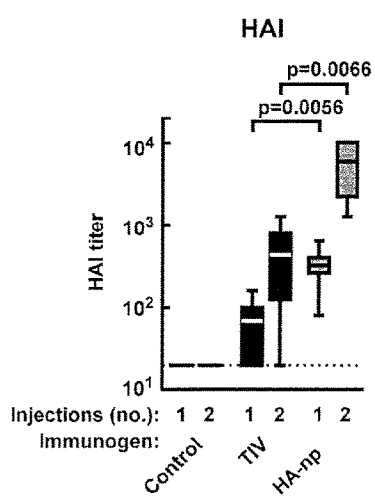
FIG. 7A-7E. Protective immunity induced in ferrets immunized with the HA-np. Ferrets were immunized twice with PBS (control), 7.5 ug (2.5 ug of H1 HA) of TIV or 2.5 ug (amount of HA) 1999 NC HA-np using Ribi adjuvant and a 4-week interval. Control animals received PBS. (A) HAI (B) IC90 neutralization, and (C) anti-HA ab endpoint titers in immunized ferrets against homologous 1999 NC HA were determined. Immune sera were collected 3 and 2 weeks after the first (R. Salomon, R. G. Webster, The influenza virus enigma. *Cell* 136, 402-410 (2009) and second (L. C. Lambert, A. S. Fauci, Influenza vaccines for the future. *N Engl J Med* 363, 2036-2044 (2010)) immunizations, respectively. The data are presented as box and whisker plots with lines at the mean (n=6). D and E Protection of immunized ferrets from an unmatched 2007 Bris virus challenge. Ferrets were challenged with $10^{6.5}$ 50% egg infectious dose (EID50) of 2007 Bris virus 5 weeks after the second immunization. (D) Virus titers in the nasal washes from 1, 3 and 5 days post challenge were determined by a 50% tissue culture infectious dose ($TCID_{50}$) assay. One of six ferrets in the TIV-immunized group showed measurable virus on day 5. Virus titers in 4 out of 6 ferrets on day 3 and 6 out of 6 ferrets on day 5 in the HA-np-immunized group were under the detection limit (<102). The mean viral loads with standard deviation (s.d.) at each time point were plotted (n=6). (E) Change in the body weight after the virus challenge was also monitored. Each data point represents the mean percent change in body weight from the pre-challenge (day 0). The mean body weight changes with standard error (s.e.) at each time point were plotted (n=6).

Three weeks after the first immunization, all ferrets receiving HA-np generated protective HAI titers against homologous H1 1999 NC virus (>1:40), while only 50% (3/6) of TIV-immunized ferrets induced HAI titers greater than 1:40 (FIG. 7A, left; p=0.0056). The same trend was also observed for both neutralization and anti-HA ab titers (FIG. 7A, middle and right; p=0.0047 and p=0.0045, respectively), documenting the superior potency of HA-np in a second species. After boosting, the HAI and $IC_{90}$ neutralization titers of the HA-np-immune sera were ~10-fold higher than those of TIV-immunized ferrets (FIG. 7A, left and middle; 457±185 vs. 5760±1541, p=0.0066, and 598±229 vs. 5515±1074, p=0.0012, respectively). A similar enhancement in HA-np vs. TIV immunization was also observed by ELISA titers (FIG. 7A, right; p=0.0038). Remarkably, a single immunization with HA-np induced immune responses comparable to two immunizations with TIV (FIG. 7A).

To determine whether HA-np could confer protection against an unmatched H1N1 virus, five weeks after the last immunization ferrets immunized with 1999 NC HA-np or TIV containing the same H1 HA were challenged with $10^{6.5}$ $EID_{50}$ of 2007 Bris virus. (1999 NC and 2007 Bris viruses are 8 years apart and their antigenic characteristics are sufficiently different to require the production of two different vaccines to confer protection in humans.) The virus was expanded in embryonated chicken eggs from a seed stock obtained from CDC (Atlanta, Ga.) and has a titer of $10^{6.5}$ $EID_{50}$ ml$^{-1}$. The virus stock was inoculated intranasally into ferrets, which had been anesthetized with ketamine/xylazine, in a volume of 500 µl per nostril. The ferrets were observed for clinical signs twice daily and weight and temperature measurements recorded daily by technicians blind to the treatment groups. Nasal washes were obtained on days 1, 3 and 5 and infectious viral titers were determined by $TCID_{50}$ assay using MDCK cells as described previously (C. J. Wei et al., Induction of broadly neutralizing H1N1 influenza antibodies by vaccination. *Science* 329, 1060-1064 (2010)).

Figure 7B:
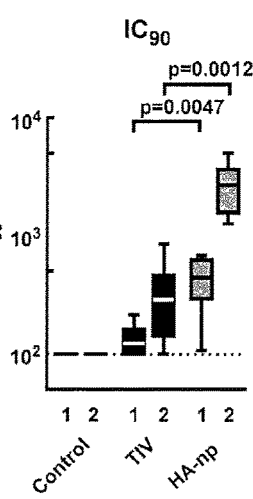
Figure 7C:
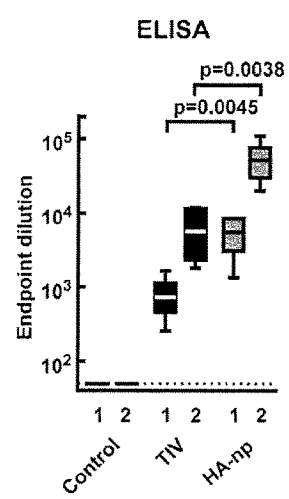
Figure 7D:
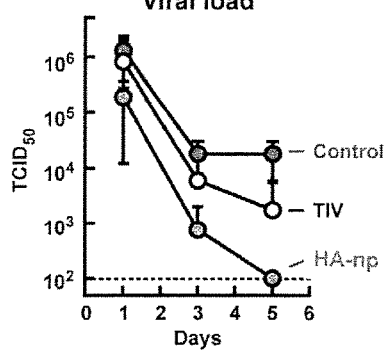
Figure 7E:
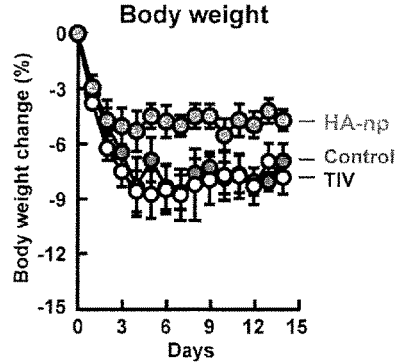

Ferrets immunized with HA-np showed a significant reduction in viral shedding beginning 1 day after challenge compared to the sham control group (FIG. 7B, left; p=0.0259). At the same time point, no reduction in viral shedding was seen in the TIV-immunized group. Four of six animals immunized with HA-np had no detectable viral load after 3 days and by day 5, all animals in this group cleared the virus, while all animals in the sham control group still had detectable virus (FIG. 7B). In addition, HA-np-immunized ferrets suffered less body weight loss compared to the TIV-immunized and sham control groups (FIG. 7B, right). These results demonstrate faster virus clearance in ferrets immunized with HA-np than with TIV and further demonstrate that HA-np effectively induced cross-protective immunity in vaccinated ferrets.

Example 7. Induction of Two Types of Neutralizing Abs (nAbs) in Ferrets

This Example demonstrates the breadth and specificity of nAbs in ferret immune sera.

Figures 8A, 8B:
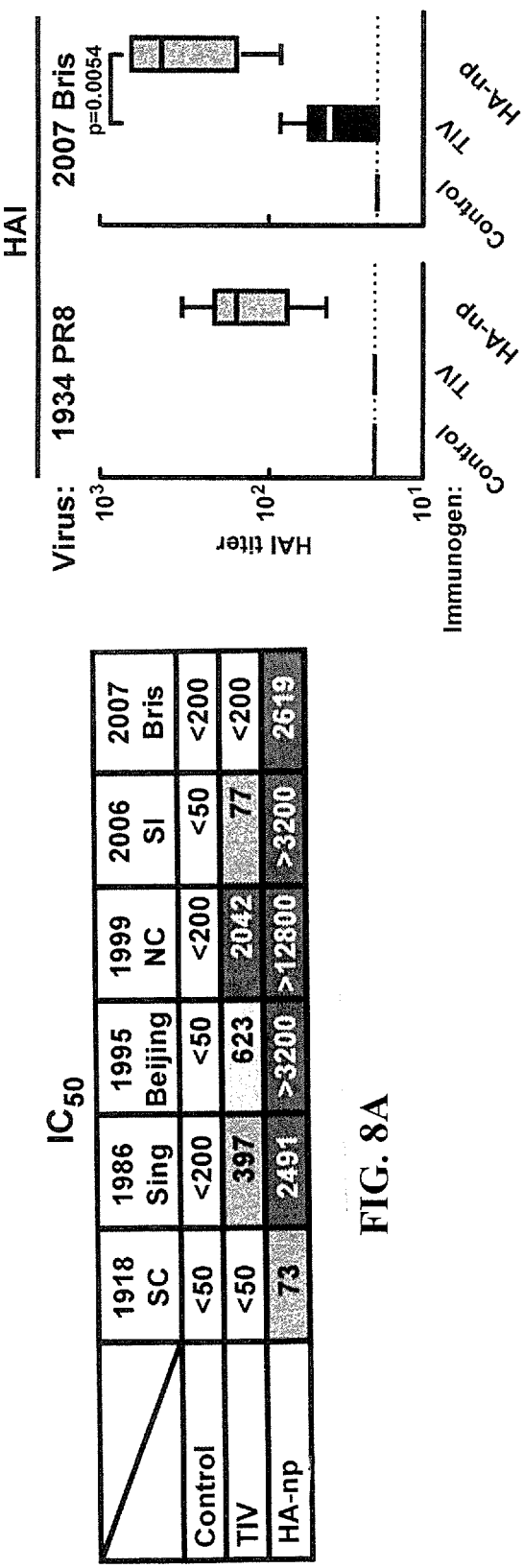

$IC_{50}$ neutralization titers against 1986 Sing, A/Beijing/262/1995 (1995 Beijing), A/Solomon Islands/3/2006 (2006 SI) and 2007 Bris were significantly higher in animals immunized with HA-np compared to immunization with TIV (FIG. 8A, left). This enhanced breadth was due not only to a quantitative increase in overall ab titer (~9-fold against matched virus) but also reflected a qualitative difference in the types of abs elicited (>40-fold enhancement against an unmatched strain). To determine whether the cross-reactivity induced by HA-np was due to nAbs to the conserved HA stem epitope, ferret immune sera were pre-absorbed with cells expressing a stem mutant (ΔStem) HA to remove non-stem directed antibodies. Briefly, ferret immune sera taken 2 weeks after the second immunization were subjected to the assay. The plasmids encoding for ΔStem and ΔRBS HAs were transfected into 293F cells. Three days after transfection, the cells were analyzed by flow cytometry to confirm expression of HA on the cell surface and used for serum absorption. One ml of the immune sera diluted at 1:100 and 1:1,000 was incubated with 100 μl of pre-washed ΔStem and ΔRBS HA-expressing 293F cell pellets, respectively. After incubating for 1 hour at 4° C., supernatants were harvested by centrifugation and binding to WT and mutant HAs was examined by ELISA previously described (C. J. Wei et al., Induction of broadly neutralizing H1N1 influenza antibodies by vaccination. *Science* 329, 1060-1064 (2010)). The ΔStem HA-pre-absorbed sera were also used for competition ELISA.

Stem-specific abs were detected in HA-np-immunized ferrets (6/6) in greater frequency and magnitude than TIV-immune ferrets (2/6) (FIG. 8B, left; p=0.0056). Moreover, binding of these pre-absorbed sera to HA was inhibited by CR6261 mAb (FIG. 8B, right; p=0.0019), further documenting the specificity of HA-np immune sera to the stem epitope. The HAI titers against heterologous 2007 Bris virus were also significantly higher in ferrets immunized with HA-np (6/6, 1:80-1:640) than with TIV (3/6, 1:40-1:80) (FIG. 8A, right; p=0.0054). Interestingly, in contrast to a previous study in which DNA prime/TIV boost was used to elicit anti-stem broadly neutralizing abs (bnAbs) (C. J. Wei et al., Induction of broadly neutralizing H1N1 influenza antibodies by vaccination. *Science* 329, 1060-1064 (2010)), sera from animals immunized with HA-np showed HAI ab titers against a highly divergent 1934 PR8 strain, with titers ≥1:40 in all ferrets. However, no HAI titers against 1934 PR8 were detected in TIV-immunized ferrets (FIG. 8A, right). These data suggested that the HA-np vaccine might elicit another class of nAb directed towards the conserved RBS in the HA head.

To determine whether HA-np elicited abs against RBS, an RBS mutant HA (ΔRBS) was generated by introducing a glycosylation site in the sialic acid binding pocket at residue 190 (FIG. 9) (D. Lingwood et al., Structural and genetic basis for development of broadly neutralizing influenza antibodies. *Nature*, in press). Ferret immune sera were absorbed with ΔRBS HA-expressing cells to remove abs to HA outside of this region and tested for binding against WT or ΔRBS HA. RBS-directed abs were detected with titers of >1:2,000 in all HA-np-immunized ferrets, but only 1 out of 6 ferrets that received TIV (FIG. 8B, middle).

Figure 8C:
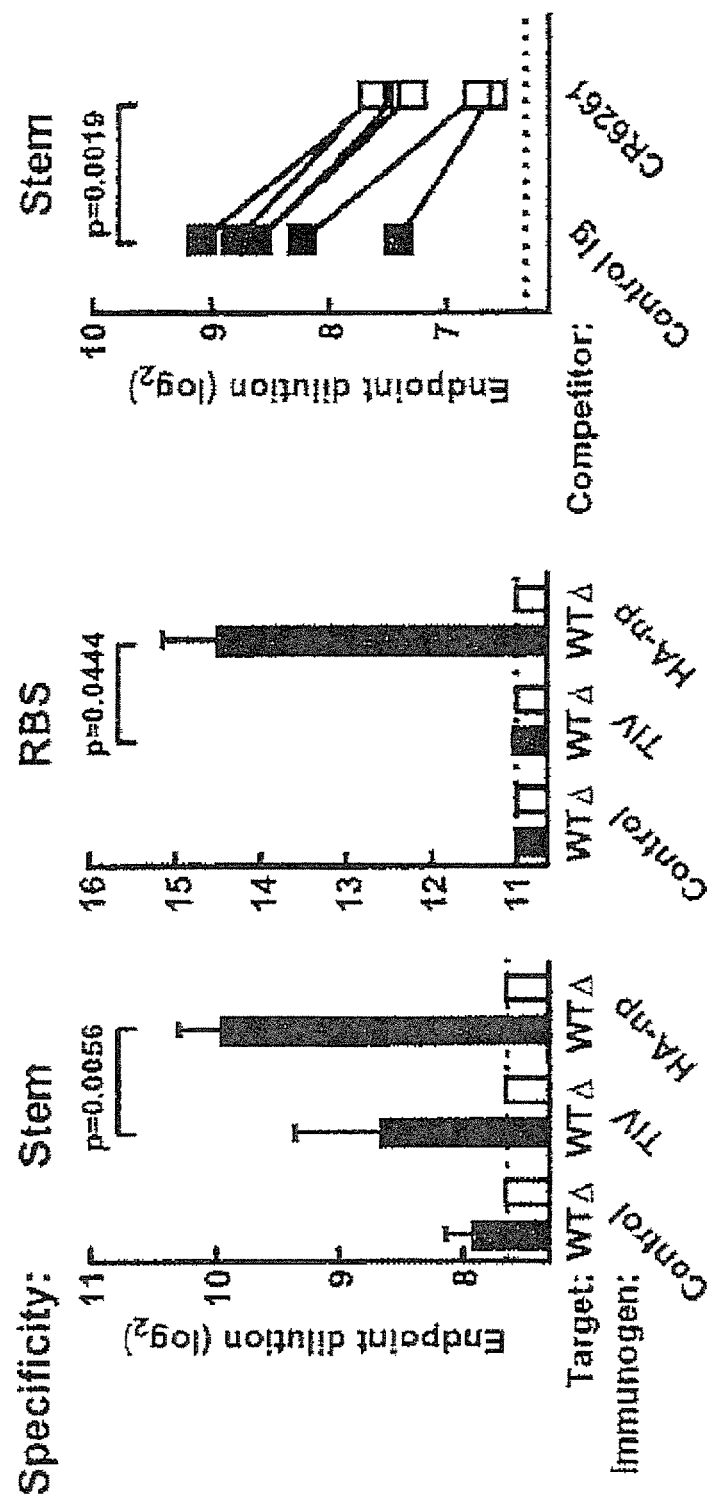

To define the relative contributions of these stem and RBS abs to the breadth of neutralization, neutralization assays were performed in the presence of competitor proteins: WT, ΔStem or ΔRBS HA. In the presence of excess ΔStem HA, only stem-directed abs can neutralize viruses; similarly, ΔRBS HA interferes with all antibodies in the serum except those proximal to the RBS. The relative contribution of stem- and RBS-directed neutralization was measured as activity remaining in the presence of the respective competitor HA. For example, with 2007 Bris, ΔRBS HA only partially inhibited neutralization, while either WT or ΔStem HA almost completely abolished the neutralization activity of the sera; hence, the neutralization against 2007 Bris was due almost entirely to RBS-directed abs (FIG. 8C). Four H1N1 strains were tested in this assay. The pattern of neutralization inhibition varied by strain. Neutralization of 1999 NC or 2007 Bris was mediated predominantly by RBS-directed abs. However, neutralization of 1986 Sing was due mainly to stem-directed abs. Interestingly, the neutralization of 1995 Beijing was more complex. Both stem- and RBS-directed abs contributed to neutralization of this virus (FIG. 8C).

These results demonstrate that HA-np induce both known types of bnAbs—stem-directed and RBS-directed. Together, these abs contribute to the breadth and potency of the immune sera elicited by HA-np. The synergy between them explains mechanistically the observed superior efficacy of the HA-np vaccine and decreases the likelihood of viral escape mutations from either antibody alone.

Taken together the above-disclosed Examples demonstrate that a ferritin-based nanoparticle is able to present trimeric HA in its native fold, rigidly and symmetrically, with sufficient spacing to ensure optimal access to potential bnAbs directed to the stem. They also demonstrate that the nanoparticles have enhanced immunogenicity and an expanded neutralization breadth to both stem and RBD antibodies.

Example 8. Immunization of Mice and Ferrets Using a Tetravalent Vaccine

This Example demonstrates the ability of a multivalent vaccine to elicit an immune response against several strains and sub-types of influenza virus.

Figure 15:
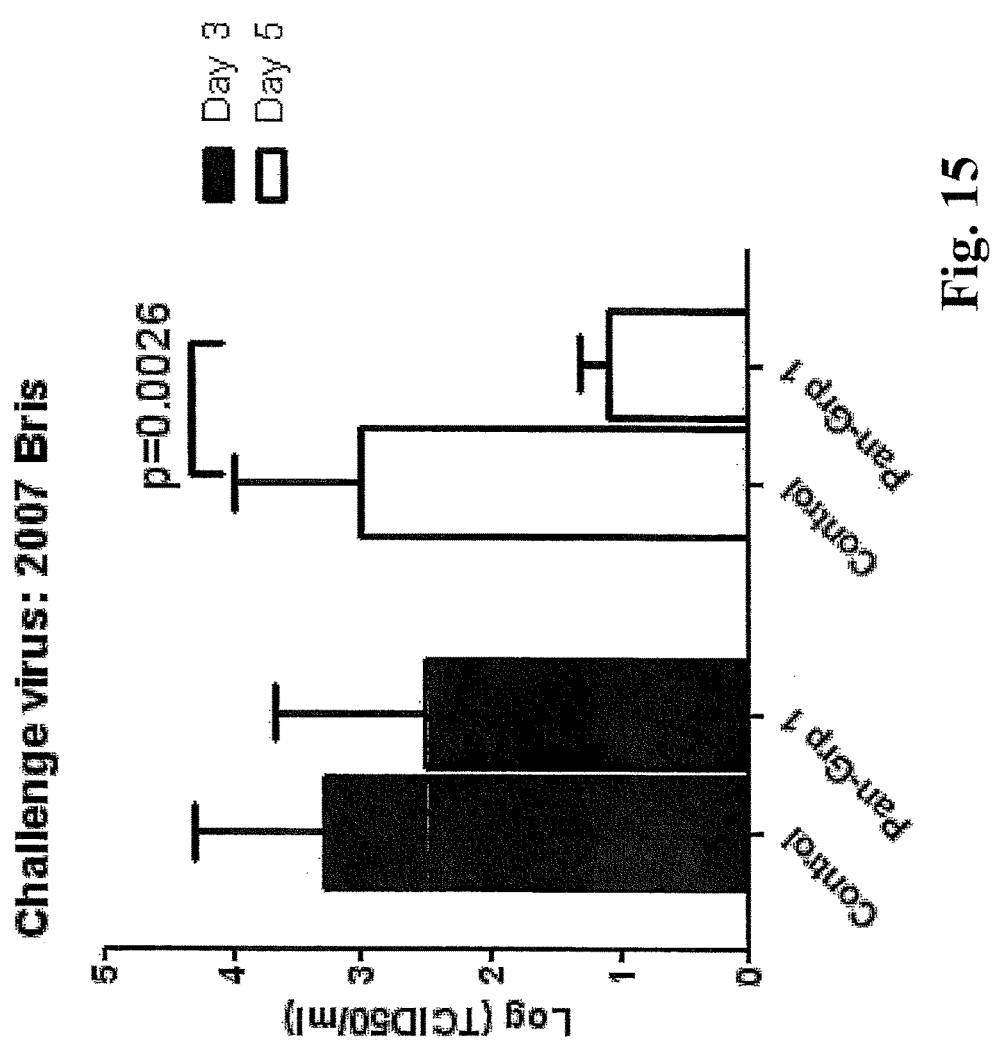
Figure 16:
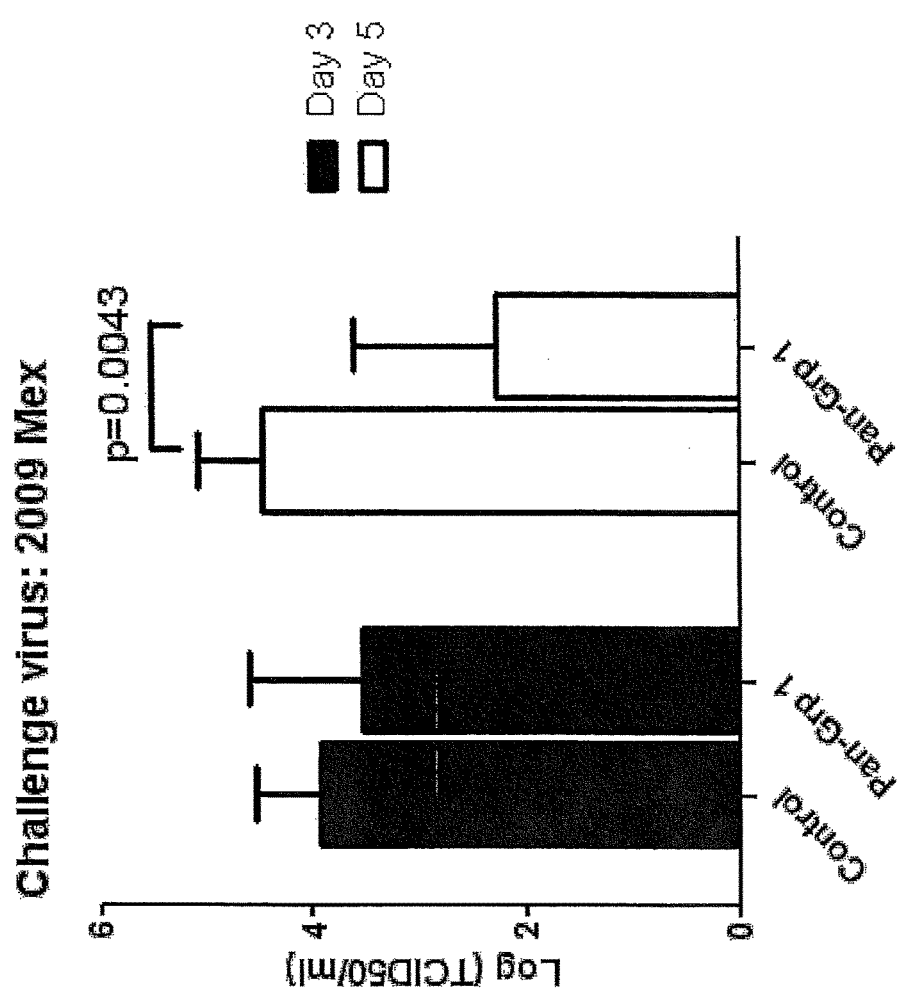
FIG. 16. Protection of ferrets from viral challenge with Influenza A/Mexico/2009 (H1N1) (2009 Mex). Two groups of ferrets (n=6) were immunized with pan Group1 HA np vaccine or PBS (control) and challenged with heterologous 2009 Mex virus ($10^{6.5}$ $EID_{50}$). Virus titers were measured in nasal swabs collected on day 3 and day 5 post challenge. Titers were determined using end-point titration in MDCK cells.

The ability of a pan-group 1 vaccine to stimulate neutralizing antibodies against a variety of influenza viruses was tested in mice and ferrets using a protocol similar to that described in Example 1, and outlined in FIG. 11. Briefly, a pan-group 1 HA-ferritin np vaccine was produced by combining four different monovalent HA-ferritin np vaccines. Specifically, HA-ferritin np, each expressing either H1 ANC/20/1999, H1 A/CA/04/2009, H2 A/Singapore/1/1957 or H5 A/Indonesia/05/2005, were combined to produce a single vaccine containing all four HA proteins. Mice were immunized twice in a four week interval using 6.8 ug total of the pan-group 1 vaccine (1.7 ug of each HA-ferritin np) in Ribi. Ferrets were immunized twice in a four week interval using 10 ug total of the pan-group 1 vaccine (2.5 ug of each HA-ferritin np) in Ribi. Blood was obtained from the immunized animals and the titer of neutralizing antibodies against various influenza viruses measured. The results of this analysis are shown in FIGS. 12-14. Immunized ferrets were also challenged with either influenza A/Brisbane/59/2007 Brisbane (H1N1) (2207 Bris) (FIG. 15) or influenza A/Mexico/2009 (H1N1) (2009 Mex) (FIG. 16) and the resulting virus titers measured on day 3 and 5 post-challenge.

Example 9. Design and Construction HA-Ferritin Stem-Region Fusion Proteins

This Example demonstrates the construction of HA-ferritin proteins and nanoparticles that present the stem region of the influenza HA protein.

As illustrated in FIG. 17, the stem region of the influenza HA protein is highly conserved among different influenza strains, and possesses a site of vulnerability for Group 1 viruses. Thus, a vaccine that elicits neutralizing antibodies against the stem region of the influenza HA protein should be broadly neutralizing. A nanoparticle displaying the stem region of the influenza stem region was constructed as a vaccine.

Design of an HA-Stabilized Stem Fusion Protein.

Figures 18A, 18B:
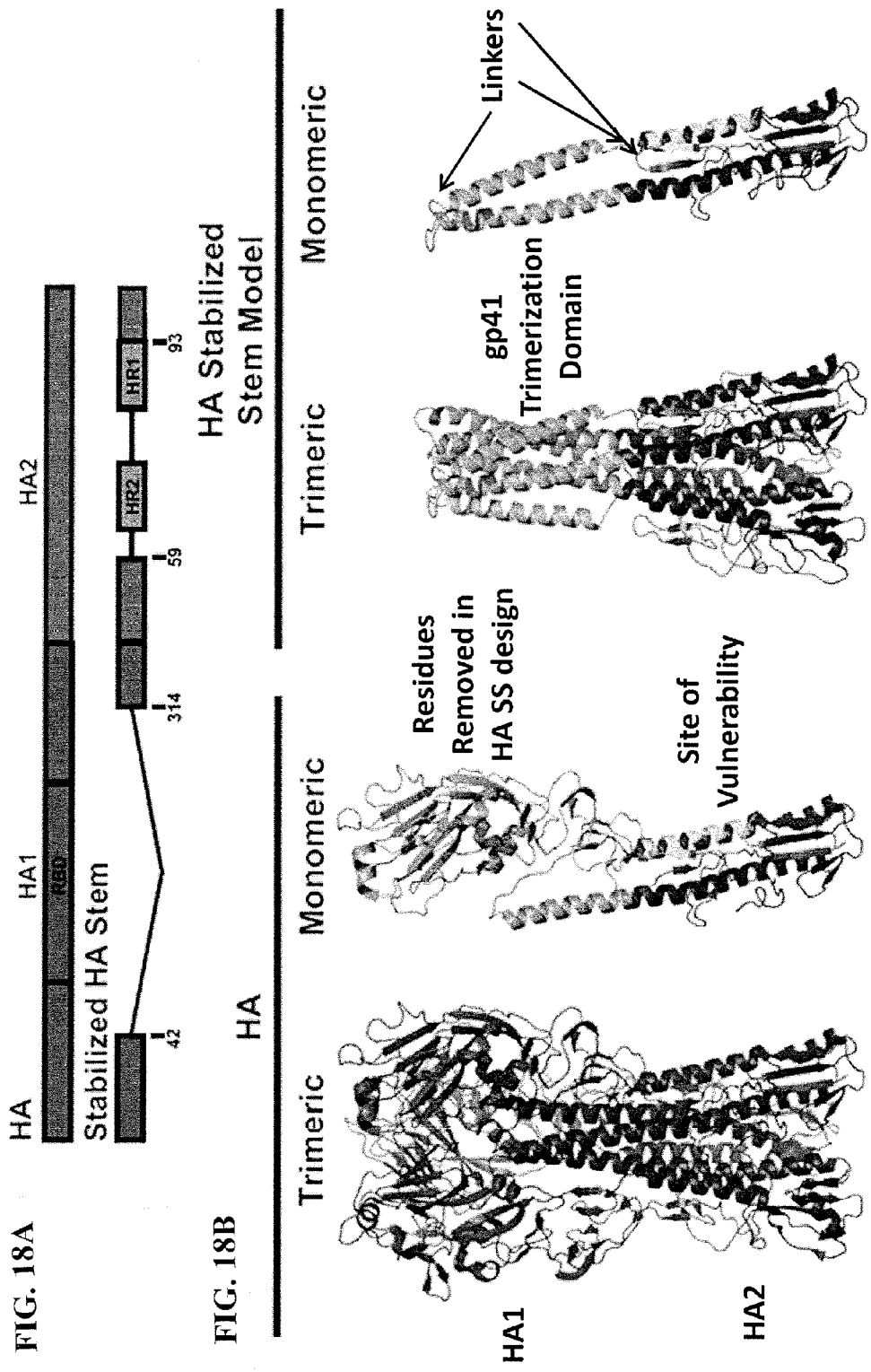
FIG. 18A-18B. Design of HA Stabilized Stem protein. (A) Schematic of the HA SS (bottom) in comparison to HA (top). HA SS was constructed by inserting a GWG linker between residues 42 and 314 of HA1 RBD head, a gp41 post-fusion trimerization motif inserted in place of residues 59 through 93 of HA2, a GG linker between HA2 and the gp41 HR2 helix and an NGTGGGSG linker between the two gp41 helices. The gene sequence of H1 NC 99 SS is provided in the supplemental materials. (B) Trimeric and monomeric representation of HA (PDB entry 1RU7) (left) in comparison to the HA SS model (right).

An HA-stabilized stem fusion protein (HA SS) was constructed as follows: residues 43-313 of the head domain of HA1 were replace with a Gly-Trp-Gly linker. The membrane distal end of HA2 (residues 59 to 93) was replaced by an HIV-1 Bal gp41 HR2 helix followed by a six residue glycine-rich linker (Asn-Gly-Thr-Gly-Gly-Gly-Ser-Gly) and the gp41 HR1 helix. The HR1 helix of gp41 was added in frame with helix C of HA2 so as to generate a long central chimeric helix. The resulting six helix bundle sitting atop the modified hemagglutinin stem provides stability to the SS trimer in lieu of the missing head residues. A schematic of the resulting protein is shown in FIG. 18A, while a ribbon diagram is shown in FIG. 18B. A second trimerization domain consisting of a 28 residue T4 foldon domain was joined to the membrane proximal C-terminus of HA2. The HA SS-ferritin nanoparticle (HA SS-np) protein was generated by joining residue 174 (H3 numbering) of HA SS to *H. pylori* ferritin (residues 5-167) with a Ser-Gly-Gly linker.

In constructing HA-SS fusion proteins, genes encoding wild-type HA proteins (A/Puerto Rico/8/1934 (H1 1934 PR8), A/Singapore/6/1986 (H1 1986 Sing), A/New Caledonia/20/1999 (H1 1999 NC), A/Brisbane/59/2007 (H1 2007 Bris), A/Vietnam/1203/2004 (H5 2004 VN), A/Canada/720/05 (H2 2005 CAN), A/Hong Kong/1/1968 (H3 1968 HK), A/Hong Kong/1073/1999 (H9 1999 HK) and their corresponding NAs, H1 NC 99 SS, RSC3 HIV gp120 control protein, and all Abs (CR6261, F16v3, and VRC01) were synthesized with human preferred codons as previously described (Wei et al. Science 2010, 329(5995):1060-4). *Helicobacter pylori* nonheme iron-containing ferritin (GenBank NP_223316) with a point mutation (N19Q) to abolish a potential N-linked glycosylation site was synthesized by PCR-based accurate synthesis (Xiong et al. *Nat Protoc* 2006, 1(2):791-797) using human-preferred codons. Coding sequences for the human CD5 leader sequence and a serine-glycine-glycine (SGG) spacer were joined to the gene fragment encoding ferritin (residues 5-167) to generate a secreted protein. HA and HA SS-np fusion proteins were generated by overlap PCR by joining the HA ectodomains at residue HA2 174 (H3 numbering) to *H. pylori* ferritin (residues 5-167) with a Ser-Gly-Gly linker. Stem mutant probes Δstem (glycosylation insertion into the CR6261 binding epitope at position 45 in HA2; H3 numbering) which prevent binding at the conserved H1 stem epitope were generated using site directed mutagenesis. Genes encoding these proteins were cloned into a CMVR plasmid backbone for efficient mammalian cell expression.

Protein Expression and Purification

Figure 19:
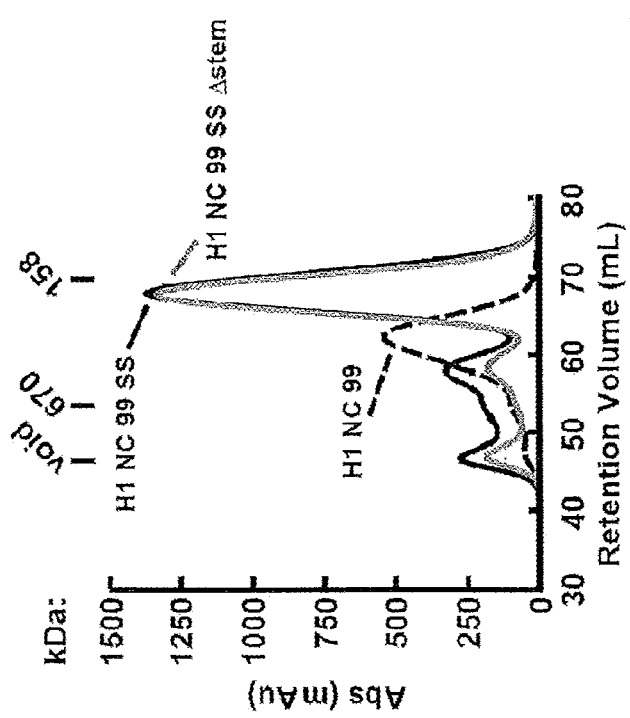
FIG. 19. Size exclusion chromatogram of HA and HA SS probes. Calibration standards are shown above the curves as vertical lines.

Plasmids encoding soluble proteins were transfected (HA ectodomain genes were cotransfected with the corresponding NA encoding plasmids) into the human embryonic kidney cell line 293F and isolated from expression supernatants 72-96 hrs post-transfection. All HA and HA SS trimeric proteins were purified first by metal chelation affinity chromatography and then by size exclusion chromatography as previously described (Wei et al. J Virol. 2008, 82(13):6200-8). IgG Abs were purified using a Protein G affinity column (GE Healthcare). The HA- and HA SS-np were purified by affinity column chromatography using *Erythrina cristagalli* agglutinin (ECA, coral tree lectin; EY Laboratories, Inc.) specific for galactose β(1,4) N-acetylglucosamine and *Galanthus nivalis* agglutinin (GNA, snowdrop lectin; EY Laboratories, Inc.) specific for α(1,3) and α(1,6) linked high mannose structures, respectively. HA- and HA SS-np were further purified by size exclusion chromatography with a Superose 6 PG XK 16/70 column (GE Healthcare) in PBS (FIG. 19).

HA SS-Ferritin Characterization.

Figures 21A, 21B:
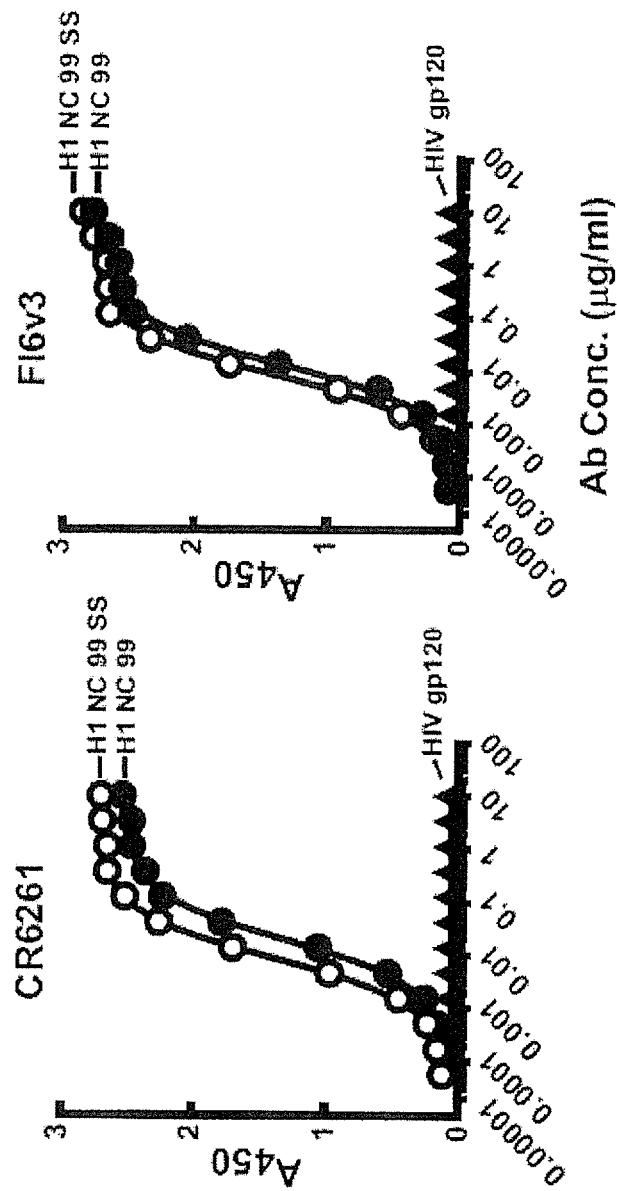
FIG. 21A-21B. Antigenic characterization of HA SS-ferritin np. The ability of purified HA SS and HA SS-np to bind to monoclonal Abs CR6261 (A) and FI6v3 (B) was characterized by ELISA. HA and HIV gp120 proteins served as controls.

HA SS-ferritin np were visualized by electron microscopy. Briefly, purified HA SS-np were negatively stained with phosphotungstic acid and ammonium molybdate, respectively, and images were recorded on a Tecnai T12 microscope (FEI) at 80 kV with a CCD camera (AMT Corp.). The results of this analysis are shown in FIG. 20. IN addition, the ability of purified HA SS and HA SS-np to bind to monoclonal Abs CR6261 and FI6v3 ($1.7 \times 10^{-4}$ to 10 µg/mL) was characterized by ELISA. HA and HIV gp120 proteins served as controls. Ab binding was detected by peroxidase-conjugated goat anti-human IgG. The results of this analysis, which are shown in FIG. 21, demonstrate that HAS S-ferritin is antigenically similar to HA protein.

Example 10. Immune Response to HA SS-Ferritin Nanoparticles

This Example demonstrates the immune response generated in animals following immunization with HA SS-ferritin np.

BALB/c mice were immunized twice intramuscularly with protein (2 or 10 µg each) formulated with Ribi adjuvant system (Sigma) at a 3 week interval. Mice received either homologous (HA SS-np prime and boost) or heterologous (HA-np prime and HA SS-np boost) immunizations. Ferrets were immunized three times intramuscularly with HA SS-np (10 µg each) formulated with Ribi adjuvant system (Sigma) at weeks 0, 4 and 14. Serum was collected from animals 2 weeks after each immunization and 1 week prior to the first immunization and heat inactivated (30 min at 56° C.).

Figure 22:
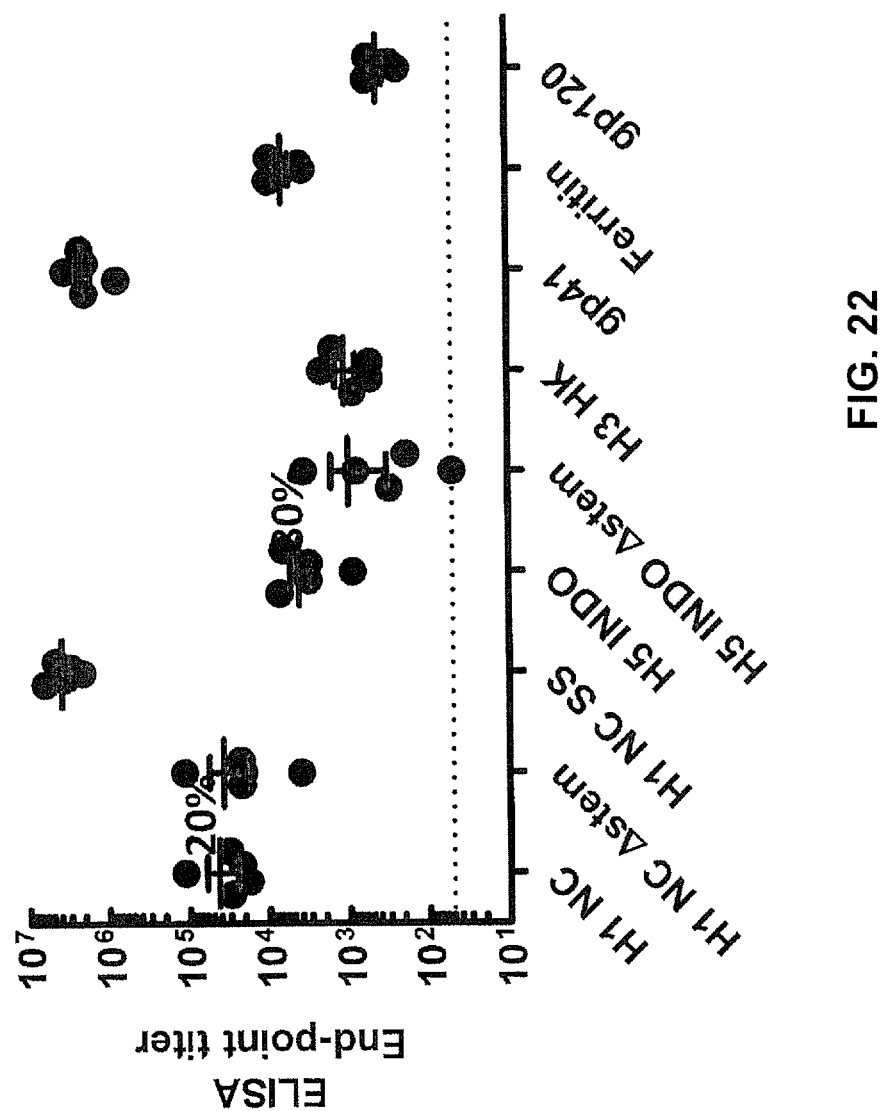
FIG. 22. Immune sera of mice immunized heterologously with HA-np prime and HA SS-np boost are reactive to the conserved HA stem epitope. Antibodies elicited by vaccination target the conserved HA stem epitope as individual mice possess differential binding (a minimum of 2-fold difference in endpoint dilution) between wt and Δstem HA variants. The percentage of mice displaying differential binding is given above matched wt and Δstem constructs. Error bars represent standard error.

Pre- and post-immune sera from immunized mice and ferrets were assayed for binding to HA and HA SS by ELISA. Briefly, sera were serially diluted (diluted 50 to 2.3×10⁶) and assayed for reactivity to soluble trimeric HA and HA SS proteins, as well as control proteins (200 ng/well with molar equivalents plated according to HA SS). Binding was detected by peroxidase conjugated anti-mouse or anti-ferret IgG, respectively. Endpoint dilutions were determined from nonlinear fit dose-response curves using a detection limit of 2× background absorbance. The result from this analysis are shown in FIG. 22 and demonstrate that stem specific cross-reactive antibodies which recognize the conserved stem-epitope are elicited by HA SS-np vaccination.

Figures 23A, 23B:
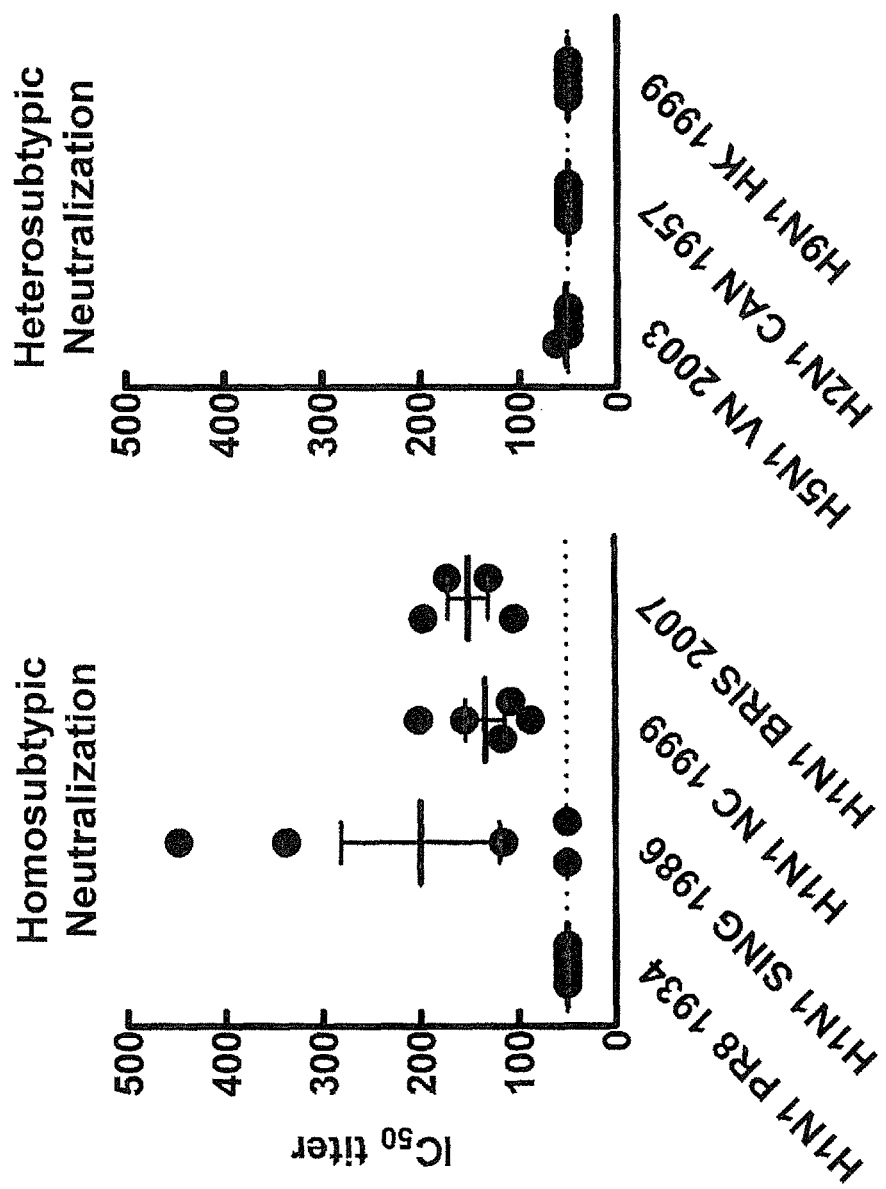
FIG. 23A-23B. Immune sera of mice immunized with HA SS neutralizes diverse pseudovirus stains. IC50 values are shown for individual mice against H1 homosubtypic (A) strains and H2, H5 and H9 group-1 heterosubtypic strains (B). Dashed lines represents the lowest dilution assayed. Error bars represent standard error FIG. 24A-24C. Boosting with HA SS-np increases neutralizing titers in ferrets against H1N1 New Calendonia. Pseudovirus neutralizing titers were calculated for preimmune (A), HA FL-np primed (B), and HA SS-np (C) boosted sera from individual mice. Error bars represent standard deviation of values.

Sera were also analyzed for neutralization of pseudotyped recombinant lentiviruses expressing wild-type HA with the corresponding NA with a luciferase reporter gene as previously described (Wei et al. Science 2010, 329(5995):1060-4) following pretreatment with receptor-destroying enzyme (RDE II; Denka Seiken Co., Ltd.). Psuedotype neutralization competition of ferret serum was performed by incubating serially diluted serum in the presence of either H1 1999 NC SS, H1 1999 NC SS Δstem probe or gp120 control (10 μg/mL [JK1]) for 1 hr (RT) before addition to pseudotyped recombinant lentiviruses and assaying for neutralization. The results from this analysis are shown in FIG. 23 and demonstrate that vaccination with HA SS-np elicits neutralizing antibodies against various group-1 strains.

Example 11. Immune Response to HA SS-Ferritin Heterologous Immunization Boost

This example demonstrates that HA SS-np can be utilized to boost antibodies directed to the conserved stem epitope.

BALB/c mice were immunized twice intramuscularly with heterologous ferritin proteins (HA-np prime and HA SS-np boost; 2 μg each) formulated with Ribi adjuvant system (Sigma) at a 3 week interval. Serum was collected from animals 2 weeks after each immunization and 1 week prior to the first immunization and heat inactivated (30 min at 56° C.).

Pre- and post-immune sera from immunized mice were assayed for binding to HA and HA SS by ELISA. Briefly, sera were serially diluted (diluted 50 to 2.3×10⁶) and assayed for reactivity to soluble trimeric HA and HA SS proteins, as well as control proteins (200 ng/well with molar equivalents plated according to HA SS). Binding was detected by peroxidase conjugated anti-mouse or anti-ferret IgG, respectively. Endpoint dilutions were determined from nonlinear fit dose-response curves using a detection limit of 2× background absorbance. The results from this analysis are shown in FIG. 22 and demonstrate that cross-reactive stem-epitope specific antibodies are being elicited.

Figure 24A:
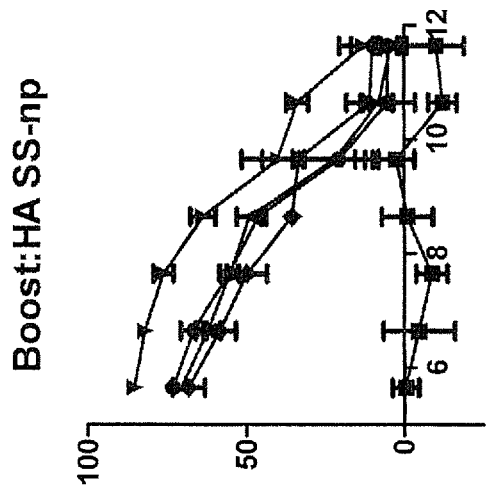
Figure 24B:
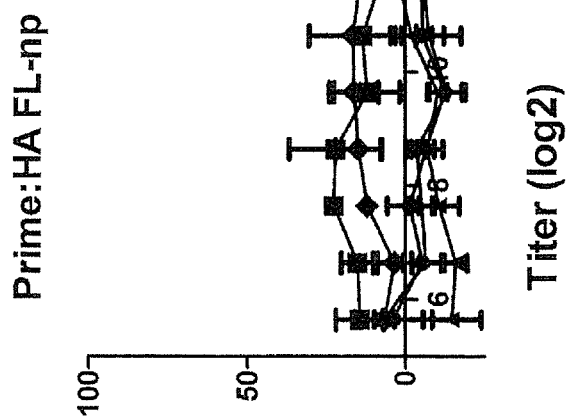
Figure 24C:
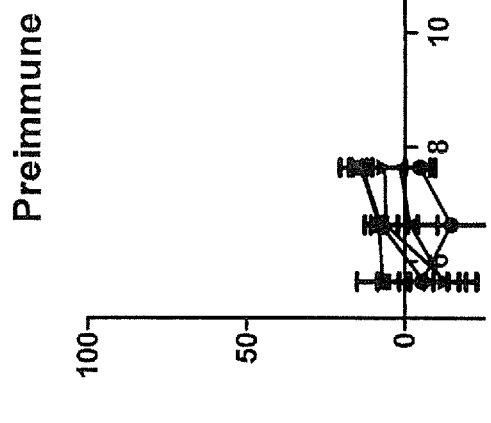

Sera were also analyzed for neutralization of pseudotyped recombinant lentiviruses expressing wild-type HA with the corresponding NA with a luciferase reporter gene as previously described (Wei et al. Science 2010, 329(5995):1060-4) following pretreatment with receptor-destroying enzyme (RDE II; Denka Seiken Co., Ltd.). The results from this analysis are shown in FIG. 24 and demonstrate that mice which have preexisting stem antibodies titers can be boosted with HA SS-np.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

SEQUENCE LISTING

<160> NUMBER OF SEQ ID NOS: 162

<210> SEQ ID NO 1
<211> LENGTH: 504
<212> TYPE: DNA
<213> ORGANISM: Helicobacter pylori

<400> SEQUENCE: 1

```
atgttatcaa aagacatcat taagttgcta aacgaacaag tgaataagga aatgaactct      60
tccaacttgt atatgagcat gagttcatgg tgctataccc atagcttaga tggcgcgggg     120
cttttcttgt ttgaccatgc ggctgaagaa tacgagcatg ctaaaaagct tattatcttc     180
ttgaatgaaa acaatgtgcc tgtgcaattg accagcatca gcgcgcctga gcataagttt     240
gaaggtttga ctcaaatttt ccaaaaagcc tatgaacatg agcaacacat cagcgagtct     300
attaacaata tcgtagatca cgccataaaa agcaaagatc atgcgacttt caatttcttg     360
caatggtatg tggctgaaca gcatgaagaa gaagtgcttt tcaaggatat tttggataaa     420
attgagttga ttggtaatga aaaccatggc ttgtatttag ccgatcagta tgtcaaaggg     480
atcgctaaaa gcaggaaatc ttaa                                            504
```

<210> SEQ ID NO 2
<211> LENGTH: 167
<212> TYPE: PRT

<213> ORGANISM: Helicobacter pylori

<400> SEQUENCE: 2

```
Met Leu Ser Lys Asp Ile Ile Lys Leu Leu Asn Glu Gln Val Asn Lys
1               5                   10                  15
Glu Met Asn Ser Ser Asn Leu Tyr Met Ser Met Ser Ser Trp Cys Tyr
            20                  25                  30
Thr His Ser Leu Asp Gly Ala Gly Leu Phe Leu Phe Asp His Ala Ala
        35                  40                  45
Glu Glu Tyr Glu His Ala Lys Lys Leu Ile Ile Phe Leu Asn Glu Asn
    50                  55                  60
Asn Val Pro Val Gln Leu Thr Ser Ile Ser Ala Pro Glu His Lys Phe
65                  70                  75                  80
Glu Gly Leu Thr Gln Ile Phe Gln Lys Ala Tyr Glu His Glu Gln His
                85                  90                  95
Ile Ser Glu Ser Ile Asn Asn Ile Val Asp His Ala Ile Lys Ser Lys
            100                 105                 110
Asp His Ala Thr Phe Asn Phe Leu Gln Trp Tyr Val Ala Glu Gln His
        115                 120                 125
Glu Glu Glu Val Leu Phe Lys Asp Ile Leu Asp Lys Ile Glu Leu Ile
    130                 135                 140
Gly Asn Glu Asn His Gly Leu Tyr Leu Ala Asp Gln Tyr Val Lys Gly
145                 150                 155                 160
Ile Ala Lys Ser Arg Lys Ser
                165
```

<210> SEQ ID NO 3
<211> LENGTH: 504
<212> TYPE: DNA
<213> ORGANISM: Helicobacter pylori

<400> SEQUENCE: 3

```
ttaagatttc ctgcttttag cgatcccttt gacatactga tcggctaaat acaagccatg      60
gttttcatta ccaatcaact caattttatc caaaatatcc ttgaaaagca cttcttcttc     120
atgctgttca gccacatacc attgcaagaa attgaaagtc gcatgatctt tgcttttat     180
ggcgtgatct acgatattgt aatagactc gctgatgtgt tgctcatgtt cataggcttt     240
ttggaaaatt tgagtcaaac cttcaaactt atgctcaggc gcgctgatgc tggtcaattg     300
cacaggcaca ttgttttcat tcaagaagat aataagcttt ttagcatgct cgtattcttc     360
agccgcatgg tcaaacaaga aaagccccgc gccatctaag ctatgggtat agcaccatga     420
actcatgctc atatacaagt tggaagagtt catttcctta ttcacttgtt cgtttagcaa     480
cttaatgatg tcttttgata acat                                            504
```

<210> SEQ ID NO 4
<211> LENGTH: 489
<212> TYPE: DNA
<213> ORGANISM: Helicobacter pylori

<400> SEQUENCE: 4

```
gacatcatca agctgctgaa cgagcaggtg aacaaggaga tgcagagcag caacctgtac      60
atgagcatga gcagctggtg ctacacccac agcctggacg gcgccggcct gttcctgttc     120
gaccacgccg ccgaggagta cgagcacgcc aagaagctga tcatcttcct gaacgagaac     180
aacgtgcccg tgcagctgac cagcatcagc gcccccgagc acaagttcga gggcctgacc     240
```

```
cagatcttcc agaaggccta cgagcacgag cagcacatca gcgagagcat caacaacatc    300
gtggaccacg ccatcaagag caaggaccac gccaccttca acttcctgca gtggtacgtg    360
gccgagcagc acgaggagga ggtgctgttc aaggacatcc tggacaagat cgagctgatc    420
ggcaacgaga accacggcct gtacctggcc gaccagtacg tgaagggcat cgccaagagc    480
aggaagagc                                                            489

<210> SEQ ID NO 5
<211> LENGTH: 163
<212> TYPE: PRT
<213> ORGANISM: Helicobacter pylori

<400> SEQUENCE: 5

Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
            20                  25                  30

Asp Gly Ala Gly Leu Phe Leu Phe Asp His Ala Ala Glu Glu Tyr Glu
        35                  40                  45

His Ala Lys Lys Leu Ile Ile Phe Leu Asn Glu Asn Asn Val Pro Val
    50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Glu Val
        115                 120                 125

Leu Phe Lys Asp Ile Leu Asp Lys Ile Glu Leu Ile Gly Asn Glu Asn
    130                 135                 140

His Gly Leu Tyr Leu Ala Asp Gln Tyr Val Lys Gly Ile Ala Lys Ser
145                 150                 155                 160

Arg Lys Ser

<210> SEQ ID NO 6
<211> LENGTH: 489
<212> TYPE: DNA
<213> ORGANISM: Helicobacter pylori

<400> SEQUENCE: 6
gctcttcctg ctcttggcga tgcccttcac gtactggtcg ccaggtaca ggccgtggtt     60 ctcgttgccg atcagctcga tcttgtccag gatgtccttg aacagcacct cctcctcgtg    120
ctgctcggcc acgtaccact gcaggaagtt gaaggtggcg tggtccttgc tcttgatggc    180
gtggtccacg atgttgttga tgctctcgct gatgtgctgc tcgtgctcgt aggccttctg    240
gaagatctgg gtcaggccct cgaacttgtg ctcggggcg ctgatgctgg tcagctgcac    300
gggcacgttg ttctcgttca ggaagatgat cagcttcttg gcgtgctcgt actcctcggc    360
ggcgtggtcg aacaggaaca ggccggcgcc gtccaggctg tggtgtagc accagctgct    420 catgctcatg tacaggttgc tgctctgcat ctccttgttc acctgctcgt tcagcagctt    480
gatgatgtc                                                            489

<210> SEQ ID NO 7
<211> LENGTH: 1695
```

<212> TYPE: DNA
<213> ORGANISM: Influenza virus

<400> SEQUENCE: 7

```
atgaaggcca aactgctggt gctgctgtgt acctttaccg ccacctacgc cgacacaatc      60
tgtatcggct accacgccaa caatagcacc gacaccgtgg atacagtgct ggagaagaac     120
gtgaccgtga cccactctgt gaacctgctg gaggacagcc acaatggcaa gctgtgtctg     180
ctgaaaggca ttgcccctct gcagctgggc aattgttctg tggccggatg gattctgggc     240
aaccccgagt gtgagctgct gatttctaag gagagctgga gctacatcgt ggagaccccc     300
aatcctgaga atggcacctg ctaccctggc tacttcgccg attacgagga gctgcgcgag     360
cagctgtcta gcgtgtccag cttcgagaga ttcgagatct cccccaagga gtccagctgg     420
cctaatcaca cagtgacagg cgtgtctgcc agctgtagcc acaacggcaa aagcagcttc     480
taccggaacc tgctgtggct gacaggcaag aatggcctgt accccaacct gagcaagagc     540
tacgtgaaca caaggaaaaa ggaagtgctg gtgctgtggg gagtgcacca ccctcccaac     600
atcggaaatc agcgggccct gtaccacaca gagaacgcct atgtgagcgt ggtgtccagc     660
cactacagca agagattcac ccccgagatc gccaagagac ccaaagtgag agaccaggag     720
ggccggatca attactactg gaccctgctg gagcctggcg ataccatcat cttcgaggcc     780
aacggcaatc tgatcgcccc ttggtatgcc tttgccctga gcagaggctt tggcagcggc     840
atcatcacaa gcaacgcccc catggatgag tgtgatgcca agtgccagac cctcagggc      900
gccatcaata gcagcctgcc cttccagaat gtgcacctg  tgaccatcgg cgagtgcccc     960
aagtatgtga agcgccaa gctgagaatg gtgaccggcc tgagaaacat ccctagcatc    1020
cagagcagag actgtttgg agccatcgcc ggattcatcg agggaggatg gacaggcatg    1080
gtggatggct ggtacggcta ccaccaccag aatgagcagg gctctggata tgccgccgat    1140
cagaagtcta cccagaacgc catcaacggc atcaccaaca aggtgaacag cgtgatcgag    1200
aagatgaaca cccagtttac cgctgtgggc aaggagttca caagctgga gcggaggatg    1260
gagaacctga caagaaggt ggacgacggc tttctggaca tctggaccta caatgccgaa    1320
ctcctggtcc tcctcgagaa tgagaggacc ctggacttcc acgacagcaa cgtgaagaac    1380
ctgtatgaga aggtgaagag ccagctgaag aacaacgcca aggagatcgg caacggctgc    1440
ttcgagttct accacaagtg taacaacgag tgtatggaga gcgtgaagaa cggcacctac    1500
gactacccta gtacagcga ggagagcaag ctgaaccggg agaagatcga tggcgtgaag    1560
ctggagagca tgggcgtgta tcagatcctg gccatctaca gcacagtggc ctcttctctg    1620
gtgctgctgg tgtctctggg cgccatctcc ttttggatgt gctccaacgg cagcctgcag    1680
tgcaggatct gtatc                                                    1695
```

<210> SEQ ID NO 8
<211> LENGTH: 565
<212> TYPE: PRT
<213> ORGANISM: Influenza virus

<400> SEQUENCE: 8

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

-continued

```
Leu Leu Glu Asp Ser His Asn Gly Lys Leu Cys Leu Leu Lys Gly Ile
     50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460
```

```
Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 9
<211> LENGTH: 1695
<212> TYPE: DNA
<213> ORGANISM: Influenza virus

<400> SEQUENCE: 9
gatacagatc ctgcactgca ggctgccgtt ggagcacatc caaaaggaga tggcgcccag       60
agacaccagc agcaccagag aagaggccac tgtgctgtag atggccagga tctgatacac      120
gcccatgctc tccagcttca cgccatcgat cttctcccgg ttcagcttgc tctcctcgct      180
gtacttaggg tagtcgtagg tgccgttctt cacgctctcc atacactcgt tgttacactt      240
gtggtagaac tcgaagcagc cgttgccgat ctccttggcg ttgttcttca gctggctctt      300 cacctctca taccggttct tcacgttgct gtcgtggaag tccagggtcc tctcattctc      360
gaggaggacc aggagttcgg cattgtaggt ccagatgtcc agaaagccgt cgtccacctt      420
cttgttcagg ttctccatcc tccgctccag cttgttgaac tccttgccca cagcggtaaa      480
ctgggtgttc atcttctcga tcacgctgtt caccttgttg gtgatgccgt tgatggcgtt      540
ctgggtagac ttctgatcgg cggcatatcc agagccctgc tcattctggt ggtggtagcc      600
gtaccagcca tccaccatgc ctgtccatcc tccctcgatg aatccggcga tggctccaaa      660
cagtcctctg ctctggatgc tagggatgtt tctcaggccg tcaccattc tcagcttggc       720 gcttctcaca tacttggggc actcgccgat ggtcacaggg tgcacattct ggaagggcag      780
gctgctattg atggcgccct gaggtgtctg gcacttggca tcacactcat ccatggggc      840 gttgcttgtg atgatgccgc tgccaaagcc tctgctcagg gcaaaggcat accaggggc       900 gatcagattg ccgttggcct cgaagatgat ggtatcgcca ggctccagca gggtccagta      960
gtaattgatc cggccctcct ggtctctcac tttgggtctc ttggcgatct cggggggtgaa    1020 tcttctgctg tagtggctgg acaccacgct cacataggcg ttctctgtgt ggtacagggc     1080
ccgctgattt ccgatgttgg gagggtggtg cactccccac agcaccagca cttccttttc     1140
cttgttgttc acgtagctct tgctcaggtt ggggtacagg ccattcttgc ctgtcagcca     1200
cagcaggttc cggtagaagc tgcttttgcc gttgtggcta cagctggcag acacgcctgt     1260
cactgtgtga ttaggccagc tggactcctt ggggaagatc tcgaatctct cgaagctgga     1320
cacgctagac agctgctcgc gcagctcctc gtaatcggcg aagtagccag ggtagcaggt     1380
gccattctca ggattggggg tctccacgat gtagctccag ctctccttag aaatcagcag     1440
ctcacactcg gggttgccca gaatccatcc ggccacagaa caattgccca gctgcagagg     1500
```

```
ggcaatgcct ttcagcagac acagcttgcc attgtggctg tcctccagca ggttcacaga   1560
gtgggtcacg tcacgttct tctccagcac tgtatccacg tgtcggtgc tattgttggc     1620 gtggtagccg atacagattg tgtcggcgta ggtggcggta aggtacaca gcagcaccag     1680 cagtttggcc ttcat                                                    1695

<210> SEQ ID NO 10
<211> LENGTH: 1551
<212> TYPE: DNA
<213> ORGANISM: Influenza virus

<400> SEQUENCE: 10
atgaaggcca aactgctggt gctgctgtgt acctttaccg ccacctacgc cgacacaatc      60
tgtatcggct accacgccaa caatagcacc gacaccgtgg atacagtgct ggagaagaac     120
gtgaccgtga cccactctgt gaacctgctg gaggacagcc acaatggcaa gctgtgtctg     180
ctgaaaggca ttgcccctct gcagctgggc aattgttctg tggccggatg gattctgggc     240
aaccccgagt gtgagctgct gatttctaag gagagctgga gctacatcgt ggagaccccc     300
aatcctgaga tggcacctg ctaccctggc tacttcgccg attacgagga gctgcgcgag      360
cagctgtctc gcgtgtccag cttcgagaga ttcgagatct cccccaagga gtccagctgg     420
cctaatcaca cagtgacagg cgtgtctgcc agctgtagcc acaacggcaa agcagcttc      480 taccggaacc tgctgtggct gacaggcaag aatggcctgt accccaacct gagcaagagc     540
tacgtgaaca caaggaaaa ggaagtgctg gtgctgtggg gagtgcacca ccctcccaac       600
atcggaaatc agcgggccct gtaccacaca gagaacgcct atgtgagcgt ggtgtccagc     660
cactacagca gaagattcac ccccgagatc gccaagagac ccaaagtgag agaccaggag     720
ggccggatca attactactg gaccctgctg gagcctggcg ataccatcat cttcgaggcc     780
aacggcaatc tgatcgcccc ttggtatgcc tttgccctga gcagaggctt tggcagcggc     840
atcatcacaa gcaacgcccc catggatgag tgtgatgcca agtgccagac cctcagggc       900 gccatcaata gcagcctgcc cttccagaat gtgcaccctg tgaccatcgg cgagtgcccc     960
aagtatgtga aagcgccaa gctgagaatg gtgaccggcc tgagaaacat ccctagcatc     1020
cagagcagag gactgtttgg agccatcgcc ggattcatcg agggaggatg gacaggcatg     1080
gtggatggct ggtacggcta ccaccaccag aatgagcagg gctctggata tgccgccgat    1140
cagaagtcta cccagaacgc catcaacggc atcaccaaca ggtgaacag cgtgatcgag      1200 aagatgaaca cccagtttac cgctgtgggc aaggagttca acaagctgga gcggaggatg    1260
gagaacctga caagaaggt ggacgacggc tttctggaca tctggaccta caatgccgaa      1320
ctcctggtcc tctcgagaa tgagaggacc ctggacttcc acgacagcaa cgtgaagaac     1380
ctgtatgaga aggtgaagag ccagctgaag aacaacgcca aggagatcgg caacggctgc    1440
ttcgagttct accacaagtg taacaacgag tgtatggaga gcgtgaagaa cggcacctac    1500
gactacccta agtacagcga ggagagcaag ctgaaccggg agaagatcga t             1551

<210> SEQ ID NO 11
<211> LENGTH: 517
<212> TYPE: PRT
<213> ORGANISM: Influenza virus

<400> SEQUENCE: 11

Met Lys Ala Lys Leu Leu Val Leu Leu Cys Thr Phe Thr Ala Thr Tyr
1               5                   10                  15
```

-continued

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
```

```
        435                 440                 445
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp
        515

<210> SEQ ID NO 12
<211> LENGTH: 1551
<212> TYPE: DNA
<213> ORGANISM: Influenza virus

<400> SEQUENCE: 12
atcgatcttc tcccggttca gcttgctctc ctcgctgtac ttagggtagt cgtaggtgcc       60
gttcttcacg ctctccatac actcgttgtt acacttgtgg tagaactcga agcagccgtt      120
gccgatctcc ttggcgttgt tcttcagctg gctcttcacc ttctcataca ggttcttcac      180
gttgctgtcg tggaagtcca gggtcctctc attctgagg aggaccagga gttcggcatt       240
gtaggtccag atgtccagaa agccgtcgtc caccttcttg ttcaggttct ccatcctccg      300
ctccagcttg ttgaactcct tgcccacagc ggtaaactgg tgttcatct tctcgatcac       360 gctgttcacc ttgttggtga tgccgttgat ggcgttctgg gtagacttct gatcggcggc      420
atatccagag ccctgctcat tctggtggtg gtagccgtac cagccatcca ccatgcctgt      480
ccatcctccc tcgatgaatc cggcgatggc tccaaacagt cctctgctct ggatgctagg      540
gatgtttctc aggccggtca ccattctcag cttggcgctt ctcacatact gggggcactc      600
gccgatggtc acagggtgca cattctggaa gggcaggctg ctattgatgg cgccctgagg      660
tgtctggcac ttggcatcac actcatccat ggggggcgttg cttgtgatga tgccgctgcc      720
aaagcctctg ctcagggcaa aggcatacca aggggcgatc agattgccgt tggcctcgaa      780
gatgatggta tcgccaggct ccagcagggt ccagtagtaa ttgatccggc cctcctggtc      840
tctcactttg ggtctcttgg cgatctcggg ggtgaatctt ctgctgtagt ggctggacac      900
cacgctcaca taggcgttct ctgtgtggta cagggcccgc tgatttccga tgttgggagg      960
gtggtgcact ccccacagca ccagcacttc ctttttccttg ttgttcacgt agctcttgct     1020
caggttgggg tacaggccat tcttgcctgt cagccacagc aggttccggt agaagctgct     1080
tttgccgttg tggctacagc tggcagacac gcctgtcact gtgtgattag gccagctgga     1140
ctccttgggg aagatctcga atctctcgaa gctggacacg ctagacagct gctcgcgcag     1200
ctcctcgtaa tcggcgaagt agccagggta gcaggtgcca ttctcaggat tgggggtctc     1260
cacgatgtag ctccagctct ccttagaaat cagcagctca cactcggggt tgcccagaat     1320
ccatccggcc acagaacaat tgcccagctg cagaggggca atgcctttca gcagacacag     1380
cttgccattg tggctgtcct ccagcaggtt cacagagtgg gtcacggtca cgttcttctc     1440
cagcactgta tccacggtgt cggtgctatt gttggcgtgg tagccgatac agattgtgtc     1500
ggcgtaggtg gcggtaaagg tacacagcag caccagcagt ttggccttca t              1551

<210> SEQ ID NO 13
```

```
<211> LENGTH: 1554
<212> TYPE: DNA
<213> ORGANISM: Influenza virus

<400> SEQUENCE: 13
atgaaggcca tcctggtggt gctgctgtac accttcgcca ccgccaacgc cgacaccctg     60
tgcatcggct accacgccaa caacagcacc gacaccgtgg acaccgtgct ggagaagaac    120
gtgaccgtga cccacagcgt gaacctgctg gaggacaagc acaacggcaa gctgtgcaag    180
ctgcggggcg tggcccccct gcacctgggc aagtgcaaca tcgccggctg gattctgggc    240
aaccccgagt gcgagagcct gagcaccgcc agcagctgga gctacatcgt ggagaccccc    300
agcagcgaca acggcacctg ctaccccggc gacttcatcg actacgagga gctgcgggag    360
cagctgagca gcgtgagcag cttcgagcgg ttcgagatct cccccaagac cagcagctgg    420
cccaaccacg acagcaacaa gggcgtgacc gccgcctgcc ccacgccgg cgccaagagc     480
ttctacaaga acctgatctg gctggtgaag aagggcaaca gctaccccaa gctgagcaag    540
agctacatca cgacaagggg caaggaggtg ctggtgctgt ggggcatcca ccaccccagc    600
accagcgccg accagcagag cctgtaccag aacgccgaca cctacgtgtt cgtgggcagc    660
agccggtaca gcaagaagtt caagcccgag atcgccatcc ggcccaaggt gcgggaccag    720
gagggccgga tgaactacta ctggaccctg gtggagcccg gcgacaagat caccttcgag    780
gccaccggca acctggtggt gccccggtac gccttcgcca tggagcggaa cgccggcagc    840
ggcatcatca tcagcgacac ccccgtgcac gactgcaaca ccacctgcca gacccccaag    900
ggcgccatca caccagcct gcccttccag aacatccacc ccatcaccat cggcaagtgc    960
cccaagtacg tgaagagcac caagctgcgg ctggccaccg gcctgcggaa catccccagc   1020
atccagagcc ggggcctgtt cggcgccatc gccggcttca tcgagggcgg ctggaccggc   1080
atggtggacg gctggtacgg ctaccaccac cagaacgagc agggcagcgg ctacgccgcc   1140
gacctgaaga gcacccagaa cgccatcgac gagatcacca caaggtgaa cagcgtgatc   1200
gagaagatga cacccagtt caccgccgtg ggcaaggagt tcaaccacct ggagaagcgg   1260
atcgagaacc tgaacaagaa ggtggacgac ggcttcctgg acatctggac ctacaacgcc   1320
gagctgctgg tgctgctgga aacgagcgg accctggact accacgacag caacgtgaag   1380
aacctgtacg agaaggtgcg gagccagctg aagaacaacg ccaaggagat cggcaacggc   1440
tgcttcgagt tctaccacaa gtgcgacaac acctgcatgg agagcgtgaa gaacggcacc   1500
tacgactacc ccaagtacag cgaggaggcc aagctgaacc gggaggagat cgac         1554

<210> SEQ ID NO 14
<211> LENGTH: 518
<212> TYPE: PRT
<213> ORGANISM: Influenza virus

<400> SEQUENCE: 14

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
```

```
                65                  70                  75                  80
Asn Pro Glu Cys Glu Ser Leu Ser Thr Ala Ser Ser Trp Ser Tyr Ile
                    85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                    165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
            210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                    245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                    325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                    405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                    485                 490                 495
```

```
            Lys Asn Gly Thr Tyr Asp Tyr Pro Lys Tyr Ser Glu Glu Ala Lys Leu
                        500                 505                 510

Asn Arg Glu Glu Ile Asp
                    515

<210> SEQ ID NO 15
<211> LENGTH: 1554
<212> TYPE: DNA
<213> ORGANISM: Influenza virus

<400> SEQUENCE: 15
gtcgatctcc tcccggttca gcttggcctc ctcgctgtac ttggggtagt cgtaggtgcc      60
gttcttcacg ctctccatgc aggtgttgtc gcacttgtgg tagaactcga agcagccgtt     120
gccgatctcc ttggcgttgt tcttcagctg gctccgcacc ttctcgtaca ggttcttcac     180
gttgctgtcg tggtagtcca gggtccgctc gttctccagc agcaccagca gctcggcgtt     240
gtaggtccag atgtccagga agccgtcgtc caccttcttg ttcaggttct cgatccgctt     300
ctccaggtgg ttgaactcct tgcccacggc ggtgaactgg tgttcatct tctcgatcac      360 gctgttcacc ttgttggtga tctcgtcgat ggcgttctgg gtgctcttca ggtcggcggc     420
gtagccgctg ccctgctcgt tctggtggtg gtagccgtac cagccgtcca ccatgccggt     480
ccagccgccc tcgatgaagc cggcgatggc gccgaacagg cccggctct ggatgctggg      540 gatgttccgc aggccggtgg ccagccgcag cttggtgctc ttcacgtact tggggcactt     600
gccgatggtg atgggtgga tgttctggaa gggcaggctg tgttgatgg cgcccttggg       660 ggtctggcag gtggtgttgc agtcgtgcac ggggtgtcg ctgatgatga tgccgctgcc      720
ggcgttccgc tccatggcga aggcgtaccg gggcaccacc aggttgccgg tggcctcgaa     780
ggtgatcttg tcgccgggct ccaccagggt ccagtagtag ttcatccggc cctcctggtc     840
ccgcaccttg gccggatgg cgatctcggg cttgaacttc ttgctgtacc ggctgctgcc      900
cacgaacacg taggtgtcgg cgttctggta caggctctgc tggtcggcgc tggtgctggg     960
gtggtggatg ccccacagca ccagcacctc cttgccttg tcgttgatgt agctcttgct     1020
cagcttgggg tagctgttgc ccttcttcac cagccagatc aggttcttgt agaagctctt    1080
ggcgccggcg tggggcagg cggcggtcac gcccttgttg ctgtcgtggt tgggccagct     1140
gctggtcttg gggaagatct cgaaccgctc gaagctgctc acgctgctca gctgctcccg    1200
cagctcctcg tagtcgatga agtcgccggg gtagcaggtg ccgttgtcgc tgctggggt     1260 ctccacgatg tagctccagc tgctggcggt gctcaggctc tcgcactcgg ggttgccag     1320 aatccagccg gcgatgttgc acttgcccag gtgcaggggg ccacgccccc gcagcttgca    1380
cagcttgcct tgtgcttgt cctccagcag gttcacgctg tgggtcacgg tcacgttctt     1440
ctccagcacg gtgtccacgg tgtcggtgct gttgttggcg tggtagccga tgcacagggt    1500
gtcggcgttg gcggtggcga aggtgtacag cagcaccacc aggatggcct tcat          1554

<210> SEQ ID NO 16
<211> LENGTH: 1542
<212> TYPE: DNA
<213> ORGANISM: Influenza virus

<400> SEQUENCE: 16
atggccatca tctacctgat cctgctgttt acagctgtgc ggggcgatca gatctgtatc      60
ggctaccacg ccaacaatag caccgagaag gtggacacca tcctggaaag aaatgtgacc    120
```

```
gtgacccacg ccaaggatat tctggaaaag acccacaacg gcaagctgtg caagctgaat    180
ggcattcctc ctctggaact gggcgattgt tctattgctg gctggctgct gggaaatcct    240
gagtgcgata gactgctgtc tgtgcctgag tggagctaca tcatggaaaa agagaaccct    300
agggacggac tgtgttaccc cggcagcttc aacgattacg aggaactgaa gcacctgctg    360
tccagcgtga agcacttcga gaaagtgaag atcctgccca aggatagatg gacccagcat    420
acaacaacag gcggaagcag agcttgtgct gtgtccggca accccagctt cttcagaaat    480
atggtctggc tgaccaagaa gggctctaat tatcctgtgg ccaagggcag ctacaataat    540
acaagcggcg agcagatgct gattatttgg ggcgtgcacc accctaatga tgagacagag    600
cagagaaccc tgtaccagaa tgtgggcaca tacgtgtctg tgggcaccag cacactgaat    660
aagagaagca cccccgatat tgccaccaga cccaaagtga atggacaggg cggcagaatg    720 gaatttttcct ggaccctgct ggatatgtgg gacaccatca actttgagag caccgggaat    780
ctgattgccc ctgagtacgg cttcaagatc agcaagagag cagcagcgg catcatgaaa    840 acagagggca ccctggaaaa ctgtgaaacc aagtgtcaga cacctctggg cgccattaat    900
accaccctgc ccttccataa tgtgcaccct ctgacaatcg gcgagtgccc taagtacgtg    960
aagtctgaga actggtgct ggccacagga ctgagaaatg tgccccagat cgagtcaaga    1020
ggcctgtttg gagccattgc cggctttatt gaaggcggat ggcagggaat ggtggatggg    1080
tggtacggct atcaccacag caatgatcag ggatctggct atgccgccga taagagagc    1140 acccagaagg cctttgacgg catcaccaac aaagtgaaca gcgtgatcga agatgaac    1200 acccagtttg aggccgtggg caaagagttc agcaatctgg aaagacggct ggaaaacctg    1260
aacaagaaaa tggaagatgg cttcctggac gtgtggacat ataatgccga gctgctggtg    1320
ctgatggaaa acgagaggac cctggacttt cacgacagca acgtgaagaa cctgtacgac    1380
aaagtgcgga tgcagctgag agacaatgtg aaagagctgg gcaacggctg ctttgagttc    1440
taccacaagt gcgacgacga gtgcatgaat agcgtgaaga acggcaccta cgactaccct    1500
aagtatgagg aagagagcaa gctgaacaga aacgagatca ag                      1542
```

<210> SEQ ID NO 17
<211> LENGTH: 514
<212> TYPE: PRT
<213> ORGANISM: Influenza virus

<400> SEQUENCE: 17

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

```
Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys

<210> SEQ ID NO 18
<211> LENGTH: 1542
<212> TYPE: DNA
```

<213> ORGANISM: Influenza virus

<400> SEQUENCE: 18

| | |
|---|---|
| cttgatctcg tttctgttca gcttgctctc ttcctcatac ttagggtagt cgtaggtgcc | 60 |
| gttcttcacg ctattcatgc actcgtcgtc gcacttgtgg tagaactcaa agcagccgtt | 120 |
| gcccagctct ttcacattgt ctctcagctg catccgcact ttgtcgtaca ggttcttcac | 180 |
| gttgctgtcg tgaaagtcca gggtcctctc gttttccatc agcaccagca gctcggcatt | 240 |
| atatgtccac acgtccagga agccatcttc cattttcttg ttcaggtttt ccagccgtct | 300 |
| ttccagattg ctgaactctt tgcccacggc ctcaaactgg gtgttcatct tctcgatcac | 360 |
| gctgttcact ttgttggtga tgccgtcaaa ggccttctgg gtgctctctt tatcggcggc | 420 |
| atagccagat ccctgatcat tgctgtggtg atagccgtac cacccatcca ccattccctg | 480 |
| ccatccgcct tcaataaagc cggcaatggc tccaaacagg cctcttgact cgatctgggg | 540 |
| cacatttctc agtcctgtgg ccagcaccag tttctcagac ttcacgtact tagggcactc | 600 |
| gccgattgtc agagggtgca cattatgaaa gggcagggtg gtattaatgg cgcccagagg | 660 |
| tgtctgacac ttggtttcac agttttccag ggtgccctct gttttcatga tgccgctgct | 720 |
| gcctctcttg ctgatcttga agccgtactc aggggcaatc agattcccgg tgctctcaaa | 780 |
| gttgatggtg tcccacatat ccagcagggt ccaggaaaat tccattctgc cgccctgtcc | 840 |
| attcactttg ggtctggtgg caatatcggg ggtgcttctc ttattcagtg gctggtgcc | 900 |
| cacagacacg tatgtgccca cattctggta cagggttctc tgctctgtct catcattagg | 960 |
| gtggtgcacg cccaaataa tcagcatctg ctcgccgctt gtattattgt agctgccctt | 1020 |
| ggccacagga taattagagc ccttcttggt cagccagacc atatttctga agaagctggg | 1080 |
| gttgccggac acagcacaag ctctgcttcc gcctgttgtt gtatgctggg tccatctatc | 1140 |
| cttgggcagg atcttcactt tctcgaagtg cttcacgctg acagcaggt gcttcagttc | 1200 |
| ctcgtaatcg ttgaagctgc cggggtaaca cagtccgtcc ctagggttct cttttttccat | 1260 |
| gatgtagctc cactcaggca cagacagcag tctatcgcac tcaggatttc ccagcagcca | 1320 |
| gccagcaata gaacaatcgc ccagttccag aggaggaatg ccattcagct tgcacagctt | 1380 |
| gccgttgtgg gtcttttcca gaatatcctt ggcgtgggtc acggtcacat ttcttttccag | 1440 |
| gatggtgtcc accttctcgg tgctattgtt ggcgtggtag ccgatacaga tctgatcgcc | 1500 |
| ccgcacagct gtaaacagca ggatcaggta gatgatggcc at | 1542 |

<210> SEQ ID NO 19
<211> LENGTH: 1557
<212> TYPE: DNA
<213> ORGANISM: Influenza virus

<400> SEQUENCE: 19

| | |
|---|---|
| atgaaaacca tcattgccct gagctacatc ttttgtctgg ctctgggcca ggatctgccc | 60 |
| ggcaatgata atagcaccgc caccctgtgt ctgggacacc acgccgtgcc taatggcacc | 120 |
| ctggtgaaaa ccattaccga cgaccagatc gaagtgacca atgccaccga gctggtgcag | 180 |
| agcagcagca ccggcaagat ctgcaacaac ccccacagaa tcctggatgg catcgactgt | 240 |
| accctgatcg atgccctgct gggcgatcct cactgcgacg tgttccagaa cgagacatgg | 300 |
| gacctgttcg tggagagaag caaggccttc agcaactgct accctacga tgtgcccgat | 360 |
| tacgcctctc tgaagagcct ggtggccagc agcggcacac tggaattcat caccgagggc | 420 |
| tttacctgga caggcgtgac ccagaatggc ggcagcaatg cctgtaaaag aggccctgcc | 480 |

-continued

```
agcggcttct tcagcagact gaactggctg accaagtccg gcagcaccta ccctgtgctg    540
aacgtgacca tgcccaacaa cgacaacttc gacaagctgt acatctgggg cgtgcaccac    600
cctagcacca atcaggaaca gaccagcctg tacgtgcagg ccagcggcag agtgaccgtg    660 tctaccgac ggtcccagca gaccatcatc cccaacatcg agtcaagacc ttgggtgcgc     720
ggcctgagca gcagaatcag catctactgg accatcgtga acctggcga cgtgctggtg     780 atcaacagca atggcaacct gatcgccccc agaggctact tcaagatgcg gaccggcaag    840
agcagcatca tgagaagcga cgcccccatc gatacctgta tcagcgagtg catcacccccc   900 aacggcagca tccccaacga caagcccttc agaacgtga acaagatcac ctacggcgcc    960
tgccctaagt acgtgaagca gaacaccctg aagctggcca ccggcatgag aaatgtgccc   1020
gagaagcaga caagaggcct gtttggcgcc attgccggct ttatcgagaa cggctgggag   1080
ggcatgatcg atgggtggta cggcttcaga caccagaatt ctgagggcac aggacaggcc   1140
gccgatctga gtctacaca ggccgccatc gaccagatca acggcaagct gaacagagtg    1200
atcgagaaaa ccaacgagaa gttccaccag atcgagaaag aattcagcga ggtggagggc   1260
agaatccagg acctggaaaa atacgtggag gacaccaaga tcgacctgtg gagctacaat   1320
gccgaactgc tggtcgccct ggaaaaccag cacaccatcg acctgaccga cagcgagatg   1380
aataagctgt tcgaaaagac cagacggcag ctgagagaaa acgccgagga catgggcaac   1440
ggctgcttca agatctacca caagtgcgac aacgcctgca tcgagagcat cagaaacggc   1500
acctacgacc acgatgtgta cagggacgag gccctgaaca cagattcca gatcaag       1557
```

<210> SEQ ID NO 20
<211> LENGTH: 519
<212> TYPE: PRT
<213> ORGANISM: Influenza virus

<400> SEQUENCE: 20

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
```

```
              180                 185                 190
Leu Tyr Ile Trp Gly Val His His Pro Ser Thr Asn Gln Glu Gln Thr
            195                 200                 205

Ser Leu Tyr Val Gln Ala Ser Gly Arg Val Thr Val Ser Thr Arg Arg
        210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys
            515

<210> SEQ ID NO 21
<211> LENGTH: 1557
<212> TYPE: DNA
<213> ORGANISM: Influenza virus

<400> SEQUENCE: 21
cttgatctgg aatctgttgt tcagggcctc gtccctgtac acatcgtggt cgtaggtgcc      60
gtttctgatg ctctcgatgc aggcgttgtc gcacttgtgg tagatcttga agcagccgtt     120
gcccatgtcc tcggcgtttt ctctcagctg ccgtctggtc ttttcgaaca gcttattcat     180
```

```
ctcgctgtcg gtcaggtcga tggtgtgctg gttttccagg gcgaccagca gttcggcatt      240
gtagctccac aggtcgatct tggtgtcctc cacgtatttt tccaggtcct ggattctgcc      300
ctccacctcg ctgaattctt tctcgatctg gtggaacttc tcgttggttt tctcgatcac      360
tctgttcagc ttgccgttga tctggtcgat ggcggcctgt gtagacttca gatcggcggc      420
ctgtcctgtg ccctcagaat tctggtgtct gaagccgtac acccatcga tcatgccctc       480 ccagccgttc tcgataaagc cggcaatggc gccaaacagg cctcttgtct gcttctcggg      540
cacatttctc atgccggtgg ccagcttcag ggtgttctgc ttcacgtact tagggcaggc      600
gccgtaggtg atcttgttca cgttctggaa gggcttgtcg ttggggatgc tgccgttggg      660
ggtgatgcac tcgctgatac aggtatcgat ggggcgtcg cttctcatga tgctgctctt       720
gccggtccgc atcttgaagt agcctctggg ggcgatcagg ttgccattgc tgttgatcac      780
cagcacgtcg ccaggtttca cgatggtcca gtagatgctg attctgctgc tcaggccgcg      840
cacccaaggt cttgactcga tgttgggat gatggtctgc tgggaccgtc tggtagacac       900
ggtcactctg ccgctggcct gcacgtacag gctggtctgt tcctgattgg tgctagggtg      960
gtgcacgccc cagatgtaca gcttgtcgaa gttgtcgttg ttgggcatgg tcacgttcag     1020
cacagggtag gtgctgccgg acttggtcag ccagttcagt ctgctgaaga gccgctgcc     1080 agggcctctt ttacaggcat tgctgccgcc attctgggtc acgcctgtcc aggtaaagcc     1140
ctcggtgatg aattccagtg tgccgctgct ggccaccagg cttctcagag aggcgtaatc     1200
gggcacatcg taggggtagc agttgctgaa ggccttgctt ctctccacga acaggtccca     1260
tgtctcgttc tggaacacgt cgcagtgagg atcgcccagc agggcatcga tcagggtaca     1320
gtcgatgcca tccaggattc tgtggggggtt gttgcagatc ttgccggtgc tgctgctctg    1380
caccagctcg gtggcattgg tcacttcgat ctggtcgtcg gtaatggttt tcaccagggt     1440
gccattaggc acggcgtggt gtcccagaca cagggtggcg gtgctattat cattgccggg     1500
cagatcctgg cccagagcca gacaaaagat gtagctcagg gcaatgatgg ttttcat        1557
```

<210> SEQ ID NO 22
<211> LENGTH: 1557
<212> TYPE: DNA
<213> ORGANISM: Influenza virus

<400> SEQUENCE: 22

```
atgaaaacca tcattgccct gagctacatc ctgtgcctgg tgttcacaca gaagctgccc       60
ggcaacgata atagcaccgc cacactgtgt ctgggacacc acgccgtgcc taatggcacc      120
atcgtgaaaa caatcaccaa cgaccagatc gaagtgacca atgccacaga gctggtgcag      180
agcagcagca caggcgagat ctgtgacagc ccccaccaga tcctggatgg cgagaactgt      240
accctgatcg atgccctgct gggcgatcct cagtgcgacg gcttccagaa caagaaatgg      300
gacctgttcg tggagagaag caaggcctac agcaactgct accccctacga cgtgcctgat     360 tacgccagcc tgagaagcct ggtggcctct agcggcaccc tggaattcaa caacgagagc      420
ttcaactgga ccggcgtgac acagaatggc accagcagcg cctgcatcag acggtccaac      480
aacagcttct tcagtagact gaattggctg acccacctga gttcaagta ccccgccctg       540 aacgtgacca tgcccaacaa tgagaagttc gacaagctgt acatctgggg agtgcaccac      600
cctggcaccg acaacgatca gatcttccct tacgcccagg ccagcggcag aatcaccgtg      660
tccaccaaga gaagccagca gaccgtgatc cccaatatcg gcagcagacc cagagtgcgg      720
aacatcccca gcaggatcag catctactgg acaatcgtga agcctggcga catcctgctg     780
```
atcaacagca ccggcaacct gatcgcccct cggggctact ttaagatcag aagcggcaag    840
agcagcatca tgagatccga cgcccccatc ggcaagtgca acagcgagtg catcacccca    900
aacggcagca tccccaacga caagcccttc cagaacgtga acaggatcac ctacggcgcc    960
tgccctagat acgtgaagca gaacaccctg aagctggcca ccggcatgag aaatgtgccc   1020
gagaagcaga ccagaggcat ctttggcgcc attgccggct ttatcgagaa tggctgggag   1080
ggaatggtgg atgggtggta cggcttcaga caccagaata gcgagggaat tggacaggcc   1140
gccgatctga atctaccca ggccgccatc gaccagatca cggcaagct gaacaggctg   1200 atcggcaaga ccaacgagaa gttccaccag atcgagaaag aattcagcga ggtggagggc   1260
agaatccagg acctggaaaa atacgtggag gacaccaaga tcgacctgtg gagctacaat   1320
gccgaactgc tggtcgccct ggaaaaccag cacacaattg atctgacaga cagtgagatg   1380
aataagctgt tcgagaaaac caagaagcag ctgagagaaa acgccgagga catgggcaac   1440
ggctgcttca agatctacca caagtgcgac aacgcctgca tcgcagcat cagaaacggc   1500 acctacgacc acgacgtgta cagagatgag gccctgaaca accggtttca gatcaag     1557

<210> SEQ ID NO 23
<211> LENGTH: 519
<212> TYPE: PRT
<213> ORGANISM: Influenza virus

<400> SEQUENCE: 23

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

```
Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys
        515

<210> SEQ ID NO 24
<211> LENGTH: 1557
<212> TYPE: DNA
<213> ORGANISM: Influenza virus

<400> SEQUENCE: 24
cttgatctga aaccggttgt tcagggcctc atctctgtac acgtcgtggt cgtaggtgcc      60
gtttctgatg ctgccgatgc aggcgttgtc gcacttgtgg tagatcttga agcagccgtt     120
gcccatgtcc tcggcgtttt ctctcagctg cttcttggtt ttctcgaaca gcttattcat     180
ctcactgtct gtcagatcaa ttgtgtgctg gttttccagg gcgaccagca gttcggcatt     240
gtagctccac aggtcgatct ggtgtcctc cacgtatttt tccaggtcct ggattctgcc     300
ctccacctcg ctgaattctt tctcgatctg gtggaacttc tcgttggtct tgccgatcag     360
cctgttcagc ttgccgttga tctggtcgat ggcggcctgg gtagatttca gatcggcggc     420
ctgtccaatt ccctcgctat tctggtgtct gaagccgtac cacccatcca ccattccctc     480
```

```
ccagccattc tcgataaagc cggcaatggc gccaaagatg cctctggtct gcttctcggg      540
cacatttctc atgccggtgg ccagcttcag ggtgttctgc ttcacgtatc tagggcaggc      600
gccgtaggtg atcctgttca cgttctggaa gggcttgtcg ttggggatgc tgccgtttgg      660
ggtgatgcac tcgctgttgc acttgccgat ggggcgtcg gatctcatga tgctgctctt      720
gccgcttctg atcttaaagt agccccgagg ggcgatcagg ttgccggtgc tgttgatcag      780
caggatgtcg ccaggcttca cgattgtcca gtagatgctg atcctgctgg ggatgttccg      840
cactctgggt ctgctgccga tattggggat cacggtctgc tggcttctct tggtggacac      900
ggtgattctg ccgctggcct gggcgtaagg gaagatctga tcgttgtcgg tgccagggtg      960
gtgcactccc cagatgtaca gcttgtcgaa cttctcattg ttgggcatgg tcacgttcag     1020
ggcggggtac ttgaacttca ggtgggtcag ccaattcagt ctactgaaga agctgttgtt     1080
ggaccgtctg atgcaggcgc tgctggtgcc attctgtgtc acgccggtcc agttgaagct     1140
ctcgttgttg aattccaggg tgccgctaga ggccaccagg cttctcaggc tggcgtaatc     1200
aggcacgtcg taggggtagc agttgctgta ggccttgctt ctctccacga acaggtccca     1260
tttcttgttc tggaagccgt cgcactgagg atcgcccagc agggcatcga tcagggtaca     1320
gttctcgcca tccaggatct ggtggggct gtcacagatc tcgcctgtgc tgctgctctg     1380
caccagctct gtggcattgg tcacttcgat ctggtcgttg gtgattgttt tcacgatggt     1440
gccattaggc acggcgtggt gtcccagaca cagtgtggcg gtgctattat cgttgccggg     1500
cagcttctgt gtgaacacca ggcacaggat gtagctcagg gcaatgatgg ttttcat       1557

<210> SEQ ID NO 25
<211> LENGTH: 1560
<212> TYPE: DNA
<213> ORGANISM: Influenza virus

<400> SEQUENCE: 25
atggaaaaga tcgtgctgct gctggccatt gtgagcctgg tgaagagcga ccagatctgc       60
attggctacc acgccaacaa tagcacagag caggtggaca ccatcatgga aaaaaacgtg      120
accgtgaccc acgctcagga catcctggaa aagacccaca cggcaagct gtgtgatctg      180 gacggcgtga agcctctgat cctgagagat tgtagcgtgg ctggatggct gctgggcaac      240
cctatgtgcg acgagttcat caacgtgccc gagtggagct atatcgtgga aaggccaac      300 cccaccaacg atctgtgtta ccccggcagc ttcaacgatt acgaggaact gaagcacctg      360
ctgtcccgga tcaaccactt cgagaagatc cagatcatcc caagtcctc ttggagcgat      420 cacgaagcct ctagcggagt gtctagcgcc tgtccttacc tgggcagccc cagcttcttc      480
agaaacgtgg tgtggctgat caagaagaac agcacctacc caccatcaa gaagagctac      540 aacaacacca accaggaaga tctgctggtc ctgtggggaa tccaccaccc taatgatgcc      600
gccgagcaga ccagactgta ccagaacccc accacctata tcagcatcgg caccagcacc      660
ctgaatcaga gactggtgcc caagatcgcc accagatcca aggtgaacgg ccagagcggc      720
aggatggaat tcttctggac catcctgaag cccaacgacg ccatcaactt cgagagcaac      780
ggcaacttta tcgcccctga gtacgcctac aagatcgtga agaagggcga cagcgccatc      840
atgaagagcg agctggaata cggcaactgc aacaccaagt gccagacacc tatgggcgcc      900
atcaacagca gcatgccctt ccacaacatc cacctctga ccatcggcga gtgccctaag      960
tacgtgaaga gcaacagact ggtgctgcc acaggcctga aaatagccc ccagcgggag     1020 agcagaagaa agaagagggg cctgtttgga gccatcgccg gctttattga aggcggctgg     1080
```

```
caggggaatgg tggatggctg gtacggctac caccacagca atgagcaggg ctctggatat  1140
gccgccgaca aagagtctac ccagaaggcc atcgacggcg tcaccaacaa ggtgaacagc  1200
atcatcgaca agatgaacac ccagttcgag gctgtgggca gagagttcaa caacctggaa  1260
cggcggatcg agaacctgaa caagaaaatg gaagatggct tcctggatgt gtggacctac  1320
aatgccgaac tgctggtgct gatggaaaac gagcggaccc tggacttcca cgacagcaac  1380
gtgaagaacc tgtacgacaa agtgcggctg cagctgagag acaacgccaa agagctgggc  1440
aacggctgct tcgagttcta ccacaagtgc gacaacgagt gcatggaaag catcaggaac  1500
ggcacctaca actaccctca gtacagcgag aagccaggc tgaagaggga agagatcagc  1560
```

<210> SEQ ID NO 26
<211> LENGTH: 520
<212> TYPE: PRT
<213> ORGANISM: Influenza virus

<400> SEQUENCE: 26

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285
```

```
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Ser Arg Arg Lys Arg Gly Leu Phe Gly Ala Ile
            340                 345                 350
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Ile Arg Asn Gly Thr Tyr Asn Tyr Pro Gln Tyr Ser Glu Glu Ala
            500                 505                 510
Arg Leu Lys Arg Glu Glu Ile Ser
        515                 520

<210> SEQ ID NO 27
<211> LENGTH: 1560
<212> TYPE: DNA
<213> ORGANISM: Influenza virus

<400> SEQUENCE: 27
gctgatctct tccctcttca gcctggcttc ctcgctgtac tgagggtagt tgtaggtgcc      60
gttcctgatg ctttccatgc actcgttgtc gcacttgtgg tagaactcga agcagccgtt     120
gcccagctct ttggcgttgt ctctcagctg cagccgcact tgtcgtaca ggttcttcac      180 gttgctgtcg tggaagtcca gggtccgctc gttttccatc agcaccagca gttcggcatt     240
gtaggtccac acatccagga agccatcttc catttcttg tcaggttct cgatccgccg       300 ttccaggttg ttgaactctc tgcccacagc ctcgaactgg tgttcatct tgtcgatgat      360 gctgttcacc ttgttggtga cgccgtcgat ggccttctgg gtagactctt gtcggcggc     420 atatccagag ccctgctcat tgctgtggtg gtagccgtac cagccatcca ccattccctg    480
ccagccgcct tcaataaagc cggcgatggc tccaaacagg cccctcttct ttcttctgct    540
ctcccgctgg gggctatttc tcaggcctgt ggccagcacc agtctgttgc tcttcacgta    600
cttagggcac tcgccgatgg tcagagggtg gatgttgtgg aagggcatgc tgctgttgat    660
ggcgcccata ggtgtctggc acttggtgtt gcagttgccg tattccagct cgctcttcat    720
gatggcgctg tcgcccttct tcacgatctt gtaggcgtac tcaggggcga taaagttgcc    780
```

```
gttgctctcg aagttgatgg cgtcgttggg cttcaggatg gtccagaaga attccatcct    840
gccgctctgg ccgttcacct tggatctggt ggcgatcttg gcaccagtc tctgattcag     900
ggtgctggtg ccgatgctga tataggtggt ggggttctgg tacagtctgg tctgctcggc    960
ggcatcatta gggtggtgga ttccccacag gaccagcaga tcttcctggt tggtgttgtt   1020
gtagctcttc ttgatggtgg ggtaggtgct gttcttcttg atcagccaca ccacgtttct   1080
gaagaagctg ggctgccca ggtaaggaca ggcgctagac actccgctag aggcttcgtg    1140
atcgctccaa gaggacttgg ggatgatctg gatcttctcg aagtggttga tccgggacag   1200
caggtgcttc agttcctcgt aatcgttgaa gctgccgggg taacacagat cgttggtggg   1260
gttggccttc tccacgatat agctccactc gggcacgttg atgaactcgt cgcacatagg   1320
gttgcccagc agccatccag ccacgctaca atctctcagg atcagaggct tcacgccgtc   1380
cagatcacac agcttgccgt tgtgggtctt ttccaggatg tcctgagcgt gggtcacggt   1440
cacgttttt tccatgatgg tgtccacctg ctctgtgcta ttgttggcgt ggtagccaat    1500
gcagatctgg tcgctcttca ccaggctcac aatggccagc agcagcacga tcttttccat   1560

<210> SEQ ID NO 28
<211> LENGTH: 1602
<212> TYPE: DNA
<213> ORGANISM: Influenza virus

<400> SEQUENCE: 28
atgaaggcca tcatcgtgct gctgatggtg gtgaccagca acgccgatag aatctgcacc      60
ggcatcacca gcagcaatag cccccatgtg gtgaaaacag ccacccaggg cgaagtgaat     120
gtgacaggcg tgatccctct gaccaccacc cccaccaaga gctacttcgc caacctgaag    180
ggcaccagaa ccagaggcaa gctgtgcccc gattgcctga actgcaccga tctggatgtg    240
gctctgggca gacctatgtg tgtgggcacc acaccatctg ccaaggccag catcctgcac    300
gaagtgaagc ctgtgaccag cggctgcttc cccatcatgc acgaccggac caagatcaga    360
cagctgccca acctgctgag aggctacgag aacatccggc tgtccaccca gaatgtgatc    420
gatgccgaga agccccctgg cggacccttat agactgggca ccagcggctc ttgtcccaat    480
gccacctcca gagcggcttt ttttgccaca atggcctggg ccgtgcctaa ggacaacaac    540
aagaacgcca ccaaccctct gaccgtggag gtgcccctaca tctgtacaga gggcgaggat    600
cagatcacag tgtggggctt ccacagcgac gacaagaccc agatgaagaa cctgtacggc    660
gacagcaacc cccagaagtt taccagcagc gccaatggcg tgaccaccca ctacgtgtcc    720
cagatcggca gctttccccga tcagacagag gatggcggac tgcctcagtc tggcaggatc    780
gtggtggact acatgatgca aaagcctggc aagaccggca ccatcgtgta tcagagaggc    840
gtgctgctgc ctcagaaagt gtggtgtgcc agcggcaggt ctaaagtgat caagggcagc    900
ctgcctctga ttggcgaggc cgactgtctg cacgaaaagt acggcggcct gaacaagagc    960
aagccctact acacaggcga gcacgccaag gccatcggca attgccccat ctgggtgaaa   1020
accccccctga gctggccaa tggcaccaag tacagacctc ccgccaagct gctgaaagag   1080
agaggcttct ttgccgccat tgccggattt ctggaaggcg gctgggaggg aatgattgcc   1140
ggctggcacg gctatacatc tcatggggcc catggcgtgg ctgtggccgc cgatctgaag   1200
tctacccagg aagccatcaa caagatcacc aagaacctga acagcctgag cgagctggaa   1260
gtgaagaatc tgcagagact gagcggcgcc atggatgagc tgcacaacga gatcctgaaa   1320
ctggacgaga aagtggatga tctccgcgcc gatacaattt cctcccagat tgaactggcc   1380
```

```
gtgctgctgt ccaacgaggg catcatcaac agcgaggatg aacacctgct ggccctggaa    1440
cggaagctga agaagatgct gggcccttct gccgtggaga tcggcaacgg ctgcttcgag    1500
acaaagcaca agtgcaacca gacctgcctg gatagaatcg ccgctggcac cttcaatgcc    1560
ggcgagttca gcctgcctac cttcgacagc ctgaatatca cc                      1602
```

```
<210> SEQ ID NO 29
<211> LENGTH: 534
<212> TYPE: PRT
<213> ORGANISM: Influenza virus

<400> SEQUENCE: 29
```

| | | | | | | | | | | | | | | | |
|---|---|---|---|---|---|---|---|---|---|---|---|---|---|---|---|
| Met | Lys | Ala | Ile | Ile | Val | Leu | Leu | Met | Val | Val | Thr | Ser | Asn | Ala | Asp |
| 1 | | | | 5 | | | | | 10 | | | | | 15 | |
| Arg | Ile | Cys | Thr | Gly | Ile | Thr | Ser | Ser | Asn | Ser | Pro | His | Val | Val | Lys |
| | | | 20 | | | | | 25 | | | | | 30 | | |
| Thr | Ala | Thr | Gln | Gly | Glu | Val | Asn | Val | Thr | Gly | Val | Ile | Pro | Leu | Thr |
| | | 35 | | | | | 40 | | | | | 45 | | | |
| Thr | Thr | Pro | Thr | Lys | Ser | Tyr | Phe | Ala | Asn | Leu | Lys | Gly | Thr | Arg | Thr |
| | 50 | | | | | 55 | | | | | 60 | | | | |
| Arg | Gly | Lys | Leu | Cys | Pro | Asp | Cys | Leu | Asn | Cys | Thr | Asp | Leu | Asp | Val |
| 65 | | | | | 70 | | | | | 75 | | | | | 80 |
| Ala | Leu | Gly | Arg | Pro | Met | Cys | Val | Gly | Thr | Thr | Pro | Ser | Ala | Lys | Ala |
| | | | | 85 | | | | | 90 | | | | | 95 | |
| Ser | Ile | Leu | His | Glu | Val | Lys | Pro | Val | Thr | Ser | Gly | Cys | Phe | Pro | Ile |
| | | | 100 | | | | | 105 | | | | | 110 | | |
| Met | His | Asp | Arg | Thr | Lys | Ile | Arg | Gln | Leu | Pro | Asn | Leu | Leu | Arg | Gly |
| | | 115 | | | | | 120 | | | | | 125 | | | |
| Tyr | Glu | Asn | Ile | Arg | Leu | Ser | Thr | Gln | Asn | Val | Ile | Asp | Ala | Glu | Lys |
| | 130 | | | | | 135 | | | | | 140 | | | | |
| Ala | Pro | Gly | Gly | Pro | Tyr | Arg | Leu | Gly | Thr | Ser | Gly | Ser | Cys | Pro | Asn |
| 145 | | | | | 150 | | | | | 155 | | | | | 160 |
| Ala | Thr | Ser | Lys | Ser | Gly | Phe | Phe | Ala | Thr | Met | Ala | Trp | Ala | Val | Pro |
| | | | | 165 | | | | | 170 | | | | | 175 | |
| Lys | Asp | Asn | Asn | Lys | Asn | Ala | Thr | Asn | Pro | Leu | Thr | Val | Glu | Val | Pro |
| | | | 180 | | | | | 185 | | | | | 190 | | |
| Tyr | Ile | Cys | Thr | Glu | Gly | Glu | Asp | Gln | Ile | Thr | Val | Trp | Gly | Phe | His |
| | | 195 | | | | | 200 | | | | | 205 | | | |
| Ser | Asp | Asp | Lys | Thr | Gln | Met | Lys | Asn | Leu | Tyr | Gly | Asp | Ser | Asn | Pro |
| | 210 | | | | | 215 | | | | | 220 | | | | |
| Gln | Lys | Phe | Thr | Ser | Ser | Ala | Asn | Gly | Val | Thr | Thr | His | Tyr | Val | Ser |
| 225 | | | | | 230 | | | | | 235 | | | | | 240 |
| Gln | Ile | Gly | Ser | Phe | Pro | Asp | Gln | Thr | Glu | Asp | Gly | Gly | Leu | Pro | Gln |
| | | | | 245 | | | | | 250 | | | | | 255 | |
| Ser | Gly | Arg | Ile | Val | Val | Asp | Tyr | Met | Met | Gln | Lys | Pro | Gly | Lys | Thr |
| | | | 260 | | | | | 265 | | | | | 270 | | |
| Gly | Thr | Ile | Val | Tyr | Gln | Arg | Gly | Val | Leu | Leu | Pro | Gln | Lys | Val | Trp |
| | | 275 | | | | | 280 | | | | | 285 | | | |
| Cys | Ala | Ser | Gly | Arg | Ser | Lys | Val | Ile | Lys | Gly | Ser | Leu | Pro | Leu | Ile |
| | 290 | | | | | 295 | | | | | 300 | | | | |
| Gly | Glu | Ala | Asp | Cys | Leu | His | Glu | Lys | Tyr | Gly | Gly | Leu | Asn | Lys | Ser |
| 305 | | | | | 310 | | | | | 315 | | | | | 320 |
| Lys | Pro | Tyr | Tyr | Thr | Gly | Glu | His | Ala | Lys | Ala | Ile | Gly | Asn | Cys | Pro |
| | | | | 325 | | | | | 330 | | | | | 335 | |

```
Ile Trp Val Lys Thr Pro Leu Lys Leu Ala Asn Gly Thr Lys Tyr Arg
                340                 345                 350
Pro Pro Ala Lys Leu Leu Lys Glu Arg Gly Phe Phe Gly Ala Ile Ala
            355                 360                 365
Gly Phe Leu Glu Gly Gly Trp Glu Gly Met Ile Ala Gly Trp His Gly
        370                 375                 380
Tyr Thr Ser His Gly Ala His Gly Val Ala Val Ala Ala Asp Leu Lys
385                 390                 395                 400
Ser Thr Gln Glu Ala Ile Asn Lys Ile Thr Lys Asn Leu Asn Ser Leu
                405                 410                 415
Ser Glu Leu Glu Val Lys Asn Leu Gln Arg Leu Ser Gly Ala Met Asp
            420                 425                 430
Glu Leu His Asn Glu Ile Leu Glu Leu Asp Glu Lys Val Asp Asp Leu
        435                 440                 445
Arg Ala Asp Thr Ile Ser Ser Gln Ile Glu Leu Ala Val Leu Leu Ser
    450                 455                 460
Asn Glu Gly Ile Ile Asn Ser Glu Asp Glu His Leu Leu Ala Leu Glu
465                 470                 475                 480
Arg Lys Leu Lys Lys Met Leu Gly Pro Ser Ala Val Glu Ile Gly Asn
                485                 490                 495
Gly Cys Phe Glu Thr Lys His Lys Cys Asn Gln Thr Cys Leu Asp Arg
            500                 505                 510
Ile Ala Ala Gly Thr Phe Asn Ala Gly Glu Phe Ser Leu Pro Thr Phe
        515                 520                 525
Asp Ser Leu Asn Ile Thr
        530

<210> SEQ ID NO 30
<211> LENGTH: 1602
<212> TYPE: DNA
<213> ORGANISM: Influenza virus

<400> SEQUENCE: 30
ggtgatattc aggctgtcga aggtaggcag gctgaactcg ccggcattga aggtgccagc      60
ggcgattcta tccaggcagg tctggttgca cttgtgcttt gtctcgaagc agccgttgcc    120
gatctccacg gcagaagggc ccagcatctt cttcagcttc cgttccaggg ccagcaggtg    180
ttcatcctcg ctgttgatga tgccctcgtt ggacagcagc acggccagtt caatctggga    240
ggaaattgta tcggcgcgga gatcatccac tttctcgtcc agttccagga tctcgttgtg    300
cagctcatcc atggcgccgc tcagtctctg cagattcttc acttccagct cgctcaggct    360
gttcaggttc ttggtgatct tgttgatggc ttcctgggta gacttcagat cggcggccac    420
agccacgcca tgggccccat gagatgtata gccgtgccag ccggcaatca ttccctccca    480
gccgccttcc agaaatccgg caatggcgcc aaagaagcct ctctctttca gcagcttggc    540
gggaggtctg tacttggtgc cattggccag cttcagggg gttttcaccc agatggggca    600
attgccgatg ccttggcgt gctcgcctgt gtagtagggc ttgctcttgt tcaggccgcc    660
gtacttttcg tgcagacagt cggcctcgcc aatcagaggc aggctgccct tgatcacttt    720
agacctgccg ctggcacacc acactttctg aggcagcagc acgcctctct gatacacgat    780
ggtgccggtc ttgccaggct ctgcatcat gtagtccacc acgatcctgc agactgagg    840
cagtccgcca tcctctgtct gatcgggaaa gctgccgatc tggacacgt agtgggtggt    900
cacgccattg gcgctgctgg taaacttctg ggggttgctg tcgccgtaca ggttcttcat    960
```

```
ctgggtcttg tcgtcgctgt ggaagcccca cactgtgatc tgatcctcgc cctctgtaca    1020
gatgtagggc acctccacgg tcagagggtt ggtggcgttc ttgttgttgt ccttaggcac    1080
ggcccaggcc attgtggcaa aaaagccgct cttggaggtg cattgggac aagagccgct     1140 ggtgcccagt ctataaggtc cgccaggggc tttctcggca tcgatcacat tctgggtgga    1200
cagccggatg ttctcgtagc ctctcagcag gttgggcagc tgtctgatct tggtccggtc    1260
gtgcatgatg gggaagcagc cgctggtcac aggcttcact tcgtgcagga tgctggcctt    1320
ggcagatggt gtggtgccca cacatagg tctgcccaga gccacatcca gatcggtgca      1380
gttcaggcaa tcgggcaca gcttgcctct ggttctggtg cccttcaggt tggcgaagta     1440
gctcttggtg ggggtggtgg tcagagggat cacgcctgtc acattcactt cgccctgggt   1500
ggctgttttc accacatggg ggctattgct gctggtgatg ccggtgcaga ttctatcggc    1560
gttgctggtc accaccatca gcagcacgat gatggccttc at                      1602

<210> SEQ ID NO 31
<211> LENGTH: 1493
<212> TYPE: DNA
<213> ORGANISM: Influenza virus

<400> SEQUENCE: 31
atgacaactc aacagccacg ctctgcttgg ggcaccatgc cgtccctaac gggaccattg      60
tgaaaaccat tactaacgat cagatagagg tgactaatgc caccgagctg gtgcaaagta    120
gctccacagg agagatctgc gatagtcccc accagattct ggacggaaag aattgtacgc    180
tgatcgacgc gctgttgggc gaccctcagt gtgacggatt cagaataag aagtgggatc     240 tgtttgtgga aggtcaaag gcttattcaa attgctaccc ttacgatgtg cctgattatg     300
ccagcctgcg gtccctcgtc gcgtctagtg ggactctgga gttcaacaac gagtcattta    360
actggactgg cgttacacag aacgggacta gttccgcttg cataaggaga agcaaaaata    420
gtttcttcag cagactgaat tggctgacac atctgaactt caagtaccct gcactgaatg    480
taaccatgcc caacaacgag cagttcgata agctttacat ttggggagtt catcatcctg    540
gcactgacaa ggatcagatc tttctgtatg cccaggcttc cggcaggatt accgtgtcta    600
caaagagaag ccagcaaact gtgtctccca atatcggcag tagacccaga gtacggaaca    660
tccctagtcg catcagtatt tactggacca tcgtgaaacc aggcgatatt ctcctgatta    720
acagtactgg caacctgatc gccccccggg gatactttaa aatccgctct ggaaagtcct    780
ccattatgag atcagatgca ccgatcggaa atgcaactc tgagtgtatc acacccaatg     840
ggagcattcc caatgacaaa ccttttccaga acgttaatcg ataacttat ggggcctgtc     900 cacggtacgt gaagcaaaat accttgaaac tggcgaccgg tatgcgcaat gtccccgaaa    960
aacagacccg cggatatttt ggggctatcg caggctttat cgagaatggc tgggaaggga   1020
tggtggatgg ttggtatggt tttagacatc aaaactccga aggcagaggc caggctgccg   1080
atctcaagag cacgcaggcc gctatagatc agatcaatgg aaagctcaac agactgatcg   1140
ggaaaaccaa cgaaaaattc catcagatcg agaaagagtt ctccgaagtc gaggggcgca   1200
tacaggacct ggagaagtat gttgaggata caaagattga tctgtggtcc tacaatgccg   1260
agctgctggt ggctctggag aatcagcaca ctattgacct gaccgattca gagatgaaca   1320
aactttttga agacgaag aagcagctta gagaaaatgc agaggacatg gggaacggat      1380
gctttaaaat atatcataag tgtgataatg cctgcatcgg atcaattaga aatggtacct   1440
```
atgatcacga tgtttacagg gacgaagcgc tgaataacag gttccagata aaa            1493

<210> SEQ ID NO 32
<211> LENGTH: 519
<212> TYPE: PRT
<213> ORGANISM: Influenza virus

<400> SEQUENCE: 32

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

```
Phe Arg His Gln Asn Ser Glu Gly Arg Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys
        515

<210> SEQ ID NO 33
<211> LENGTH: 1493
<212> TYPE: DNA
<213> ORGANISM: Influenza virus

<400> SEQUENCE: 33
```

| | | | | | |
|---|---|---|---|---|---|
| ttttatctgg | aacctgttat | tcagcgcttc | gtccctgtaa | acatcgtgat | cataggtacc | 60 |
| atttctaatt | gatccgatgc | aggcattatc | acacttatga | tatattttaa | agcatccgtt | 120 |
| ccccatgtcc | tctgcatttt | ctctaagctg | cttcttcgtc | ttctcaaaaa | gtttgttcat | 180 |
| ctctgaatcg | gtcaggtcaa | tagtgtgctg | attctccaga | gccaccagca | gctcggcatt | 240 |
| gtaggaccac | agatcaatct | ttgtatcctc | aacatacttc | tccaggtcct | gtatgcgccc | 300 |
| ctcgacttcg | gagaactctt | tctcgatctg | atggaatttt | tcgttggttt | tcccgatcag | 360 |
| tctgttgagc | tttccattga | tctgatctat | agcggcctgc | gtgctcttga | tcggcagc | 420 |
| ctggcctctg | ccttcggagt | tttgatgtct | aaaaccatac | caaccatcca | ccatcccttc | 480 |
| ccagccattc | tcgataaagc | ctgcgatagc | ccaaatatcc | cgcgggtct | gttttttcggg | 540 |
| gacattgcgc | ataccggtcg | ccagtttcaa | ggtattttgc | ttcacgtacc | gtggacaggc | 600 |
| cccataagtt | attcgattaa | cgttctggaa | aggtttgtca | ttgggaatgc | tcccattggg | 660 |
| tgtgatacac | tcagagttgc | attttccgat | cggtgcatct | gatctcataa | tggaggactt | 720 |
| tccagagcgg | attttaaagt | atccccgggg | ggcgatcagg | ttgccagtac | tgttaatcag | 780 |
| gagaatatcg | cctggtttca | cgatggtcca | gtaaatactg | atgcgactag | ggatgttccg | 840 |
| tactctgggt | ctactgccga | tattgggaga | cacagtttgc | tggcttctct | ttgtagacac | 900 |
| ggtaatcctg | ccggaagcct | gggcatacag | aaagatctga | tccttgtcag | tgccaggatg | 960 |
| atgaactccc | caaatgtaaa | gcttatcgaa | ctgctcgttg | ttgggcatgg | ttacattcag | 1020 |
| tgcagggtac | ttgaagttca | gatgtgtcag | ccaattcagt | ctgctgaaga | aactattttt | 1080 |
| gcttctcctt | atgcaagcgg | aactagtccc | gttctgtgta | acgccagtcc | agttaaatga | 1140 |
| ctcgttgttg | aactccagag | tcccactaga | cgcgacgagg | gaccgcaggc | tggcataatc | 1200 |
| aggcacatcg | taagggtagc | aatttgaata | agcctttgac | cttttccacaa | acagatccca | 1260 |

```
cttcttattc tgaaatccgt cacactgagg gtcgcccaac agcgcgtcga tcagcgtaca   1320
attctttccg tccagaatct ggtggggact atcgcagatc tctcctgtgg agctactttg   1380
caccagctcg gtggcattag tcacctctat ctgatcgtta gtaatggttt tcacaatggt   1440
cccgttaggg acggcatggt gccccaagca gagcgtggct gttgagttgt cat          1493
```

<210> SEQ ID NO 34
<211> LENGTH: 1551
<212> TYPE: DNA
<213> ORGANISM: Influenza virus

<400> SEQUENCE: 34

```
atgaaagtga agctgctggt gctgctgtgt acctttaccg ccacctacgc cgataccatc     60
tgtatcggct accacgccaa caatagcacc gacaccgtgg ataccgtgct ggaaaagaac    120
gtgaccgtga cccacagcgt gaacctgctg aaaacagcc acaacggcaa gctgtgtctg    180
ctgaaaggca ttgcccctct gcagctggga aattgtagcg tggccggctg gattctgggc    240
aatcctgagt gcgagctgct gatttccaaa gagtcctggt cctacatcgt ggagaagccc    300
aaccctgaga tggcacctg ctaccctggc cacttcgccg attacgagga actgagagaa      360
cagctgtcca gcgtgtccag cttcgagaga ttcgagatct cccccaaaga gagcagctgg    420
cccaatcata cagtgaccgg cgtgagcgcc tcttgtagcc acaatggcga gagcagcttc    480
tacagaaacc tgctgtggct gaccggcaag aacggcctgt accccaacct gagcaagagc    540
tacgccaaca caaagaaaaa gaagtgctg gtcctctggg gagtgcacca ccctcctaac    600
atcggcatcc agaaggccct gtaccacacc gagaatgcct acgtgtccgt ggtgtccagc    660
cactacagca gaaagttcac ccccgagatc gccaaaagac ccaaagtgcg ggaccaggaa    720
ggcaggatca actactactg gaccctgctg gaacctggcg acaccatcat cttcgaggcc    780
aacggcaatc tgatcgcccc tagatacgcc tttgccctga gcagaggctt tggcagcggc    840
atcatcaaca gcaacgcccc catggacaag tgtgacgcca gtgtcagac accacaggga    900 gctatcaata gcagcctgcc cttccagaat gtgcaccctg tgaccatcgg cgagtgtcct    960
aaatacgtgc ggagcgccaa gctgagaatg gtgaccggcc tgaggaatat ccccagcatc   1020
cagagcagag gcctgtttgg cgccattgcc ggctttatcg agggcggatg gacaggcatg   1080
gtggatgggt ggtacggcta ccaccaccag aatgagcagg gatctggcta tgccgccgat   1140
cagaagagca cccagaacgc catcaacggc atcaccaaca agtgaacag cgtgatcgag   1200 aagatgaaca cccagttcac cgccgtgggc aaagagttca acaagctgga acggcggatg   1260
gaaaacctga acaagaaggt ggacgacggc ttcatcgaca tctggaccta caacgccgaa   1320
ctcctggtcc tcctggaaaa tgagaggacc ctggacttcc acgacagcaa cgtgaagaac   1380
ctgtacgaga aagtgaagag ccagctgaag aacaacgcca agagatcgg caacggctgc   1440 ttcgagttct accacaagtg caacgacgag tgcatggaaa gcgtgaagaa cggcacctac   1500
gactacccca agtacagcga ggaaagcaag ctgaaccggg agaagatcga t            1551
```

<210> SEQ ID NO 35
<211> LENGTH: 517
<212> TYPE: PRT
<213> ORGANISM: Influenza virus

<400> SEQUENCE: 35

```
Met Lys Val Lys Leu Leu Val Leu Leu Cys Thr Phe Thr Ala Thr Tyr
1               5                   10                  15
```

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Ile Gln Lys Ala Leu Tyr
        195                 200                 205

His Thr Glu Asn Ala Tyr Val Ser Val Val Ser Ser His Tyr Ser Arg
        210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430
```

```
Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp
        515

<210> SEQ ID NO 36
<211> LENGTH: 1551
<212> TYPE: DNA
<213> ORGANISM: Influenza virus

<400> SEQUENCE: 36
atcgatcttc tcccggttca gcttgctttc ctcgctgtac ttggggtagt cgtaggtgcc     60
gttcttcacg ctttccatgc actcgtcgtt gcacttgtgg tagaactcga agcagccgtt    120
gccgatctct ttggcgttgt tcttcagctg gctcttcact ttctcgtaca ggttcttcac    180
gttgctgtcg tggaagtcca gggtcctctc attttccagg aggaccagga gttcggcgtt    240
gtaggtccag atgtcgatga agccgtcgtc caccttcttg ttcaggtttt ccatccgccg    300
ttccagcttg ttgaactctt tgcccacggc ggtgaactgg gtgttcatct tctcgatcac    360
gctgttcact tgttggtga tgccgttgat ggcgttctgg gtgctcttct gatcggcggc    420
atagccagat ccctgctcat tctggtggtg gtagccgtac cacccatcca ccatgcctgt    480
ccatccgccc tcgataaagc cggcaatggc gccaaacagg cctctgctct ggatgctggg    540
gatattcctc aggccggtca ccattctcag cttggcgctc cgcacgtatt taggacactc    600
gccgatggtc acagggtgca cattctggaa gggcaggctg ctattgatag ctccctgtgg    660
tgtctgacac ttggcgtcac acttgtccat ggggcgttg ctgttgatga tgccgctgcc    720
aaagcctctg ctcagggcaa aggcgtatct aggggcgatc agattgccgt tggcctcgaa    780
gatgatggtg tcgccaggtt ccagcagggt ccagtagtag ttgatcctgc cttcctggtc    840
ccgcactttg ggtctttggg cgatctcggg ggtgaacttt ctgctgtagt ggctggacac    900
cacggacacg taggcattct cggtgtggta cagggcctc tggatgccga tgttaggagg    960
gtggtgcact ccccagagga ccagcacttc tttttctttg ttgttggcgt agctcttgct   1020
caggttgggg tacaggccgt tcttgccggt cagccacagc aggtttctgt agaagctgct   1080
ctcgccattg tggctacaag aggcgctcac gccggtcact gtatgattgg gccagctgct   1140
ctctttgggg aagatctcga atctctcgaa gctggacacg ctggacagct gttctctcag   1200
ttcctcgtaa tcggcgaagt ggccagggta gcaggtgcca ttctcagggt tgggcttctc   1260
cacgatgtag gaccaggact ctttggaaat cagcagctcg cactcaggat tgcccagaat   1320
ccagccggcc acgctacaat ttcccagctg cagaggggca atgcctttca gcagacacag   1380
cttgccgttg tggctgtttt ccagcaggtt cacgctgtgg gtcacggtca cgttcttttc   1440
cagcacggta tccacggtgt cggtgctatt gttggcgtgg tagccgatac agatggtatc   1500
ggcgtaggtg gcggtaaagg tacacagcag caccagcagc ttcactttca t            1551
```

<210> SEQ ID NO 37
<211> LENGTH: 1605
<212> TYPE: DNA
<213> ORGANISM: Influenza virus

<400> SEQUENCE: 37

| | | | | | |
|---|---|---|---|---|---|
| atgaaggcca | tcatcgtgct | gctgatggtg | gtcacaagca | acgccgatag | aatctgtacc | 60 |
| ggcatcacca | gcagcaatag | ccctcacgtc | gtgaaaacag | ctacacaggg | cgaagtgaat | 120 |
| gtgaccggcg | tgatccctct | gaccacaaca | cctacaaaga | gccacttcgc | caatctgaag | 180 |
| ggcacagaga | caagaggcaa | gctgtgtccc | aagtgcctga | attgcacaga | tctggatgtg | 240 |
| gctctgggca | gacctaagtg | tacaggcaaa | atccctagcg | ccagagtgtc | cattctgcat | 300 |
| gaagtgcgac | tgtgaccag | cggctgtttt | cctattatgc | acgaccggac | caagatcaga | 360 |
| cagctgccta | atctgctgag | aggctacgag | cacatcagac | tgagcaccca | caatgtgatc | 420 |
| aacgccgaaa | atgctcctgg | cggcccttat | aagatcggca | catctggcag | ctgccccaac | 480 |
| attacaaatg | gcaatggctt | ctttgccacc | atggcttggg | ccgtgcctaa | gaacgataag | 540 |
| aacaagaccg | ccaccaaccc | cctgacaatc | gaggtgccat | atatctgtac | agagggcgag | 600 |
| gatcagatca | ccgtgtgggg | atttcacagc | gacaacgaaa | cacagatggc | caagctgtac | 660 |
| ggcgatagca | agcctcagaa | gtttaccagc | tctgccaatg | gcgtgaccac | acactatgtg | 720 |
| tctcagatcg | gcggcttccc | taatcagaca | gaagatggcg | gactgcctca | gtctggaaga | 780 |
| atcgtggtgg | attacatggt | gcagaagtct | ggcaagaccg | gcaccatcac | atatcagaga | 840 |
| ggaatcctgc | tgccccagaa | agtgtggtgc | gcttctggaa | gatccaaagt | gatcaagggc | 900 |
| agcctgcctc | tgattggaga | agccgattgt | ctgcacgaga | atacggcgg | cctgaacaag | 960 |
| agcaagcctt | actatacagg | cgagcacgcc | aaggccatcg | gcaattgtcc | tatttgggtc | 1020 |
| aagacccctc | tgaagctggc | caatggcaca | agtatagac | ctccagccaa | gctgctgaaa | 1080 |
| gagagaggct | tttttggagc | tatcgccggc | tttctggaag | gcggatggga | gggaatgatt | 1140 |
| gctggatggc | atgctacac | atctcatggc | gcacatggcg | tggcagtggc | tgctgatctg | 1200 |
| aaatctacac | aggaagccat | caacaagatc | accaagaacc | tgaacagcct | gagcgagctg | 1260 |
| gaagtgaaga | atctgcagag | actgtctggc | gccatggacg | aactgcacaa | tgagatcctg | 1320 |
| gaactggacg | agaaggtgga | cgatctgaga | gccgatacaa | tcagcagcca | gattgaactg | 1380 |
| gctgtgctgc | tgtctaacga | gggcatcatc | aatagcgagg | acgaacatct | gctggccctg | 1440 |
| gaaagaaagc | tgaagaagat | gctgggacct | agcgccgtgg | aaatcggcaa | tggatgcttt | 1500 |
| gagacaaagc | acaagtgcaa | ccagacctgc | ctggataaga | ttgccgccgg | aacatttgat | 1560 |
| gccggcgagt | tttctctgcc | caccttcgat | agcctgaata | tcaca | | 1605 |

<210> SEQ ID NO 38
<211> LENGTH: 535
<212> TYPE: PRT
<213> ORGANISM: Influenza virus

<400> SEQUENCE: 38

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr

```
            50                  55                  60
Arg Gly Lys Leu Cys Pro Lys Cys Leu Asn Cys Thr Asp Leu Asp Val
 65                  70                  75                  80

Ala Leu Gly Arg Pro Lys Cys Thr Gly Lys Ile Pro Ser Ala Arg Val
                 85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Lys Phe Thr Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
                290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
                370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
                450                 455                 460

Ser Asn Glu Gly Ile Ile Asn Ser Glu Asp Glu His Leu Leu Ala Leu
465                 470                 475                 480
```

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr
    530                 535

<210> SEQ ID NO 39
<211> LENGTH: 1605
<212> TYPE: DNA
<213> ORGANISM: Influenza virus

<400> SEQUENCE: 39
tgtgatattc aggctatcga aggtgggcag agaaaactcg ccggcatcaa atgttccggc      60
ggcaattcta tccaggcagg tctggttgca cttgtgcttt gtctcaaagc atccattgcc     120
gatttccacg gcgctaggtc ccagcatctt cttcagcttt ctttccaggg ccagcagatg     180
ttcgtcctcg ctattgatga tgccctcgtt agacagcagc acagccagtt caatctggct     240
gctgattgta tcggctctca gatcgtccac cttctcgtcc agttccagga tctcattgtg     300
cagttcgtcc atggcgccag acagtctctg cagattcttc acttccagct cgctcaggct     360
gttcaggttc ttggtgatct tgttgatggc ttcctgtgta gatttcagat cagcagccac     420
tgccacgcca tgtgcgccat gagatgtgta gccatgccat ccagcaatca ttccctccca     480
tccgccttcc agaaagccgg cgatagctcc aaaaaagcct ctctctttca gcagcttggc     540
tggaggtcta tactttgtgc cattggccag cttcagaggg tcttgaccc aaataggaca      600
attgccgatg ccttggcgt gctcgcctgt atagtaaggc ttgctcttgt tcaggccgcc      660
gtatttctcg tgcagacaat cggcttctcc aatcagaggc aggctgccct tgatcacttt     720
ggatcttcca gaagcgcacc acactttctg gggcagcagg attcctctct gatatgtgat     780
ggtgccggtc ttgccagact ctgcaccat gtaatccacc acgattcttc cagactgagg      840
cagtccgcca tcttctgtct gattagggaa gccgccgatc tgagacacat agtgtgtggt     900
cacgccattg gcagagctgg taaacttctg aggcttgcta cgccgtaca gcttggccat      960
ctgtgtttcg ttgtcgctgt gaaatcccca cacggtgatc tgatcctcgc cctctgtaca    1020
gatatatggc acctcgattg tcaggggggtt ggtggcggtc ttgttcttat cgttcttagg    1080
cacggcccaa gccatggtgg caagaagcc attgccattt gtaatgttgg ggcagctgcc    1140
agatgtgccg atcttataag ggccgccagg agcattttcg gcgttgatca cattgtgggt    1200
gctcagtctg atgtgctcgt agcctctcag cagattaggc agctgtctga tcttggtccg    1260
gtcgtgcata ataggaaaac agccgctggt cacaggtcgc acttcatgca gaatggacac    1320
tctggcgcta gggattttgc ctgtacactt aggtctgccc agagccacat ccagatctgt    1380
gcaattcagg cacttgggac acagcttgcc tcttgtctct gtgcccttca gattggcgaa    1440
gtggctcttt gtaggtgttg tggtcagagg gatcacgccg gtcacattca cttcgccctg    1500
tgtagctgtt ttcacgacgt gagggctatt gctgctggtg atgccggtac agattctatc    1560
ggcgttgctt gtgaccacca tcagcagcac gatgatggcc ttcat                    1605

<210> SEQ ID NO 40
<211> LENGTH: 2058
<212> TYPE: DNA

<213> ORGANISM: Artificial Sequence
<220> FEATURE:
<223> OTHER INFORMATION: Synthetic

<400> SEQUENCE: 40

```
atgaaggcca aactgctggt gctgctgtgt acctttaccg ccacctacgc cgacacaatc      60
tgtatcggct accacgccaa caatagcacc gacaccgtgg atacagtgct ggagaagaac     120
gtgaccgtga cccactctgt gaacctgctg gaggacagcc acaatggcaa gctgtgtctg     180
ctgaaaggca ttgcccctct gcagctgggc aattgttctg tggccggatg gattctgggc     240
aaccccgagt gtgagctgct gatttctaag gagagctgga gctacatcgt ggagacccc      300
aatcctgaga atggcacctg ctaccctggc tacttcgccg attacgagga gctgcgcgag     360
cagctgtcta gcgtgtccag cttcgagaga ttcgagatct cccccaagga gtccagctgg     420
cctaatcaca cagtgacagg cgtgtctgcc agctgtagcc acaacggcaa aagcagcttc     480
taccggaacc tgctgtggct gacaggcaag aatggcctgt accccaacct gagcaagagc     540
tacgtgaaca acaaggaaaa ggaagtgctg gtgctgtggg agtgcacca  ccctcccaac     600
atcggaaatc agcgggccct gtaccacaca gagaacgcct atgtgagcgt ggtgtccagc     660
cactacagca gaagattcac ccccgagatc gccaagagac ccaaagtgag agaccaggag     720
ggccggatca attactactg gacctgctg gagcctggcg ataccatcat cttcgaggcc     780
aacggcaatc tgatcgcccc ttggtatgcc tttgccctga gcagaggctt tggcagcggc     840
atcatcacaa gcaacgcccc catggatgag tgtgatgcca agtgccagac cctcagggc      900
gccatcaata gcagcctgcc cttccagaat gtgcaccctg tgaccatcgg cgagtgcccc     960
aagtatgtga aagcgccaa gctgagaatg gtgaccggcc tgagaaacat ccctcagagg    1020
gagaccagag gactgtttgg agccatcgcc ggattcatcg agggaggatg gacaggcatg    1080
gtggatggct ggtacggcta ccaccaccag aatgagcagg gctctggata tgccgccgat    1140
cagaagtcta cccagaacgc catcaacggg atcaccaaca aggtgaacag cgtgatcgag    1200
aagatgaaca cccagtttac cgctgtgggc aaggagttca caagctgga gcggaggatg    1260
gagaacctga acaagaaggt ggacgacggc tttctggaca tctggaccta caatgccgaa    1320
ctcctggtcc tcctcgagaa tgagaggacc ctggacttcc acgacagcaa cgtgaagaac    1380
ctgtatgaga aggtgaagag ccagctgaag aacaacgcca aggagatcgg caacggctgc    1440
ttcgagttct accacaagtg taacaacgag tgtatggaga gcgtgaagaa cggcacctac    1500
gactacccta gtacagcga ggagagcaag ctgaaccggg agaagatcga ttccggaggc    1560
gacatcatca gctgctgaa cgagcaggtg aacaaggaga tgcagagcag caacctgtac    1620
atgagcatga gcagctggtg ctacacccac agcctggacg cgccggcct gttcctgttc    1680
gaccacgccg ccgaggagta cgagcacgcc aagaagctga tcatcttcct gaacgagaac    1740
aacgtgcccg tgcagctgac cagcatcagc gcccccgagc acaagttcga gggcctgacc    1800
cagatcttcc agaaggccta cgagcacgag cagcacatca gcgagagcat caacaacatc    1860
gtggaccacg ccatcaagag caaggaccac gccaccttca ctttcctgca gtggtacgtg    1920
gccgagcagc acgaggagga ggtgctgttc aaggacatcc tggacaagat cgagctgatc    1980
ggcaacgaga accacggcct gtacctggcc gaccagtacg tgaagggcat cgccaagagc    2040
aggaagagcg gatcctag                                                 2058
```

<210> SEQ ID NO 41
<211> LENGTH: 685

```
<212> TYPE: PRT
<213> ORGANISM: Artificial Sequence
<220> FEATURE:
<223> OTHER INFORMATION: Synthetic

<400> SEQUENCE: 41

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Gln Arg Glu Thr Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
370                 375                 380
```

-continued

```
Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
            405                 410                 415

Glu Arg Arg Met Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
    435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
            485                 490                 495

Asn Gly Thr Tyr Asp Tyr Pro Lys Tyr Ser Glu Glu Ser Lys Leu Asn
        500                 505                 510

Arg Glu Lys Ile Asp Ser Gly Gly Asp Ile Ile Lys Leu Leu Asn Glu
    515                 520                 525

Gln Val Asn Lys Glu Met Gln Ser Ser Asn Leu Tyr Met Ser Met Ser
530                 535                 540

Ser Trp Cys Tyr Thr His Ser Leu Asp Gly Ala Gly Leu Phe Leu Phe
545                 550                 555                 560

Asp His Ala Ala Glu Glu Tyr Glu His Ala Lys Lys Leu Ile Ile Phe
            565                 570                 575

Leu Asn Glu Asn Asn Val Pro Val Gln Leu Thr Ser Ile Ser Ala Pro
        580                 585                 590

Glu His Lys Phe Glu Gly Leu Thr Gln Ile Phe Gln Lys Ala Tyr Glu
    595                 600                 605

His Glu Gln His Ile Ser Glu Ser Ile Asn Asn Ile Val Asp His Ala
610                 615                 620

Ile Lys Ser Lys Asp His Ala Thr Phe Asn Phe Leu Gln Trp Tyr Val
625                 630                 635                 640

Ala Glu Gln His Glu Glu Val Leu Phe Lys Asp Ile Leu Asp Lys
            645                 650                 655

Ile Glu Leu Ile Gly Asn Glu Asn His Gly Leu Tyr Leu Ala Asp Gln
        660                 665                 670

Tyr Val Lys Gly Ile Ala Lys Ser Arg Lys Ser Gly Ser
    675                 680                 685
```

<210> SEQ ID NO 42
<211> LENGTH: 2058
<212> TYPE: DNA
<213> ORGANISM: Artificial Sequence
<220> FEATURE:
<223> OTHER INFORMATION: Synthetic

<400> SEQUENCE: 42

```
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aagtggcgt ggtccttgct    180 cttgatggcg tggtccacga tgttgttgat gctctcgctg atgtgctgct cgtgctcgta   240
ggccttctgg aagatctggg tcaggccctc gaacttgtgc tcgggggcgc tgatgctggt   300
cagctgcacg ggcacgttgt tctcgttcag gaagatgatc agcttcttgg cgtgctcgta   360
```

```
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc tccggaatc gatcttctcc cggttcagct tgctctcctc    540
gctgtactta gggtagtcgt aggtgccgtt cttcacgctc tccatacact cgttgttaca    600
cttgtggtag aactcgaagc agccgttgcc gatctccttg gcgttgttct tcagctggct    660
cttcaccttc tcatacaggt tcttcacgtt gctgtcgtgg aagtccaggg tcctctcatt    720
ctcgaggagg accaggagtt cggcattgta ggtccagatg tccagaaagc cgtcgtccac    780
cttcttgttc aggttctcca tcctccgctc cagcttgttg aactccttgc ccacagcggt    840
aaactgggtg ttcatcttct cgatcacgct gttcaccttg ttggtgatgc cgttgatggc    900
gttctgggta gacttctgat cggcggcata tccagagccc tgctcattct ggtggtggta    960
gccgtaccag ccatccacca tgcctgtcca tcctccctcg atgaatccgg cgatggctcc   1020
aaacagtcct ctggtctccc tctgagggat gtttctcagg ccggtcacca ttctcagctt   1080
ggcgcttctc acatacttgg ggcactcgcc gatggtcaca gggtgcacat tctggaaggg   1140
caggctgcta ttgatggcgc cctgaggtgt ctggcacttg gcatcacact catccatggg   1200
ggcgttgctt gtgatgatgc cgctgccaaa gcctctgctc agggcaaagg cataccaagg   1260
ggcgatcaga ttgccgttgg cctcgaagat gatggtatcg ccaggctcca gcagggtcca   1320
gtagtaattg atccggccct cctggtctct cactttgggt ctcttggcga ctcgggggt    1380 gaatcttctg ctgtagtggc tggacaccac gctcacatag gcgttctctg tgtggtacag   1440
ggcccgctga tttccgatgt tgggagggtg gtgcactccc cacagcacca gcacttcctt   1500
ttccttgttg ttcacgtagc tcttgctcag gttggggtac aggccattct tgcctgtcag   1560
ccacagcagg ttccggtaga agctgctttt gccgttgtgg ctacagctgg cagacacgcc   1620
tgtcactgtg tgattaggcc agctggactc cttggggaag atctcgaatc tctcgaagct   1680
ggacacgcta gacagctgct cgcgcagctc ctcgtaatcg gcgaagtagc cagggtagca   1740
ggtgccattc tcaggattgg gggtctccac gatgtagctc cagctctcct tagaaatcag   1800
cagctcacac tcggggttgc ccagaatcca tccggccaca gaacaattgc ccagctgcag   1860
aggggcaatg cctttcagca gacacagctt gccattgtgg ctgtcctcca gcaggttcac   1920
agagtgggtc acggtcacgt tcttctccag cactgtatcc acggtgtcgg tgctattgtt   1980
ggcgtggtag ccgatacaga ttgtgtcggc gtaggtggcg gtaaaggtac acagcagcac   2040
cagcagtttg gccttcat                                                 2058
```

<210> SEQ ID NO 43
<211> LENGTH: 2061
<212> TYPE: DNA
<213> ORGANISM: Artificial Sequence
<220> FEATURE:
<223> OTHER INFORMATION: Synthetic

<400> SEQUENCE: 43

```
atgaaggcca tcctggtggt gctgctgtac accttcgcca ccgccaacgc cgacaccctg     60
tgcatcggct accacgccaa caacagcacc gacaccgtgg acaccgtgct ggagaagaac    120
gtgaccgtga cccacagcgt gaacctgctg gaggacaagc acaacggcaa gctgtgcaag    180 ctgcgggggcg tggccccccct gcacctgggc aagtgcaaca tcgccggctg gattctgggc    240
aaccccgagt gcgagagcct gagcaccgcc agcagctgga gctacatcgt ggagaccccc    300
agcagcgaca acggcacctg ctaccccggc gacttcatcg actacgagga gctgcgggag    360
```

```
cagctgagca gcgtgagcag cttcgagcgg ttcgagatct tccccaagac cagcagctgg    420
cccaaccacg acagcaacaa gggcgtgacc gccgcctgcc ccacgccgg cgccaagagc    480 ttctacaaga acctgatctg gctggtgaag aagggcaaca gctaccccaa gctgagcaag    540
agctacatca cgacaaggg caaggaggtg ctggtgctgt ggggcatcca ccaccccagc    600
accagcgccg accagcagag cctgtaccag aacgccgaca cctacgtgtt cgtgggcagc    660
agccggtaca gcaagaagtt caagcccgag atcgccatcc ggcccaaggt gcgggaccag    720
gagggccgga tgaactacta ctggaccctg gtggagcccg cgacaagat caccttcgag    780 gccaccggca acctggtggt gccccggtac gccttcgcca tggagcggaa cgccggcagc    840
ggcatcatca tcagcgacac ccccgtgcac gactgcaaca ccacctgcca gacccccaag    900
ggcgccatca acaccagcct gcccttccag aacatccacc ccatcaccat cggcaagtgc    960
cccaagtacg tgaagagcac caagctgcgg ctggccaccg gcctgcggaa catccccagc    1020
atccagagcc ggggcctgtt cggcgccatc gccggcttca tcgagggcgg ctggaccggc    1080
atggtggacg gctggtacgg ctaccaccac cagaacgagc agggcagcgg ctacgccgcc    1140
gacctgaaga gcacccagaa cgccatcgac gagatcacca caaggtgaa cagcgtgatc    1200 gagaagatga cacccagtt caccgccgtg gcaaggagt tcaaccacct ggagaagcgg    1260
atcgagaacc tgaacaagaa ggtggacgac ggcttcctgg acatctggac ctacaacgcc    1320
gagctgctgg tgctgctgga aacgagcgg accctggact accacgacag caacgtgaag    1380
aacctgtacg agaaggtgcg gagccagctg aagaacaacg ccaaggagat cggcaacggc    1440
tgcttcgagt tctaccacaa gtgcgacaac acctgcatgg agagcgtgaa gaacggcacc    1500
tacgactacc ccaagtacag cgaggaggcc aagctgaacc gggaggagat cgactccgga    1560
ggcgacatca tcaagctgct gaacgagcag gtgaacaagg agatgcagag cagcaacctg    1620
tacatgagca tgagcagctg gtgctacacc cacagcctgg acggcgccgg cctgttcctg    1680
ttcgaccacc ccgccgagga gtacgagcac gccaagaagc tgatcatctt cctgaacgag    1740
aacaacgtgc ccgtgcagct gaccagcatc agcgcccccg agcacaagtt cgagggcctg    1800
acccagatct tccagaaggc ctacgagcac gagcagcaca tcagcgagag catcaacaac    1860
atcgtggacc acgccatcaa gagcaaggac cacgccacct tcaacttcct gcagtggtac    1920
gtggccgagc agcacgagga ggaggtgctg ttcaaggaca tcctggacaa gatcgagctg    1980
atcggcaacg agaaccacgg cctgtacctg gccgaccagt acgtgaaggg catcgccaag    2040
agcaggaaga gcggatccta g                                              2061
```

<210> SEQ ID NO 44
<211> LENGTH: 686
<212> TYPE: PRT
<213> ORGANISM: Artificial Sequence
<220> FEATURE:
<223> OTHER INFORMATION: Synthetic

<400> SEQUENCE: 44

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
```

```
            50                  55                  60
Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480
```

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Ser Gly Gly Asp Ile Ile Lys Leu Leu Asn
            515                 520                 525

Glu Gln Val Asn Lys Glu Met Gln Ser Ser Asn Leu Tyr Met Ser Met
        530                 535                 540

Ser Ser Trp Cys Tyr Thr His Ser Leu Asp Gly Ala Gly Leu Phe Leu
545                 550                 555                 560

Phe Asp His Ala Ala Glu Glu Tyr Glu His Ala Lys Lys Leu Ile Ile
                565                 570                 575

Phe Leu Asn Glu Asn Asn Val Pro Val Gln Leu Thr Ser Ile Ser Ala
            580                 585                 590

Pro Glu His Lys Phe Glu Gly Leu Thr Gln Ile Phe Gln Lys Ala Tyr
        595                 600                 605

Glu His Glu Gln His Ile Ser Glu Ser Ile Asn Asn Ile Val Asp His
    610                 615                 620

Ala Ile Lys Ser Lys Asp His Ala Thr Phe Asn Phe Leu Gln Trp Tyr
625                 630                 635                 640

Val Ala Glu Gln His Glu Glu Val Leu Phe Lys Asp Ile Leu Asp
                645                 650                 655

Lys Ile Glu Leu Ile Gly Asn Glu Asn His Gly Leu Tyr Leu Ala Asp
            660                 665                 670

Gln Tyr Val Lys Gly Ile Ala Lys Ser Arg Lys Ser Gly Ser
        675                 680                 685

<210> SEQ ID NO 45
<211> LENGTH: 2061
<212> TYPE: DNA
<213> ORGANISM: Artificial Sequence
<220> FEATURE:
<223> OTHER INFORMATION: Synthetic

<400> SEQUENCE: 45
ctaggatccg ctcttcctgc tcttggcgat gcccttcacg tactggtcgg ccaggtacag     60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggcgc tgatgctggt    300 cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggagtc gatctcctcc cggttcagct tggcctcctc    540
gctgtacttg gggtagtcgt aggtgccgtt cttcacgctc tccatgcagg tgttgtcgca    600
cttgtggtag aactcgaagc agccgttgcc gatctccttg gcgttgttct tcagctggct    660
ccgcaccttc tcgtacaggt tcttcacgtt gctgtcgtgg tagtccaggg tccgctcgtt    720
ctccagcagc accagcagct cggcgttgta ggtccagatg tccaggaagc gtcgtccac    780 cttcttgttc aggttctcga tccgcttctc caggtggttg aactccttgc ccacggcggt    840
gaactgggtg ttcatcttct cgatcacgct gttcaccttg ttggtgatct cgtcgatggc    900

```
gttctgggtg ctcttcaggt cggcggcgta gccgctgccc tgctcgttct ggtggtggta      960
gccgtaccag ccgtccacca tgccggtcca gccgccctcg atgaagccgg cgatggcgcc     1020
gaacaggccc cggctctgga tgctggggat gttccgcagg ccggtggcca gccgcagctt     1080
ggtgctcttc acgtacttgg ggcacttgcc gatggtgatg gggtggatgt tctggaaggg     1140
caggctggtg ttgatggcgc ccttgggggt ctggcaggtg gtgttgcagt cgtgcacggg     1200
ggtgtcgcta tgatgatgc cgctgccggc gttccgctcc atggcgaagg cgtaccgggg      1260
caccaccagg ttgccggtgg cctcgaaggt gatcttgtcg ccgggctcca ccagggtcca     1320
gtagtagttc atccggccct cctggtcccg caccttgggc cggatggcga tctcgggctt     1380
gaacttcttg ctgtaccggc tgctgcccac gaacacgtag gtgtcggcgt tctggtacag     1440
gctctgctgg tcggcgctgg tgctggggtg gtggatgccc cacagcacca gcacctcctt     1500
gcccttgtcg ttgatgtagc tcttgctcag cttggggtag ctgttgccct tcttcaccag     1560
ccagatcagg ttcttgtaga agctcttggc gccggcgtgg gggcaggcgg cggtcacgcc     1620
cttgttgctg tcgtggttgg gccagctgct ggtcttgggg aagatctcga accgctcgaa     1680
gctgctcacg ctgctcagct gctcccgcag ctcctcgtag tcgatgaagt cgccggggta     1740
gcaggtgccg ttgtcgctgc tgggggtctc cacgatgtag ctccagctgc tggcggtgct     1800
caggctctcg cactcgggt tgcccagaat ccagccggcg atgttgcact gcccaggtg      1860 caggggggcc acgccccgca gcttgcacag cttgccgttg tgcttgtcct ccagcaggtt     1920
cacgctgtgg gtcacggtca cgttcttctc cagcacggtg tccacggtgt cggtgctgtt     1980
gttggcgtgg tagccgatgc acagggtgtc ggcgttggcg gtggcgaagg tgtacagcag     2040
caccaccagg atggccttca t                                               2061

<210> SEQ ID NO 46
<211> LENGTH: 2049
<212> TYPE: DNA
<213> ORGANISM: Artificial Sequence
<220> FEATURE:
<223> OTHER INFORMATION: Synthetic

<400> SEQUENCE: 46
atggccatca tctacctgat cctgctgttt acagctgtgc ggggcgatca gatctgtatc       60
ggctaccacg ccaacaatag caccgagaag gtggacacca tcctggaaag aaatgtgacc      120
gtgacccacg ccaaggatat tctggaaaag acccacaacg gcaagctgtg caagctgaat      180
ggcattcctc tctggaact gggcgattgt tctattgctg ctggctgct gggaaatcct        240 gagtgcgata gactgctgtc tgtgcctgag tggagctaca tcatggaaaa agagaaccct      300
agggacggac tgtgttaccc cggcagcttc aacgattacg aggaactgaa gcacctgctg      360
tccagcgtga agcacttcga gaaagtgaag atcctgccca aggatagatg gacccagcat      420
acaacaacag gcggaagcag agcttgtgct gtgtccggca accccagctt ttcagaaat       480 atggtctggc tgaccaagaa gggctctaat tatcctgtgg ccaagggcag ctacaataat      540
acaagcggcg agcagatgct gattatttgg ggcgtgcacc accctaatga tgagacagag      600
cagagaaccc tgtaccagaa tgtgggcaca tacgtgtctg tgggcaccag cacactgaat      660
aagagaagca ccccgatat tgccaccaga cccaaagtga atggacaggg cggcagaatg       720
gaattttcct ggaccctgct ggatatgtgg gacaccatca actttgagag caccgggaat      780
ctgattgccc ctgagtacgg cttcaagatc agcaagagag gcagcagcgg catcatgaaa      840
```

```
acagagggca ccctggaaaa ctgtgaaacc aagtgtcaga cacctctggg cgccattaat   900
accaccctgc ccttccataa tgtgcaccct ctgacaatcg gcgagtgccc taagtacgtg   960
aagtctgaga aactggtgct ggccacagga ctgagaaatg tgccccagat cgagtcaaga  1020
ggcctgtttg gagccattgc cggctttatt gaaggcggat ggcagggaat ggtggatggg  1080
tggtacggct atcaccacag caatgatcag ggatctggct atgccgccga taaagagagc  1140
acccagaagg cctttgacgg catcaccaac aaagtgaaca gcgtgatcga agatgaac     1200
acccagtttg aggccgtggg caaagagttc agcaatctgg aaagacggct ggaaaacctg  1260
aacaagaaaa tggaagatgg cttcctggac gtgtggacat ataatgccga gctgctggtg  1320
ctgatggaaa acgagaggac cctggacttt cacgacagca cgtgaagaa cctgtacgac   1380
aaagtgcgga tgcagctgag agacaatgtg aaagagctgg gcaacggctg ctttgagttc  1440
taccacaagt gcgacgacga gtgcatgaat agcgtgaaga acggcaccta cgactaccct  1500
aagtatgagg aagagagcaa gctgaacaga aacgagatca gtccggagg cgacatcatc   1560
aagctgctga cgagcaggt gaacaaggag atgcagagca gcaacctgta catgagcatg    1620
agcagctggt gctacaccca cagcctggac ggcgccggcc tgttcctgtt cgaccacgcc  1680
gccgaggagt acgagcacgc caagaagctg atcatcttcc tgaacgagaa caacgtgccc  1740
gtgcagctga ccagcatcag cgcccccgag cacaagttcg agggcctgac ccagatcttc  1800
cagaaggcct acgagcacga gcagcacatc agcgagagca tcaacaacat cgtggaccac  1860
gccatcaaga gcaaggacca cgccaccttc aacttcctgc agtggtacgt ggccgagcag  1920
cacgaggagg aggtgctgtt caaggacatc ctggacaaga tcgagctgat cggcaacgag  1980
aaccacggcc tgtacctggc cgaccagtac gtgaagggca tcgccaagag caggaagagc  2040
ggatcctag                                                          2049
```

<210> SEQ ID NO 47
<211> LENGTH: 682
<212> TYPE: PRT
<213> ORGANISM: Artificial Sequence
<220> FEATURE:
<223> OTHER INFORMATION: Synthetic

<400> SEQUENCE: 47

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140
```

-continued

```
Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Ser Gly Gly Asp Ile Ile Lys Leu Leu Asn Glu Gln Val Asn
        515                 520                 525

Lys Glu Met Gln Ser Ser Asn Leu Tyr Met Ser Met Ser Ser Trp Cys
    530                 535                 540

Tyr Thr His Ser Leu Asp Gly Ala Gly Leu Phe Leu Phe Asp His Ala
545                 550                 555                 560

Ala Glu Glu Tyr Glu His Ala Lys Lys Leu Ile Ile Phe Leu Asn Glu
```

```
                     565                 570                 575

Asn Asn Val Pro Val Gln Leu Thr Ser Ile Ser Ala Pro Glu His Lys
            580                 585                 590

Phe Glu Gly Leu Thr Gln Ile Phe Gln Lys Ala Tyr Glu His Glu Gln
            595                 600                 605

His Ile Ser Glu Ser Ile Asn Asn Ile Val Asp His Ala Ile Lys Ser
        610                 615                 620

Lys Asp His Ala Thr Phe Asn Phe Leu Gln Trp Tyr Val Ala Glu Gln
625                 630                 635                 640

His Glu Glu Val Leu Phe Lys Asp Ile Leu Asp Lys Ile Glu Leu
                645                 650                 655

Ile Gly Asn Glu Asn His Gly Leu Tyr Leu Ala Asp Gln Tyr Val Lys
            660                 665                 670

Gly Ile Ala Lys Ser Arg Lys Ser Gly Ser
            675                 680

<210> SEQ ID NO 48
<211> LENGTH: 2049
<212> TYPE: DNA
<213> ORGANISM: Artificial Sequence
<220> FEATURE:
<223> OTHER INFORMATION: Synthetic

<400> SEQUENCE: 48
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300 cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttg atgatgtcgc ctccggactt gatctcgttt ctgttcagct tgctctcttc   540
ctcatactta gggtagtcgt aggtgccgtt cttcacgcta ttcatgcact cgtcgtcgca   600
cttgtggtag aactcaaagc agccgttgcc cagctctttc acattgtctc tcagctgcat   660
ccgcactttg tcgtacaggt tcttcacgtt gctgtcgtga agtccaggg tcctctcgtt   720 ttccatcagc accagcagct cggcattata tgtccacacg tccaggaagc catcttccat   780
tttcttgttc aggttttcca gccgtctttc cagattgctg aactctttgc ccacggcctc   840
aaactgggtg ttcatcttct cgatcacgct gttcactttg ttggtgatgc cgtcaaaggc   900
cttctgggtg ctctctttat cggcggcata gccagatccc tgatcattgc tgtggtgata   960
gccgtaccac ccatccacca ttccctgcca tccgccttca ataaagccgg caatggctcc  1020
aaacaggcct cttgactcga tctggggcac atttctcagt cctgtggcca gcaccagttt  1080
ctcagacttc acgtacttag ggcactcgcc gattgtcaga gggtgcacat tatggaaggg  1140
cagggtggta ttaatggcgc ccagaggtgt ctgacacttg gtttcacagt tttccagggt  1200
gccctctgtt ttcatgatgc cgctgctgcc tctcttgctg atcttgaagc cgtactcagg  1260
ggcaatcaga ttcccggtgc tctcaaagtt gatggtgtcc cacatatcca gcagggtcca  1320
ggaaaattcc attctgccgc cctgtccatt cactttgggt ctggtggcaa tatcgggggt  1380
```

| | |
|---|---|
| gcttctctta ttcagtgtgc tggtgcccac agacacgtat gtgcccacat tctggtacag | 1440 |
| ggttctctgc tctgtctcat cattagggtg gtgcacgccc caaataatca gcatctgctc | 1500 |
| gccgcttgta ttattgtagc tgcccttggc cacaggataa ttagagccct tcttggtcag | 1560 |
| ccagaccata tttctgaaga agctgggggtt gccggacaca gcacaagctc tgcttccgcc | 1620 |
| tgttgttgta tgctgggtcc atctatcctt gggcaggatc ttcactttct cgaagtgctt | 1680 |
| cacgctggac agcaggtgct tcagttcctc gtaatcgttg aagctgccgg ggtaacacag | 1740 |
| tccgtcccta gggttctctt tttccatgat gtagctccac tcaggcacag acagcagtct | 1800 |
| atcgcactca ggatttccca gcagccagcc agcaatagaa caatcgccca gttccagagg | 1860 |
| aggaatgcca ttcagcttgc acagcttgcc gttgtgggtc ttttccagaa tatccttggc | 1920 |
| gtgggtcacg gtcacatttc tttccaggat ggtgtccacc ttctcggtgc tattgttggc | 1980 |
| gtggtagccg atacagatct gatcgccccg cacagctgta aacagcagga tcaggtagat | 2040 |
| gatggccat | 2049 |

<210> SEQ ID NO 49
<211> LENGTH: 2064
<212> TYPE: DNA
<213> ORGANISM: Artificial Sequence
<220> FEATURE:
<223> OTHER INFORMATION: Synthetic

<400> SEQUENCE: 49

| | |
|---|---|
| atgaaaacca tcattgccct gagctacatc ttttgtctgg ctctgggcca ggatctgccc | 60 |
| ggcaatgata tagcaccgc caccctgtgt ctgggacacc acgccgtgcc taatggcacc | 120 |
| ctggtgaaaa ccattaccga cgaccagatc gaagtgacca tgccaccga gctggtgcag | 180 |
| agcagcagca ccgcaagat ctgcaacaac ccccacagaa tcctggatgg catcgactgt | 240 |
| accctgatcg atgccctgct gggcgatcct cactgcgacg tgttccagaa cgagacatgg | 300 |
| gacctgttcg tggagagaag caaggccttc agcaactgct accccacga tgtgcccgat | 360 |
| tacgcctctc tgagaagcct ggtggccagc agcggcacac tggaattcat caccgagggc | 420 |
| tttacctgga caggcgtgac ccagaatggc ggcagcaatg cctgtaaaag aggccctggc | 480 |
| agcggcttct tcagcagact gaactggctg accaagtccg gcagcaccta ccctgtgctg | 540 |
| aacgtgacca tgcccaacaa cgacaacttc gacaagctgt acatctgggg cgtgcaccac | 600 |
| cctagcacca tcaggaaca gaccagcctg tacgtgcagg ccagcggcag agtgaccgtg | 660 |
| tctaccagac ggtcccagca gaccatcatc cccaacatcg agtcaagacc ttgggtgcgc | 720 |
| ggcctgagca gcagaatcag catctactgg accatcgtga aacctggcga cgtgctggtg | 780 |
| atcaacagca atggcaacct gatcgcccc agaggctact tcaagatgcg gaccggcaag | 840 |
| agcagcatca tgagaagcga cgcccccatc gatacctgta tcagcgagtg catcacccc | 900 |
| aacggcagca tccccaacga caagcccttc cagaacgtga acaagatcac ctacggcgcc | 960 |
| tgccctaagt acgtgaagca gaacaccctg aagctggcca ccggcatgag aaatgtgccc | 1020 |
| gagaagcaga caagaggcct gtttggcgcc attgccggct ttatcgagaa cggctgggag | 1080 |
| ggcatgatcg atgggtggta cggcttcaga caccagaatt ctgagggcac aggacaggcc | 1140 |
| gccgatctga agtctacaca ggccgccatc gaccagatca cggcaagct gaacagagtg | 1200 |
| atcgagaaaa ccaacgagaa gttccaccag atcgagaaag aattcagcga ggtggagggc | 1260 |
| agaatccagg acctggaaaa atacgtggag gacaccaaga tcgacctgtg gagctacaat | 1320 |
| gccgaactgc tggtcgccct ggaaaaccag cacaccatcg acctgaccga cagcgagatg | 1380 |

```
aataagctgt tcgaaaagac cagacggcag ctgagagaaa acgccgagga catgggcaac  1440
ggctgcttca agatctacca caagtgcgac aacgcctgca tcgagagcat cagaaacggc  1500
acctacgacc acgatgtgta cagggacgag gccctgaaca acagattcca gatcaagtcc  1560
ggaggcgaca tcatcaagct gctgaacgag caggtgaaca aggagatgca gagcagcaac  1620
ctgtacatga gcatgagcag ctggtgctac acccacagcc tggacggcgc cggcctgttc  1680
ctgttcgacc acgccgccga ggagtacgag cacgccaaga agctgatcat cttcctgaac  1740
gagaacaacg tgcccgtgca gctgaccagc atcagcgccc ccgagcacaa gttcgagggc  1800
ctgacccaga tcttccagaa ggcctacgag cacgagcagc acatcagcga gagcatcaac  1860
aacatcgtgg accacgccat caagagcaag gaccacgcca ccttcaactt cctgcagtgg  1920
tacgtggccg agcagcacga ggaggaggtg ctgttcaagg acatcctgga caagatcgag  1980
ctgatcggca cgagaaccca cggcctgtac ctggccgacc agtacgtgaa gggcatcgcc  2040
aagagcagga agagcggatc ctag                                       2064

<210> SEQ ID NO 50
<211> LENGTH: 687
<212> TYPE: PRT
<213> ORGANISM: Artificial Sequence
<220> FEATURE:
<223> OTHER INFORMATION: Synthetic

<400> SEQUENCE: 50

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Ser Ser Thr
        50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240
```

-continued

```
Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
                260                 265                 270

Tyr Phe Lys Met Arg Thr Gly Lys Ser Ser Ile Met Arg Ser Asp Ala
            275                 280                 285

Pro Ile Asp Thr Cys Ile Ser Glu Cys Ile Thr Pro Asn Gly Ser Ile
        290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Ser Gly Gly Asp Ile Ile Lys Leu Leu
        515                 520                 525

Asn Glu Gln Val Asn Lys Glu Met Gln Ser Ser Asn Leu Tyr Met Ser
    530                 535                 540

Met Ser Ser Trp Cys Tyr Thr His Ser Leu Asp Gly Ala Gly Leu Phe
545                 550                 555                 560

Leu Phe Asp His Ala Ala Glu Glu Tyr Glu His Ala Lys Lys Leu Ile
                565                 570                 575

Ile Phe Leu Asn Glu Asn Asn Val Pro Val Gln Leu Thr Ser Ile Ser
            580                 585                 590

Ala Pro Glu His Lys Phe Glu Gly Leu Thr Gln Ile Phe Gln Lys Ala
        595                 600                 605

Tyr Glu His Glu Gln His Ile Ser Glu Ser Ile Asn Asn Ile Val Asp
    610                 615                 620

His Ala Ile Lys Ser Lys Asp His Ala Thr Phe Asn Phe Leu Gln Trp
625                 630                 635                 640

Tyr Val Ala Glu Gln His Glu Glu Glu Val Leu Phe Lys Asp Ile Leu
                645                 650                 655
```

```
Asp Lys Ile Glu Leu Ile Gly Asn Glu Asn His Gly Leu Tyr Leu Ala
            660                 665                 670

Asp Gln Tyr Val Lys Gly Ile Ala Lys Ser Arg Lys Ser Gly Ser
        675                 680                 685
```

<210> SEQ ID NO 51
<211> LENGTH: 2064
<212> TYPE: DNA
<213> ORGANISM: Artificial Sequence
<220> FEATURE:
<223> OTHER INFORMATION: Synthetic

<400> SEQUENCE: 51

| | | | | | |
|---|---|---|---|---|---|
| ctaggatccg | ctcttcctgc | tcttggcgat | gcccttcacg | tactggtcgg | ccaggtacag | 60 |
| gccgtggttc | tcgttgccga | tcagctcgat | cttgtccagg | atgtccttga | acagcacctc | 120 |
| ctcctcgtgc | tgctcggcca | cgtaccactg | caggaagttg | aaggtggcgt | ggtccttgct | 180 |
| cttgatggcg | tggtccacga | tgttgttgat | gctctcgctg | atgtgctgct | cgtgctcgta | 240 |
| ggccttctgg | aagatctggg | tcaggccctc | gaacttgtgc | tcggggcgc | tgatgctggt | 300 |
| cagctgcacg | ggcacgttgt | tctcgttcag | gaagatgatc | agcttcttgg | cgtgctcgta | 360 |
| ctcctcggcg | gcgtggtcga | acaggaacag | gccggcgccg | tccaggctgt | gggtgtagca | 420 |
| ccagctgctc | atgctcatgt | acaggttgct | gctctgcatc | tccttgttca | cctgctcgtt | 480 |
| cagcagcttg | atgatgtcgc | ctccggactt | gatctggaat | ctgttgttca | gggcctcgtc | 540 |
| cctgtacaca | tcgtggtcgt | aggtgccgtt | tctgatgctc | tcgatgcagg | cgttgtcgca | 600 |
| cttgtggtag | atcttgaagc | agccgttgcc | catgtcctcg | gcgttttctc | tcagctgccg | 660 |
| tctggtctt | tcgaacagct | tattcatctc | gctgtcggtc | aggtcgatgg | tgtgctggtt | 720 |
| ttccagggcg | accagcagtt | cggcattgta | gctccacagg | tcgatcttgg | tgtcctccac | 780 |
| gtattttcc | aggtcctgga | ttctgccctc | cacctcgctg | aattctttct | cgatctggtg | 840 |
| gaacttctcg | ttggttttct | cgatcactct | gttcagcttg | ccgttgatct | ggtcgatggc | 900 |
| ggcctgtgta | gacttcagat | cggcggcctg | tcctgtgccc | tcagaattct | ggtgtctgaa | 960 |
| gccgtaccac | ccatcgatca | tgccctccca | gccgttctcg | ataaagccgg | caatggcgcc | 1020 |
| aaacaggcct | cttgtctgct | tctcgggcac | atttctcatg | ccggtggcca | gcttcagggt | 1080 |
| gttctgcttc | acgtacttag | ggcaggcgcc | gtaggtgatc | ttgttcacgt | tctgaaggg | 1140 |
| cttgtcgttg | gggatgctgc | cgttgggggt | gatgcactcg | ctgatacagg | tatcgatggg | 1200 |
| ggcgtcgctt | tcatgatgc | tgctcttgcc | ggtccgcatc | ttgaagtagc | ctctggggc | 1260 |
| gatcaggttg | ccattgctgt | tgatcaccag | cacgtcgcca | ggtttcacga | tggtccagta | 1320 |
| gatgctgatt | ctgctgctca | ggccgcgcac | ccaaggtctt | gactcgatgt | tgggatgat | 1380 |
| ggtctgctgg | gaccgtctgg | tagacacggt | cactctgccg | ctggcctgca | cgtacaggct | 1440 |
| ggtctgttcc | tgattggtgc | tagggtggtg | cacgccccag | atgtacagct | tgtcgaagtt | 1500 |
| gtcgttgttg | ggcatggtca | cgttcagcac | agggtaggtg | ctgccggact | tggtcagcca | 1560 |
| gttcagtctg | ctgaagaagc | cgctgccagg | gcctctttta | caggcattgc | tgccgccatt | 1620 |
| ctgggtcacg | cctgtccagg | taaagccctc | ggtgatgaat | tccagtgtgc | cgctgctggc | 1680 |
| caccaggctt | ctcagagagg | cgtaatcggg | cacatcgtag | gggtagcagt | tgctgaaggc | 1740 |
| cttgcttctc | tccacgaaca | ggtcccatgt | ctcgttctgg | aacacgtcgc | agtgaggatc | 1800 |
| gcccagcagg | gcatcgatca | gggtacagtc | gatgccatcc | aggattctgt | ggggggttgtt | 1860 |
| gcagatcttg | ccggtgctgc | tgctctgcac | cagctcggtg | gcattggtca | cttcgatctg | 1920 |

```
gtcgtcggta atggttttca ccagggtgcc attaggcacg gcgtggtgtc ccagacacag    1980
ggtggcggtg ctattatcat tgccgggcag atcctggccc agagccagac aaaagatgta    2040
gctcagggca atgatggttt tcat                                           2064
```

<210> SEQ ID NO 52
<211> LENGTH: 2064
<212> TYPE: DNA
<213> ORGANISM: Artificial Sequence
<220> FEATURE:
<223> OTHER INFORMATION: Synthetic

<400> SEQUENCE: 52

```
atgaaaacca tcattgccct gagctacatc ctgtgcctgg tgttcacaca gaagctgccc      60
ggcaacgata tagcaccgc cacactgtgt ctgggacacc acgccgtgcc taatggcacc      120
atcgtgaaaa caatcaccaa cgaccagatc gaagtgacca atgccacaga gctggtgcag      180
agcagcagca caggcgagat ctgtgacagc ccccaccaga tcctggatgg cgagaactgt      240
accctgatcg atgccctgct gggcgatcct cagtgcgacg gcttccagaa caagaaatgg      300
gacctgttcg tggagagaag caaggcctac agcaactgct accccctacga cgtgcctgat      360 tacgccagcc tgagaagcct ggtggcctct agcggcaccc tggaattcaa caacgagagc      420
ttcaactgga ccggcgtgac acagaatggc accagcagcg cctgcatcag acggtccaac      480
aacagcttct tcagtagact gaattggctg acccacctga gttcaagta ccccgccctg      540 aacgtgacca tgcccaacaa tgagaagttc gacaagctgt acatctgggg agtgcaccac      600
cctggcaccg acaacgatca gatcttccct tacgcccagg ccagcggcag aatcaccgtg      660
tccaccaaga aagccagca gaccgtgatc cccaatatcg gcagcagacc cagagtgcgg      720
aacatcccca gcaggatcag catctactgg acaatcgtga agcctggcga catcctgctg      780
atcaacagca ccggcaacct gatcgcccct cggggctact ttaagatcag aagcggcaag      840
agcagcatca tgagatccga cgcccccatc ggcaagtgca cagcgagtg catcaccccca      900 aacggcagca tccccaacga caagcccttc cagaacgtga caggatcac ctacggcgcc      960 tgccctagat acgtgaagca gaacaccctg aagctggcca ccggcatgag aaatgtgccc     1020
gagaagcaga ccagaggcat cttttggcgc attgccggct ttatcgagaa tggctgggag     1080
ggaatggtgg atgggtggta cggcttcaga caccagaata gcgagggaat tggacaggcc     1140
gccgatctga aatctacca ggccgccatc gaccagatca cggcaagct gaacaggctg     1200 atcggcaaga ccaacgagaa gttccaccag atcgagaaag aattcagcga ggtggagggc     1260
agaatccagg acctggaaaa atacgtggag gacaccaaga tcgacctgtg gagctacaat     1320
gccgaactgc tggtcgccct ggaaaaccag cacacaattg atctgacaga cagtgagatg     1380
aataagctgt tcgagaaaac caagaagcag ctgagagaaa acgccgagga catgggcaac     1440
ggctgcttca gatctacca agtgcgac aacgcctgca tcggcagcat cagaaacggc     1500
acctacgacc acgacgtgta cagagatgag gccctgaaca accggtttca gatcaagtcc     1560
ggaggcgaca tcatcaagct gctgaacgag caggtgaaca aggagatgca gagcagcaac     1620
ctgtacatga gcatgagcag ctggtgctac acccacagcc tggacggcgc cggcctgttc     1680
ctgttcgacc acgccgccga ggagtacgag cacgccaaga gctgatcat cttcctgaac     1740 gagaacaacg tgcccgtgca gctgaccagc atcagcgccc ccgagcacaa gttcgagggc     1800
ctgacccaga tcttccagaa ggcctacgag cacgagcagc acatcagcga gagcatcaac     1860
```

-continued

```
aacatcgtgg accacgccat caagagcaag gaccacgcca ccttcaactt cctgcagtgg    1920
tacgtggccg agcagcacga ggaggaggtg ctgttcaagg acatcctgga caagatcgag    1980
ctgatcggca acgagaacca cggcctgtac ctggccgacc agtacgtgaa gggcatcgcc    2040
aagagcagga agagcggatc ctag                                          2064
```

<210> SEQ ID NO 53  
<211> LENGTH: 687  
<212> TYPE: PRT  
<213> ORGANISM: Artificial Sequence  
<220> FEATURE:  
<223> OTHER INFORMATION: Synthetic

<400> SEQUENCE: 53

```
Met Lys Thr Ile Ile Ala Leu Ser Tyr Ile Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
```

```
            325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Ile Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
            405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
    450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
            485                 490                 495
Ile Arg Asn Gly Thr Tyr Asp His Asp Val Tyr Arg Asp Glu Ala Leu
            500                 505                 510
Asn Asn Arg Phe Gln Ile Lys Ser Gly Gly Asp Ile Ile Lys Leu Leu
    515                 520                 525
Asn Glu Gln Val Asn Lys Glu Met Gln Ser Ser Asn Leu Tyr Met Ser
    530                 535                 540
Met Ser Ser Trp Cys Tyr Thr His Ser Leu Asp Gly Ala Gly Leu Phe
545                 550                 555                 560
Leu Phe Asp His Ala Ala Glu Glu Tyr Glu His Ala Lys Lys Leu Ile
            565                 570                 575
Ile Phe Leu Asn Glu Asn Asn Val Pro Val Gln Leu Thr Ser Ile Ser
            580                 585                 590
Ala Pro Glu His Lys Phe Glu Gly Leu Thr Gln Ile Phe Gln Lys Ala
            595                 600                 605
Tyr Glu His Glu Gln His Ile Ser Glu Ser Ile Asn Asn Ile Val Asp
    610                 615                 620
His Ala Ile Lys Ser Lys Asp His Ala Thr Phe Asn Phe Leu Gln Trp
625                 630                 635                 640
Tyr Val Ala Glu Gln His Glu Glu Val Leu Phe Lys Asp Ile Leu
            645                 650                 655
Asp Lys Ile Glu Leu Ile Gly Asn Glu Asn His Gly Leu Tyr Leu Ala
            660                 665                 670
Asp Gln Tyr Val Lys Gly Ile Ala Lys Ser Arg Lys Ser Gly Ser
    675                 680                 685

<210> SEQ ID NO 54
<211> LENGTH: 2064
<212> TYPE: DNA
<213> ORGANISM: Artificial Sequence
<220> FEATURE:
<223> OTHER INFORMATION: Synthetic

<400> SEQUENCE: 54
ctaggatccg ctcttcctgc tcttggcgat gcccttcacg tactggtcgg ccaggtacag      60
```

```
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcgggggcgc tgatgctggt    300
cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggactt gatctgaaac cggttgttca gggcctcatc    540
tctgtacacg tcgtggtcgt aggtgccgtt tctgatgctg ccgatgcagg cgttgtcgca    600
cttgtggtag atcttgaagc agccgttgcc catgtcctcg gcgttttctc tcagctgctt    660
cttggttttc tcgaacagct tattcatctc actgtctgtc agatcaattg tgtgctggtt    720
ttccagggcg accagcagtt cggcattgta gctccacagg tcgatcttgg tgtcctccac    780 gtattttttcc aggtcctgga ttctgccctc cacctcgctg aattctttct cgatctggtg    840
gaacttctcg ttggtcttgc cgatcagcct gttcagcttg ccgttgatct ggtcgatggc    900
ggcctgggta gatttcagat cggcggcctg tccaattccc tcgctattct ggtgtctgaa    960
gccgtaccac ccatccacca ttccctccca gccattctcg ataaagccgg caatggcgcc   1020
aaagatgcct ctggtctgct ctcgggcac atttctcatg ccggtggcca gcttcagggt   1080
gttctgcttc acgtatctag ggcaggcgcc gtaggtgatc ctgttcacgt tctggaaggg   1140
cttgtcgttg gggatgctgc cgtttggggt gatgcactcg ctgttgcact gccgatggg    1200 ggcgtcggat ctcatgatgc tgctcttgcc gcttctgatc ttaaagtagc cccgaggggc   1260
gatcaggttg ccggtgctgt tgatcagcag gatgtcgcca ggcttcacga ttgtccagta   1320
gatgctgatc ctgctgggga tgttccgcac tctgggtctg ctgccgatat tggggatcac   1380
ggtctgctgg cttctcttgg tggacacggt gattctgccg ctggcctggg cgtaagggaa   1440
gatctgatcg ttgtcggtgc cagggtggtg cactccccag atgtacagct tgtcgaactt   1500
ctcattgttg ggcatggtca cgttcagggc ggggtacttg aacttcaggt gggtcagcca   1560
attcagtcta ctgaagaagc tgttgttgga ccgtctgatg caggcgctgc tggtgccatt   1620
ctgtgtcacg ccggtccagt tgaagctctc gttgttgaat tccagggtgc cgctagaggc   1680
caccaggctt ctcaggctgg cgtaatcagg cacgtcgtag gggtagcagt tgctgtaggc   1740
cttgcttctc tccacgaaca ggtcccattt cttgttctgg aagccgtcgc actgaggatc   1800
gcccagcagg gcatcgatca gggtacagtt ctcgccatcc aggatctggt ggggggctgtc   1860 acagatctcg cctgtgctgc tgctctgcac cagctctgtg gcattggtca cttcgatctg   1920
gtcgttggtg attgttttca cgatggtgcc attaggcacg gcgtggtgtc ccagacacag   1980
tgtggcggtg ctattatcgt tgccgggcag cttctgtgtg aacaccaggc acaggatgta   2040
gctcagggca atgatggttt tcat                                           2064
```

<210> SEQ ID NO 55
<211> LENGTH: 2067
<212> TYPE: DNA
<213> ORGANISM: Artificial Sequence
<220> FEATURE:
<223> OTHER INFORMATION: Synthetic

<400> SEQUENCE: 55

```
atggaaaaga tcgtgctgct gctggccatt gtgagcctgg tgaagagcga ccagatctgc    60
attggctacc acgccaacaa tagcacagag caggtggaca ccatcatgga aaaaaacgtg   120
accgtgaccc acgctcagga catcctggaa aagacccaca acggcaagct gtgtgatctg   180
gacggcgtga agcctctgat cctgagagat tgtagcgtgg ctggatggct gctgggcaac   240
cctatgtgcg acgagttcat caacgtgccc gagtggagct atatcgtgga aaggccaac   300
cccaccaacg atctgtgtta ccccggcagc ttcaacgatt acgaggaact gaagcacctg   360
ctgtcccgga tcaaccactt cgagaagatc cagatcatcc ccaagtcctc ttggagcgat   420
cacgaagcct ctagcggagt gtctagcgcc tgtccttacc tgggcagccc cagcttcttc   480
agaaacgtgg tgtggctgat caagaagaac agcacctacc ccaccatcaa gaagagctac   540
aacaacacca accaggaaga tctgctggtc ctgtggggaa tccaccaccc taatgatgcc   600
gccgagcaga ccagactgta ccagaacccc accacctata tcagcatcgg caccagcacc   660
ctgaatcaga gactggtgcc caagatcgcc accagatcca aggtgaacgg ccagagcggc   720
aggatggaat tcttctggac catcctgaag cccaacgacg ccatcaactt cgagagcaac   780
ggcaacttta tcgcccctga gtacgcctac aagatcgtga agaagggcga cagcgccatc   840
atgaagagcg agctggaata cggcaactgc aacaccaagt gccagacacc tatgggcgcc   900
atcaacagca gcatgccctt ccacaacatc cacctctga ccatcggcga gtgccctaag   960
tacgtgaaga gcaacagact ggtgctggcc acaggcctga aaatagccc ccagcggag  1020
agcagaagaa agaagagggg cctgtttgga gccatcgccg gctttattga aggcggctgg  1080
cagggaatgg tggatggctg gtacggctac caccacagca atgagcaggg ctctggatat  1140
gccgccgaca aagagtctac ccagaaggcc atcgacggcg tcaccaacaa ggtgaacagc  1200
atcatcgaca agatgaacac ccagttcgag gctgtgggca gagagttcaa caacctggaa  1260
cggcggatcg agaacctgaa caagaaaatg gaagatggct tcctggatgt gtggacctac  1320
aatgccgaac tgctggtgct gatggaaaac gagcggaccc tggacttcca cgacagcaac  1380
gtgaagaacc tgtacgacaa agtgcggctg cagctgagag acaacgccaa agagctgggc  1440
aacggctgct tcgagttcta ccacaagtgc gacaacgagt gcatggaaag catcaggaac  1500
ggcacctaca actacccctca gtacagcgag gaagccaggc tgaagaggga agagatcagc  1560
tccggaggcg acatcatcaa gctgctgaac gagcaggtga caaggagat gcagagcagc  1620
aacctgtaca tgagcatgag cagctggtgc tacacccaca gcctggacgg cgccggcctg  1680
ttcctgttcg accacgccgc cgaggagtac gagcacgcca gaagctgat catcttcctg  1740
aacgagaaca acgtgcccgt gcagctgacc agcatcagcg ccccgagca aagttcgag  1800
ggcctgaccc agatcttcca gaaggcctac gagcacgagc agcacatcag cgagagcatc  1860
aacaacatcg tggaccacgc catcaagagc aaggaccacg ccaccttcaa cttcctgcag  1920
tggtacgtgg ccgagcagca cgaggaggag gtgctgttca aggacatcct ggacaagatc  1980
gagctgatcg caacgagaa ccacggcctg tacctggccg accagtacgt gaagggcatc  2040
gccaagagca ggaagagcgg atcctag                                     2067
```

<210> SEQ ID NO 56
<211> LENGTH: 688
<212> TYPE: PRT
<213> ORGANISM: Artificial Sequence
<220> FEATURE:
<223> OTHER INFORMATION: Synthetic

<400> SEQUENCE: 56

-continued

```
Met Glu Lys Ile Val Leu Leu Ala Ile Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415
```

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Ser Gly Gly Asp Ile Ile Lys Leu
        515                 520                 525

Leu Asn Glu Gln Val Asn Lys Glu Met Gln Ser Ser Asn Leu Tyr Met
    530                 535                 540

Ser Met Ser Ser Trp Cys Tyr Thr His Ser Leu Asp Gly Ala Gly Leu
545                 550                 555                 560

Phe Leu Phe Asp His Ala Ala Glu Glu Tyr Glu His Ala Lys Lys Leu
                565                 570                 575

Ile Ile Phe Leu Asn Glu Asn Asn Val Pro Val Gln Leu Thr Ser Ile
            580                 585                 590

Ser Ala Pro Glu His Lys Phe Glu Gly Leu Thr Gln Ile Phe Gln Lys
        595                 600                 605

Ala Tyr Glu His Glu Gln His Ile Ser Glu Ser Ile Asn Asn Ile Val
    610                 615                 620

Asp His Ala Ile Lys Ser Lys Asp His Ala Thr Phe Asn Phe Leu Gln
625                 630                 635                 640

Trp Tyr Val Ala Glu Gln His Glu Glu Val Leu Phe Lys Asp Ile
                645                 650                 655

Leu Asp Lys Ile Glu Leu Ile Gly Asn Glu Asn His Gly Leu Tyr Leu
            660                 665                 670

Ala Asp Gln Tyr Val Lys Gly Ile Ala Lys Ser Arg Lys Ser Gly Ser
        675                 680                 685

<210> SEQ ID NO 57
<211> LENGTH: 2067
<212> TYPE: DNA
<213> ORGANISM: Artificial Sequence
<220> FEATURE:
<223> OTHER INFORMATION: Synthetic

<400> SEQUENCE: 57
ctaggatccg ctcttcctgc tcttggcgat gcccttcacg tactggtcgg ccaggtacag     60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggggcgc tgatgctggt    300 cagctgcacg gcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggagct gatctcttcc ctcttcagcc tggcttcctc    540

| | |
|---|---|
| gctgtactga gggtagttgt aggtgccgtt cctgatgctt tccatgcact cgttgtcgca | 600 |
| cttgtggtag aactcgaagc agccgttgcc cagctctttg gcgttgtctc tcagctgcag | 660 |
| ccgcactttg tcgtacaggt tcttcacgtt gctgtcgtgg aagtccaggg tccgctcgtt | 720 |
| ttccatcagc accagcagtt cggcattgta ggtccacaca tccaggaagc catcttccat | 780 |
| tttcttgttc aggttctcga tccgccgttc caggttgttg aactctctgc ccacagcctc | 840 |
| gaactgggtg ttcatcttgt cgatgatgct gttcaccttg ttggtgacgc cgtcgatggc | 900 |
| cttctgggta gactctttgt cggcggcata tccagagccc tgctcattgc tgtggtggta | 960 |
| gccgtaccag ccatccacca ttccctgcca gccgccttca ataaagccgg cgatggctcc | 1020 |
| aaacaggccc ctcttctttc ttctgctctc ccgctggggg ctatttctca ggcctgtggc | 1080 |
| cagcaccagt ctgttgctct tcacgtactt agggcactcg ccgatggtca gagggtggat | 1140 |
| gttgtggaag ggcatgctgc tgttgatggc gcccataggt gtctggcact tggtgttgca | 1200 |
| gttgccgtat tccagctcgc tcttcatgat ggcgctgtcg ccttcttca cgatcttgta | 1260 |
| ggcgtactca ggggcgataa agttgccgtt gctctcgaag ttgatggcgt cgttgggctt | 1320 |
| caggatggtc cagaagaatt ccatcctgcc gctctggccg ttcaccttgg atctggtggc | 1380 |
| gatcttgggc accagtctct gattcagggt gctggtgccg atgctgatat aggtggtggg | 1440 |
| gttctggtac agtctggtct gctcggcggc atcattaggg tggtggattc cccacaggac | 1500 |
| cagcagatct tcctggttgg tgttgttgta gctcttcttg atggtggggt aggtgctgtt | 1560 |
| cttcttgatc agccacacca cgtttctgaa gaagctgggg ctgcccaggt aaggacaggc | 1620 |
| gctagacact ccgctagagg cttcgtgatc gctccaagag gcttggggga tgatctggat | 1680 |
| cttctcgaag tggttgatcc gggacagcag gtgcttcagt tcctcgtaat cgttgaagct | 1740 |
| gccggggtaa cacagatcgt tggtggggtt ggccttctcc acgatatagc tccactcggg | 1800 |
| cacgttgatg aactcgtcgc catagggtt gcccagcagc catccagcca cgctacaatc | 1860 |
| tctcaggatc agaggcttca cgccgttcag atcacacagc ttgccgttgt gggtcttttc | 1920 |
| caggatgtcc tgagcgtggg tcacggtcac gttttttttcc atgatggtgt ccacctgctc | 1980 |
| tgtgctattg ttggcgtggt agccaatgca gatctggtcg ctcttcacca ggctcacaat | 2040 |
| ggccagcagc agcacgatct tttccat | 2067 |

<210> SEQ ID NO 58
<211> LENGTH: 2109
<212> TYPE: DNA
<213> ORGANISM: Artificial Sequence
<220> FEATURE:
<223> OTHER INFORMATION: Synthetic

<400> SEQUENCE: 58

| | |
|---|---|
| atgaaggcca tcatcgtgct gctgatggtg gtgaccagca acgccgatag aatctgcacc | 60 |
| ggcatcacca gcagcaatag ccccccatgtg gtgaaaacag ccaccagggg cgaagtgaat | 120 |
| gtgacaggcg tgatccctct gaccaccacc cccaccaaga gctacttcgc caacctgaag | 180 |
| ggcaccagaa ccagaggcaa gctgtgcccc gattgcctga actgcaccga tctggatgtg | 240 |
| gctctgggca gacctatgtg tgtgggcacc acaccatctg ccaaggccag catcctgcac | 300 |
| gaagtgaagc ctgtgaccag cggctgcttc cccatcatgc acgaccggac caagatcaga | 360 |
| cagctgccca acctgctgag aggctacgag aacatccggc tgtccaccca gaatgtgatc | 420 |
| gatgccgaga agcccctgg cggaccttat agactgggca ccagcggctc ttgtcccaat | 480 |
| gccacctcca agagcggctt ttttgccaca atggcctggg ccgtgcctaa ggacaacaac | 540 |

```
aagaacgcca ccaaccctct gaccgtggag gtgccctaca tctgtacaga gggcgaggat    600
cagatcacag tgtggggctt ccacagcgac gacaagaccc agatgaagaa cctgtacggc    660
gacagcaacc cccagaagtt taccagcagc gccaatggcg tgaccaccca ctacgtgtcc    720
cagatcggca gctttcccga tcagacagag gatggcggac tgcctcagtc tggcaggatc    780
gtggtggact acatgatgca gaagcctggc aagaccggca ccatcgtgta tcagagaggc    840
gtgctgctgc ctcagaaagt gtggtgtgcc agcggcaggt ctaaagtgat caagggcagc    900
ctgcctctga ttggcgaggc cgactgtctg cacgaaaagt acggcggcct gaacaagagc    960
aagccctact acacaggcga gcacgccaag gccatcggca ttgccccat ctgggtgaaa    1020 accccccctga agctggccaa tggcaccaag tacagacctc ccgccaagct gctgaaagag    1080
agaggcttct ttggcgccat tgccggattt ctggaaggcg gctgggaggg aatgattgcc    1140
ggctggcacg gctatacatc tcatggggcc catggcgtgg ctgtggccgc cgatctgaag    1200
tctacccagg aagccatcaa caagatcacc aagaacctga cagcctgag cgagctggaa    1260 gtgaagaatc tgcagagact gagcggcgcc atggatgagc tgcacaacga tcctggaa    1320 ctggacgaga agtggatga tctccgcgcc gatacaattt cctcccagat tgaactggcc    1380
gtgctgctgt ccaacgaggg catcatcaac agcgaggatg aacacctgct ggccctggaa    1440
cggaagctga agaagatgct gggcccttct gccgtggaga tcggcaacgg ctgcttcgag    1500
acaaagcaca agtgcaacca gacctgcctg gatagaatcg ccgctggcac cttcaatgcc    1560
ggcgagttca gcctgcctac cttcgacagc ctgaatatca cctccggagg cgacatcatc    1620
aagctgctga acgagcaggt gaacaaggag atgcagagca gcaacctgta catgagcatg    1680
agcagctggt gctacaccca cagcctggac ggcgccggcc tgttcctgtt cgaccacgcc    1740
gccgaggagt acgagcacgc caagaagctg atcatcttcc tgaacgagaa caacgtgccc    1800
gtgcagctga ccagcatcag cgcccccgag cacaagttcg agggcctgac ccagatcttc    1860
cagaaggcct acgagcacga gcagcacatc agcgagagca tcaacaacat cgtggaccac    1920
gccatcaaga gcaaggacca cgccaccttc aacttcctgc agtggtacgt ggccgagcag    1980
cacgaggagg aggtgctgtt caaggacatc ctggacaaga tcgagctgat cggcaacgag    2040
aaccacggcc tgtacctggc cgaccagtac gtgaagggca tcgccaagag caggaagagc    2100
ggatcctag                                                            2109
```

<210> SEQ ID NO 59
<211> LENGTH: 702
<212> TYPE: PRT
<213> ORGANISM: Artificial Sequence
<220> FEATURE:
<223> OTHER INFORMATION: Synthetic

<400> SEQUENCE: 59

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

```
Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495
```

```
Gly Cys Phe Glu Thr Lys His Lys Cys Asn Gln Thr Cys Leu Asp Arg
            500                 505                 510
Ile Ala Ala Gly Thr Phe Asn Ala Gly Glu Phe Ser Leu Pro Thr Phe
        515                 520                 525
Asp Ser Leu Asn Ile Thr Ser Gly Asp Ile Ile Lys Leu Leu Asn
    530                 535                 540
Glu Gln Val Asn Lys Glu Met Gln Ser Ser Asn Leu Tyr Met Ser Met
545                 550                 555                 560
Ser Ser Trp Cys Tyr Thr His Ser Leu Asp Gly Ala Gly Leu Phe Leu
                565                 570                 575
Phe Asp His Ala Ala Glu Glu Tyr Glu His Ala Lys Lys Leu Ile Ile
            580                 585                 590
Phe Leu Asn Glu Asn Asn Val Pro Val Gln Leu Thr Ser Ile Ser Ala
        595                 600                 605
Pro Glu His Lys Phe Glu Gly Leu Thr Gln Ile Phe Gln Lys Ala Tyr
    610                 615                 620
Glu His Glu Gln His Ile Ser Glu Ser Ile Asn Asn Ile Val Asp His
625                 630                 635                 640
Ala Ile Lys Ser Lys Asp His Ala Thr Phe Asn Phe Leu Gln Trp Tyr
                645                 650                 655
Val Ala Glu Gln His Glu Glu Val Leu Phe Lys Asp Ile Leu Asp
            660                 665                 670
Lys Ile Glu Leu Ile Gly Asn Glu Asn His Gly Leu Tyr Leu Ala Asp
        675                 680                 685
Gln Tyr Val Lys Gly Ile Ala Lys Ser Arg Lys Ser Gly Ser
    690                 695                 700

<210> SEQ ID NO 60
<211> LENGTH: 2109
<212> TYPE: DNA
<213> ORGANISM: Artificial Sequence
<220> FEATURE:
<223> OTHER INFORMATION: Synthetic

<400> SEQUENCE: 60
ctaggatccg ctcttcctgc tcttggcgat gcccttcacg tactggtcgg ccaggtacag     60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggcgc tgatgctggt    300
cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggaggt gatattcagg ctgtcgaagg taggcaggct    540
gaactcgccg gcattgaagg tgccagcggc gattctatcc aggcaggtct ggttgcactt    600
gtgctttgtc tcgaagcagc cgttgccgat ctccacggca aagggcccca gcatcttctt    660
cagcttccgt tccagggcca gcaggtgttc atcctcgctg ttgatgatgc cctcgttgga    720
cagcagcacg gccagttcaa tctgggagga aattgtatcg gcgcggagat catccacttt    780
ctcgtccagt tccaggatct cgttgtgcag ctcatccatg gcgccgctca gtctctgcag    840
attcttcact tccagctcgc tcaggctgtt caggttcttg gtgatcttgt tgatggcttc    900
```

| | |
|---|---|
| ctgggtagac ttcagatcgg cggccacagc cacgccatgg gccccatgag atgtatagcc | 960 |
| gtgccagccg gcaatcattc cctcccagcc gccttccaga aatccggcaa tggcgccaaa | 1020 |
| gaagcctctc tctttcagca gcttggcggg aggtctgtac ttggtgccat tggccagctt | 1080 |
| cagggggtt ttcacccaga tggggcaatt gccgatggcc ttggcgtgct cgcctgtgta | 1140 |
| gtagggcttg ctcttgttca ggccgccgta cttttcgtgc agacagtcgg cctcgccaat | 1200 |
| cagaggcagg ctgcccttga tcactttaga cctgccgctg gcacaccaca ctttctgagg | 1260 |
| cagcagcacg cctctctgat acacgatggt gccggtcttg ccaggcttct gcatcatgta | 1320 |
| gtccaccacg atcctgccag actgaggcag tccgccatcc tctgtctgat cgggaaagct | 1380 |
| gccgatctgg gacacgtagt gggtggtcac gccattggcg ctgctggtaa acttctgggg | 1440 |
| gttgctgtcg ccgtacaggt tcttcatctg ggtcttgtcg tcgctgtgga agccccacac | 1500 |
| tgtgatctga tcctcgccct ctgtacagat gtagggcacc tccacggtca gagggttggt | 1560 |
| ggcgttcttg ttgttgtcct taggcacggc ccaggccatt gtggcaaaaa agccgctctt | 1620 |
| ggaggtggca ttgggacaag agccgctggt gcccagtcta taaggtccgc caggggcttt | 1680 |
| ctcggcatcg atcacattct gggtggacag ccggatgttc tcgtagcctc tcagcaggtt | 1740 |
| gggcagctgt ctgatcttgg tccggtcgtg catgatgggg aagcagccgc tggtcacagg | 1800 |
| cttcacttcg tgcaggatgc tggccttggc agatggtgtg gtgcccacac acataggtct | 1860 |
| gcccagagcc acatccagat cggtgcagtt caggcaatcg gggcacagct tgcctctggt | 1920 |
| tctggtgccc ttcaggttgg cgaagtagct cttggtgggg gtggtggtca gagggatcac | 1980 |
| gcctgtcaca ttcacttcgc cctgggtggc tgttttcacc acatgggggc tattgctgct | 2040 |
| ggtgatgccg gtgcagattc tatcggcgtt gctggtcacc accatcagca gcacgatgat | 2100 |
| ggccttcat | 2109 |

<210> SEQ ID NO 61
<211> LENGTH: 2064
<212> TYPE: DNA
<213> ORGANISM: Artificial Sequence
<220> FEATURE:
<223> OTHER INFORMATION: Synthetic

<400> SEQUENCE: 61

| | |
|---|---|
| atgaaaacca taattgcgct gtcctacata ctgtgtctgg tgtttgccca gaaactgccg | 60 |
| ggcaatgaca actcaacagc cacgctctgc ttggggcacc atgccgtccc taacgggacc | 120 |
| attgtgaaaa ccattactaa cgatcagata gaggtgacta atgccaccga gctggtgcaa | 180 |
| agtagctcca caggagagat ctgcgatagt ccccaccaga ttctggacgg aaagaattgt | 240 |
| acgctgatcg acgcgctgtt gggcgaccct cagtgtgacg gatttcagaa taagaagtgg | 300 |
| gatctgtttg tggaaaggtc aaaggcttat tcaaattgct acccttacga tgtgcctgat | 360 |
| tatgccagcc tgcggtccct cgtcgcgtct agtgggactc tggagttcaa caacgagtca | 420 |
| tttaactgga ctggcgttac acagaacggg actagttccg cttgcataag gagaagcaaa | 480 |
| aatagtttct tcagcagact gaattggctg acacatctga acttcaagta ccctgcactg | 540 |
| aatgtaacca tgcccaacaa cgagcagttc gataagcttt acatttgggg agttcatcat | 600 |
| cctggcactg acaaggatca gatctttctg tatgcccagg cttccggcag gattaccgtg | 660 |
| tctacaaaga gaagccagca aactgtgtct cccaatatcg gcagtagacc cagagtacgg | 720 |
| aacatcccta gtcgcatcag tatttactgg accatcgtga aaccaggcga tattctcctg | 780 |
| attaacagta ctggcaacct gatcgccccc cggggatact ttaaaatccg ctctggaaag | 840 |

```
tcctccatta tgagatcaga tgcaccgatc ggaaaatgca actctgagtg tatcacaccc      900
aatgggagca ttcccaatga caaacctttc cagaacgtta atcgaataac ttatggggcc      960
tgtccacggt acgtgaagca aaataccttg aaactggcga ccggtatgcg caatgtcccc     1020
gaaaaacaga cccgcgggat atttggggct atcgcaggct ttatcgagaa tggctgggaa     1080
gggatggtgg atggttggta tggttttaga catcaaaact ccgaaggcag aggccaggct     1140
gccgatctca agagcacgca ggccgctata gatcagatca atggaaagct caacagactg     1200
atcgggaaaa ccaacgaaaa attccatcag atcgagaaag agttctccga agtcgagggg     1260
cgcatacagg acctggagaa gtatgttgag gatacaaaga ttgatctgtg gtcctacaat     1320
gccgagctgc tggtggctct ggagaatcag cacactattg acctgaccga ttcagagatg     1380
aacaaacttt ttgagaagac gaagaagcag cttagagaaa atgcagagga catggggaac     1440
ggatgcttta aaatatatca taagtgtgat aatgcctgca tcggatcaat tagaaatggt     1500
acctatgatc acgatgttta cagggacgaa gcgctgaata acaggttcca gataaaatcc     1560
ggaggcgaca tcatcaagct gctgaacgag caggtgaaca aggagatgca gagcagcaac     1620
ctgtacatga gcatgagcag ctggtgctac acccacagcc tggacggcgc cggcctgttc     1680
ctgttcgacc acgccgccga ggagtacgag cacgccaaga agctgatcat cttcctgaac     1740
gagaacaacg tgcccgtgca gctgaccagc atcagcgccc ccgagcacaa gttcgagggc     1800
ctgacccaga tcttccagaa ggcctacgag cacgagcagc acatcagcga gagcatcaac     1860
aacatcgtgg accacgccat caagagcaag gaccacgcca ccttcaactt cctgcagtgg     1920
tacgtggccg agcagcacga ggaggaggtg ctgttcaagg acatcctgga caagatcgag     1980
ctgatcggca cgagaaccg cggcctgtac ctggccgacc agtacgtgaa gggcatcgcc     2040
aagagcagga gagcggatc ctag                                             2064
```

<210> SEQ ID NO 62
<211> LENGTH: 687
<212> TYPE: PRT
<213> ORGANISM: Artificial Sequence
<220> FEATURE:
<223> OTHER INFORMATION: Synthetic

<400> SEQUENCE: 62

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140
```

```
Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Ser Gly Gly Asp Ile Ile Lys Leu Leu
        515                 520                 525

Asn Glu Gln Val Asn Lys Glu Met Gln Ser Ser Asn Leu Tyr Met Ser
    530                 535                 540

Met Ser Ser Trp Cys Tyr Thr His Ser Leu Asp Gly Ala Gly Leu Phe
545                 550                 555                 560
```

```
Leu Phe Asp His Ala Ala Glu Glu Tyr Glu His Ala Lys Lys Leu Ile
                565                 570                 575

Ile Phe Leu Asn Glu Asn Asn Val Pro Val Gln Leu Thr Ser Ile Ser
            580                 585                 590

Ala Pro Glu His Lys Phe Glu Gly Leu Thr Gln Ile Phe Gln Lys Ala
        595                 600                 605

Tyr Glu His Glu Gln His Ile Ser Glu Ser Ile Asn Asn Ile Val Asp
    610                 615                 620

His Ala Ile Lys Ser Lys Asp His Ala Thr Phe Asn Phe Leu Gln Trp
625                 630                 635                 640

Tyr Val Ala Glu Gln His Glu Glu Val Leu Phe Lys Asp Ile Leu
                645                 650                 655

Asp Lys Ile Glu Leu Ile Gly Asn Glu Asn His Gly Leu Tyr Leu Ala
            660                 665                 670

Asp Gln Tyr Val Lys Gly Ile Ala Lys Ser Arg Lys Ser Gly Ser
        675                 680                 685
```

<210> SEQ ID NO 63
<211> LENGTH: 2064
<212> TYPE: DNA
<213> ORGANISM: Artificial Sequence
<220> FEATURE:
<223> OTHER INFORMATION: Synthetic

<400> SEQUENCE: 63

| | | | | | | |
|---|---|---|---|---|---|---|
| ctaggatccg | ctcttcctgc | tcttggcgat | gcccttcacg | tactggtcgg | ccaggtacag | 60 |
| gccgtggttc | tcgttgccga | tcagctcgat | cttgtccagg | atgtccttga | acagcacctc | 120 |
| ctcctcgtgc | tgctcggcca | cgtaccactg | caggaagttg | aaggtggcgt | ggtccttgct | 180 |
| cttgatggcg | tggtccacga | tgttgttgat | gctctcgctg | atgtgctgct | cgtgctcgta | 240 |
| ggccttctgg | aagatctggg | tcaggccctc | gaacttgtgc | tcggggcgc | tgatgctggt | 300 |
| cagctgcacg | ggcacgttgt | tctcgttcag | gaagatgatc | agcttcttgg | cgtgctcgta | 360 |
| ctcctcggcg | gcgtggtcga | acaggaacag | gccggcgccg | tccaggctgt | gggtgtagca | 420 |
| ccagctgctc | atgctcatgt | acaggttgct | gctctgcatc | tccttgttca | cctgctcgtt | 480 |
| cagcagcttg | atgatgtcgc | tccggatttt | tatctggaac | tgttattca | gcgcttcgtc | 540 |
| cctgtaaaca | tcgtgatcat | aggtaccatt | tctaattgat | ccgatgcagg | cattatcaca | 600 |
| cttatgatat | attttaaagc | atccgttccc | catgtcctct | gcattttctc | taagctgctt | 660 |
| cttcgtcttc | tcaaaaagtt | tgttcatctc | tgaatcggtc | aggtcaatag | tgtgctgatt | 720 |
| ctccagagcc | accagcagct | cggcattgta | ggaccacaga | tcaatctttg | tatcctcaac | 780 |
| atacttctcc | aggtcctgta | tgcgcccctc | gacttcggag | aactctttct | cgatctgatg | 840 |
| gaattttttcg | ttggttttcc | cgatcagtct | gttgagcttt | ccattgatct | gatctatagc | 900 |
| ggcctgcgtg | ctcttgagat | cggcagcctg | gcctctgcct | tcggagtttt | gatgtctaaa | 960 |
| accataccaa | ccatccacca | tcccttccca | gccattctcg | ataaagcctg | cgatagcccc | 1020 |
| aaatatcccg | cgggtctgtt | tttcggggac | attgcgcata | ccggtcgcca | gtttcaaggt | 1080 |
| attttgcttc | acgtaccgtg | gacaggcccc | ataagttatt | cgattaacgt | tctggaaagg | 1140 |
| tttgtcattg | ggaatgctcc | cattgggtgt | gatacactca | gagttgcatt | ttccgatcgg | 1200 |
| tgcatctgat | ctcataatgg | aggactttcc | agagcggatt | ttaaagtatc | cccgggggc | 1260 |
| gatcaggttg | ccagtactgt | taatcaggag | aatatcgcct | ggtttcacga | tggtccagta | 1320 |
| aatactgatg | cgactaggga | tgttccgtac | tctgggtcta | ctgccgatat | tgggagacac | 1380 |

```
agtttgctgg cttctctttg tagacacggt aatcctgccg gaagcctggg catacagaaa      1440
gatctgatcc ttgtcagtgc caggatgatg aactccccaa atgtaaagct tatcgaactg      1500
ctcgttgttg ggcatggtta cattcagtgc agggtacttg aagttcagat gtgtcagcca      1560
attcagtctg ctgaagaaac tattttgct tctccttatg caagcggaac tagtcccgtt       1620
ctgtgtaacg ccagtccagt taaatgactc gttgttgaac tccagagtcc cactagacgc      1680
gacgagggac cgcaggctgg cataatcagg cacatcgtaa gggtagcaat ttgaataagc      1740
ctttgacctt tccacaaaca gatcccactt cttattctga aatccgtcac actgagggtc      1800
gcccaacagc gcgtcgatca gcgtacaatt cttttccgtcc agaatctggt ggggactatc     1860
gcagatctct cctgtggagc tactttgcac cagctcggtg gcattagtca cctctatctg      1920
atcgttagta atggttttca caatggtccc gttaggacg gcatggtgcc ccaagcagag       1980
cgtggctgtt gagttgtcat tgcccggcag tttctgggca aacaccagac acagtatgta     2040
ggacagcgca attatggttt tcat                                             2064
```

<210> SEQ ID NO 64
<211> LENGTH: 2058
<212> TYPE: DNA
<213> ORGANISM: Artificial Sequence
<220> FEATURE:
<223> OTHER INFORMATION: Synthetic

<400> SEQUENCE: 64

```
atgaaagtga agctgctggt gctgctgtgt acctttaccg ccacctacgc cgataccatc       60
tgtatcggct accacgccaa caatagcacc gacaccgtgg ataccgtgct ggaaaagaac      120
gtgaccgtga cccacagcgt gaacctgctg gaaaacagcc acaacggcaa gctgtgtctg      180
ctgaaaggca ttgcccctct gcagctggga aattgtagcg tggccggctg gattctgggc      240
aatcctgagt gcgagctgct gatttccaaa gagtcctggt cctacatcgt ggagaagccc      300
aaccctgaga atggcacctg ctaccctggc cacttcgccg attacgagga actgagagaa      360
cagctgtcca gcgtgtccag cttcgagaga ttcgagatct tccccaaaga gagcagctgg      420
cccaatcata cagtgaccgg cgtgagcgcc tcttgtagcc acaatggcga gagcagcttc      480
tacagaaacc tgctgtggct gaccggcaag aacggcctgt accccaacct gagcaagagc      540
tacgccaaca acaaagaaaa agaagtgctg gtcctctggg gagtgcacca ccctcctaac      600
atcggcatcc agaaggccct gtaccacacc gagaatgcct acgtgtccgt ggtgtccagc      660
cactacagca gaaagttcac ccccgagatc gccaaaagac ccaaagtgcg ggaccaggaa      720
ggcaggatca actactactg gaccctgctg gaacctggcg acaccatcat cttcgaggcc      780
aacggcaatc tgatcgcccc tagatacgcc tttgccctga cagaggcttt ggcagcggc      840 atcatcaaca gcaacgcccc catggacaag tgtgacgcca agtgtcagac accacaggga      900
gctatcaata gcagcctgcc cttccagaat gtgcaccctg tgaccatcgg cgagtgtcct      960
aaatacgtgc ggagcgccaa gctgagaatg gtgaccggcc tgaggaatat ccccagcatc     1020
cagagcagag gcctgtttgg cgccattgcc ggctttatcg agggcggatg gacaggcatg     1080
gtggatgggt ggtacggcta ccaccaccag aatgagcagg gatctggcta tgccgccgat     1140
cagaagagca cccagaacgc catcaacggc atcaccaaca aagtgaacag cgtgatcgag     1200
aagatgaaca cccagttcac cgccgtgggc aaagagttca acaagctgga acggcggatg     1260
gaaaacctga acaagaaggt ggacgacggc ttcatcgaca tctggaccta caacgccgaa     1320
```

```
ctcctggtcc tcctggaaaa tgagaggacc ctggacttcc acgacagcaa cgtgaagaac    1380
ctgtacgaga aagtgaagag ccagctgaag aacaacgcca agagatcgg caacggctgc     1440 ttcgagttct accacaagtg caacgacgag tgcatggaaa gcgtgaagaa cggcacctac    1500
gactacccca gtacagcga ggaaagcaag ctgaaccggg agaagatcga ttccggaggc     1560
gacatcatca agctgctgaa cgagcaggtg aacaaggaga tgcagagcag caacctgtac    1620
atgagcatga gcagctggtg ctacacccac agcctggacg gcgccggcct gttcctgttc    1680
gaccacgccg ccgaggagta cgagcacgcc aagaagctga tcatcttcct gaacgagaac    1740
aacgtgcccg tgcagctgac cagcatcagc gcccccgagc acaagttcga gggcctgacc    1800
cagatcttcc agaaggccta cgagcacgag cagcacatca gcgagagcat caacaacatc    1860
gtggaccacg ccatcaagag caaggaccac gccaccttca acttcctgca gtggtacgtg    1920
gccgagcagc acgaggagga ggtgctgttc aaggacatct ggacaagat cgagctgatc     1980 ggcaacgaga accacggcct gtacctggcc gaccagtacg tgaagggcat cgccaagagc    2040
aggaagagcg gatcctag                                                  2058
```

<210> SEQ ID NO 65
<211> LENGTH: 685
<212> TYPE: PRT
<213> ORGANISM: Artificial Sequence
<220> FEATURE:
<223> OTHER INFORMATION: Synthetic

<400> SEQUENCE: 65

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Ile Gln Lys Ala Leu Tyr
        195                 200                 205

His Thr Glu Asn Ala Tyr Val Ser Val Ser Ser His Tyr Ser Arg
    210                 215                 220

Lys Phe Thr Pro Glu Ile Ala Lys Arg Pro Lys Val Arg Asp Gln Glu
```

-continued

```
             225                 230                 235                 240
     Gly Arg Ile Asn Tyr Tyr Trp Thr Leu Leu Glu Pro Gly Asp Thr Ile
                         245                 250                 255
     Ile Phe Glu Ala Asn Gly Asn Leu Ile Ala Pro Arg Tyr Ala Phe Ala
                         260                 265                 270
     Leu Ser Arg Gly Phe Gly Ser Gly Ile Ile Asn Ser Asn Ala Pro Met
                         275                 280                 285
     Asp Lys Cys Asp Ala Lys Cys Gln Thr Pro Gln Gly Ala Ile Asn Ser
                         290                 295                 300
     Ser Leu Pro Phe Gln Asn Val His Pro Val Thr Ile Gly Glu Cys Pro
     305                 310                 315                 320
     Lys Tyr Val Arg Ser Ala Lys Leu Arg Met Val Thr Gly Leu Arg Asn
                         325                 330                 335
     Ile Pro Ser Ile Gln Ser Arg Gly Leu Phe Gly Ala Ile Ala Gly Phe
                         340                 345                 350
     Ile Glu Gly Gly Trp Thr Gly Met Val Asp Gly Trp Tyr Gly Tyr His
                         355                 360                 365
     His Gln Asn Glu Gln Gly Ser Gly Tyr Ala Ala Asp Gln Lys Ser Thr
                         370                 375                 380
     Gln Asn Ala Ile Asn Gly Ile Thr Asn Lys Val Asn Ser Val Ile Glu
     385                 390                 395                 400
     Lys Met Asn Thr Gln Phe Thr Ala Val Gly Lys Glu Phe Asn Lys Leu
                         405                 410                 415
     Glu Arg Arg Met Glu Asn Leu Asn Lys Lys Val Asp Asp Gly Phe Ile
                         420                 425                 430
     Asp Ile Trp Thr Tyr Asn Ala Glu Leu Leu Val Leu Leu Glu Asn Glu
                         435                 440                 445
     Arg Thr Leu Asp Phe His Asp Ser Asn Val Lys Asn Leu Tyr Glu Lys
                         450                 455                 460
     Val Lys Ser Gln Leu Lys Asn Asn Ala Lys Glu Ile Gly Asn Gly Cys
     465                 470                 475                 480
     Phe Glu Phe Tyr His Lys Cys Asn Asp Glu Cys Met Glu Ser Val Lys
                         485                 490                 495
     Asn Gly Thr Tyr Asp Tyr Pro Lys Tyr Ser Glu Glu Ser Lys Leu Asn
                         500                 505                 510
     Arg Glu Lys Ile Asp Ser Gly Gly Asp Ile Ile Lys Leu Leu Asn Glu
                         515                 520                 525
     Gln Val Asn Lys Glu Met Gln Ser Ser Asn Leu Tyr Met Ser Met Ser
                         530                 535                 540
     Ser Trp Cys Tyr Thr His Ser Leu Asp Gly Ala Gly Leu Phe Leu Phe
     545                 550                 555                 560
     Asp His Ala Ala Glu Glu Tyr Glu His Ala Lys Lys Leu Ile Ile Phe
                         565                 570                 575
     Leu Asn Glu Asn Asn Val Pro Val Gln Leu Thr Ser Ile Ser Ala Pro
                         580                 585                 590
     Glu His Lys Phe Glu Gly Leu Thr Gln Ile Phe Gln Lys Ala Tyr Glu
                         595                 600                 605
     His Glu Gln His Ile Ser Glu Ser Ile Asn Asn Ile Val Asp His Ala
                         610                 615                 620
     Ile Lys Ser Lys Asp His Ala Thr Phe Asn Phe Leu Gln Trp Tyr Val
     625                 630                 635                 640
     Ala Glu Gln His Glu Glu Val Leu Phe Lys Asp Ile Leu Asp Lys
                         645                 650                 655
```

Ile Glu Leu Ile Gly Asn Glu Asn His Gly Leu Tyr Leu Ala Asp Gln
            660                 665                 670

Tyr Val Lys Gly Ile Ala Lys Ser Arg Lys Ser Gly Ser
            675                 680                 685

<210> SEQ ID NO 66
<211> LENGTH: 2058
<212> TYPE: DNA
<213> ORGANISM: Artificial Sequence
<220> FEATURE:
<223> OTHER INFORMATION: Synthetic

<400> SEQUENCE: 66
ctaggatccg ctcttcctgc tcttggcgat gcccttcacg tactggtcgg ccaggtacag      60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggcgc tgatgctggt    300 cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggaatc gatcttctcc cggttcagct tgctttcctc    540
gctgtacttg gggtagtcgt aggtgccgtt cttcacgctt ccatgcact cgtcgttgca    600 cttgtggtag aactcgaagc agccgttgcc gatctctttg gcgttgttct tcagctggct    660
cttcactttc tcgtacaggt tcttcacgtt gctgtcgtgg aagtccaggg tcctctcatt    720
ttccaggagg accaggagtt cggcgttgta ggtccagatg tcgatgaagc cgtcgtccac    780
cttcttgttc aggttttcca tccgccgttc cagcttgttg aactctttgc ccacggcggt    840
gaactgggtg ttcatcttct cgatcacgct gttcactttg ttggtgatgc cgttgatggc    900
gttctgggtg ctcttctgat cggcggcata gccagatccc tgctcattct ggtggtggta    960
gccgtaccac ccatccacca tgcctgtcca tccgccctcg ataaagccgg caatggcgcc   1020
aaacaggcct ctgctctgga tgctggggat attcctcagg ccggtcacca ttctcagctt   1080
ggcgctccgc acgtatttag gacactcgcc gatggtcaca gggtgcacat tctgaagggg   1140
caggctgcta ttgatagctc cctgtggtgt ctgacacttg gcgtcacact tgtccatggg   1200
ggcgttgctg ttgatgatgc cgctgccaaa gcctctgctc agggcaaagg cgtatctagg   1260
ggcgatcaga ttgccgttgg cctcgaagat gatggtgtcg ccaggttcca gcagggtcca   1320
gtagtagttg atcctgcctt cctggtcccg cactttgggt cttttggcga ctcggggggt   1380
gaactttctg ctgtagtggc tggacaccac ggacacgtag gcattctcgg tgtggtacag   1440
ggccttctgg atgccgatgt taggagggtg gtgcactccc cagaggacca gcacttcttt   1500
ttctttgttg ttggcgtagc tcttgctcag gttggggtac aggccgttct gccggtcag   1560 ccacagcagg tttctgtaga agctgctctc gccattgtgg ctacaagagg cgctcacgcc   1620
ggtcactgta tgattgggcc agctgctctc tttggggaag atctcgaatc tctcgaagct   1680
ggacacgctg gacagctgtt ctctcagttc ctcgtaatcg gcgaagtggc cagggtagca   1740
ggtgccattc tcagggttgg gcttctccac gatgtaggac caggactctt tggaaatcag   1800
cagctcgcac tcaggattgc ccagaatcca gccggccacg ctacaatttc cagctgcag   1860

| | |
|---|---|
| aggggcaatg cctttcagca gacacagctt gccgttgtgg ctgttttcca gcaggttcac | 1920 |
| gctgtgggtc acggtcacgt tcttttccag cacggtatcc acggtgtcgg tgctattgtt | 1980 |
| ggcgtggtag ccgatacaga tggtatcggc gtaggtggcg gtaaaggtac acagcagcac | 2040 |
| cagcagcttc actttcat | 2058 |

```
<210> SEQ ID NO 67
<211> LENGTH: 2112
<212> TYPE: DNA
<213> ORGANISM: Artificial Sequence
<220> FEATURE:
<223> OTHER INFORMATION: Synthetic

<400> SEQUENCE: 67
```

| | |
|---|---|
| atgaaggcca tcatcgtgct gctgatggtg gtcacaagca acgccgatag aatctgtacc | 60 |
| ggcatcacca gcagcaatag ccctcacgtc gtgaaaacag ctacacaggg cgaagtgaat | 120 |
| gtgaccggcg tgatccctct gaccacaaca cctacaaaga gccacttcgc caatctgaag | 180 |
| ggcacagaga caagaggcaa gctgtgtccc aagtgcctga attgcacaga tctggatgtg | 240 |
| gctctgggca gacctaagtg tacaggcaaa atccctagcg ccagagtgtc cattctgcat | 300 |
| gaagtgcgac ctgtgaccag cggctgtttt cctattatgc acgaccggac caagatcaga | 360 |
| cagctgccta atctgctgag aggctacgag cacatcagac tgagcaccca caatgtgatc | 420 |
| aacgccgaaa atgctcctgg cggcccttat aagatcggca catctggcag ctgccccaac | 480 |
| attacaaatg gcaatggctt ctttgccacc atggcttggg ccgtgcctaa gaacgataag | 540 |
| aacaagaccg ccaccaaccc cctgacaatc gaggtgccat atatctgtac agagggcgag | 600 |
| gatcagatca ccgtgtgggg atttcacagc gacaacgaaa cacagatggc caagctgtac | 660 |
| ggcgatagca agcctcagaa gtttaccagc tctgccaatg gcgtgaccac acactatgtg | 720 |
| tctcagatcg gcggcttccc taatcagaca gaagatggcg gactgcctca gtctggaaga | 780 |
| atcgtggtgg attacatggt gcagaagtct ggcaagaccg gcaccatcac atatcagaga | 840 |
| ggaatcctgc tgccccagaa agtgtggtgc gcttctggaa gatccaaagt gatcaagggc | 900 |
| agcctgcctc tgattggaga agccgattgt ctgcacgaga atacggcgg cctgaacaag | 960 |
| agcaagcctt actatacagg cgagcacgcc aaggccatcg gcaattgtcc tatttgggtc | 1020 |
| aagacccctc tgaagctggc caatggcaca aagtatagac ctccagccaa gctgctgaaa | 1080 |
| gagagaggct tttttggagc tatcgccggc tttctggaag gcggatggga gggaatgatt | 1140 |
| gctggatggc atggctacac atctcatggc gcacatggcg tggcagtggc tgctgatctg | 1200 |
| aaatctacac aggaagccat caacaagatc accaagaacc tgaacagcct gagcgagctg | 1260 |
| gaagtgaaga tctgcagag actgtctggc gccatggacg aactgcacaa tgagatcctg | 1320 |
| gaactggacg agaaggtgga cgatctgaga gccgatacaa tcagcagcca gattgaactg | 1380 |
| gctgtgctgc tgtctaacga gggcatcatc aatagcgagg acgaacatct gctggccctg | 1440 |
| gaaagaaagc tgaagaagat gctgggacct agcgccgtgg aaatcggcaa tggatgcttt | 1500 |
| gagacaaagc acaagtgcaa ccagacctgc ctggatagaa ttgccgccgg aacatttgat | 1560 |
| gccggcgagt ttctctctgcc caccttcgat agcctgaata tcacatccgg aggcgacatc | 1620 |
| atcaagctgc tgaacgagca ggtgaacaag agatgcagaa gcagcaacct gtacatgagc | 1680 |
| atgagcagct ggtgctacac ccacagcctg acggcgccg gctgttcct gttcgaccac | 1740 |
| gccgccgagg agtacgagca cgccaagaag ctgatcatct tcctgaacga gaacaacgtg | 1800 |
| cccgtgcagc tgaccagcat cagcgcccc gagcacaagt cgagggcct gacccagatc | 1860 |

```
ttccagaagg cctacgagca cgagcagcac atcagcgaga gcatcaacaa catcgtggac    1920
cacgccatca agagcaagga ccacgccacc ttcaacttcc tgcagtggta cgtggccgag    1980
cagcacgagg aggaggtgct gttcaaggac atcctggaca agatcgagct gatcggcaac    2040
gagaaccacg gcctgtacct ggccgaccag tacgtgaagg gcatcgccaa gagcaggaag    2100
agcggatcct ag                                                       2112
```

<210> SEQ ID NO 68
<211> LENGTH: 703
<212> TYPE: PRT
<213> ORGANISM: Artificial Sequence
<220> FEATURE:
<223> OTHER INFORMATION: Synthetic

<400> SEQUENCE: 68

```
Met Lys Ala Ile Ile Val Leu Leu Met Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
```

```
                    305                 310                 315                 320
            Ser Lys Pro Tyr Tyr Thr Gly Glu His Ala Lys Ala Ile Gly Asn Cys
                            325                 330                 335

Pro Ile Trp Val Lys Thr Pro Leu Lys Leu Ala Asn Gly Thr Lys Tyr
                        340                 345                 350

Arg Pro Pro Ala Lys Leu Leu Lys Glu Arg Gly Phe Phe Gly Ala Ile
                    355                 360                 365

Ala Gly Phe Leu Glu Gly Gly Trp Gly Met Ile Ala Gly Trp His
                370                 375                 380

Gly Tyr Thr Ser His Gly Ala His Gly Val Ala Val Ala Ala Asp Leu
            385                 390                 395                 400

Lys Ser Thr Gln Glu Ala Ile Asn Lys Ile Thr Lys Asn Leu Asn Ser
                            405                 410                 415

Leu Ser Glu Leu Glu Val Lys Asn Leu Gln Arg Leu Ser Gly Ala Met
                        420                 425                 430

Asp Glu Leu His Asn Glu Ile Leu Glu Leu Asp Glu Lys Val Asp Asp
                    435                 440                 445

Leu Arg Ala Asp Thr Ile Ser Ser Gln Ile Glu Leu Ala Val Leu Leu
                450                 455                 460

Ser Asn Glu Gly Ile Ile Asn Ser Glu Asp Glu His Leu Leu Ala Leu
            465                 470                 475                 480

Glu Arg Lys Leu Lys Lys Met Leu Gly Pro Ser Ala Val Glu Ile Gly
                            485                 490                 495

Asn Gly Cys Phe Glu Thr Lys His Lys Cys Asn Gln Thr Cys Leu Asp
                        500                 505                 510

Arg Ile Ala Ala Gly Thr Phe Asp Ala Gly Glu Phe Ser Leu Pro Thr
                    515                 520                 525

Phe Asp Ser Leu Asn Ile Thr Ser Gly Gly Asp Ile Ile Lys Leu Leu
                530                 535                 540

Asn Glu Gln Val Asn Lys Glu Met Gln Ser Ser Asn Leu Tyr Met Ser
            545                 550                 555                 560

Met Ser Ser Trp Cys Tyr Thr His Ser Leu Asp Gly Ala Gly Leu Phe
                            565                 570                 575

Leu Phe Asp His Ala Ala Glu Glu Tyr Glu His Ala Lys Lys Leu Ile
                        580                 585                 590

Ile Phe Leu Asn Glu Asn Asn Val Pro Val Gln Leu Thr Ser Ile Ser
                    595                 600                 605

Ala Pro Glu His Lys Phe Glu Gly Leu Thr Gln Ile Phe Gln Lys Ala
                610                 615                 620

Tyr Glu His Glu Gln His Ile Ser Glu Ser Ile Asn Asn Ile Val Asp
            625                 630                 635                 640

His Ala Ile Lys Ser Lys Asp His Ala Thr Phe Asn Phe Leu Gln Trp
                            645                 650                 655

Tyr Val Ala Glu Gln His Glu Glu Val Leu Phe Lys Asp Ile Leu
                        660                 665                 670

Asp Lys Ile Glu Leu Ile Gly Asn Glu Asn His Gly Leu Tyr Leu Ala
                    675                 680                 685

Asp Gln Tyr Val Lys Gly Ile Ala Lys Ser Arg Lys Ser Gly Ser
                690                 695                 700

<210> SEQ ID NO 69
<211> LENGTH: 2112
<212> TYPE: DNA
<213> ORGANISM: Artificial Sequence
```

<220> FEATURE:
<223> OTHER INFORMATION: Synthetic

<400> SEQUENCE: 69

```
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt    300
cagctgcacg gcacgttgt tctcgttcag gaagatgatc agcttcttgg cgtgctcgta    360
ctcctcggcg cgtggtcga acaggaacag gccggcgccg tccaggctgt gggtgtagca    420
ccagctgctc atgctcatgt acaggttgct gctctgcatc tccttgttca cctgctcgtt   480
cagcagcttg atgatgtcgc ctccggatgt gatattcagg ctatcgaagg tgggcagaga   540
aaactcgccg gcatcaaatg ttccggcggc aattctatcc aggcaggtct ggttgcactt   600
gtgctttgtc tcaaagcatc cattgccgat ttccacggcg ctaggtccca gcatcttctt   660
cagctttctt tccagggcca gcagatgttc gtcctcgcta ttgatgatgc cctcgttaga   720
cagcagcaca gccagttcaa tctggctgct gattgtatcg gctctcagat cgtccacctt   780
ctcgtccagt tccaggatct cattgtgcag ttcgtccatg cgccagaca gtctctgcag    840
attcttcact ccagctcgc tcaggctgtt caggttcttg gtgatcttgt tgatggcttc    900
ctgtgtagat ttcagatcag cagccactgc cacgccatgt gcgccatgag atgtgtagcc   960
atgccatcca gcaatcattc cctcccatcc gccttccaga aagccggcga tagctccaaa  1020
aaagcctctc tctttcagca gcttggctgg aggtctatac tttgtgccat ggccagctt   1080
cagagggtc ttgacccaaa taggacaatt gccgatggcc ttggcgtgct cgcctgtata  1140
gtaaggcttg ctcttgttca ggccgccgta tttctcgtgc agacaatcgg cttctccaat  1200
cagaggcagg ctgcccttga tcactttgga tcttccagaa gcgcaccaca ctttctgggg  1260
cagcaggatt cctctctgat atgtgatggt gccggtcttg ccagacttct gcaccatgta  1320
atccaccacg attcttccag actgaggcag tccgccatct tctgtctgat tagggaagcc   1380
gccgatctga gacacatagt gtgtggtcac gccattggca gagctggtaa acttctgagg   1440
cttgctatcg ccgtacagct tggccatctg tgtttcgttg tcgctgtgaa atccccacac   1500
ggtgatctga tcctcgccct ctgtacagat atatggcacc tcgattgtca ggggggttggt  1560
ggcggtcttg ttcttatcgt tcttaggcac ggcccaagcc atggtggcaa agaagccatt  1620
gccatttgta atgttggggc agctgccaga tgtgccgatc ttataagggc cgccaggagc  1680
atttcggcg ttgatcacat tgtgggtgct cagtctgatg tgctcgtagc ctctcagcag  1740
attaggcagc tgtctgatct tggtccggtc gtgcataata ggaaaacagc cgctggtcac  1800
aggtcgcact tcatgcagaa tggacactct ggcgctaggg attttgcctg tacacttagg  1860
tctgcccaga gccacatcca gatctgtgca attcaggcac ttgggacaca gcttgcctct  1920
tgtctctgtg cccttcagat tggcgaagtg gctctttgta ggtgttgtgg tcagagggat  1980
cacgccggtc acattcactt cgccctgtgt agctgttttc acgacgtgag ggctattgct  2040
gctggtgatg ccggtacaga ttctatcggc gttgcttgtg accaccatca gcagcacgat  2100
gatggccttc at                                                       2112
```

<210> SEQ ID NO 70

```
<211> LENGTH: 837
<212> TYPE: DNA
<213> ORGANISM: Influenza virus

<400> SEQUENCE: 70
atgaaggcca agctgctggt gctgctgtgc acctttaccg ccacctacgc cgacaccatc    60
tgcattggct accacgccaa caacagcacc gacaccgtgg ataccgtgct ggaaaagaac   120
gtgaccgtga cccacagcgt gaacctggga tccggactga aatggtcac cggcctgaga    180 aacatcccca gcatccagag cagaggcctg tttggagcca ttgccggctt tattgagggc   240
ggatggaccg gaatggtgga tgggtggtac ggctaccacc accagaatga gcagggctct   300
ggctatgccg ccgatcagaa gtctacccag aacgccatca cggcatcac caacaaagtg    360 aacagcgtga tcgagaagat gggcggcgat cctgaatggg acagagagat caacaactac   420
accagcatca tctacagcct gatcgaggaa agccagaacc agcaggaaaa cggcacaggc   480
ggcggatctg gaattgtgca gcagcagaac aacctgctga gagccattga ggcccagcag   540
catctgctgc agctgacagt gtgggcatc aagcagctgc agacctacaa tgccgagctg    600
ctggtcctcc tggaaaacga gagaaccctg gacttccacg acagcaacgt gaagaacctg   660
tacgagaaag tgaagtccca gctgaagaac aacgccaaag atcggcaa cggctgcttc    720 gagttctacc acaagtgcaa caacgagtgc atggaaagcg tgaagaacgg cacctacgac   780
taccccaagt acagcgagga aagcaagctg aacagagaga gatcgactc cggaggc       837

<210> SEQ ID NO 71
<211> LENGTH: 279
<212> TYPE: PRT
<213> ORGANISM: Influenza virus

<400> SEQUENCE: 71

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
```

-continued

```
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asn Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Ser Gly Gly
        275
```

```
<210> SEQ ID NO 72
<211> LENGTH: 837
<212> TYPE: DNA
<213> ORGANISM: Influenza virus

<400> SEQUENCE: 72
gcctccggag tcgatcttct ctctgttcag cttgctttcc tcgctgtact tggggtagtc     60
gtaggtgccg ttcttcacgc tttccatgca ctcgttgttg cacttgtggt agaactcgaa    120
gcagccgttg ccgatctctt tggcgttgtt cttcagctgg gacttcactt tctcgtacag    180
gttcttcacg ttgctgtcgt ggaagtccag ggttctctcg ttttccagga ggaccagcag    240
ctcggcattg taggtctgca gctgcttgat gccccacact gtcagctgca gcagatgctg    300
ctgggcctca atggctctca gcaggttgtt ctgctgctgc acaattccag atccgccgcc    360
tgtgccgttt tcctgctggt tctggctttc ctcgatcagg ctgtagatga tgctggtgta    420
gttgttgatc tctctgtccc attcaggatc gccgcccatc ttctcgatca cgctgttcac    480
tttgttggtg atgccgttga tggcgttctg ggtagacttc tgatcggcgg catagccaga    540
gccctgctca ttctggtggt ggtagccgta ccacccatcc accattccgg tccatccgcc    600
ctcaataaag ccggcaatgg ctccaaacag gcctctgctc tggatgctgg ggatgtttct    660
caggccggtg accattctca gtccggatcc caggttcacg ctgtgggtca cggtcacgtt    720
cttttccagc acggtatcca cggtgtcggt gctgttgttg gcgtggtagc caatgcagat    780
ggtgtcggcg taggtggcgg taaaggtgca cagcagcacc agcagcttgg ccttcat       837
```

```
<210> SEQ ID NO 73
<211> LENGTH: 828
<212> TYPE: DNA
<213> ORGANISM: Influenza virus

<400> SEQUENCE: 73
atgaaggcta tcctggtggt gctgctgtac acctttgcca ccgccaatgc cgacaccctg     60
tgtattggct accacgccaa caacagcacc gacaccgtgg ataccgtgct ggaaaagaac    120
gtgaccgtga cccacagcgt gaacctgggc tccggcctga gactggccac cggcctgaga    180
aacatcccca gcattcagag cagaggcctg tttggagcca ttgccggctt tattgagggc    240
ggatggaccg gaatggtgga tgggtggtac ggctaccacc accagaatga gcagggctct    300
ggctatgccg ccgacctgaa gtctacccag aacgccatcg acgagatcac caacaaagtg    360
aacagcgtga tcgagaagat gggcggctgg gacccatggg acagagagat caacaactac    420
accagcatca tctacagcct gatcgaggaa agccagaacc agcaggaaaa cggcacaggc    480
ggcggatctg gaattgtgca gcagcagaac aacctgctga gagccattga ggcccagcag    540
```

```
catctgctgc agctgacagt gtggggcatc aagcagctgc agacctacaa cgccgagctg      600
ctggtgctgc tcgagaatga gagaaccctg gactaccacg acagcaacgt gaagaacctg      660
tacgagaaag tgcggagcca gctgaagaac aacgccaaag agatcggcaa cggctgcttc      720
gagttctacc acaagtgcga caatacctgc atggaaagcg tgaagaacgg cacctacgac      780
taccccaagt acagcgagga agccaagctg aaccgggaag agatcgat                   828
```

```
<210> SEQ ID NO 74
<211> LENGTH: 276
<212> TYPE: PRT
<213> ORGANISM: Influenza virus

<400> SEQUENCE: 74
```

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Gly Ser Gly Leu Arg Leu Ala Thr Gly Leu Arg Asn Ile Pro Ser
        50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Leu Lys Ser Thr Gln Asn Ala
            100                 105                 110

Ile Asp Glu Ile Thr Asn Lys Val Asn Ser Val Ile Glu Lys Met Gly
        115                 120                 125

Gly Trp Asp Pro Trp Asp Arg Glu Ile Asn Asn Tyr Thr Ser Ile Ile
130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Tyr His Asp Ser Asn Val Lys Asn Leu Tyr Glu Lys Val
        210                 215                 220

Arg Ser Gln Leu Lys Asn Asn Ala Lys Glu Ile Gly Asn Gly Cys Phe
225                 230                 235                 240

Glu Phe Tyr His Lys Cys Asp Asn Thr Cys Met Glu Ser Val Lys Asn
                245                 250                 255

Gly Thr Tyr Asp Tyr Pro Lys Tyr Ser Glu Glu Ala Lys Leu Asn Arg
            260                 265                 270

Glu Glu Ile Asp
        275
```

```
<210> SEQ ID NO 75
<211> LENGTH: 828
<212> TYPE: DNA
<213> ORGANISM: Influenza virus

<400> SEQUENCE: 75
```

```
atcgatctct tcccggttca gcttggcttc ctcgctgtac ttggggtagt cgtaggtgcc     60
gttcttcacg ctttccatgc aggtattgtc gcacttgtgg tagaactcga agcagccgtt    120
gccgatctct ttggcgttgt tcttcagctg gctccgcact ttctcgtaca ggttcttcac    180
gttgctgtcg tggtagtcca gggttctctc attctcgagc agcaccagca gctcggcgtt    240
gtaggtctgc agctgcttga tgccccacac tgtcagctgc agcagatgct gctgggcctc    300
aatggctctc agcaggttgt tctgctgctg cacaattcca gatccgccgc ctgtgccgtt    360
ttcctgctgg ttctggcttt cctcgatcag gctgtagatg atgctggtgt agttgttgat    420
ctctctgtcc catgggtccc agccgccat cttctcgatc acgctgttca ctttgttggt     480
gatctcgtcg atggcgttct gggtagactt caggtcggcg gcatagccag agccctgctc    540
attctggtgg tggtagccgt accacccatc caccattccg gtccatccgc cctcaataaa    600
gccggcaatg gctccaaaca ggcctctgct ctgaatgctg gggatgtttc tcaggccggt    660
ggccagtctc aggccggagc ccaggttcac gctgtgggtc acggtcacgt tcttttccag    720
cacggtatcc acggtgtcgg tgctgttgtt ggcgtggtag ccaatacaca gggtgtcggc    780
attggcggtg gcaaaggtgt acagcagcac caccaggata gccttcat              828

<210> SEQ ID NO 76
<211> LENGTH: 822
<212> TYPE: DNA
<213> ORGANISM: Influenza virus

<400> SEQUENCE: 76
atggccatca tctacctgat tctgctgttt acagccgtca gaggcgatca gatctgtatt     60
ggctaccacg ccaacaatag caccgagaaa gtggatacca tcctggaaag aaatgtgaca    120
gtgacacacg ccaaggatat tggatcagga ctggtgctgg ctacaggact gagaaatgtg    180
cctcagattg agagcagagg cctgtttgga gccattgctg gctttattga aggcggatgg    240
cagggaatga ttgatgggtg gtacggctac caccactcta tgatcagggg atctggatat    300
gccgccgaca agaatctac acagaaagcc ttcgacggca tcaccaacaa agtgaatagc    360
gtgatcgaga agatgggcgg agatcccgaa tgggacagag agatcaacaa ctacaccagc    420
atcatctaca gcctgatcga ggaaagccag aatcagcagg aaaatggaac aggcggagga    480
tctggaattg tgcagcagca gaacaatctg ctgagagcta ttgaagctca gcagcatctg    540
ctgaatctga cagtgtgggg aatcaaacag ctgcagacat acaatgctga gctgctggtg    600
ctgatggaaa atgagagaac cctggacttc cacgacagca atgtgaagaa cctgtacgac    660
aaagtgcgga tgcagctgag agacaatgtg aaagaactgg gcaatggctg cttcgagttc    720
taccacaagt gcgacgatga gtgtatgaac agcgtgaaga acggcaccta cgactaccct    780
aagtacgagg aagagagcaa gctgaacaga atgagatca ag                        822

<210> SEQ ID NO 77
<211> LENGTH: 274
<212> TYPE: PRT
<213> ORGANISM: Influenza virus

<400> SEQUENCE: 77

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30
```

```
Thr Ile Leu Glu Arg Asn Val Thr Val Thr His Ala Lys Asp Ile Gly
             35                  40                  45
Ser Gly Leu Val Leu Ala Thr Gly Leu Arg Asn Val Pro Gln Ile Glu
 50                  55                  60
Ser Arg Gly Leu Phe Gly Ala Ile Ala Gly Phe Ile Glu Gly Gly Trp
 65                  70                  75                  80
Gln Gly Met Ile Asp Gly Trp Tyr Gly Tyr His His Ser Asn Asp Gln
                 85                  90                  95
Gly Ser Gly Tyr Ala Ala Asp Lys Glu Ser Thr Gln Lys Ala Phe Asp
                100                 105                 110
Gly Ile Thr Asn Lys Val Asn Ser Val Ile Glu Lys Met Gly Gly Asp
            115                 120                 125
Pro Glu Trp Asp Arg Glu Ile Asn Asn Tyr Thr Ser Ile Ile Tyr Ser
130                 135                 140
Leu Ile Glu Glu Ser Gln Asn Gln Gln Glu Asn Gly Thr Gly Gly Gly
145                 150                 155                 160
Ser Gly Ile Val Gln Gln Asn Asn Leu Leu Arg Ala Ile Glu Ala
                165                 170                 175
Gln Gln His Leu Leu Asn Leu Thr Val Trp Gly Ile Lys Gln Leu Gln
            180                 185                 190
Thr Tyr Asn Ala Glu Leu Leu Val Leu Met Glu Asn Glu Arg Thr Leu
        195                 200                 205
Asp Phe His Asp Ser Asn Val Lys Asn Leu Tyr Asp Lys Val Arg Met
210                 215                 220
Gln Leu Arg Asp Asn Val Lys Glu Leu Gly Asn Gly Cys Phe Glu Phe
225                 230                 235                 240
Tyr His Lys Cys Asp Asp Glu Cys Met Asn Ser Val Lys Asn Gly Thr
                245                 250                 255
Tyr Asp Tyr Pro Lys Tyr Glu Glu Glu Ser Lys Leu Asn Arg Asn Glu
                260                 265                 270
Ile Lys

<210> SEQ ID NO 78
<211> LENGTH: 822
<212> TYPE: DNA
<213> ORGANISM: Influenza virus

<400> SEQUENCE: 78
cttgatctca tttctgttca gcttgctctc ttcctcgtac ttagggtagt cgtaggtgcc      60
gttcttcacg ctgttcatac actcatcgtc gcacttgtgg tagaactcga agcagccatt     120
gcccagttct ttcacattgt ctctcagctg catccgcact tgtcgtaca ggttcttcac      180
attgctgtcg tggaagtcca gggttctctc attttccatc agcaccagca gctcagcatt     240
gtatgtctgc agctgtttga ttccccacac tgtcagattc agcagatgct gctgagcttc     300
aatagctctc agcagattgt tctgctgctg cacaattcca gatcctccgc tgttccatt      360
ttcctgctga ttctggcttt cctcgatcag gctgtagatg atgctggtgt agttgttgat     420
ctctctgtcc cattcgggat ctccgcccat cttctcgatc acgctattca ctttgttggt     480
gatgccgtcg aaggctttct gtgtagattc tttgtcggcg gcatatccag atccctgatc     540
attagagtgg tggtagccgt accacccatc aatcattccc tgccatccgc cttcaataaa     600
gccagcaatg gctccaaaca ggcctctgct ctcaatctga ggcacatttc tcagtcctgt     660
agccagcacc agtcctgatc caatatcctt ggcgtgtgtc actgtcacat ttcttttccag    720
```

| | | |
|---|---|---|
| gatggtatcc actttctcgg tgctattgtt ggcgtggtag ccaatacaga tctgatcgcc | 780 | |
| tctgacggct gtaaacagca gaatcaggta gatgatggcc at | 822 | |

<210> SEQ ID NO 79
<211> LENGTH: 858
<212> TYPE: DNA
<213> ORGANISM: Influenza virus

<400> SEQUENCE: 79

| | |
|---|---|
| atgaagacca tcatcgccct gagctacatc ttctgcctgg ccctgggcca ggacctgccc | 60 |
| ggcaacgaca acagcaccgc caccctgtgc ctgggccacc acgccgtgcc caacggcacc | 120 |
| ctggtgaaga ccatcaccga cgaccagatc gaggtgacca acgccaccga gctgggctcc | 180 |
| ggcctgaagc tggccaccgg catgcggaac gtgcccgaga gcagacccg ggcctgttc | 240 |
| ggcgccatcg ccggcttcat cgagaacggc tgggagggca tgatcgacgg ctggtacggc | 300 |
| ttccggcacc agaacagcga gggcaccggc caggccgccg acctgaagag cacccaggcc | 360 |
| gccatcgacc agatcaacgg caagctgaac cgggtgatcg agaagaccgg cggcgatccc | 420 |
| gagtgggacc gggagatcaa caactacacc agcatcatct acagcctgat cgaggagagc | 480 |
| cagaaccagc aggagaacgg caccggcggc ggcagcggca cgtgcagca gcagaacaac | 540 |
| ctgctgcggg ccatcgaggc ccagcagcac ctgctgcagc tgaccgtgtg gggcatcaag | 600 |
| cagctgcaga gctacaacgc cgagctgctg gtggccctgg agaaccagca ccatcgac | 660 |
| ctgaccgaca gcgagatgaa caagctgttc gagaagaccc ggcggcagct gcgggagaac | 720 |
| gccgaggaca tgggcaacgg ctgcttcaag atctaccaca gtgcgacaa cgcctgcatc | 780 |
| gagagcatcc ggaacggcac ctacgaccac gacgtgtacc gggacgaggc cctgaacaac | 840 |
| cggttccaga tcaagggc | 858 |

<210> SEQ ID NO 80
<211> LENGTH: 286
<212> TYPE: PRT
<213> ORGANISM: Influenza virus

<400> SEQUENCE: 80

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Leu Phe
65                  70                  75                  80

Gly Ala Ile Ala Gly Phe Ile Glu Asn Gly Trp Glu Gly Met Ile Asp
                85                  90                  95

Gly Trp Tyr Gly Phe Arg His Gln Asn Ser Glu Gly Thr Gly Gln Ala
            100                 105                 110

Ala Asp Leu Lys Ser Thr Gln Ala Ala Ile Asp Gln Ile Asn Gly Lys
        115                 120                 125

Leu Asn Arg Val Ile Glu Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

```
Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Arg Arg Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Glu Ser Ile Arg Asn Gly Thr Tyr Asp His Asp Val
            260                 265                 270

Tyr Arg Asp Glu Ala Leu Asn Asn Arg Phe Gln Ile Lys Gly
        275                 280                 285

<210> SEQ ID NO 81
<211> LENGTH: 858
<212> TYPE: DNA
<213> ORGANISM: Influenza virus

<400> SEQUENCE: 81
gcccttgatc tggaaccggt tgttcagggc ctcgtcccgg tacacgtcgt ggtcgtaggt      60
gccgttccgg atgctctcga tgcaggcgtt gtcgcacttg tggtagatct tgaagcagcc    120
gttgcccatg tcctcggcgt tctcccgcag ctgccgccgg tcttctcga acagcttgtt     180 catctcgctg tcggtcaggt cgatggtgtg ctggttctcc agggccacca gcagctcggc    240
gttgtagctc tgcagctgct tgatgcccca cacggtcagc tgcagcaggt gctgctgggc    300
ctcgatggcc cgcagcaggt tgttctgctg ctgcacgatg ccgctgccgc cgccggtgcc    360
gttctcctgc tggttctggc tctcctcgat caggctgtag atgatgctgg tgtagttgtt    420 gatctccccgg tcccactcgg gatcgccgcc ggtcttctcg atcacccggt tcagcttgcc    480
gttgatctgg tcgatggcgg cctgggtgct cttcaggtcg gcggcctggc cggtgccctc    540
gctgttctgg tgccggaagc cgtaccagcc gtcgatcatg ccctcccagc cgttctcgat    600
gaagccggcg atggcgccga acaggccccg ggtctgcttc tcgggcacgt tccgcatgcc    660
ggtggccagc ttcaggccgg agcccagctc ggtggcgttg gtcacctcga tctggtcgtc    720
ggtgatggtc ttcaccaggg tgccgttggg cacggcgtgg tgcccaggc acagggtggc     780 ggtgctgttg tcgttgccgg gcaggtcctg cccagggcc aggcagaaga tgtagctcag     840
ggcgatgatg gtcttcat                                                   858

<210> SEQ ID NO 82
<211> LENGTH: 867
<212> TYPE: DNA
<213> ORGANISM: Influenza virus

<400> SEQUENCE: 82
atgaaaacca tcattgccct gagctacatc ctgtgcctgg tgttcacaca gaagctgccc      60
ggcaacgata tagcaccgc cacactgtgt ctgggacacc acgccgtgcc taatggcacc     120
atcgtgaaaa caatcaccaa cgaccagatc gaagtgacca atgccacaga gctgggctcc    180
ggcctgaagc tggccaccgg catgagaaat gtgcccgaga gcagaccag aggcatcttt    240
```

-continued

| | | | | |
|---|---|---|---|---|
| ggcgccattg | ccggctttat | cgagaatggc | tgggagggaa tggtggatgg | gtggtacggc | 300 |
| ttcagacacc | agaatagcga | gggaattgga | caggccgccg | atctgaaatc tacccaggcc | 360 |
| gccatcgacc | agatcaacgg | caagctgaac | aggctgatcg | gcaagaccgg cggcgatccc | 420 |
| gagtgggacc | gggagatcaa | caactacacc | agcatcatct | acagcctgat cgaggagagc | 480 |
| cagaaccagc | aggagaacgg | caccggcggc | ggcagcggca | tcgtgcagca gcagaacaac | 540 |
| ctgctgcggg | ccatcgaggc | ccagcagcac | ctgctgcagc | tgaccgtgtg gggcatcaag | 600 |
| cagctgcaga | gctacaatgc | cgaactgctg | gtcgccctgg | aaaaccagca cacaattgat | 660 |
| ctgacagaca | gtgagatgaa | taagctgttc | gagaaaacca | gaagcagct gagagaaaac | 720 |
| gccgaggaca | tgggcaacgg | ctgcttcaag | atctaccaca | agtgcgacaa cgcctgcatc | 780 |
| ggcagcatca | gaaacggcac | ctacgaccac | gacgtgtaca | gagatgaggc cctgaacaac | 840 |
| cggtttcaga | tcaagggctc | cggaggc | | | 867 |

<210> SEQ ID NO 83
<211> LENGTH: 289
<212> TYPE: PRT
<213> ORGANISM: Influenza virus

<400> SEQUENCE: 83

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Ile Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
```

260                 265                 270
Tyr Arg Asp Glu Ala Leu Asn Asn Arg Phe Gln Ile Lys Gly Ser Gly
            275                 280                 285

Gly

<210> SEQ ID NO 84
<211> LENGTH: 867
<212> TYPE: DNA
<213> ORGANISM: Influenza virus

<400> SEQUENCE: 84
gcctccggag cccttgatct gaaaccggtt gttcagggcc tcatctctgt acacgtcgtg     60
gtcgtaggtg ccgtttctga tgctgccgat gcaggcgttg tcgcacttgt ggtagatctt    120
gaagcagccg ttgcccatgt cctcggcgtt ttctctcagc tgcttcttgg ttttctcgaa    180
cagcttattc atctcactgt ctgtcagatc aattgtgtgc tggttttcca gggcgaccag    240
cagttcggca ttgtagctct gcagctgctt gatgccccac acggtcagct gcagcaggtg    300
ctgctgggcc tcgatggccc gcagcaggtt gttctgctgc tgcacgatgc cgctgccgcc    360
gccggtgccg ttctcctgct ggttctggct ctcctcgatc aggctgtaga tgatgctggt    420
gtagttgttg atctcccggt cccactcggg atcgccgccg tcttgccga tcagcctgtt     480
cagcttgccg ttgatctggt cgatggcggc ctgggtagat ttcagatcgg cggcctgtcc    540
aattccctcg ctattctggt gtctgaagcc gtaccaccca tccaccattc cctcccagcc    600
attctcgata aagccggcaa tggcgccaaa gatgcctctg gtctgcttct cgggcacatt    660
tctcatgccg gtggccagct tcaggccgga gcccagctct gtggcattgg tcacttcgat    720
ctggtcgttg gtgattgttt tcacgatggt gccattaggc acggcgtggt gtcccagaca    780
cagtgtggcg gtgctattat cgttgccggg cagcttctgt gtgaacacca ggcacaggat    840
gtagctcagg gcaatgatgg ttttcat                                       867

<210> SEQ ID NO 85
<211> LENGTH: 837
<212> TYPE: DNA
<213> ORGANISM: Influenza virus

<400> SEQUENCE: 85
atggagaaga tcgtgctgct gctggccatc gtgagcctgg tgaagagcga ccagatctgc     60
atcggctacc acgccaacaa cagcaccgag caggtggaca ccatcatgga agaaacgtg     120
accgtgaccc acgcccagga catcggctcc ggcctggtgc tggccaccgg cctgcggaac    180
agcccccagc gggagagccg gcggaagaag cggggcctgt tcggcgccat cgccggcttc    240
atcgagggcg gctggcaggg catggtggac ggctggtacg gctaccacca cagcaacgag    300
cagggcagcg gctacgccgc cgacaaggag agcacccaga aggccatcga cggcgtgacc    360
aacaaggtga acagcatcat cgacaagatg ggcggcgatc ccgagtggga ccgggagatc    420
aacaactaca ccagcatcat ctacagcctg atcgaggaga ccagaaacca gcaggagaac    480
ggcaccggcg gcggcagcgg catcgtgcag cagcagaaca acctgctgcg ggccatcgag    540
gcccagcagc acctgctgca gctgaccgtg tgggcatca agcagctgca gacctacaac    600
gccgagctgc tggtgctgat ggagaacgag cggaccctgg acttccacga cagcaacgtg    660
aagaacctgt acgacaaggt gcggctgcag ctgcgggaca acgccaagga gctgggcaac    720
ggctgcttcg agttctacca caagtgcgac aacgagtgca tggagagcat ccggaacggc    780

```
acctacaact accccccagta cagcgaggag gcccggctga agcgggagga gatcagc       837
```

<210> SEQ ID NO 86
<211> LENGTH: 279
<212> TYPE: PRT
<213> ORGANISM: Influenza virus

<400> SEQUENCE: 86

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Gly Ser Gly Leu Val Leu Ala Thr Gly Leu Arg Asn Ser Pro Gln Arg
    50                  55                  60

Glu Ser Arg Arg Lys Lys Arg Gly Leu Phe Gly Ala Ile Ala Gly Phe
65                  70                  75                  80

Ile Glu Gly Gly Trp Gln Gly Met Val Asp Gly Trp Tyr Gly Tyr His
                85                  90                  95

His Ser Asn Glu Gln Gly Ser Gly Tyr Ala Ala Asp Lys Glu Ser Thr
            100                 105                 110

Gln Lys Ala Ile Asp Gly Val Thr Asn Lys Val Asn Ser Ile Ile Asp
        115                 120                 125

Lys Met Gly Gly Asp Pro Glu Trp Asp Arg Glu Ile Asn Asn Tyr Thr
130                 135                 140

Ser Ile Ile Tyr Ser Leu Ile Glu Glu Ser Gln Asn Gln Gln Glu Asn
145                 150                 155                 160

Gly Thr Gly Gly Gly Ser Gly Ile Val Gln Gln Gln Asn Asn Leu Leu
                165                 170                 175

Arg Ala Ile Glu Ala Gln Gln His Leu Leu Gln Leu Thr Val Trp Gly
            180                 185                 190

Ile Lys Gln Leu Gln Thr Tyr Asn Ala Glu Leu Leu Val Leu Met Glu
        195                 200                 205

Asn Glu Arg Thr Leu Asp Phe His Asp Ser Asn Val Lys Asn Leu Tyr
210                 215                 220

Asp Lys Val Arg Leu Gln Leu Arg Asp Asn Ala Lys Glu Leu Gly Asn
225                 230                 235                 240

Gly Cys Phe Glu Phe Tyr His Lys Cys Asp Asn Glu Cys Met Glu Ser
                245                 250                 255

Ile Arg Asn Gly Thr Tyr Asn Tyr Pro Gln Tyr Ser Glu Glu Ala Arg
            260                 265                 270

Leu Lys Arg Glu Glu Ile Ser
        275
```

<210> SEQ ID NO 87
<211> LENGTH: 837
<212> TYPE: DNA
<213> ORGANISM: Influenza virus

<400> SEQUENCE: 87

```
gctgatctcc tcccgcttca gccgggcctc ctcgctgtac tgggggtagt tgtaggtgcc    60
gttccggatg ctctccatgc actcgttgtc gcacttgtgg tagaactcga agcagccgtt   120
gcccagctcc ttggcgttgt cccgcagctg cagccgcacc ttgtcgtaca ggttcttcac   180
gttgctgtcg tggaagtcca gggtccgctc gttctccatc agcaccagca gctcggcgtt   240
```

```
gtaggtctgc agctgcttga tgccccacac ggtcagctgc agcaggtgct gctgggcctc    300
gatggcccgc agcaggttgt tctgctgctg cacgatgccg ctgccgccgc cggtgccgtt    360
ctcctgctgg ttctggctct cctcgatcag gctgtagatg atgctggtgt agttgttgat    420
ctcccggtcc cactcgggat cgccgcccat cttgtcgatg atgctgttca ccttgttggt    480
cacgccgtcg atggccttct gggtgctctc cttgtcggcg gcgtagccgc tgccctgctc    540
gttgctgtgg tggtagccgt accagccgtc caccatgccc tgccagccgc cctcgatgaa    600
gccggcgatg gcgccgaaca ggccccgctt cttccgccgg ctctcccgct ggggggctgtt   660 ccgcaggccg gtggccagca ccaggccgga gccgatgtcc tgggcgtggg tcacggtcac    720
gttcttctcc atgatggtgt ccacctgctc ggtgctgttg ttggcgtggt agccgatgca    780
gatctggtcg ctcttcacca ggctcacgat ggccagcagc agcacgatct tctccat      837
```

<210> SEQ ID NO 88
<211> LENGTH: 837
<212> TYPE: DNA
<213> ORGANISM: Influenza virus

<400> SEQUENCE: 88

```
atgaaggcca tcatcgtgct gctgatggtg gtgaccagca acgccgatag aatctgcacc    60
ggcatcacca gcagcaatag cccccatgtg gtgaaaacag ccacccaggg cgaagtgaat   120
gtgacaggcg tgatccctct gggatcagga ctgaagctgg ccaatggcac caagtacaga   180
cctcccgcca agctgctgaa agagagaggc ttctttggcg ccattgccgg atttctggaa   240
ggcggctggg agggaatgat tgccggctgg cacggctata catctcatgg ggcccatggc   300
gtggctgtgg ccgccgatct gaagtctacc caggaagcca tcaacaagat caccaagaac   360
ctgaacagcc tgagcgagct ggaaggaggc gaccccgagt gggatcgcga aatcaacaac   420
tacacatcta tcatctacag tctgattgag aaagccaga accagcagga gaatgggact    480
gggggaggct ccggaatcgt gcagcagcag aacaatctgc tgcgagccat tgaagctcag   540
cagcacctgc tgcagctgac agtgtggggc atcaagcagc tgcaggggtc ccagattgaa   600
ctggccgtgc tgctgtccaa cgagggcatc atcaacagcg aggatgaaca cctgctggcc   660
ctggaacgga agctgaagaa gatgctgggc ccttctgccg tggagatcgg caacggctgc   720
ttcgagacaa agcacaagtg caaccagacc tgcctggata gaatcgccgc tggcaccttc   780
aatgccggcg agttcagcct gcctaccttc gacagcctga atatcacctc cggaggc      837
```

<210> SEQ ID NO 89
<211> LENGTH: 279
<212> TYPE: PRT
<213> ORGANISM: Influenza virus

<400> SEQUENCE: 89

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Gly
        35                  40                  45

Ser Gly Leu Lys Leu Ala Asn Gly Thr Lys Tyr Arg Pro Pro Ala Lys
    50                  55                  60

Leu Leu Lys Glu Arg Gly Phe Phe Gly Ala Ile Ala Gly Phe Leu Glu
65                  70                  75                  80

Gly Gly Trp Glu Gly Met Ile Ala Gly Trp His Gly Tyr Thr Ser His
                    85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
    130                 135                 140

Ile Tyr Ser Leu Ile Glu Glu Ser Gln Asn Gln Gln Glu Asn Gly Thr
145                 150                 155                 160

Gly Gly Gly Ser Gly Ile Val Gln Gln Gln Asn Asn Leu Leu Arg Ala
                165                 170                 175

Ile Glu Ala Gln Gln His Leu Leu Gln Leu Thr Val Trp Gly Ile Lys
            180                 185                 190

Gln Leu Gln Gly Ser Gln Ile Glu Leu Ala Val Leu Leu Ser Asn Glu
        195                 200                 205

Gly Ile Ile Asn Ser Glu Asp Glu His Leu Leu Ala Leu Glu Arg Lys
    210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asn Ala Gly Glu Phe Ser Leu Pro Thr Phe Asp Ser
            260                 265                 270

Leu Asn Ile Thr Ser Gly Gly
        275

<210> SEQ ID NO 90
<211> LENGTH: 837
<212> TYPE: DNA
<213> ORGANISM: Influenza virus

<400> SEQUENCE: 90
gcctccggag gtgatattca ggctgtcgaa ggtaggcagg ctgaactcgc cggcattgaa      60
ggtgccagcg gcgattctat ccaggcaggt ctggttgcac ttgtgctttg tctcgaagca     120
gccgttgccg atctccacgg cagaagggcc cagcatcttc ttcagcttcc gttccagggc     180
cagcaggtgt tcatcctcgc tgttgatgat gccctcgttg acagcagca cggccagttc      240 aatctgggac cctgcagct gcttgatgcc ccacactgtc agctgcagca ggtgctgctg      300
agcttcaatg gctcgcagca gattgttctg ctgctgcacg attccggagc ctcccccagt     360
cccattctcc tgctggttct ggctttcctc aatcagactg tagatgatag atgtgtagtt     420
gttgatttcg cgatcccact cggggtcgcc tccttccagc tcgctcaggc tgttcaggtt     480
cttggtgatc ttgttgatgg cttcctgggt agacttcaga tcggcggcca gccacgcc      540 atgggcccca tgagatgtat agccgtgcca gccggcaatc attccctccc agccgccttc     600
cagaaatccg gcaatggcgc caaagaagcc tctctctttc agcagcttgg cgggaggtct     660
gtacttggtg ccattggcca gcttcagtcc tgatcccaga gggatcacgc tgtcacatt      720 cacttcgccc tgggtggctg ttttcaccac atgggggcta ttgctgctgg tgatgccggt     780
gcagattcta tcggcgttgc tggtcaccac catcagcagc acgatgatgg ccttcat        837

<210> SEQ ID NO 91
<211> LENGTH: 867

<212> TYPE: DNA
<213> ORGANISM: Influenza virus

<400> SEQUENCE: 91

```
atgaaaacca taattgcgct gtcctacata ctgtgtctgg tgtttgccca gaaactgccg    60
ggcaatgaca actcaacagc cacgctctgc ttggggcacc atgccgtccc taacgggacc   120
attgtgaaaa ccattactaa cgatcagata gaggtgacta atgccaccga gctgggctcc   180
ggcttgaaac tggcgaccgg tatgcgcaat gtccccgaaa acagacccg cgggatattt    240
ggggctatcg caggctttat cgagaatggc tgggaaggga tggtggatgg ttggtatggt   300
tttagacatc aaaactccga aggcagaggc caggctgccg atctcaagag cacgcaggcc   360
gctatagatc agatcaatgg aaagctcaac agactgatcg ggaaaaccgg cggcgatccc   420
gagtgggacc gggagatcaa caactacacc agcatcatct acagcctgat cgaggagagc   480
cagaaccagc aggagaacgg caccggcggc ggcagcggca tcgtgcagca gcagaacaac   540
ctgctgcggg ccatcgaggc ccagcagcac ctgctgcagc tgaccgtgtg gggcatcaag   600
cagctgcagt cctacaatgc cgagctgctg gtggctctgg agaatcagca cactattgac   660
ctgaccgatt cagagatgaa caaactttttt gagaagacga agaagcagct tagagaaaat   720
gcagaggaca tggggaacgg atgctttaaa atatatcata agtgtgataa tgcctgcatc   780
ggatcaatta gaaatggtac ctatgatcac gatgtttaca gggacgaagc gctgaataac   840
aggttccaga taaaaggctc cggaggc                                       867
```

<210> SEQ ID NO 92
<211> LENGTH: 289
<212> TYPE: PRT
<213> ORGANISM: Influenza virus

<400> SEQUENCE: 92

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Arg Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190
```

```
Gln Leu Thr Val Trp Gly Ile Lys Gln Leu Gln Ser Tyr Asn Ala Glu
            195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Lys Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly

<210> SEQ ID NO 93
<211> LENGTH: 867
<212> TYPE: DNA
<213> ORGANISM: Influenza virus

<400> SEQUENCE: 93
gcctccggag cctttatct ggaacctgtt attcagcgct tcgtccctgt aaacatcgtg      60
atcataggta ccatttctaa ttgatccgat gcaggcatta tcacacttat gatatatttt    120
aaagcatccg ttccccatgt cctctgcatt ttctctaagc tgcttcttcg tcttctcaaa    180
aagtttgttc atctctgaat cggtcaggtc aatagtgtgc tgattctcca gagccaccag    240
cagctcggca ttgtaggact gcagctgctt gatgccccac acggtcagct gcagcaggtg    300
ctgctgggcc tcgatggccc gcagcaggtt gttctgctgc tgcacgatgc cgctgccgcc    360
gccggtgccg ttctcctgct ggttctggct ctcctcgatc aggctgtaga tgatgctggt    420
gtagttgttg atctcccggt cccactcggg atcgccgccg ttttcccga tcagtctgtt     480 gagctttcca ttgatctgat ctatagcggc ctgcgtgctc ttgagatcgg cagcctggcc    540
tctgccttcg gagttttgat gtctaaaacc ataccaacca tccaccatcc cttcccagcc    600
attctcgata aagcctgcga tagccccaaa tatcccgcgg gtctgttttt cggggacatt    660
gcgcataccg gtcgccagtt tcaagccgga gcccagctcg gtggcattag tcacctctat    720
ctgatcgtta gtaatggttt tcacaatggt cccgttaggg acggcatggt gccccaagca    780
gagcgtggct gttgagttgt cattgcccgg cagtttctgg gcaaacacca gacacagtat    840
gtaggacagc gcaattatgg ttttcat                                        867

<210> SEQ ID NO 94
<211> LENGTH: 837
<212> TYPE: DNA
<213> ORGANISM: Influenza virus

<400> SEQUENCE: 94
atgaaagtga agctgctggt gctgctgtgt accttaccg ccacctacgc cgataccatc       60
tgtatcggct accacgccaa caatagcacc gacaccgtgg ataccgtgct ggaaaagaac     120
gtgaccgtga cccacagcgt gaacctggga tcaggactga atggtgac cggcctgagg      180 aatatcccca gcatccagag cagaggcctg tttggcgcca ttgccggctt tatcgagggc    240
ggatggacag gcatggtgga tgggtggtac ggctaccacc accagaatga gcagggatct    300
ggctatgccg ccgatcagaa gagcacccag aacgccatca cggcatcac caacaaagtg    360 aacagcgtga tcgagaagat gggcggcgat cctgaatggg acagagagat caacaactac    420
```

```
accagcatca tctacagcct gatcgaggaa agccagaacc agcaggaaaa cggcacaggc    480
ggcggatctg gaattgtgca gcagcagaac aacctgctga gagccattga ggcccagcag    540
catctgctgc agctgacagt gtggggcatc aagcagctgc agacctacaa cgccgaactc    600
ctggtcctcc tggaaaatga gaggaccctg gacttccacg acagcaacgt gaagaacctg    660
tacgagaaag tgaagagcca gctgaagaac aacgccaaag agatcggcaa cggctgcttc    720
gagttctacc acaagtgcaa cgacgagtgc atggaaagcg tgaagaacgg cacctacgac    780
taccccaagt acagcgagga aagcaagctg aaccgggaga gatcgattc cggaggc       837
```

<210> SEQ ID NO 95
<211> LENGTH: 276
<212> TYPE: PRT
<213> ORGANISM: Influenza virus

<400> SEQUENCE: 95

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asp Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp
        275
```

<210> SEQ ID NO 96

<211> LENGTH: 837
<212> TYPE: DNA
<213> ORGANISM: Influenza virus

<400> SEQUENCE: 96

```
gcctccggaa tcgatcttct cccggttcag cttgctttcc tcgctgtact tggggtagtc    60
gtaggtgccg ttcttcacgc tttccatgca ctcgtcgttg cacttgtggt agaactcgaa   120
gcagccgttg ccgatctctt tggcgttgtt cttcagctgg ctcttcactt tctcgtacag   180
gttcttcacg ttgctgtcgt ggaagtccag ggtcctctca ttttccagga ggaccaggag   240
ttcggcgttg taggtctgca gctgcttgat gccccacact gtcagctgca gcagatgctg   300
ctgggcctca atggctctca gcaggttgtt ctgctgctgc acaattccag atccgccgcc   360
tgtgccgttt cctgctggt  tctggctttc ctcgatcagg ctgtagatga tgctggtgta   420
gttgttgatc tctctgtccc attcaggatc gccgcccatc ttctcgatca cgctgttcac   480
tttgttggtg atgccgttga tggcgttctg ggtgctcttc tgatcggcgg catagccaga   540
tccctgctca ttctggtggt ggtagccgta ccacccatcc accatgcctg tccatccgcc   600
ctcgataaag ccggcaatgg cgccaaacag gcctctgctc tggatgctgg ggatattcct   660
caggccggtc accattctca gtcctgatcc caggttcacg ctgtgggtca cggtcacgtt   720
cttttccagc acggtatcca cggtgtcggt gctattgttg cgtggtagc  cgatacagat   780
ggtatcggcg taggtggcgg taaaggtaca cagcagcacc agcagcttca ctttcat     837
```

<210> SEQ ID NO 97
<211> LENGTH: 837
<212> TYPE: DNA
<213> ORGANISM: Influenza virus

<400> SEQUENCE: 97

```
atgaaggcca tcatcgtgct gctgatggtg gtcacaagca acgccgatag aatctgtacc    60
ggcatcacca gcagcaatag ccctcacgtc gtgaaaacag ctacacaggg cgaagtgaat   120
gtgaccggcg tgatccctct gggatcagga ctgaagctgg ccaatggcac aaagtataga   180
cctccagcca gctgctgaa  agagagaggc ttttttggag ctatcgccgg ctttctggaa   240
ggcggatggg agggaatgat tgctggatgg catggctaca catctcatgg cgcacatggc   300
gtggcagtgg ctgctgatct gaaatctaca caggaagcca tcaacaagat caccaagaac   360
ctgaacagcc tgagcgagct ggaaggaggc gaccccgagt gggatcgcga aatcaacaac   420
tacacatcta tcatctacag tctgattgag aaagccaga  accagcagga gaatgggact   480
gggggaggct ccggaatcgt gcagcagcag aacaatctgc tgcgagccat tgaagctcag   540
cagcacctgc tgcagctgac agtgtggggc atcaagcagc tgcaggggag ccagattgaa   600
ctggctgtgc tgctgtctaa cgagggcatc atcaatagcg aggacgaaca tctgctggcc   660
ctggaaagaa agctgaagaa gatgctggga cctagcgccg tggaaatcgg caatggatgc   720
tttgagacaa agcacaagtg caaccagacc tgcctggata gaattgccgc cggaacatt   780
gatgccggcg agttttctct gcccaccttc gatagcctga atatcacatc cggaggc      837
```

<210> SEQ ID NO 98
<211> LENGTH: 279
<212> TYPE: PRT
<213> ORGANISM: Influenza virus

<400> SEQUENCE: 98

Met Lys Ala Ile Ile Val Leu Leu Met Val Val Thr Ser Asn Ala Asp

|  |  |  |  |  |  |  |  |  |  |  |  |  |  |  |
|---|---|---|---|---|---|---|---|---|---|---|---|---|---|---|
| 1 |  |  |  | 5 |  |  |  |  | 10 |  |  |  |  | 15 |

Arg Ile Cys Thr Gly Ile Thr Ser Ser Asn Ser Pro His Val Lys
                        20                      25                      30

Thr Ala Thr Gln Gly Glu Val Asn Val Thr Gly Val Ile Pro Leu Gly
                35                      40                      45

Ser Gly Leu Lys Leu Ala Asn Gly Thr Lys Tyr Arg Pro Pro Ala Lys
  50                      55                      60

Leu Leu Lys Glu Arg Gly Phe Phe Gly Ala Ile Ala Gly Phe Leu Glu
65                      70                      75                      80

Gly Gly Trp Glu Gly Met Ile Ala Gly Trp His Gly Tyr Thr Ser His
                        85                      90                      95

Gly Ala His Gly Val Ala Val Ala Ala Asp Leu Lys Ser Thr Gln Glu
                100                     105                     110

Ala Ile Asn Lys Ile Thr Lys Asn Leu Asn Ser Leu Ser Glu Leu Glu
                115                     120                     125

Gly Gly Asp Pro Glu Trp Asp Arg Glu Ile Asn Asn Tyr Thr Ser Ile
130                     135                     140

Ile Tyr Ser Leu Ile Glu Glu Ser Gln Asn Gln Gln Glu Asn Gly Thr
145                     150                     155                     160

Gly Gly Gly Ser Gly Ile Val Gln Gln Gln Asn Asn Leu Leu Arg Ala
                        165                     170                     175

Ile Glu Ala Gln Gln His Leu Leu Gln Leu Thr Val Trp Gly Ile Lys
                180                     185                     190

Gln Leu Gln Gly Ser Gln Ile Glu Leu Ala Val Leu Leu Ser Asn Glu
                195                     200                     205

Gly Ile Ile Asn Ser Glu Asp Glu His Leu Leu Ala Leu Glu Arg Lys
210                     215                     220

Leu Lys Lys Met Leu Gly Pro Ser Ala Val Glu Ile Gly Asn Gly Cys
225                     230                     235                     240

Phe Glu Thr Lys His Lys Cys Asn Gln Thr Cys Leu Asp Arg Ile Ala
                        245                     250                     255

Ala Gly Thr Phe Asp Ala Gly Glu Phe Ser Leu Pro Thr Phe Asp Ser
                260                     265                     270

Leu Asn Ile Thr Ser Gly Gly
        275

<210> SEQ ID NO 99
<211> LENGTH: 837
<212> TYPE: DNA
<213> ORGANISM: Influenza virus

<400> SEQUENCE: 99

```
gcctccggat gtgatattca ggctatcgaa ggtgggcaga gaaaactcgc cggcatcaaa      60
tgttccggcg gcaattctat ccaggcaggt ctggttgcac ttgtgctttg tctcaaagca     120
tccattgccg atttccacgg cgctaggtcc cagcatcttc ttcagctttc tttccagggc     180
cagcagatgt tcgtcctcgc tattgatgat gccctcgtta dacagcagca cagccagttc     240
aatctggctc ccctgcagct gcttgatgcc ccacactgtc agctgcagca ggtgctgctg     300
agcttcaatg gctcgcagca gattgttctg ctgctgcacg attccggagc ctcccccagt     360
cccattctcc tgctggttct ggctttcctc aatcagactg tagatgatag atgtgtagtt     420
gttgatttcg cgatcccact cggggtcgcc tccttccagc tcgctcaggc tgttcaggtt     480
cttggtgatc ttgttgatgg cttcctgtgt agatttcaga tcagcagcca ctgccacgcc     540
```

```
atgtgcgcca tgagatgtgt agccatgcca tccagcaatc attccctccc atccgccttc    600
cagaaagccg gcgatagctc caaaaaagcc tctctctttc agcagcttgg ctggaggtct    660
atactttgtg ccattggcca gcttcagtcc tgatcccaga gggatcacgc cggtcacatt    720
cacttcgccc tgtgtagctg ttttcacgac gtgagggcta ttgctgctgg tgatgccggt    780
acagattcta tcggcgttgc ttgtgaccac catcagcagc acgatgatgg ccttcat      837
```

<210> SEQ ID NO 100
<211> LENGTH: 1332
<212> TYPE: DNA
<213> ORGANISM: Artificial Sequence
<220> FEATURE:
<223> OTHER INFORMATION: Synthetic

<400> SEQUENCE: 100

```
atgaaggcca agctgctggt gctgctgtgc acctttaccg ccacctacgc cgacaccatc     60
tgcattggct accacgccaa caacagcacc gacaccgtgg ataccgtgct ggaaaagaac    120
gtgaccgtga cccacagcgt gaacctggga tccggactga aatggtcac  cggcctgaga    180 aacatcccca gcatccagag cagaggcctg tttggagcca ttgccggctt tattgagggc    240
ggatggaccg gaatggtgga tgggtggtac ggctaccacc accagaatga gcagggctct    300
ggctatgccg ccgatcagaa gtctacccag aacgccatca acggcatcac caacaaagtg    360
aacagcgtga tcgagaagat gggcggcgat cctgaatggg acagagagat caacaactac    420
accagcatca tctacagcct gatcgaggaa gccagaacc agcaggaaaa cggcacaggc    480
ggcggatctg gaattgtgca gcagcagaac aacctgctga gagccattga gcccagcag    540 catctgctgc agctgacagt gtggggcatc aagcagctgc agacctacaa tgccgagctg    600
ctggtcctcc tggaaaacga gagaaccctg gacttccacg cagcaacgt gaagaacctg    660 tacgagaaag tgaagtccca gctgaagaac aacgccaaag atcggcaa  cggctgcttc    720 gagttctacc acaagtgcaa caacgagtgc atggaaagcg tgaagaacgg cacctacgac    780
taccccaagt acagcgagga aagcaagctg aacagagaga gatcgactc cggaggcgac    840 atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac   1020
gtgcccgtgc agctgaccag catcagcgcc cccgagcaca gttcgaggg cctgacccag   1080 atcttccaga aggcctacga gcacgagcag cacatcagcg agagcatcaa caacatcgtg   1140
gaccacgcca tcaagagcaa ggaccacgcc accttcaact tcctgcagtg gtacgtggcc   1200
gagcagcacg aggaggaggt gctgttcaag gacatcctgg acaagatcga gctgatcggc   1260
aacgagaacc acggcctgta cctggccgac cagtacgtga agggcatcgc caagagcagg   1320
aagagcggat cc                                                     1332
```

<210> SEQ ID NO 101
<211> LENGTH: 444
<212> TYPE: PRT
<213> ORGANISM: Artificial Sequence
<220> FEATURE:
<223> OTHER INFORMATION: Synthetic

<400> SEQUENCE: 101

```
Met Lys Ala Lys Leu Leu Val Leu Leu Cys Thr Phe Thr Ala Thr Tyr
1               5                   10                  15
```

-continued

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asn Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
    290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
            340                 345                 350

His Lys Phe Glu Gly Leu Thr Gln Ile Phe Gln Lys Ala Tyr Glu His
        355                 360                 365

Glu Gln His Ile Ser Glu Ser Ile Asn Asn Ile Val Asp His Ala Ile
    370                 375                 380

Lys Ser Lys Asp His Ala Thr Phe Asn Phe Leu Gln Trp Tyr Val Ala
385                 390                 395                 400

Glu Gln His Glu Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
            420                 425                 430

Val Lys Gly Ile Ala Lys Ser Arg Lys Ser Gly Ser

<210> SEQ ID NO 102
<211> LENGTH: 1332
<212> TYPE: DNA
<213> ORGANISM: Artificial Sequence
<220> FEATURE:
<223> OTHER INFORMATION: Synthetic

<400> SEQUENCE: 102

| | |
|---|---|
| ggatccgctc ttcctgctct tggcgatgcc cttcacgtac tggtcggcca ggtacaggcc | 60 |
| gtggttctcg ttgccgatca gctcgatctt gtccaggatg tccttgaaca gcacctcctc | 120 |
| ctcgtgctgc tcggccacgt accactgcag gaagttgaag gtggcgtggt ccttgctctt | 180 |
| gatggcgtgg tccacgatgt tgttgatgct ctcgctgatg tgctgctcgt gctcgtaggc | 240 |
| cttctggaag atctgggtca ggccctcgaa cttgtgctcg ggggcgctga tgctggtcag | 300 |
| ctgcacgggc acgttgttct cgttcaggaa gatgatcagc ttcttggcgt gctcgtactc | 360 |
| ctcggcggcg tggtcgaaca ggaacaggcc ggcgccgtcc aggctgtggg tgtagcacca | 420 |
| gctgctcatg ctcatgtaca ggttgctgct ctgcatctcc ttgttcacct gctcgttcag | 480 |
| cagcttgatg atgtcgcctc cggagtcgat cttctctctg ttcagcttgc tttcctcgct | 540 |
| gtacttgggg tagtcgtagg tgccgttctt cacgctttcc atgcactcgt tgttgcactt | 600 |
| gtggtagaac tcgaagcagc cgttgccgat ctctttggcg ttgttcttca gctgggactt | 660 |
| cactttctcg tacaggttct tcacgttgct gtcgtggaag tccagggttc tctcgttttc | 720 |
| caggaggacc agcagctcgg cattgtaggt ctgcagctgc ttgatgcccc acactgtcag | 780 |
| ctgcagcaga tgctgctggg cctcaatggc tctcagcagg ttgttctgct gctgcacaat | 840 |
| tccagatccg ccgcctgtgc cgttttcctg ctggttctgg ctttcctcga tcaggctgta | 900 |
| gatgatgctg gtgtagttgt tgatctctct gtcccattca ggatcgccgc ccatcttctc | 960 |
| gatcacgctg ttcactttgt tggtgatgcc gttgatggcg ttctgggtag acttctgatc | 1020 |
| ggcggcatag ccagagccct gctcattctg gtggtggtag ccgtaccacc catccaccat | 1080 |
| tccggtccat ccgccctcaa taaagccggc aatggctcca acaggcctc tgctctggat | 1140 |
| gctggggatg tttctcaggc cggtgaccat tctcagtccg gatcccaggt tcacgctgtg | 1200 |
| ggtcacggtc acgttctttt ccagcacggt atccacggtg tcggtgctgt tgttggcgtg | 1260 |
| gtagccaatg cagatggtgt cggcgtaggt ggcggtaaag gtgcacagca gcaccagcag | 1320 |
| cttggccttc at | 1332 |

<210> SEQ ID NO 103
<211> LENGTH: 1332
<212> TYPE: DNA
<213> ORGANISM: Artificial Sequence
<220> FEATURE:
<223> OTHER INFORMATION: Synthetic

<400> SEQUENCE: 103

| | |
|---|---|
| atgaaggcta tcctggtggt gctgctgtac acctttgcca ccgccaatgc cgacaccctg | 60 |
| tgtattggct accacgccaa caacagcacc gacaccgtgg ataccgtgct ggaaaagaac | 120 |
| gtgaccgtga cccacagcgt gaacctgggc tccggcctga ctggccacg gcctgaga | 180 |
| aacatcccca gcattcagag cagaggcctg tttggagcca ttgccggctt tattgagggc | 240 |
| ggatggaccg gaatggtgga tgggtggtac ggctaccacc accagaatga gcagggctct | 300 |
| ggctatgccg ccgacctgaa gtctacccag aacgccatcg acgagatcac caacaaagtg | 360 |

```
aacagcgtga tcgagaagat gggcggctgg gacccatggg acagagagat caacaactac    420
accagcatca tctacagcct gatcgaggaa agccagaacc agcaggaaaa cggcacaggc    480
ggcggatctg gaattgtgca gcagcagaac aacctgctga gagccattga ggcccagcag    540
catctgctgc agctgacagt gtggggcatc aagcagctgc agacctacaa cgccgagctg    600
ctggtgctgc tcgagaatga gagaaccctg gactaccacg acagcaacgt gaagaacctg    660
tacgagaaag tgcggagcca gctgaagaac aacgccaaag atcggcaa cggctgcttc     720
gagttctacc acaagtgcga caatacctgc atggaaagcg tgaagaacgg cacctacgac    780
taccccaagt acagcgagga agccaagctg aaccgggaag atcgattc cggaggcgac     840
atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac    1020
gtgcccgtgc agctgaccag catcagcgcc cccgagcaca gttcgaggg cctgacccag     1080
atcttccaga aggcctacga gcacgagcag cacatcagcg agagcatcaa caacatcgtg    1140
gaccacgcca tcaagagcaa ggaccacgcc accttcaact tcctgcagtg gtacgtggcc    1200
gagcagcacg aggaggaggt gctgttcaag gacatcctgg acaagatcga gctgatcggc    1260
aacgagaacc acggcctgta cctggccgac cagtacgtga agggcatcgc caagagcagg    1320
aagagcggat cc                                                       1332

<210> SEQ ID NO 104
<211> LENGTH: 444
<212> TYPE: PRT
<213> ORGANISM: Artificial Sequence
<220> FEATURE:
<223> OTHER INFORMATION: Synthetic

<400> SEQUENCE: 104

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Leu Ala Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Leu Lys Ser Thr Gln Asn Ala
            100                 105                 110

Ile Asp Glu Ile Thr Asn Lys Val Asn Ser Val Ile Glu Lys Met Gly
        115                 120                 125

Gly Trp Asp Pro Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
```

```
                180                 185                 190
Leu Gln Thr Tyr Asn Ala Glu Leu Leu Val Leu Leu Glu Asn Glu Arg
                195                 200                 205

Thr Leu Asp Tyr His Asp Ser Asn Val Lys Asn Leu Tyr Glu Lys Val
                210                 215                 220

Arg Ser Gln Leu Lys Asn Asn Ala Lys Glu Ile Gly Asn Gly Cys Phe
225                 230                 235                 240

Glu Phe Tyr His Lys Cys Asp Asn Thr Cys Met Glu Ser Val Lys Asn
                245                 250                 255

Gly Thr Tyr Asp Tyr Pro Lys Tyr Ser Glu Glu Ala Lys Leu Asn Arg
                260                 265                 270

Glu Glu Ile Asp Ser Gly Gly Asp Ile Ile Lys Leu Leu Asn Glu Gln
                275                 280                 285

Val Asn Lys Glu Met Gln Ser Ser Asn Leu Tyr Met Ser Met Ser Ser
                290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
                340                 345                 350

His Lys Phe Glu Gly Leu Thr Gln Ile Phe Gln Lys Ala Tyr Glu His
                355                 360                 365

Glu Gln His Ile Ser Glu Ser Ile Asn Asn Ile Val Asp His Ala Ile
                370                 375                 380

Lys Ser Lys Asp His Ala Thr Phe Asn Phe Leu Gln Trp Tyr Val Ala
385                 390                 395                 400

Glu Gln His Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
                420                 425                 430

Val Lys Gly Ile Ala Lys Ser Arg Lys Ser Gly Ser
                435                 440

<210> SEQ ID NO 105
<211> LENGTH: 1332
<212> TYPE: DNA
<213> ORGANISM: Artificial Sequence
<220> FEATURE:
<223> OTHER INFORMATION: Synthetic

<400> SEQUENCE: 105
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300 ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggaatcgat ctcttcccgg ttcagcttgg cttcctcgct     540
gtacttgggg tagtcgtagg tgccgttctt cacgctttcc atgcaggtat tgtcgcactt     600
```

```
gtggtagaac tcgaagcagc cgttgccgat ctctttggcg ttgttcttca gctggctccg    660
cactttctcg tacaggttct tcacgttgct gtcgtggtag tccagggttc tctcattctc    720
gagcagcacc agcagctcgg cgttgtaggt ctgcagctgc ttgatgcccc acactgtcag    780
ctgcagcaga tgctgctggg cctcaatggc tctcagcagg ttgttctgct gctgcacaat    840
tccagatccg ccgcctgtgc cgtttcctg ctggttctgg ctttcctcga tcaggctgta    900
gatgatgctg gtgtagttgt tgatctctct gtcccatggg tcccagccgc ccatcttctc    960
gatcacgctg ttcactttgt tggtgatctc gtcgatggcg ttctgggtag acttcaggtc   1020
ggcggcatag ccagagccct gctcattctg gtggtggtag ccgtaccacc catccaccat   1080
tccggtccat ccgccctcaa taaagccggc aatggctcca acaggcctc tgctctgaat   1140 gctggggatg tttctcaggc cggtggccag tctcaggccg gagcccaggt tcacgctgtg   1200
ggtcacggtc acgttctttt ccagcacggt atccacggtg tcggtgctgt tgttggcgtg   1260
gtagccaata cacagggtgt cggcattggc ggtggcaaag gtgtacagca gcaccaccag   1320
gatagccttc at                                                        1332

<210> SEQ ID NO 106
<211> LENGTH: 1326
<212> TYPE: DNA
<213> ORGANISM: Artificial Sequence
<220> FEATURE:
<223> OTHER INFORMATION: Synthetic

<400> SEQUENCE: 106
atggccatca tctacctgat tctgctgttt acagccgtca gaggcgatca gatctgtatt     60
ggctaccacg ccaacaatag caccgagaaa gtggatacca tcctggaaag aaatgtgaca    120
gtgacacacg ccaaggatat tggatcagga ctggtgctgg ctacaggact gagaaatgtg    180
cctcagattg agagcagagg cctgtttgga gccattgctg gctttattga aggcggatgg    240
cagggaatga ttgatgggtg gtacggctac caccactcta atgatcaggg atctggatat    300
gccgccgaca agaatctac acagaaagcc ttcgacggca tcaccaacaa agtgaatagc    360
gtgatcgaga agatgggcgg agatcccgaa tgggacagag agatcaacaa ctacaccagc    420
atcatctaca gcctgatcga ggaaagccag aatcagcagg aaaatggaac aggcggagga    480
tctggaattg tgcagcagca gaacaatctg ctgagagcta ttgaagctca gcagcatctg    540
ctgaatctga cagtgtgggg aatcaaacag ctgcagacat acaatgctga gctgctggtg    600
ctgatggaaa atgagagaac cctggacttc acgacagca atgtgaagaa cctgtacgac    660
aaagtgcgga tgcagctgag agacaatgtg aagaactgg caatggctg cttcgagttc    720 taccacaagt gcgacgatga gtgtatgaac agcgtgaaga acggcaccta cgactaccct    780
aagtacgagg aagagagcaa gctgaacaga atgagatca agtccggagg cgacatcatc    840
aagctgctga cgagcaggt gaacaaggag atgcagagca gcaacctgta catgagcatg    900
agcagctggt gctacaccca gcctggac ggcgccggcc tgttcctgtt cgaccacgcc    960
gccgaggagt acgagcacgc caagaagctg atcatcttcc tgaacgagaa caacgtgccc   1020
gtgcagctga ccagcatcag cgcccccgag cacaagttcg agggcctgac ccagatcttc   1080
cagaaggcct acgagcacga gcagcacatc agcgagagca tcaacaacat cgtggaccac   1140
gccatcaaga gcaaggacca cgccaccttc aacttcctgc agtggtacgt ggccgagcag   1200
cacgaggagg aggtgctgtt caaggacatc ctggacaaga tcgagctgat cggcaacgag   1260
```

-continued

```
aaccacggcc tgtacctggc cgaccagtac gtgaagggca tcgccaagag caggaagagc    1320
ggatcc                                                                1326
```

<210> SEQ ID NO 107
<211> LENGTH: 442
<212> TYPE: PRT
<213> ORGANISM: Artificial Sequence
<220> FEATURE:
<223> OTHER INFORMATION: Synthetic

<400> SEQUENCE: 107

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Gly
        35                  40                  45

Ser Gly Leu Val Leu Ala Thr Gly Leu Arg Asn Val Pro Gln Ile Glu
    50                  55                  60

Ser Arg Gly Leu Phe Gly Ala Ile Ala Gly Phe Ile Glu Gly Gly Trp
65                  70                  75                  80

Gln Gly Met Ile Asp Gly Trp Tyr Gly Tyr His His Ser Asn Asp Gln
                85                  90                  95

Gly Ser Gly Tyr Ala Ala Asp Lys Glu Ser Thr Gln Lys Ala Phe Asp
            100                 105                 110

Gly Ile Thr Asn Lys Val Asn Ser Val Ile Glu Lys Met Gly Gly Asp
        115                 120                 125

Pro Glu Trp Asp Arg Glu Ile Asn Asn Tyr Thr Ser Ile Ile Tyr Ser
    130                 135                 140

Leu Ile Glu Glu Ser Gln Asn Gln Gln Glu Asn Gly Thr Gly Gly Gly
145                 150                 155                 160

Ser Gly Ile Val Gln Gln Gln Asn Asn Leu Leu Arg Ala Ile Glu Ala
                165                 170                 175

Gln Gln His Leu Leu Asn Leu Thr Val Trp Gly Ile Lys Gln Leu Gln
            180                 185                 190

Thr Tyr Asn Ala Glu Leu Leu Val Leu Met Glu Asn Glu Arg Thr Leu
        195                 200                 205

Asp Phe His Asp Ser Asn Val Lys Asn Leu Tyr Asp Lys Val Arg Met
    210                 215                 220

Gln Leu Arg Asp Asn Val Lys Glu Leu Gly Asn Gly Cys Phe Glu Phe
225                 230                 235                 240

Tyr His Lys Cys Asp Asp Glu Cys Met Asn Ser Val Lys Asn Gly Thr
                245                 250                 255

Tyr Asp Tyr Pro Lys Tyr Glu Glu Ser Lys Leu Asn Arg Asn Glu
            260                 265                 270

Ile Lys Ser Gly Gly Asp Ile Ile Lys Leu Leu Asn Glu Gln Val Asn
        275                 280                 285

Lys Glu Met Gln Ser Ser Asn Leu Tyr Met Ser Met Ser Ser Trp Cys
    290                 295                 300

Tyr Thr His Ser Leu Asp Gly Ala Gly Leu Phe Leu Phe Asp His Ala
305                 310                 315                 320

Ala Glu Glu Tyr Glu His Ala Lys Lys Leu Ile Ile Phe Leu Asn Glu
                325                 330                 335

Asn Asn Val Pro Val Gln Leu Thr Ser Ile Ser Ala Pro Glu His Lys
            340                 345                 350
```

```
Phe Glu Gly Leu Thr Gln Ile Phe Gln Lys Ala Tyr Glu His Glu Gln
            355                 360                 365

His Ile Ser Glu Ser Ile Asn Asn Ile Val Asp His Ala Ile Lys Ser
    370                 375                 380

Lys Asp His Ala Thr Phe Asn Phe Leu Gln Trp Tyr Val Ala Glu Gln
385                 390                 395                 400

His Glu Glu Val Leu Phe Lys Asp Ile Leu Asp Lys Ile Glu Leu
                405                 410                 415

Ile Gly Asn Glu Asn His Gly Leu Tyr Leu Ala Asp Gln Tyr Val Lys
            420                 425                 430

Gly Ile Ala Lys Ser Arg Lys Ser Gly Ser
            435                 440
```

<210> SEQ ID NO 108
<211> LENGTH: 1326
<212> TYPE: DNA
<213> ORGANISM: Artificial Sequence
<220> FEATURE:
<223> OTHER INFORMATION: Synthetic

<400> SEQUENCE: 108

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggacttgat ctcatttctg ttcagcttgc tctcttcctc     540
gtacttaggg tagtcgtagg tgccgttctt cacgctgttc atacactcat cgtcgcactt     600
gtggtagaac tcgaagcagc cattgcccag ttctttcaca ttgtctctca gctgcatccg     660
cactttgtcg tacaggttct tcacattgct gtcgtggaag tccagggttc tctcattttc     720
catcagcacc agcagctcag cattgtatgt ctgcagctgt tgattcccc acactgtcag     780
attcagcaga tgctgctgag cttcaatagc tctcagcaga ttgttctgct gctgcacaat     840
tccagatcct ccgcctgttc cattttcctg ctgattctgg ctttcctcga tcaggctgta     900
gatgatgctg gtgtagttgt tgatctctct gtcccattcg ggatctccgc ccatcttctc     960
gatcacgcta ttcactttgt tggtgatgcc gtcgaaggct ttctgtgtag attctttgtc    1020
ggcggcatat ccagatccct gatcattaga gtggtggtag ccgtaccacc catcaatcat    1080
tccctgccat ccgccttcaa taaagccagc aatggctcca acaggcctc tgctctcaat    1140
ctgaggcaca tttctcagtc ctgtagccag caccagtcct gatccaatat ccttggcgtg    1200
tgtcactgtc acatttcttt ccaggatggt atccactttc tcggtgctat tgttggcgtg    1260
gtagccaata cagatctgat cgcctctgac ggctgtaaac agcagaatca ggtagatgat    1320
ggccat                                                                1326
```

<210> SEQ ID NO 109
<211> LENGTH: 1362
<212> TYPE: DNA

<213> ORGANISM: Artificial Sequence
<220> FEATURE:
<223> OTHER INFORMATION: Synthetic

<400> SEQUENCE: 109

```
atgaagacca tcatcgccct gagctacatc ttctgcctgg ccctgggcca ggacctgccc      60
ggcaacgaca acagcaccgc caccctgtgc ctgggccacc acgccgtgcc caacggcacc     120
ctggtgaaga ccatcaccga cgaccagatc gaggtgacca acgccaccga gctgggctcc     180
ggcctgaagc tggccaccgg catgcggaac gtgcccgaga agcagacccg gggcctgttc     240
ggcgccatcg ccggcttcat cgagaacggc tgggagggca tgatcgacgg ctggtacggc     300
ttccggcacc agaacagcga gggcaccggc caggccgccg acctgaagag cacccaggcc     360
gccatcgacc agatcaacgg caagctgaac cgggtgatcg agaagaccgg cggcgatccc     420
gagtgggacc gggagatcaa caactacacc agcatcatct acagcctgat cgaggagagc     480
cagaaccagc aggagaacgg caccggcggc ggcagcggca tcgtgcagca gcagaacaac     540
ctgctgcggg ccatcgaggc ccagcagcac ctgctgcagc tgaccgtgtg gggcatcaag     600
cagctgcaga gctacaacgc cgagctgctg gtggccctgg agaaccagca ccatcgac     660
ctgaccgaca gcgagatgaa caagctgttc gagaagaccc ggcggcagct gcgggagaac     720
gccgaggaca tgggcaacgg ctgcttcaag atctaccaca gtgcgacaa cgcctgcatc     780
gagagcatcc ggaacggcac ctacgaccac acgtgtacc gggacgaggc cctgaacaac     840
cggttccaga tcaagggctc cggaggcgac atcatcaagc tgctgaacga gcaggtgaac     900
aaggagatgc agagcagcaa cctgtacatg agcatgagca gctggtgcta cacccacagc     960
ctggacggcg ccggcctgtt cctgttcgac cacgccgccg aggagtacga gcacgccaag    1020
aagctgatca tcttcctgaa cgagaacaac gtgcccgtgc agctgaccag catcagcgcc    1080
cccgagcaca gttcgaggg cctgacccag atcttccaga aggcctacga gcacgagcag    1140
cacatcagcg agagcatcaa caacatcgtg gaccacgcca tcaagagcaa ggaccacgcc    1200
accttcaact tcctgcagtg gtacgtggcc gagcagcacg aggaggaggt gctgttcaag    1260
gacatcctgg acaagatcga gctgatcggc aacgagaacc acggcctgta cctggccgac    1320
cagtacgtga agggcatcgc caagagcagg aagagcggat cc                       1362
```

<210> SEQ ID NO 110
<211> LENGTH: 454
<212> TYPE: PRT
<213> ORGANISM: Artificial Sequence
<220> FEATURE:
<223> OTHER INFORMATION: Synthetic

<400> SEQUENCE: 110

```
Met Lys Thr Ile Ile Ala Leu Ser Tyr Ile Phe Cys Leu Ala Leu Gly
  1               5                  10                  15

Gln Asp Leu Pro Gly Asn Asp Asn Ser Thr Ala Thr Leu Cys Leu Gly
             20                  25                  30

His His Ala Val Pro Asn Gly Thr Leu Val Lys Thr Ile Thr Asp Asp
         35                  40                  45

Gln Ile Glu Val Thr Asn Ala Thr Glu Leu Gly Ser Gly Leu Lys Leu
     50                  55                  60

Ala Thr Gly Met Arg Asn Val Pro Glu Lys Gln Thr Arg Gly Leu Phe
 65                  70                  75                  80

Gly Ala Ile Ala Gly Phe Ile Glu Asn Gly Trp Glu Gly Met Ile Asp
                 85                  90                  95
```

Gly Trp Tyr Gly Phe Arg His Gln Asn Ser Glu Gly Thr Gly Gln Ala
                100                 105                 110

Ala Asp Leu Lys Ser Thr Gln Ala Ile Asp Gln Ile Asn Gly Lys
            115                 120                 125

Leu Asn Arg Val Ile Glu Lys Thr Gly Gly Asp Pro Glu Trp Asp Arg
        130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Arg Arg Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Glu Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly Asp Ile Ile Lys Leu Leu Asn Glu Gln Val Asn Lys Glu Met Gln
    290                 295                 300

Ser Ser Asn Leu Tyr Met Ser Met Ser Ser Trp Cys Tyr Thr His Ser
305                 310                 315                 320

Leu Asp Gly Ala Gly Leu Phe Leu Phe Asp His Ala Ala Glu Glu Tyr
                325                 330                 335

Glu His Ala Lys Lys Leu Ile Ile Phe Leu Asn Glu Asn Asn Val Pro
            340                 345                 350

Val Gln Leu Thr Ser Ile Ser Ala Pro Glu His Lys Phe Glu Gly Leu
        355                 360                 365

Thr Gln Ile Phe Gln Lys Ala Tyr Glu His Glu Gln His Ile Ser Glu
    370                 375                 380

Ser Ile Asn Asn Ile Val Asp His Ala Ile Lys Ser Lys Asp His Ala
385                 390                 395                 400

Thr Phe Asn Phe Leu Gln Trp Tyr Val Ala Glu Gln His Glu Glu Glu
                405                 410                 415

Val Leu Phe Lys Asp Ile Leu Asp Lys Ile Glu Leu Ile Gly Asn Glu
            420                 425                 430

Asn His Gly Leu Tyr Leu Ala Asp Gln Tyr Val Lys Gly Ile Ala Lys
        435                 440                 445

Ser Arg Lys Ser Gly Ser
    450

<210> SEQ ID NO 111
<211> LENGTH: 1362
<212> TYPE: DNA
<213> ORGANISM: Artificial Sequence
<220> FEATURE:
<223> OTHER INFORMATION: Synthetic

<400> SEQUENCE: 111

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggagccctt gatctggaac cggttgttca gggcctcgtc     540
ccggtacacg tcgtggtcgt aggtgccgtt ccggatgctc tcgatgcagg cgttgtcgca     600
cttgtggtag atcttgaagc agccgttgcc catgtcctcg gcgttctccc gcagctgccg     660
ccgggtcttc tcgaacagct tgttcatctc gctgtcggtc aggtcgatgg tgtgctggtt     720
ctccagggcc accagcagct cggcgttgta gctctgcagc tgcttgatgc cccacacggt     780
cagctgcagc aggtgctgct gggcctcgat ggcccgcagc aggttgttct gctgctgcac     840
gatgccgctg ccgccgccgg tgccgttctc ctgctggttc tggctctcct cgatcaggct     900
gtagatgatg ctggtgtagt tgttgatctc ccggtcccac tcgggatcgc cgccggtctt     960
ctcgatcacc cggttcagct tgccgttgat ctggtcgatg gcggcctggg tgctcttcag    1020
gtcggcggcc tggccggtgc cctcgctgtt ctggtgccgg aagccgtacc agccgtcgat    1080
catgccctcc cagccgttct cgatgaagcc ggcgatggcg ccgaacaggc cccgggtctg    1140
cttctcgggc acgttccgca tgccggtggc cagcttcagg ccggagccca gctcggtggc    1200
gttggtcacc tcgatctggt cgtcggtgat ggtcttcacc agggtgccgt tgggcacggc    1260
gtggtggccc aggcacaggg tggcggtgct gttgtcgttg ccgggcaggt cctggcccag    1320
ggccaggcag aagatgtagc tcagggcgat gatggtcttc at                       1362

<210> SEQ ID NO 112
<211> LENGTH: 1341
<212> TYPE: DNA
<213> ORGANISM: Artificial Sequence
<220> FEATURE:
<223> OTHER INFORMATION: Synthetic

<400> SEQUENCE: 112
atggagaaga tcgtgctgct gctggccatc gtgagcctgg tgaagagcga ccagatctgc      60
atcggctacc acgccaacaa cagcaccgag caggtggaca ccatcatgga agaacgtg       120 accgtgaccc cgcccagga catcggctcc ggcctggtgc tggccaccgg cctgcggaac      180
agcccccagc gggagagccg gcggaagaag cggggcctgt tcggcgccat cgccggcttc      240
atcgagggcg gctggcaggg catggtggac ggctggtacg gctaccacca cagcaacgag      300
cagggcagcg gctacgccgc cgacaaggag agcacccaga aggccatcga cggcgtgacc      360
aacaaggtga acagcatcat cgacaagatg ggcggcgatc cgagtgggca ccgggagatc      420
aacaactaca ccagcatcat ctacagcctg atcgaggaga ccagaaacca gcaggagaac      480
ggcaccggcg gcggcagcgg catcgtgcag cagcagaaca acctgctgcg ggccatcgag      540
gcccagcagc acctgctgca gctgaccgtg tggggcatca agcagctgca gacctacaac      600
gccgagctgc tggtgctgat ggagaacgag cggaccctgg acttccacga cagcaacgtg      660
```

```
aagaacctgt acgacaaggt gcggctgcag ctgcgggaca cgccaagga gctgggcaac        720 ggctgcttcg agttctacca caagtgcgac aacgagtgca tggagagcat ccggaacggc        780
acctacaact accccccagta cagcgaggag gcccggctga agcgggagga gatcagctcc       840
ggaggcgaca tcatcaagct gctgaacgag caggtgaaca aggagatgca gagcagcaac        900
ctgtacatga gcatgagcag ctggtgctac acccacagcc tggacggcgc cggcctgttc        960
ctgttcgacc acgccgccga ggagtacgag cacgccaaga agctgatcat cttcctgaac       1020
gagaacaacg tgcccgtgca gctgaccagc atcagcgccc ccgagcacaa gttcgagggc       1080
ctgacccaga tcttccagaa ggcctacgag cacgagcagc acatcagcga gagcatcaac       1140
aacatcgtgg accacgccat caagagcaag gaccacgcca ccttcaactt cctgcagtgg       1200
tacgtggccg agcagcacga ggaggaggtg ctgttcaagg acatcctgga caagatcgag       1260
ctgatcggca cgagaaccca cggcctgtac ctggccgacc agtacgtgaa gggcatcgcc       1320
aagagcagga agagcggatc c                                                 1341
```

<210> SEQ ID NO 113
<211> LENGTH: 447
<212> TYPE: PRT
<213> ORGANISM: Artificial Sequence
<220> FEATURE:
<223> OTHER INFORMATION: Synthetic

<400> SEQUENCE: 113

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Gly Ser Gly Leu Val Leu Ala Thr Gly Leu Arg Asn Ser Pro Gln Arg
    50                  55                  60

Glu Ser Arg Arg Lys Lys Arg Gly Leu Phe Gly Ala Ile Ala Gly Phe
65                  70                  75                  80

Ile Glu Gly Gly Trp Gln Gly Met Val Asp Gly Trp Tyr Gly Tyr His
                85                  90                  95

His Ser Asn Glu Gln Gly Ser Gly Tyr Ala Ala Asp Lys Glu Ser Thr
            100                 105                 110

Gln Lys Ala Ile Asp Gly Val Thr Asn Lys Val Asn Ser Ile Ile Asp
        115                 120                 125

Lys Met Gly Gly Asp Pro Glu Trp Asp Arg Glu Ile Asn Asn Tyr Thr
    130                 135                 140

Ser Ile Ile Tyr Ser Leu Ile Glu Glu Ser Gln Asn Gln Gln Glu Asn
145                 150                 155                 160

Gly Thr Gly Gly Gly Ser Gly Ile Val Gln Gln Gln Asn Asn Leu Leu
                165                 170                 175

Arg Ala Ile Glu Ala Gln Gln His Leu Leu Gln Leu Thr Val Trp Gly
            180                 185                 190

Ile Lys Gln Leu Gln Thr Tyr Asn Ala Glu Leu Leu Val Leu Met Glu
        195                 200                 205

Asn Glu Arg Thr Leu Asp Phe His Asp Ser Asn Val Lys Asn Leu Tyr
    210                 215                 220

Asp Lys Val Arg Leu Gln Leu Arg Asp Asn Ala Lys Glu Leu Gly Asn
225                 230                 235                 240
```

| | | | | | | | | | | | |
|---|---|---|---|---|---|---|---|---|---|---|---|
|Gly|Cys|Phe|Glu|Phe|Tyr|His|Lys|Cys|Asp|Asn|Glu|Cys|Met|Glu|Ser|
| | | | |245| | | |250| | | |255| | | |

Ile Arg Asn Gly Thr Tyr Asn Tyr Pro Gln Tyr Ser Glu Glu Ala Arg
            260                 265                 270

Leu Lys Arg Glu Glu Ile Ser Ser Gly Gly Asp Ile Ile Lys Leu Leu
        275                 280                 285

Asn Glu Gln Val Asn Lys Glu Met Gln Ser Ser Asn Leu Tyr Met Ser
    290                 295                 300

Met Ser Ser Trp Cys Tyr Thr His Ser Leu Asp Gly Ala Gly Leu Phe
305                 310                 315                 320

Leu Phe Asp His Ala Ala Glu Glu Tyr Glu His Ala Lys Lys Leu Ile
                325                 330                 335

Ile Phe Leu Asn Glu Asn Asn Val Pro Val Gln Leu Thr Ser Ile Ser
            340                 345                 350

Ala Pro Glu His Lys Phe Glu Gly Leu Thr Gln Ile Phe Gln Lys Ala
        355                 360                 365

Tyr Glu His Glu Gln His Ile Ser Glu Ser Ile Asn Asn Ile Val Asp
    370                 375                 380

His Ala Ile Lys Ser Lys Asp His Ala Thr Phe Asn Phe Leu Gln Trp
385                 390                 395                 400

Tyr Val Ala Glu Gln His Glu Glu Val Leu Phe Lys Asp Ile Leu
                405                 410                 415

Asp Lys Ile Glu Leu Ile Gly Asn Glu Asn His Gly Leu Tyr Leu Ala
                420                 425                 430

Asp Gln Tyr Val Lys Gly Ile Ala Lys Ser Arg Lys Ser Gly Ser
    435                 440                 445

<210> SEQ ID NO 114
<211> LENGTH: 1341
<212> TYPE: DNA
<213> ORGANISM: Artificial Sequence
<220> FEATURE:
<223> OTHER INFORMATION: Synthetic

<400> SEQUENCE: 114

```
ggatccgctc ttcctgctct tggcgatgcc cttcacgtac tggtcggcca ggtacaggcc    60
gtggttctcg ttgccgatca gctcgatctt gtccaggatg tccttgaaca gcacctcctc   120
ctcgtgctgc tcggccacgt accactgcag gaagttgaag gtggcgtggt ccttgctctt   180
gatggcgtgg tccacgatgt tgttgatgct ctcgctgatg tgctgctcgt gctcgtaggc   240
cttctggaag atctgggtca ggccctcgaa cttgtgctcg gggcgctga tgctggtcag   300 ctgcacgggc acgttgttct cgttcaggaa gatgatcagc ttcttggcgt gctcgtactc   360
ctcggcggcg tggtcgaaca ggaacaggcc ggcgccgtcc aggctgtggg tgtagcacca   420
gctgctcatg ctcatgtaca ggttgctgct ctgcatctcc ttgttcacct gctcgttcag   480
cagcttgatg atgtcgcctc cggagctgat ctcctcccgc ttcagccggg cctcctcgct   540
gtactggggg tagttgtagg tgccgttccg gatgctctcc atgcactcgt tgtcgcactt   600
gtggtagaac tcgaagcagc cgttgcccag ctccttggcg ttgtcccgca gctgcagccg   660
caccttgtcg tacaggttct tcacgttgct gtcgtggaag tccagggtcc gctcgttctc   720
catcagcacc agcagctcgg cgttgtaggt ctgcagctgc ttgatgcccc acacggtcag   780
ctgcagcagg tgctgctggg cctcgatggc ccgcagcagg ttgttctgct gctgcacgat   840
gccgctgccg ccgccggtgc cgttctcctg ctggttctgg ctctcctcga tcaggctgta   900
```

```
gatgatgctg gtgtagttgt tgatctcccg gtcccactcg ggatcgccgc ccatcttgtc    960
gatgatgctg ttcaccttgt tggtcacgcc gtcgatggcc ttctgggtgc tctccttgtc   1020
ggcggcgtag ccgctgccct gctcgttgct gtggtggtag ccgtaccagc cgtccaccat   1080
gccctgccag ccgccctcga tgaagccggc gatggcgccg aacaggcccc gcttcttccg   1140
ccggctctcc cgctgggggc tgttccgcag gccggtggcc agcaccaggc cggagccgat   1200
gtcctgggcg tgggtcacgg tcacgttctt ctccatgatg gtgtccacct gctcggtgct   1260
gttgttggcg tggtagccga tgcagatctg gtcgctcttc accaggctca cgatggccag   1320
cagcagcacg atcttctcca t                                             1341

<210> SEQ ID NO 115
<211> LENGTH: 1332
<212> TYPE: DNA
<213> ORGANISM: Artificial Sequence
<220> FEATURE:
<223> OTHER INFORMATION: Synthetic

<400> SEQUENCE: 115
atgaaagtga agctgctggt gctgctgtgt acctttaccg ccacctacgc cgataccatc     60
tgtatcggct accacgccaa caatagcacc gacaccgtgg ataccgtgct ggaaaagaac    120
gtgaccgtga cccacagcgt gaacctggga tcaggactga aatggtgac cggcctgagg     180 aatatcccca gcatccagag cagaggcctg tttggcgcca ttgccggctt tatcgagggc    240
ggatggacag gcatggtgga tgggtggtac ggctaccacc accagaatga gcagggatct    300
ggctatgccg ccgatcagaa gagcacccag aacgccatca cggcatcac caacaaagtg    360 aacagcgtga tcgagaagat gggcggcgat cctgaatggg acagagagat caacaactac    420
accagcatca tctacagcct gatcgaggaa gccagaacc agcaggaaaa cggcacaggc    480
ggcggatctg gaattgtgca gcagcagaac aacctgctga gagccattga ggcccagcag    540
catctgctgc agctgacagt gtggggcatc aagcagctgc agacctacaa cgccgaactc    600
ctggtcctcc tggaaaatga gaggaccctg gacttccacg acagcaacgt gaagaacctg    660
tacgagaaag tgaagagcca gctgaagaac aacgccaaag atcggcaa cggctgcttc    720 gagttctacc acaagtgcaa cgacgagtgc atggaaagcg tgaagaacgg cacctacgac    780
taccccaagt acagcgagga aagcaagctg aaccgggaga gatcgattc cggaggcgac    840 atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac   1020
gtgcccgtgc agctgaccag catcagcgcc cccgagcaca gttcgaggg cctgacccag   1080 atcttccaga aggcctacga gcacgagcag cacatcagcg agagcatcaa caacatcgtg   1140
gaccacgcca tcaagagcaa ggaccacgcc accttcaact tcctgcagtg gtacgtggcc   1200
gagcagcacg aggaggaggt gctgttcaag gacatcctgg acaagatcga gctgatcggc   1260
aacgagaacc acggcctgta cctggccgac cagtacgtga agggcatcgc caagagcagg   1320
aagagcggat cc                                                       1332

<210> SEQ ID NO 116
<211> LENGTH: 444
<212> TYPE: PRT
<213> ORGANISM: Artificial Sequence
<220> FEATURE:
<223> OTHER INFORMATION: Synthetic
```

<400> SEQUENCE: 116

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asp Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
            340                 345                 350

His Lys Phe Glu Gly Leu Thr Gln Ile Phe Gln Lys Ala Tyr Glu His
        355                 360                 365

Glu Gln His Ile Ser Glu Ser Ile Asn Asn Ile Val Asp His Ala Ile
370                 375                 380

Lys Ser Lys Asp His Ala Thr Phe Asn Phe Leu Gln Trp Tyr Val Ala
385                 390                 395                 400

Glu Gln His Glu Glu Glu Val Leu Phe Lys Asp Ile Leu Asp Lys Ile

|  |  |  |  | 405 |  |  |  | 410 |  |  |  | 415 |  |
|---|---|---|---|---|---|---|---|---|---|---|---|---|---|
| Glu | Leu | Ile | Gly | Asn | Glu | Asn | His | Gly | Leu | Tyr | Leu | Ala | Asp | Gln | Tyr |
|  |  |  | 420 |  |  |  | 425 |  |  |  | 430 |  |  |

| Val | Lys | Gly | Ile | Ala | Lys | Ser | Arg | Lys | Ser | Gly | Ser |
|---|---|---|---|---|---|---|---|---|---|---|---|
|  |  |  | 435 |  |  |  | 440 |  |  |  |  |

<210> SEQ ID NO 117
<211> LENGTH: 1332
<212> TYPE: DNA
<213> ORGANISM: Artificial Sequence
<220> FEATURE:
<223> OTHER INFORMATION: Synthetic

<400> SEQUENCE: 117

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggaatcgat cttctcccgg ttcagcttgc tttcctcgct     540
gtacttgggg tagtcgtagg tgccgttctt cacgctttcc atgcactcgt cgttgcactt     600
gtggtagaac tcgaagcagc cgttgccgat ctctttggcg ttgttcttca gctggctctt     660
cactttctcg tacaggttct tcacgttgct gtcgtgaag tccagggtcc tctcattttc     720
caggaggacc aggagttcgg cgttgtaggt ctgcagctgc ttgatgcccc acactgtcag     780
ctgcagcaga tgctgctggg cctcaatggc tctcagcagg ttgttctgct gctgcacaat     840
tccagatccg ccgcctgtgc cgttttcctg ctggttctgg ctttcctcga tcaggctgta     900
gatgatgctg gtgtagttgt tgatctctct gtcccattca ggatcgccgc ccatcttctc     960
gatcacgctg ttcactttgt tggtgatgcc gttgatggcg ttctgggtgc tcttctgatc    1020
ggcggcatag ccagatccct gctcattctg gtggtggtag ccgtaccacc catccaccat    1080
gcctgtccat ccgccctcga taaagccggc aatggcgcca acaggcctc tgctctggat    1140
gctggggata ttcctcaggc cggtcaccat tctcagtcct gatcccaggt tcacgctgtg    1200
ggtcacggtc acgttctttt ccagcacggt atccacggtg tcggtgctat tgttggcgtg    1260
gtagccgata cagatggtat cggcgtaggt ggcggtaaag gtacacagca gcaccagcag    1320
cttcactttc at                                                        1332
```

<210> SEQ ID NO 118
<211> LENGTH: 1362
<212> TYPE: DNA
<213> ORGANISM: Artificial Sequence
<220> FEATURE:
<223> OTHER INFORMATION: Synthetic

<400> SEQUENCE: 118

```
atgaaaacca tcattgccct gagctacatc ctgtgcctgg tgttcacaca gaagctgccc      60
ggcaacgata atagcaccgc cacactgtgt ctgggacacc acgccgtgcc taatggcacc     120
atcgtgaaaa caatcaccaa cgaccagatc gaagtgacca atgccacaga gctgggctcc     180
```

```
ggcctgaagc tggccaccgg catgagaaat gtgcccgaga agcagaccag aggcatcttt    240
ggcgccattg ccggctttat cgagaatggc tgggagggaa tggtggatgg gtggtacggc    300
ttcagacacc agaatagcga gggaattgga caggccgccg atctgaaatc tacccaggcc    360
gccatcgacc agatcaacgg caagctgaac aggctgatcg gcaagaccgg cggcgatccc    420
gagtgggacc gggagatcaa caactacacc agcatcatct acagcctgat cgaggagagc    480
cagaaccagc aggagaacgg caccggcggc ggcagcggca tcgtgcagca gcagaacaac    540
ctgctgcggg ccatcgaggc ccagcagcac ctgctgcagc tgaccgtgtg gggcatcaag    600
cagctgcaga gctacaatgc cgaactgctg gtcgccctgg aaaaccagca cacaattgat    660
ctgacagaca gtgagatgaa taagctgttc gagaaaacca gaagcagct gagagaaaac     720 gccgaggaca tgggcaacgg ctgcttcaag atctaccaca gtgcgacaa cgcctgcatc     780 ggcagcatca gaaacggcac ctacgaccac gacgtgtaca gagatgaggc cctgaacaac    840
cggtttcaga tcaagggctc cggaggcgac atcatcaagc tgctgaacga gcaggtgaac    900
aaggagatgc agagcagcaa cctgtacatg agcatgagca gctggtgcta cacccacagc    960
ctggacggcg ccggcctgtt cctgttcgac cacgccgccg aggagtacga gcacgccaag    1020
aagctgatca tcttcctgaa cgagaacaac gtgcccgtgc agctgaccag catcagcgcc    1080
cccgagcaca gttcgaggg cctgacccag atcttccaga aggcctacga gcacgagcag    1140
cacatcagcg agagcatcaa caacatcgtg gaccacgcca tcaagagcaa ggaccacgcc    1200
accttcaact tcctgcagtg gtacgtggcc gagcagcacg aggaggaggt gctgttcaag    1260
gacatcctgg acaagatcga gctgatcggc aacgagaacc acggcctgta cctggccgac    1320
cagtacgtga agggcatcgc caagagcagg aagagcggat cc                       1362
```

<210> SEQ ID NO 119
<211> LENGTH: 454
<212> TYPE: PRT
<213> ORGANISM: Artificial Sequence
<220> FEATURE:
<223> OTHER INFORMATION: Synthetic

<400> SEQUENCE: 119

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Ile Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
```

| | | | | | | | | | | | | | | | |
|---|---|---|---|---|---|---|---|---|---|---|---|---|---|---|---|
| | 145 | | | | 150 | | | | | 155 | | | | 160 | |
| Gln | Asn | Gln | Gln | Glu | Asn | Gly | Thr | Gly | Gly | Ser | Gly | Ile | Val | Gln | |
| | | | | 165 | | | | | 170 | | | | | 175 | |
| Gln | Gln | Asn | Asn | Leu | Leu | Arg | Ala | Ile | Glu | Ala | Gln | Gln | His | Leu | Leu |
| | | | 180 | | | | | 185 | | | | | 190 | | |
| Gln | Leu | Thr | Val | Trp | Gly | Ile | Lys | Gln | Leu | Gln | Ser | Tyr | Asn | Ala | Glu |
| | | 195 | | | | | 200 | | | | | 205 | | | |
| Leu | Leu | Val | Ala | Leu | Glu | Asn | Gln | His | Thr | Ile | Asp | Leu | Thr | Asp | Ser |
| | 210 | | | | | 215 | | | | | 220 | | | | |
| Glu | Met | Asn | Lys | Leu | Phe | Glu | Lys | Thr | Lys | Lys | Gln | Leu | Arg | Glu | Asn |
| 225 | | | | | 230 | | | | | 235 | | | | | 240 |
| Ala | Glu | Asp | Met | Gly | Asn | Gly | Cys | Phe | Lys | Ile | Tyr | His | Lys | Cys | Asp |
| | | | | 245 | | | | | 250 | | | | | 255 | |
| Asn | Ala | Cys | Ile | Gly | Ser | Ile | Arg | Asn | Gly | Thr | Tyr | Asp | His | Asp | Val |
| | | | 260 | | | | | 265 | | | | | 270 | | |
| Tyr | Arg | Asp | Glu | Ala | Leu | Asn | Asn | Arg | Phe | Gln | Ile | Lys | Gly | Ser | Gly |
| | | 275 | | | | | 280 | | | | | 285 | | | |
| Gly | Asp | Ile | Ile | Lys | Leu | Leu | Asn | Glu | Gln | Val | Asn | Lys | Glu | Met | Gln |
| | 290 | | | | | 295 | | | | | 300 | | | | |
| Ser | Ser | Asn | Leu | Tyr | Met | Ser | Met | Ser | Ser | Trp | Cys | Tyr | Thr | His | Ser |
| 305 | | | | | 310 | | | | | 315 | | | | | 320 |
| Leu | Asp | Gly | Ala | Gly | Leu | Phe | Leu | Phe | Asp | His | Ala | Ala | Glu | Glu | Tyr |
| | | | | 325 | | | | | 330 | | | | | 335 | |
| Glu | His | Ala | Lys | Lys | Leu | Ile | Ile | Phe | Leu | Asn | Glu | Asn | Asn | Val | Pro |
| | | | 340 | | | | | 345 | | | | | 350 | | |
| Val | Gln | Leu | Thr | Ser | Ile | Ser | Ala | Pro | Glu | His | Lys | Phe | Glu | Gly | Leu |
| | | 355 | | | | | 360 | | | | | 365 | | | |
| Thr | Gln | Ile | Phe | Gln | Lys | Ala | Tyr | Glu | His | Glu | Gln | His | Ile | Ser | Glu |
| | 370 | | | | | 375 | | | | | 380 | | | | |
| Ser | Ile | Asn | Asn | Ile | Val | Asp | His | Ala | Ile | Lys | Ser | Lys | Asp | His | Ala |
| 385 | | | | | 390 | | | | | 395 | | | | | 400 |
| Thr | Phe | Asn | Phe | Leu | Gln | Trp | Tyr | Val | Ala | Glu | Gln | His | Glu | Glu | Glu |
| | | | | 405 | | | | | 410 | | | | | 415 | |
| Val | Leu | Phe | Lys | Asp | Ile | Leu | Asp | Lys | Ile | Glu | Leu | Ile | Gly | Asn | Glu |
| | | | 420 | | | | | 425 | | | | | 430 | | |
| Asn | His | Gly | Leu | Tyr | Leu | Ala | Asp | Gln | Tyr | Val | Lys | Gly | Ile | Ala | Lys |
| | | 435 | | | | | 440 | | | | | 445 | | | |
| Ser | Arg | Lys | Ser | Gly | Ser | | | | | | | | | | |
| | 450 | | | | | | | | | | | | | | |

<210> SEQ ID NO 120
<211> LENGTH: 1362
<212> TYPE: DNA
<213> ORGANISM: Artificial Sequence
<220> FEATURE:
<223> OTHER INFORMATION: Synthetic

<400> SEQUENCE: 120

| | | |
|---|---|---|
| ggatccgctc ttcctgctct tggcgatgcc cttcacgtac tggtcggcca ggtacaggcc | 60 |
| gtggttctcg ttgccgatca gctcgatctt gtccaggatg tccttgaaca gcacctcctc | 120 |
| ctcgtgctgc tcggccacgt accactgcag gaagttgaag gtggcgtggt ccttgctctt | 180 |
| gatggcgtgg tccacgatgt tgttgatgct ctcgctgatg tgctgctcgt gctcgtaggc | 240 |
| cttctggaag atctgggtca ggccctcgaa cttgtgctcg ggggcgctga tgctggtcag | 300 |

```
ctgcacgggc acgttgttct cgttcaggaa gatgatcagc ttcttggcgt gctcgtactc      360
ctcggcggcg tggtcgaaca ggaacaggcc ggcgccgtcc aggctgtggg tgtagcacca      420
gctgctcatg ctcatgtaca ggttgctgct ctgcatctcc ttgttcacct gctcgttcag      480
cagcttgatg atgtcgcctc cggagcccct gatctgaaac cggttgttca gggcctcatc      540
tctgtacacg tcgtggtcgt aggtgccgtt tctgatgctg ccgatgcagg cgttgtcgca      600
cttgtggtag atcttgaagc agccgttgcc catgtcctcg gcgttttctc tcagctgctt      660
cttggttttc tcgaacagct tattcatctc actgtctgtc agatcaattg tgtgctggtt      720
ttccagggcg accagcagtt cggcattgta gctctgcagc tgcttgatgc cccacacggt      780
cagctgcagc aggtgctgct gggcctcgat ggcccgcagc aggttgttct gctgctgcac      840
gatgccgctg ccgccgccgg tgccgttctc ctgctggttc tggctctcct cgatcaggct      900
gtagatgatg ctggtgtagt tgttgatctc ccggtcccac tcgggatcgc cgccggtctt      960
gccgatcagc ctgttcagct tgccgttgat ctggtcgatg gcggcctggg tagatttcag     1020
atcggcggcc tgtccaattc cctcgctatt ctggtgtctg aagccgtacc acccatccac     1080
cattccctcc cagccattct cgataaagcc ggcaatggcg ccaaagatgc ctctggtctg     1140
cttctcgggc acatttctca tgccggtggc cagcttcagg ccggagccca gctctgtggc     1200
attggtcact tcgatctggt cgttggtgat tgttttcacg atggtgccat taggcacggc     1260
gtggtgtccc agacacagtg tggcggtgct attatcgttg ccgggcagct tctgtgtgaa     1320
caccaggcac aggatgtagc tcagggcaat gatggttttc at                       1362
```

<210> SEQ ID NO 121
<211> LENGTH: 1362
<212> TYPE: DNA
<213> ORGANISM: Artificial Sequence
<220> FEATURE:
<223> OTHER INFORMATION: Synthetic

<400> SEQUENCE: 121

```
atgaaaacca taattgcgct gtcctacata ctgtgtctgg tgtttgccca gaaactgccg       60
ggcaatgaca actcaacagc cacgctctgc ttggggcacc atgccgtccc taacgggacc      120
attgtgaaaa ccattactaa cgatcagata gaggtgacta atgccaccga gctgggctcc      180
ggcttgaaac tggcgaccgg tatgcgcaat gtccccgaaa aacagacccg cgggatattt      240
ggggctatcg caggctttat cgagaatggc tgggaaggga tggtggatgg ttggtatggt      300
tttagacatc aaaactccga aggcagaggc caggctgccg atctcaagag cacgcaggcc      360
gctatagatc agatcaatgg aaagctcaac agactgatcg ggaaaaccgg cggcgatccc      420
gagtgggacc gggagatcaa caactacacc agcatcatct acagcctgat cgaggagagc      480
cagaaccagc aggagaacgg caccggcggc ggcagcggca tcgtgcagca gcagaacaac      540
ctgctgcggg ccatcgaggc ccagcagcac ctgctgcagc tgaccgtgtg ggcatcaag      600 cagctgcagt cctacaatgc cgagctgctg gtggctctgg agaatcagca cactattgac      660
ctgaccgatt cagagatgaa caaactttttt gagaagacga agaagcagct tagagaaaat      720
gcagaggaca tggggaacgg atgctttaaa atatatcata gtgtgataa tgcctgcatc      780 ggatcaatta gaaatggtac ctatgatcac gatgtttaca gggacgaagc gctgaataac      840
aggttccaga taaaaggctc cggaggcgaa atcatcaagc tgctgaacga gcaggtgaac      900
aaggagatgc agagcagcaa cctgtacatg agcatgagca gctggtgcta cacccacagc      960
ctggacggcg ccggcctgtt cctgttcgac cacgccgccg aggagtacga gcacgccaag     1020
```

```
aagctgatca tcttcctgaa cgagaacaac gtgcccgtgc agctgaccag catcagcgcc    1080
cccgagcaca agttcgaggg cctgacccag atcttccaga aggcctacga gcacgagcag    1140
cacatcagcg agagcatcaa caacatcgtg gaccacgcca tcaagagcaa ggaccacgcc    1200
accttcaact tcctgcagtg gtacgtggcc gagcagcacg aggaggaggt gctgttcaag    1260
gacatcctgg acaagatcga gctgatcggc aacgagaacc acggcctgta cctggccgac    1320
cagtacgtga agggcatcgc caagagcagg aagagcggat cc                      1362
```

<210> SEQ ID NO 122
<211> LENGTH: 454
<212> TYPE: PRT
<213> ORGANISM: Artificial Sequence
<220> FEATURE:
<223> OTHER INFORMATION: Synthetic

<400> SEQUENCE: 122

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Arg Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly Asp Ile Ile Lys Leu Leu Asn Glu Gln Val Asn Lys Glu Met Gln
    290                 295                 300
```

```
Ser Ser Asn Leu Tyr Met Ser Met Ser Ser Trp Cys Tyr Thr His Ser
305                 310                 315                 320

Leu Asp Gly Ala Gly Leu Phe Leu Phe Asp His Ala Ala Glu Glu Tyr
                325                 330                 335

Glu His Ala Lys Lys Leu Ile Ile Phe Leu Asn Glu Asn Asn Val Pro
            340                 345                 350

Val Gln Leu Thr Ser Ile Ser Ala Pro Glu His Lys Phe Glu Gly Leu
        355                 360                 365

Thr Gln Ile Phe Gln Lys Ala Tyr Glu His Glu Gln His Ile Ser Glu
370                 375                 380

Ser Ile Asn Asn Ile Val Asp His Ala Ile Lys Ser Lys Asp His Ala
385                 390                 395                 400

Thr Phe Asn Phe Leu Gln Trp Tyr Val Ala Glu Gln His Glu Glu Glu
                405                 410                 415

Val Leu Phe Lys Asp Ile Leu Asp Lys Ile Glu Leu Ile Gly Asn Glu
            420                 425                 430

Asn His Gly Leu Tyr Leu Ala Asp Gln Tyr Val Lys Gly Ile Ala Lys
        435                 440                 445

Ser Arg Lys Ser Gly Ser
    450
```

<210> SEQ ID NO 123
<211> LENGTH: 1362
<212> TYPE: DNA
<213> ORGANISM: Artificial Sequence
<220> FEATURE:
<223> OTHER INFORMATION: Synthetic

<400> SEQUENCE: 123

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggagccttt tatctggaac tgttattca gcgcttcgtc     540
cctgtaaaca tcgtgatcat aggtaccatt tctaattgat ccgatgcagg cattatcaca     600
cttatgatat attttaaagc atccgttccc catgtcctct gcattttctc taagctgctt     660
cttcgtcttc tcaaaaagtt tgttcatctc tgaatcggtc aggtcaatag tgtgctgatt     720
ctccagagcc accagcagct cggcattgta ggactgcagc tgcttgatgc ccacacggt     780
cagctgcagc aggtgctgct gggcctcgat ggcccgcagc aggttgttct gctgctgcac     840
gatgccgctg ccgccgccgg tgccgttctc ctgctggttc tggctctcct cgatcaggct     900
gtagatgatg ctggtgtagt tgttgatctc ccggtcccac tcgggatcgc cgccggtttt     960
cccgatcagt ctgttgagct ttccattgat ctgatctata gcggcctgcg tgctcttgag    1020
atcggcagcc tggcctctgc cttcggagtt ttgatgtcta aaaccatacc aaccatccac    1080
catcccttcc cagccattct cgataaagcc tgcgatagcc caaatatcc gcgggtctg     1140
```

```
tttttcgggg acattgcgca taccggtcgc cagtttcaag ccggagccca gctcggtggc    1200
attagtcacc tctatctgat cgttagtaat ggttttcaca atggtcccgt tagggacggc    1260
atggtgcccc aagcagagcg tggctgttga gttgtcattg cccggcagtt tctgggcaaa    1320
caccagacac agtatgtagg acagcgcaat tatggttttc at                      1362
```

<210> SEQ ID NO 124
<211> LENGTH: 1332
<212> TYPE: DNA
<213> ORGANISM: Artificial Sequence
<220> FEATURE:
<223> OTHER INFORMATION: Synthetic

<400> SEQUENCE: 124

```
atgaaggcca tcatcgtgct gctgatggtg gtcacaagca acgccgatag aatctgtacc     60
ggcatcacca gcagcaatag ccctcacgtc gtgaaaacag ctacacaggg cgaagtgaat    120
gtgaccggcg tgatccctct gggatcagga ctgaagctgg ccaatggcac aaagtataga    180
cctccagcca agctgctgaa agagagaggc ttttttggag ctatcgccgg ctttctggaa    240
ggcggatggg agggaatgat tgctggatgg catggctaca catctcatgg cgcacatggc    300
gtggcagtgg ctgctgatct gaaatctaca caggaagcca tcaacaagat caccaagaac    360
ctgaacagcc tgagcgagct ggaaggaggc gaccccgagt gggatcgcga aatcaacaac    420
tacacatcta tctcctacag tctgattgag aaagccaga accagcagga gaatgggact    480
gggggaggct ccggaatcgt gcagcagcag aacaatctgc tgcgagccat tgaagctcag    540
cagcacctgc tgcagctgac agtgtggggc atcaagcagc tgcaggggag ccagattgaa    600
ctggctgtgc tgctgtctaa cgagggcatc atcaatagcg aggacgaaca tctgctggcc    660
ctggaaagaa agctgaagaa gatgctggga cctagcgccg tggaaatcgg caatggatgc    720
tttgagacaa agcacaagtg caaccagacc tgcctggata gaattgccgc cggaacattt    780
gatgccggcg agttttctct gcccaccttc gatagcctga atatcacatc cggaggcgac    840
atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac   1020
gtgcccgtgc agctgaccag catcagcgcc cccgagcaca gttcgaggg cctgacccag   1080 atcttccaga aggcctacga gcacgagcag cacatcagcg agagcatcaa caacatcgtg   1140
gaccacgcca tcaagagcaa ggaccacgcc accttcaact tcctgcagtg gtacgtggcc   1200
gagcagcacg aggaggaggt gctgttcaag gacatcctgg acaagatcga gctgatcggc   1260
aacgagaacc acggcctgta cctggccgac cagtacgtga agggcatcgc caagagcagg   1320
aagagcggat cc                                                      1332
```

<210> SEQ ID NO 125
<211> LENGTH: 444
<212> TYPE: PRT
<213> ORGANISM: Artificial Sequence
<220> FEATURE:
<223> OTHER INFORMATION: Synthetic

<400> SEQUENCE: 125

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30
```

```
Thr Ala Thr Gln Gly Glu Val Asn Val Thr Gly Val Ile Pro Leu Gly
         35                  40                  45

Ser Gly Leu Lys Leu Ala Asn Gly Thr Lys Tyr Arg Pro Pro Ala Lys
 50                  55                  60

Leu Leu Lys Glu Arg Gly Phe Phe Gly Ala Ile Ala Gly Phe Leu Glu
 65                  70                  75                  80

Gly Gly Trp Glu Gly Met Ile Ala Gly Trp His Gly Tyr Thr Ser His
                 85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
            115                 120                 125

Gly Gly Asp Pro Glu Trp Asp Arg Glu Ile Asn Asn Tyr Thr Ser Ile
        130                 135                 140

Ile Tyr Ser Leu Ile Glu Glu Ser Gln Asn Gln Gln Glu Asn Gly Thr
145                 150                 155                 160

Gly Gly Gly Ser Gly Ile Val Gln Gln Gln Asn Asn Leu Leu Arg Ala
                165                 170                 175

Ile Glu Ala Gln Gln His Leu Leu Gln Leu Thr Val Trp Gly Ile Lys
            180                 185                 190

Gln Leu Gln Gly Ser Gln Ile Glu Leu Ala Val Leu Leu Ser Asn Glu
        195                 200                 205

Gly Ile Ile Asn Ser Glu Asp Glu His Leu Leu Ala Leu Glu Arg Lys
        210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asp Ala Gly Glu Phe Ser Leu Pro Thr Phe Asp Ser
            260                 265                 270

Leu Asn Ile Thr Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
        290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
            340                 345                 350

His Lys Phe Glu Gly Leu Thr Gln Ile Phe Gln Lys Ala Tyr Glu His
            355                 360                 365

Glu Gln His Ile Ser Glu Ser Ile Asn Asn Ile Val Asp His Ala Ile
        370                 375                 380

Lys Ser Lys Asp His Ala Thr Phe Asn Phe Leu Gln Trp Tyr Val Ala
385                 390                 395                 400

Glu Gln His Glu Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
            420                 425                 430

Val Lys Gly Ile Ala Lys Ser Arg Lys Ser Gly Ser
            435                 440
```

<210> SEQ ID NO 126
<211> LENGTH: 1332
<212> TYPE: DNA
<213> ORGANISM: Artificial Sequence
<220> FEATURE:
<223> OTHER INFORMATION: Synthetic

<400> SEQUENCE: 126

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggatgtgat attcaggcta tcgaaggtgg cagagaaaa      540
ctcgccggca tcaaatgttc cggcggcaat tctatccagg caggtctggt tgcacttgtg     600
ctttgtctca aagcatccat tgccgatttc acggcgcta ggtcccagca tcttcttcag      660
cttcttttcc agggccagca gatgttcgtc ctcgctattg atgatgccct cgttagacag     720
cagcacagcc agttcaatct ggctcccctg cagctgcttg atgccccaca ctgtcagctg     780
cagcaggtgc tgctgagctt caatggctcg cagcagattg ttctgctgct gcacgattcc     840
ggagcctccc ccagtcccat tctcctgctg gttctggctt cctcaatca gactgtagat      900
gatagatgtg tagttgttga tttcgcgatc ccactcgggg tcgcctcctt ccagctcgct     960
caggctgttc aggttcttgg tgatcttgtt gatggcttcc tgtgtagatt tcagatcagc    1020
agccactgcc acgccatgtg cgccatgaga tgtgtagcca tgccatccag caatcattcc    1080
ctcccatccg ccttccagaa agccggcgat agctccaaaa aagcctctct ctttcagcag    1140
cttggctgga gtctatact tgtgccatt ggccagcttc agtcctgatc ccagagggat      1200
cacgccggtc acattcactt cgccctgtgt agctgttttc acgacgtgag gctattgct     1260
gctggtgatg ccggtacaga ttctatcggc gttgcttgtg accaccatca gcagcacgat    1320
gatggccttc at                                                         1332
```

<210> SEQ ID NO 127
<211> LENGTH: 1332
<212> TYPE: DNA
<213> ORGANISM: Artificial Sequence
<220> FEATURE:
<223> OTHER INFORMATION: Synthetic

<400> SEQUENCE: 127

```
atgaaggcca tcatcgtgct gctgatggtg gtgaccagca cgccgataga atctgcacc       60
ggcatcacca gcagcaatag cccccatgtg gtgaaaacag ccacccaggg cgaagtgaat     120
gtgacaggcg tgatccctct gggatcagga ctgaagctgg ccaatggcac caagtacaga     180
cctcccgcca agctgctgaa agagagaggc ttctttggcg ccattgccgg atttctggaa     240
ggcggctggg agggaatgat tgccggctgg cacggctata catctcatgg gcccatggc     300
gtggctgtgg ccgccgatct gaagtctacc caggaagcca tcaacaagat caccaagaac     360
ctgaacagcc tgagcgagct ggaaggaggc gaccccgagt gggatcgcga aatcaacaac    420
```

-continued

```
tacacatcta tcatctacag tctgattgag aaagccaga accagcagga gaatgggact      480
gggggaggct ccggaatcgt gcagcagcag aacaatctgc tgcgagccat tgaagctcag      540
cagcacctgc tgcagctgac agtgtggggc atcaagcagc tgcagggtc ccagattgaa      600
ctggccgtgc tgctgtccaa cgagggcatc atcaacagcg aggatgaaca cctgctggcc      660
ctggaacgga agctgaagaa gatgctgggc ccttctgccg tggagatcgg caacggctgc      720
ttcgagacaa agcacaagtg caaccagacc tgcctggata gaatcgccgc tggcaccttc      780
aatgccggcg agttcagcct gcctaccttc gacagcctga atatcacctc cggaggcgac      840
atcatcaagc tgctgaacga gcaggtgaac aaggagatgc agagcagcaa cctgtacatg      900
agcatgagca gctggtgcta cacccacagc ctggacggcg ccggcctgtt cctgttcgac      960
cacgccgccg aggagtacga gcacgccaag aagctgatca tcttcctgaa cgagaacaac     1020
gtgcccgtgc agctgaccag catcagcgcc cccgagcaca gttcgaggg cctgacccag     1080
atcttccaga aggcctacga gcacgagcag cacatcagcg agagcatcaa caacatcgtg     1140
gaccacgcca tcaagagcaa ggaccacgcc accttcaact tcctgcagtg gtacgtggcc     1200
gagcagcacg aggaggaggt gctgttcaag gacatcctgg acaagatcga gctgatcggc     1260
aacgagaacc acggcctgta cctggccgac cagtacgtga agggcatcgc caagagcagg     1320
aagagcggat cc                                                         1332
```

<210> SEQ ID NO 128
<211> LENGTH: 444
<212> TYPE: PRT
<213> ORGANISM: Artificial Sequence
<220> FEATURE:
<223> OTHER INFORMATION: Synthetic

<400> SEQUENCE: 128

```
Met Lys Ala Ile Ile Val Leu Leu Met Val Val Thr Ser Asn Ala Asp
 1               5                  10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Gly
        35                  40                  45

Ser Gly Leu Lys Leu Ala Asn Gly Thr Lys Tyr Arg Pro Pro Ala Lys
    50                  55                  60

Leu Leu Lys Glu Arg Gly Phe Phe Gly Ala Ile Ala Gly Phe Leu Glu
65                  70                  75                  80

Gly Gly Trp Glu Gly Met Ile Ala Gly Trp His Gly Tyr Thr Ser His
                85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
    130                 135                 140

Ile Tyr Ser Leu Ile Glu Glu Ser Gln Asn Gln Gln Glu Asn Gly Thr
145                 150                 155                 160

Gly Gly Gly Ser Gly Ile Val Gln Gln Asn Asn Leu Leu Arg Ala
                165                 170                 175

Ile Glu Ala Gln Gln His Leu Leu Gln Leu Thr Val Trp Gly Ile Lys
            180                 185                 190
```

Gln Leu Gln Gly Ser Gln Ile Glu Leu Ala Val Leu Leu Ser Asn Glu
            195                 200                 205

Gly Ile Ile Asn Ser Glu Asp Glu His Leu Leu Ala Leu Glu Arg Lys
        210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asn Ala Gly Glu Phe Ser Leu Pro Thr Phe Asp Ser
            260                 265                 270

Leu Asn Ile Thr Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
            340                 345                 350

His Lys Phe Glu Gly Leu Thr Gln Ile Phe Gln Lys Ala Tyr Glu His
        355                 360                 365

Glu Gln His Ile Ser Glu Ser Ile Asn Asn Ile Val Asp His Ala Ile
370                 375                 380

Lys Ser Lys Asp His Ala Thr Phe Asn Phe Leu Gln Trp Tyr Val Ala
385                 390                 395                 400

Glu Gln His Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
            420                 425                 430

Val Lys Gly Ile Ala Lys Ser Arg Lys Ser Gly Ser
        435                 440

<210> SEQ ID NO 129
<211> LENGTH: 1332
<212> TYPE: DNA
<213> ORGANISM: Artificial Sequence
<220> FEATURE:
<223> OTHER INFORMATION: Synthetic

<400> SEQUENCE: 129
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggaggtgat attcaggctg tcgaaggtag gaggctgaa     540 ctcgccggca ttgaaggtgc cagcggcgat ctatccagg caggtctggt tgcacttgtg     600
ctttgtctcg aagcagccgt tgccgatctc cacggcagaa gggcccagca tcttcttcag     660

```
cttccgttcc agggccagca ggtgttcatc ctcgctgttg atgatgccct cgttggacag    720
cagcacggcc agttcaatct gggacccctg cagctgcttg atgccccaca ctgtcagctg    780
cagcaggtgc tgctgagctt caatggctcg cagcagattg ttctgctgct gcacgattcc    840
ggagcctccc ccagtcccat tctcctgctg gttctggctt tcctcaatca gactgtagat    900
gatagatgtg tagttgttga tttcgcgatc ccactcgggg tcgcctcctt ccagctcgct    960
caggctgttc aggttcttgg tgatcttgtt gatggcttcc tgggtagact tcagatcggc   1020
ggccacagcc acgccatggg ccccatgaga tgtatagccg tgccagccgg caatcattcc   1080
ctcccagccg ccttccagaa atccggcaat ggcgccaaag aagcctctct ctttcagcag   1140
cttggcggga ggtctgtact tggtgccatt ggccagcttc agtcctgatc ccagagggat   1200
cacgcctgtc acattcactt cgccctgggg ggctgttttc accacatggg ggctattgct   1260
gctggtgatg ccggtgcaga ttctatcggc gttgctggtc accaccatca gcagcacgat   1320
gatggccttc at                                                       1332
```

<210> SEQ ID NO 130
<211> LENGTH: 6506
<212> TYPE: DNA
<213> ORGANISM: Artificial Sequence
<220> FEATURE:
<223> OTHER INFORMATION: Synthetic sequence of plasmid CMV8x/R-H1NC
      HA(517)_SGG_egm

<400> SEQUENCE: 130

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt cctacttgg    660 cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt gttttgact caccaaaatc aacgggaatt cccaaaatgt cgtaacaact    840
ccgccccatt gacgcaaatg gcggtaggc gtgtacggtg gaggtctat ataagcagag    900 ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct    1140 ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
```

-continued

```
tcttttctgc agtcaccgtc gtcgacacgt gtgatcagat atcgcggccg ctctagagat    1380
atcgccacca tgaaggccaa actgctggtg ctgctgtgta cctttaccgc cacctacgcc    1440
gacacaatct gtatcggcta ccacgccaac aatagcaccg acaccgtgga tacagtgctg    1500
gagaagaacg tgaccgtgac ccactctgtg aacctgctgg aggacagcca caatggcaag    1560
ctgtgtctgc tgaaaggcat tgcccctctg cagctgggca ttgttctgt ggccggatgg     1620
attctgggca accccgagtg tgagctgctg atttctaagg agagctggag ctacatcgtg    1680
gagacccca atcctgagaa tggcacctgc taccctggct acttcgccga ttacgaggag     1740
ctgcgcgagc agctgtctag cgtgtccagc ttcgagagat tcgagatctt ccccaaggag    1800
tccagctggc taatcacac agtgacaggc gtgtctgcca gctgtagcca acggcaaa      1860
agcagcttct accggaacct gctgtggctg acaggcaaga atggcctgta ccccaacctg    1920
agcaagagct acgtgaacaa caaggaaaag gaagtgctgg tgctgtgggg agtgcaccac    1980
cctcccaaca tcggaaatca gcgggccctg taccacacag agaacgccta tgtgagcgtg    2040
gtgtccagcc actacagcag aagattcacc cccgagatcg ccaagagacc caaagtgaga    2100
gaccaggagg gccggatcaa ttactactgg accctgctgg agcctggcga taccatcatc    2160
ttcgaggcca acggcaatct gatcgcccct tggtatgcct ttgccctgag cagaggcttt    2220
ggcagcggca tcatcacaag caacgccccc atggatgagt gtgatgccaa gtgccagaca    2280
cctcagggcg ccatcaatag cagcctgccc ttccagaatg tgcaccctgt gaccatcggc    2340
gagtgcccca gtatgtgag aagcgccaag ctgagaatgg tgaccggcct gagaaacatc     2400
cctcagaggg agaccagagg actgtttgga gccatcgccg gattcatcga gggaggatgg    2460
acaggcatgg tggatggctg gtacggctac caccaccaga tgagcagggg ctctggatat    2520
gccgccgatc agaagtctac ccagaacgcc atcaacggca tcaccaacaa ggtgaacagc    2580
gtgatcgaga gatgaacac ccagtttacc gctgtgggca aggagttcaa caagctggag    2640
cggaggatgg agaacctgaa caagaaggtg gacgacggct tctggacat ctggacctac   2700
aatgccgaac tcctggtcct cctcgagaat gagaggaccc tggacttcca cgacagcaac    2760
gtgaagaacc tgtatgagaa ggtgaagagc cagctgaaga caacgccaa ggagatcggc     2820
aacggctgct tcgagttcta ccacaagtgt aacaacgagt gtatggagag cgtgaagaac    2880
ggcacctacg actaccctaa gtacagcgag gagagcaagc tgaaccggga gaagatcgat    2940
tccggaggcg acatcatcaa gctgctgaac gagcaggtga acaaggagat gcagagcagc    3000
aacctgtaca tgagcatgag cagctggtgc tacacccaca gcctggacgg cgccggcctg    3060
ttcctgttcg accacgccgc cgaggagtac gagcacgcca agaagctgat catcttcctg    3120
aacgagaaca acgtgcccgt gcagctgacc agcatcagcg ccccgagca aagttcgag      3180
ggcctgaccc agatcttcca gaaggcctac gagcacgagc agcacatcag cgagagcatc    3240
aacaacatcg tggaccacgc catcaagagc aaggaccacg ccaccttcaa cttcctgcag    3300
tggtacgtgg ccgagcagca cgaggaggag gtgctgttca aggacatcct ggacaagatc    3360
gagctgatcg gcaacgagaa ccacggcctg tacctggccg accagtacgt gaagggcatc    3420
gccaagagca ggaagagcgg atcctagcat catcatcatc attagtctgg aagggcgaat    3480
tgatccagat ctgctgtgcc ttctagttgc cagccatctg ttgtttgccc ctccccgtg      3540
ccttccttga ccctggaagg tgccactccc actgtccttt cctaataaaa tgaggaaatt    3600
gcatcgcatt gtctgagtag gtgtcattct attctggggg gtggggtggg gcaggacagc    3660
```

| | |
|---|---|
| aaggggagg attgggaaga caatagcagg catgctgggg atgcggtggg ctctatggt | 3720 |
| acccaggtgc tgaagaattg acccggttcc tcctgggcca gaaagaagca ggcacatccc | 3780 |
| cttctctgtg acacaccctg tccacgcccc tggttcttag ttccagcccc actcatagga | 3840 |
| cactcatagc tcaggagggc tccgccttca atcccacccg ctaaagtact tggagcggtc | 3900 |
| tctccctccc tcatcagccc accaaaccaa acctagcctc caagagtggg aagaaattaa | 3960 |
| agcaagatag gctattaagt gcagagggag agaaaatgcc tccaacatgt gaggaagtaa | 4020 |
| tgagagaaat catagaattt taaggccatg atttaaggcc atcatggcct taatcttccg | 4080 |
| cttcctcgct cactgactcg ctgcgctcgg tcgttcggct gcggcgagcg gtatcagctc | 4140 |
| actcaaaggc ggtaatacgg ttatccacag aatcagggga taacgcagga agaacatgt | 4200 |
| gagcaaaagg ccagcaaaag gccaggaacc gtaaaaaggc cgcgttgctg gcgttttttcc | 4260 |
| ataggctccg ccccctgac gagcatcaca aaaatcgacg ctcaagtcag aggtggcgaa | 4320 |
| acccgacagg actataaaga taccaggcgt ttccccctgg aagctccctc gtgcgctctc | 4380 |
| ctgttccgac cctgccgctt accggatacc tgtccgcctt tctcccttcg ggaagcgtgg | 4440 |
| cgctttctca tagctcacgc tgtaggtatc tcagttcggt gtaggtcgtt cgctccaagc | 4500 |
| tgggctgtgt gcacgaaccc cccgttcagc ccgaccgctg cgccttatcc ggtaactatc | 4560 |
| gtcttgagtc caacccggta agacacgact tatcgccact ggcagcagcc actggtaaca | 4620 |
| ggattagcag agcgaggtat gtaggcggtg ctacagagtt cttgaagtgg tggcctaact | 4680 |
| acggctacac tagaagaaca gtatttggta tctgcgctct gctgaagcca gttaccttcg | 4740 |
| gaaaaagagt tggtagctct tgatccggca acaaaccac cgctggtagc ggtggttttt | 4800 |
| ttgtttgcaa gcagcagatt acgcgcagaa aaaaggatc tcaagaagat cctttgatct | 4860 |
| tttctacggg gtctgacgct cagtggaacg aaaactcacg ttaagggatt ttggtcatga | 4920 |
| gattatcaaa aaggatcttc acctagatcc ttttaaatta aaaatgaagt tttaaatcaa | 4980 |
| tctaaagtat atatgagtaa acttggtctg acagttacca atgcttaatc agtgaggcac | 5040 |
| ctatctcagc gatctgtcta tttcgttcat ccatagttgc ctgactcggg gggggggc | 5100 |
| gctgaggtct gcctcgtgaa gaaggtgttg ctgactcata ccaggcctga atcgccccat | 5160 |
| catccagcca gaaagtgagg gagccacggt tgatgagagc tttgttgtag gtggaccagt | 5220 |
| tggtgatttt gaacttttgc tttgccacg aacggtctgc gttgtcggga agatgcgtga | 5280 |
| tctgatcctt caactcagca aaagttcgat ttattcaaca aagccgccgt cccgtcaagt | 5340 |
| cagcgtaatg ctctgccagt gttacaacca attaaccaat tctgattaga aaaactcatc | 5400 |
| gagcatcaaa tgaaactgca atttattcat atcaggatta tcaataccat atttttgaaa | 5460 |
| aagccgtttc tgtaatgaag gagaaaactc accgaggcag ttccatagga tgcaagatc | 5520 |
| ctggtatcgg tctgcgattc cgactcgtcc aacatcaata caacctatta atttcccctc | 5580 |
| gtcaaaaata aggttatcaa gtgagaaatc accatgagtg acgactgaat ccggtgagaa | 5640 |
| tggcaaaagc ttatgcattt cttttccagac ttgttcaaca ggccagccat tacgctcgtc | 5700 |
| atcaaaatca ctcgcatcaa ccaaaccgtt attcattcgt gattgcgcct gagcgagacg | 5760 |
| aaatacgcga tcgctgttaa aaggacaatt acaaacagga tcgaatgca accgcgcag | 5820 |
| gaacactgcc agcgcatcaa caatattttc acctgaatca ggatattctt ctaatacctg | 5880 |
| gaatgctgtt ttcccgggga tcgcagtggt gagtaaccat gcatcatcag gagtacggat | 5940 |
| aaaatgcttg atggtcggaa gaggcataaa ttccgtcagc cagtttagtc tgaccatctc | 6000 |
| atctgtaaca tcattggcaa cgctaccttt gccatgtttc agaaacaact ctggcgcatc | 6060 |

```
gggcttccca tacaatcgat agattgtcgc acctgattgc ccgacattat cgcgagccca      6120
tttataccca tataaatcag catccatgtt ggaatttaat cgcggcctcg agcaagacgt      6180
ttcccgttga atatggctca taacacccct tgtattactg tttatgtaag cagacagttt      6240
tattgttcat gatgatatat ttttatcttg tgcaatgtaa catcagagat tttgagacac      6300
aacgtggctt tccccccccc cccattattg aagcatttat cagggttatt gtctcatgag      6360
cggatacata tttgaatgta tttagaaaaa taaacaaata ggggttccgc gcacatttcc      6420
ccgaaaagtg ccacctgacg tctaagaaac cattattatc atgacattaa cctataaaaa      6480
taggcgtatc acgaggccct ttcgtc                                           6506
```

<210> SEQ ID NO 131
<211> LENGTH: 2058
<212> TYPE: DNA
<213> ORGANISM: Artificial Sequence
<220> FEATURE:
<223> OTHER INFORMATION: Synthetic nucleic acid sequence encoding SEQ
      ID NO:41 (contains stop codon)

<400> SEQUENCE: 131

```
atgaaggcca aactgctggt gctgctgtgt acctttaccg ccacctacgc cgacacaatc        60
tgtatcggct accacgccaa caatagcacc gacaccgtgg atacagtgct ggagaagaac       120
gtgaccgtga cccactctgt gaacctgctg aggacagcc acaatggcaa gctgtgtctg       180
ctgaaaggca ttgcccctct gcagctgggc aattgttctg tggccggatg gattctgggc       240
aaccccgagt gtgagctgct gatttctaag gagagctgga gctacatcgt ggagaccccc       300
aatcctgaga atggcacctg ctaccctggc tacttcgccg attacgagga gctgcgcgag       360
cagctgtcta gcgtgtccag cttcgagaga ttcgagatct tccccaagga gtccagctgg       420
cctaatcaca cagtgacagg cgtgtctgcc agctgtagcc acaacggcaa agcagcttc       480 taccggaacc tgctgtggct gacaggcaag aatggcctgt accccaacct gagcaagagc       540
tacgtgaaca caaggaaaa ggaagtgctg gtgctgtggg gagtgcacca ccctcccaac       600
atcggaaatc agcgggccct gtaccacaca gagaacgcct atgtgagcgt ggtgtccagc       660
cactacagca gaagattcac ccccgagatc gccaagagac ccaaagtgag agaccaggag       720
ggccggatca attactactg gaccctgctg gagcctggcg ataccatcat cttcgaggcc       780
aacggcaatc tgatcgcccc ttggtatgcc tttgccctga gcagaggctt tggcagcggc       840
atcatcacaa gcaacgcccc catggatgag tgtgatgcca gtgccagac acctcagggc       900 gccatcaata gcagcctgcc cttccagaat gtgcaccctg tgaccatcgg cgagtgcccc       960
aagtatgtga aagcgccaa gctgagaatg gtgaccggcc tgagaaacat ccctcagagg      1020
gagaccagag gactgtttgg agccatcgcc ggattcatcg agggaggatg gacaggcatg      1080
gtggatggct ggtacggcta ccaccaccag aatgagcagg gctctggata tgccgccgat      1140
cagaagtcta cccagaacgc catcaacggc atcaccaaca aggtgaacag cgtgatcgag      1200
aagatgaaca cccagtttac cgctgtgggc aaggagttca acaagctgga gcggaggatg      1260
gagaacctga acaagaaggt ggacgacggc tttctggaca tctggaccta caatgccgaa      1320
ctcctggtcc tcctcgagaa tgagaggacc ctggacttcc acgacagcaa cgtgaagaac      1380
ctgtatgaga aggtgaagag ccagctgaag aacaacgcca aggagatcgg caacggctgc      1440
ttcgagttct accacaagtg taacaacgag tgtatggaga gcgtgaagaa cggcacctac      1500
gactacccta gtacagcga ggagagcaag ctgaaccggg agaagatcga ttccggaggc      1560
```

```
gacatcatca agctgctgaa cgagcaggtg aacaaggaga tgcagagcag caacctgtac    1620
atgagcatga gcagctggtg ctacacccac agcctggacg gcgccggcct gttcctgttc    1680
gaccacgccg ccgaggagta cgagcacgcc aagaagctga tcatcttcct gaacgagaac    1740
aacgtgcccg tgcagctgac cagcatcagc gcccccgagc acaagttcga gggcctgacc    1800
cagatcttcc agaaggccta cgagcacgag cagcacatca gcgagagcat caacaacatc    1860
gtggaccacg ccatcaagag caaggaccac gccaccttca acttcctgca gtggtacgtg    1920
gccgagcagc acgaggagga ggtgctgttc aaggacatcc tggacaagat cgagctgatc    1980
ggcaacgaga accacggcct gtacctggcc gaccagtacg tgaagggcat cgccaagagc    2040
aggaagagcg gatcctag                                                  2058
```

<210> SEQ ID NO 132
<211> LENGTH: 6509
<212> TYPE: DNA
<213> ORGANISM: Artificial Sequence
<220> FEATURE:
<223> OTHER INFORMATION: Synthetic sequence of plasmid CMV8x/R-H1CA
      HA(518)_

<400> SEQUENCE: 132

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga cccccgccca ttgacgtcaa taatgacgta tgttcccata     480
gtaacgccaa tagggaactt ccattgacgt caatgggtgg agtatttacg gtaaactgcc     540
cacttggcag tacatcaagt gtatcatatg ccaagtacgc cccctattga cgtcaatgacg     600 ggaacttcca agcttgcatt atgcccagta catgacctat gggaattcct atgaccttgg     660
cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg ggcggtaggc gtgtacggtg ggaggtctat ataagcagag     900
ctcgtttagt gaaccgtcag atcgcctgga cgccatcc acgctgtttt gacctccata     960
gaagacaccg ggaccgatcc agcctccatc ggctcgcatc tctccttcac gcgcccgccg    1020
ccctacctga gccgccatc cacgccggtt gagtcgcgtt ctgccgcctc ccgcctgtgg    1080
tgcctcctga actgcgtccg ccgtctaggt aagtttaaag ctcaggtcga gaccgggcct    1140
ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tgaaggccat cctggtggtg ctgctgtaca ccttcgccac cgccaacgcc    1440 gacacctgt gcatcggcta ccacgccaac aacagcaccg acaccgtgga caccgtgctg    1500
```

```
gagaagaacg tgaccgtgac ccacagcgtg aacctgctgg aggacaagca caacggcaag    1560
ctgtgcaagc tgcggggcgt ggccccctg  cacctgggca agtgcaacat cgccggctgg    1620
attctgggca accccgagtg cgagagcctg agcaccgcca gcagctggag ctacatcgtg    1680
gagaccccca gcagcgacaa cggcacctgc taccccggcg acttcatcga ctacgaggag    1740
ctgcgggagc agctgagcag cgtgagcagc ttcgagcggt tcgagatctt ccccaagacc    1800
agcagctggc ccaaccacga cagcaacaag ggcgtgaccg ccgcctgccc ccacgccggc    1860
gccaagagct tctacaagaa cctgatctgg ctggtgaaga gggcaacag  ctaccccaag    1920 ctgagcaaga gctacatcaa cgacaagggc aaggaggtgc tggtgctgtg gggcatccac    1980
caccccagca ccagcgccga ccagcagagc ctgtaccaga cgccgacac  ctacgtgttc    2040 gtgggcagca gccggtacag caagaagttc aagcccgaga tcgccatccg gcccaaggtg    2100
cgggaccagg agggccggat gaactactac tggaccctgg tggagcccgg cgacaagatc    2160
accttcgagg ccaccggcaa cctggtggtg ccccggtacg ccttcgccat ggagcggaac    2220
gccggcagcg gcatcatcat cagcgacacc cccgtgcacg actgcaacac cacctgccag    2280 accccccaagg gcgccatcaa caccagcctg cccttccaga acatccaccc catcaccatc    2340
ggcaagtgcc ccaagtacgt gaagagcacc aagctgcggc tggccaccgg cctgcggaac    2400
atccccagca tccagagccg gggcctgttc ggcgccatcg ccggcttcat cgagggcggc    2460
tggaccggca tggtggacgg ctggtacggc taccaccacc agaacgagca gggcagcggc    2520
tacgccgccg acctgaagag cacccagaac gccatcgacg agatcaccaa caaggtgaac    2580
agcgtgatcg agaagatgaa cacccagttc accgccgtgg gcaaggagtt caaccacctg    2640
gagaagcgga tcgagaacct gaacaagaag gtggacgacg gcttcctgga catctggacc    2700
tacaacgccg agctgctggt gctgctggag aacgagcgga ccctggacta ccacgacagc    2760
aacgtgaaga acctgtacga aaggtgcgc  agccagctga gaacaacgc  caaggagatc    2820 ggcaacggct gcttcgagtt ctaccacaag tgcgacaaca cctgcatgga gagcgtgaag    2880
aacggcacct acgactaccc caagtacagc gaggaggcca agctgaaccg ggaggagatc    2940
gactccggag gcgacatcat caagctgctg aacgagcagg tgaacaagga gatgcagagc    3000
agcaacctgt acatgagcat gagcagctgg tgctacaccc acagcctgga cggcgccggc    3060
ctgttcctgt tcgaccacgc cgccgaggag tacgagcacg ccaagaagct gatcatcttc    3120
ctgaacgaga caacgtgcc  cgtgcagctg accagcatca gcgccccga  gcacaagttc    3180 gagggcctga cccagatctt ccagaaggcc tacgagcacg agcagcacat cagcgagagc    3240
atcaacaaca tcgtggacca cgccatcaag agcaaggacc acgccacctt caacttcctg    3300
cagtggtacg tggccgagca gcacgaggag gaggtgctgt tcaaggacat cctggacaag    3360
atcgagctga tcggcaacga gaaccacggc ctgtacctgg ccgaccagta cgtgaagggc    3420
atcgccaaga gcaggaagag cggatcctag catcatcatc atcattagtc tggaagggcg    3480
aattgatcca gatctgctgt gccttctagt tgccagccat ctgttgtttg cccctccccc    3540
gtgccttcct tgaccctgga aggtgccact cccactgtcc tttcctaata aaatgaggaa    3600
attgcatcgc attgtctgag taggtgtcat tctattctgg ggggtggggt ggggcaggac    3660 agcaagggg  aggattggga agacaatagc aggcatgctg gggatgcggt gggctctatg    3720
ggtacccagg tgctgaagaa ttgacccggt tcctcctggg ccagaaagaa gcaggcacat    3780
ccccttctct gtgacacacc ctgtccacgc ccctggttct tagttccagc cccactcata    3840
```

```
ggacactcat agctcaggag ggctccgcct tcaatcccac ccgctaaagt acttggagcg    3900
gtctctccct ccctcatcag cccaccaaac caaacctagc ctccaagagt gggaagaaat    3960
taaagcaaga taggctatta agtgcagagg gagagaaaat gcctccaaca tgtgaggaag    4020
taatgagaga aatcatagaa ttttaaggcc atgatttaag gccatcatgg ccttaatctt    4080
ccgcttcctc gctcactgac tcgctgcgct cggtcgttcg gctgcggcga gcggtatcag    4140
ctcactcaaa ggcggtaata cggttatcca cagaatcagg ggataacgca ggaaagaaca    4200
tgtgagcaaa aggccagcaa aaggccagga accgtaaaaa ggccgcgttg ctggcgtttt    4260
tccataggct ccgcccccct gacgagcatc acaaaaatcg acgctcaagt cagaggtggc    4320
gaaacccgac aggactataa agataccagg cgtttccccc tggaagctcc ctcgtgcgct    4380
ctcctgttcc gaccctgccg cttaccggat acctgtccgc ctttctccct tcgggaagcg    4440
tggcgctttc tcatagctca cgctgtaggt atctcagttc ggtgtaggtc gttcgctcca    4500
agctgggctg tgtgcacgaa ccccccgttc agcccgaccg ctgcgcctta tccggtaact    4560
atcgtcttga gtccaacccg gtaagacacg acttatcgcc actggcagca gccactggta    4620
acaggattag cagagcgagg tatgtaggcg gtgctacaga gttcttgaag tggtggccta    4680
actacggcta cactagaaga acagtatttg gtatctgcgc tctgctgaag ccagttacct    4740
tcggaaaaag agttggtagc tcttgatccg gcaaacaaac caccgctggt agcggtggtt    4800
tttttgtttg caagcagcag attacgcgca gaaaaaaagg atctcaagaa gatcctttga    4860
tcttttctac ggggtctgac gctcagtgga acgaaaactc acgttaaggg attttggtca    4920
tgagattatc aaaaaggatc ttcacctaga tccttttaaa ttaaaaatga agttttaaat    4980
caatctaaag tatatatgag taaacttggt ctgacagtta ccaatgctta atcagtgagg    5040
cacctatctc agcgatctgt ctatttcgtt catccatagt tgcctgactc ggggggggggg    5100 ggcgctgagg tctgcctcgt gaagaaggtg ttgctgactc ataccaggcc tgaatcgccc    5160
catcatccag ccagaaagtg agggagccac ggttgatgag agctttgttg taggtggacc    5220
agttggtgat tttgaacttt tgctttgcca cggaacggtc tgcgttgtcg ggaagatgcg    5280
tgatctgatc cttcaactca gcaaaagttc gatttattca acaaagccgc cgtcccgtca    5340
agtcagcgta atgctctgcc agtgttacaa ccaattaacc aattctgatt agaaaaactc    5400
atcgagcatc aaatgaaact gcaatttatt catatcagga ttatcaatac catatttttg    5460
aaaaagccgt ttctgtaatg aaggagaaaa ctcaccgagg cagttccata ggatggcaag    5520
atcctggtat cggtctgcga ttccgactcg tccaacatca atacaaccta ttaatttccc    5580
ctcgtcaaaa ataaggttat caagtgagaa atcaccatga gtgacgactg aatccggtga    5640
gaatggcaaa agcttatgca tttctttcca gacttgttca acaggccagc cattacgctc    5700
gtcatcaaaa tcactcgcat caaccaaacc gttattcatt cgtgattgcg cctgagcgag    5760
acgaaatacg cgatcgctgt taaaaggaca attacaaaca ggaatcgaat gcaaccggcg    5820
caggaacact gccagcgcat caacaatatt ttcacctgaa tcaggatatt cttctaatac    5880
ctggaatgct gttttcccgg ggatcgcagt ggtgagtaac catgcatcat caggagtacg    5940
gataaaatgc ttgatggtcg gaagaggcat aaattccgtc agccagttta gtctgaccat    6000
ctcatctgta acatcattgg caacgctacc tttgccatgt ttcagaaaca actctggcgc    6060
atcgggcttc ccatacaatc gatagattgt cgcacctgat tgcccgacat tatcgcgagc    6120
ccatttatac ccatataaat cagcatccat gttggaattt aatcgcggcc tcgagcaaga    6180
cgtttcccgt tgaatatggc tcataacacc ccttgtatta ctgtttatgt aagcagacag    6240
```

```
ttttattgtt catgatgata tatttttatc ttgtgcaatg taacatcaga gattttgaga    6300
cacaacgtgg ctttcccccc ccccccatta ttgaagcatt tatcagggtt attgtctcat    6360
gagcggatac atatttgaat gtatttagaa aaataaacaa ataggggttc cgcgcacatt    6420
tccccgaaaa gtgccacctg acgtctaaga aaccattatt atcatgacat taacctataa    6480
aaataggcgt atcacgaggc cctttcgtc                                      6509
```

<210> SEQ ID NO 133
<211> LENGTH: 2058
<212> TYPE: DNA
<213> ORGANISM: Artificial Sequence
<220> FEATURE:
<223> OTHER INFORMATION: Synthetic nucleic acid sequence encoding SEQ
      ID NO:44 (lacks stop codon)

<400> SEQUENCE: 133

```
atgaaggcca tcctggtggt gctgctgtac accttcgcca ccgccaacgc cgacaccctg     60
tgcatcggct accacgccaa caacagcacc gacaccgtgg acaccgtgct ggagaagaac    120
gtgaccgtga cccacagcgt gaacctgctg gaggacaagc acaacggcaa gctgtgcaag    180
ctgcggggcg tggccccccct gcacctgggc aagtgcaaca tcgccggctg gattctgggc    240
aaccccgagt gcgagagcct gagcaccgcc agcagctgga gctacatcgt ggagacccccc    300 agcagcgaca acggcacctg ctaccccggc gacttcatcg actacgagga gctgcgggag    360
cagctgagca gcgtgagcag cttcgagcgg ttcgagatct ccccaagac cagcagctgg    420 cccaaccacg acagcaacaa gggcgtgacc gccgcctgcc ccacgccgg cgccaagagc    480 ttctacaaga acctgatctg gctggtgaag aagggcaaca gctaccccaa gctgagcaag    540
agctacatca cgacaaggg caaggaggtg ctggtgctgt ggggcatcca ccaccccagc    600
accagcgccg accagcagag cctgtaccag aacgccgaca cctacgtgtt cgtgggcagc    660
agccggtaca gcaagaagtt caagcccgag atcgccatcc ggcccaaggt gcgggaccag    720
gagggccgga tgaactacta ctggaccctg gtggagcccg gcgacaagat caccttcgag    780
gccaccggca cctggtggt gccccggtac gccttcgcca tggagcggaa cgccggcagc    840
ggcatcatca tcagcgacac ccccgtgcac gactgcaaca ccacctgcca gacccccaag    900
ggcgccatca acaccagcct gcccttccag aacatccacc ccatcaccat cggcaagtgc    960
cccaagtacg tgaagagcac caagctgcgg ctggccaccg gcctgcggaa catccccagc    1020
atccagagcc ggggcctgtt cggcgccatc gccggcttca tcgagggcgg ctggaccggc    1080
atggtggacg gctggtacgg ctaccaccac cagaacgagc agggcagcgg ctacgccgcc    1140
gacctgaaga gcacccagaa cgccatcgac gagatcacca caaggtgaa cagcgtgatc    1200 gagaagatga acacccagtt caccgccgtg ggcaaggagt tcaaccacct ggagaagcgg    1260
atcgagaacc tgaacaagaa ggtggacgac ggcttcctgg acatctggac ctacaacgcc    1320
gagctgctgg tgctgctgga aaacgagcgg accctggact accacgacag caacgtgaag    1380
aacctgtacg agaaggtgcg gagccagctg aagaacaacg ccaaggagat cggcaacggc    1440
tgcttcgagt tctaccacaa gtgcgacaac acctgcatgg agagcgtgaa gaacggcacc    1500
tacgactacc ccaagtacag cgaggaggcc aagctgaacc gggaggagat cgactccgga    1560
ggcgacatca tcaagctgct gaacgagcag gtgaacaagg agatgcagag cagcaacctg    1620
tacatgagca tgagcagctg gtgctacacc cacagcctgg acggcgccgg cctgttcctg    1680
ttcgaccacg ccgccgagga gtacgagcac gccaagaagc tgatcatctt cctgaacgag    1740
```

```
aacaacgtgc cgtgcagct gaccagcatc agcgccccg agcacaagtt cgagggcctg    1800
acccagatct tccagaaggc ctacgagcac gagcagcaca tcagcgagag catcaacaac    1860
atcgtggacc acgccatcaa gagcaaggac cacgccacct tcaacttcct gcagtggtac    1920
gtggccgagc agcacgagga ggaggtgctg ttcaaggaca tcctggacaa gatcgagctg    1980
atcggcaacg agaaccacgg cctgtacctg gccgaccagt acgtgaaggg catcgccaag    2040
agcaggaaga gcggatcc                                                  2058

<210> SEQ ID NO 134
<211> LENGTH: 6497
<212> TYPE: DNA
<213> ORGANISM: Artificial Sequence
<220> FEATURE:
<223> OTHER INFORMATION: Synthetic sequence of plasmid CMV8x/R-H2SING
      HA(514)_SGG_egm

<400> SEQUENCE: 134
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga ccccgccca ttgacgtcaa taatgacgta tgttcccata     480
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg gcggtaggc gtgtacggtg ggaggtctat ataagcagag     900
ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga ggccgccatc cacgccggtt gagtcgcgtt ctgccgcctc cgcctgtgg    1080 tgcctcctga actgcgtccg ccgtctaggt aagtttaaag ctcaggtcga ccgggcct      1140 ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tggccatcat ctacctgatc ctgctgttta cagctgtgcg gggcgatcag    1440
atctgtatcg gctaccacgc caacaatagc accgagaagg tggacaccat cctggaaaga    1500
aatgtgaccg tgacccacgc caaggatatt ctgaaaaaga cccacaacgg caagctgtgc    1560
aagctgaatg gcattcctcc tctgaactg ggcgattgtt ctattgctgg ctggctgctg    1620
ggaaatcctg agtgcgatag actgctgtct gtgcctgagt ggagctacat catggaaaaa    1680
```

```
gagaaccctag ggacggactg tgttaccccg gcagcttcaa cgattacgag gaactgaag      1740
cacctgctgt ccagcgtgaa gcacttcgag aaagtgaaga tcctgcccaa ggatagatgg      1800
acccagcata caacaacagg cggaagcaga gcttgtgctg tgtccggcaa ccccagcttc      1860
ttcagaaata tggtctggct gaccaagaag ggctctaatt atcctgtggc caagggcagc      1920
tacaataata caagcggcga gcagatgctg attatttggg gcgtgcacca ccctaatgat      1980
gagacagagc agagaaccct gtaccagaat gtgggcacat acgtgtctgt gggcaccagc      2040
acactgaata agagaagcac ccccgatatt gccaccagac ccaaagtgaa tggacagggc      2100
ggcagaatgg aattttcctg gacccctgctg atatgtgggg acaccatcaa ctttgagagc      2160
accgggaatc tgattgcccc tgagtacggc ttcaagatca gcaagagagg cagcagcggc      2220
atcatgaaaa cagagggcac cctggaaaac tgtgaaacca agtgtcagac acctctgggc      2280
gccattaata ccaccctgcc cttccataat gtgcaccctc tgacaatcgg cgagtgccct      2340
aagtacgtga agtctgagaa actggtgctg ccacaggac tgagaaatgt gccccagatc      2400
gagtcaagag gcctgtttgg agccattgcc ggctttattg aaggcggatg cagggaatg      2460
gtggatgggt ggtacggcta tcaccacagc aatgatcagg gatctggcta tgccgccgat      2520
aaagagagca cccagaaggc ctttgacggc atcaccaaca aagtgaacag cgtgatcgag      2580
aagatgaaca cccagtttga ggccgtgggc aaagagttca gcaatctgga aagacgctg      2640
gaaaacctga caagaaaat ggaagatggc ttcctggacg tgtggacata taatgccgag      2700
ctgctggtgc tgatggaaaa cgagaggacc ctggactttc acgacagcaa cgtgaagaac      2760
ctgtacgaca aagtgcggat gcagctgaga gacaatgtga aagagctggg caacggctgc      2820
tttgagttct accacaagtg cgacgacgag tgcatgaata gcgtgaagaa cggcacctac      2880
gactacccta agtatgagga agagagcaag ctgaacagaa acgagatcaa gtccggaggc      2940
gacatcatca gctgctgaa cgagcaggtg aacaaggaga tgcagagcag caacctgtac      3000
atgagcatga gcagctggtg ctacacccac agcctggacg gcgccggcct gttcctgttc      3060
gaccacgccg ccgaggagta cgagcacgcc aagaagctga tcatcttcct gaacgagaac      3120
aacgtgcccg tgcagctgac cagcatcagc gcccccgagc acaagttcga gggcctgacc      3180
cagatcttcc agaaggccta cgagcacgag cagcacatca gcgagagcat caacaacatc      3240
gtggaccacg ccatcaagag caaggaccac gccaccttca cttcctgca gtggtacgtg      3300
gccgagcagc acgaggagga ggtgctgttc aaggacatcc tggacaagat cgagctgatc      3360
ggcaacgaga ccacggcct gtacctggcc gaccagtacg tgaagggcat cgccaagagc      3420
aggaagagcg gatcctagca tcatcatcat cattagtctg aagggcgaa ttgatccaga      3480
tctgctgtgc cttctagttg ccagccatct gttgtttgcc cctcccccgt gccttccttg      3540
accctggaag gtgccactcc cactgtcctt tcctaataaa atgaggaaat tgcatcgcat      3600
tgtctgagta ggtgtcattc tattctgggg gtgtgggtgg gcaggacag caaggggggag      3660
gattgggaag acaatagcag gcatgctggg gatgcggtgg gctctatggg tacccaggtg      3720
ctgaagaatt gacccggttc ctcctgggcc agaaagaagc aggcacatcc ccttctctgt      3780
gacacaccct gtccacgccc ctggttctta gttccagccc cactcatagg acactcatag      3840
ctcaggaggg ctccgccttc aatcccaccc gctaaagtac ttggagcggt ctctccctcc      3900
ctcatcagcc caccaaacca aacctagcct ccaagagtgg gaagaaatta aagcaagata      3960
ggctattaag tgcagaggga gagaaaatgc ctccaacatg tgaggaagta atgagagaaa      4020
```

```
tcatagaatt ttaaggccat gatttaaggc catcatggcc ttaatcttcc gcttcctcgc    4080
tcactgactc gctgcgctcg gtcgttcggc tgcggcgagc ggtatcagct cactcaaagg    4140
cggtaatacg gttatccaca gaatcagggg ataacgcagg aaagaacatg tgagcaaaag    4200
gccagcaaaa ggccaggaac cgtaaaaagg ccgcgttgct ggcgtttttc cataggctcc    4260
gcccccctga cgagcatcac aaaaatcgac gctcaagtca gaggtggcga acccgacag    4320
gactataaag ataccaggcg tttccccctg gaagctccct cgtgcgctct cctgttccga    4380
ccctgccgct taccggatac ctgtccgcct ttctcccttc gggaagcgtg gcgctttctc    4440
atagctcacg ctgtaggtat ctcagttcgg tgtaggtcgt tcgctccaag ctgggctgtg    4500
tgcacgaacc ccccgttcag cccgaccgct gcgccttatc cggtaactat cgtcttgagt    4560
ccaacccggt aagacacgac ttatcgccac tggcagcagc cactggtaac aggattagca    4620
gagcgaggta tgtaggcggt gctacagagt tcttgaagtg gtggcctaac tacggctaca    4680
ctagaagaac agtatttggt atctgcgctc tgctgaagcc agttaccttc ggaaaaagag    4740
ttggtagctc ttgatccggc aaacaaacca ccgctggtag cggtggtttt tttgtttgca    4800
agcagcagat tacgcgcaga aaaaaaggat ctcaagaaga tcctttgatc ttttctacgg    4860
ggtctgacgc tcagtggaac gaaaactcac gttaagggat tttggtcatg agattatcaa    4920
aaaggatctt cacctagatc cttttaaatt aaaaatgaag ttttaaatca atctaaagta    4980
tatatgagta aacttggtct gacagttacc aatgcttaat cagtgaggca cctatctcag    5040
cgatctgtct atttcgttca tccatagttg cctgactcgg ggggggggg cgctgaggtc    5100
tgcctcgtga agaaggtgtt gctgactcat accaggcctg aatcgcccca tcatccagcc    5160
agaaagtgag ggagccacgg ttgatgagag ctttgttgta ggtggaccag ttggtgattt    5220
tgaacttttg ctttgccacg gaacggtctg cgttgtcggg aagatgcgtg atctgatcct    5280
tcaactcagc aaaagttcga tttattcaac aaagccgccg tcccgtcaag tcagcgtaat    5340
gctctgccag tgttacaacc aattaaccaa ttctgattag aaaaactcat cgagcatcaa    5400
atgaaactgc aatttattca tatcaggatt atcaatacca tatttttgaa aaagccgttt    5460
ctgtaatgaa ggagaaaact caccgaggca gttccatagg atggcaagat cctggtatcg    5520
gtctgcgatt ccgactcgtc aacatcaat acaacctatt aatttcccct cgtcaaaaat    5580
aaggttatca agtgagaaat caccatgagt gacgactgaa tccggtgaga atggcaaaag    5640
cttatgcatt tctttccaga cttgttcaac aggccagcca ttacgctcgt catcaaaatc    5700
actcgcatca accaaaccgt tattcattcg tgattgcgcc tgagcgagac gaaatacgcg    5760
atcgctgtta aaaggacaat tacaaacagg aatcgaatgc aaccggcgca ggaacactgc    5820
cagcgcatca acaatatttt cacctgaatc aggatattct tctaatacct ggaatgctgt    5880
tttcccgggg atcgcagtgg tgagtaacca tgcatcatca ggagtacgga taaaatgctt    5940
gatggtcgga agaggcataa attccgtcag ccagtttagt ctgaccatct catctgtaac    6000
atcattggca acgctacctt tgccatgttt cagaaacaac tctggcgcat cgggcttccc    6060
atacaatcga tagattgtcg cacctgattg cccgacatta tcgcgagccc atttataccc    6120
atataaatca gcatccatgt tggaatttaa tcgcggcctc gagcaagacg tttcccgttg    6180
aatatggctc ataacacccc ttgtattact gtttatgtaa gcagacagtt ttattgttca    6240
tgatgatata ttttatctt gtgcaatgta acatcagaga ttttgagaca caacgtggct    6300
ttcccccccc ccccattatt gaagcattta tcagggttat tgtctcatga gcggatacat    6360
atttgaatgt atttagaaaa ataaacaaat agggggttccg cgcacatttc cccgaaaagt    6420
```

```
gccacctgac gtctaagaaa ccattattat catgacatta acctataaaa ataggcgtat    6480
cacgaggccc tttcgtc                                                   6497

<210> SEQ ID NO 135
<211> LENGTH: 2046
<212> TYPE: DNA
<213> ORGANISM: Artificial Sequence
<220> FEATURE:
<223> OTHER INFORMATION: Synthetic nucleic acid sequence encoding SEQ
      ID NO:47 (lacks stop codon)

<400> SEQUENCE: 135
atggccatca tctacctgat cctgctgttt acagctgtgc ggggcgatca gatctgtatc      60
ggctaccacg ccaacaatag caccgagaag gtggacacca tcctggaaag aaatgtgacc     120
gtgacccacg ccaaggatat tctggaaaag acccacaacg gcaagctgtg caagctgaat     180
ggcattcctc tctctggaact gggcgattgt tctattgctg ctggctgct gggaaatcct     240 gagtgcgata gactgctgtc tgtgcctgag tggagctaca tcatggaaaa agagaaccct     300
agggacggac tgtgttaccc cggcagcttc aacgattacg aggaactgaa gcacctgctg     360
tccagcgtga agcacttcga gaaagtgaag atcctgccca aggatagatg gacccagcat     420
acaacaacag gcggaagcag agcttgtgct gtgtccggca accccagctt cttcagaaat     480
atggtctggc tgaccaagaa gggctctaat tatcctgtgg ccaagggcag ctacaataat     540
acaagcggcg agcagatgct gattatttgg ggcgtgcacc accctaatga tgagacagag     600
cagagaaccc tgtaccagaa tgtgggcaca tacgtgtctg tgggcaccag cacactgaat     660
aagagaagca ccccgatat tgccaccaga cccaaagtga atggacaggg cggcagaatg     720 gaatttttcct ggaccctgct ggatatgtgg gacaccatca actttgagag caccgggaat     780
ctgattgccc ctgagtacgg cttcaagatc agcaagagag gcagcagcgg catcatgaaa     840
acagagggca ccctggaaaa ctgtgaaacc aagtgtcaga cacctctggg cgccattaat     900
accaccctgc ccttccataa tgtgcaccct ctgacaatcg gcgagtgccc taagtacgtg     960
aagtctgaga actggctgct ggccacagga ctgagaaatg tgcccccagat cgagtcaaga    1020 ggcctgtttg gagccattgc cggctttatt gaaggcggat ggcagggaat ggtggatggg    1080
tggtacggct atcaccacag caatgatcag ggatctggct atgccgccga taaagagagc    1140
acccagaagg cctttgacgg catcaccaac aaagtgaaca gcgtgatcga aagatgaac    1200 acccagtttg aggccgtggg caaagagttc agcaatctgg aaagacggct ggaaaacctg    1260
aacaagaaaa tggaagatgg cttcctggac gtgtggacat ataatgccga gctgctggtg    1320
ctgatggaaa acgagaggac cctggacttt cacgacagca acgtgaagaa cctgtacgac    1380
aaagtgcgga tgcagctgag agacaatgtg aaagagctgg gcaacggctg ctttgagttc    1440
taccacaagt gcgacgacga gtgcatgaat agcgtgaaga acggcaccta cgactaccct    1500
aagtatgagg aagagagcaa gctgaacaga acgagatca agtccggagg cgacatcatc    1560
aagctgctga cgagcaggt gaacaaggag atgcagagca gcaacctgta catgagcatg    1620
agcagctggt gctacaccca gcctggac ggcgccggcc tgttcctgtt cgaccacgcc    1680
gccgaggagt acgagcacgc caagaagctg atcatcttcc tgaacgagaa caacgtgccc    1740
gtgcagctga ccagcatcag cgccccgag cacaagttcg agggcctgac ccagatcttc    1800
cagaaggcct acgagcacga gcagcacatc agcgagagca tcaacaacat cgtgaccac    1860 gccatcaaga gcaaggacca cgccaccttc aacttcctgc agtggtacgt ggccgagcag    1920
```

```
cacgaggagg aggtgctgtt caaggacatc ctggacaaga tcgagctgat cggcaacgag    1980
aaccacggcc tgtacctggc cgaccagtac gtgaagggca tcgccaagag caggaagagc    2040
ggatcc                                                                2046
```

<210> SEQ ID NO 136
<211> LENGTH: 6512
<212> TYPE: DNA
<213> ORGANISM: Artificial Sequence
<220> FEATURE:
<223> OTHER INFORMATION: Synthetic sequence of plasmid CMV8x/R-H3HK
      HA(519)_SGG_egm

<400> SEQUENCE: 136

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga cgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct    1140 ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tgaaaaccat cattgccctg agctacatct ttgtctggc tctgggccag   1440 gatctgcccg gcaatgataa tagcaccgcc accctgtgtc tggacacca cgccgtgcct   1500 aatggcaccc tggtgaaaac cattaccgac gaccagatcg aagtgaccaa tgccaccgag   1560
ctggtgcaga gcagcagcac cggcaagatc tgcaacaacc cccacagaat cctggatggc   1620
atcgactgta cccctgatcg atgccctgctg ggcgatcctc actgcgacgt gttccagaac   1680
gagacatggg acctgttcgt ggagagaagc aaggccttca gcaactgcta cccctacgat   1740
gtgcccgatt acgcctctct gagaagcctg gtggccagca cggcacact ggaattcatc   1800 accgagggct ttacctggac aggcgtgacc cagaatggcg gcagcaatgc ctgtaaaaga   1860
```

```
ggccctggca gcggcttctt cagcagactg aactggctga ccaagtccgg cagcacctac    1920
cctgtgctga acgtgaccat gcccaacaac gacaacttcg acaagctgta catctggggc    1980
gtgcaccacc ctagcaccaa tcaggaacag accagcctgt acgtgcaggc cagcggcaga    2040
gtgaccgtgt ctaccagacg gtcccagcag accatcatcc caacatcga gtcaagacct    2100 tgggtgcgcg gcctgagcag cagaatcagc atctactgga ccatcgtgaa acctggcgac    2160
gtgctggtga tcaacagcaa tggcaacctg atcgccccca gaggctactt caagatgcgg    2220
accggcaaga gcagcatcat gagaagcgac gcccccatcg atacctgtat cagcgagtgc    2280
atcaccccca acggcagcat ccccaacgac aagcccttcc agaacgtgaa caagatcacc    2340
tacggcgcct gccctaagta cgtgaagcag aacaccctga agctggccac cggcatgaga    2400
aatgtgcccg agaagcagac aagaggcctg tttggcgcca ttgccggctt tatcgagaac    2460
ggctgggagg gcatgatcga tgggtggtac ggcttcagac accagaattc tgagggcaca    2520
ggacaggccg ccgatctgaa gtctacacag gccgccatcg accagatcaa cggcaagctg    2580
aacagagtga tcgagaaaac caacgagaag ttccaccaga tcgagaaaga attcagcgag    2640
gtggagggca gaatccagga cctggaaaaa tacgtggagg acaccaagat cgacctgtgg    2700
agctacaatg ccgaactgct ggtcgccctg gaaaaccagc acaccatcga cctgaccgac    2760
agcgagatga ataagctgtt cgaaaagacc agacggcagc tgagagaaaa cgccgaggac    2820
atgggcaacg gctgcttcaa gatctaccac aagtgcgaca cgcctgcat cgagagcatc    2880 agaaacggca cctacgacca cgatgtgtac agggacgagg ccctgaacaa cagattccag    2940
atcaagtccg gaggcgacat catcaagctg ctgaacgagc aggtgaacaa ggagatgcag    3000
agcagcaacc tgtacatgag catgagcagc tggtgctaca cccacagcct ggacggcgcc    3060
ggcctgttcc tgttcgacca cgccgccgag gagtacgagc acgccaagaa gctgatcatc    3120
ttcctgaacg agaacaacgt gcccgtgcag ctgaccagca tcagcgcccc cgagcacaag    3180
ttcgagggcc tgacccagat cttccagaag gcctacgagc acgagcagca catcagcgag    3240
agcatcaaca catcgtgga ccacgccatc aagagcaagg accacgccac cttcaacttc    3300
ctgcagtggt acgtggccga gcagcacgag gaggaggtgc tgttcaagga catcctggac    3360
aagatcgagc tgatcggcaa cgagaaccac ggcctgtacc tggccgacca gtacgtgaag    3420
ggcatcgcca gagcaggaa gagcggatcc tagcatcatc atcatcatta gtctggaagg    3480
gcgaattgat ccagatctgc tgtgccttct agttgccagc catctgttgt ttgcccctcc    3540
cccgtgcctt ccttgaccct ggaaggtgcc actcccactg tcctttccta ataaaatgag    3600
gaaattgcat cgcattgtct gagtaggtgt cattctattc tggggggtgg ggtggggcag    3660
gacagcaagg gggaggattg ggaagacaat agcaggcatg ctggggatgc ggtgggctct    3720
atgggtaccc aggtgctgaa gaattgaccc ggttcctcct gggccagaaa gaagcaggca    3780 catcccttc tctgtgacac accctgtcca cgccctggt tcttagttcc agccccactc    3840
ataggacact catagctcag gagggctccg ccttcaatcc cacccgctaa agtacttgga    3900
gcggtctctc cctccctcat cagcccacca aaccaaacct agcctccaag agtgggaaga    3960
aattaaagca agataggcta ttaagtgcag agggagagaa aatgcctcca acatgtgagg    4020
aagtaatgag agaaatcata gaattttaag gccatgattt aaggccatca tggccttaat    4080
cttccgcttc ctcgctcact gactcgctgc gctcggtcgt tcggctgcgg cgagcggtat    4140
cagctcactc aaaggcggta atacggttat ccacagaatc aggggataac gcaggaaaga    4200
```

-continued

```
acatgtgagc aaaaggccag caaaaggcca ggaaccgtaa aaaggccgcg ttgctggcgt    4260
ttttccatag gctccgcccc cctgacgagc atcacaaaaa tcgacgctca agtcagaggt    4320
ggcgaaaccc gacaggacta taaagatacc aggcgtttcc ccctggaagc tccctcgtgc    4380
gctctcctgt tccgaccctg ccgcttaccg gatacctgtc cgcctttctc ccttcgggaa    4440
gcgtggcgct ttctcatagc tcacgctgta ggtatctcag ttcggtgtag gtcgttcgct    4500
ccaagctggg ctgtgtgcac gaaccccccg ttcagcccga ccgctgcgcc ttatccggta    4560
actatcgtct tgagtccaac ccggtaagac acgacttatc gccactggca gcagccactg    4620
gtaacaggat tagcagagcg aggtatgtag gcggtgctac agagttcttg aagtggtggc    4680
ctaactacgg ctacactaga agaacagtat ttggtatctg cgctctgctg aagccagtta    4740
ccttcggaaa aagagttggt agctcttgat ccggcaaaca aaccaccgct ggtagcggtg    4800
gttttttttgt ttgcaagcag cagattacgc gcagaaaaaa aggatctcaa gaagatcctt    4860
tgatcttttc tacggggtct gacgctcagt ggaacgaaaa ctcacgttaa gggattttgg    4920
tcatgagatt atcaaaaagg atcttcacct agatcctttt aaattaaaaa tgaagtttta    4980
aatcaatcta agtatatat gagtaaactt ggtctgacag ttaccaatgc ttaatcagtg    5040
aggcacctat ctcagcgatc tgtctatttc gttcatccat agttgcctga ctcggggggg    5100
gggggcgctg aggtctgcct cgtgaagaag gtgttgctga ctcataccag gcctgaatcg    5160
ccccatcatc cagccagaaa gtgagggagc cacggttgat gagagctttg ttgtaggtgg    5220
accagttggt gattttgaac ttttgctttg ccacggaacg gtctgcgttg tcgggaagat    5280
gcgtgatctg atccttcaac tcagcaaaag ttcgatttat tcaacaaagc cgccgtcccg    5340
tcaagtcagc gtaatgctct gccagtgtta caaccaatta accaattctg attagaaaaa    5400
ctcatcgagc atcaaatgaa actgcaattt attcatatca ggattatcaa taccatattt    5460
ttgaaaaagc cgtttctgta atgaaggaga aaactcaccg aggcagttcc ataggatggc    5520
aagatcctgg tatcggtctg cgattccgac tcgtccaaca tcaatacaac ctattaattt    5580
cccctcgtca aaaataaggt tatcaagtga gaaatcacca tgagtgacga ctgaatccgg    5640
tgagaatggc aaaagcttat gcatttcttt ccagacttgt tcaacaggcc agccattacg    5700
ctcgtcatca aaatcactcg catcaaccaa accgttattc attcgtgatt gcgcctgagc    5760
gagacgaaat acgcgatcgc tgttaaaagg acaattacaa acaggaatcg aatgcaaccg    5820
gcgcaggaac actgccagcg catcaacaat attttcacct gaatcaggat attcttctaa    5880
tacctggaat gctgttttcc cggggatcgc agtggtgagt aaccatgcat catcaggagt    5940
acggataaaa tgcttgatgg tcggaagagg cataaattcc gtcagccagt ttagtctgac    6000
catctcatct gtaacatcat tggcaacgct acctttgcca tgtttcagaa acaactctgg    6060
cgcatcgggc ttcccataca atcgatagat tgtcgcacct gattgcccga cattatcgcg    6120
agcccattta cccatata aatcagcatc catgttggaa tttaatcgcg gcctcgagca    6180
agacgtttcc cgttgaatat ggctcataac accccttgta ttactgttta tgtaagcaga    6240
cagtttatt gttcatgatg atatattttt atcttgtgca atgtaacatc agagattttg    6300
agacacaacg tggctttccc ccccccccca ttattgaagc atttatcagg gttattgtct    6360
catgagcgga tacatatttg aatgtattta gaaaaataaa caataggggg ttccgcgcac    6420
atttccccga aaagtgccac ctgacgtcta agaaaccatt attatcatga cattaaccta    6480
taaaatagg cgtatcacga ggccctttcg tc                                   6512
```

<210> SEQ ID NO 137
<211> LENGTH: 2061
<212> TYPE: DNA
<213> ORGANISM: Artificial Sequence
<220> FEATURE:
<223> OTHER INFORMATION: Synthetic nucleic acid sequence encoding SEQ
      ID NO:50 (lacks stop codon)

<400> SEQUENCE: 137

```
atgaaaacca tcattgccct gagctacatc ttttgtctgg ctctgggcca ggatctgccc      60
ggcaatgata atagcaccgc caccctgtgt ctgggacacc acgccgtgcc taatggcacc     120
ctggtgaaaa ccattaccga cgaccagatc gaagtgacca atgccaccga gctggtgcag     180
agcagcagca ccggcaagat ctgcaacaac ccccacagaa tcctggatgg catcgactgt     240
accctgatcg atgccctgct gggcgatcct cactgcgacg tgttccagaa cgagacatgg     300
gacctgttcg tggagagaag caaggccttc agcaactgct accectacga tgtgcccgat     360
tacgcctctc tgagaagcct ggtgccagc agcggcacac tggaattcat caccgagggc     420
tttacctgga caggcgtgac ccagaatggc ggcagcaatg cctgtaaaag gggccctggc     480
agcggcttct tcagcagact gaactggctg accaagtccg gcagcaccta ccctgtgctg     540
aacgtgacca tgcccaacaa cgacaacttc gacaagctgt acatctgggg cgtgcaccac     600
cctagcacca tcaggaaca gaccagcctg tacgtgcagg ccagcggcag agtgaccgtg     660
tctaccagac ggtcccagca gaccatcatc cccaacatcg agtcaagacc ttgggtgcgc     720
ggcctgagca gcagaatcag catctactgg accatcgtga acctggcga cgtgctggtg     780
atcaacagca atggcaacct gatcgccccc agaggctact tcaagatgcg gaccggcaag     840
agcagcatca tgagaagcga cgccccatc gatacctgta tcagcgagtg catcacccc      900
aacggcagca tccccaacga caagcccttc cagaacgtga caagatcac ctacggcgcc     960
tgccctaagt acgtgaagca gaacaccctg aagctggcca ccggcatgag aaatgtgccc    1020
gagaagcaga caagaggcct gtttggcgcc attgccggct ttatcgagaa cggctgggag    1080
ggcatgatcg atgggtggta cggcttcaga caccagaatt ctgagggcac aggacaggcc    1140
gccgatctga gtctacaca ggccgccatc gaccagatca cggcaagct gaacagagtg    1200
atcgagaaaa ccaacgagaa gttccaccag atcgagaaag aattcagcga ggtggagggc    1260
agaatccagg acctggaaaa atacgtggag gacaccaaga tcgacctgtg gagctacaat    1320
gccgaactgc tggtcgccct ggaaaaccag cacaccatcg acctgaccga cagcgagatg    1380
aataagctgt tcgaaaagac cagacggcag ctgagagaaa acgccgagga catgggcaac    1440
ggctgcttca agatctacca caagtgcgac aacgcctgca tcgagagcat cagaaacggc    1500
acctacgacc acgatgtgta cagggacgag gccctgaaca cagattcca gatcaagtcc    1560
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag cacgccaaga gctgatcat cttcctgaac    1740
gagaacaacg tgcccgtgca gctgaccagc atcagcgccc ccgagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggaggtg ctgttcaagg acatcctgga caagatcgag    1980
ctgatcggca cgagaaacca cggcctgtac ctggccgacc agtacgtgaa gggcatcgcc    2040
aagagcagga gagcggatc c                                                2061
```

<210> SEQ ID NO 138
<211> LENGTH: 6512
<212> TYPE: DNA
<213> ORGANISM: Artificial Sequence
<220> FEATURE:
<223> OTHER INFORMATION: Synthetic sequence of plasmid CMV8x/R-H3Bris
      HA(519)_SGG_egm

<400> SEQUENCE: 138

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| gggaacttcc | atagcccata | tatggagttc | cgcgttacat | aacttacggg | aatttccaaa | 420 |
| cctggctgac | cgcccaacga | cccccgccca | ttgacgtcaa | taatgacgta | tgttcccata | 480 |
| gtaacgccaa | tagggaactt | ccattgacgt | caatgggtgg | agtatttacg | gtaaactgcc | 540 |
| cacttgggaa | tttccaagtg | tatcatatgc | caagtacgcc | ccctattgac | gtcaatgacg | 600 |
| ggaacttcca | taagcttgca | ttatgcccag | tacatgacct | tatgggaatt | tcctacttgg | 660 |
| cagtacatct | acgtattagt | catcgctatt | accatggtga | tgcggttttg | gcagtacatc | 720 |
| aatgggcgtg | gatagcggtt | tgactcacgg | gaacttccaa | gtctccaccc | cattgacgtc | 780 |
| aatgggagtt | tgttttgact | caccaaaatc | aacgggaatt | cccaaaatgt | cgtaacaact | 840 |
| ccgccccatt | gacgcaaatg | ggcggtaggc | gtgtacggtg | ggaggtctat | ataagcagag | 900 |
| ctcgtttagt | gaaccgtcag | atcgcctgga | gacgccatcc | acgctgtttt | gacctccata | 960 |
| gaagacaccg | ggaccgatcc | agcctccatc | ggctcgcatc | tctccttcac | gcgcccgccg | 1020 |
| ccctacctga | ggccgccatc | cacgccggtt | gagtcgcgtt | ctgccgcctc | ccgcctgtgg | 1080 |
| tgcctcctga | actgcgtccg | ccgtctaggt | aagtttaaag | ctcaggtcga | gaccgggcct | 1140 |
| ttgtccggcg | ctcccttgga | gcctacctag | actcagccgg | ctctccacgc | tttgcctgac | 1200 |
| cctgcttgct | caactctagt | taacggtgga | gggcagtgta | gtctgagcag | tactcgttgc | 1260 |
| tgccgcgcgc | gccaccagac | ataatagctg | acagactaac | agactgttcc | tttccatggg | 1320 |
| tcttttctgc | agtcaccgtc | gtcgacacgt | gtgatcagat | cgcggccg | ctctagagat | 1380 |
| atcgccacca | tgaaaaccat | cattgccctg | agctacatcc | tgtgcctggt | gttcacacag | 1440 |
| aagctgcccg | gcaacgataa | tagcaccgcc | acactgtgtc | tgggacacca | cgccgtgcct | 1500 |
| aatggcacca | tcgtgaaaac | aatcaccaac | gaccagatcg | aagtgaccaa | tgccacagag | 1560 |
| ctggtgcaga | gcagcagcac | aggcgagatc | tgtgacagcc | ccaccagat | cctggatggc | 1620 |
| gagaactgta | ccctgatcga | tgccctgctg | ggcgatcctc | agtgcgacgg | cttccagaac | 1680 |
| aagaaatggg | acctgttcgt | ggagagaagc | aaggcctaca | gcaactgcta | ccctacgac | 1740 |
| gtgcctgatt | acgccagcct | gagaagcctg | gtggcctcta | gcggcaccct | ggaattcaac | 1800 |
| aacgagagct | tcaactggac | cggcgtgaca | cagaatggca | ccagcagcgc | ctgcatcaga | 1860 |
| cggtccaaca | acagcttctt | cagtagactg | aattggctga | cccacctgaa | gttcaagtac | 1920 |
| cccgccctga | acgtgaccat | gcccaacaat | gagaagttcg | acaagctgta | catctgggga | 1980 |
| gtgcaccacc | ctggcaccga | caacgatcag | atcttcccct | acgcccaggc | cagcggcaga | 2040 |

-continued

```
atcaccgtgt ccaccaagag aagccagcag accgtgatcc ccaatatcgg cagcagaccc      2100
agagtgcgga acatcccag caggatcagc atctactgga caatcgtgaa gcctggcgac       2160
atcctgctga tcaacagcac cggcaacctg atcgcccctc ggggctactt taagatcaga      2220
agcggcaaga gcagcatcat gagatccgac gcccccatcg gcaagtgcaa cagcgagtgc     2280
atcaccccaa acggcagcat ccccaacgac aagcccttcc agaacgtgaa caggatcacc      2340
tacggcgcct gccctagata cgtgaagcag aacaccctga gctggccac cggcatgaga      2400 aatgtgcccg agaagcagac cagaggcatc tttggcgcca ttgccggctt tatcgagaat     2460
ggctgggagg aatggtgga tgggtggtac ggcttcagac accagaatag cgagggaatt      2520
ggacaggccg ccgatctgaa atctacccag gccgccatcg accagatcaa cggcaagctg     2580
aacaggctga tcggcaagac caacgagaag ttccaccaga tcgagaaaga attcagcgag     2640
gtggagggca gaatccagga cctggaaaaa tacgtggagg acaccaagat cgacctgtgg     2700
agctacaatg ccgaactgct ggtcgccctg gaaaaccagc acacaattga tctgacagac      2760
agtgagatga ataagctgtt cgagaaaacc aagaagcagc tgagagaaaa cgccgaggac     2820
atgggcaacg gctgcttcaa gatctaccac aagtgcgaca acgcctgcat cggcagcatc      2880
agaaacggca cctacgacca cgacgtgtac agagatgagg ccctgaacaa ccggtttcag     2940
atcaagtccg gaggcgacat catcaagctg ctgaacgagc aggtgaacaa ggagatgcag     3000
agcagcaacc tgtacatgag catgagcagc tggtgctaca cccacagcct ggacggcgcc      3060
ggcctgttcc tgttcgacca cgccgccgag gagtacgagc acgccaagaa gctgatcatc      3120
ttcctgaacg agaacaacgt gcccgtgcag ctgaccagca tcagcgcccc cgagcacaag      3180
ttcgagggcc tgacccagat cttccagaag gcctacgagc acgagcagca catcagcgag     3240
agcatcaaca acatcgtgga ccacgccatc aagagcaagg accacgccac cttcaacttc      3300
ctgcagtggt acgtggccga gcagcacgag gaggaggtgc tgttcaagga catcctggac      3360
aagatcgagc tgatcggcaa cgagaaccac ggcctgtacc tggccgacca gtacgtgaag     3420
ggcatcgcca agagcaggaa gagcggatcc tagcatcatc atcatcatta gtctggaagg     3480
gcgaattgat ccagatctgc tgtgccttct agttgccagc catctgttgt ttgccctcc       3540 cccgtgcctt ccttgaccct ggaaggtgcc actcccactg tcctttccta ataaaatgag      3600
gaaattgcat cgcattgtct gagtaggtgt cattctattc tggggggtgg ggtggggcag      3660
gacagcaagg gggaggattg gaagacaat agcaggcatg ctgggatgc ggtgggctct        3720 atgggtaccc aggtgctgaa gaattgaccc ggttcctcct gggccagaaa gaagcaggca      3780
catccccttc tctgtgacac accctgtcca cgcccctggt tcttagttcc agccccactc      3840
ataggacact catagctcag gagggctccg ccttcaatcc cacccgctaa agtacttgga      3900
gcggtctctc cctccctcat cagcccacca aaccaaacct agcctccaag agtgggaaga     3960
aattaaagca agataggcta ttaagtgcag agggagagaa aatgcctcca acatgtgagg     4020
aagtaatgag agaaatcata gaattttaag gccatgattt aaggccatca tggccttaat     4080
cttccgcttc ctcgctcact gactcgctgc gctcggtcgt tcggctgcgg cgagcggtat      4140
cagctcactc aaaggcggta atacggttat ccacagaatc aggggataac gcaggaaaga     4200
acatgtgagc aaaaggccag caaaaggcca ggaaccgtaa aaaggccgcg ttgctggcgt     4260
ttttccatag gctccgcccc cctgacgagc atcacaaaaa tcgacgctca agtcagaggt     4320
ggcgaaaccc gacaggacta taaagatacc aggcgtttcc ccctggaagc tccctcgtgc     4380
```

-continued

```
gctctcctgt tccgaccctg ccgcttaccg gatacctgtc cgcctttctc ccttcgggaa      4440
gcgtggcgct ttctcatagc tcacgctgta ggtatctcag ttcggtgtag gtcgttcgct      4500
ccaagctggg ctgtgtgcac gaaccccccg ttcagcccga ccgctgcgcc ttatccggta      4560
actatcgtct tgagtccaac ccggtaagac acgacttatc gccactggca gcagccactg      4620
gtaacaggat tagcagagcg aggtatgtag gcggtgctac agagttcttg aagtggtggc      4680
ctaactacgg ctacactaga agaacagtat ttggtatctg cgctctgctg aagccagtta      4740
ccttcggaaa aagagttggt agctcttgat ccggcaaaca accaccgct ggtagcggtg       4800
gtttttttgt ttgcaagcag cagattacgc gcagaaaaaa aggatctcaa gaagatcctt      4860
tgatcttttc tacggggtct gacgctcagt ggaacgaaaa ctcacgttaa gggattttgg      4920
tcatgagatt atcaaaaagg atcttcacct agatcctttt aaattaaaaa tgaagtttta      4980
aatcaatcta agtatatat gagtaaactt ggtctgacag ttaccaatgc ttaatcagtg       5040
aggcacctat ctcagcgatc tgtctatttc gttcatccat agttgcctga ctcggggggg      5100
gggggcgctg aggtctgcct cgtgaagaag gtgttgctga ctcataccag gcctgaatcg      5160
ccccatcatc cagccagaaa gtgagggagc cacggttgat gagagctttg ttgtaggtgg      5220
accagttggt gattttgaac ttttgctttg ccacggaacg gtctgcgttg tcgggaagat      5280
gcgtgatctg atccttcaac tcagcaaaag ttcgatttat tcaacaaagc cgccgtcccg      5340
tcaagtcagc gtaatgctct gccagtgtta caaccaatta accaattctg attagaaaaa      5400
ctcatcgagc atcaaatgaa actgcaattt attcatatca ggattatcaa taccatattt      5460
ttgaaaaagc cgtttctgta atgaaggaga aaactcaccg aggcagttcc ataggatggc      5520
aagatcctgg tatcggtctg cgattccgac tcgtccaaca tcaatacaac ctattaattt     5580
cccctcgtca aaataaggt tatcaagtga aaatcacca tgagtgacga ctgaatccgg        5640
tgagaatggc aaaagcttat gcatttcttt ccagacttgt tcaacaggcc agccattacg      5700
ctcgtcatca aaatcactcg catcaaccaa accgttattc attcgtgatt gcgcctgagc      5760
gagacgaaat acgcgatcgc tgttaaaagg acaattacaa acaggaatcg aatgcaaccg      5820
gcgcaggaac actgccagcg catcaacaat attttcacct gaatcaggat attcttctaa      5880
tacctggaat gctgttttcc cggggatcgc agtggtgagt aaccatgcat catcaggagt      5940
acggataaaa tgcttgatgg tcggaagagg cataaattcc gtcagccagt ttagtctgac      6000
catctcatct gtaacatcat tggcaacgct acctttgcca tgtttcagaa acaactctgg     6060
cgcatcgggc ttcccataca atcgatagat tgtcgcacct gattgcccga cattatcgcg     6120
agcccattta tacccatata aatcagcatc catgttggaa tttaatcgcg gcctcgagca     6180
agacgtttcc cgttgaatat ggctcataac accccttgta ttactgttta tgtaagcaga     6240
cagttttatt gttcatgatg atatatttt atcttgtgca atgtaacatc agagattttg      6300
agacacaacg tggctttccc ccccccccca ttattgaagc atttatcagg gttattgtct     6360
catgagcgga tacatatttg aatgtattta gaaaaataaa caaatagggg ttccgcgcac     6420
atttccccga aaagtgccac ctgacgtcta agaaaccatt attatcatga cattaaccta     6480
taaaaatagg cgtatcacga ggccctttcg tc                                    6512
```

<210> SEQ ID NO 139
<211> LENGTH: 2061
<212> TYPE: DNA
<213> ORGANISM: Artificial Sequence
<220> FEATURE:
<223> OTHER INFORMATION: Synthetic nucleic acid sequence encoding SEQ ID NO:53 (nearly identical to SEQ ID NO:52 but lacks stop codon)

<400> SEQUENCE: 139

```
atgaaaacca tcattgccct gagctacatc ctgtgcctgg tgttcacaca gaagctgccc      60
ggcaacgata tagcaccgc cacactgtgt ctgggacacc acgccgtgcc taatggcacc     120
atcgtgaaaa caatcaccaa cgaccagatc gaagtgacca atgccacaga gctggtgcag     180
agcagcagca caggcgagat ctgtgacagc ccccaccaga tcctggatgg cgagaactgt     240
accctgatcg atgccctgct gggcgatcct cagtgcgacg gcttccagaa caagaaatgg     300
gacctgttcg tggagagaag caaggcctac agcaactgct accctacga cgtgcctgat     360
tacgccagcc tgagaagcct ggtggcctct agcggcaccc tggaattcaa caacgagagc     420
ttcaactgga ccggcgtgac acagaatggc accagcagcg cctgcatcag acggtccaac     480
aacagcttct tcagtagact gaattggctg acccacctga gttcaagta ccccgccctg     540
aacgtgacca tgcccaacaa tgagaagttc gacaagctgt acatctgggg agtgcaccac     600
cctggcaccg acaacgatca gatcttccct tacgcccagg ccagcggcag aatcaccgtg     660
tccaccaaga aagccagca gaccgtgatc cccaatatcg gcagcagacc cagagtgcgg     720
aacatcccca gcaggatcag catctactgg acaatcgtga gcctggcga catcctgctg     780
atcaacagca ccggcaacct gatcgcccct cggggctact ttaagatcag aagcggcaag     840
agcagcatca tgagatccga cgcccccatc ggcaagtgca cagcgagtg catcaccccca    900
aacggcagca tccccaacga caagcccttc agaacgtga acaggatcac ctacggcgcc     960
tgccctagat acgtgaagca gaacaccctg aagctggcca ccggcatgag aaatgtgccc    1020
gagaagcaga ccagaggcat ctttggcgcc attgccggct ttatcgagaa tggctgggag    1080
ggaatggtgg atgggtggta cggcttcaga caccagaata gcgagggaat tggacaggcc    1140
gccgatctga atctaccca ggccgccatc gaccagatca cggcaagct gaacaggctg    1200
atcggcaaga ccaacgagaa gttccaccag atcgagaaag aattcagcga ggtggagggc    1260
agaatccagg acctggaaaa atacgtggag gacaccaaga tcgacctgtg gagctacaat    1320
gccgaactgc tggtcgccct ggaaaaccag cacacaattg atctgacaga cagtgagatg    1380
aataagctgt tcgagaaaac caagaagcag ctgagagaaa acgccgagga catgggcaac    1440
ggctgcttca gatctacca caagtgcgac aacgcctgca tcggcagcat cagaaacggc    1500
acctacgacc acgacgtgta cagagatgag gccctgaaca accggtttca gatcaagtcc    1560
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag cacgccaaga agctgatcat cttcctgaac    1740
gagaacaacg tgcccgtgca gctgaccagc atcagcgccc ccgagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggagtg ctgttcaagg acatcctgga caagatcgag    1980
ctgatcggca cgagaacca cggcctgtac ctggccgacc agtacgtgaa gggcatcgcc    2040
aagagcagga gagcggatc c                                              2061
```

<210> SEQ ID NO 140
<211> LENGTH: 6515
<212> TYPE: DNA
<213> ORGANISM: Artificial Sequence
<220> FEATURE:
<223> OTHER INFORMATION: Synthetic sequence of plasmid CMV8x/R-H5Indo
HA(520)_SGG_egm

<400> SEQUENCE: 140

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggaaaagat cgtgctgctg ctggccattg tgagcctggt gaagagcgac   1440
cagatctgca ttggctacca cgccaacaat agcacagagc aggtggacac catcatggaa   1500
aaaaacgtga ccgtgaccca cgctcaggac atcctggaaa agacccacaa cggcaagctg   1560
tgtgatctgg acggcgtgaa gcctctgatc ctgagagatt gtagcgtggc tggatggctg   1620
ctgggcaacc ctatgtgcga cgagttcatc aacgtgcccg agtggagcta tatcgtggag   1680
aaggccaacc ccaccaacga tctgtgttac cccggcagct tcaacgatta cgaggaactg   1740
aagcacctgc tgtcccggat caaccacttc gagaagatcc agatcatccc caagtcctct   1800
tggagcgatc acgaagcctc tagcggagtg tctagcgcct gtccttacct gggcagcccc   1860
agcttcttca gaaacgtggt gtggctgatc aagaagaaca gcacctaccc caccatcaag   1920
aagagctaca acaacaccaa ccaggaagat ctgctggtcc tgtggggaat ccaccaccct   1980
aatgatgccg ccgagcagac cagactgtac cagaacccca ccacctatat cagcatcggc   2040
accagcaccc tgaatcagag actggtgccc aagatcgcca ccagatccaa ggtgaacggc   2100
cagagcggca ggatggaatt cttctggacc atcctgaagc ccaacgacgc catcaacttc   2160
gagagcaacg gcaactttat cgcccctgag tacgcctaca agatcgtgaa gaagggcgac   2220
```

```
agcgccatca tgaagagcga gctggaatac ggcaactgca acaccaagtg ccagacacct   2280
atgggcgcca tcaacagcag catgcccttc cacaacatcc accctctgac catcggcgag   2340
tgccctaagt acgtgaagag caacagactg gtgctggcca caggcctgag aaatagcccc   2400 cagcggggaga gcagaagaaa gaagaggggc ctgtttggag ccatcgccgg ctttattgaa   2460
ggcggctggc agggaatggt ggatggctgg tacggctacc accacagcaa tgagcagggc   2520
tctggatatg ccgccgacaa agagtctacc cagaaggcca tcgacggcgt caccaacaag   2580
gtgaacagca tcatcgacaa gatgaacacc cagttcgagg ctgtgggcag agagttcaac   2640
aacctggaac ggcggatcga gaacctgaac aagaaaatgg aagatggctt cctggatgtg   2700
tggacctaca atgccgaact gctggtgctg atggaaaacg agcggaccct ggacttccac   2760
gacagcaacg tgaagaacct gtacgacaaa gtgcggctgc agctgagaga caacgccaaa   2820
gagctgggca cggctgctt cgagttctac cacaagtgcg acaacgagtg catggaaagc   2880
atcaggaacg gcacctacaa ctaccctcag tacagcgagg aagccaggct gaagagggaa   2940
gagatcagct ccggaggcga catcatcaag ctgctgaacg agcaggtgaa caaggagatg   3000
cagagcagca acctgtacat gagcatgagc agctggtgct acacccacag cctggacggc   3060
gccggcctgt tcctgttcga ccacgccgcc gaggagtacg agcacgccaa gaagctgatc   3120
atcttcctga cgagaacaa cgtgcccgtg cagctgacca gcatcagcgc ccccgagcac   3180
aagttcgagg gcctgaccca gatcttccag aaggcctacg agcacgagca gcacatcagc   3240
gagagcatca caacatcgt ggaccacgcc atcaagagca aggaccacgc caccttcaac   3300
ttcctgcagt ggtacgtggc cgagcagcac gaggaggagg tgctgttcaa ggacatcctg   3360
gacaagatcg agctgatcgg caacgagaac cacggcctgt acctggccga ccagtacgtg   3420
aagggcatcg ccaagagcag gaagagcgga tcctagcatc atcatcatca ttagtctgga   3480
agggcgaatt gatccagatc tgctgtgcct tctagttgcc agccatctgt tgtttgcccc   3540
tcccccgtgc cttccttgac cctggaaggt gccactccca ctgtcctttc ctaataaaat   3600
gaggaaattg catcgcattg tctgagtagg tgtcattcta ttctgggggg tggggtgggg   3660
caggacagca agggggagga ttgggaagac aatagcaggc atgctgggga tgcggtgggc   3720
tctatgggta cccaggtgct gaagaattga cccggttcct cctgggccag aaagaagcag   3780
gcacatcccc ttctctgtga cacaccctgt ccacgcccct ggttcttagt tccagcccca   3840
ctcataggac actcatagct caggagggct ccgccttcaa tcccacccgc taaagtactt   3900
ggagcggtct ctccctccct catcagccca ccaaaccaaa cctagcctcc aagagtggga   3960
agaaattaaa gcaagatagg ctattaagtg cagagggaga gaaaatgcct ccaacatgtg   4020
aggaagtaat gagagaaatc atagaatttt aaggccatga tttaaggcca tcatggcctt   4080
aatcttccgc ttcctcgctc actgactcgc tgcgctcggt cgttcggctg cggcgagcgg   4140
tatcagctca ctcaaaggcg gtaatacggt tatccacaga atcaggggat aacgcaggaa   4200
agaacatgtg agcaaaaggc cagcaaaagg ccaggaaccg taaaaaggcc gcgttgctgg   4260
cgttttccca taggctccgc ccccctgacg agcatcacaa aaatcgacgc tcaagtcaga   4320
ggtggcgaaa cccgacagga ctataaagat accaggcgtt ccccctggaa gctccctcg   4380 tgcgctctcc tgttccgacc ctgccgctta ccggatacct gtccgccttt ctcccttcgg   4440
gaagcgtggc gctttctcat agctcacgct gtaggtatct cagttcggtg taggtcgttc   4500
gctccaagct gggctgtgtg cacgaacccc ccgttcagcc cgaccgctgc gccttatccg   4560
```

| | |
|---|---|
| gtaactatcg tcttgagtcc aacccggtaa gacacgactt atcgccactg gcagcagcca | 4620 |
| ctggtaacag gattagcaga gcgaggtatg taggcggtgc tacagagttc ttgaagtggt | 4680 |
| ggcctaacta cggctacact agaagaacag tatttggtat ctgcgctctg ctgaagccag | 4740 |
| ttaccttcgg aaaaagagtt ggtagctctt gatccggcaa acaaaccacc gctggtagcg | 4800 |
| gtggtttttt tgtttgcaag cagcagatta cgcgcagaaa aaaggatctc aagaagatc | 4860 |
| ctttgatctt ttctacgggg tctgacgctc agtggaacga aaactcacgt taagggattt | 4920 |
| tggtcatgag attatcaaaa aggatcttca cctagatcct tttaaattaa aaatgaagtt | 4980 |
| ttaaatcaat ctaaagtata tatgagtaaa cttggtctga cagttaccaa tgcttaatca | 5040 |
| gtgaggcacc tatctcagcg atctgtctat ttcgttcatc catagttgcc tgactcgggg | 5100 |
| ggggggggcg ctgaggtctg cctcgtgaag aaggtgttgc tgactcatac caggcctgaa | 5160 |
| tcgccccatc atccagccag aaagtgaggg agccacggtt gatgagagct ttgttgtagg | 5220 |
| tggaccagtt ggtgattttg aacttttgct ttgccacgga acggtctgcg ttgtcgggaa | 5280 |
| gatgcgtgat ctgatccttc aactcagcaa aagttcgatt tattcaacaa agccgccgtc | 5340 |
| ccgtcaagtc agcgtaatgc tctgccagtg ttacaaccaa ttaaccaatt ctgattagaa | 5400 |
| aaactcatcg agcatcaaat gaaactgcaa tttattcata tcaggattat caataccata | 5460 |
| tttttgaaaa agccgtttct gtaatgaagg agaaaactca ccgaggcagt tccataggat | 5520 |
| ggcaagatcc tggtatcggt ctgcgattcc gactcgtcca acatcaatac aacctattaa | 5580 |
| tttcccctcg tcaaaaataa ggttatcaag tgagaaatca ccatgagtga cgactgaatc | 5640 |
| cggtgagaat ggcaaaagct tatgcatttc tttccagact tgttcaacag gccagccatt | 5700 |
| acgctcgtca tcaaaatcac tcgcatcaac caaaccgtta ttcattcgtg attgcgcctg | 5760 |
| agcgagacga atacgcgat cgctgttaaa aggacaatta caaacaggaa tcgaatgcaa | 5820 |
| ccggcgcagg aacactgcca gcgcatcaac aatattttca cctgaatcag gatattcttc | 5880 |
| taatacctgg aatgctgttt tcccggggat cgcagtggtg agtaaccatg catcatcagg | 5940 |
| agtacggata aaatgcttga tggtcggaag aggcataaat tccgtcagcc agtttagtct | 6000 |
| gaccatctca tctgtaacat cattggcaac gctacctttg ccatgtttca gaaacaactc | 6060 |
| tggcgcatcg ggcttcccat acaatcgata gattgtcgca cctgattgcc cgacattatc | 6120 |
| gcgagcccat ttatacccat ataaatcagc atccatgttg gaatttaatc gcggcctcga | 6180 |
| gcaagacgtt tcccgttgaa tatggctcat aacacccctt gtattactgt ttatgtaagc | 6240 |
| agacagtttt attgttcatg atgatatatt tttatcttgt gcaatgtaac atcagagatt | 6300 |
| ttgagacaca acgtggcttt cccccccccc ccattattga agcatttatc agggttattg | 6360 |
| tctcatgagc ggatacatat ttgaatgtat ttagaaaaat aaacaaatag gggttccgcg | 6420 |
| cacatttccc cgaaaagtgc cacctgacgt ctaagaaacc attattatca tgacattaac | 6480 |
| ctataaaaat aggcgtatca cgaggcccct tcgtc | 6515 |

<210> SEQ ID NO 141
<211> LENGTH: 2064
<212> TYPE: DNA
<213> ORGANISM: Artificial Sequence
<220> FEATURE:
<223> OTHER INFORMATION: Synthetic nucleic acid sequence encoding SEQ
      ID NO:56 (nearly identical to SEQ ID NO:55 but lacks stop codon)

<400> SEQUENCE: 141

| | |
|---|---|
| atggaaaaga tcgtgctgct gctggccatt gtgagcctgg tgaagagcga ccagatctgc | 60 |

| | |
|---|---|
| attggctacc acgccaacaa tagcacagag caggtggaca ccatcatgga aaaaaacgtg | 120 |
| accgtgaccc acgctcagga catcctggaa aagacccaca acggcaagct gtgtgatctg | 180 |
| gacggcgtga agcctctgat cctgagagat tgtagcgtgg ctggatggct gctgggcaac | 240 |
| cctatgtgcg acgagttcat caacgtgccc gagtggagct atatcgtgga aaggccaac | 300 |
| cccaccaacg atctgtgtta ccccggcagc ttcaacgatt acgaggaact gaagcacctg | 360 |
| ctgtcccgga tcaaccactt cgagaagatc cagatcatcc ccaagtcctc ttggagcgat | 420 |
| cacgaagcct ctagcggagt gtctagcgcc tgtccttacc tgggcagccc cagcttcttc | 480 |
| agaaacgtgg tgtggctgat caagaagaac agcacctacc ccaccatcaa gaagagctac | 540 |
| aacaacacca accaggaaga tctgctggtc ctgtgggaa tccaccaccc taatgatgcc | 600 |
| gccgagcaga ccagactgta ccagaacccc accacctata tcagcatcgg caccagcacc | 660 |
| ctgaatcaga gactggtgcc caagatcgcc accagatcca aggtgaacgg ccagagcggc | 720 |
| aggatggaat tcttctggac catcctgaag cccaacgacg ccatcaactt cgagagcaac | 780 |
| ggcaacttta tcgcccctga gtacgcctac aagatcgtga agaagggcga cagcgccatc | 840 |
| atgaagagcg agctggaata cggcaactgc aacaccaagt gccagacacc tatgggcgcc | 900 |
| atcaacagca gcatgccctt ccacaacatc cacccctctga ccatcggcga gtgccctaag | 960 |
| tacgtgaaga gcaacagact ggtgctggcc acaggcctga aaatagccc ccagcgggag | 1020 |
| agcagaagaa agaagagggg cctgtttgga gccatcgccg gctttattga aggcggctgg | 1080 |
| cagggaatgg tggatggctg gtacggctac accacagca atgagcaggg ctctggatat | 1140 |
| gccgccgaca aagagtctac ccagaaggcc atcgacggcg tcaccaacaa ggtgaacagc | 1200 |
| atcatcgaca agatgaacac ccagttcgag gctgtgggca gagagttcaa caacctggaa | 1260 |
| cggcggatcg agaacctgaa caagaaaatg gaagatggct tcctggatgt gtggacctac | 1320 |
| aatgccgaac tgctggtgct gatggaaaac gagcggaccc tggacttcca cgacagcaac | 1380 |
| gtgaagaacc tgtacgacaa agtgcggctg cagctgagag acaacgccaa agagctgggc | 1440 |
| aacggctgct tcgagttcta ccacaagtgc gacaacgagt gcatggaaag catcaggaac | 1500 |
| ggcacctaca actaccctca gtacagcgag gaagccaggc tgaagaggga agagatcagc | 1560 |
| tccggaggcg acatcatcaa gctgctgaac gagcaggtga caaggagat gcagagcagc | 1620 |
| aacctgtaca tgagcatgag cagctggtgc tacacccaca gcctgacgg cgccggcctg | 1680 |
| ttcctgttcg accacgccgc cgaggagtac gagcacgcca gaagctgat catcttcctg | 1740 |
| aacgagaaca acgtgcccgt gcagctgacc agcatcagcg cccccgagca caagttcgag | 1800 |
| ggcctgaccc agatcttcca gaaggcctac gagcacgagc agcacatcag cgagagcatc | 1860 |
| aacaacatcg tggaccacgc catcaagagc aaggaccacg ccaccttcaa cttcctgcag | 1920 |
| tggtacgtgg ccgagcagca cgaggaggag gtgctgttca aggacatcct ggacaagatc | 1980 |
| gagctgatcg gcaacgagaa ccacggcctg tacctggccg accagtacgt gaagggcatc | 2040 |
| gccaagagca ggaagagcgg atcc | 2064 |

<210> SEQ ID NO 142
<211> LENGTH: 6557
<212> TYPE: DNA
<213> ORGANISM: Artificial Sequence
<220> FEATURE:
<223> OTHER INFORMATION: Synthetic sequence of plasmid CMV8x/R-B.Florida
    HA(534)_SGG_egm

<400> SEQUENCE: 142

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
gggaacttcc atagcccata tatggagttc cgcgttacat aacttacggg aatttccaaa      420
cctggctgac cgcccaacga ccccgccca ttgacgtcaa taatgacgta tgttcccata      480
gtaacgccaa tagggaactt ccattgacgt caatgggtgg agtatttacg gtaaactgcc      540
cacttgggaa tttccaagtg tatcatatgc caagtacgcc ccctattgac gtcaatgacg      600
ggaacttcca taagcttgca ttatgcccag tacatgacct tatgggaatt tcctacttgg      660
cagtacatct acgtattagt catcgctatt accatggtga tgcggttttg gcagtacatc      720
aatgggcgtg gatagcggtt tgactcacgg gaacttccaa gtctcaccc cattgacgtc      780
aatgggagtt tgttttgact caccaaaatc aacgggaatt cccaaaatgt cgtaacaact      840
ccgccccatt gacgcaaatg gcggtaggc gtgtacggtg ggaggtctat ataagcagag      900
ctcgtttagt gaaccgtcag atcgcctgga gacgccatcc acgctgtttt gacctccata      960
gaagacaccg ggaccgatcc agcctccatc ggctcgcatc tctccttcac gcgcccgccg     1020
ccctacctga ggccgccatc cacgccggtt gagtcgcgtt ctgccgcctc ccgcctgtgg     1080
tgcctcctga actgcgtccg ccgtctaggt aagtttaaag ctcaggtcga ccgggcct      1140
ttgtccggcg ctcccttgga gcctacctag actcagccgg ctctccacgc tttgcctgac     1200
cctgcttgct caactctagt taacggtgga gggcagtgta gtctgagcag tactcgttgc     1260
tgccgcgcgc gccaccagac ataatagctg acagactaac agactgttcc tttccatggg     1320
tcttttctgc agtcaccgtc gtcgacacgt gtgatcagat atcgcggccg ctctagagat     1380
atcgccacca tgaaggccat catcgtgctg ctgatggtgg tgaccagcaa cgccgataga     1440
atctgcaccg gcatcaccag cagcaatagc ccccatgtgg tgaaaacagc cacccagggc     1500
gaagtgaatg tgacaggcgt gatccctctg accaccaccc ccaccaagag ctacttcgcc     1560
aacctgaagg gcaccagaac cagaggcaag ctgtgccccg attgcctgaa ctgcaccgat     1620
ctggatgtgg ctctgggcag acctatgtgt gtgggcacca ccatctgc caaggccagc     1680
atcctgcacg aagtgaagcc tgtgaccagc ggctgcttcc ccatcatgca cgaccggacc     1740
aagatcagac agctgcccaa cctgctgaga ggctacgaga acatccggct gtccacccag     1800
aatgtgatcg atgccgagaa agcccctggc ggaccttata gactgggcac cagcggctct     1860
tgtcccaatg ccacctccaa gagcggcttt tttgccacaa tggcctgggc cgtgcctaag     1920
gacaacaaca agaacgccac caaccctctg accgtggagg tgccctacat ctgtacagag     1980
ggcgaggatc agatcacagt gtggggcttc cacagcgacg acaagaccca gatgaagaac     2040
ctgtacggcg acagcaaccc ccagaagttt accagcagcg ccaatggcgt gaccaccac      2100
tacgtgtccc agatcggcag ctttcccgat cagacagagg atggcggact gcctcagtct     2160
ggcaggatcg tggtggacta catgatgcag aagcctggca gaccggcac catcgtgtat     2220
cagagaggcg tgctgctgcc tcagaaagtg tggtgtgcca gcggcaggtc taaagtgatc     2280
aagggcagct gcctctgat tggcgaggcc gactgtctgc acgaaaagta cggcggcctg     2340
aacaagagca gccctactaca cacaggcgag cacgccaagg ccatcggcaa ttgccccatc     2400
```

```
tgggtgaaaa ccccctgaa gctggccaat ggcaccaagt acagacctcc cgccaagctg   2460
ctgaaagaga gaggcttctt tggcgccatt gccggatttc tggaaggcgg ctgggaggga   2520
atgattgccg gctggcacgg ctatacatct catggggccc atggcgtggc tgtggccgcc   2580
gatctgaagt ctacccagga agccatcaac aagatcacca agaacctgaa cagcctgagc   2640
gagctggaag tgaagaatct gcagagactg agcggcgcca tggatgagct gcacaacgag   2700
atcctggaac tggacgagaa agtggatgat ctccgcgccg atacaatttc ctcccagatt   2760
gaactggccg tgctgctgtc caacgagggc atcatcaaca gcgaggatga acacctgctg   2820 gccctgaac ggaagctgaa gagatgctg gcccttctg ccgtggagat cggcaacggc   2880
tgcttcgaga caaagcacaa gtgcaaccag acctgctgg atagaatcgc cgctggcacc   2940
ttcaatgccg gcgagttcag cctgcctacc ttcgacagcc tgaatatcac ctccggaggc   3000
gacatcatca gctgctgaa cgagcaggtg aacaaggaga tgcagagcag caacctgtac   3060
atgagcatga gcagctggtg ctacacccac agcctggacg gcgccggcct gttcctgttc   3120
gaccacgccg ccgaggagta cgagcacgcc aagaagctga tcatcttcct gaacgagaac   3180
aacgtgcccg tgcagctgac cagcatcagc gcccccgagc acaagttcga gggcctgacc   3240
cagatcttcc agaaggccta cgagcacgag cagcacatca gcgagagcat caacaacatc   3300
gtggaccacg ccatcaagag caaggaccac gccaccttca acttcctgca gtggtacgtg   3360
gccgagcagc acgaggagga ggtgctgttc aaggacatcc tggacaagat cgagctgatc   3420
ggcaacgaga accacggcct gtacctggcc gaccagtacg tgaagggcat cgccaagagc   3480
aggaagagcg atcctagca tcatcatcat cattagtctg aagggcgaa ttgatccaga   3540 tctgctgtgc cttctagttg ccagccatct gttgtttgcc cctccccgt gccttccttg   3600 accctggaag gtgccactcc cactgtcctt tcctaataaa atgaggaaat tgcatcgcat   3660
tgtctgagta ggtgtcattc tattctgggg ggtggggtgg ggcaggacag caaggggag   3720 gattgggaag acaatagcag gcatgctggg gatgcggtgg gctctatggg tacccaggtg   3780
ctgaagaatt gacccggttc ctcctgggcc agaaagaagc aggcacatcc ccttctctgt   3840
gacacaccct gtccacgccc ctggttctta gttccagccc cactcatagg acactcatag   3900
ctcaggaggg ctccgccttc aatcccaccc gctaaagtac ttggagcggt ctctccctcc   3960
ctcatcagcc caccaaacca aacctagcct caagagtgg gaagaaatta agcaagata   4020 ggctattaag tgcagaggga gagaaaatgc ctccaacatg tgaggaagta atgagagaaa   4080
tcatagaatt ttaaggccat gatttaaggc catcatggcc ttaatcttcc gcttcctcgc   4140
tcactgactc gctgcgctcg gtcgttcggc tgcggcgagc ggtatcagct cactcaaagg   4200
cggtaatacg gttatccaca gaatcagggg ataacgcagg aaagaacatg tgagcaaaag   4260
gccagcaaaa ggccaggaac cgtaaaaagg ccgcgttgct ggcgtttttc cataggctcc   4320 gccccctga cgagcatcac aaaatcgac gctcaagtca gaggtggcga acccgacag   4380 gactataaag ataccaggcg tttccccctg gaagctccct cgtgcgctct cctgttccga   4440
ccctgccgct accggatac ctgtccgcct ttctcccttc gggaagcgtg gcgctttctc   4500
atagctcacg ctgtaggtat ctcagttcgg tgtaggtcgt tcgctccaag ctgggctgtg   4560
tgcacgaacc ccccgttcag cccgaccgct gcgccttatc cggtaactat cgtcttgagt   4620
ccaacccggt aagacacgac ttatcgccac tggcagcagc cactggtaac aggattagca   4680
gagcgaggta tgtaggcggt gctacagagt tcttgaagtg gtggcctaac tacggctaca   4740
```

-continued

```
ctagaagaac agtatttggt atctgcgctc tgctgaagcc agttaccttc ggaaaaagag    4800
ttggtagctc ttgatccggc aaacaaacca ccgctggtag cggtggtttt tttgtttgca    4860
agcagcagat tacgcgcaga aaaaaggat ctcaagaaga tcctttgatc ttttctacgg     4920
ggtctgacgc tcagtggaac gaaaactcac gttaagggat tttggtcatg agattatcaa    4980
aaaggatctt cacctagatc cttttaaatt aaaaatgaag ttttaaatca atctaaagta    5040
tatatgagta aacttggtct gacagttacc aatgcttaat cagtgaggca cctatctcag    5100
cgatctgtct atttcgttca tccatagttg cctgactcgg ggggggggg cgctgaggtc     5160 tgcctcgtga agaaggtgtt gctgactcat accaggcctg aatcgcccca tcatccagcc    5220
agaaagtgag ggagccacgg ttgatgagag ctttgttgta ggtggaccag ttggtgattt    5280
tgaacttttg ctttgccacg gaacggtctg cgttgtcggg aagatgcgtg atctgatcct    5340
tcaactcagc aaaagttcga tttattcaac aaagccgccg tcccgtcaag tcagcgtaat    5400
gctctgccag tgttacaacc aattaaccaa ttctgattag aaaaactcat cgagcatcaa    5460
atgaaactgc aatttattca tatcaggatt atcaatacca tatttttgaa aaagccgttt    5520
ctgtaatgaa ggagaaaact caccgaggca gttccatagg atggcaagat cctggtatcg    5580
gtctgcgatt ccgactcgtc caacatcaat acaacctatt aatttcccct cgtcaaaaat    5640
aaggttatca agtgagaaat caccatgagt gacgactgaa tccggtgaga atggcaaaag    5700
cttatgcatt tctttccaga cttgttcaac aggccagcca ttacgctcgt catcaaaatc    5760
actcgcatca accaaaccgt tattcattcg tgattgcgcc tgagcgagac gaaatacgcg    5820
atcgctgtta aaaggacaat tacaaacagg aatcgaatgc aaccggcgca ggaacactgc    5880
cagcgcatca acaatatttt cacctgaatc aggatattct tctaatacct ggaatgctgt    5940
tttcccgggg atcgcagtgg tgagtaacca tgcatcatca ggagtacgga taaaatgctt    6000
gatggtcgga agaggcataa attccgtcag ccagtttagt ctgaccatct catctgtaac    6060
atcattggca acgctacctt tgccatgttt cagaaacaac tctggcgcat cgggcttccc    6120
atacaatcga tagattgtcg cacctgattg cccgacatta tcgcgagccc atttataccc    6180
atataaatca gcatccatgt tggaatttaa tcgcggcctc gagcaagacg tttcccgttg    6240
aatatggctc ataacacccc ttgtattact gtttatgtaa gcagacagtt ttattgttca    6300
tgatgatata ttttatctt gtgcaatgta acatcagaga ttttgagaca caacgtggct    6360 ttccccccc cccattatt gaagcattta tcagggttat tgtctcatga gcggatacat    6420
atttgaatgt atttagaaaa ataaacaaat agggggttccg cgcacatttc cccgaaaagt    6480
gccacctgac gtctaagaaa ccattattat catgacatta acctataaaa ataggcgtat    6540
cacgaggccc tttcgtc                                                  6557
```

<210> SEQ ID NO 143
<211> LENGTH: 2106
<212> TYPE: DNA
<213> ORGANISM: Artificial Sequence
<220> FEATURE:
<223> OTHER INFORMATION: Synthetic nucleic acid sequence encoding SEQ
      ID NO:59 (nearly identical to SEQ ID NO:58 but lacks stop codon)

<400> SEQUENCE: 143

```
atgaaggcca tcatcgtgct gctgatggtg gtgaccagca cgccgatag aatctgcacc      60 ggcatcacca gcagcaatag cccccatgtg gtgaaaacag ccaccaggg cgaagtgaat    120 gtgacaggcg tgatccctct gaccaccacc cccaccaaga gctacttcgc caacctgaag    180
```

```
ggcaccagaa ccagaggcaa gctgtgcccc gattgcctga actgcaccga tctggatgtg      240
gctctgggca gacctatgtg tgtgggcacc acaccatctg ccaaggccag catcctgcac      300
gaagtgaagc tctgtgaccag cggctgcttc cccatcatgc acgaccggac caagatcaga     360
cagctgccca acctgctgag aggctacgag aacatccggc tgtccaccca gaatgtgatc      420
gatgccgaga agcccctggc ggaccttat agactgggca ccagcggctc ttgtcccaat       480
gccacctcca gagcggcttt ttttgccaca atggcctggg ccgtgcctaa ggacaacaac      540
aagaacgcca ccaaccctct gaccgtggag gtgccctaca tctgtacaga gggcgaggat     600
cagatcacag tgtggggctt ccacagcgac gacaagaccc agatgaagaa cctgtacggc     660
gacagcaacc cccagaagtt taccagcagc gccaatggcg tgaccaccca ctacgtgtcc     720
cagatcggca gctttcccga tcagacagag gatggcggac tgcctcagtc tggcaggatc     780
gtggtggact acatgatgca gaagcctggc aagaccggca ccatcgtgta tcagagaggc     840
gtgctgctgc ctcagaaagt gtggtgtgcc agcggcaggt ctaaagtgat caagggcagc     900
ctgcctctga ttggcgaggc cgactgtctg cacgaaaagt acgcggcct gaacaagagc      960 aagccctact acacaggcga gcacgccaag gccatcggca attgccccat ctgggtgaaa     1020 accccctga agctggccaa tggcaccaag tacagacctc ccgccaagct gctgaaagag      1080
agaggcttct ttggcgccat tgccggattt ctggaaggcg gctgggaggg aatgattgcc     1140
ggctggcacg gctatacatc tcatggggcc catggcgtgg ctgtggccgc cgatctgaag     1200
tctacccagg aagccatcaa caagatcacc aagaacctga acagcctgag cgagctggaa     1260
gtgaagaatc tgcagagact gagcggcgcc atggatgagc tgcacaacga tcctggaa      1320 ctggacgaga agtggatga tctccgcgcc gatacaattt cctcccagat tgaactggcc      1380
gtgctgctgt ccaacgaggg catcatcaac agcgaggatg aacacctgct ggccctggaa     1440
cggaagctga agaagatgct gggcccttct gccgtggaga tcggcaacgg ctgcttcgag     1500
acaaagcaca gtgcaacca gacctgcctg gatagaatcg ccgctggcac cttcaatgcc      1560
ggcgagttca gcctgcctac cttcgacagc ctgaatatca cctccggagg cgacatcatc     1620
aagctgctga cgagcaggt gaacaaggag atgcagagca gcaacctgta catgagcatg     1680
agcagctggt gctacaccca cagcctggac ggcgccggcc tgttcctgtt cgaccacgcc     1740
gccgaggagt acgagcacgc caagaagctg atcatcttcc tgaacgagaa caacgtgccc     1800
gtgcagctga ccagcatcag cgcccccgag cacaagttcg agggcctgac ccagatcttc     1860
cagaaggcct acgagcacga gcagcacatc agcgagagca tcaacaacat cgtgaccac    1920 gccatcaaga gcaaggacca cgccaccttc aacttcctgc agtggtacgt ggccgagcag    1980
cacgaggagg aggtgctgtt caaggacatc ctggacaaga tcgagctgat cggcaacgag    2040
aaccacggcc tgtacctggc cgaccagtac gtgaagggca tcgccaagag caggaagagc    2100
ggatcc                                                                2106
```

<210> SEQ ID NO 144
<211> LENGTH: 6512
<212> TYPE: DNA
<213> ORGANISM: Artificial Sequence
<220> FEATURE:
<223> OTHER INFORMATION: Synthetic sequence of plasmid CMV8x/R-H3-Perth
     HA(519)_SGG_egm

<400> SEQUENCE: 144

```
tcgcgcgttt cggtgatgac ggtgaaaacc tctgacacat gcagctcccg g

```
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
gggaacttcc atagcccata tatggagttc cgcgttacat aacttacggg aatttccaaa      420
cctggctgac cgcccaacga ccccgccca ttgacgtcaa taatgacgta tgttcccata      480
gtaacgccaa tagggaactt ccattgacgt caatgggtgg agtatttacg gtaaactgcc      540
cacttgggaa tttccaagtg tatcatatgc caagtacgcc ccctattgac gtcaatgacg      600
ggaacttcca taagcttgca ttatgcccag tacatgacct tatgggaatt cctacttgg      660 cagtacatct acgtattagt catcgctatt accatggtga tgcggttttg gcagtacatc      720
aatgggcgtg gatagcggtt tgactcacgg gaacttccaa gtctccaccc cattgacgtc      780
aatgggagtt tgttttgact caccaaaatc aacgggaatt cccaaaatgt cgtaacaact      840
ccgccccatt gacgcaaatg ggcggtaggc gtgtacggtg ggaggtctat ataagcagag      900
ctcgtttagt gaaccgtcag atcgcctgga cacgccatcc acgctgtttt gacctccata      960
gaagacaccg ggaccgatcc agcctccatc ggctcgcatc tctccttcac gcgcccgccg     1020
ccctacctga ggccgccatc cacgccggtt gagtcgcgtt ctgccgcctc cgcctgtgg      1080 tgcctcctga actgcgtccg ccgtctaggt aagtttaaag ctcaggtcga gaccgggcct     1140
ttgtccggcg ctcccttgga gcctacctag actcagccgg ctctccacgc tttgcctgac     1200
cctgcttgct caactctagt aacggtgga gggcagtgta gtctgagcag tactcgttgc      1260
tgccgcgcgc gccaccagac ataatagctg acagactaac agactgttcc tttccatggg     1320
tcttttctgc agtcaccgtc gtcgacacgt gtgatcagat atcgcggccg ctctagagat     1380
atcgccacca tgaaaccat aattgcgctg tcctacatac tgtgtctggt gtttgcccag     1440
aaactgccgg gcaatgacaa ctcaacagcc acgctctgct ggggcacca tgccgtccct     1500 aacgggacca ttgtgaaaac cattactaac gatcagatag aggtgactaa tgccaccgag     1560
ctggtgcaaa gtagctccac aggagagatc tgcgatagtc cccaccagat tctggacgga     1620
aagaattgta cgctgatcga cgcgctgttg ggcgaccctc agtgtgacgg atttcagaat     1680
aagaagtggg atctgtttgt ggaaaggtca aaggcttatt caaattgcta cccttacgat     1740
gtgcctgatt atgccagcct gcggtccctc gtcgcgtcta gtgggactct ggagttcaac     1800
aacgagtcat ttaactggac tggcgttaca cagaacggga ctagttccgc ttgcataagg     1860
agaagcaaaa atagtttctt cagcagactg aattggctga cacatctgaa cttcaagtac     1920
cctgcactga atgtaaccat gcccaacaac gagcagttcg ataagcttta catttgggga     1980
gttcatcatc ctgcactgaa caaggatcag atctttctgt atgcccaggc ttccggcagg     2040
attaccgtgt ctacaaagag aagccagcaa actgtgtctc ccaatatcgg cagtagaccc     2100
agagtacgga acatccctag tcgcatcagt atttactgga ccatcgtgaa accaggcgat     2160
attctcctga ttaacagtac tggcaacctg atcgccccc ggggatactt aaaaatccgc     2220
tctggaaagt cctccattat gagatcagat gcaccgatcg gaaaatgcaa ctctgagtgt     2280
atcacaccca tgggagcat tcccaatgac aaacctttcc agaacgttaa tcgaataact     2340 tatgggcct gtcacggta cgtgaagcaa atacccttga aactggcgac cggtatgcgc     2400
aatgtccccg aaaaacagac ccgcgggata tttgggcta tcgcaggctt tatcgagaat     2460
```

-continued

```
ggctgggaag ggatggtgga tggttggtat ggttttagac atcaaaactc cgaaggcaga    2520
ggccaggctg ccgatctcaa gagcacgcag gccgctatag atcagatcaa tggaaagctc    2580
aacagactga tcgggaaaac caacgaaaaa ttccatcaga tcgagaaaga gttctccgaa    2640
gtcgaggggc gcatacagga cctgagaag tatgttgagg atacaaagat tgatctgtgg    2700
tcctacaatg ccgagctgct ggtggctctg gagaatcagc acactattga cctgaccgat    2760
tcagagatga acaaactttt tgagaagacg aagaagcagc ttagagaaaa tgcagaggac    2820
atggggaacg gatgctttaa aatatatcat aagtgtgata atgcctgcat cggatcaatt    2880
agaaatggta cctatgatca cgatgtttac agggacgaag cgctgaataa caggttccag    2940
ataaaatccg gaggcgacat catcaagctg ctgaacgagc aggtgaacaa ggagatgcag    3000
agcagcaacc tgtacatgag catgagcagc tggtgctaca cccacagcct ggacggcgcc    3060
ggcctgttcc tgttcgacca cgccgccgag gagtacgagc acgccaagaa gctgatcatc    3120
ttcctgaacg agaacaacgt gcccgtgcag ctgaccagca tcagcgcccc cgagcacaag    3180
ttcgagggcc tgacccagat cttccagaag gcctacgagc acgagcagca catcagcgag    3240
agcatcaaca catcgtgga ccacgccatc aagagcaagg accacgccac cttcaacttc    3300
ctgcagtggt acgtggccga gcagcacgag gaggaggtgc tgttcaagga catcctggac    3360
aagatcgagc tgatcggcaa cgagaaccac ggcctgtacc tggccgacca gtacgtgaag    3420
ggcatcgcca agagcaggaa gagcggatcc tagcatcatc atcatcatta gtctggaagg    3480
gcgaattgat ccagatctgc tgtgccttct agttgccagc catctgttgt ttgcccctcc    3540
cccgtgcctt ccttgaccct ggaaggtgcc actcccactg tcctttccta ataaaatgag    3600
gaaattgcat cgcattgtct gagtaggtgt cattctattc tggggggtgg ggtggggcag    3660
gacagcaagg gggaggattg gaagacaat agcaggcatg ctggggatgc ggtgggctct    3720
atgggtaccc agtgctgaa gaattgaccc ggttcctcct gggccagaaa gaagcaggca    3780 catcccttc tctgtgacac accctgtcca cgccctggt tcttagttcc agccccactc    3840
ataggacact catagctcag gagggctccg ccttcaatcc cacccgctaa agtacttgga    3900
gcggtctctc cctccctcat cagccccacca aaccaaacct agcctccaag agtgggaaga    3960
aattaaagca agataggcta ttaagtgcag agggagagaa aatgcctcca acatgtgagg    4020
aagtaatgag agaaatcata gaattttaag gccatgattt aaggccatca tggccttaat    4080
cttccgcttc ctcgctcact gactcgctgc gctcggtcgt tcggctgcgg cgagcggtat    4140
cagctcactc aaaggcggta atacggttat ccacagaatc aggggataac gcaggaaaga    4200
acatgtgagc aaaaggccag caaaaggcca ggaaccgtaa aaaggccgcg ttgctggcgt    4260
ttttccatag gctccgcccc cctgacgagc atcacaaaaa tcgacgctca agtcagaggt    4320
ggcgaaaccc gacaggacta taaagatacc aggcgtttcc ccctggaagc tccctcgtgc    4380
gctctcctgt tccgaccctg ccgcttaccg gatacctgtc cgcctttctc ccttcggaa    4440 gcgtggcgct ttctcatagc tcacgctgta ggtatctcag ttcggtgtag gtcgttcgct    4500
ccaagctggg ctgtgtgcac gaaccccccg ttcagcccga ccgctgcgcc ttatccggta    4560
actatcgtct tgagtccaac ccggtaagac acgacttatc gccactggca gcagccactg    4620
gtaacaggat tagcagagcg aggtatgtag gcggtgctac agagttcttg aagtggtggc    4680
ctaactacgg ctacactaga agaacagtat ttggtatctg cgctctgctg aagccagtta    4740
ccttcggaaa aagagttggt agctcttgat ccggcaaaca aaccaccgct ggtagcggtg    4800
```

```
gtttttttgt tgcaagcag cagattacgc gcagaaaaaa aggatctcaa gaagatcctt    4860
tgatcttttc tacggggtct gacgctcagt ggaacgaaaa ctcacgttaa gggattttgg    4920
tcatgagatt atcaaaaagg atcttcacct agatcctttt aaattaaaaa tgaagtttta    4980
aatcaatcta agtatatat gagtaaactt ggtctgacag ttaccaatgc ttaatcagtg    5040
aggcacctat ctcagcgatc tgtctatttc gttcatccat agttgcctga ctcgggggg    5100
ggggcgctg aggtctgcct cgtgaagaag gtgttgctga ctcataccag gcctgaatcg    5160
ccccatcatc cagccagaaa gtgagggagc cacggttgat gagagctttg ttgtaggtgg    5220
accagttggt gattttgaac ttttgctttg ccacggaacg gtctgcgttg tcgggaagat    5280
gcgtgatctg atccttcaac tcagcaaaag ttcgatttat tcaacaaagc cgccgtcccg    5340
tcaagtcagc gtaatgctct gccagtgtta caaccaatta accaattctg attagaaaaa    5400
ctcatcgagc atcaaatgaa actgcaattt attcatatca ggattatcaa taccatattt    5460
ttgaaaaagc cgtttctgta atgaaggaga aaactcaccg aggcagttcc ataggatggc    5520
aagatcctgg tatcggtctg cgattccgac tcgtccaaca tcaatacaac ctattaattt    5580
cccctcgtca aaaataaggt tatcaagtga gaaatcacca tgagtgacga ctgaatccgg    5640
tgagaatggc aaaagcttat gcatttcttt ccagacttgt tcaacaggcc agccattacg    5700
ctcgtcatca aaatcactcg catcaaccaa accgttattc attcgtgatt gcgcctgagc    5760
gagacgaaat acgcgatcgc tgttaaaagg acaattacaa caggaatcg aatgcaaccg    5820
gcgcaggaac actgccagcg catcaacaat attttcacct gaatcaggat attcttctaa    5880
tacctggaat gctgttttcc cggggatcgc agtggtgagt aaccatgcat catcaggagt    5940
acggataaaa tgcttgatgg tcggaagagg cataaattcc gtcagccagt ttagtctgac    6000
catctcatct gtaacatcat tggcaacgct acctttgcca tgtttcagaa acaactctgg    6060
cgcatcgggc ttcccataca atcgatagat tgtcgcacct gattgcccga cattatcgcg    6120
agcccattta tacccatata aatcagcatc catgttggaa tttaatcgcg gcctcgagca    6180
agacgtttcc cgttgaatat ggctcataac accccttgta ttactgttta tgtaagcaga    6240
cagttttatt gttcatgatg atatattttt atcttgtgca atgtaacatc agagattttg    6300
agacacaacg tggctttccc ccccccccca ttattgaagc atttatcagg gttattgtct    6360
catgagcgga tacatatttg aatgtatta gaaaataaa caaataggg ttccgcgcac    6420
atttccccga aaagtgccac ctgacgtcta agaaaccatt attatcatga cattaaccta    6480
taaaaatagg cgtatcacga ggccctttcg tc                              6512
```

<210> SEQ ID NO 145  
<211> LENGTH: 2061  
<212> TYPE: DNA  
<213> ORGANISM: Artificial Sequence  
<220> FEATURE:  
<223> OTHER INFORMATION: Synthetic nucleic acid sequence encoding SEQ  
ID NO:62 (nearly identical to SEQ ID NO:61 but lacks stop codon)

<400> SEQUENCE: 145

```
atgaaaacca taattgcgct gtcctacata ctgtgtctgg tgtttgccca gaaactgccg     60
ggcaatgaca actcaacagc cacgctctgc ttggggcacc atgccgtccc taacgggacc    120
attgtgaaaa ccattactaa cgatcagata gaggtgacta atgccaccga gctggtgcaa    180
agtagctcca caggagagat ctgcgatagt ccccaccaga ttctggacgg aaagaattgt    240
acgctgatcg acgcgctgtt gggcgaccct cagtgtgacg gatttcagaa taagaagtgg    300
```

```
gatctgtttg tggaaaggtc aaaggcttat tcaaattgct acccttacga tgtgcctgat      360
tatgccagcc tgcggtccct cgtcgcgtct agtgggactc tggagttcaa caacgagtca      420
tttaactgga ctggcgttac acagaacggg actagttccg cttgcataag gagaagcaaa      480
aatagtttct tcagcagact gaattggctg acacatctga acttcaagta ccctgcactg      540
aatgtaacca tgcccaacaa cgagcagttc gataagcttt catttgggg agttcatcat       600
cctggcactg acaaggatca gatctttctg tatgcccagg cttccggcag gattaccgtg      660
tctacaaaga gaagccagca aactgtgtct cccaatatcg gcagtagacc cagagtacgg      720
aacatcccta gtcgcatcag tatttactgg accatcgtga accaggcga tattctcctg       780
attaacagta ctggcaacct gatcgccccc cggggatact ttaaaatccg ctctggaaag      840
tcctccatta tgagatcaga tgcaccgatc ggaaaatgca actctgagtg tatcacaccc      900
aatgggagca ttcccaatga caaacctttc cagaacgtta atcgaataac ttatggggcc     960
tgtccacggt acgtgaagca aaataccttg aaactggcga ccggtatgcg caatgtcccc    1020
gaaaaacaga cccgcgggat atttggggct atcgcaggct ttatcgagaa tggctgggaa    1080
gggatggtgg atggttggta tggttttaga catcaaaact ccgaaggcag aggccaggct    1140
gccgatctca gagcacgca ggccgctata gatcagatca tggaaagct caacagactg       1200
atcgggaaaa ccaacgaaaa attccatcag atcgagaaag agttctccga agtcgagggg    1260
cgcatacagg acctggagaa gtatgttgag gatacaaaga ttgatctgtg gtcctacaat    1320
gccgagctgc tggtggctct ggagaatcag cacactattg acctgaccga ttcagagatg    1380
aacaaacttt ttgagaagac gaagaagcag cttagagaaa atgcagagga catggggaac    1440
ggatgcttta aaatatatca taagtgtgat aatgcctgca tcggatcaat tagaaatggt    1500
acctatgatc acgatgttta cagggacgaa gcgctgaata acaggttcca gataaaatcc    1560
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag cacgccaaga agctgatcat cttcctgaac    1740
gagaacaacg tgcccgtgca gctgaccagc atcagcgccc ccagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggaggtg ctgttcaagg acatcctgga caagatcgag    1980
ctgatcggca cgagaaacca cggcctgtac ctggccgacc agtacgtgaa gggcatcgcc    2040
aagagcagga agagcggatc c                                              2061
```

<210> SEQ ID NO 146
<211> LENGTH: 6506
<212> TYPE: DNA
<213> ORGANISM: Artificial Sequence
<220> FEATURE:
<223> OTHER INFORMATION: Synthetic sequence of plasmid CMV8x/R-H1Bris
      HA(517)_SGG_egm

<400> SEQUENCE: 146

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
```

```
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg atagcggttt gactcacgg gaacttccaa gtctcaccc cattgacgtc    780 aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga gaccgggcct    1140
ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tgaaagtgaa gctgctggtg ctgctgtgta cctttaccgc cacctacgcc    1440
gataccatct gtatcggcta ccacgccaac aatagcaccg acaccgtgga taccgtgctg    1500
gaaaagaacg tgaccgtgac ccacagcgtg aacctgctgg aaaacagcca caacggcaag    1560
ctgtgtctgc tgaaaggcat tgcccctctg cagctgggaa attgtagcgt ggccggctgg    1620
attctgggca atcctgagtg cgagctgctg atttccaaag agtcctggtc ctacatcgtg    1680
gagaagccca accctgagaa tggcacctgc taccctggcc acttcgccga ttacgaggaa    1740
ctgagagaac agctgtccag cgtgtccagc ttcgagagat cgagatcttc ccccaaagag    1800
agcagctggc ccaatcatac agtgaccggc gtgagcgcct cttgtagcca caatggcgag    1860
agcagcttct acagaaacct gctgtggctg accggcaaga acggcctgta ccccaacctg    1920
agcaagagct acgccaacaa caaagaaaaa gaagtgctgg tcctctgggg agtgcaccac    1980
cctcctaaca tcggcatcca gaaggccctg taccacaccg agaatgccta cgtgtccgtg    2040
gtgtccagcc actacagcag aaagttcacc cccgagatcg ccaaaagacc caaagtgcgg    2100
gaccaggaag gcaggatcaa ctactactgg accctgctgg aacctggcga caccatcatc    2160
ttcgaggcca acggcaatct gatcgcccct agatacgcct ttgccctgag cagaggctt    2220 ggcagcggca tcatcaacag caacgccccc atggacaagt gtgacgccaa gtgtcagaca    2280
ccacagggag ctatcaatag cagcctgccc ttccagaatg tgcaccctgt gaccatcggc    2340
gagtgtccta aatacgtgcg gagcgccaag ctgagaatgg tgaccggcct gaggaatatc    2400
cccagcatcc agagcagagg cctgtttggc gccattgccg ctttatcga gggcggatgg    2460 acaggcatgg tggatgggtg gtacggctac caccaccaga atgagcaggg atctggctat    2520
gccgccgatc agaagagcac ccagaacgcc atcaacggca tcaccaacaa agtgaacagc    2580
gtgatcgaga agatgaacac ccagttcacc gccgtgggca aagagttcaa caagctggaa    2640
```

```
cggcggatgg aaaacctgaa caagaaggtg gacgacggct tcatcgacat ctggacctac    2700
aacgccgaac tcctggtcct cctggaaaat gagaggaccc tggacttcca cgacagcaac    2760
gtgaagaacc tgtacgagaa agtgaagagc cagctgaaga caacgccaa agagatcggc     2820 aacggctgct tcgagttcta ccacaagtgc aacgacgagt gcatggaaag cgtgaagaac    2880
ggcacctacg actaccccaa gtacagcgag gaaagcaagc tgaaccggga agatcgat     2940 tccggaggcg acatcatcaa gctgctgaac gagcaggtga acaaggagat gcagagcagc   3000
aacctgtaca tgagcatgag cagctggtgc tacacccaca gcctggacgg cgccggcctg    3060
ttcctgttcg accacgccgc cgaggagtac gagcacgcca agaagctgat catcttcctg    3120
aacgagaaca acgtgcccgt gcagctgacc agcatcagcg ccccgagca caagttcgag     3180 ggcctgaccc agatcttcca gaaggcctac gagcacgagc agcacatcag cgagagcatc    3240
aacaacatcg tggaccacgc catcaagagc aaggaccacg ccaccttcaa cttcctgcag    3300
tggtacgtgg ccgagcagca cgaggaggag gtgctgttca aggacatcct ggacaagatc    3360
gagctgatcg gcaacgagaa ccacggcctg tacctggccg accagtacgt gaagggcatc    3420
gccaagagca ggaagagcgg atcctagcat catcatcatc attagtctgg aagggcgaat    3480
tgatccagat ctgctgtgcc ttctagttgc cagccatctg ttgtttgccc ctccccgtg     3540 ccttccttga ccctggaagg tgccactccc actgtccttt cctaataaaa tgaggaaatt    3600
gcatcgcatt gtctgagtag gtgtcattct attctggggg gtggggtggg gcaggacagc    3660 aaggggagg attgggaaga caatagcagg catgctgggg atgcggtggg ctctatgggt     3720
acccaggtgc tgaagaattg acccggttcc tcctgggcca gaaagaagca ggcacatccc    3780
cttctctgtg acacccctg tccacgcccc tggttcttag ttccagcccc actcatagga     3840
cactcatagc tcaggagggc tccgccttca atcccacccg ctaaagtact ggagcggtc     3900 tctcctccc tcatcagccc accaaaccaa acctagcctc caagagtggg aagaaattaa    3960
agcaagatag gctattaagt gcagagggag agaaaatgcc tccaacatgt gaggaagtaa    4020
tgagagaaat catagaattt taaggccatg atttaaggcc atcatggcct taatcttccg     4080
cttcctcgct cactgactcg ctgcgctcgg tcgttcggct gcggcgagcg gtatcagctc    4140
actcaaaggc ggtaatacgg ttatccacag aatcagggga taacgcagga agaacatgt    4200 gagcaaaagg ccagcaaaag gccaggaacc gtaaaaaggc cgcgttgctg gcgttttttcc   4260 ataggctccg ccccctgac gagcatcaca aaaatcgacg ctcaagtcag aggtggcgaa    4320
acccgacagg actataaaga taccaggcgt ttcccctgg aagctccctc gtgcgctctc     4380
ctgttccgac cctgccgctt accggatacc tgtccgcctt ctcccttcg ggaagcgtgg     4440 cgctttctca tagctcacgc tgtaggtatc tcagttcggt gtaggtcgtt cgctccaagc    4500
tgggctgtgt gcacgaaccc cccgttcagc ccgaccgctg cgccttatcc ggtaactatc    4560
gtcttgagtc caacccggta agacacgact tatcgccact ggcagcagcc actggtaaca    4620
ggattagcag agcgaggtat gtaggcggtg ctacagagtt cttgaagtgg tggcctaact    4680
acggctacac tagaagaaca gtatttggta tctgcgctct gctgaagcca gttaccttcg    4740
gaaaaagagt tggtagctct tgatccggca aacaaaccac cgctggtagc ggtggttttt    4800
ttgtttgcaa gcagcagatt acgcgcagaa aaaaggatc tcaagaagat cctttgatct    4860
tttctacggg gtctgacgct cagtggaacg aaaactcacg ttaagggatt ttggtcatga    4920
gattatcaaa aaggatcttc acctagatcc ttttaaatta aaaatgaagt tttaaatcaa    4980
```

```
tctaaagtat atatgagtaa acttggtctg acagttacca atgcttaatc agtgaggcac    5040
ctatctcagc gatctgtcta tttcgttcat ccatagttgc ctgactcggg ggggggggc     5100
gctgaggtct gcctcgtgaa gaaggtgttg ctgactcata ccaggcctga atcgcccat     5160
catccagcca gaaagtgagg gagccacggt tgatgagagc tttgttgtag gtggaccagt    5220
tggtgatttt gaacttttgc tttgccacgg aacggtctgc gttgtcggga agatgcgtga    5280
tctgatcctt caactcagca aaagttcgat ttattcaaca aagccgccgt cccgtcaagt    5340
cagcgtaatg ctctgccagt gttacaacca attaaccaat tctgattaga aaaactcatc    5400
gagcatcaaa tgaaactgca atttattcat atcaggatta tcaataccat atttttgaaa    5460
aagccgtttc tgtaatgaag gagaaaactc accgaggcag ttccatagga tgcaagatc     5520
ctggtatcgg tctgcgattc cgactcgtcc aacatcaata caacctatta atttcccctc    5580
gtcaaaaata aggttatcaa gtgagaaatc accatgagtg acgactgaat ccggtgagaa    5640
tggcaaaagc ttatgcattt cttcccagac ttgttcaaca ggccagccat tacgctcgtc    5700
atcaaaatca ctcgcatcaa ccaaaccgtt attcattcgt gattgcgcct gagcgagacg    5760
aaatacgcga tcgctgttaa aaggacaatt acaaacagga tcgaatgcaa ccggcgcag    5820
gaacactgcc agcgcatcaa caatattttc acctgaatca ggatattctt ctaatacctg    5880
gaatgctgtt ttcccgggga tcgcagtggt gagtaaccat gcatcatcag gagtacggat    5940
aaaatgcttg atggtcggaa gaggcataaa ttccgtcagc cagtttagtc tgaccatctc    6000
atctgtaaca tcattggcaa cgctacccttt gccatgtttc agaaacaact ctggcgcatc    6060
gggcttccca tacaatcgat agattgtcgc acctgattgc ccgacattat cgcgagccca    6120
tttataccca tataaatcag catccatgtt ggaatttaat cgcggcctcg agcaagacgt    6180
ttcccgttga atatggctca taacacccct tgtattactg tttatgtaag cagacagttt    6240
tattgttcat gatgatatat ttttatcttg tgcaatgtaa catcagagat tttgagacac    6300
aacgtggctt tccccccccc cccattattg aagcatttat cagggttatt gtctcatgag    6360
cggatacata tttgaatgta tttagaaaaa taaacaaata ggggttccgc gcacatttcc    6420
ccgaaaagtg ccacctgacg tctaagaaac cattattatc atgacattaa cctataaaaa    6480
taggcgtatc acgaggccct ttcgtc                                         6506
```

<210> SEQ ID NO 147
<211> LENGTH: 2055
<212> TYPE: DNA
<213> ORGANISM: Artificial Sequence
<220> FEATURE:
<223> OTHER INFORMATION: Synthetic nucleic acid sequence encoding SEQ
      ID NO:65 (nearly identical to SEQ ID NO:64 but lacks stop codon)

<400> SEQUENCE: 147

```
atgaaagtga agctgctggt gctgctgtgt acctttaccg ccacctacgc cgataccatc     60
tgtatcggct accacgccaa caatagcacc gacaccgtgg ataccgtgct ggaaaagaac    120
gtgaccgtga cccacagcgt gaacctgctg aaaacagcc acaacggcaa gctgtgtctg    180
ctgaaaggca ttgcccctct gcagctggga aattgtagcg tggccggctg gattctgggc    240
aatcctgagt gcgagctgct gatttccaaa gagtcctggt cctacatcgt ggagaagccc    300
aaccctgaga atggcaccctg ctaccctggc cacttcgccg attacgagga actgagagaa    360
cagctgtcca gcgtgtccag cttcgagaga ttcgagatct ccccaaaga gagcagctgg    420
cccaatcata cagtgaccgg cgtgagcgcc tcttgtagcc acaatggcga gagcagcttc    480
```

-continued

```
tacagaaacc tgctgtggct gaccggcaag aacggcctgt accccaacct gagcaagagc    540
tacgccaaca acaaagaaaa agaagtgctg gtcctctggg gagtgcacca ccctcctaac    600
atcggcatcc agaaggccct gtaccacacc gagaatgcct acgtgtccgt ggtgtccagc    660
cactacagca gaaagttcac ccccgagatc gccaaaagac ccaaagtgcg ggaccaggaa    720
ggcaggatca actactactg gaccctgctg gaacctggcg acaccatcat cttcgaggcc    780
aacggcaatc tgatcgcccc tagatacgcc tttgccctga gcagaggctt tggcagcggc    840
atcatcaaca gcaacgcccc catggacaag tgtgacgcca agtgtcagac accacaggga    900
gctatcaata gcagcctgcc cttccagaat gtgcaccctg tgaccatcgg cgagtgtcct    960
aaatacgtgc ggagcgccaa gctgagaatg gtgaccggcc tgaggaatat ccccagcatc   1020
cagagcagag gcctgtttgg cgccattgcc ggctttatcg agggcggatg gacaggcatg   1080
gtggatgggt ggtacggcta ccaccaccag aatgagcagg gatctggcta tgccgccgat   1140
cagaagagca cccagaacgc catcaacggc atcaccaaca aagtgaacag cgtgatcgag   1200
aagatgaaca cccagttcac cgccgtgggc aaagagttca acaagctgga acggcggatg   1260
gaaaacctga acaagaaggt ggacgacggc ttcatcgaca tctggaccta caacgccgaa   1320
ctcctggtcc tcctggaaaa tgagaggacc ctggacttcc acgacagcaa cgtgaagaac   1380
ctgtacgaga aagtgaagag ccagctgaag aacaacgcca aagagatcgg caacggctgc   1440
ttcgagttct accacaagtg caacgacgag tgcatggaaa gcgtgaagaa cggcacctac   1500
gactacccca agtacagcga ggaaagcaag ctgaaccggg agaagatcga ttccggaggc   1560
gacatcatca agctgctgaa cgagcaggtg aacaaggaga tgcagagcag caacctgtac   1620
atgagcatga gcagctggtg ctacacccac agcctggacg gcgccggcct gttcctgttc   1680
gaccacgccg ccgaggagta cgagcacgcc aagaagctga tcatcttcct gaacgagaac   1740
aacgtgcccg tgcagctgac cagcatcagc gcccccgagc acaagttcga gggcctgacc   1800
cagatcttcc agaaggccta cgagcacgag cagcacatca gcgagagcat caacaacatc   1860
gtggaccacg ccatcaagag caaggaccac gccaccttca acttcctgca gtggtacgtg   1920
gccgagcagc acgaggagga ggtgctgttc aaggacatcc tggacaagat cgagctgatc   1980
ggcaacgaga accacggcct gtacctggcc gaccagtacg tgaagggcat cgccaagagc   2040
aggaagagcg gatcc                                                    2055
```

<210> SEQ ID NO 148
<211> LENGTH: 6560
<212> TYPE: DNA
<213> ORGANISM: Artificial Sequence
<220> FEATURE:
<223> OTHER INFORMATION: Synthetic sequence of plasmid CMV8x/R-B.Bris HA(535)_SGG_egm

<400> SEQUENCE: 148

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
```

-continued

```
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg gaggtctat ataagcagag     900 ctcgtttagt gaaccgtcag atcgcctgga gacgccatcc acgctgtttt gacctccata    960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga ccgggcct     1140 ttgtccggcg ctcccttgga gcctacctag actcagccgg ctctcacgc tttgcctgac    1200 cctgcttgct caactctagt aacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tgaaggccat catcgtgctg ctgatggtgg tcacaagcaa cgccgataga    1440
atctgtaccg gcatcaccag cagcaatagc cctcacgtcg tgaaaacagc tacacagggc    1500
gaagtgaatg tgaccggcgt gatccctctg accacaacac ctacaaagag ccacttcgcc    1560
aatctgaagg gcacagagac aagaggcaag ctgtgtccca gtgcctgaa ttgcacagat     1620 ctggatgtgc tctgggcag acctaagtgt acaggcaaaa tccctagcgc cagagtgtcc    1680
attctgcatg aagtgcgacc tgtgaccagc ggctgttttc ctattatgca cgaccggacc    1740
aagatcagac agctgcctaa tctgctgaga ggctacgagc acatcagact gagcacccac    1800
aatgtgatca acgccgaaaa tgctcctggc ggcccttata agatcggcac atctggcagc    1860
tgccccaaca ttacaaatgg caatggcttc tttgccacca tggcttgggc cgtgcctaag    1920
aacgataaga caagaccgc caccaacccc ctgacaatcg aggtgccata tatctgtaca    1980
gagggcgagg atcagatcac cgtgtgggga tttcacagcg acaacgaaac acagatggcc    2040
aagctgtacg gcgatagcaa gcctcagaag tttaccagct ctgccaatgg cgtgaccaca    2100
cactatgtgt ctcagatcgg cggcttccct aatcagacag aagatggcgg actgcctcag    2160
tctggaagaa tcgtggtgga ttacatggtg cagaagtctg gcaagaccgg caccatcaca    2220
tatcagagag gaatcctgct gcccagaaa gtgtggtgcg cttctggaag atccaaagtg    2280
atcaagggca gcctgcctct gattggagaa gccgattgtc tgcacgagaa atacggcggc    2340
ctgaacaaga gcaagcctta ctatacaggc gagcacgcca aggccatcgg caattgtcct    2400
atttgggtca agacccctct gaagctggcc aatggcacaa agtatagacc tccagccaag    2460
ctgctgaaag agagaggctt ttttggagct atcgccggct ttctggaagg cggatgggag    2520
ggaatgattg ctggatggca tggctacaca tctcatggcg cacatggcgt ggcagtggct    2580
gctgatctga atctacaca ggaagccatc aacaagatca ccaagaacct gaacagcctg     2640
agcgagctgg aagtgaagaa tctgcagaga ctgtctggcg ccatggacga actgcacaat    2700
gagatcctga actggacga aaggtggac gatctgagag ccgatacaat cagcagccag     2760
attgaactgg ctgtgctgct gtctaacgag ggcatcatca atagcgagga cgaacatctg    2820
```

```
ctggccctgg aaagaaagct gaagaagatg ctgggaccta gcgccgtgga aatcggcaat    2880
ggatgctttg agacaaagca caagtgcaac cagacctgcc tggatagaat tgccgccgga    2940
acatttgatg ccggcgagtt ttctctgccc accttcgata gcctgaatat cacatccgga    3000
ggcgacatca tcaagctgct gaacgagcag gtgaacaagg agatgcagag cagcaacctg    3060
tacatgagca tgagcagctg gtgctacacc cacagcctgg acggcgccgg cctgttcctg    3120
ttcgaccacg ccgccgagga gtacgagcac gccaagaagc tgatcatctt cctgaacgag    3180
aacaacgtgc ccgtgcagct gaccagcatc agcgcccccg agcacaagtt cgagggcctg    3240
acccagatct tccagaaggc ctacgagcac gagcagcaca tcagcgagag catcaacaac    3300
atcgtggacc acgccatcaa gagcaaggac cacgccacct tcaacttcct gcagtggtac    3360
gtggccgagc agcacgagga ggaggtgctg ttcaaggaca tcctggacaa gatcgagctg    3420
atcggcaacg agaaccacgg cctgtacctg gccgaccagt acgtgaaggg catcgccaag    3480
agcaggaaga gcggatccta gcatcatcat catcattagt ctggaagggc gaattgatcc    3540
agatctgctg tgccttctag ttgccagcca tctgttgttt gcccctcccc cgtgccttcc    3600
ttgaccctgg aaggtgccac tcccactgtc ctttcctaat aaaatgagga aattgcatcg    3660
cattgtctga gtaggtgtca ttctattctg ggggtgggg tggggcagga cagcaagggg    3720
gaggattggg aagacaatag caggcatgct ggggatgcgg tgggctctat gggtacccag    3780
gtgctgaaga attgacccgg ttcctcctgg gccagaaaga agcaggcaca tccccttctc    3840
tgtgacacac cctgtccacg cccctggttc ttagttccag ccccactcat aggacactca    3900
tagctcagga gggctccgcc ttcaatccca cccgctaaag tacttggagc ggtctctccc    3960
tccctcatca gcccaccaaa ccaaacctag cctccaagag tgggaagaaa ttaaagcaag    4020
ataggctatt aagtgcagag ggagagaaaa tgcctccaac atgtgaggaa gtaatgagag    4080
aaatcataga attttaaggc catgatttaa ggccatcatg ccttaatctt ccgcttcct    4140
cgctcactga ctcgctgcgc tcggtcgttc ggctgcggcg agcggtatca gctcactcaa    4200
aggcggtaat acggttatcc acagaatcag gggataacgc aggaaagaac atgtgagcaa    4260
aaggccagca aaaggccagg aaccgtaaaa aggccgcgtt gctggcgttt ttccataggc    4320
tccgcccccc tgacgagcat cacaaaaatc gacgctcaag tcagaggtgg cgaaacccga    4380
caggactata aagataccag gcgtttcccc ctggaagctc cctcgtgcgc tctcctgttc    4440
cgacccgcc gcttaccgga tacctgtccg cctttctccc ttcgggaagc gtggcgcttt    4500
ctcatagctc acgctgtagg tatctcagtt cggtgtaggt cgttcgctcc aagctgggct    4560
gtgtgcacga acccccgtt cagcccgacc gctgcgcctt atccggtaac tatcgtcttg    4620
agtccaaccc ggtaagacac gacttatcgc cactggcagc agccactggt aacaggatta    4680
gcagagcgag gtatgtaggc ggtgctacag agttcttgaa gtggtggcct aactacggct    4740
acactagaag aacagtattt ggtatctgcg ctctgctgaa gccagttacc ttcggaaaaa    4800
gagttggtag ctcttgatcc ggcaaacaaa ccaccgctgg tagcggtggt ttttttgttt    4860
gcaagcagca gattacgcgc agaaaaaaag gatctcaaga gatcctttg atcttttcta    4920
cggggtctga cgctcagtgg aacgaaaact cacgttaagg gattttggtc atgagattat    4980
caaaaaggat cttcacctag atccttttaa attaaaaatg aagttttaaa tcaatctaaa    5040
gtatatatga gtaaacttgg tctgacagtt accaatgctt aatcagtgag gcacctatct    5100
cagcgatctg tctatttcgt tcatccatag ttgcctgact cggggggggg gggcgctgag    5160
```

```
gtctgcctcg tgaagaaggt gttgctgact cataccaggc ctgaatcgcc ccatcatcca   5220
gccagaaagt gagggagcca cggttgatga gagctttgtt gtaggtggac cagttggtga   5280
ttttgaactt ttgctttgcc acggaacggt ctgcgttgtc gggaagatgc gtgatctgat   5340
ccttcaactc agcaaaagtt cgatttattc aacaaagccg ccgtcccgtc aagtcagcgt   5400
aatgctctgc cagtgttaca accaattaac caattctgat tagaaaaact catcgagcat   5460
caaatgaaac tgcaatttat tcatatcagg attatcaata ccatattttt gaaaaagccg   5520
tttctgtaat gaaggagaaa actcaccgag gcagttccat aggatggcaa gatcctggta   5580
tcggtctgcg attccgactc gtccaacatc aatacaacct attaatttcc cctcgtcaaa   5640
aataaggtta tcaagtgaga atcaccatg agtgacgact gaatccggtg agaatggcaa   5700
aagcttatgc atttctttcc agacttgttc aacaggccag ccattacgct cgtcatcaaa   5760
atcactcgca tcaaccaaac cgttattcat tcgtgattgc gcctgagcga acgaaatac   5820 gcgatcgctg ttaaaaggac aattacaaac aggaatcgaa tgcaaccggc gcaggaacac   5880
tgccagcgca tcaacaatat tttcacctga atcaggatat tcttctaata cctggaatgc   5940
tgttttcccg gggatcgcag tggtgagtaa ccatgcatca tcaggagtac ggataaaatg   6000
cttgatggtc ggaagaggca taaattccgt cagccagttt agtctgacca tctcatctgt   6060
aacatcattg gcaacgctac ctttgccatg tttcagaaac aactctggcg catcgggctt   6120
cccatacaat cgatagattg tcgcacctga ttgcccgaca ttatcgcgag cccatttata   6180
cccatataaa tcagcatcca tgttggaatt taatcgcggc ctcgagcaag acgtttcccg   6240
ttgaatatgg ctcataacac cccttgtatt actgtttatg taagcagaca gttttattgt   6300
tcatgatgat atattttat cttgtgcaat gtaacatcag agattttgag acacaacgtg   6360
gctttccccc ccccccatt attgaagcat ttatcagggt tattgtctca tgagcggata   6420
catatttgaa tgtatttaga aaaataaaca atagggggtt ccgcgcacat ttccccgaaa   6480
agtgccacct gacgtctaag aaaccattat tatcatgaca ttaacctata aaaataggcg   6540
tatcacgagg ccctttcgtc                                              6560
```

<210> SEQ ID NO 149
<211> LENGTH: 2109
<212> TYPE: DNA
<213> ORGANISM: Artificial Sequence
<220> FEATURE:
<223> OTHER INFORMATION: Synthetic nucleic acid sequence encoding SEQ
      ID NO:68 (nearly identical to SEQ ID NO:67 but lacks stop codon)

<400> SEQUENCE: 149

```
atgaaggcca tcatcgtgct gctgatggtg gtcacaagca acgccgatag aatctgtacc     60
ggcatcacca gcagcaatag ccctcacgtc gtgaaaacag ctacacaggg cgaagtgaat    120
gtgaccggcg tgatccctct gaccacaaca cctacaaaga gccacttcgc caatctgaag    180
ggcacagaga caagaggcaa gctgtgtccc aagtgcctga attgcacaga tctggatgtg    240
gctctgggca gacctaagtg tacaggcaaa atccctagcg ccagagtgtc cattctgcat    300
gaagtgcgac ctgtgaccag cggctgtttt cctattatgc acgaccggac caagatcaga    360
cagctgccta tctgctgag aggctacgag cacatcgact gagcacccca atgtgatc       420 aacgccgaaa atgctcctgg cggcccttat aagatcggca tctggcag ctgccccaac      480 attacaaatg gcaatggctt ctttgccacc atggcttggg ccgtgcctaa gaacgataag    540
aacaagaccg ccaccaaccc cctgacaatc gaggtgccat atatctgtac agagggcgag    600
```

-continued

```
gatcagatca ccgtgtgggg atttcacagc gacaacgaaa cacagatggc caagctgtac      660
ggcgatagca agcctcagaa gtttaccagc tctgccaatg gcgtgaccac acactatgtg      720
tctcagatcg gcggcttccc taatcagaca gaagatggcg gactgcctca gtctggaaga      780
atcgtggtgg attacatggt gcagaagtct ggcaagaccg gcaccatcac atatcagaga      840
ggaatcctgc tgccccagaa agtgtggtgc gcttctggaa gatccaaagt gatcaagggc      900
agcctgcctc tgattggaga agccgattgt ctgcacgaga atacggcgg cctgaacaag      960 agcaagcctt actatacagg cgagcacgcc aaggccatcg gcaattgtcc tatttgggtc     1020
aagacccctc tgaagctggc caatggcaca agtatagac ctccagccaa gctgctgaaa      1080
gagagaggct tttttggagc tatcgccggc tttctggaag gcggatggga gggaatgatt     1140
gctggatggc atggctacac atctcatggc gcacatggcg tggcagtggc tgctgatctg     1200
aaatctacac aggaagccat caacaagatc accaagaacc tgaacagcct gagcgagctg     1260
gaagtgaaga atctgcagag actgtctggc gccatggacg aactgcacaa tgagatcctg     1320
gaactggacg agaaggtgga cgatctgaga gccgatacaa tcagcagcca gattgaactg     1380
gctgtgctgc tgtctaacga gggcatcatc aatagcgagg acgaacatct gctggccctg     1440
gaaagaaagc tgaagaagat gctgggacct agcgccgtgg aaatcggcaa tggatgcttt     1500
gagacaaagc acaagtgcaa ccagacctgc ctggatagaa ttgccgccgg aacatttgat     1560
gccggcgagt ttctctgcc caccttcgat agcctgaata tcacatccgg aggcgacatc     1620
atcaagctgc tgaacgagca ggtgaacaag gagatgcaga gcagcaacct gtacatgagc     1680
atgagcagct ggtgctacac ccacagcctg acggcgccg gcctgttcct gttcgaccac     1740
gccgccgagg agtacgagca cgccaagaag ctgatcatct tcctgaacga gaacaacgtg     1800
cccgtgcagc tgaccagcat cagcgccccc gagcacaagt cgagggcct gacccagatc     1860 ttccagaagg cctacgagca cgagcagcac atcagcgaga gcatcaacaa catcgtggac     1920
cacgccatca agagcaagga ccacgccacc ttcaacttcc tgcagtggta cgtggccgag     1980
cagcacgagg aggaggtgct gttcaaggac atcctggaca agatcgagct gatcggcaac     2040
gagaaccacg gcctgtacct ggccgaccag tacgtgaagg gcatcgccaa gagcaggaag     2100
agcggatcc                                                             2109
```

<210> SEQ ID NO 150
<211> LENGTH: 5783
<212> TYPE: DNA
<213> ORGANISM: Artificial Sequence
<220> FEATURE:
<223> OTHER INFORMATION: Synthetic sequence of plasmid CMV8x/R-H1NC SS
    Gen4.55_SGG_egm

<400> SEQUENCE: 150

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg       120 ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
gggaacttcc atagcccata tatggagttc cgcgttacat aacttacggg aatttccaaa      420
cctggctgac cgcccaacga cccccgccca ttgacgtcaa taatgacgta tgttcccata      480
```

-continued

```
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt tgttttgact caccaaaatc aacgggaatt cccaaaatgt cgtaacaact     840
ccgcccatt gacgcaaatg gcggtaggc gtgtacggtg ggaggtctat ataagcagag     900
ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga gccgccatc acgccggtt gagtcgcgtt ctgccgcctc ccgcctgtgg    1080
tgcctcctga actgcgtccg ccgtctaggt aagtttaaag ctcaggtcga gaccgggcct    1140
ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tgaaggccaa gctgctggtg ctgctgtgca cctttaccgc cacctacgcc    1440
gacaccatct gcattggcta ccacgccaac aacagcaccg acaccgtgga taccgtgctg    1500
gaaaagaacg tgaccgtgac ccacagcgtg aacctgggat ccggactgag aatggtcacc    1560
ggcctgagaa acatccccag catccagagc agaggcctgt ttggagccat gccggctttt    1620
attgagggcg gatggaccgg aatggtggat gggtggtacg gctaccacca ccagaatgag    1680
cagggctctg gctatgccgc cgatcagaag tctacccaga acgccatcaa cggcatcacc    1740
aacaaagtga acagcgtgat cgagaagatg ggcggcgatc tgaatgggga cagagagatc    1800
aacaactaca ccagcatcat ctacagcctg atcgaggaaa gccagaacca gcaggaaaac    1860
ggcacaggcg gcggatctgg aattgtgcag cagcagaaca acctgctgag agccattgag    1920
gcccagcagc atctgctgca gctgacagtg tggggcatca gcagctgca gacctacaat    1980
gccgagctgc tggtcctcct ggaaaacgag agaaccctgg acttccacga cagcaacgtg    2040
aagaacctgt acgagaaagt gaagtcccag ctgaagaaca cgccaaaga gatcggcaac    2100
ggctgcttcg agttctacca caagtgcaac aacgagtgca tggaaagcgt gaagaacggc    2160
acctacgact accccaagta cagcgaggaa agcaagctga acagagagaa gatcgactcc    2220
ggaggcgaca tcatcaagct gctgaacgag caggtgaaca aggagatgca gagcagcaac    2280
ctgtacatga gcatgagcag ctggtgctac ccccacagcc tggacggcgc cggcctgttc    2340
ctgttcgacc acgccgccga ggagtacgag cacgccaaga agctgatcat cttcctgaac    2400
gagaacaacg tgcccgtgca gctgaccagc atcagcgccc ccgagcacaa gttcgagggc    2460
ctgacccaga tcttccagaa ggcctacgag cacgagcagc acatcagcga gagcatcaac    2520
aacatcgtgg accacgccat caagagcaag gaccacgcca ccttcaactt cctgcagtgg    2580
tacgtggccg agcagcacga ggaggagtg ctgttcaagg acatcctgga caagatcgag    2640
ctgatcggca acgagaacca cggcctgtac ctggccgacc agtacgtgaa gggcatcgcc    2700
aagagcagga gagcggatc ctagcatcat catcatcatt agtctggaag gcgaattga    2760
tccagatctg ctgtgccttc tagttgccag ccatctgttg tttgcccctc ccccgtgcct    2820
tccttgaccc tggaaggtgc cactcccact gtcctttcct aataaaatga ggaaattgca    2880
```

```
tcgcattgtc tgagtaggtg tcattctatt ctggggggtg gggtgggggca ggacagcaag    2940 ggggaggatt gggaagacaa tagcaggcat gctggggatg cggtgggctc tatgggtacc    3000
caggtgctga agaattgacc cggttcctcc tgggccagaa agaagcaggc acatcccctt    3060
ctctgtgaca caccctgtcc acgccctgg  ttcttagttc cagccccact cataggacac    3120
tcatagctca ggagggctcc gccttcaatc ccacccgcta agtacttgg  agcggtctct    3180 ccctccctca tcagcccacc aaaccaaacc tagcctccaa gagtgggaag aaattaaagc    3240
aagataggct attaagtgca gagggagaga aaatgcctcc aacatgtgag gaagtaatga    3300
gagaaatcat agaattttaa ggccatgatt taaggccatc atggccttaa tcttccgctt    3360
cctcgctcac tgactcgctg cgctcggtcg ttcggctgcg gcgagcggta tcagctcact    3420
caaaggcggt aatacggtta tccacagaat caggggataa cgcaggaaag aacatgtgag    3480
caaaaggcca gcaaaaggcc aggaaccgta aaaaggccgc gttgctggcg ttttttccata   3540 ggctccgccc ccctgacgag catcacaaaa atcgacgctc aagtcagagg tggcgaaacc    3600
cgacaggact ataaagatac caggcgtttc ccctggaag  ctccctcgtg cgctctcctg    3660
ttccgaccct gccgcttacc ggatacctgt ccgcctttct cccttcggga agcgtggcgc    3720
tttctcatag ctcacgctgt aggtatctca gttcggtgta ggtcgttcgc tccaagctgg    3780
gctgtgtgca cgaaccccc  gttcagcccg accgctgcgc cttatccggt aactatcgtc    3840
ttgagtccaa cccggtaaga cacgacttat cgccactggc agcagccact ggtaacagga    3900
ttagcagagc gaggtatgta ggcggtgcta cagagttctt gaagtggtgg cctaactacg    3960
gctacactag aagaacagta tttggtatct gcgctctgct gaagccagtt accttcggaa    4020
aaagagttgg tagctcttga tccggcaaac aaaccaccgc tggtagcggt ggtttttttg    4080
tttgcaagca gcagattacg cgcagaaaaa aaggatctca agaagatcct ttgatctttt    4140
ctacggggtc tgacgctcag tggaacgaaa actcacgtta agggattttg gtcatgagat    4200
tatcaaaaag gatcttcacc tagatccttt taaattaaaa atgaagtttt aaatcaatct    4260
aaagtatata tgagtaaact tggtctgaca gttaccaatg cttaatcagt gaggcaccta    4320
tctcagcgat ctgtctattt cgttcatcca tagttgcctg actcggggg  ggggggcgct    4380 gaggtctgcc tcgtgaagaa ggtgttgctg actcatacca ggcctgaatc gccccatcat    4440
ccagccagaa agtgagggag ccacggttga tgagagcttt gttgtaggtg gaccagttgg    4500
tgattttgaa cttttgcttt gccacggaac ggtctgcgtt gtcgggaaga tgcgtgatct    4560
gatccttcaa ctcagcaaaa gttcgattta ttcaacaaag ccgccgtccc gtcaagtcag    4620
cgtaatgctc tgccagtgtt acaaccaatt aaccaattct gattagaaaa actcatcgag    4680
catcaaatga aactgcaatt tattcatatc aggattatca ataccatatt tttgaaaaag    4740
ccgtttctgt aatgaaggag aaaactcacc gaggcagttc cataggatgg caagatcctg    4800
gtatcggtct gcgattccga ctcgtccaac atcaatacaa cctattaatt tcccctcgtc    4860
aaaaataagg ttatcaagtg agaaatcacc atgagtgacg actgaatccg gtgagaatgg    4920
caaaagctta tgcatttctt tccagacttg ttcaacaggc cagccattac gctcgtcatc    4980
aaaatcactc gcatcaacca aaccgttatt cattcgtgat tgcgcctgag cgagacgaaa    5040
tacgcgatcg ctgttaaaag gacaattaca acaggaatc  gaatgcaacc ggcgcaggaa    5100
cactgccagc gcatcaacaa tattttcacc tgaatcagga tattcttcta atacctggaa    5160
tgctgttttc ccggggatcg cagtggtgag taaccatgca tcatcaggag tacggataaa    5220
```

| | |
|---|---|
| atgcttgatg gtcggaagag gcataaattc cgtcagccag tttagtctga ccatctcatc | 5280 |
| tgtaacatca ttggcaacgc tacctttgcc atgtttcaga acaactctg gcgcatcggg | 5340 |
| cttcccatac aatcgataga ttgtcgcacc tgattgcccg acattatcgc gagcccattt | 5400 |
| atacccatat aaatcagcat ccatgttgga atttaatcgc ggcctcgagc aagacgtttc | 5460 |
| ccgttgaata tggctcataa caccccttgt attactgttt atgtaagcag acagttttat | 5520 |
| tgttcatgat gatatatttt tatcttgtgc aatgtaacat cagagatttt gagacacaac | 5580 |
| gtggctttcc ccccccccc attattgaag catttatcag ggttattgtc tcatgagcgg | 5640 |
| atacatattt gaatgtattt agaaaaataa acaaataggg gttccgcgca catttccccg | 5700 |
| aaaagtgcca cctgacgtct aagaaaccat tattatcatg acattaacct ataaaaatag | 5760 |
| gcgtatcacg aggccctttc gtc | 5783 |

<210> SEQ ID NO 151
<211> LENGTH: 1332
<212> TYPE: DNA
<213> ORGANISM: Artificial Sequence
<220> FEATURE:
<223> OTHER INFORMATION: Synthetic nucleic acid sequence encoding SEQ
      ID NO:101 (identical to SEQ ID NO:100, but lacks stop codon)

<400> SEQUENCE: 151

| | |
|---|---|
| atgaaggcca agctgctggt gctgctgtgc acctttaccg ccacctacgc cgacaccatc | 60 |
| tgcattggct accacgccaa caacagcacc gacaccgtgg ataccgtgct ggaaaagaac | 120 |
| gtgaccgtga cccacagcgt gaacctggga tccggactga aatggtcac cggcctgaga | 180 |
| aacatcccca gcatccagag cagaggcctg tttggagcca ttgccggctt tattgagggc | 240 |
| ggatggaccg gaatggtgga tgggtggtac ggctaccacc accagaatga gcagggctct | 300 |
| ggctatgccg ccgatcagaa gtctacccag aacgccatca cggcatcac caacaaagtg | 360 |
| aacagcgtga tcgagaagat gggcggcgat cctgaatggg acagagagat caacaactac | 420 |
| accagcatca tctacagcct gatcgaggaa agccagaacc agcaggaaaa cggcacaggc | 480 |
| ggcggatctg gaattgtgca gcagcagaac aacctgctga gagccattga ggcccagcag | 540 |
| catctgctgc agctgacagt gtggggcatc aagcagctgc agacctacaa tgccgagctg | 600 |
| ctggtcctcc tggaaaacga gagaaccctg gacttccacg acagcaacgt gaagaacctg | 660 |
| tacgagaaag tgaagtccca gctgaagaac aacgccaaag atcggcaa cggctgcttc | 720 |
| gagttctacc acaagtgcaa caacgagtgc atggaaagcg tgaagaacgg cacctacgac | 780 |
| taccccaagt acagcgagga aagcaagctg aacagagaga gatcgactc cggaggcgac | 840 |
| atcatcaagc tgctgaacga gcaggtgaac aaggagatgc agagcagcaa cctgtacatg | 900 |
| agcatgagca gctggtgcta cacccacagc ctggacggcg ccggcctgtt cctgttcgac | 960 |
| cacgccgccg aggagtacga gcacgccaag aagctgatca tcttcctgaa cgagaacaac | 1020 |
| gtgcccgtgc agctgaccag catcagcgcc cccgagcaca gttcgaggg cctgacccag | 1080 |
| atcttccaga aggcctacga gcacgagcag cacatcagcg agagcatcaa caacatcgtg | 1140 |
| gaccacgcca tcaagagcaa ggaccacgcc accttcaact tcctgcagtg gtacgtggcc | 1200 |
| gagcagcacg aggaggaggt gctgttcaag gacatcctgg acaagatcga gctgatcggc | 1260 |
| aacgagaacc acggcctgta cctggccgac cagtacgtga agggcatcgc caagagcagg | 1320 |
| aagagcggat cc | 1332 |

<210> SEQ ID NO 152

<211> LENGTH: 5782
<212> TYPE: DNA
<213> ORGANISM: Artificial Sequence
<220> FEATURE:
<223> OTHER INFORMATION: Synthetic sequence of plasmid H1CA
      SS/Gen4.55/Ferritin

<400> SEQUENCE: 152

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgaccccccg cccattgacg tcaataatga cgtatgttcc     480
catagtaacg ccaatagggg ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgccgg cgctctagag    1380
atatcgccac catgaaggct atcctggtgg tgctgctgta cacctttgcc accgccaatg    1440
ccgacaccct gtgtattggc taccgcgcca acaacagcac cgacaccgtg gataccgtgc    1500
tggaaaagaa cgtgaccgtg acccacagcg tgaacctggg ctccggcctg agactggcca    1560
ccggcctgag aaacatcccc agcattcaga gcagaggcct gtttggagcc attgccggct    1620
ttattgaggg cggatggacc ggaatggtgg atggtggta cggctaccac caccagaatg    1680
agcagggctc tggctatgcc gccgacctga gtctacccca gaacgccatc gacgagatca    1740
ccaacaaagt gaacagcgtg atcgagaaga tgggcggctg ggacccatgg gacagagaga    1800
tcaacaacta caccagcatc atctacagcc tgatcgagga agccagaac cagcaggaaa    1860 acgggacagg cggcggatct ggaattgtgc agcagcagaa caacctgctg agagccattg    1920
aggcccagca gcatctgctg cagctgacag tgtggggcat caagcagctg cagacctaca    1980
acgccgagct gctggtgctg ctcgagaatg agagaaccct ggactaccac acagcaacg    2040 tgaagaacct gtacgagaaa gtgcggagcc agctgaagaa caacgccaaa gagatcggca    2100
```

-continued

```
acggctgctt cgagttctac cacaagtgcg acaatacctg catggaaagc gtgaagaacg    2160
gcacctacga ctaccccaag tacagcgagg aagccaagct gaaccgggaa gagatcgatt    2220
ccggaggcga catcatcaag ctgctgaacg agcaggtgaa caaggagatg cagagcagca    2280
acctgtacat gagcatgagc agctggtgct acacccacag cctggacggc gccggcctgt    2340
tcctgttcga ccacgccgcc gaggagtacg agcacgccaa gaagctgatc atcttcctga    2400
acgagaacaa cgtgcccgtg cagctgacca gcatcagcgc ccccgagcac aagttcgagg    2460
gcctgaccca gatcttccag aaggcctacg agcacgagca gcacatcagc gagagcatca    2520
acaacatcgt ggaccacgcc atcaagagca aggaccacgc caccttcaac ttcctgcagt    2580
ggtacgtggc cgagcagcac gaggaggagg tgctgttcaa ggacatcctg acaagatcg     2640 agctgatcgg caacgagaac cacgcctgt acctggccga ccagtacgtg aagggcatcg      2700
ccaagagcag gaagagcgga tcctagcatc atcatcatca tcattagtct gaagggcgaa    2760
ttgatccagc tgtgccttct agttgccagc catctgttgt ttgcccctcc cccgtgcctt    2820
ccttgaccct ggaaggtgcc actcccactg tcctttccta ataaaatgag gaaattgcat    2880
cgcattgtct gagtaggtgt cattctattc tggggggtgg ggtggggcag gacagcaagg    2940
gggaggattg gaagacaat agcaggcatg ctggggatgc ggtgggctct atgggtaccc      3000
aggtgctgaa gaattgaccc ggttcctcct gggccagaaa gaagcaggca tccccttc      3060 tctgtgacac accctgtcca cgccctggt cttagttcc agccccactc ataggacact       3120
catagctcag gagggctccg ccttcaatcc cacccgctaa agtacttgga gcggtctctc    3180
cctccctcat cagcccacca aaccaaacct agcctccaag agtgggaaga aattaaagca    3240
agataggcta ttaagtgcag agggagagaa aatgcctcca acatgtgagg aagtaatgag    3300
agaaatcata gaattttaag gccatgattt aaggccatca tggccttaat cttccgcttc    3360
ctcgctcact gactcgctgc gctcggtcgt tcggctgcgg cgagcggtat cagctcactc    3420
aaaggcggta atacggttat ccacagaatc aggggataac gcaggaaaga acatgtgagc    3480
aaaaggccag caaaaggcca ggaaccgtaa aaaggccgcg ttgctggcgt ttttccatag    3540
gctccgcccc cctgacgagc atcacaaaaa tcgacgctca agtcagaggt ggcgaaaccc    3600
gacaggacta taaagatacc aggcgtttcc ccctggaagc tccctcgtgc gctctcctgt    3660
tccgaccctg ccgcttaccg gatacctgtc cgcctttctc ccttcgggaa gcgtggcgct    3720
ttctcatagc tcacgctgta ggtatctcag ttcggtgtag gtcgttcgct ccaagctggg    3780
ctgtgtgcac gaaccccccg ttcagcccga ccgctgcgcc ttatccggta actatcgtct    3840
tgagtccaac ccggtaagac acgacttatc gccactggca gcagccactg gtaacaggat    3900
tagcagagcg aggtatgtag gcggtgctac agagttcttg aagtggtggc ctaactacgg    3960
ctacactaga agaacagtat ttggtatctg cgctctgctg aagccagtta ccttcggaaa    4020
aagagttggt agctcttgat ccggcaaaca aaccaccgct ggtagcggtg ttttttttgt    4080
ttgcaagcag cagattacgc gcagaaaaaa aggatctcaa gaagatcctt tgatcttttc    4140
tacggggtct gacgctcagt ggaacgaaaa ctcacgttaa gggattttgg tcatgagatt    4200
atcaaaaagg atcttcacct agatcctttt aaattaaaaa tgaagtttta atcaatcta     4260 aagtatatat gagtaaactt ggtctgacag ttaccaatgc ttaatcagtg aggcacctat    4320
ctcagcgatc tgtctatttc gttcatccat agttgcctga ctcggggggg ggggcgctg    4380 aggtctgcct cgtgaagaag gtgttgctga ctcataccag gctgaatcg ccccatcatc     4440 cagccagaaa gtgagggagc cacggttgat gagagctttg ttgtaggtgg accagttggt    4500
```

```
gattttgaac ttttgctttg ccacggaacg gtctgcgttg tcgggaagat gcgtgatctg   4560
atccttcaac tcagcaaaag ttcgatttat tcaacaaagc cgccgtcccg tcaagtcagc   4620
gtaatgctct gccagtgtta caaccaatta accaattctg attagaaaaa ctcatcgagc   4680
atcaaatgaa actgcaattt attcatatca ggattatcaa taccatattt ttgaaaaagc   4740
cgtttctgta atgaaggaga aaactcaccg aggcagttcc ataggatggc aagatcctgg   4800
tatcggtctg cgattccgac tcgtccaaca tcaatacaac ctattaattt ccctcgtca    4860 aaaataaggt tatcaagtga gaaatcacca tgagtgacga ctgaatccgg tgagaatggc   4920
aaaagcttat gcatttcttt ccagacttgt tcaacaggcc agccattacg ctcgtcatca   4980
aaatcactcg catcaaccaa accgttattc attcgtgatt gcgcctgagc gagacgaaat   5040
acgcgatcgc tgttaaaagg acaattacaa acaggaatcg aatgcaaccg gcgcaggaac   5100
actgccagcg catcaacaat attttcacct gaatcaggat attcttctaa tacctggaat   5160
gctgttttcc cggggatcgc agtggtgagt aaccatgcat catcaggagt acggataaaa   5220
tgcttgatgg tcggaagagg cataaattcc gtcagccagt ttagtctgac catctcatct   5280
gtaacatcat tggcaacgct acctttgcca tgtttcagaa acaactctgg cgcatcgggc   5340
ttcccataca atcgatagat tgtcgcacct gattgcccga cattatcgcg agcccattta   5400
tacccatata atcagcatc  catgttggaa tttaatcgcg gcctcgagca agacgtttcc   5460
cgttgaatat ggctcataac accccttgta ttactgttta tgtaagcaga cagtttatt    5520 gttcatgatg atatatttt  atcttgtgca atgtaacatc agagattttg agacacaacg    5580
tggctttccc cccccccca  ttattgaagc atttatcagg gttattgtct catgagcgga    5640
tacatatttg aatgtattta gaaaaataaa caaatagggg ttccgcgcac atttccccga   5700
aaagtgccac ctgacgtcta agaaaccatt attatcatga cattaaccta taaaaatagg   5760
cgtatcacga ggccctttcg tc                                            5782
```

<210> SEQ ID NO 153
<211> LENGTH: 5782
<212> TYPE: DNA
<213> ORGANISM: Artificial Sequence
<220> FEATURE:
<223> OTHER INFORMATION: Synthetic sequence of plasmid H1Bris
      SS/Gen4.55/Ferritin

<400> SEQUENCE: 153

```
tcgcgcgttt cggtgatgac ggtgaaaacc tctgacacat gcagctcccg gagacggtca     60
cagcttgtct gtaagcggat gccggagca  gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
```

```
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctcca tcggctcgca tctctccttc acgcgcccgc     1020
cgccctacct gaggccgcca tccacgccgg ttgagtcgcg ttctgccgcc tcccgcctgt     1080
ggtgcctcct gaactgcgtc cgccgtctag gtaagtttaa agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacac gtgtgatcag atatcgcggc cgctctagag     1380
atatcgccac catgaaagtg aagctgctgg tgctgctgtg tacctttacc gccacctacg     1440
ccgataccat ctgtatcggc taccacgcca acaatagcac cgacaccgtg gataccgtgc     1500
tggaaaagaa cgtgaccgtg acccacgcg tgaacctggg atcaggactg agaatggtga     1560
ccggcctgag gaatatcccc agcatccaga gcagaggcct gtttggcgcc attgccggct     1620
ttatcgaggg cggatggaca ggcatggtgg atggtggta cggctaccac caccagaatg     1680
agcagggatc tggctatgcc gccgatcaga agagcaccca gaacgccatc aacggcatca     1740
ccaacaaagt gaacagcgtg atcgagaaga tgggcggcga tcctgaatgg gacagagaga     1800
tcaacaacta caccagcatc atctacagcc tgatcgagga aagccagaac cagcaggaaa     1860
acggcacagg cggcggatct ggaattgtgc agcagcagaa caacctgctg agagccattg     1920
aggcccagca gcatctgctg cagctgacag tgtgggcat caagcagctg cagacctaca     1980
acgccgaact cctggtcctc ctggaaaatg agaggaccct ggacttccac gacagcaacg     2040
tgaagaacct gtacgagaaa gtgaagagcc agctgaagaa caacgccaaa gagatcggca     2100
acggctgctt cgagttctac cacaagtgca acgacgagtg catggaaagc gtgaagaacg     2160
gcacctacga ctaccccaag tacagcgagg aaagcaagct gaaccgggag aagatcgatt     2220
ccggaggcga catcatcaag ctgctgaacg agcaggtgaa caaggagatg cagagcagca     2280
acctgtacat gagcatgagc agctggtgct acacccacag cctggacggc gccggcctgt     2340
tcctgttcga ccacgccgcc gaggagtacg agcacgccaa gagctgatc atcttcctga     2400 acgagaacaa cgtgcccgtg cagctgacca gcatcagcgc ccccgagcac aagttcgagg     2460
gcctgaccca gatcttccag aaggcctacg agcacgagca gcacatcagc gagagcatca     2520
acaacatcgt ggaccacgcc atcaagcaca aggaccacgc caccttcaac ttcctgcagt     2580
ggtacgtggc cgagcagcac gaggaggagg tgctgttcaa ggacatcctg acaagatcg     2640 agctgatcgg caacgagaac cacggcctgt acctggccga ccagtacgtg aagggcatcg     2700
ccaagagcag gaagagcgga tcctagcatc atcatcatca tcattagtct gaagggcgaa     2760
ttgatccagc tgtgccttct agttgccagc catctgttgt ttgcccctcc cccgtgcctt     2820
ccttgacccc ggaaggtgcc actcccactg tcctttccta taaaatgag gaaattgcat     2880 cgcattgtct gagtaggtgt cattctattc tggggggtgg ggtggggcag gacagcaagg     2940
gggaggattg ggaagacaat agcaggcatg ctggggatgc ggtgggctct atgggtaccc     3000
aggtgctgaa gaattgaccc ggttcctcct gggccagaaa gaagcaggca catcccttc      3060
```

```
tctgtgacac accctgtcca cgcccctggt tcttagttcc agccccactc ataggacact    3120
catagctcag gagggctccg ccttcaatcc cacccgctaa agtacttgga gcggtctctc    3180
cctccctcat cagcccacca aaccaaacct agcctccaag agtgggaaga aattaaagca    3240
agataggcta ttaagtgcag agggagagaa aatgcctcca acatgtgagg aagtaatgag    3300
agaaatcata gaattttaag gccatgattt aaggccatca tggccttaat cttccgcttc    3360
ctcgctcact gactcgctgc gctcggtcgt tcggctgcgg cgagcggtat cagctcactc    3420
aaaggcggta atacggttat ccacagaatc agggaataac gcaggaaaga acatgtgagc    3480
aaaaggccag caaaaggcca ggaaccgtaa aaaggccgcg ttgctggcgt ttttccatag    3540
gctccgcccc cctgacgagc atcacaaaaa tcgacgctca agtcagaggt ggcgaaaccc    3600
gacaggacta taaagatacc aggcgtttcc ccctggaagc tccctcgtgc gctctcctgt    3660
tccgaccctg ccgcttaccg gatacctgtc cgcctttctc ccttcgggaa gcgtggcgct    3720
ttctcatagc tcacgctgta ggtatctcag ttcggtgtag gtcgttcgct ccaagctggg    3780
ctgtgtgcac gaaccccccg ttcagcccga ccgctgcgcc ttatccggta actatcgtct    3840
tgagtccaac ccggtaagac acgacttatc gccactggca gcagccactg gtaacaggat    3900
tagcagagcg aggtatgtag gcggtgctac agagttcttg aagtggtggc ctaactacgg    3960
ctacactaga agaacagtat ttggtatctg cgctctgctg aagccagtta ccttcggaaa    4020
aagagttggt agctcttgat ccggcaaaca aaccaccgct ggtagcggtg gtttttttgt    4080
ttgcaagcag cagattacgc gcagaaaaaa aggatctcaa gaagatcctt tgatcttttc    4140
tacgggtct gacgctcagt ggaacgaaaa ctcacgttaa gggattttgg tcatgagatt    4200
atcaaaaagg atcttcacct agatcctttt aaattaaaaa tgaagtttta aatcaatcta    4260
aagtatatat gagtaaactt ggtctgacag ttaccaatgc ttaatcagtg aggcacctat    4320
ctcagcgatc tgtctatttc gttcatccat agttgcctga ctcgggggg gggggcgctg    4380
aggtctgcct cgtgaagaag gtgttgctga ctcataccag gcctgaatcg ccccatcatc    4440
cagccagaaa gtgagggagc cacggttgat gagagctttg ttgtaggtgg accagttggt    4500
gattttgaac ttttgctttg ccacggaacg gtctgcgttg tcgggaagat gcgtgatctg    4560
atccttcaac tcagcaaaag ttcgatttat tcaacaaagc cgccgtcccg tcaagtcagc    4620
gtaatgctct gccagtgtta caaccaatta accaattctg attagaaaaa ctcatcgagc    4680
atcaaatgaa actgcaattt attcatatca ggattatcaa taccatattt ttgaaaaagc    4740
cgtttctgta atgaaggaga aaactcaccg aggcagttcc ataggatggc aagatcctgg    4800
tatcggtctg cgattccgac tcgtccaaca tcaatacaac ctattaattt cccctcgtca    4860
aaaataaggt tatcaagtga gaaatcacca tgagtgacga ctgaatccgg tgagaatggc    4920
aaaagcttat gcatttcttt ccagacttgt tcaacaggcc agccattacg ctcgtcatca    4980
aaatcactcg catcaaccaa accgttattc attcgtgatt gcgcctgagc gagacgaaat    5040
acgcgatcgc tgttaaaagg acaattacaa acaggaatcg aatgcaaccg gcgcaggaac    5100
actgccagcg catcaacaat attttcacct gaatcaggat attcttctaa tacctggaat    5160
gctgttttcc cggggatcgc agtggtgagt aaccatgcat catcaggagt acggataaaa    5220
tgcttgatgg tcggaagagg cataaattcc gtcagccagt ttagtctgac catctcatct    5280
gtaacatcat tggcaacgct acctttgcca tgtttcagaa acaactctgg cgcatcgggc    5340
ttcccataca atcgatagat tgtcgcacct gattgcccga cattatcgcg agcccattta    5400
tacccatata aatcagcatc catgttggaa tttaatcgcg gcctcgagca agacgtttcc    5460
```

```
cgttgaatat ggctcataac accccttgta ttactgttta tgtaagcaga cagttttatt    5520
gttcatgatg atatattttt atcttgtgca atgtaacatc agagattttg agacacaacg    5580
tggctttccc ccccccccca ttattgaagc atttatcagg gttattgtct catgagcgga    5640
tacatatttg aatgtattta gaaaataaac aaatagggg ttccgcgcac atttcccga     5700 aaagtgccac ctgacgtcta agaaaccatt attatcatga cattaaccta taaaaatagg    5760
cgtatcacga ggccctttcg tc                                              5782
```

<210> SEQ ID NO 154
<211> LENGTH: 5776
<212> TYPE: DNA
<213> ORGANISM: Artificial Sequence
<220> FEATURE:
<223> OTHER INFORMATION: Synthetic sequence of plasmid H1Sing
      SS/Gen4.55/Ferritin

<400> SEQUENCE: 154

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagag    1380
atatcgccac catggccatc atctacctga ttctgctgtt tacagccgtc agaggcgatc    1440
agatctgtat tggctaccac gccaacaata gcaccgagaa agtggatacc atcctggaaa    1500
gaaatgtgac agtgacacac gccaaggata ttggatcagg actggtgctg gctacaggac    1560
tgagaaatgt gcctcagatt gagagcagag gcctgtttgg agccattgct ggctttattg    1620
aaggcggatg gcaggggaatg attgatgggt ggtacggcta ccaccactct aatgatcagg    1680
```

```
gatctggata tgccgccgac aaagaatcta cacagaaagc cttcgacggc atcaccaaca      1740
aagtgaatag cgtgatcgag aagatgggcg gagatcccga atgggacaga gagatcaaca      1800
actacaccag catcatctac agcctgatcg aggaaagcca gaatcagcag gaaaatggaa      1860
caggcggagg atctggaatt gtgcagcagc agaacaatct gctgagagct attgaagctc      1920
agcagcatct gctgaatctg acagtgtggg gaatcaaaca gctgcagaca tacaatgctg      1980
agctgctggt gctgatggaa aatgagagaa ccctggactt ccacgacagc aatgtgaaga      2040
acctgtacga caaagtgcgg atgcagctga gagacaatgt gaaagaactg ggcaatggct      2100
gcttcgagtt ctaccacaag tgcgacgatg agtgtatgaa cagcgtgaag aacggcacct      2160
acgactaccc taagtacgag gaagagagca agctgaacag aaatgagatc aagtccggag      2220
gcgacatcat caagctgctg aacgagcagg tgaacaagga gatgcagagc agcaacctgt      2280
acatgagcat gagcagctgg tgctacaccc acagcctgga cggcgccggc ctgttcctgt      2340
tcgaccacgc cgccgaggag tacgagcacg ccaagaagct gatcatcttc ctgaacgaga      2400
acaacgtgcc cgtgcagctg accagcatca gcgcccccga gcacaagttc gagggcctga      2460
cccagatctt ccagaaggcc tacgagcacg agcagcacat cagcgagagc atcaacaaca      2520
tcgtggacca cgccatcaag agcaaggacc acgccaccct caacttcctg cagtggtacg      2580
tggccgagca gcacgaggag gaggtgctgt tcaaggacat cctggacaag atcgagctga      2640
tcggcaacga gaaccacggc ctgtacctgg ccgaccagta cgtgaagggc atcgccaaga      2700
gcaggaagag cggatcctag catcatcatc atcatcatta gtctgaaggg cgaattgatc      2760
cagctgtgcc ttctagttgc cagccatctg ttgtttgccc ctcccccgtg ccttccttga      2820
ccctggaagg tgccactccc actgtccttt cctaataaaa tgaggaaatt gcatcgcatt      2880
gtctgagtag gtgtcattct attctggggg gtggggtggg gcaggacagc aagggggagg      2940
attgggaaga caatagcagg catgctgggg atgcggtggg ctctatgggt acccaggtgc      3000
tgaagaattg acccggttcc tcctgggcca gaaagaagca ggcacatccc cttctctgtg      3060
acacaccctg tccacgcccc tggttcttag ttccagcccc actcatagga cactcatagc      3120
tcaggagggc tccgccttca atcccacccg ctaaagtact tggagcggtc tctccctccc      3180
tcatcagccc accaaaccaa acctagcctc aagagtggga agaaattaa agcaagatag      3240 gctattaagt gcagagggag agaaaatgcc tccaacatgt gaggaagtaa tgagagaaat      3300
catagaattt taaggccatg atttaaggcc atcatggcct taatcttccg cttcctcgct      3360
cactgactcg ctgcgctcgg tcgttcggct gcggcgagcg gtatcagctc actcaaaggc      3420
ggtaatacgg ttatccacag aatcagggga taacgcagga agaacatgt gagcaaaagg      3480 ccagcaaaag gccaggaacc gtaaaaaggc cgcgttgctg gcgttttcc ataggctccg      3540 ccccccctgac gagcatcaca aaaatcgacg ctcaagtcag aggtggcgaa acccgacagg      3600
actataaaga taccaggcgt ttccccctgg aagctccctc gtgcgctctc ctgttccgac      3660
cctgccgctt accggatacc tgtccgcctt tctcccttcg ggaagcgtgg cgctttctca      3720
tagctcacgc tgtaggtatc tcagttcggt gtaggtcgtt cgctccaagc tgggctgtgt      3780
gcacgaaccc cccgttcagc ccgaccgctg cgccttatcc ggtaactatc gtcttgagtc      3840
caacccggta agacacgact tatcgccact ggcagcagcc actggtaaca ggattagcag      3900
agcgaggtat gtaggcggtg ctacagagtt cttgaagtgg tggcctaact acggctacac      3960
tagaagaaca gtatttggta tctgcgctct gctgaagcca gttaccttcg gaaaaagagt      4020
```

```
tggtagctct tgatccggca acaaaccac cgctggtagc ggtggttttt ttgtttgcaa    4080
gcagcagatt acgcgcagaa aaaaggatc tcaagaagat cctttgatct tttctacggg    4140
gtctgacgct cagtggaacg aaaactcacg ttaagggatt ttggtcatga gattatcaaa    4200
aaggatcttc acctagatcc ttttaaatta aaaatgaagt tttaaatcaa tctaaagtat    4260
atatgagtaa acttggtctg acagttacca atgcttaatc agtgaggcac ctatctcagc    4320
gatctgtcta tttcgttcat ccatagttgc ctgactcggg ggggggggc gctgaggtct    4380 gcctcgtgaa gaaggtgttg ctgactcata ccaggcctga atcgccccat catccagcca    4440
gaaagtgagg gagccacggt tgatgagagc tttgttgtag gtggaccagt tggtgatttt    4500
gaacttttgc tttgccacgg aacggtctgc gttgtcggga agatgcgtga tctgatcctt    4560
caactcagca aaagttcgat ttattcaaca aagccgccgt cccgtcaagt cagcgtaatg    4620
ctctgccagt gttacaacca attaaccaat tctgattaga aaaactcatc gagcatcaaa    4680
tgaaactgca atttattcat atcaggatta tcaataccat tttttgaaa agccgtttc     4740 tgtaatgaag gagaaaactc accgaggcag ttccatagga tggcaagatc ctggtatcgg    4800
tctgcgattc cgactcgtcc aacatcaata caacctatta atttcccctc gtcaaaaata    4860
aggttatcaa gtgagaaatc accatgagtg acgactgaat ccggtgagaa tggcaaaagc    4920
ttatgcattt ctttccagac ttgttcaaca ggccagccat tacgctcgtc atcaaaatca    4980
ctcgcatcaa ccaaaccgtt attcattcgt gattgcgcct gagcgagacg aaatacgcga    5040
tcgctgttaa aaggacaatt acaaacagga tcgaatgca accggcgcag gaacactgcc    5100
agcgcatcaa caatatttc acctgaatca ggatattctt ctaatacctg gaatgctgtt    5160
ttcccgggga tcgcagtggt gagtaaccat gcatcatcag gagtacggat aaaatgcttg    5220
atggtcggaa gaggcataaa ttccgtcagc cagtttagtc tgaccatctc atctgtaaca    5280
tcattggcaa cgctaccttt gccatgtttc agaaacaact ctggcgcatc gggcttccca    5340
tacaatcgat agattgtcgc acctgattgc ccgacattat cgcgagccca tttatatccca    5400 tataaatcag catccatgtt ggaatttaat cgcggcctcg agcaagacgt ttcccgttga    5460
atatggctca taacacccct tgtattactg tttatgtaag cagacagttt tattgttcat    5520
gatgatatat ttttatcttg tgcaatgtaa catcagagat tttgagacac aacgtggctt    5580
tccccccccc cccattattg aagcatttat caggttatt gtctcatgag cggatacata    5640
tttgaatgta tttagaaaaa taaacaaata ggggttccgc gcacatttcc ccgaaaagtg    5700
ccacctgacg tctaagaaac cattattatc atgacattaa cctataaaaa taggcgtatc    5760
acgaggccct ttcgtc                                                   5776

<210> SEQ ID NO 155
<211> LENGTH: 5810
<212> TYPE: DNA
<213> ORGANISM: Artificial Sequence
<220> FEATURE:
<223> OTHER INFORMATION: Synthetic sequence of plasmid H3Bris
      SS/Gen4.55/Ferritin

<400> SEQUENCE: 155
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
```

-continued

```
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg atagcggttt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg gcggtaggcg tgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct    1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tgaaaaccat cattgccctg agctacatcc tgtgcctggt gttcacacag   1440
aagctgcccg gcaacgataa tagcaccgcc acactgtgtc tgggacacca cgccgtgcct   1500
aatggcacca tcgtgaaaac aatcaccaac gaccagatcg aagtgaccaa tgccacagag   1560
ctgggctccg gcctgaagct ggccaccggc atgagaaatg tgcccgagaa gcagaccaga   1620
ggcatctttg gcgccattgc cggctttatc gagaatggct gggagggaat ggtggatggg   1680
tggtacggct tcagacacca gaatagcgag ggaattggac aggccgccga tctgaaatct   1740
acccaggccg ccatcgacca gatcaacggc aagctgaaca ggctgatcgg caagaccggc   1800
ggcgatcccg agtgggaccg ggagatcaac aactacacca gcatcatcta cagcctgatc   1860
gaggagagcc agaaccagca ggagaacggc accggcggcg gcagcggcat cgtgcagcag   1920
cagaacaacc tgctgcgggc catcgaggcc cagcagcacc tgctgcagct gaccgtgtgg   1980
ggcatcaagc agctgcagag ctacaatgcc gaactgctgg tcgccctgga aaaccagcac   2040
acaattgatc tgacagacag tgagatgaat aagctgttcg agaaaaccaa gaagcagctg   2100
agagaaaacg ccgaggacat gggcaacggc tgcttcaaga tctaccacaa gtgcgacaac   2160
gcctgcatcg gcagcatcag aaacggcacc tacgaccacg acgtgtacag agatgaggcc   2220
ctgaacaacc ggtttcagat caagggctcc ggaggcgaca tcatcaagct gctgaacgag   2280
caggtgaaca aggagatgca gagcagcaac ctgtacatga gcatgagcag ctggtgctac   2340
acccacagcc tggacggcgc cggcctgttc ctgttcgacc acgccgccga ggagtacgag   2400
cacgccaaga agctgatcat cttcctgaac gagaacaacg tgcccgtgca gctgaccagc   2460
atcagcgccc ccgagcacaa gttcgagggc ctgacccaga tcttccagaa ggcctacgag   2520
cacgagcagc acatcagcga gagcatcaac aacatcgtgg accacgccat caagagcaag   2580
gaccacgcca ccttcaactt cctgcagtgg tacgtggccg agcagcacga ggaggaggtg   2640
```

```
ctgttcaagg acatcctgga caagatcgag ctgatcggca acgagaacca cggcctgtac    2700
ctggccgacc agtacgtgaa gggcatcgcc aagagcagga gagcggatc ctagcatcat    2760
catcatcatc attagtctga agggcgaatt gatccagctg tgccttctag ttgccagcca    2820
tctgttgttt gccctcccc cgtgccttcc ttgaccctgg aaggtgccac tcccactgtc    2880
ctttcctaat aaaatgagga aattgcatcg cattgtctga gtaggtgtca ttctattctg    2940
gggggtgggg tggggcagga cagcaagggg gaggattggg aagacaatag caggcatgct    3000
ggggatgcgg tgggctctat gggtacccag gtgctgaaga attgacccgg ttcctcctgg    3060
gccagaaaga agcaggcaca tccccttctc tgtgacacac cctgtccacg cccctggttc    3120
ttagttccag ccccactcat aggacactca tagctcagga gggctccgcc ttcaatccca    3180
cccgctaaag tacttggagc ggtctctccc tccctcatca gcccaccaaa ccaaacctag    3240
cctccaagag tgggaagaaa ttaaagcaag ataggctatt aagtgcagag ggagagaaaa    3300
tgcctccaac atgtgaggaa gtaatgagag aaatcataga attttaaggc catgatttaa    3360
ggccatcatg gccttaatct tccgcttcct cgctcactga ctcgctgcgc tcggtcgttc    3420
ggctgcggcg agcggtatca gctcactcaa aggcggtaat acggttatcc acagaatcag    3480
gggataacgc aggaaagaac atgtgagcaa aaggccagca aaaggccagg aaccgtaaaa    3540
aggccgcgtt gctggcgttt ttccataggc tccgccccc tgacgagcat cacaaaaatc    3600
gacgctcaag tcagaggtgg cgaaacccga caggactata agataccag gcgtttcccc    3660
ctggaagctc cctcgtgcgc tctcctgttc cgaccctgcc gcttaccgga tacctgtccg    3720
cctttctccc ttcgggaagc gtggcgcttt ctcatagctc acgctgtagg tatctcagtt    3780
cggtgtaggt cgttcgctcc aagctgggct gtgtgcacga accccccgtt cagcccgacc    3840
gctgcgcctt atccggtaac tatcgtcttg agtccaaccc ggtaagacac gacttatcgc    3900
cactggcagc agccactggt aacaggatta gcagagcgag gtatgtaggc ggtgctacag    3960
agttcttgaa gtggtggcct aactacggct acactagaag aacagtattt ggtatctgcg    4020
ctctgctgaa gccagttacc ttcggaaaaa gagttggtag ctcttgatcc ggcaaacaaa    4080
ccaccgctgg tagcggtggt ttttttgttt gcaagcagca gattacgcgc agaaaaaaag    4140
gatctcaaga agatcctttg atcttttcta cggggtctga cgctcagtgg aacgaaaact    4200
cacgttaagg gattttggtc atgagattat caaaaaggat cttcacctag atccttttaa    4260
attaaaaatg aagttttaaa tcaatctaaa gtatatatga gtaaacttgg tctgacagtt    4320
accaatgctt aatcagtgag gcacctatct cagcgatctg tctatttcgt tcatccatag    4380
ttgcctgact cggggggggg gggcgctgag gtctgcctcg tgaagaaggt gttgctgact    4440
cataccaggc ctgaatcgcc ccatcatcca gccagaaagt gagggagcca cggttgatga    4500
gagctttgtt gtaggtggac cagttggtga ttttgaactt ttgctttgcc acggaacggt    4560
ctgcgttgtc gggaagatgc gtgatctgat ccttcaactc agcaaaagtt cgatttattc    4620
aacaaagccg ccgtcccgtc aagtcagcgt aatgctctgc cagtgttaca accaattaac    4680
caattctgat tagaaaaact catcgagcat caaatgaaac tgcaattat tcatatcagg    4740
attatcaata ccatatttt gaaaagccg tttctgtaat gaaggagaaa actcaccgag    4800
gcagttccat aggatggcaa gatcctggta tcggtctgcg attccgactc gtccaacatc    4860
aatacaacct attaatttcc cctcgtcaaa aataaggtta tcaagtgaga atcaccatg    4920
agtgacgact gaatccggtg agaatggcaa aagcttatgc atttctttcc agacttgttc    4980
```

| | |
|---|---:|
| aacaggccag ccattacgct cgtcatcaaa atcactcgca tcaaccaaac cgttattcat | 5040 |
| tcgtgattgc gcctgagcga gacgaaatac gcgatcgctg ttaaaaggac aattacaaac | 5100 |
| aggaatcgaa tgcaaccggc gcaggaacac tgccagcgca tcaacaatat tttcacctga | 5160 |
| atcaggatat tcttctaata cctggaatgc tgttttcccg gggatcgcag tggtgagtaa | 5220 |
| ccatgcatca tcaggagtac ggataaaatg cttgatggtc ggaagaggca taaattccgt | 5280 |
| cagccagttt agtctgacca tctcatctgt aacatcattg gcaacgctac ctttgccatg | 5340 |
| tttcagaaac aactctggcg catcgggctt cccatacaat cgatagattg tcgcacctga | 5400 |
| ttgcccgaca ttatcgcgag cccatttata cccatataaa tcagcatcca tgttggaatt | 5460 |
| taatcgcggc ctcgagcaag acgtttcccg ttgaatatgg ctcataacac cccttgtatt | 5520 |
| actgtttatg taagcagaca gttttattgt tcatgatgat atattttat cttgtgcaat | 5580 |
| gtaacatcag agattttgag acacaacgtg ctttccccc cccccccatt attgaagcat | 5640 |
| ttatcagggt tattgtctca tgagcggata catatttgaa tgtatttaga aaataaaca | 5700 |
| aatagggtt ccgcgcacat ttccccgaaa agtgccacct gacgtctaag aaaccattat | 5760 |
| tatcatgaca ttaacctata aaaataggcg tatcacgagg ccctttcgtc | 5810 |

<210> SEQ ID NO 156
<211> LENGTH: 5810
<212> TYPE: DNA
<213> ORGANISM: Artificial Sequence
<220> FEATURE:
<223> OTHER INFORMATION: Synthetic sequence of plasmid H1Perth
SS/Gen4.55/Ferritin

<400> SEQUENCE: 156

| | |
|---|---:|
| tcgcgcgttt cggtgatgac ggtgaaaacc tctgacacat gcagctcccg gagacggtca | 60 |
| cagcttgtct gtaagcggat gccggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| gggaacttcc atagcccata tatggagttc cgcgttacat aacttacggg aatttccaaa | 420 |
| cctggctgac cgcccaacga cccccgccca ttgacgtcaa taatgacgta tgttcccata | 480 |
| gtaacgccaa tagggaactt ccattgacgt caatgggtgg agtatttacg gtaaactgcc | 540 |
| cacttggaa tttccaagtg tatcatatgc caagtacgcc ccctattgac gtcaatgacg | 600 |
| ggaacttcca taagcttgca ttatgcccag tacatgacct tatgggaatt cctacttgg | 660 |
| cagtacatct acgtattagt catcgctatt accatggtga tgcggttttg gcagtacatc | 720 |
| aatgggcgtg gatagcggtt tgactcacgg gaacttccaa gtctccaccc cattgacgtc | 780 |
| aatgggagtt tgttttgact caccaaaatc aacgggaatt cccaaaatgt cgtaacaact | 840 |
| ccgccccatt gacgcaaatg ggcggtaggc gtgtacggtg ggaggtctat ataagcagag | 900 |
| ctcgtttagt gaaccgtcag atcgcctgga gacgccatcc acgctgtttt gacctccata | 960 |
| gaagacaccg ggaccgatcc agcctccatc ggctcgcatc tctccttcac gcgcccgccg | 1020 |
| ccctacctga ggccgccatc cacgccggtt gagtcgcgtt ctgccgcctc cgcctgtgg | 1080 |
| tgcctcctga actgcgtccg ccgtctaggt aagtttaaag ctcaggtcga gaccgggcct | 1140 |
| ttgtccggcg ctcccttgga gcctacctag actcagccgg ctctccacgc tttgcctgac | 1200 |

```
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tgaaaaccat aattgcgctg tcctacatac tgtgtctggt gtttgcccag   1440
aaactgccgg gcaatgacaa ctcaacagcc acgctctgct ggggcacca tgccgtccct    1500
aacgggacca ttgtgaaaac cattactaac gatcagatag aggtgactaa tgccaccgag   1560
ctgggctccg gcttgaaact ggcgaccggt atgcgcaatg tccccgaaaa acagacccgc   1620
gggatatttg gggctatcgc aggctttatc gagaatggct gggaagggat ggtggatggt   1680
tggtatggtt ttagacatca aaactccgaa ggcagaggcc aggctgccga tctcaagagc   1740
acgcaggccg ctatagatca gatcaatgga aagctcaaca gactgatcgg aaaaaccggc   1800
ggcgatcccg agtgggaccg ggagatcaac aactacacca gcatcatcta cagcctgatc   1860
gaggagagcc agaaccagca ggagaacggc accggcggcg gcagcggcat cgtgcagcag   1920
cagaacaacc tgctgcgggc catcgaggcc cagcagcacc tgctgcagct gaccgtgtgg   1980
ggcatcaagc agctgcagtc ctacaatgcc gagctgctgg tggctctgga aatcagcac    2040
actattgacc tgaccgattc agagatgaac aaacttttg agaagacgaa gaagcagctt     2100
agagaaaatg cagaggacat ggggaacgga tgctttaaaa tatatcataa gtgtgataat   2160
gcctgcatcg gatcaattag aaatggtacc tatgatcacg atgtttacag ggacgaagcg   2220
ctgaataaca ggttccagat aaaaggctcc ggaggcgaca tcatcaagct gctgaacgag   2280
caggtgaaca aggagatgca gagcagcaac ctgtacatga gcatgagcag ctggtgctac   2340
acccacagcc tggacggcgc cggcctgttc ctgttcgacc acgccgccga ggagtacgag   2400
cacgccaaga agctgatcat cttcctgaac gagaacaacg tgcccgtgca gctgaccagc   2460
atcagcgccc ccgagcacaa gttcgagggc ctgacccaga tcttccagaa ggcctacgag   2520
cacgagcagc acatcagcga gagcatcaac aacatcgtgg accacgccat caagagcaag   2580
gaccacgcca ccttcaactt cctgcagtgg tacgtggccg agcagcacga ggaggaggtg   2640
ctgttcaagg acatcctgga caagatcgag ctgatcggca cgagaaccca cggcctgtac   2700
ctggccgacc agtacgtgaa gggcatcgcc aagagcagga gagcggatc ctagcatcat   2760
catcatcatc attagtctga agggcgaatt gatccagctg tgccttctag ttgccagcca   2820
tctgttgttt gcccctcccc cgtgccttcc ttgaccctgg aaggtgccac tcccactgtc   2880
ctttcctaat aaaatgagga aattgcatcg cattgtctga gtaggtgtca ttctattctg   2940
gggggtgggg tggggcagga cagcaagggg gaggattggg aagacaatag caggcatgct   3000
ggggatgcgg tgggctctat ggtacccag gtgctgaaga attgacccgg ttcctcctgg    3060
gccagaaaga agcaggcaca tccccttctc tgtgacacac cctgtccacg cccctggttc   3120
ttagttccag ccccactcat aggacactca tagctcagga gggctccgcc ttcaatccca   3180
cccgctaaag tacttggagc ggtctctccc tccctcatca gcccaccaaa ccaaacctag   3240
cctccaagag tgggaagaaa ttaaagcaag ataggctatt aagtgcagag ggagagaaaa   3300
tgcctccaac atgtgaggaa gtaatgagag aaatcataga attttaaggc catgatttaa   3360
ggccatcatg gccttaatct tccgcttcct cgctcactga ctcgctgcgc tcggtcgttc   3420
ggctgcggcg agcggtatca gctcactcaa aggcggtaat acggttatcc acagaatcag   3480
gggataacgc aggaaagaac atgtgagcaa aaggccagca aaaggccagg aaccgtaaaa   3540
aggccgcgtt gctggcgttt ttccataggc tccgcccccc tgacgagcat cacaaaaatc   3600
```

```
gacgctcaag tcagaggtgg cgaaacccga caggactata aagataccag gcgtttcccc    3660
ctggaagctc cctcgtgcgc tctcctgttc cgaccctgcc gcttaccgga tacctgtccg    3720
cctttctccc ttcgggaagc gtggcgcttt ctcatagctc acgctgtagg tatctcagtt    3780
cggtgtaggt cgttcgctcc aagctgggct gtgtgcacga accccccgtt cagcccgacc    3840
gctgcgcctt atccggtaac tatcgtcttg agtccaaccc ggtaagacac gacttatcgc    3900
cactggcagc agccactggt aacaggatta gcagagcgag gtatgtaggc ggtgctacag    3960
agttcttgaa gtggtggcct aactacggct acactagaag aacagtattt ggtatctgcg    4020
ctctgctgaa gccagttacc ttcggaaaaa gagttggtag ctcttgatcc ggcaaacaaa    4080
ccaccgctgg tagcggtggt ttttttgttt gcaagcagca gattacgcgc agaaaaaaag    4140
gatctcaaga agatcctttg atcttttcta cggggtctga cgctcagtgg aacgaaaact    4200
cacgttaagg gattttggtc atgagattat caaaaaggat cttcacctag atccttttaa    4260
attaaaaatg aagttttaaa tcaatctaaa gtatatatga gtaaacttgg tctgacagtt    4320
accaatgctt aatcagtgag gcacctatct cagcgatctg tctatttcgt tcatccatag    4380
ttgcctgact cggggggggg gggcgctgag gtctgcctcg tgaagaaggt gttgctgact    4440
cataccaggc ctgaatcgcc ccatcatcca gccagaaagt gagggagcca cggttgatga    4500
gagctttgtt gtaggtggac cagttggtga ttttgaactt ttgctttgcc acggaacggt    4560
ctgcgttgtc gggaagatgc gtgatctgat ccttcaactc agcaaaagtt cgatttattc    4620
aacaaagccg ccgtcccgtc aagtcagcgt aatgctctgc cagtgttaca accaattaac    4680
caattctgat tagaaaaact catcgagcat caaatgaaac tgcaatttat tcatatcagg    4740
attatcaata ccatattttt gaaaaagccg tttctgtaat gaaggagaaa actcaccgag    4800
gcagttccat aggatggcaa gatcctggta tcggtctgcg attccgactc gtccaacatc    4860
aatacaacct attaatttcc cctcgtcaaa aataaggtta tcaagtgaga atcaccatg    4920 agtgacgact gaatccggtg agaatggcaa aagcttatgc atttctttcc agacttgttc    4980
aacaggccag ccattacgct cgtcatcaaa atcactcgca tcaaccaaac cgttattcat    5040
tcgtgattgc gcctgagcga gacgaaatac gcgatcgctg ttaaaaggac aattacaaac    5100
aggaatcgaa tgcaaccggc gcaggaacac tgccagcgca tcaacaatat tttcacctga    5160
atcaggatat tcttctaata cctggaatgc tgttttcccg gggatcgcag tggtgagtaa    5220
ccatgcatca tcaggagtac ggataaaatg cttgatggtc ggaagaggca taaattccgt    5280
cagccagttt agtctgacca tctcatctgt aacatcattg gcaacgctac ctttgccatg    5340
tttcagaaac aactctggcg catcgggctt cccatacaat cgatagattg tcgcacctga    5400
ttgcccgaca ttatcgcgag cccatttata cccatataaa tcagcatcca tgttggaatt    5460
taatcgcggc ctcgagcaag acgtttcccg ttgaatatgg ctcataacac cccttgtatt    5520
actgtttatg taagcagaca gttttattgt tcatgatgat atattttat cttgtgcaat    5580 gtaacatcag agattttgag acacaacgtg ctttcccccc cccccccatt attgaagcat    5640
ttatcagggt tattgtctca tgagcggata catatttgaa tgtatttaga aaataaaca    5700 aatagggggtt ccgcgcacat ttccccgaaa agtgccacct gacgtctaag aaaccattat    5760
tatcatgaca ttaacctata aaaataggcg tatcacgagg ccctttcgtc                5810

<210> SEQ ID NO 157
<211> LENGTH: 5812
<212> TYPE: DNA
```

<213> ORGANISM: Artificial Sequence
<220> FEATURE:
<223> OTHER INFORMATION: Synthetic sequence of plasmid H3 HK68 SS/Gen4.55/Ferritin

<400> SEQUENCE: 157

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| ggggtcatta | gttcatagcc | catatatgga | gttccgcgtt | acataactta | cggtaaatgg | 420 |
| cccgcctggc | tgaccgccca | acgaccccg | cccattgacg | tcaataatga | cgtatgttcc | 480 |
| catagtaacg | ccaataggga | ctttccattg | acgtcaatgg | gtggagtatt | tacggtaaac | 540 |
| tgcccacttg | gcagtacatc | aagtgtatca | tatgccaagt | acgccccta | ttgacgtcaa | 600 |
| tgacggtaaa | tggcccgcct | ggcattatgc | ccagtacatg | accttatggg | actttcctac | 660 |
| ttggcagtac | atctacgtat | tagtcatcgc | tattaccatg | gtgatgcggt | tttggcagta | 720 |
| catcaatggg | cgtggatagc | ggtttgactc | acggggattt | ccaagtctcc | accccattga | 780 |
| cgtcaatggg | agtttgtttt | ggcaccaaaa | tcaacgggac | tttccaaaat | gtcgtaacaa | 840 |
| ctccgcccca | ttgacgcaaa | tgggcggtag | gcgtgtacgg | tgggaggtct | atataagcag | 900 |
| agctcgttta | gtgaaccgtc | agatcgcctg | gagacgccat | ccacgctgtt | ttgacctcca | 960 |
| tagaagacac | cgggaccgat | ccagcctcca | tcggctcgca | tctctccttc | acgcgcccgc | 1020 |
| cgccctacct | gaggccgcca | tccacgccgg | ttgagtcgcg | ttctgccgcc | tcccgcctgt | 1080 |
| ggtgcctcct | gaactgcgtc | cgccgtctag | gtaagtttaa | agctcaggtc | gagaccgggc | 1140 |
| ctttgtccgg | cgctcccttg | gagcctacct | agactcagcc | ggctctccac | gctttgcctg | 1200 |
| accctgcttg | ctcaactcta | gttaacggtg | gagggcagtg | tagtctgagc | agtactcgtt | 1260 |
| gctgccgcgc | gcgccaccag | acataatagc | tgacagacta | acagactgtt | cctttccatg | 1320 |
| ggtcttttct | gcagtcaccg | tcgtcgacac | gtgtgatcag | atatcgcggc | cgctctagag | 1380 |
| atatcgccac | catgaagacc | atcatcgccc | tgagctacat | cttctgcctg | gcctgggcc | 1440 |
| aggacctgcc | cggcaacgac | aacagcaccg | ccaccctgtg | cctgggccac | cacgccgtgc | 1500 |
| ccaacggcac | cctggtgaag | accatcaccg | acgaccagat | cgaggtgacc | aacgccaccg | 1560 |
| agctgggctc | cggcctgaag | ctggccaccg | gcatgcggaa | cgtgcccgag | aagcagaccc | 1620 |
| ggggcctgtt | cggcgccatc | gccggcttca | tcgagaacgg | ctgggagggc | atgatcgacg | 1680 |
| gctggtacgg | cttccggcac | cagaacagcg | agggcaccgg | ccaggccgcc | gacctgaaga | 1740 |
| gcacccaggc | cgccatcgac | cagatcaacg | gcaagctgaa | ccgggtgatc | gagaagaccg | 1800 |
| gcggcgatcc | gagtgggac | cgggagatca | acaactacac | cagcatcatc | tacagcctga | 1860 |
| tcgaggagag | ccagaaccag | caggagaacg | gcaccggcgg | cggcagcggc | atcgtgcagc | 1920 |
| agcagaacaa | cctgctgcgg | gccatcgagg | cccagcagca | cctgctgcag | ctgaccgtgt | 1980 |
| ggggcatcaa | gcagctgcag | agctacaacg | ccgagctgct | ggtggccctg | agaaccagc | 2040 |
| acaccatcga | cctgaccgac | agcgagatga | acaagctgtt | cgagaagacc | cggcggcagc | 2100 |
| tgcgggagaa | cgccgaggac | atgggcaacg | gctgcttcaa | gatctaccac | aagtgcgaca | 2160 |

-continued

```
acgcctgcat cgagagcatc cggaacggca cctacgacca cgacgtgtac cgggacgagg    2220
ccctgaacaa ccggttccag atcaagggct ccggaggcga catcatcaag ctgctgaacg    2280
agcaggtgaa caaggagatg cagagcagca acctgtacat gagcatgagc agctggtgct    2340
acacccacag cctggacggc gccggcctgt cctgttcga ccacgccgcc gaggagtacg    2400
agcacgccaa gaagctgatc atcttcctga acgagaacaa cgtgcccgtg cagctgacca    2460
gcatcagcgc ccccgagcac aagttcgagg gcctgaccca gatcttccag aaggcctacg    2520
agcacgagca gcacatcagc gagagcatca acaacatcgt ggaccacgcc atcaagagca    2580
aggaccacgc caccttcaac ttcctgcagt ggtacgtggc cgagcagcac gaggaggagg    2640
tgctgttcaa ggacatcctg acaagatcg agctgatcgg caacgagaac cacggcctgt    2700
acctggccga ccagtacgtg aagggcatcg ccaagagcag gaagagcgga tcctagcatc    2760
atcatcatca tcattagtct gaagggcgaa ttgatccagc tgtgccttct agttgccagc    2820
catctgttgt ttgcccctcc cccgtgcctt ccttgaccct ggaaggtgcc actcccactg    2880
tcctttccta ataaaatgag gaaattgcat cgcattgtct gagtaggtgt cattctattc    2940
tggggggtgg ggtggggcag gacagcaagg gggaggattg gaagacaat agcaggcatg    3000 ctggggatgc ggtgggctct atgggtaccc aggtgctgaa gaattgaccc ggttcctcct    3060
gggccagaaa gaagcaggca catcccttc tctgtgacac accctgtcca cgccctggt    3120 tcttagttcc agccccactc ataggacact catagctcag gagggctccg ccttcaatcc    3180
cacccgctaa agtacttgga gcggtctctc cctccctcat cagcccacca aaccaaacct    3240
agcctccaag agtgggaaga aattaaagca agataggcta ttaagtgcag agggagagaa    3300
aatgcctcca acatgtgagg aagtaatgag agaaatcata gaattttaag gccatgattt    3360
aaggccatca tggcccttaat cttccgcttc ctcgctcact gactcgctgc gctcggtcgt    3420
tcggctgcgg cgagcggtat cagctcactc aaaggcggta atacggttat ccacagaatc    3480
aggggataac gcaggaaaga acatgtgagc aaaaggccag caaaaggcca ggaaccgtaa    3540
aaaggccgcg ttgctggcgt ttttccatag gctccgcccc cctgacgagc atcacaaaaa    3600
tcgacgctca agtcagaggt ggcgaaaccc gacaggacta taaagatacc aggcgtttcc    3660
ccctggaagc tccctcgtgc gctctcctgt tccgaccctg ccgcttaccg gatacctgtc    3720
cgcctttctc ccttcgggaa gcgtggcgct ttctcatagc tcacgctgta ggtatctcag    3780
ttcggtgtag gtcgttcgct ccaagctggg ctgtgtgcac gaaccccccg ttcagcccga    3840
ccgctgcgcc ttatccggta actatcgtct tgagtccaac ccggtaagac acgacttatc    3900
gccactggca gcagccactg gtaacaggat tagcagagcg aggtatgtag gcggtgctac    3960
agagttcttg aagtggtggc ctaactacgg ctacactaga agaacagtat ttggtatctg    4020
cgctctgctg aagccagtta ccttcggaaa aagagttggt agctcttgat ccggcaaaca    4080
aaccaccgct ggtagcggtg gtttttttgt ttgcaagcag cagattacgc gcagaaaaaa    4140
aggatctcaa gaagatcctt tgatctttc tacgggtct gacgctcagt ggaacgaaaa    4200
ctcacgttaa gggattttgg tcatgagatt atcaaaaagg atcttcacct agatcctttt    4260
aaattaaaaa tgaagtttta atcaatcta agtatatat gagtaaactt ggtctgacag    4320
ttaccaatgc ttaatcagtg aggcacctat ctcagcgatc tgtctatttc gttcatccat    4380
agttgcctga ctcgggggg gggggcgctg aggtctgcct cgtgaagaag gtgttgctga    4440
ctcataccag gcctgaatcg ccccatcatc cagccagaaa gtgagggagc acgttgat    4500 gagagctttg ttgtaggtgg accagttggt gattttgaac ttttgctttg ccacggaacg    4560
```

| gtctgcgttg tcgggaagat gcgtgatctg atccttcaac tcagcaaaag ttcgatttat | 4620 |
| tcaacaaagc cgccgtcccg tcaagtcagc gtaatgctct gccagtgtta caaccaatta | 4680 |
| accaattctg attagaaaaa ctcatcgagc atcaaatgaa actgcaattt attcatatca | 4740 |
| ggattatcaa taccatattt ttgaaaaagc cgtttctgta atgaaggaga aaactcaccg | 4800 |
| aggcagttcc ataggatggc aagatcctgg tatcggtctg cgattccgac tcgtccaaca | 4860 |
| tcaatacaac ctattaattt cccctcgtca aaataaggt tatcaagtga aaatcacca | 4920 |
| tgagtgacga ctgaatccgg tgagaatggc aaaagcttat gcatttcttt ccagacttgt | 4980 |
| tcaacaggcc agccattacg ctcgtcatca aaatcactcg catcaaccaa accgttattc | 5040 |
| attcgtgatt gcgcctgagc gagacgaaat acgcgatcgc tgttaaaagg acaattacaa | 5100 |
| acaggaatcg aatgcaaccg gcgcaggaac actgccagcg catcaacaat attttcacct | 5160 |
| gaatcaggat attcttctaa tacctggaat gctgttttcc cggggatcgc agtggtgagt | 5220 |
| aaccatgcat catcaggagt acggataaaa tgcttgatgg tcggaagagg cataaattcc | 5280 |
| gtcagccagt ttagtctgac catctcatct gtaacatcat tggcaacgct acctttgcca | 5340 |
| tgtttcagaa acaactctgg cgcatcgggc ttcccataca atcgatagat tgtcgcacct | 5400 |
| gattgcccga cattatcgcg agcccattta tacccatata aatcagcatc catgttggaa | 5460 |
| tttaatcgcg gcctcgagca agacgtttcc cgttgaatat ggctcataac accccttgta | 5520 |
| ttactgttta tgtaagcaga cagttttatt gttcatgatg atatattttt atcttgtgca | 5580 |
| atgtaacatc agagattttg agacacaacg tggctttccc ccccccccca ttattgaagc | 5640 |
| atttatcagg gttattgtct catgagcgga tacatatttg aatgtattta gaaaaataaa | 5700 |
| caaataggg ttccgcgcac atttcccga aaagtgccac ctgacgtcta agaaaccatt | 5760 |
| attatcatga cattaaccta taaaaatagg cgtatcacga ggccctttcg tc | 5812 |

<210> SEQ ID NO 158
<211> LENGTH: 5789
<212> TYPE: DNA
<213> ORGANISM: Artificial Sequence
<220> FEATURE:
<223> OTHER INFORMATION: Synthetic sequence of plasmid H5Indo
      SS/Gen4.55/Ferritin

<400> SEQUENCE: 158

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggacttcc atagcccata tatggagttc cgcgttacat aacttacggg aatttccaaa | 420 |
| cctggctgac cgcccaacga ccccgccca ttgacgtcaa taatgacgta tgttcccata | 480 |
| gtaacgccaa tagggaactt ccattgacgt caatgggtgg agtatttacg gtaaactgcc | 540 |
| cacttggcaa tttccaagtg tatcatatgc caagtacgcc ccctattgac gtcaatgacg | 600 |
| ggaacttcca taagcttgca ttatgcccag tacatgacct tatgggaatt cctacttgg | 660 |
| cagtacatct acgtattagt catcgctatt accatggtga tgcggttttg gcagtacatc | 720 |
| aatgggcgtg gatagcggtt tgactcacgg ggaacttccaa gtctccaccc cattgacgtc | 780 |

-continued

```
aatgggagtt tgttttgact caccaaaatc aacgggaatt cccaaaatgt cgtaacaact      840
ccgccccatt gacgcaaatg ggcggtaggc gtgtacggtg ggaggtctat ataagcagag      900
ctcgtttagt gaaccgtcag atcgcctgga gacgccatcc acgctgtttt gacctccata      960
gaagacaccg ggaccgatcc agcctccatc ggctcgcatc tctccttcac gcgcccgccg     1020
ccctacctga ggccgccatc cacgccggtt gagtcgcgtt ctgccgcctc ccgcctgtgg     1080
tgcctcctga actgcgtccg ccgtctaggt aagtttaaag ctcaggtcga gacgggcct      1140
ttgtccggcg ctcccttgga gcctacctag actcagccgg ctctccacgc tttgcctgac     1200
cctgcttgct caactctagt taacggtgga gggcagtgta gtctgagcag tactcgttgc     1260
tgccgcgcgc gccaccagac ataatagctg acagactaac agactgttcc tttccatggg     1320
tcttttctgc agtcaccgtc gtcgacacgt gtgatcagat atcgcggccg ctctagagat     1380
atcgccacca tggagaagat cgtgctgctg ctggccatcg tgagcctggt gaagagcgac     1440
cagatctgca tcggctacca cgccaacaac agcaccgagc aggtggacac catcatggag     1500
aagaacgtga ccgtgaccca cgcccaggac atcggctccg gcctggtgct ggccaccggc     1560
ctgcggaaca gcccccagcg ggagagccgg cggaagaagc ggggcctgtt cggcgccatc     1620
gccggcttca tcgagggcgg ctggcagggc atggtggacg gctggtacgg ctaccaccac     1680
agcaacgagc agggcagcgg ctacgccgcc gacaaggaga gcacccagaa ggccatcgac     1740
ggcgtgacca acaaggtgaa cagcatcatc gacaagatgg gcggcgatcc cgagtgggac     1800
cgggagatca caactacac cagcatcatc tacagcctga tcgaggagag ccagaaccag     1860
caggagaacg gcaccggcgg cggcagcggc atcgtgcagc agcagaacaa cctgctgcgg     1920
gccatcgagg cccagcagca cctgctgcag ctgaccgtgt ggggcatcaa gcagctgcag     1980
acctacaacg ccgagctgct ggtgctgatg gagaacgagc ggaccctgga cttccacgac     2040
agcaacgtga agaacctgta cgacaaggtg cggctgcagc tgcgggacaa cgccaaggag     2100
ctgggcaacg gctgcttcga gttctaccac aagtgcgaca cgagtgcat ggagagcatc     2160
cggaacggca cctacaacta cccccagtac agcgaggagg cccggctgaa gcggaggag      2220
atcagctccg gaggcgacat catcaagctg ctgaacgagc aggtgaacaa ggagatgcag     2280
agcagcaacc tgtacatgag catgagcagc tggtgctaca cccacagcct ggacggcgcc     2340
ggcctgttcc tgttcgacca cgccgccgag gagtacgagc acgccaagaa gctgatcatc     2400
ttcctgaacg agaacaacgt gccgtgcag ctgaccagca tcagcgcccc cgagcacaag     2460
ttcgagggcc tgacccagat cttccagaag gcctacgagc acgagcagca catcagcgag     2520
agcatcaaca acatcgtgga ccacgccatc aagagcaagg accacgccac cttcaacttc     2580
ctgcagtggt acgtggccga gcagcacgag gaggaggtgc tgttcaagga catcctggac     2640
aagatcgagc tgatcggcaa cgagaaccac ggcctgtacc tggccgacca gtacgtgaag     2700
ggcatcgcca agagcaggaa gagcggatcc tagcatcatc atcatcatca ttagtctgaa     2760
gggcgaattg atccagctgt gccttctagt tgccagccat ctgttgtttg cccctccccc     2820
gtgccttcct tgaccctgga aggtgccact cccactgtcc tttcctaata aaatgaggaa     2880
attgcatcgc attgtctgag taggtgtcat tctattctgg ggggtgggt ggggcaggac      2940
agcaagggg aggattggga agacaatagc aggcatgctg gggatgcggt gggctctatg      3000
ggtacccagg tgctgaagaa ttgacccggt tcctcctggg ccagaaagaa gcaggcacat     3060
cccttctct gtgacacacc ctgtccacgc ccctggttct tagttccagc cccactcata      3120
```

```
ggacactcat agctcaggag ggctccgcct tcaatcccac ccgctaaagt acttggagcg    3180
gtctctccct ccctcatcag cccaccaaac caaacctagc ctccaagagt gggaagaaat    3240
taaagcaaga taggctatta agtgcagagg gagagaaaat gcctccaaca tgtgaggaag    3300
taatgagaga aatcatagaa ttttaaggcc atgatttaag gccatcatgg ccttaatctt    3360
ccgcttcctc gctcactgac tcgctgcgct cggtcgttcg gctgcggcga gcggtatcag    3420
ctcactcaaa ggcggtaata cggttatcca cagaatcagg ggataacgca ggaaagaaca    3480
tgtgagcaaa aggccagcaa aaggccagga accgtaaaaa ggccgcgttg ctggcgtttt    3540
tccataggct ccgcccccct gacgagcatc acaaaaatcg acgctcaagt cagaggtggc    3600
gaaacccgac aggactataa agataccagg cgtttccccc tggaagctcc ctcgtgcgct    3660
ctcctgttcc gaccctgccg cttaccggat acctgtccgc ctttctccct tcgggaagcg    3720
tggcgctttc tcatagctca cgctgtaggt atctcagttc ggtgtaggtc gttcgctcca    3780
agctgggctg tgtgcacgaa ccccccgttc agcccgaccg ctgcgcctta tccggtaact    3840
atcgtcttga gtccaacccg gtaagacacg acttatcgcc actggcagca gccactggta    3900
acaggattag cagagcgagg tatgtaggcg gtgctacaga gttcttgaag tggtggccta    3960
actacggcta cactagaaga acagtatttg gtatctgcgc tctgctgaag ccagttacct    4020
tcggaaaaag agttggtagc tcttgatccg gcaaacaaac caccgctggt agcggtggtt    4080 ttttttgtttg caagcagcag attacgcgca gaaaaaaagg atctcaagaa gatcctttga    4140
tcttttctac ggggtctgac gctcagtgga acgaaaactc acgttaaggg attttggtca    4200
tgagattatc aaaaaggatc ttcacctaga tccttttaaa ttaaaaatga agttttaaat    4260
caatctaaag tatatatgag taaacttggt ctgacagtta ccaatgctta atcagtgagg    4320
cacctatctc agcgatctgt ctatttcgtt catccatagt tgcctgactc ggggggggg    4380 ggcgctgagg tctgcctcgt gaagaaggtg ttgctgactc ataccaggcc tgaatcgccc    4440
catcatccag ccagaaagtg agggagccac ggttgatgag agctttgttg taggtggacc    4500
agttggtgat tttgaacttt tgctttgcca cggaacggtc tgcgttgtcg ggaagatgcg    4560
tgatctgatc cttcaactca gcaaaagttc gatttattca acaaagccgc cgtcccgtca    4620
agtcagcgta atgctctgcc agtgttacaa ccaattaacc aattctgatt agaaaaactc    4680
atcgagcatc aaatgaaact gcaatttatt catatcagga ttatcaatac catatttttg    4740
aaaaagccgt ttctgtaatg aaggagaaaa ctcaccgagg cagttccata ggatggcaag    4800
atcctggtat cggtctgcga ttccgactcg tccaacatca atacaaccta ttaatttccc    4860
ctcgtcaaaa ataaggttat caagtgagaa atcaccatga gtgacgactg aatccggtga    4920
gaatggcaaa agcttatgca tttctttcca gacttgttca acaggccagc cattacgctc    4980
gtcatcaaaa tcactcgcat caaccaaacc gttattcatt cgtgattgcg cctgagcgag    5040
acgaaatacg cgatcgctgt taaaaggaca attacaaaca ggaatcgaat gcaaccggcg    5100
caggaacact gccagcgcat caacaatatt ttcacctgaa tcaggatatt cttctaatac    5160
ctggaatgct gttttcccgg ggatcgcagt ggtgagtaac catgcatcat caggagtacg    5220
gataaaatgc ttgatggtcg gaagaggcat aaattccgtc agccagttta gtctgaccat    5280
ctcatctgta acatcattgg caacgctacc tttgccatgt ttcagaaaca actctggcgc    5340
atcgggcttc ccatacaatc gatagattgt cgcacctgat tgcccgacat tatcgcgagc    5400
ccatttatac ccatataaat cagcatccat gttggaattt aatcgcggcc tcgagcaaga    5460
cgtttcccgt tgaatatggc tcataacacc ccttgtatta ctgtttatgt aagcagacag    5520
```

```
tttattgtt catgatgata tattttatc ttgtgcaatg taacatcaga gattttgaga    5580
cacaacgtgg ctttccccccc ccccccatta ttgaagcatt tatcagggtt attgtctcat    5640
gagcggatac atatttgaat gtatttagaa aaataaacaa ataggggttc cgcgcacatt    5700
tccccgaaaa gtgccacctg acgtctaaga accattatt atcatgacat taacctataa    5760
aaataggcgt atcacgaggc cctttcgtc                                       5789
```

<210> SEQ ID NO 159
<211> LENGTH: 5783
<212> TYPE: DNA
<213> ORGANISM: Artificial Sequence
<220> FEATURE:
<223> OTHER INFORMATION: Synthetic sequence of plasmid B Bris SS/Gen4.55/Ferritin

<400> SEQUENCE: 159

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcattc atagcccata tatggagttc cgcgttacat aacttacggg aatttccaaa     420
cctggctgac cgcccaacga ccccgccca ttgacgtcaa taatgacgta tgttcccata     480
gtaacgccaa tagggaactt ccattgacgt caatgggtgg agtatttacg gtaaactgcc     540 cacttggaa tttccaagtg tatcatatgc caagtacgcc ccctattgac gtcaatgacg     600
ggaacttcca taagcttgca ttatgcccag tacatgacct tatgggaatt cctacttgg     660 cagtacatct acgtattagt catcgctatt accatggtga tgcggttttg gcagtacatc     720
aatgggcgtg atagcggttt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg ggcggtaggc gtgtacggtg ggaggtctat ataagcagag     900
ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga gcccgccatc cacgccggtt gagtcgcgtt ctgccgcctc cgcctgtgg    1080 tgcctcctga actgcgtccg ccgtctaggt aagtttaaag ctcaggtcga ccgggcct     1140 ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tgaaggccat catcgtgctg ctgatggtgg tcacaagcaa cgccgataga    1440
atctgtaccg gcatcaccag cagcaatagc cctcacgtcg tgaaaacagc tacacagggc    1500
gaagtgaatg tgaccggcgt gatccctctg ggatcaggac tgaagctggc caatggcaca    1560
aagtatagac ctccagccaa gctgctgaaa gagagaggct tttttggagc tatcgccggc    1620
tttctggaag gcggatggga gggaatgatt gctggatggc atggctacac atctcatggc    1680
gcacatggcg tggcagtggc tgctgatctg aaatctacac aggaagccat caacaagatc    1740
```

-continued

```
accaagaacc tgaacagcct gagcgagctg aaggaggcg accccgagtg ggatcgcgaa    1800
atcaacaact acacatctat catctacagt ctgattgagg aaagccagaa ccagcaggag    1860
aatgggactg ggggaggctc cggaatcgtg cagcagcaga acaatctgct gcgagccatt    1920
gaagctcagc agcacctgct gcagctgaca gtgtggggca tcaagcagct gcaggggagc    1980
cagattgaac tggctgtgct gctgtctaac gagggcatca tcaatagcga ggacgaacat    2040
ctgctggccc tggaaagaaa gctgaagaag atgctgggac ctagcgccgt ggaaatcggc    2100
aatggatgct ttgagacaaa gcacaagtgc aaccagacct gcctggatag aattgccgcc    2160
ggaacatttg atgccggcga gttttctctg cccaccttcg atagcctgaa tatcacatcc    2220
ggaggcgaca tcatcaagct gctgaacgag caggtgaaca aggagatgca gagcagcaac    2280
ctgtacatga gcatgagcag ctggtgctac acccacagcc tggacggcgc cggcctgttc    2340
ctgttcgacc acgccgccga ggagtacgag cacgccaaga agctgatcat cttcctgaac    2400
gagaacaacg tgcccgtgca gctgaccagc atcagcgccc ccgagcacaa gttcgagggc    2460
ctgacccaga tcttccagaa ggcctacgag cacgagcagc acatcagcga gagcatcaac    2520
aacatcgtgg accacgccat caagagcaag gaccacgcca ccttcaactt cctgcagtgg    2580
tacgtggccg agcagcacga ggaggaggtg ctgttcaagg acatcctgga caagatcgag    2640
ctgatcggca acgagaacca cggcctgtac ctggccgacc agtacgtgaa gggcatcgcc    2700
aagagcagga agagcggatc ctagtagcat catcatcatc atcattagtc tgaagggcga    2760
attgatccag ctgtgccttc tagttgccag ccatctgttg tttgcccctc ccccgtgcct    2820
tccttgaccc tggaaggtgc cactcccact gtcctttcct aataaaatga ggaaattgca    2880
tcgcattgtc tgagtaggtg tcattctatt ctgggggtg gggtggggca ggacagcaag    2940
ggggaggatt gggaagacaa tagcaggcat gctggggatg cggtgggctc tatgggtacc    3000
caggtgctga agaattgacc cggttcctcc tgggccagaa agaagcaggc acatcccctt    3060
ctctgtgaca caccctgtcc acgcccctgg ttcttagttc cagccccact cataggacac    3120
tcatagctca ggagggctcc gccttcaatc ccacccgcta agtacttgg agcggtctct    3180
ccctccctca tcagcccacc aaaccaaacc tagcctccaa gagtgggaag aaattaaagc    3240
aagataggct attaagtgca gagggagaga aaatgcctcc aacatgtgag gaagtaatga    3300
gagaaatcat agaatttaa ggccatgatt taaggccatc atggccttaa tcttccgctt    3360
cctcgctcac tgactcgctg cgctcggtcg ttcggctgcg gcgagcggta tcagctcact    3420
caaaggcggt aatacggtta tccacagaat caggggataa cgcaggaaag aacatgtgag    3480
caaaaggcca gcaaaaggcc aggaaccgta aaaaggccgc gttgctggcg ttttccata    3540
ggctccgccc cctgacgag catcacaaaa atcgacgctc aagtcagagg tggcgaaacc    3600
cgacaggact ataaagatac caggcgtttc cccctggaag ctccctcgtg cgctctcctg    3660
ttccgacccct gccgcttacc ggatacctgt ccgcctttct cccttcggga agcgtggcgc    3720
tttctcatag ctcacgctgt aggtatctca gttcggtgta ggtcgttcgc tccaagctgg    3780
gctgtgtgca cgaacccccc gttcagcccg accgctgcgc cttatccggt aactatcgtc    3840
ttgagtccaa cccggtaaga cacgacttat cgccactggc agcagccact ggtaacagga    3900
ttagcagagc gaggtatgta ggcggtgcta cagagttctt gaagtggtgg cctaactacg    3960
gctacactag aagaacagta tttggtatct gcgctctgct gaagccagtt accttcggaa    4020
aaagagttgg tagctcttga tccggcaaac aaaccaccgc tggtagcggt ggtttttttg    4080
```

-continued

| | | | | | |
|---|---|---|---|---|---|
| tttgcaagca | gcagattacg | cgcagaaaaa | aaggatctca | agaagatcct | tgatcttttt | 4140 |
| ctacggggtc | tgacgctcag | tggaacgaaa | actcacgtta | agggattttg | gtcatgagat | 4200 |
| tatcaaaaag | gatcttcacc | tagatccttt | taaattaaaa | atgaagtttt | aaatcaatct | 4260 |
| aaagtatata | tgagtaaact | tggtctgaca | gttaccaatg | cttaatcagt | gaggcaccta | 4320 |
| tctcagcgat | ctgtctattt | cgttcatcca | tagttgcctg | actcggggggg | gggggggcgct | 4380 |
| gaggtctgcc | tcgtgaagaa | ggtgttgctg | actcatacca | ggcctgaatc | gccccatcat | 4440 |
| ccagccagaa | agtgagggag | ccacggttga | tgagagcttt | gttgtaggtg | gaccagttgg | 4500 |
| tgattttgaa | cttttgcttt | gccacggaac | ggtctgcgtt | gtcgggaaga | tgcgtgatct | 4560 |
| gatccttcaa | ctcagcaaaa | gttcgattta | ttcaacaaag | ccgccgtccc | gtcaagtcag | 4620 |
| cgtaatgctc | tgccagtgtt | acaaccaatt | aaccaattct | gattagaaaa | actcatcgag | 4680 |
| catcaaatga | aactgcaatt | tattcatatc | aggattatca | ataccatatt | tttgaaaaag | 4740 |
| ccgtttctgt | aatgaaggag | aaaactcacc | gaggcagttc | cataggatgg | caagatcctg | 4800 |
| gtatcggtct | gcgattccga | ctcgtccaac | atcaatacaa | cctattaatt | tcccctcgtc | 4860 |
| aaaaataagg | ttatcaagtg | agaaatcacc | atgagtgacg | actgaatccg | gtgagaatgg | 4920 |
| caaaagctta | tgcatttctt | tccagacttg | ttcaacaggc | cagccattac | gctcgtcatc | 4980 |
| aaaatcactc | gcatcaacca | aaccgttatt | cattcgtgat | tgcgcctgag | cgagacgaaa | 5040 |
| tacgcgatcg | ctgttaaaag | gacaattaca | acaggaatc | gaatgcaacc | ggcgcaggaa | 5100 |
| cactgccagc | gcatcaacaa | tattttcacc | tgaatcagga | tattcttcta | atacctggaa | 5160 |
| tgctgttttc | ccggggatcg | cagtggtgag | taaccatgca | tcatcaggag | tacggataaa | 5220 |
| atgcttgatg | gtcggaagag | gcataaattc | cgtcagccag | tttagtctga | ccatctcatc | 5280 |
| tgtaacatca | ttggcaacgc | tacctttgcc | atgtttcaga | aacaactctg | gcgcatcggg | 5340 |
| cttcccatac | aatcgataga | ttgtcgcacc | tgattgcccg | acattatcgc | gagcccattt | 5400 |
| atacccatat | aaatcagcat | ccatgttgga | atttaatcgc | ggcctcgagc | aagacgtttc | 5460 |
| ccgttgaata | tggctcataa | caccccttgt | attactgttt | atgtaagcag | acagttttat | 5520 |
| tgttcatgat | gatatatttt | tatcttgtgc | aatgtaacat | cagagatttt | gagacacaac | 5580 |
| gtggctttcc | ccccccccc | attattgaag | catttatcag | ggttattgtc | tcatgagcgg | 5640 |
| atacatattt | gaatgtattt | agaaaaataa | acaaataggg | gttccgcgca | catttccccg | 5700 |
| aaaagtgcca | cctgacgtct | aagaaaccat | tattatcatg | acattaacct | ataaaaatag | 5760 |
| gcgtatcacg | aggccctttc | gtc | | | | 5783 |

<210> SEQ ID NO 160
<211> LENGTH: 5783
<212> TYPE: DNA
<213> ORGANISM: Artificial Sequence
<220> FEATURE:
<223> OTHER INFORMATION: Synthetic sequence of plasmid B FL
      SS/Gen4.55/Ferritin

<400> SEQUENCE: 160

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |

-continued

```
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatggqtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg gcggtaggc gtgtacggtg gaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct    1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tgaaggccat catcgtgctg ctgatggtgg tgaccagcaa cgccgataga   1440
atctgcaccg gcatcaccag cagcaatagc ccccatgtgg tgaaaacagc cacccagggc   1500
gaagtgaatg tgacaggcgt gatccctctg ggatcaggac tgaagctggc caatggcacc   1560
aagtacagac ctcccgccaa gctgctgaaa gagagaggct tctttggcgc cattgccgga   1620
tttctggaag cgggctggga gggaatgatt gccggctggc acggctatac atctcatggg   1680
gcccatggcg tggctgtggc cgccgatctg aagtctaccc aggaagccat caacaagatc   1740
accaagaacc tgaacagcct gagcgagctg gaaggaggcg accccgagtg ggatcgcgaa   1800
atcaacaact acacatctat catctacagt ctgattgagg aaagccagaa ccagcaggag   1860
aatgggactg gggaggctc cggaatcgtg cagcagcaga caatctgct gcgagccatt   1920
gaagctcagc agcacctgct gcagctgaca gtgtggggca tcaagcagct gcagggtcc   1980
cagattgaac tggccgtgct gctgtccaac gagggcatca tcaacagcga ggatgaacac   2040
ctgctggccc tggaacggaa gctgaagaag atgctgggcc cttctgccgt ggagatcggc   2100
aacggctgct tcgagacaaa gcacaagtgc aaccagacct gcctggatag aatcgccgct   2160
ggcaccttca tgccggcga gttcagcctg cctaccttcg acagcctgaa tatcacctcc   2220
ggaggcgaca tcatcaagct gctgaacgag caggtgaaca aggagatgca gagcagcaac   2280
ctgtacatga gcatgagcag ctggtgctac acccacagcc tggacggcgc cggcctgttc   2340
ctgttcgacc acgccgccga ggagtacgag cacgccaaga agctgatcat cttcctgaac   2400
gagaacaacg tgcccgtgca gctgaccagc atcagcgccc ccgagcacaa gttcgagggc   2460
ctgacccaga tcttccagaa ggcctacgag cacgagcagc acatcagcga gagcatcaac   2520
aacatcgtgg accacgccat caagagcaag gaccacgcca ccttcaactt cctgcagtgg   2580
tacgtggccg agcagcacga ggaggagtg ctgttcaagg acatcctgga caagatcgag   2640
ctgatcggca acgagaacca cggcctgtac ctggccgacc agtacgtgaa gggcatcgcc   2700
```

-continued

```
aagagcagga agagcggatc ctagtagcat catcatcatc atcattagtc tgaagggcga      2760
attgatccag ctgtgccttc tagttgccag ccatctgttg tttgcccctc ccccgtgcct      2820
tccttgaccc tggaaggtgc cactcccact gtcctttcct aataaaatga ggaaattgca      2880
tcgcattgtc tgagtaggtg tcattctatt ctggggggtg gggtggggca ggacagcaag      2940
ggggaggatt gggaagacaa tagcaggcat gctgggyatg cggtgggctc tatgggtacc      3000
caggtgctga agaattgacc cggttcctcc tgggccagaa agaagcaggc acatcccctt      3060
ctctgtgaca caccctgtcc acgcccctgg ttcttagttc cagccccact cataggacac      3120
tcatagctca ggagggctcc gccttcaatc ccacccgcta agtacttgg agcggtctct       3180 ccctccctca tcagcccacc aaaccaaacc tagcctccaa gagtgggaag aaattaaagc      3240
aagataggct attaagtgca gagggagaga aaatgcctcc aacatgtgag gaagtaatga      3300
gagaaatcat agaattttaa ggccatgatt taaggccatc atggccttaa tcttccgctt      3360
cctcgctcac tgactcgctg cgctcggtcg ttcggctgcg gcgagcggta tcagctcact      3420
caaaggcggt aatacggtta ccacagaat caggggataa cgcaggaaag aacatgtgag       3480
caaaaggcca gcaaaaggcc aggaaccgta aaaaggccgc gttgctggcg ttttttccata     3540 ggctccgccc ccctgacgag catcacaaaa atcgacgctc aagtcagagg tggcgaaacc     3600
cgacaggact ataaagatac caggcgtttc ccctggaag ctcccgtcg cgctctcctg       3660 ttccgaccct gccgcttacc ggatacctgt ccgcctttct cccttcggga agcgtggcgc     3720
tttctcatag ctcacgctgt aggtatctca gttcggtgta ggtcgttcgc tccaagctgg    3780
gctgtgtgca cgaaccccccc gttcagcccg accgctgcgc cttatccggt aactatcgtc   3840
ttgagtccaa cccggtaaga cacgacttat cgccactggc agcagccact ggtaacagga    3900
ttagcagagc gaggtatgta ggcggtgcta cagagttctt gaagtggtgg cctaactacg    3960
gctacactag aagaacagta tttggtatct gcgctctgct gaagccagtt accttcggaa    4020
aaagagttgg tagctcttga tccggcaaac aaaccaccgc tggtagcggt ggttttttg     4080 tttgcaagca gcagattacg cgcagaaaaa aaggatctca agaagatcct ttgatctttt    4140
ctacggggtc tgacgctcag tggaacgaaa actcacgtta agggattttg gtcatgagat    4200
tatcaaaaag gatcttcacc tagatccttt taaattaaa atgaagtttt aaatcaatct     4260
aaagtatata tgagtaaact tggtctgaca gttaccaatg cttaatcagt gaggcaccta    4320
tctcagcgat ctgtctattt cgttcatcca tagttgcctg actcgggggg ggggggcgct    4380
gaggtctgcc tcgtgaagaa ggtgttgctg actcatacca ggcctgaatc gccccatcat    4440
ccagccagaa agtgagggag ccacggttga tgagagcttt gttgtaggtg gaccagttgg    4500
tgattttgaa cttttgcttt gccacggaac ggtctgcgtt gtcgggaaga tgcgtgatct    4560
gatccttcaa ctcagcaaaa gttcgattta ttcaacaaag ccgccgtccc gtcaagtcag    4620
cgtaatgctc tgccagtgtt acaaccaatt aaccaattct gattagaaaa actcatcgag    4680
catcaaatga aactgcaatt tattcatatc aggattatca ataccatatt tttgaaaaag    4740
ccgtttctgt aatgaaggag aaaactcacc gaggcagttc cataggatgg caagatcctg    4800
gtatcggtct gcgattccga ctcgtccaac atcaatacaa cctattaatt tcccctcgtc    4860
aaaaataagg ttatcaagtg agaaatcacc atgagtgacg actgaatccg gtgagaatgg    4920
caaaagctta tgcatttctt tccagacttg ttcaacaggc cagccattac gctcgtcatc    4980
aaaatcactc gcatcaacca aaccgttatt cattcgtgat tgcgcctgag cgagacgaaa    5040
```

```
tacgcgatcg ctgttaaaag gacaattaca aacaggaatc gaatgcaacc ggcgcaggaa    5100
cactgccagc gcatcaacaa tattttcacc tgaatcagga tattcttcta atacctggaa    5160
tgctgttttc ccggggatcg cagtggtgag taaccatgca tcatcaggag tacggataaa    5220
atgcttgatg gtcggaagag gcataaattc cgtcagccag tttagtctga ccatctcatc    5280
tgtaacatca ttggcaacgc tacctttgcc atgtttcaga aacaactctg gcgcatcggg    5340
cttcccatac aatcgataga ttgtcgcacc tgattgcccg acattatcgc gagcccattt    5400
atacccatat aaatcagcat ccatgttgga atttaatcgc ggcctcgagc aagacgtttc    5460
ccgttgaata tggctcataa caccccttgt attactgttt atgtaagcag acagttttat    5520
tgttcatgat gatatatttt tatcttgtgc aatgtaacat cagagatttt gagacacaac    5580
gtggctttcc cccccccccc attattgaag catttatcag ggttattgtc tcatgagcgg    5640
atacatattt gaatgtattt agaaaaataa acaaataggg gttccgcgca catttccccg    5700
aaaagtgcca cctgacgtct aagaaaccat tattatcatg acattaacct ataaaaatag    5760
gcgtatcacg aggcccttc gtc                                             5783
```

<210> SEQ ID NO 161
<211> LENGTH: 8
<212> TYPE: PRT
<213> ORGANISM: Artificial Sequence
<220> FEATURE:
<223> OTHER INFORMATION: Synthetic sequence

<400> SEQUENCE: 161

Asn Gly Thr Gly Gly Gly Ser Gly
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic sequence

<400> SEQUENCE: 162

Asn Gly Thr Gly Gly Ser Gly
1               5

What is claimed is:

1. A nucleic acid molecule comprising a nucleotide sequence encoding a fusion protein comprising a monomeric ferritin subunit protein joined to an influenza hemagglutinin protein, wherein the monomeric ferritin subunit comprises a domain that allows the fusion protein to self-assemble into nanoparticles.

2. The nucleic acid molecule of claim 1, wherein the monomeric ferritin subunit protein is selected from the group consisting of a bacterial ferritin, a plant ferritin, an algal ferritin, an insect ferritin, a fungal ferritin and a mammalian ferritin.

3. The nucleic acid molecule of claim 1, wherein the monomeric subunit is a monomeric subunit of a *Helicobacter pylori* ferritin protein.

4. The nucleic acid molecule of claim 1, wherein the monomeric ferritin subunit protein comprises a region corresponding to amino acids 5-167 of SEQ ID NO:2.

5. The nucleic acid molecule of claim 1, wherein the monomeric subunit comprises an amino acid sequence selected from the group consisting of SEQ ID NO:2 and SEQ ID NO:5.

6. The nucleic acid molecule of claim 1, wherein the hemagglutinin protein comprises a region selected from the group consisting of:
   a) a region comprising an amino acid sequence comprising at least 25 amino acids from a hemagglutinin protein from an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and, B/Brisbane/60/2008 (2008 Bris, B);
   b) a region corresponding to amino acids 1-519 of SEQ ID NO:8;
   c) a region comprising amino acids 1-519 of SEQ ID NO:8; and d) a region comprising an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

7. The nucleic acid molecule of claim 1, wherein the hemagglutinin protein is capable of eliciting an immune response to a protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

8. The nucleic acid molecule of claim 1, wherein the fusion protein comprises an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68.

9. The nucleic acid molecule of claim 1, wherein the influenza hemagglutinin protein is selected from the group consisting of:
   a) an influenza hemagglutinin protein comprising a region selected from the group consisting of a region capable of allowing trimerization of the hemagglutinin protein, a stem region, an ectodomain, and a region comprising the amino acid sequence from the amino acid residue immediately distal to the last amino acid of the second helical coiled coil to the amino acid residue proximal to the first amino acid of the transmembrane domain;
   b) an influenza hemagglutinin protein comprising the stem region from an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and, B/Brisbane/60/2008 (2008 Bris, B);
   c) an influenza hemagglutinin protein comprising a region corresponding to amino acids 1-519 of SEQ ID NO:8;
   d) an influenza hemagglutinin protein comprising an amino acid sequence at least about 80% identical to SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, or SEQ ID NO:98; and,
   e) an influenza hemagglutinin protein comprising an amino acid sequence selected from the group consisting of amino acids 1-519 of SEQ ID NO:8 and SEQ ID NO:11.

10. The nucleic acid molecule of claim 1, wherein the fusion protein comprises a sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

11. The nucleic acid molecule of claim 1, wherein the nucleotide sequence is functionally linked to a promoter.

12. The nucleic acid molecule of claim 1, wherein the portion of the nucleotide sequence encoding the influenza hemagglutinin protein comprises a sequence at least 80% identical to a sequence selected from the group consisting of SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, and SEQ ID NO:97.

13. The nucleic acid molecule of claim 1, wherein the nucleotide sequence comprises a sequence selected from the group consisting of SEQ ID NO:40, SEQ ID NO:43, SEQ ID NO:46, SEQ ID NO:49, SEQ ID NO:52, SEQ ID NO:55, SEQ ID NO:58, SEQ ID NO:61, SEQ ID NO:64, SEQ ID NO:67, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, and SEQ ID NO:127.

14. A method of producing a nanoparticle, comprising:
   a) introducing into a cell a nucleic acid molecule comprising a nucleotide sequence encoding a fusion protein, wherein the fusion protein comprises a monomeric ferritin subunit joined to an influenza hemagglutinin protein, and wherein the monomeric ferritin subunit protein comprises a domain that allows the fusion protein to self-assemble into nanoparticles; and, b) purifying the nanoparticles from the cell.

15. The method of claim 14, wherein the monomeric ferritin subunit protein is selected from the group consisting of a bacterial ferritin, a plant ferritin, an algal ferritin, an insect ferritin, a fungal ferritin and a mammalian ferritin.

16. The method of claim 14, wherein the monomeric subunit is a monomeric subunit of a *Helicobacter pylori* ferritin protein.

17. A method to produce a vaccine against influenza virus, the method comprising:
   a) introducing into a cell a nucleic acid molecule comprising a nucleotide sequence encoding a fusion protein, wherein the fusion protein comprises a monomeric ferritin subunit joined to an influenza hemagglutinin protein, and wherein the monomeric ferritin subunit protein comprises a domain that allows the fusion protein to self-assemble into nanoparticles; and,
   b) purifying the nanoparticles from the cell to produce the vaccine.

* * * * *